United States Patent
Wrona et al.

(10) Patent No.: US 12,268,687 B2
(45) Date of Patent: Apr. 8, 2025

(54) COMPOUNDS AND USES THEREOF

(71) Applicant: JANSSEN PHARMACEUTICA NV, Beerse (BE)

(72) Inventors: Iwona Wrona, Sharon, MA (US); Kerem Ozboya, Cambridge, MA (US); Matthew Lucas, Lexington, MA (US); Bhaumik Pandya, Bedford, MA (US); Bertrand Le Bourdonnec, Northborough, MA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 248 days.

(21) Appl. No.: 17/776,952

(22) PCT Filed: Nov. 13, 2020

(86) PCT No.: PCT/US2020/060455
§ 371 (c)(1),
(2) Date: May 13, 2022

(87) PCT Pub. No.: WO2021/097240
PCT Pub. Date: May 20, 2021

(65) Prior Publication Data
US 2023/0116101 A1    Apr. 13, 2023

(51) Int. Cl.
| A61K 45/06 | (2006.01) |
| A61K 31/166 | (2006.01) |
| A61K 31/17 | (2006.01) |
| A61K 31/4188 | (2006.01) |
| A61K 31/436 | (2006.01) |
| A61K 31/439 | (2006.01) |
| A61K 31/4439 | (2006.01) |
| A61K 31/454 | (2006.01) |
| A61K 31/4545 | (2006.01) |
| A61K 31/497 | (2006.01) |
| A61K 31/501 | (2006.01) |
| A61K 31/55 | (2006.01) |
| A61K 39/395 | (2006.01) |

(52) U.S. Cl.
CPC .......... *A61K 31/501* (2013.01); *A61K 31/166* (2013.01); *A61K 31/17* (2013.01); *A61K 31/4188* (2013.01); *A61K 31/436* (2013.01); *A61K 31/439* (2013.01); *A61K 31/4439* (2013.01); *A61K 31/454* (2013.01); *A61K 31/4545* (2013.01); *A61K 31/497* (2013.01); *A61K 31/55* (2013.01); *A61K 39/3955* (2013.01)

(58) Field of Classification Search
CPC .. A61K 45/06; A61K 39/3955; A61K 31/501; A61K 31/166; A61K 31/17; A61K 31/4188; A61K 31/436; A61K 31/439; A61K 31/4439; A61K 31/454; A61K 31/4545; A61K 31/497; A61K 31/55
See application file for complete search history.

(56) References Cited

U.S. PATENT DOCUMENTS

| 4,782,071 A | 11/1988 | Butler et al. |
|---|---|---|
| 5,780,472 A | 7/1998 | Cho et al. |
| 6,727,247 B2 | 4/2004 | Flohr et al. |
| 7,074,809 B2 | 7/2006 | Arora et al. |
| 7,132,424 B2 | 11/2006 | Picard |
| 7,381,749 B2 | 6/2008 | Malecha et al. |
| 7,459,562 B2 | 12/2008 | Borzilleri et al. |
| 7,767,677 B2 | 8/2010 | Kamboj et al. |
| 7,790,408 B1 | 9/2010 | Ntambi et al. |
| 8,044,052 B2 * | 10/2011 | Fay ............ C07D 401/14 514/252.03 |
| 8,063,224 B2 | 11/2011 | Lachance et al. |
| 8,129,376 B2 | 3/2012 | Sundaresan et al. |
| 8,207,147 B2 | 6/2012 | Fyfe et al. |
| 8,207,199 B2 | 6/2012 | Aoki et al. |
| 8,258,160 B2 | 9/2012 | Dales et al. |
| 8,314,138 B2 | 11/2012 | Dales et al. |
| 8,541,457 B2 | 9/2013 | Fu et al. |
| 8,563,539 B2 | 10/2013 | Baldino et al. |
| 8,673,917 B2 | 3/2014 | Zoller et al. |
| 8,791,136 B2 | 7/2014 | Goff et al. |
| 8,822,513 B2 | 9/2014 | Lu et al. |
| 8,946,225 B2 | 2/2015 | Dupont-Passelaique et al. |
| 9,266,832 B2 | 2/2016 | Griffioen et al. |
| 9,290,465 B2 | 3/2016 | Derryberry et al. |
| 9,296,711 B2 | 3/2016 | Erickson et al. |
| 10,941,134 B2 | 3/2021 | Goff et al. |
| 10,973,810 B2 | 4/2021 | Vincent et al. |
| 2002/0019389 A1 | 2/2002 | Kim et al. |
| 2002/0133005 A1 | 9/2002 | Iino et al. |
| 2004/0023973 A1 | 2/2004 | Nagato et al. |
| 2004/0097483 A1 | 5/2004 | Zeng et al. |
| 2004/0127521 A1 | 7/2004 | Cai et al. |
| 2004/0146872 A1 | 7/2004 | Winther et al. |

(Continued)

FOREIGN PATENT DOCUMENTS

| CN | 1177352 A | 3/1998 |
| CN | 1630650 A | 6/2005 |

(Continued)

OTHER PUBLICATIONS

Huestis et al., "The Vinyl Moiety as a Handle for regiocontrol in the Preparation of Unsymmetrical 2,3-Aliphatic-Substituted Indoles and Pyrroles," Angew Chem Int Ed Engl. 50(6):1338-41 (2011).
Jarvis et al., "A-803467, a potent and selective Nav1.8 sodium channel blocker, attenuates neuropathic and inflammatory pain in the rat," Proc Natl Acad Sci U.S.A. 104(20):8520-5 (2007).
PubChem Compound Summary for CID 127868748, dated Jun. 18, 2017 (9 pages).
PubChem Compound Summary for CID 7059272, dated Jul. 29, 2006 (12 pages).

(Continued)

*Primary Examiner* — Sun Jae Yoo
(74) *Attorney, Agent, or Firm* — Wan Chieh Lee; Haug Partners LLP

(57) ABSTRACT

The present invention features compounds useful in the treatment of neurological disorders and primary brain cancer. The compounds of the invention, alone or in combination with other pharmaceutically active agents, can be used for treating or preventing neurological disorders and primary brain cancer.

29 Claims, No Drawings

(56) References Cited

U.S. PATENT DOCUMENTS

| | | |
|---|---|---|
| 2005/0032859 A1 | 2/2005 | Chen |
| 2005/0119242 A1 | 6/2005 | Deluca et al. |
| 2005/0256068 A1 | 11/2005 | McSwiggen et al. |
| 2006/0116382 A1 | 6/2006 | Yao et al. |
| 2006/0167044 A1 | 7/2006 | Arnaiz et al. |
| 2006/0270686 A1 | 11/2006 | Kelly et al. |
| 2007/0087363 A1 | 4/2007 | Bartel et al. |
| 2008/0015230 A1 | 1/2008 | Kamboj et al. |
| 2008/0021028 A1 | 1/2008 | Swinnen et al. |
| 2008/0132542 A1 | 6/2008 | Lachance et al. |
| 2008/0207587 A1 | 8/2008 | Kamboj et al. |
| 2008/0249100 A1 | 10/2008 | Chisholm et al. |
| 2008/0255130 A1 | 10/2008 | Koltun et al. |
| 2008/0255161 A1 | 10/2008 | Koltun et al. |
| 2008/0280891 A1 | 11/2008 | Kelly et al. |
| 2009/0098105 A1 | 4/2009 | Hopf et al. |
| 2009/0118296 A1 | 5/2009 | Black et al. |
| 2009/0149466 A1 | 6/2009 | Gillespie et al. |
| 2009/0163545 A1 | 6/2009 | Goldfarb |
| 2009/0170822 A1 | 7/2009 | DeLuca et al. |
| 2009/0170828 A1 | 7/2009 | Isabel et al. |
| 2009/0221597 A1 | 9/2009 | Hadida et al. |
| 2009/0239810 A1 | 9/2009 | Sundaresan et al. |
| 2009/0246137 A1 | 10/2009 | Hadida Ruah et al. |
| 2009/0253693 A1 | 10/2009 | Koltun et al. |
| 2009/0253738 A1 | 10/2009 | Koltun et al. |
| 2009/0325956 A1 | 12/2009 | Taniguchi et al. |
| 2010/0022486 A1 | 1/2010 | Bouillot et al. |
| 2010/0029722 A1 | 2/2010 | Dales et al. |
| 2010/0041696 A1 | 2/2010 | Daugan et al. |
| 2010/0160323 A1 | 6/2010 | Bischoff et al. |
| 2010/0210649 A1 | 8/2010 | Djaballah et al. |
| 2012/0010186 A1 | 1/2012 | Lachance et al. |
| 2012/0178678 A1 | 7/2012 | Dupont-Passelaigue et al. |
| 2012/0196844 A1 | 8/2012 | Alper et al. |
| 2012/0252850 A1 | 10/2012 | Milne et al. |
| 2012/0316182 A1 | 12/2012 | Whitten et al. |
| 2013/0011361 A1 | 1/2013 | Dales et al. |
| 2013/0225529 A1 | 8/2013 | Rigas |
| 2013/0317020 A1 | 11/2013 | Ruah et al. |
| 2014/0364393 A1 | 12/2014 | Yang et al. |
| 2015/0051206 A1 | 2/2015 | Loren et al. |
| 2015/0087673 A1 | 3/2015 | Hitoshi et al. |
| 2015/0246893 A1 | 9/2015 | Devaraj et al. |
| 2015/0252032 A1 | 9/2015 | Bolli et al. |
| 2016/0046568 A1 | 2/2016 | Uto et al. |
| 2016/0223559 A1 | 8/2016 | Devaraj et al. |
| 2016/0251336 A1 | 9/2016 | Yang et al. |
| 2016/0332989 A1 | 11/2016 | Wu et al. |
| 2017/0015654 A1 | 1/2017 | Imamura et al. |
| 2017/0174699 A1 | 6/2017 | Hadari et al. |
| 2017/0226086 A1 | 8/2017 | Li et al. |
| 2018/0015068 A1 | 1/2018 | Inoue et al. |
| 2018/0193325 A1 | 7/2018 | Vincent et al. |
| 2019/0302121 A1 | 10/2019 | Copland, III et al. |
| 2019/0330198 A1 | 10/2019 | Wrona et al. |
| 2020/0010462 A1 | 1/2020 | Lucas et al. |
| 2020/0262828 A1 | 8/2020 | Lucas et al. |
| 2021/0139471 A1 | 5/2021 | Wrona et al. |
| 2022/0040167 A1 | 2/2022 | Vincent et al. |

FOREIGN PATENT DOCUMENTS

| | | |
|---|---|---|
| CN | 101083994 A | 12/2007 |
| CN | 101128435 A | 2/2008 |
| CN | 101137363 A | 3/2008 |
| CN | 101589039 A | 11/2009 |
| CN | 101641347 A | 2/2010 |
| CN | 101835776 A | 9/2010 |
| CN | 103221408 A | 7/2013 |
| CN | 103328482 A | 9/2013 |
| CN | 103619825 A | 3/2014 |
| CN | 103748087 A | 4/2014 |
| CN | 104163794 | 11/2014 |
| EP | 1193255 | 4/2002 |
| EP | 1 737 451 A2 | 1/2007 |
| EP | 2 455 080 A1 | 5/2012 |
| EP | 2 455 081 A1 | 5/2012 |
| EP | 2598483 | 6/2013 |
| EP | 2462121 | 2/2015 |
| EP | 2 980 077 A1 | 2/2016 |
| EP | 2990400 | 3/2016 |
| EP | 3 284 738 A1 | 2/2018 |
| EP | 3 381 908 A1 | 10/2018 |
| JP | H11501021 A | 1/1999 |
| JP | 2005213233 | 8/2005 |
| JP | 2008513514 A | 5/2008 |
| JP | 2008525478 A | 7/2008 |
| JP | 2008526796 A | 7/2008 |
| JP | 2008539275 | 11/2008 |
| JP | 2008545760 A | 12/2008 |
| JP | 2009019013 | 1/2009 |
| JP | 2009501733 A | 3/2009 |
| JP | 201043052 | 2/2010 |
| JP | 2010506859 A | 3/2010 |
| JP | 2010510272 | 4/2010 |
| JP | 2010510993 A | 4/2010 |
| JP | 2010513400 | 4/2010 |
| JP | 2010516714 A | 5/2010 |
| JP | 2010535847 A | 11/2010 |
| JP | 2011516420 | 5/2011 |
| JP | 2011529102 A | 12/2011 |
| JP | 2012518603 A | 8/2012 |
| JP | 2013537180 A | 9/2013 |
| JP | 2014501274 A | 1/2014 |
| JP | 2014509600 A | 4/2014 |
| JP | 2014510708 A | 5/2014 |
| JP | 2014513071 A | 5/2014 |
| JP | 2014518240 A | 7/2014 |
| KR | 20150014719 | 2/2015 |
| KR | 20150015305 | 2/2015 |
| KR | 20160020616 | 2/2016 |
| WO | WO-9626937 A1 | 9/1996 |
| WO | WO-9963979 | 12/1999 |
| WO | WO-0020414 A | 4/2000 |
| WO | WO-0114339 | 3/2001 |
| WO | WO-0105769 | 11/2001 |
| WO | WO-02066470 | 8/2002 |
| WO | WO-03070885 | 8/2003 |
| WO | WO-03084948 A1 | 10/2003 |
| WO | WO-2004014892 | 2/2004 |
| WO | WO-2005011654 | 2/2005 |
| WO | WO-2005011655 | 2/2005 |
| WO | WO-2005011656 | 2/2005 |
| WO | WO-2005011657 | 2/2005 |
| WO | WO-2005014607 | 2/2005 |
| WO | WO-2005023833 | 3/2005 |
| WO | WO-2005026137 A2 | 3/2005 |
| WO | WO2005/117867 | 12/2005 |
| WO | WO-2006012325 | 2/2006 |
| WO | WO-2006014168 | 2/2006 |
| WO | WO-2006015621 | 2/2006 |
| WO | WO-2006022442 | 3/2006 |
| WO | WO-2006034279 | 3/2006 |
| WO | WO-2006034312 | 3/2006 |
| WO | WO-2006034315 | 3/2006 |
| WO | WO-2006034338 | 3/2006 |
| WO | WO-2006034341 | 3/2006 |
| WO | WO-2006034440 A2 | 3/2006 |
| WO | WO-2006034441 | 3/2006 |
| WO | WO-2006034446 | 3/2006 |
| WO | WO-2006057902 | 6/2006 |
| WO | WO-2006067531 | 6/2006 |
| WO | WO-2006071730 A1 | 7/2006 |
| WO | WO-2006072436 A1 | 7/2006 |
| WO | WO-2006074025 | 7/2006 |
| WO | WO-2006086445 | 8/2006 |
| WO | WO-2006086447 | 8/2006 |
| WO | WO-2006116713 | 11/2006 |
| WO | WO-2006125179 | 11/2006 |
| WO | WO-2006125181 | 11/2006 |
| WO | WO-2006125194 | 11/2006 |
| WO | WO-2006/130986 A1 | 12/2006 |
| WO | WO2006/137465 | 12/2006 |

(56) References Cited

FOREIGN PATENT DOCUMENTS

| | | |
|---|---|---|
| WO | WO-2007009236 A1 | 1/2007 |
| WO | WO-2007044085 | 4/2007 |
| WO | WO-2007046868 | 4/2007 |
| WO | WO-2007056846 | 5/2007 |
| WO | WO-2007076055 A2 | 7/2007 |
| WO | WO-2007079180 | 7/2007 |
| WO | WO-2007/120702 A2 | 10/2007 |
| WO | WO-2007130075 | 11/2007 |
| WO | WO-2007134457 | 11/2007 |
| WO | WO-2007136746 | 11/2007 |
| WO | WO-2007143597 | 12/2007 |
| WO | WO-2007143823 | 12/2007 |
| WO | WO-2007143824 | 12/2007 |
| WO | WO 2008/008852 A2 | 1/2008 |
| WO | WO 2008/008854 A2 | 1/2008 |
| WO | WO-2008003753 | 1/2008 |
| WO | WO-2008008059 | 1/2008 |
| WO | WO-2008017161 | 2/2008 |
| WO | WO-2008023720 A1 | 2/2008 |
| WO | WO-2008024139 | 2/2008 |
| WO | WO-2008024390 | 2/2008 |
| WO | WO-2008029266 A1 | 3/2008 |
| WO | WO-2008036715 | 3/2008 |
| WO | WO-2008043087 | 4/2008 |
| WO | WO-2008044767 | 4/2008 |
| WO | WO-2008046226 A1 | 4/2008 |
| WO | WO-2008056687 | 5/2008 |
| WO | WO-2008057280 | 5/2008 |
| WO | WO-2008061795 | 5/2008 |
| WO | WO-2008062276 | 5/2008 |
| WO | WO 2008/076356 A1 | 6/2008 |
| WO | WO-2008064474 A1 | 6/2008 |
| WO | WO-2008074824 | 6/2008 |
| WO | WO-2008074832 | 6/2008 |
| WO | WO-2008074833 | 6/2008 |
| WO | WO-2008074834 | 6/2008 |
| WO | WO-2008074835 | 6/2008 |
| WO | WO-2008089580 A1 | 7/2008 |
| WO | WO-2008096746 | 8/2008 |
| WO | WO-2008104524 | 9/2008 |
| WO | WO-2008116898 | 10/2008 |
| WO | WO-2008120744 | 10/2008 |
| WO | WO-2008120759 | 10/2008 |
| WO | WO-2008123469 | 10/2008 |
| WO | WO-2008127349 | 10/2008 |
| WO | WO-2008128335 | 10/2008 |
| WO | WO-2008139845 | 11/2008 |
| WO | WO-2008141455 | 11/2008 |
| WO | WO-2008157844 | 12/2008 |
| WO | WO-2009010560 | 1/2009 |
| WO | WO-2009012573 | 1/2009 |
| WO | WO-2009016216 | 2/2009 |
| WO | WO-2009019566 | 2/2009 |
| WO | WO-2009021990 A1 | 2/2009 |
| WO | WO-2009037542 | 3/2009 |
| WO | WO-2009/060053 A1 | 5/2009 |
| WO | WO-2009056556 | 5/2009 |
| WO | WO-2009060054 | 5/2009 |
| WO | WO-2009070533 | 6/2009 |
| WO | WO-2009073973 | 6/2009 |
| WO | WO-2009103739 | 8/2009 |
| WO | WO-2009106991 | 9/2009 |
| WO | WO-2009117659 | 9/2009 |
| WO | WO-2009123896 | 10/2009 |
| WO | WO-2009124259 | 10/2009 |
| WO | WO-2009129625 | 10/2009 |
| WO | WO-2009150196 | 12/2009 |
| WO | WO-2009156484 | 12/2009 |
| WO | WO-2010006962 | 1/2010 |
| WO | WO-2010007482 | 1/2010 |
| WO | WO-2010007966 A1 | 1/2010 |
| WO | WO-2010/022055 A2 | 2/2010 |
| WO | WO-2010013037 A1 | 2/2010 |
| WO | WO-2010025553 | 3/2010 |
| WO | WO-2010/039186 A2 | 4/2010 |
| WO | WO2010/048149 | 4/2010 |
| WO | WO-2010035052 | 4/2010 |
| WO | WO-2010037225 | 4/2010 |
| WO | WO-2010043052 | 4/2010 |
| WO | WO-2010045371 | 4/2010 |
| WO | WO-2010045374 | 4/2010 |
| WO | WO-2010056230 | 5/2010 |
| WO | WO-2010057833 | 5/2010 |
| WO | WO-2010060996 | 6/2010 |
| WO | WO-201 0094126 A | 8/2010 |
| WO | WO-2010094120 | 8/2010 |
| WO | WO-2010/108268 A1 | 9/2010 |
| WO | WO-2010101964 | 9/2010 |
| WO | WO-2010112520 | 10/2010 |
| WO | WO-2011011506 | 1/2011 |
| WO | WO-2011011508 | 1/2011 |
| WO | WO-2011011872 | 2/2011 |
| WO | WO-2011015629 | 2/2011 |
| WO | WO-2011025690 A | 3/2011 |
| WO | WO-2011030312 | 3/2011 |
| WO | WO-2011039358 | 4/2011 |
| WO | WO-2011047481 | 4/2011 |
| WO | WO-2011109059 | 9/2011 |
| WO | WO-2011123681 | 10/2011 |
| WO | WO-2011131593 | 10/2011 |
| WO | WO-2011157793 | 12/2011 |
| WO | WO-2012009134 | 1/2012 |
| WO | WO2012/016133 | 2/2012 |
| WO | WO-2012016217 | 2/2012 |
| WO | WO-2012035023 A1 | 3/2012 |
| WO | WO-2012046681 | 4/2012 |
| WO | WO-2012066077 A1 | 5/2012 |
| WO | WO-2012080729 | 6/2012 |
| WO | WO-2012082817 | 6/2012 |
| WO | WO-2012093809 A2 | 7/2012 |
| WO | WO-2012123449 A1 | 9/2012 |
| WO | WO-2012136492 A1 | 10/2012 |
| WO | WO-2012169649 A1 | 12/2012 |
| WO | WO-2013004642 A1 | 1/2013 |
| WO | WO-2013026587 A1 | 2/2013 |
| WO | WO 2013/046136 A1 | 4/2013 |
| WO | WO-2013/056148 A2 | 4/2013 |
| WO | WO 2013/070660 A1 | 5/2013 |
| WO | WO-2013085954 | 6/2013 |
| WO | WO-2013085957 | 6/2013 |
| WO | WO 2013/098373 A1 | 7/2013 |
| WO | WO-2013134546 | 9/2013 |
| WO | WO-2013160811 | 10/2013 |
| WO | WO-2013170072 | 11/2013 |
| WO | WO-2013175474 | 11/2013 |
| WO | WO-2014003153 | 1/2014 |
| WO | WO2014031928 | 2/2014 |
| WO | WO-2014092104 A1 | 6/2014 |
| WO | WO-2014116386 | 7/2014 |
| WO | WO-2015048547 | 4/2015 |
| WO | WO-2015101293 A1 | 7/2015 |
| WO | WO 2015/113920 A1 | 8/2015 |
| WO | WO-2015132610 | 9/2015 |
| WO | WO-2015137385 | 9/2015 |
| WO | WO-2015140130 A1 | 9/2015 |
| WO | WO-2016022626 | 2/2016 |
| WO | WO-2016022955 | 2/2016 |
| WO | WO-2016040794 | 3/2016 |
| WO | WO-2016049586 A2 | 3/2016 |
| WO | WO 2016/098005 A1 | 6/2016 |
| WO | WO-2016107603 | 7/2016 |
| WO | WO-2017066705 | 4/2017 |
| WO | WO 2017/112777 A1 | 6/2017 |
| WO | WO-2017093263 | 6/2017 |
| WO | WO-2017212425 | 12/2017 |
| WO | WO 2018/026663 A1 | 2/2018 |
| WO | WO-2018/081167 A1 | 5/2018 |
| WO | WO-2018112077 | 6/2018 |
| WO | WO-2018129403 | 7/2018 |
| WO | WO-2018160717 | 9/2018 |
| WO | WO-2018161033 | 9/2018 |
| WO | WO 2018/195450 A1 | 10/2018 |
| WO | WO-2019018795 | 1/2019 |
| WO | WO-2019084157 | 5/2019 |

(56) References Cited

FOREIGN PATENT DOCUMENTS

| WO | WO-2019123375 | 6/2019 |
|---|---|---|
| WO | WO-2019123378 | 6/2019 |
| WO | WO-2019140188 | 7/2019 |
| WO | WO-2019173394 | 9/2019 |
| WO | WO-2019183587 | 9/2019 |
| WO | WO-2019209948 | 10/2019 |
| WO | WO-2019209962 | 10/2019 |
| WO | WO-2020023657 | 1/2020 |
| WO | WO-2020132378 | 6/2020 |
| WO | WO-2020154571 | 7/2020 |
| WO | WO-2020198026 | 10/2020 |
| WO | WO-2021092240 | 5/2021 |
| WO | WO-2021092262 | 5/2021 |
| WO | WO-2021097240 | 5/2021 |
| WO | WO-2021139595 | 7/2021 |
| WO | WO-2021154571 | 8/2021 |

OTHER PUBLICATIONS

PubChem Compound Summary for CID 126485826, dated Apr. 22, 2017 (6 pages).
PubChem Compound Summary for CID 53003909, dated Jun. 21, 2011 (7 pages).
PubChem Compound Summary for CID 56980069, dated Jun. 13, 2012 (11 pages).
PubChem Compound Summary for CID 127012056, dated Jun. 2, 2017 (12 pages).
PubChem Compound Summary for CID 15985883, "5-[5-[4-[(4-Chlorophenyl)methyl]piperidin-1-yl]-5-oxopentyl]-1H-pyridin-2-one," created Mar. 27, 2007, retrieved Mar. 25, 2020 (7 pages).
"List of neurological conditions and disorders," <https://en.wikipedia.org/wiki/List_of_neurological_conditions_and_disorders>. retrieved on Jun. 27, 2019 (12 pages).
Astarita et al., "Elevated stearoyl-CoA desaturase in brains of patients with Alzheimer's disease," PLoS One. 6(10):e24777 (2011) (9 pages).
Bähler et al., "Heterologous modules for efficient and versatile PCR-based gene targeting in Schizosaccharomyces pombe." Yeast. 14(10):943-51 (1998).
Berge et al., "Pharmaceutical salts," J Pharm Sci. 66(1):1-19 (1977).
Berlin et al., 16(4) Bioorg. & Med. Chem. Letts., pp. 989-994 (2006).
Black et al., "Advances and limitations in the evaluation of analgesic combination therapy," Neurology. 65(12 Suppl 4):S3-6 (2005) (14 pages).
Chung et al., "Identification and rescue of alpha-synuclein toxicity in Parkinson patient-drived neurons," available in PMC Nov. 22, 2014, published in final edited form as: Science. 342(6161):983-7 (2013) (12 pages).
Cingolani et al., "A program for annotating and predicting the effects of single nucleotide polymorphisms, SnpEff: SNPs in the genome of Drosophila melanogaster strain w1118; iso-2; iso-3," Fly(Austin). 6(2):80-92 (2012).
Cooper et al., "Alpha-synuclein blocks ER-Golgi traffic and Rab1 rescues neuron loss in Parkinson's models," available in PMC Sep. 19, 2007, published in final edited form as: Science. 313(5785):324-8 (2006) (12 pages).
Crews et al., "Role of Svnucleins in Alzheimer's Disease," Neurotox Res. 16(3):306-317 (2009).
Dai et al., "SCD1 Confes Temozolomide Resistance to Human Glioma Cells via Akt/GSK3β/β-Catenin Signaling Axis," Frontiers in Pharmacology, vol. 8, Art. 960 (2018).
Debenham et al., "Discovery of N-[Bis(4-methoxyphenyl)methyl]-4-hydroxy-2-(pyridazin-3-yl)pyrimidine-5-carboxamide (MK-8617), an Orally Active Pan-Inhibitor of Hypoxia-Inducible Factor Prolyl Hydroxylase1-3 (HIF PHD1-3) for the Treatment of Anemia," J. Med. Chem. 59, 11039-11049 (2016).
Dillon et al., "Development of a novel LC(MS method to quantitate cellular stearoyl-CoA desaturase activity," Anal Chim Acta. 627(1):99-104 (2008).

Fatutta et al., "Comportamento di alcune idrazidi di fronte a composti y-dicarbonilici. (*)",Gazzetta Chimica Italiana, Societa Chimica Italiana, IT, vol. 90, Jan. 1, 1960 (Jan. 1, 1960), pp. 1645-1657.
Friedrich et al., "Mechanism of amyloid plaque formation suggests an intracellular basis of Abeta pathogenicity," Proc Natl Acad Sci U.S.A. 107(5):1942-7 (2010).
Gallagher et al., "Ceapins are a new class of unfolded protein response inhibitors, selectively targeting the ATF6α branch," eLife 2016; 5: e11878, 1-33 (2016).
Garrison et al., "Haplotype-based variant detection from short-read sequencing," <https:((arxiv.org/pdf/1207.3907.pdf> (2012) (9 pages).
Gietz, "Yeast transformation by the LiAc/SS carrier DNA/PEG method," Methods Mol Biol. 1205:1-12 (2014).
Goedert, M., "Parkinson's disease and other alpha-synucleinopathies," Clin Chem Lab Med. 39(4):308-12 (2001) (Abstract onlv).
Hamilton et al., "Aberrant Lipid Metabolism in the Forebrain Niche Suppresses Adult Neural Stem Cell Proliferation in an Animal Model of Alzheimer's Disease," Cell Stem Cell. 17(4):397-411 (2015) (16 pages).
Kamboh et al., "A novel mutation in the apolipoprotein E gene (APOE*4 Pittsburgh) is associated with the risk of late-onset Alzheimer's disease " Neurosci Lett. 263(2-3):129-32 (1999).
Larson et al., "Soluble α-synuclein is a novel modulator of Alzheimer's disease pathophysiology," Available in PMC Jan. 25, 2013, published in final edited form as: J Neurosci. 32(30):10253-66 (2012) (28 pages).
Li et al., "Fast and accurate long-read alignment with Burrows-Wheeler transform," Bioinformatics. 26(5):589-95 (2010).
Li et al., "Fast and accurate short read alignment with Burrows-Wheeler transform," Bioinformatics. 25(14):1754-60 (2009).
Li et al., "The sequence alignment/map format and SAMtools," Bioinformatics. 25(16):2078-9 (2009).
Longtine et al., "Additional modules for versatile and economical PCR-based gene deletion and modification in Saccharomyces cerevisiae," Yeast. 14(10):953-61 (1998).
Maya S. Salnikova, "Rational Development of Protein Formulations in Solid and Solution States," 2007.
Mikolaenko et al., "Alpha-synuclein lesions in normal aging, Parkinson disease, and Alzheimer disease: evidence from the Baltimore Longitudinal Study of Aging (BLSA)," J Neuropathol Exp Neurol. 64(2):156-62 (2005).
Miyazaki et al., "The biosynthesis of hepatic cholesterol esters and triglycerides is impaired in mice with a disruption of the gene for stearoyl-CoA desaturase 1," J Biol Chem. 275(39):30132-8 (2000).
Oatman et al. "Mechanisms of stearoyl CoA desaturase inhibitor sensitivity and acquired resistance in cancer" Science Advances. Feb. 10, 2021 vol 7, p. 1-19.
Pankratz et al., "Presence of an APOE4 Allele Results in Significantly Earlier Onset of Parkinson's Disease and a Higher Risk With Dementia," Mov Disord. 21(1):45-49 (2006).
Piotrowski et al., "Plant-derived antifungal agent poacic acid targets beta-1,3-glucan," Proc Natl Acad Sci U S A. 112(12):E1490-7 (2015).
Ponomarenko et al., "The Size of the Human Proteome: The Width and Depth," Int J Anal Chem. 2016:7426849 (2016) (6 pages).
Shanklin et al., "Stearoyl-acyl-carrier-protein desaturase from higher plants is structurally unrelated to the animal and fungal homologs," Proc Natl Acad Sci US A. 88(6):2510-4 (1991 ).
Simon et al., "Total ApoE and ApoE4 isoform assays in an Alzheimer's disease case-control study by targeted mass spectrometry (n=669): a pilot assay for methionine-containing proteotypic peptides." Mol Cell Proteomics. 11(11):1389-403 (2012).
Sinner et al., "StearoylCoA Desaturase-5: A novel regulator of neuronal cell proliferation and differentiation" PLoS One. 7(6):e39787 (2012) (12 pages).
Skedelj et al., "ATP-Binding Site of Bacterial Enzymes as a Target for Antibacterial Drug Design", Journal of Medicinal Chemistry, vol. 54, No. 4, Jan. 14, 2011 (Jan. 14, 2011), pp. 915-929.
Soulard et al., "Development of a high-throughput screening assay for stearoyl-CoA desaturase using rat liver microsomes, deuterium labeled stearoyl-CoA and mass spectrometry," Anal Chim Acta. 627(1):105-11 (2008).

(56) References Cited

OTHER PUBLICATIONS

Su et al., "Compounds from an unbiased chemical screen reverse both ER-to-Golgi trafficking defects and mitochondrial dysfunction in Parkinson's disease models," Dis Model Mech. 3(3-4):194-208 (2010).
Suzuki et al., "Knocking out multi-gene redundancies via cycles of sexual assortment and fluorescence selection," available in PMC Aug. 1, 2011, published in final edited form as: Nat Methods. 8(2):159-64 (Feb. 2011) (15 pages).
Tafesse et al., "Disruption of Sphingolipid Biosynthesis Blocks Phagocytosis of Candida albicans," PLoS Pathog. 11(10):e1005188 (2015) (27 pages).
Terry-Kantor et al., "Rapid Alpha-Synuclein Toxicity in a Neural Cell Model and Its Rescue by a Stearoyl-CoA Desaturase Inhibitor," Int. J. Mol. Sci., 21, 5193, 1-16 (Jul. 22. 2020).
Tesfay et al., "Steroyl-CoA Desaturase (SCD1) protects ovarian cancer cells from ferroptotic cell death," Cancer Res. 79(20): 5355-5366 (Oct. 15, 2019).
Tindale et al., "Rare and common variants in the Apolipoprotein E gene in healthy oldest old," Neurobiol Aging. 35(3):727.e1-3 (2014) (3 pages).
Verghese et al., "Roles of Apolipoprotein E in Alzheimer's disease and other neurological disorders," Lancet Neurol. 10(3):241-252 (2011 ).
Wang et al., "Characterization of HSCD5, a novel human stearoyl-CoA desaturase unique to primates," Biochem Biophys Res Commun. 332(3):735-42 (2005).
Zhang et al., "Revisiting the Medical Management of Parkinson's Disease: Levodopa Versus Dopamine Agonist," Curr Neuropharmacol. 14(4):356-363 (2016).
Zhang et al., "Opportunities and Challenges in Develping Stearoyl-Coenzyme A Desaturase-1 Inhibitors as Novel Therapeutics for Human Disease," J. Med. Chem., 57, 5039-5056 (2014).
Zhou, Youping, Zhong, et al. Inhibition of stearoyl-coenzyme A desaturase 1 ameliorates hepatic steatosis by inducing AMPK-mediated lipophagy. Aging, 12(8):7350-7362 (Apr. 23, 2020).
NCBI, Gene ID: 79966, "SCD5 stearoyl-CoA desaturase 5 [*Homo sapiens* (human)]," <https://web.archive.org/web/20150828032953/http://www.ncbi.nlm.nih.gov:80/gene/79966>, last modified Jul. 23, 2015 (5 pages).
PubChem CID 91412014, Create Date: Mar. 17, 2015 (Mar. 17, 2015), p. 2, Fig.
STN RN 1358463-36-1 (entered STN Feb. 29, 2012).
STN RN1266245-83-3 (entered STN Mar. 3, 2011).
Madia Valentina Noemi et al., "Novel Benzazole Derivatives Endowed with Potent Antiheparanase Activity", Journal of Medicinal Chemistry, vol. 61, No. 15, Jul. 16, 2018 (Jul. 16, 2018), pp. 6918-6936, XP093025853, US.
Trivedi Prakruti et al., "Design, synthesis and biological screening of 2-aminobenzamides as selective HDAC3 inhibitors with promising anticancer effects", European Journal of Pharmaceutical Sciences, Elsevier Amsterdam, NL, vol. 124, Aug. 29, 2018 (Aug. 29, 2018), pp. 165-181, XP085483648.
Tang Qidong et al., "Discovery of novel 7-azaindole derivatives bearing dihydropyridazine moiety as c-Met kinase inhibitors", European Journal of Medicinal Chemistry, vol. 133, Jun. 1, 2017 (Jun. 1, 2017), pp. 97-106, XP093026184.
Wang Lin Xiao et al., "Discovery of novel pyrrolo-pyridine/pyrimidine derivatives bearing pyridazinone moiety as c-Met kinase inhibitors", European Journal of Medicinal Chemistry, vol. 141, Oct. 13, 2017 (Oct. 13, 2017), pp. 538-551, XP085259430.
Byrd Katherine M. et al., "Synthesis and Biological Evaluation of Stilbene Analogues as Hsp90 C-Terminal Inhibitors", Chemmedchem Communications, vol. 12, No. 24, Nov. 30, 2017 (Nov. 30, 2017), pp. 2022-2029, XP093025869.
STN Search Report provided by Chinese Patent Office labelled CPCH2062597 with First Office Action dated Mar. 23, 2023.
Database Registry Chemical Abstracts Service, Columbus, Ohio, Accession No. RN 276236-86-3, Entered STN: Jul. 11, 2000.
Database Registry Chemical Abstracts Service, Columbus, Ohio, Accession No. RN 887202-53-1, Entered STN: Jun. 8, 2006.
Horan et al., "Piperazinyl-oxadiazoles as selective sphingosine-1-phosphate receptor agonists," Bioorq Med Chem Lett. 24(20):4807-11 (2014) (5 pages).
Krasavin et al., "Antiproliferative 4-(1,2,4-oxadiazol-5-yl)piperidine-1-carboxamides, a new tubulin inhibitor chemotvpe," Bioorg Med Chem Lett. 24(18): 4477-4481 (2014) (5 pages).
Kumar et al., "Design and Synthesis of 3,5-Disubstituted-1,2,4-Oxadiazoles as Potent Inhibitors of Phosphodiesterase4B2," Chem Biol Drug Des. 79(5):810-8 (2012).
Muraglia et al., "N-(2-alkylaminoethyl)-4-(1,2,4-oxadiazol-5-yl)piperazine-1-carboxamides as highly potent smoothened antagonists," Bioorg Med Chem Lett. 21(18): 5283-8 (2011) (6 pages).
Ontoria et al., "Identification of a series of 4-[3-(quinolin-2-y1)-1,2,4-oxadiazol-5-yl]piperazinyl ureas as potent smoothened antagonist hedgehog pathway inhibitors," 21(18): 5274-82 (2011) (9 pages).
PubChem Compound Summary for CID 71908265, retrieved from <https://pubchem.ncbi.nlm.nih.gov/compound/71908265>, created Nov. 29, 2013, retrieved Jan. 4, 2021 (8 pages).
Registry, Database Registry (online). Retrieved from STN, 2012. Search Date: Jul. 21, 2021 (13 pages).
Shen et al., "Discovery of a Highly Potent, Selective, and Bioavailable Soluble Epoxide Hydrolase Inhibitor with Excellent Ex Vivo Target Engagement," J Med Chem. 52(16):5009-12 (2009).
Tiwari et al., "Synthesis of 3-(5-bromo-2,3-dimethoxy-phenyl)-[1, 2, 4] oxadiazole analogues and their evaluation as anti-Parkinson's agents," Med Chem Res. 17:386-398 (2008) (12 pages).
Ng Davis et al: "Reviewing editor",Jul. 20, 2016 (Jul. 20, 2016), pp. 1-33, XP055921015, Retrieved from the Internet: URL:https://www.ncbi.nlm.nih.gov/pmc/artic les/PMC4954757/pdf/elife-11878.pdf [retrieved on May 13, 2022].
STN Search Report provided by SIPO for CN201980034106.4 listing RN1330502-23-2, RN1330502-23-2.
PubChem CID 17518963, created Nov. 13, 2007 (retrieved on Feb. 5, 2024 from https://pubchem.ncbi.nlm.nih.gov/compound/17518963).
PubChem CID 16583059, created Jul. 31, 2007 (retrieved on Feb. 5, 2024 from https://pubchem.ncbi.nlm.nih.gov/compound/16583059).
PubChem CID 23792053, created Feb. 20, 2008 (retrieved on Feb. 5, 2024 https://pubchem.ncbi.nlm.nih.gov/compound/23792053).
PubChem CID 23732517, created Feb. 20, 2008 (retrieved on Feb. 5, 2024 from https://pubchem.ncbi.nlm.nih.gov/compound/23732517).
PubChem CID 9449802, created Jul. 31, 2006 (retrieved on Feb. 5, 2024 from https://pubchem.ncbi.nlm.nih.gov/compound/9449802).
PubChem CID 23792381, created Feb. 20, 2008 (retrieved on Feb. 5, 2024 from https://pubchem.ncbi.nlm.nih.gov/compound/23792381.
PubChem CID 32148052, created May 29, 2009 (retrieved on Feb. 5, 2024 from https://pubchem.ncbi.nlm.nih.gov/compound/32148052).
PubChem CID 30035386, created May 28, 2009 (retrieved on Feb. 5, 2024 from https://pubchem.ncbi.nlm.nih.gov/compound/30035386).

\* cited by examiner

COMPOUNDS AND USES THEREOF

PRIORITY CLAIM

This application is a § 371 national phase filing of PCT Application No. PCT/US2020/060455 filed Nov. 13, 2020, which claims priority to U.S. Provisional Application Ser. No. 62/934,900 filed Nov. 13, 2019, the entire contents of each of these applications identified are hereby incorporated by reference herein in their entirety.

BACKGROUND

An incomplete understanding of the molecular perturbations that cause disease, as well as a limited arsenal of robust model systems, has contributed to a failure to generate successful disease-modifying therapies against common and progressive neurological disorders, such as Parkinson's Disease (PD) and Alzheimer's Disease (AD). Progress is being made on many fronts to find agents that can arrest the progress of these disorders. However, the present therapies for most, if not all, of these diseases provide very little relief. In particular, a need exists for better methods and compositions for the treatment of neurodegenerative diseases in order to improve the quality of the lives of those afflicted by such diseases.

Further, cancers of the brain and nervous system are among the most difficult to treat. Prognosis for patients with these cancers depends on the type and location of the tumor as well as its stage of development. For many types of brain cancer, average life expectancy after symptom onset may be months or a year or two. Treatment consists primarily of surgical removal and radiation therapy. Chemotherapy is also used, but the range of suitable chemotherapeutic agents is limited. Using known chemotherapeutics along with surgery and radiation rarely extends survival much beyond that produced by surgery and radiation alone.

Accordingly, a need exists to develop therapies that can alter the course of diseases of the brain (including primary brain cancer) and neurodegenerative diseases.

SUMMARY OF THE INVENTION

The invention features methods of treating primary brain cancer by administering an effective amount of a compound disclosed herein or a pharmaceutically acceptable salt thereof. In some embodiments, the compound modulates the activity of SCDs (e.g., SCD1 and/or SCD5), pharmaceutical compositions including such compounds.

In some embodiments, the compound is a compound of formula (I):

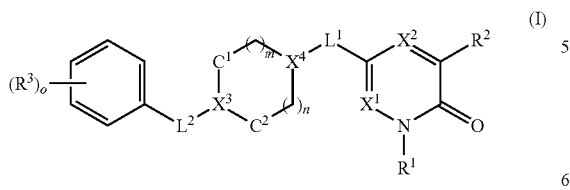

wherein: m is 0 or 1; n is 0, 1, or 2; o is 0, 1, 2, 3, 4, or 5; $C^1$ and $C^2$ optionally combine to form a bond; each of $R^1$, $R^2$, $R^5$, and $R^6$ is, independently, H or optionally substituted $C_{1-6}$ alkyl; $R^3$ is halo, cyano, $C_{1-6}$ perfluoroalkyl, optionally substituted $C_{1-6}$ alkoxy, or optionally substituted $C_{1-6}$ alkyl; each of $X^1$ and $X^2$ is, independently, CH or N, wherein $X^1$ and $X^2$ are not both N; $X^3$ is $CR^4$ or N; or $X^3$ and $C^1$ or $C^2$ combine to form an optionally substituted alkene; $X^4$ is CH or N; wherein at least one of $X^3$ and $X^4$ is N; $R^4$ is H, $OR^6$, optionally substituted $C_{1-6}$ alkyl, or halo; $L^1$ is optionally substituted $C_{5-10}$ heteroaryl or —C(O)—$X^5$—; $X^5$ is NH, O, or optionally substituted $C_{1-6}$ alkyl; and $L^2$ is O, $NR^5$, optionally substituted $C_{1-6}$ alkyl, optionally substituted $C_{1-6}$ heteroalkyl, or absent; or $X^3$ and $L^2$ combine to form an optionally substituted alkene, or a pharmaceutically acceptable salt thereof; wherein the compound does not have the structure of Compound 6, Compound 12, Compound 13, Compound 40, or Compound 106.

In some embodiments, $L^1$ is

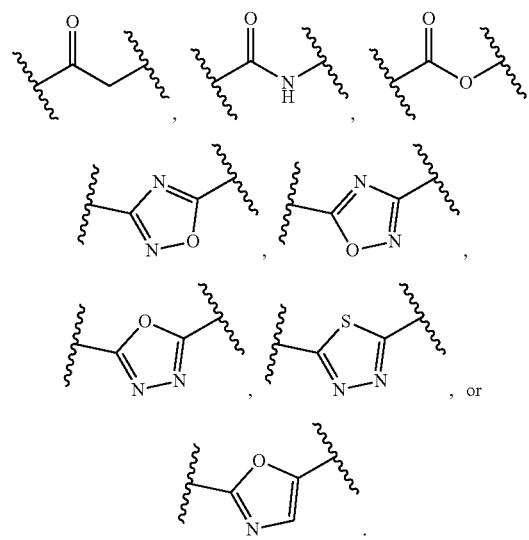

, or

In some embodiments, $L^2$ is absent, $NR^5$, optionally substituted $C_{1-6}$ alkyl, optionally substituted $C_{1-6}$ heteroalkyl, O, NH,

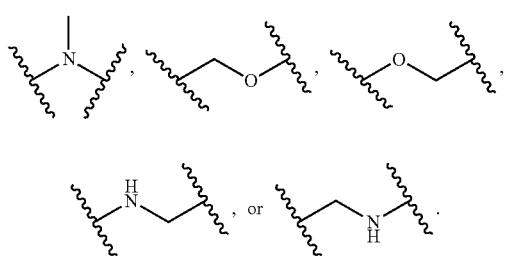

In some embodiments, m is 0 and n is 0; m is 0 and n is 1; m is 0 and n is 2; m is 1 and n is 0; m is 1 and n is 1; or m is 1 and n is 2.

In further embodiments, $R^3$ is halo (e.g., F, Cl, Br, or I), cyano, optionally substituted $C_{1-6}$ alkyl, (e.g., methyl, ethyl), optionally substituted $C_{1-6}$ alkoxy (e.g., methoxy), or $C_{1-6}$ perfluoroalkyl (e.g., perfluoromethyl).

In certain embodiments, the compound has the structure of formula (II):

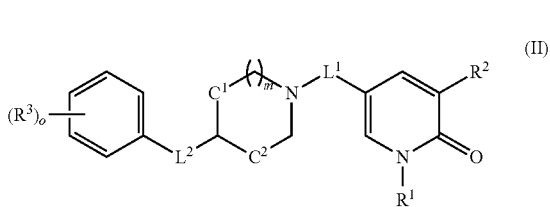

wherein: m is 0 or 1; o is 0, 1, 2, 3, 4, or 5; $C^1$ and $C^2$ optionally combine to form a bond; each of $R^1$, $R^2$, and $R^5$ is, independently, H or optionally substituted $C_{1-6}$ alkyl; $R^3$ is halo, cyano, $C_{1-6}$ perfluoroalkyl, optionally substituted $C_{1-6}$ alkoxy, or optionally substituted $C_{1-6}$ alkyl; $L^1$ is optionally substituted $C_{5-10}$ heteroaryl or —C(O)—$X^5$—; $X^5$ is NH, O, or optionally substituted $C_{1-6}$ alkyl; and $L^2$ is O, $NR^5$, optionally substituted $C_{1-6}$ alkyl, optionally substituted $C_{1-6}$ heteroalkyl, or absent; or a pharmaceutically acceptable salt thereof; wherein the compound does not have the structure of Compound 6, Compound 12, or Compound 13.

In some embodiments, $R^2$ is H. In some embodiments, $R^1$ is H. In some embodiments, m is 1.

In some embodiments, $L^1$ is

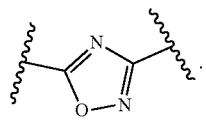 [SMILES: *c1noc(*)n1]

In some embodiments, $L^2$ is optionally substituted $C_{1-6}$ alkyl. In some embodiments, o is 2. In some embodiments, $R^3$ is halo. In particular embodiments, the compound is

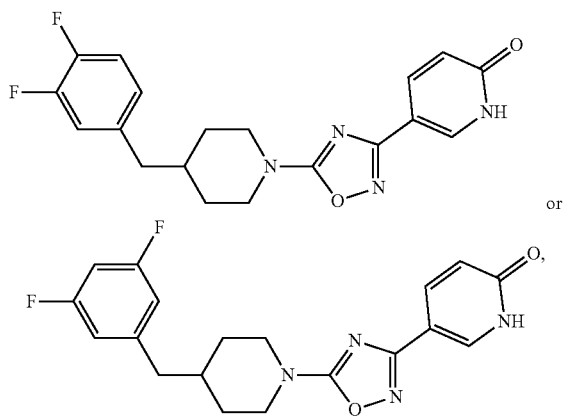

or a pharmaceutically acceptable salt thereof.

In some embodiments, $R^1$ is methyl. In some embodiments, m is 0. In some embodiments, $L^1$ is

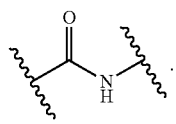 [SMILES: *NC(*)=O]

In further embodiments, $L^2$ is optionally substituted $C_{1-6}$ alkyl. In yet further embodiments, o is 2. In some embodiments, $R^3$ is halo. In particular embodiments, the compound is

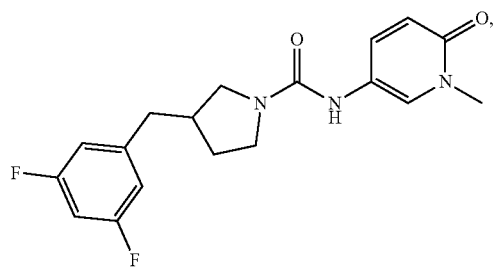 [SMILES: Cn1cc(NC(=O)N2CCC(Cc3cc(F)cc(F)c3)C2)ccc1=O]

or a pharmaceutically acceptable salt thereof.

In other embodiments, m is 1. In further embodiments, $L^1$ is

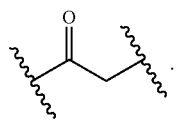 [SMILES: *CC(*)=O]

In some embodiments, $L^2$ is optionally substituted $C_{1-6}$ alkyl. In some embodiments, o is 1. In some embodiments, $R^3$ is halo. In specific embodiments, the compound is

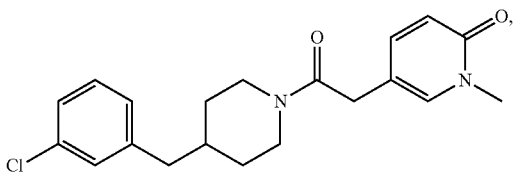 [SMILES: Cn1cc(CC(=O)N2CCC(Oc3cccc(Cl)c3)CC2)ccc1=O]

or a pharmaceutically acceptable salt thereof. In further embodiments, $L^2$ is O. In some embodiments, o is 1. In some embodiments, $R^3$ is halo. In particular embodiments, the compound is

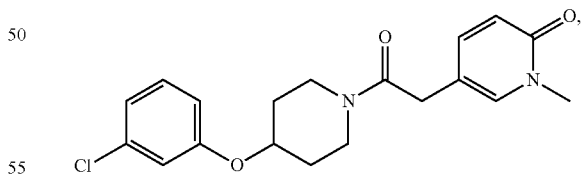

or a pharmaceutically acceptable salt thereof.

In yet other embodiments, $L^1$ is

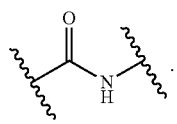 [SMILES: *NC(*)=O]

In some embodiments, $L^2$ is optionally substituted $C_{1-6}$ alkyl. In some embodiments, o is 1 or 2. In some embodiments, $R^3$ is halo. In still other embodiments, the compound is

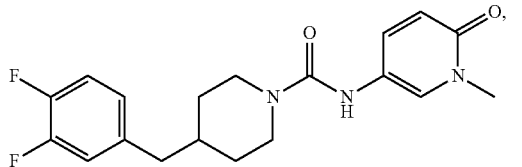

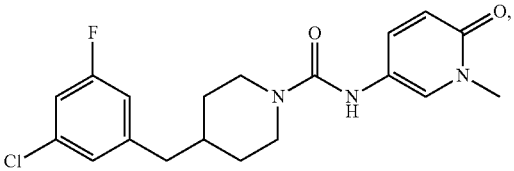

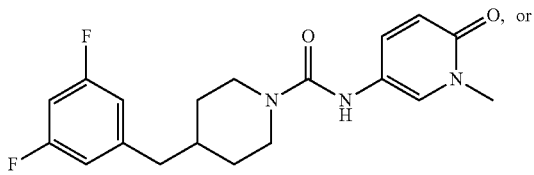

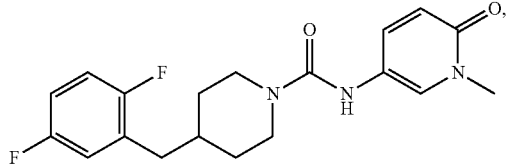

or a pharmaceutically acceptable salt thereof. In other embodiments, $L^2$ is NH. In some embodiments, o is 2. In some embodiments, $R^3$ is halo. In particular embodiments, the compound is

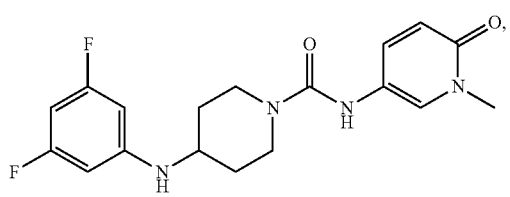

or a pharmaceutically acceptable salt thereof. In still other embodiments, $L^2$ is O. In further embodiments, o is 1. In some embodiments, $R^3$ is halo.

In further embodiments, $L^1$ is

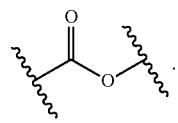 [SMILES: *OC(*)=O]

In some embodiments, $L^2$ is O. In some embodiments, o is 1 or 2. In some embodiments, $R^3$ is halo. In certain embodiments, the compound is

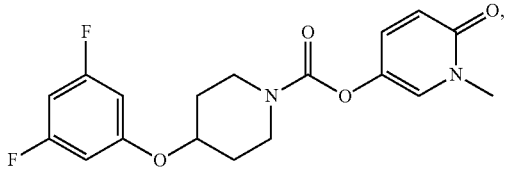

or a pharmaceutically acceptable salt thereof.

In yet further embodiments, $L^1$ is optionally substituted $C_{5-10}$ heteroaryl. In some embodiments, $L^1$ is

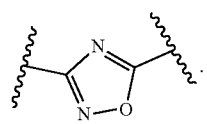 [SMILES: *c1noc(*)n1]

In some embodiments, $L^2$ is O. In some embodiments, o is 2. In some embodiments, $R^3$ is halo. In particular embodiments, the compound is

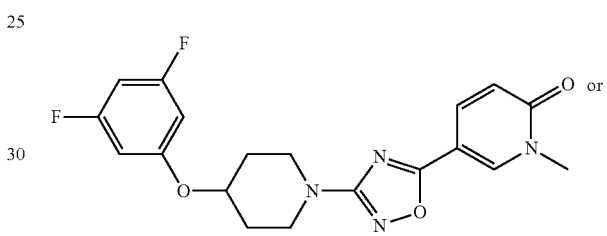

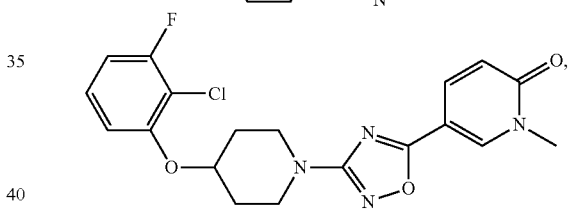

or a pharmaceutically acceptable salt thereof. In other embodiments, $L^2$ is optionally substituted $C_{1-6}$ alkyl. In some embodiments, o is 2. In further embodiments, $R^3$ is halo. In certain embodiments, the compound is

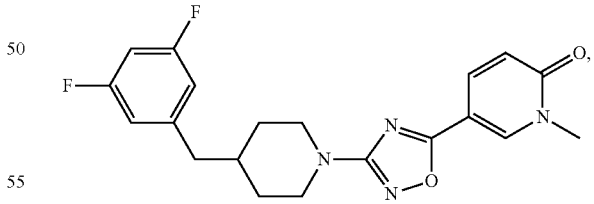

or a pharmaceutically acceptable salt thereof.

In further embodiments, $L^1$ is

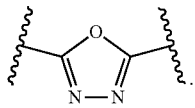

In some embodiments, L is optionally substituted $C_{1-6}$ alkyl. In some embodiments, o is 1 or 2. In some embodiments, $R^3$ is halo. In particular embodiments, the compound is

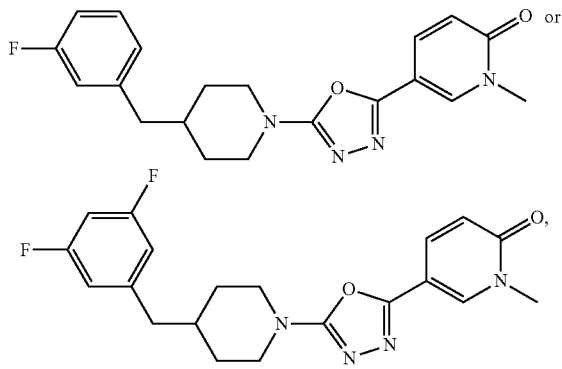

or a pharmaceutically acceptable salt thereof.

In still other embodiments, $L^1$ is

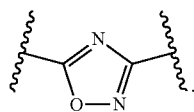

In some embodiments, $L^2$ is optionally substituted $C_{1-6}$ alkyl. In some embodiments, o is 2. In some embodiments, $R^3$ is halo. In specific embodiments, the compound is

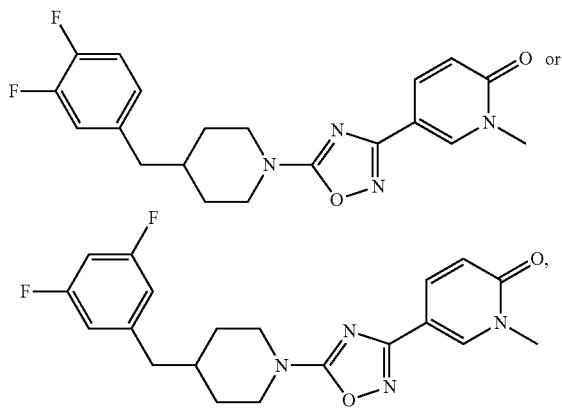

or a pharmaceutically acceptable salt thereof.

In further embodiments, the compound has the structure of formula (III):

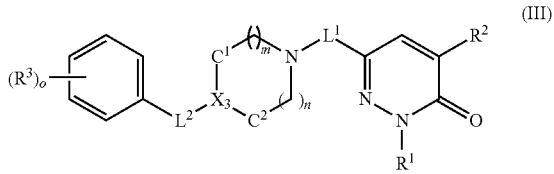

wherein: m is 0 or 1; n is 0, 1, or 2; o is 0, 1, 2, 3, 4, or 5; $C^1$ and $C^2$ optionally combine to form a bond; each of $R^1$, $R^2$, $R^5$, and $R^6$ is, independently, H or optionally substituted $C_{1-6}$ alkyl; $R^3$ is halo, cyano, $C_{1-6}$ perfluoroalkyl, optionally substituted $C_{1-6}$ alkoxy, or optionally substituted $C_{1-6}$ alkyl; $X^3$ is $CR^4$ or N; or $X^3$ and $C^1$ or $C^2$ combine to form an optionally substituted alkene; $R^4$ is H, $OR^6$, optionally substituted $C_{1-6}$ alkyl, or halo; $L^1$ is optionally substituted $C_{5-10}$ heteroaryl or —C(O)—$X^5$—; $X^5$ is NH, O, or optionally substituted $C_{1-6}$ alkyl; and $L^2$ is O, $NR^5$, optionally substituted $C_{1-6}$ alkyl, optionally substituted $C_{1-6}$ heteroalkyl, or absent; or $X^3$ and $L^2$ combine to form an optionally substituted alkene, or a pharmaceutically acceptable salt thereof; wherein the compound does not have the structure of Compound 40 or Compound 106.

In some embodiments, the compound has the structure of formula (III-A):

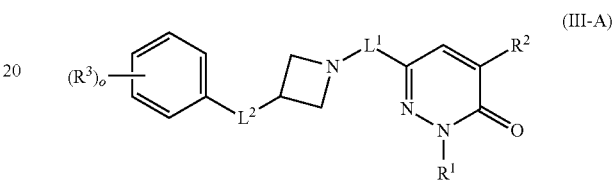

wherein: o is 0, 1, 2, 3, 4, or 5; each of $R^1$, $R^2$, and $R^5$ is, independently, H or optionally substituted $C_{1-6}$ alkyl; $R^3$ is halo, cyano, $C_{1-6}$ perfluoroalkyl, optionally substituted $C_{1-6}$ alkoxy, or optionally substituted $C_{1-6}$ alkyl; $L^1$ is optionally substituted $C_{5-10}$ heteroaryl or —C(O)—$X^5$—; $X^5$ is NH, O, or optionally substituted $C_{1-6}$ alkyl; and $L^2$ is O, $NR^5$, optionally substituted $C_{1-6}$ alkyl, optionally substituted $C_{1-6}$ heteroalkyl, or absent; or a pharmaceutically acceptable salt thereof.

In some embodiments, $R^2$ is H. In some embodiments, $R^1$ is methyl. In some embodiments, $L^1$ is

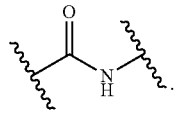 [SMILES: *NC(*)=O]

In further embodiments, $L^2$ is optionally substituted $C_{1-6}$ alkyl. In further embodiments, o is 1. In yet further embodiments, $R^3$ is halo. In particular embodiments, the compound is

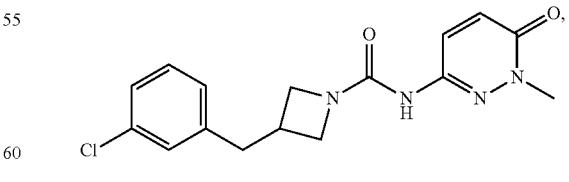

or a pharmaceutically acceptable salt thereof. In other embodiments, $L^2$ is O. In some embodiments, o is 2. In some embodiments, $R^3$ is halo. In certain embodiments, the compound is

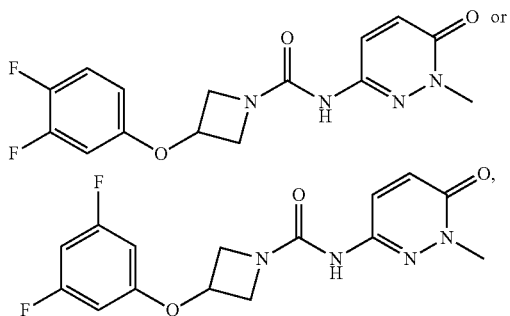

or a pharmaceutically acceptable salt thereof.

In further embodiments, the compound has the structure of formula (III-B):

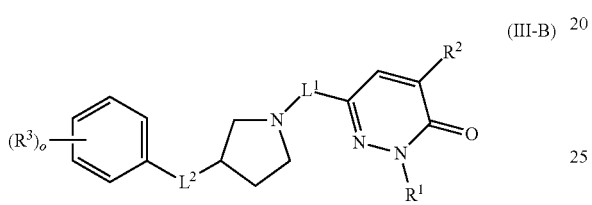
(III-B)

wherein: o is 0, 1, 2, 3, 4, or 5; each of $R^1$, $R^2$, and $R^5$ is, independently, H or optionally substituted $C_{1-6}$ alkyl; $R^3$ is halo, cyano, $C_{1-6}$ perfluoroalkyl, optionally substituted $C_{1-6}$ alkoxy, or optionally substituted $C_{1-6}$ alkyl; $L^1$ is optionally substituted $C_{5-10}$ heteroaryl or —C(O)—$X^5$—; $X^5$ is NH, O, or optionally substituted $C_{1-6}$ alkyl; and $L^2$ is O, $NR^5$, optionally substituted $C_{1-6}$ alkyl, optionally substituted $C_{1-6}$ heteroalkyl, or absent; or a pharmaceutically acceptable salt thereof.

In some embodiments, $R^2$ is H. In some embodiments, $R^1$ is methyl. In some embodiments, $L^1$ is

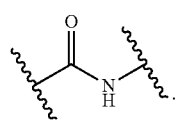

In further embodiments, $L^2$ is optionally substituted $C_{1-6}$ alkyl. In some embodiments, o is 1 or 2. In some embodiments, $R^3$ is halo. In particular embodiments, the compound is

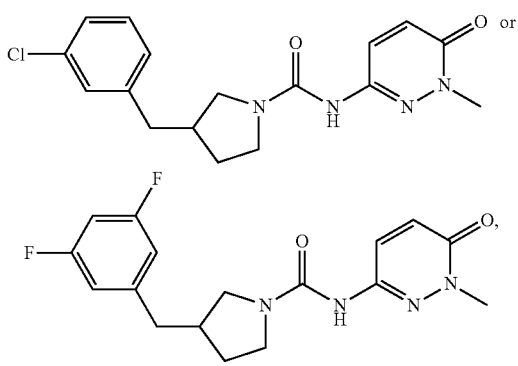

or a pharmaceutically acceptable salt thereof. In further embodiments, $L^2$ is O. In some embodiments, o is 2. In still other embodiments, $R^3$ is halo. In some embodiments, the compound is

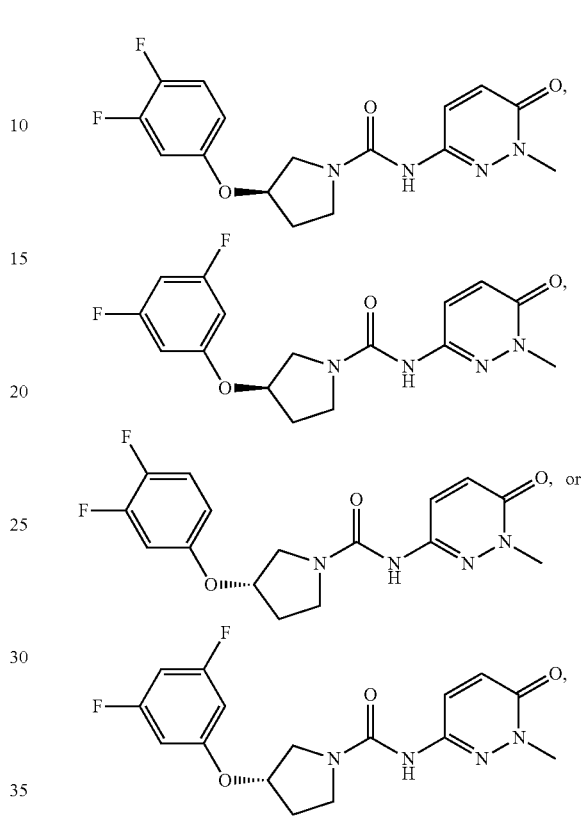

or a pharmaceutically acceptable salt thereof.

In yet other embodiments, the compound has the structure of formula (III-C):

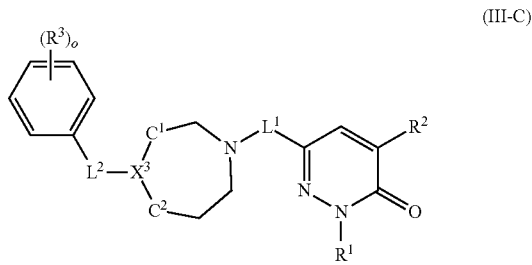
(III-C)

wherein: o is 0, 1, 2, 3, 4, or 5; $C^1$ and $C^2$ optionally combine to form a bond; each of $R^1$, $R^2$, $R^5$, and $R^6$ is, independently, H or optionally substituted $C_{1-6}$ alkyl; $R^3$ is halo, cyano, $C_{1-6}$ perfluoroalkyl, optionally substituted $C_{1-6}$ alkoxy, or optionally substituted $C_{1-6}$ alkyl; $X^3$ is $CR^4$ or N; or $X^3$ and $C^1$ or $C^2$ combine to form an optionally substituted alkene; $R^4$ is H, $OR^6$, optionally substituted $C_{1-6}$ alkyl, or halo; $L^1$ is optionally substituted $C_{5-10}$ heteroaryl or —C(O)—$X^5$—; $X^5$ is NH, O, or optionally substituted $C_{1-6}$ alkyl; and $L^2$ is O, $NR^5$, optionally substituted $C_{1-6}$ alkyl, optionally substituted $C_{1-6}$ heteroalkyl, or absent; or $X^3$ and $L^2$ combine to form an optionally substituted alkene, or a pharmaceutically acceptable salt thereof.

In some embodiments, $R^2$ is H. In some embodiments, $R^1$ is methyl. In further embodiments, $L^1$ is

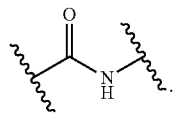 [SMILES: *NC(*)=O]

In some embodiments, $L^2$ is absent. In some embodiments, o is 1 or 2. In further embodiments, $R^3$ is halo. In specific embodiments, the compound is

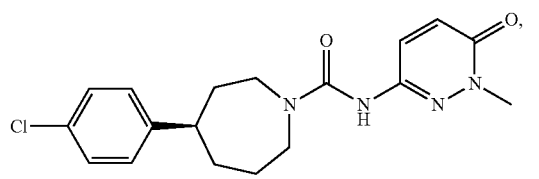

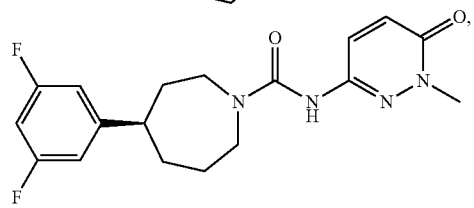

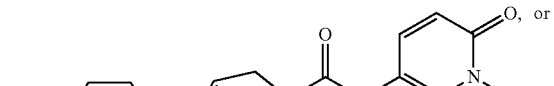

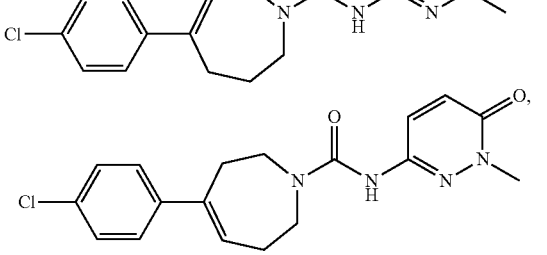

or a pharmaceutically acceptable salt thereof.

In further embodiments, the compound has the structure of formula (III-D):

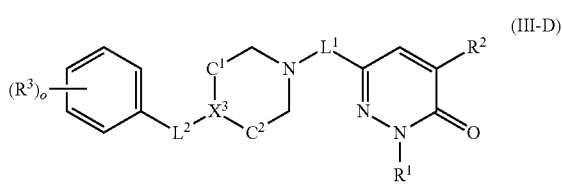

(III-D)

wherein: o is 0, 1, 2, 3, 4, or 5; $C^1$ and $C^2$ optionally combine to form a bond; each of $R^1$, $R^2$, $R^5$, and $R^6$ is, independently, H or optionally substituted $C_{1-6}$ alkyl; $R^3$ is halo, cyano, $C_{1-6}$ perfluoroalkyl, optionally substituted $C_{1-6}$ alkoxy, or optionally substituted $C_{1-6}$ alkyl; $X^3$ is $CR^4$ or N; or $X^3$ and $C^1$ or $C^2$ combine to form an optionally substituted alkene; $R^4$ is H, $OR^6$, optionally substituted $C_{1-6}$ alkyl, or halo; $L^1$ is optionally substituted $C_{5-10}$ heteroaryl or —C(O)—$X^5$—; $X^5$ is NH, O, or optionally substituted $C_{1-6}$ alkyl; and $L^2$ is O, $NR^5$, optionally substituted $C_{1-6}$ alkyl, optionally substituted $C_{1-6}$ heteroalkyl, or absent; or $X^3$ and $L^2$ combine to form an optionally substituted alkene, or a pharmaceutically acceptable salt thereof; wherein the compound does not have the structure of Compound 40 or Compound 106.

In some embodiments, $R^2$ is H. In certain embodiments, $R^1$ is methyl. In some embodiments, $L^1$ is

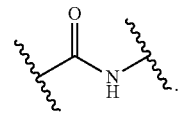 [SMILES: *NC(*)=O]

In further embodiments, $X^3$ and $L^2$ combine to form an optionally substituted alkene. In some embodiments, o is 2. In some embodiments, $R^3$ is halo. In particular embodiments, the compound

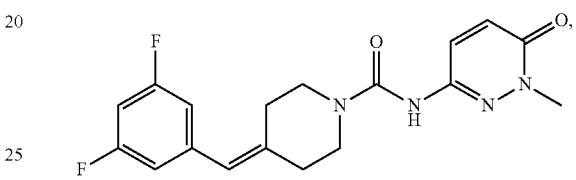

or a pharmaceutically acceptable salt thereof.

In some embodiments, the compound has the structure of formula (III-D-1):

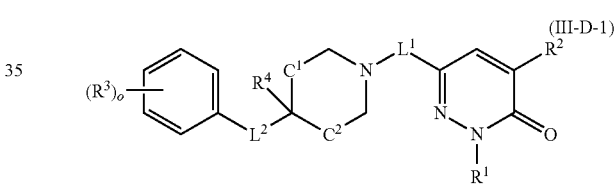

(III-D-1)

wherein: o is 0, 1, 2, 3, 4, or 5; $C^1$ and $C^2$ optionally combine to form a bond; each of $R^1$, $R^2$, $R^5$, and $R^6$ is, independently, H or optionally substituted $C_{1-6}$ alkyl; $R^3$ is halo, cyano, $C_{1-6}$ perfluoroalkyl, optionally substituted $C_{1-6}$ alkoxy, or optionally substituted $C_{1-6}$ alkyl; $R^4$ is H, $OR^6$, optionally substituted $C_{1-6}$ alkyl, or halo; $L^1$ is optionally substituted $C_{5-10}$ heteroaryl or —C(O)—$X^5$—; $X^5$ is NH, O, or optionally substituted $C_{1-6}$ alkyl; and $L^2$ is O, $NR^5$, optionally substituted $C_{1-6}$ alkyl, optionally substituted $C_{1-6}$ heteroalkyl, or absent; or a pharmaceutically acceptable salt thereof; wherein the compound does not have the structure of Compound 40 or Compound 106.

In some embodiments, $R^2$ is H. In some embodiments, $R^1$ is H. In some embodiments, $L^1$ is

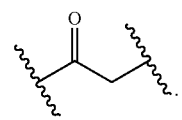 [SMILES: *CC(*)=O]

In further embodiments, $L^2$ is optionally substituted $C_{1-6}$ alkyl. In some embodiments, o is 1 or 2. In some embodiments, $R^3$ is halo. In some embodiments, $R^4$ is H. In certain embodiments, the compound is

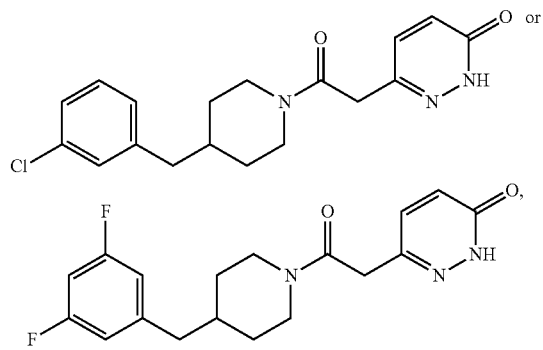

or a pharmaceutically acceptable salt thereof. In further embodiments, $L^2$ is O. In some embodiments, o is 1. In some embodiments, $R^3$ is halo. In some embodiments, $R^4$ is H. In some embodiments, the compound

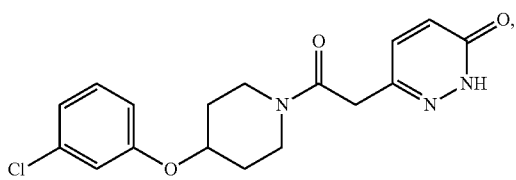 [SMILES: O=C(Cc1ccc(=O)[nH]n1)N1CCC(Oc2cccc(Cl)c2)CC1]

or a pharmaceutically acceptable salt thereof.

In further embodiments, $R^1$ is methyl. In some embodiments, $L^1$ is

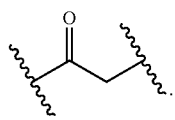 [SMILES: *CC(*)=O]

In some embodiments, $L^2$ is optionally substituted $C_{1-6}$ alkyl. In some embodiments, o is 1 or 2. In further embodiments, $R^3$ is halo. In still further embodiments, $R^4$ is H. In particular embodiments, the compound

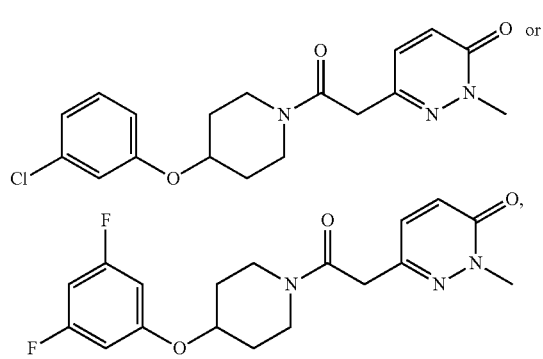

or a pharmaceutically acceptable salt thereof. In other embodiments, $L^2$ is O. In some embodiments, o is 1. In some embodiments, $R^3$ is halo. In some embodiments, $R^4$ is H. In further embodiments, the compound is

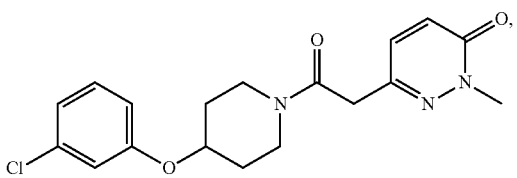 [SMILES: Cn1nc(CC(=O)N2CCC(Oc3cccc(Cl)c3)CC2)ccc1=O]

or a pharmaceutically acceptable salt thereof.

In yet other embodiments, $L^1$ is

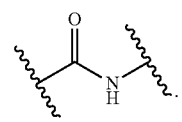

In some embodiments, $L^2$ is optionally substituted $C_{1-6}$ alkyl. In some embodiments, o is 1. In some embodiments, $R^3$ is halo. In some embodiments, $R^4$ is H. In further embodiments, the compound is

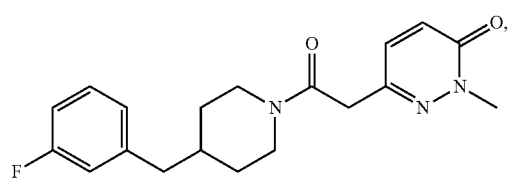

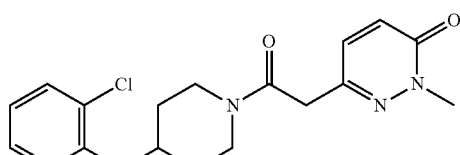

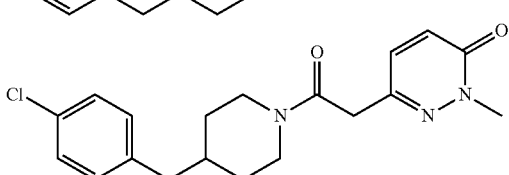

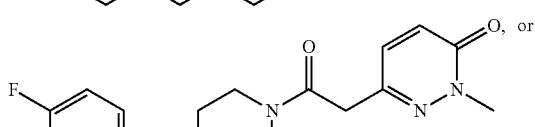

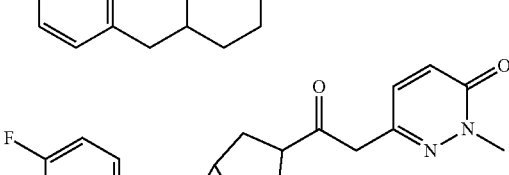

or a pharmaceutically acceptable salt thereof. In other embodiments, $R^4$ is fluoro. In certain embodiments, the compound is

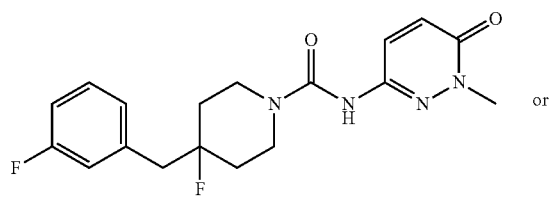

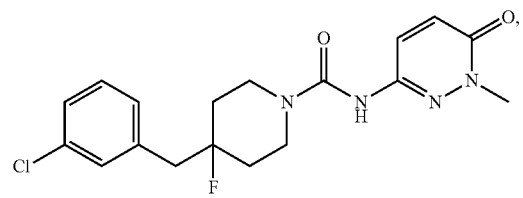

or a pharmaceutically acceptable salt thereof. In still further embodiments, $R^4$ is $OR^6$. In some embodiments, the compound is

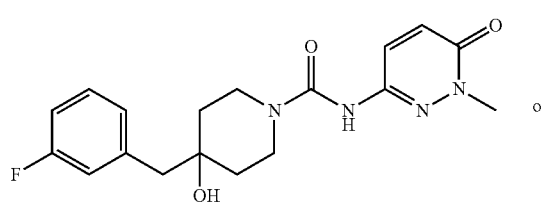

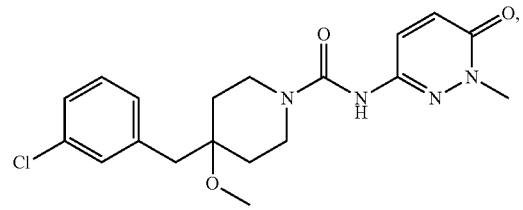

or a pharmaceutically acceptable salt thereof.

In other embodiments, o is 2. In some embodiments, $R^3$ is, independently, halo or cyano. In some embodiments, $R^4$ is H. In certain embodiments, the compound is

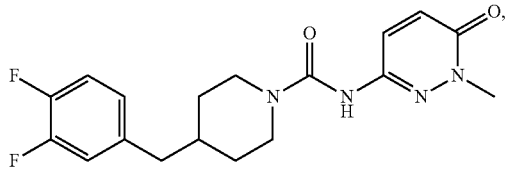

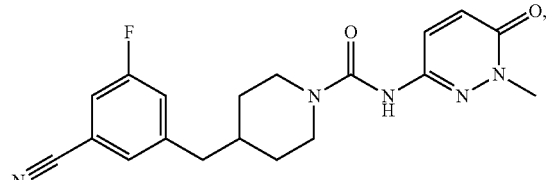

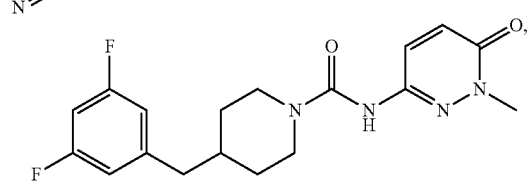

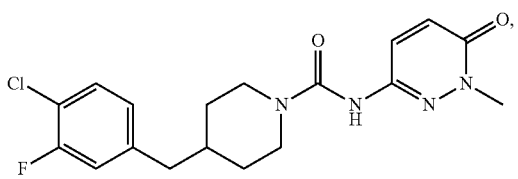

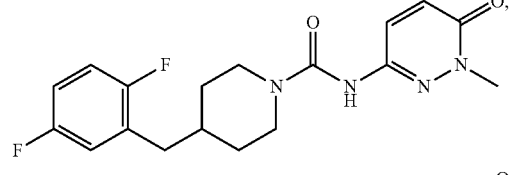

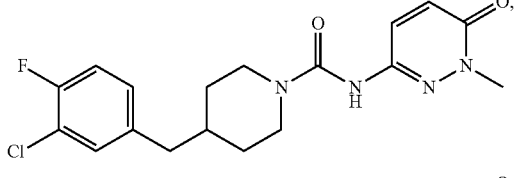

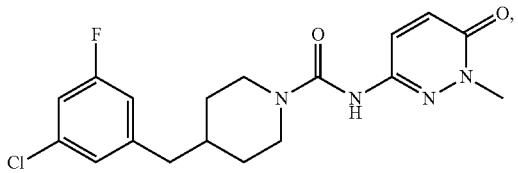

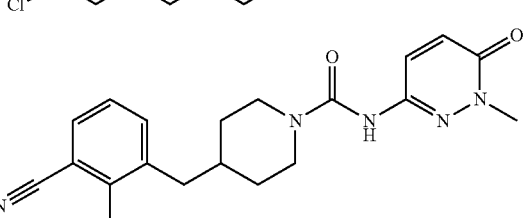

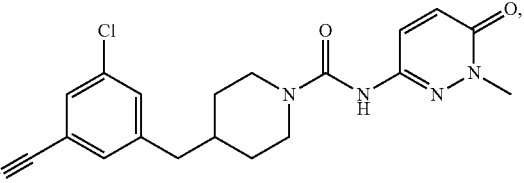

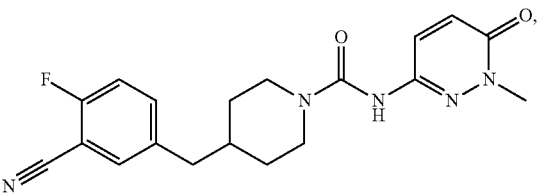 [SMILES: Cn1nc(NC(=O)N2CCC(Cc3ccc(F)c(C#N)c3)CC2)ccc1=O]

or a pharmaceutically acceptable salt thereof. In still other embodiments, $R^4$ is fluoro. In some embodiments, the compound is

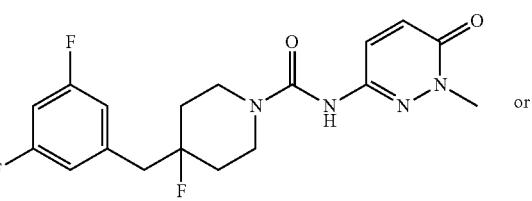

-continued

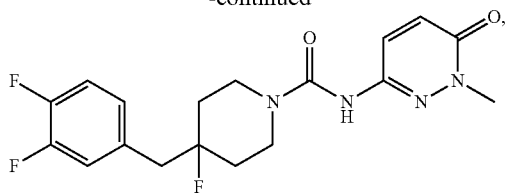

or a pharmaceutically acceptable salt thereof.

In further embodiments, o is 3. In some embodiments, each $R^3$ is, independently, halo or cyano. In some embodiments, $R^4$ is H. In particular embodiments, the compound is

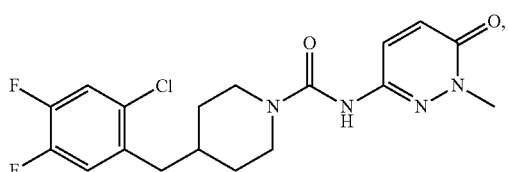

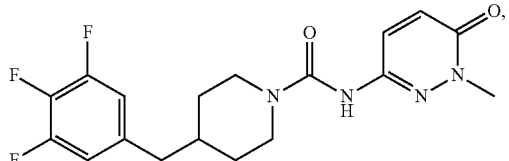

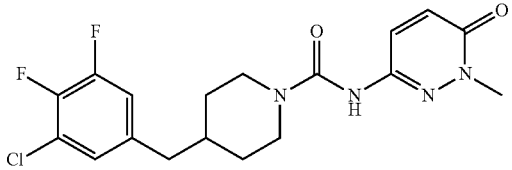

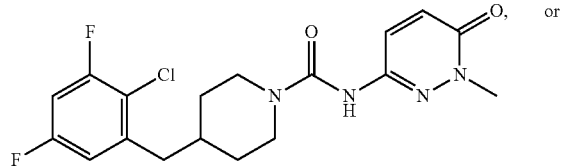

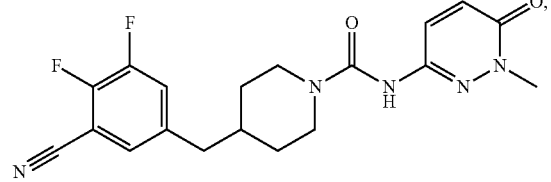

or a pharmaceutically acceptable salt thereof. In other embodiments, $R^4$ is fluoro. In some embodiments, the compound is

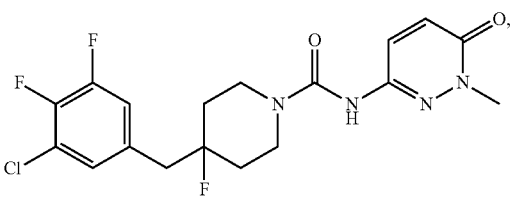 [SMILES: Cn1nc(NC(=O)N2CCC(F)(Cc3cc(F)c(F)c(Cl)c3)CC2)ccc1=O]

or a pharmaceutically acceptable salt thereof.

In some embodiments, $L^2$ is O. In further embodiments, o is 0. In some embodiments, $R^4$ is H.

In some embodiments, the compound is

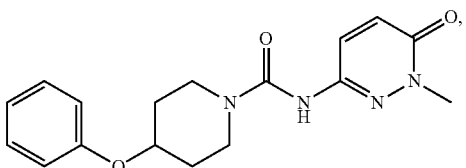

or a pharmaceutically acceptable salt thereof. In other embodiments, o is 1. In some embodiments, $R^3$ is halo, optionally substituted $C_{1-6}$ alkyl, optionally substituted $C_{1-6}$ alkoxy, or $C_{1-6}$ perfluoroalkyl. In further embodiments, $R^4$ is H. In particular embodiments, the compound is

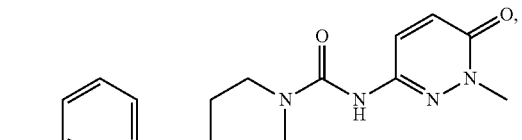

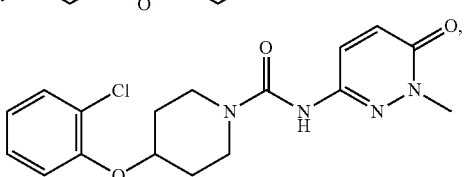

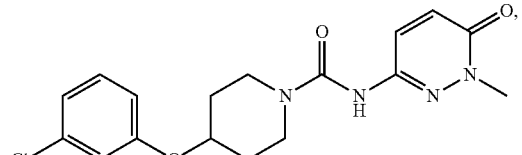

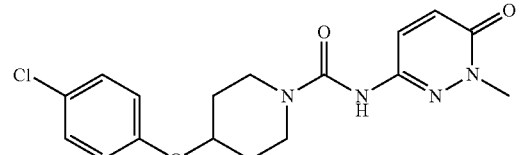

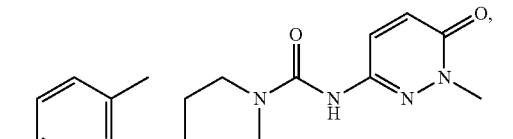

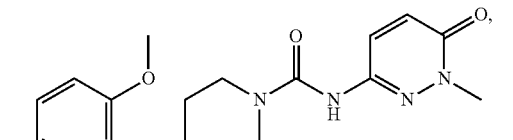

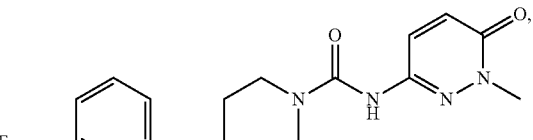

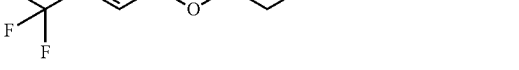

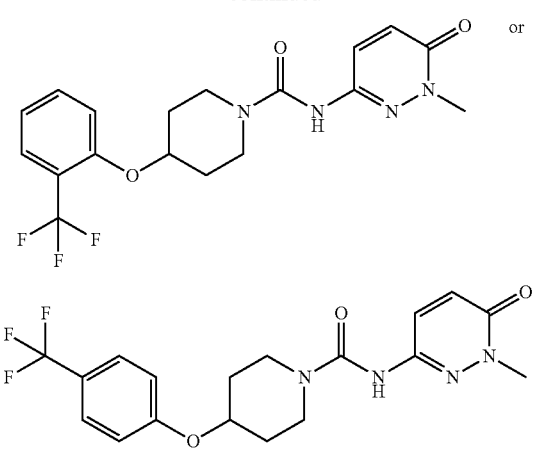

or a pharmaceutically acceptable salt thereof.

In still further embodiments, o is 2. In some embodiments, each $R^3$ is, independently, halo, $C_{1-6}$ perfluoroalkyl, or cyano. In some embodiments, $R^4$ is H. In specific embodiments, the compound is

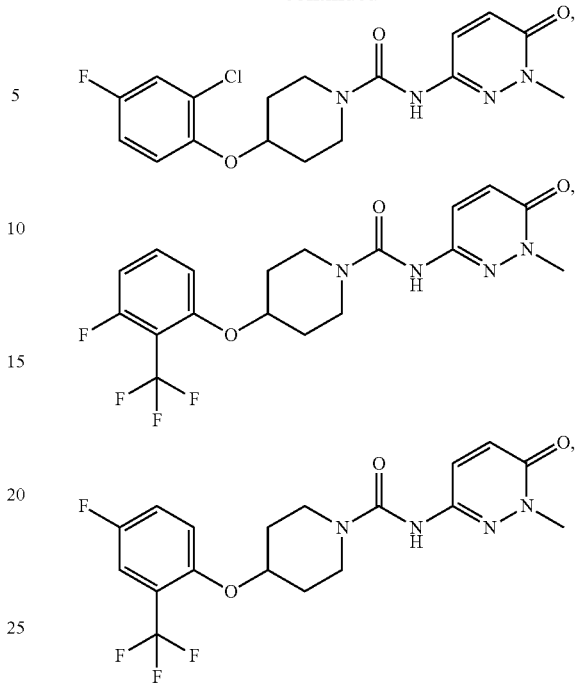

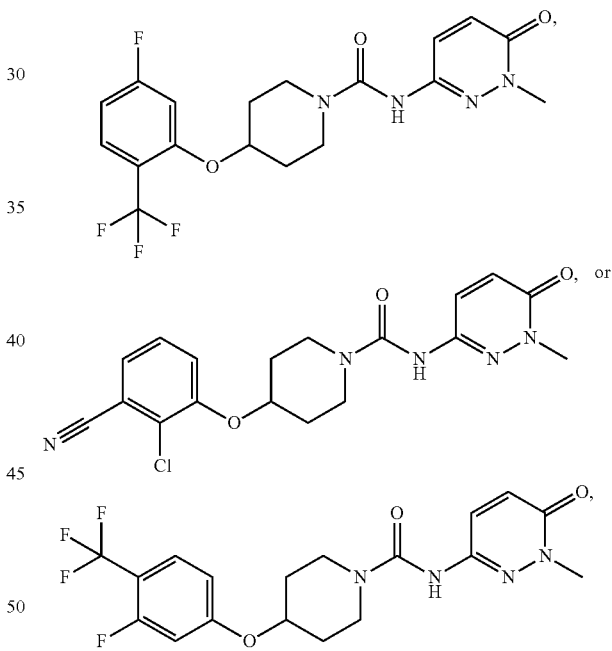

or a pharmaceutically acceptable salt thereof.

In some embodiments, o is 3. In certain embodiments, $R^3$ is halo or cyano. In further embodiments, $R^4$ is H. In particular embodiments, the compound is

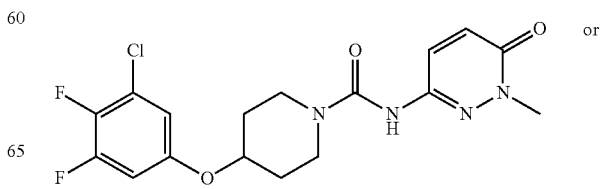

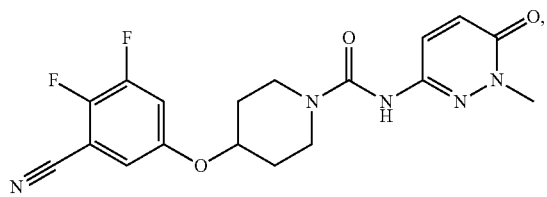

or a pharmaceutically acceptable salt thereof.

In still further embodiments, $L^2$ id $NR^5$. In certain embodiments, $L^2$ is NH. In some embodiments, o is 0, 1, or 2. In some embodiments, $R^3$ is halo or $C_{1-6}$ perfluoroalkyl. In some embodiments, $R^4$ is H. In certain embodiments, the compound is

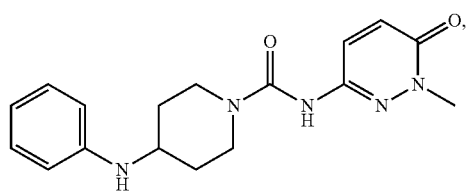

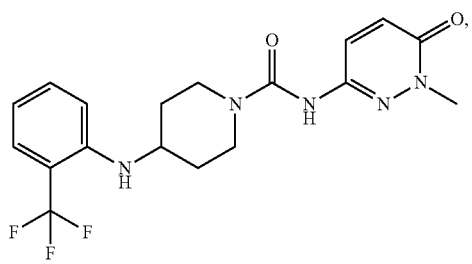

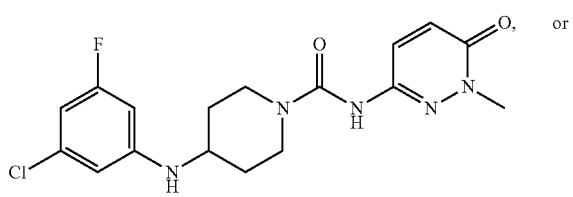

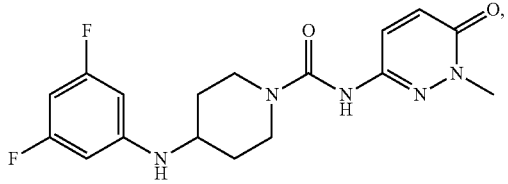

or a pharmaceutically acceptable salt thereof. In other embodiments, $L^2$ is

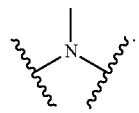 [SMILES: *N(*)C]

In some embodiments, o is 2. In some embodiments, $R^3$ is halo. In further embodiments, $R^4$ is H. In some embodiments, the compound is

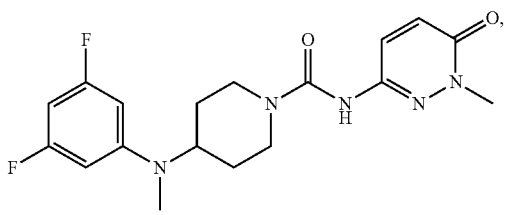 [SMILES: CN(c1cc(F)cc(F)c1)C1CCN(C(=O)Nc2ccc(=O)n(C)n2)CC1]

or a pharmaceutically acceptable salt thereof.

In other embodiments, $L^2$ is optionally substituted $C_{1-6}$ heteroalkyl. In particular embodiments, $L^2$ is

In some embodiments, o is 1. In some embodiments, $R^3$ is halo. In some embodiments, $R^4$ is H. In further embodiments, the compound is

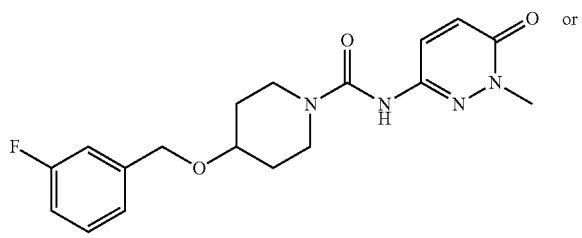

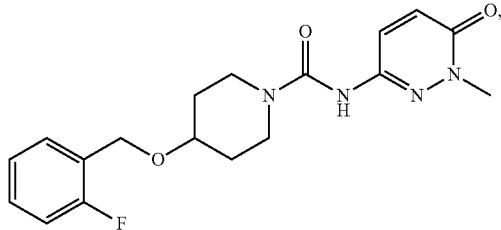

or a pharmaceutically acceptable salt thereof. In further embodiments, $L^2$ is

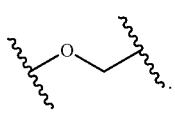

In some embodiments, o is 1. In certain embodiments, $R^3$ is halo or $C_{1-6}$ perfluoroalkyl. In some embodiments, $R^4$ is H. In particular embodiments, the compound is

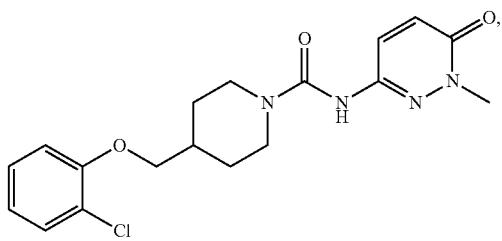

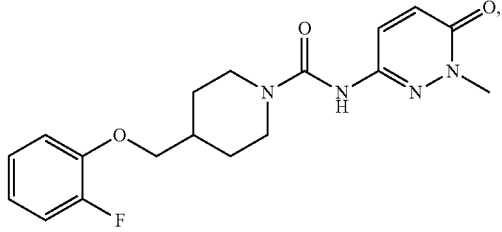

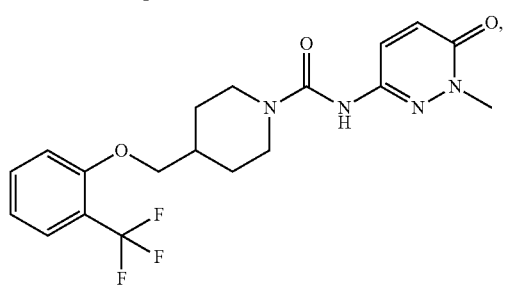

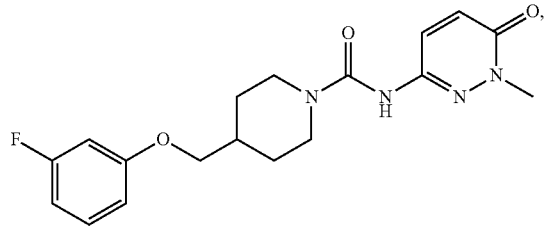

or a pharmaceutically acceptable salt thereof.

In yet further embodiments, L² is

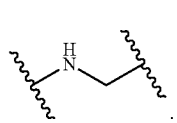

In some embodiments, o is 1 or 2. In some embodiments, R³ is halo or $C_{1-6}$ perfluoroalkyl. In further embodiments, R⁴ is H. In particular embodiments, the compound is

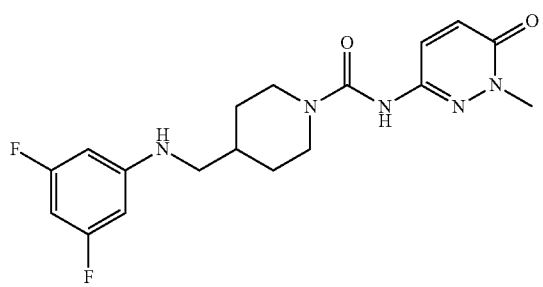

or

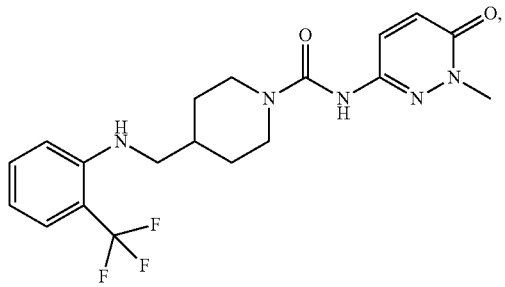

or a pharmaceutically acceptable salt thereof. In other embodiments, L² is

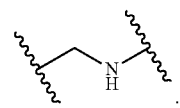 [SMILES: *CN*]

In certain embodiments, o is 1 or 2. In further embodiments, R³ is halo or $C_{1-6}$ perfluoroalkyl. In some embodiments, R⁴ is H. In some embodiments, the compound is

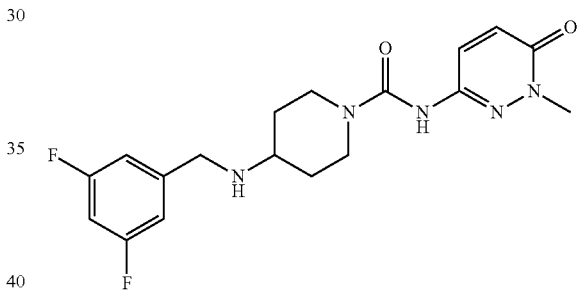

or or a pharmaceutically acceptable salt thereof.

In still other embodiments, L¹ is

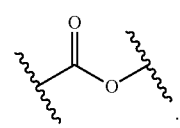 [SMILES: *OC(*)=O]

In some embodiments, L² is O. In some embodiments, o is 1 or 2. In some embodiments, R³ is halo. In further embodiments, R⁴ is H. In particular embodiments, the compound is

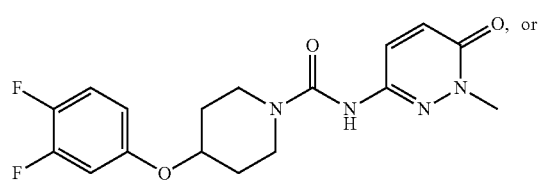

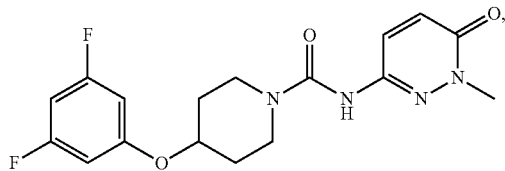

or a pharmaceutically acceptable salt thereof. In further embodiments, L² is optionally substituted C₁₋₆ alkyl. In some embodiments, o is 2. In certain embodiments, R³ is halo. In some embodiments, R⁴ is H. In some embodiments, the compound is

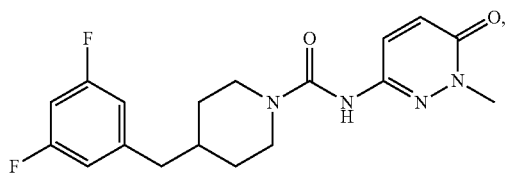

or a pharmaceutically acceptable salt thereof.

In further embodiments, L¹ is optionally substituted C₅₋₁₀ heteroaryl. In particular embodiments, L¹ is

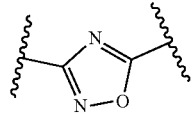

In some embodiments, L² is NH. In some embodiments, o is 2. In some embodiments, R³ is halo. In further embodiments, R⁴ is H. In particular embodiments, the compound is

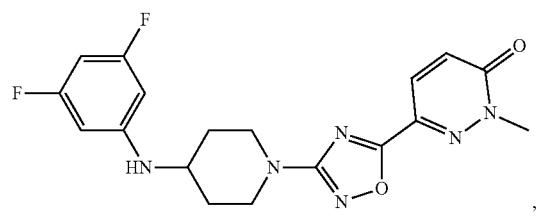 [SMILES: Cn1nc(-c2nc(N3CCC(Nc4cc(F)cc(F)c4)CC3)no2)ccc1=O]

or a pharmaceutically acceptable salt thereof. In further embodiments, L² is O. In some embodiments, o is 2. In still further embodiments, R³ is halo. In some embodiments, R⁴ is H. In particular embodiments, the compound is

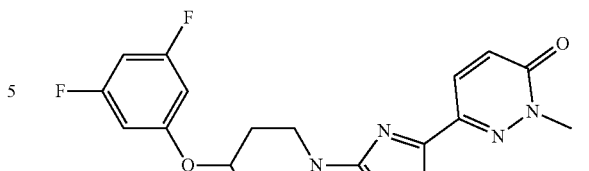

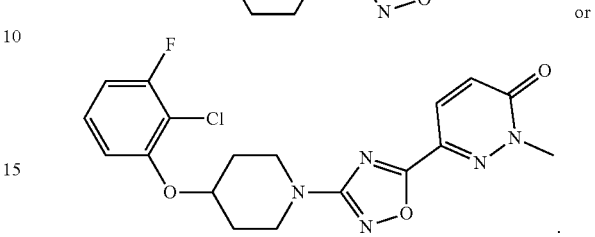

or a pharmaceutically acceptable salt thereof.

In still other embodiments, L² is optionally substituted C₁₋₆ alkyl. In some embodiments, o is 0, 1, or 2. In some embodiments, each R³ is, independently, halo or cyano. In some embodiments, R⁴ is H.

In further embodiments, the compound is

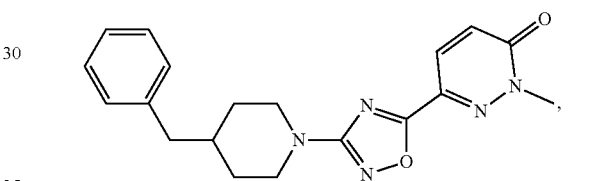

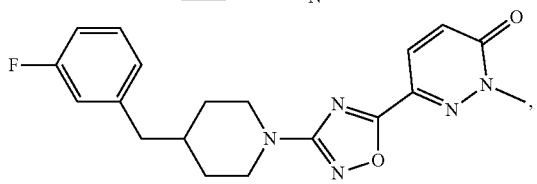

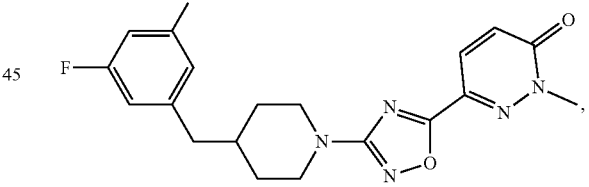

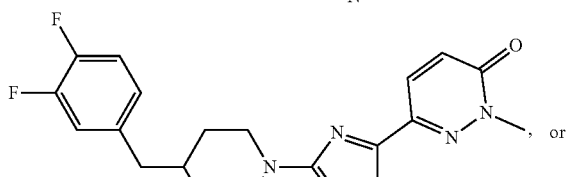

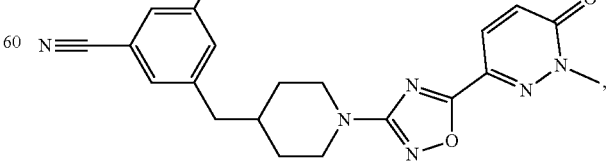

or a pharmaceutically acceptable salt thereof.

In further embodiments, $L^1$ is

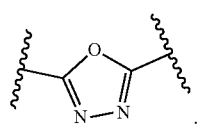 [SMILES: *c1nnc(*)o1]

In some embodiments, $L^2$ is optionally substituted $C_{1-6}$ alkyl. In certain embodiments, o is 1 or 2. In some embodiments, $R^3$ is halo. In some embodiments, $R^4$ is H. In specific embodiments, the compound is

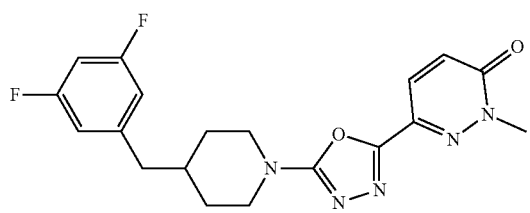

or

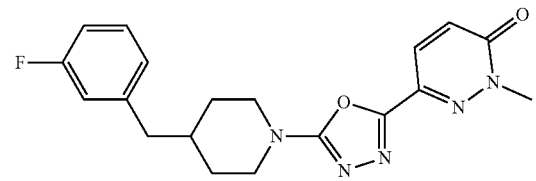

or a pharmaceutically acceptable salt thereof.

In yet other embodiments, $L^1$ is

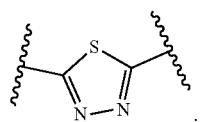 [SMILES: *c1nnc(*)s1]

In some embodiments, $L^2$ is NH. In further embodiments, o is 2. In some embodiments, $R^3$ is halo. In some embodiments, $R^4$ is H. In certain embodiments, the compound is

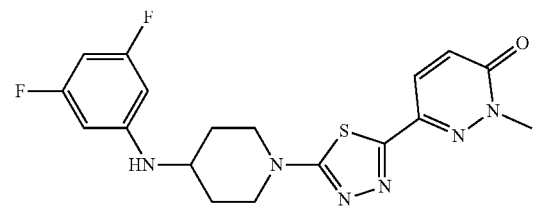

or a pharmaceutically acceptable salt thereof. In further embodiments, $L^2$ is optionally substituted $C_{1-6}$ alkyl. In particular embodiments, o is 2. In some embodiments, $R^3$ is halo. In some embodiments, $R^4$ is H. In certain embodiments, the compound is

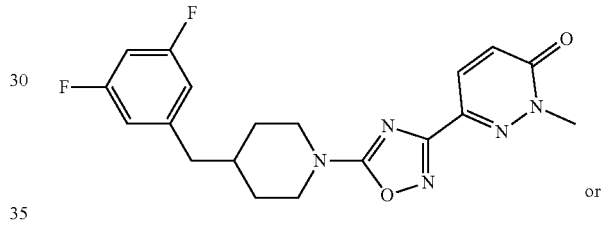

or a pharmaceutically acceptable salt thereof.

In still further embodiments, $L^1$ is

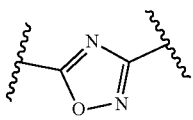

In some embodiments, $L^2$ is optionally substituted $C_{1-6}$ alkyl. In some embodiments, o is 2. In further embodiments, $R^3$ is halo. In some embodiments, $R^4$ is H. In further embodiments, the compound is

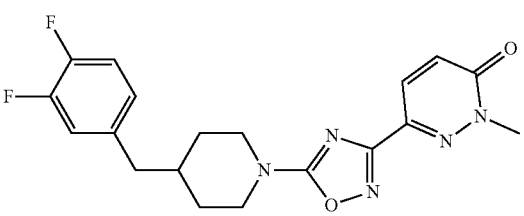

or

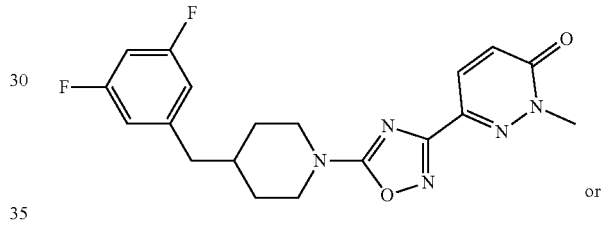

or a pharmaceutically acceptable salt thereof.

In other embodiments, $L^1$ is

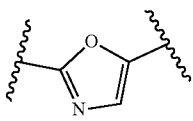

In some embodiments, $L^2$ is optionally substituted $C_{1-6}$ alkyl. In some embodiments, o is 2. In some embodiments, $R^3$ is halo. In some embodiments, $R^4$ is H. In some embodiments, the compound is

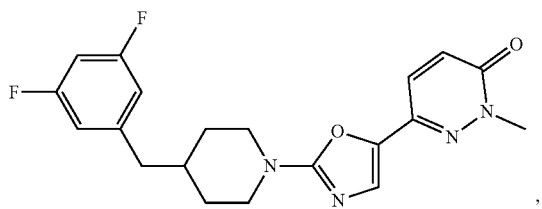 [SMILES: Cn1nc(-c2cnc(N3CCC(Cc4cc(F)cc(F)c4)CC3)o2)ccc1=O]

or a pharmaceutically acceptable salt thereof.

In still other embodiments, $R^1$ is ethyl. In some embodiments, $L^1$ is

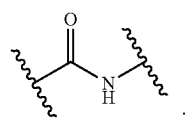 [SMILES: *NC(*)=O]

In some embodiments, $L^2$ is optionally substituted $C_{1-6}$ alkyl. In further embodiments, o is 2. In some embodiments, $R^3$ is halo. In some embodiments, $R^4$ is H. In certain embodiments, the compound is

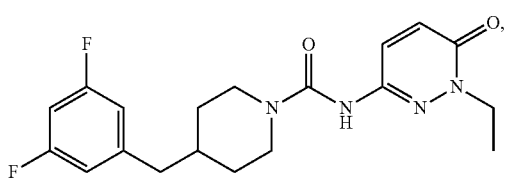 [SMILES: CCn1nc(NC(=O)N2CCC(Cc3cc(F)cc(F)c3)CC2)ccc1=O]

or a pharmaceutically acceptable salt thereof. In specific embodiments, $R^2$ is methyl. In certain embodiments, $R^1$ is methyl. In some embodiments, $L^1$ is

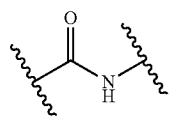

In some embodiments, $L^2$ is O. In further embodiments, o is 2. In some embodiments, $R^3$ is halo. In some embodiments, $R^4$ is H. In particular embodiments, the compound is

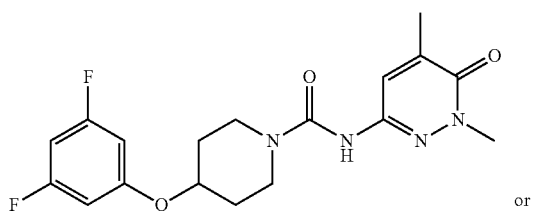

or

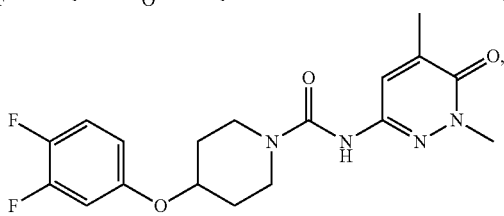

or a pharmaceutically acceptable salt thereof. In other embodiments, $L^2$ is optionally substituted $C_{1-6}$ alkyl. In some embodiments, o is 2. In some embodiments, $R^3$ is halo. In some embodiments, $R^4$ is H. In certain embodiments, the compound is

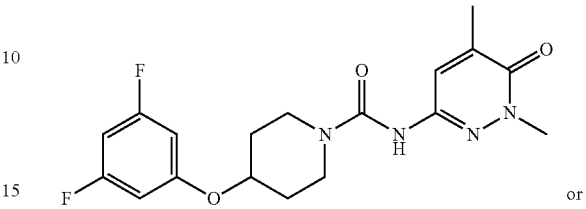

or

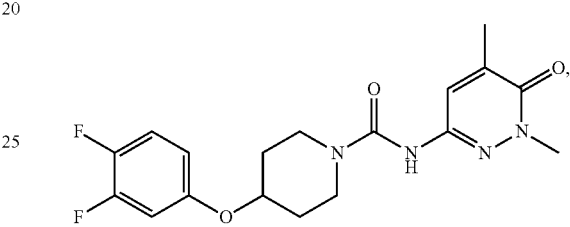

or a pharmaceutically acceptable salt thereof.

In other embodiments, the compound has the structure of formula (III-D-2):

(III-D-2)

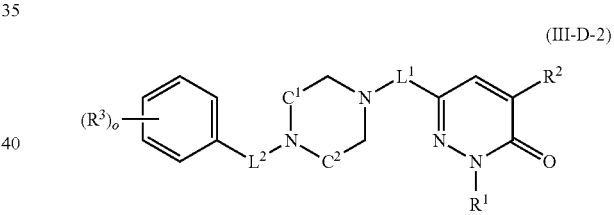

wherein: o is 0, 1, 2, 3, 4, or 5; $C^1$ and $C^2$ optionally combine to form a bond; each of $R^1$, $R^2$, and $R^5$ is, independently, H or optionally substituted $C_{1-6}$ alkyl; $R^3$ is halo, cyano, $C_{1-6}$ perfluoroalkyl, optionally substituted $C_{1-6}$ alkoxy, or optionally substituted $C_{1-6}$ alkyl; $L^1$ is optionally substituted $C_{5-10}$ heteroaryl or —C(O)—$X^5$—; $X^5$ is NH, O, or optionally substituted $C_{1-6}$ alkyl; and $L^2$ is O, $NR^5$, optionally substituted $C_{1-6}$ alkyl, optionally substituted $C_{1-6}$ heteroalkyl, or absent; or a pharmaceutically acceptable salt thereof.

In some embodiments, $R^1$ is methyl. In certain embodiments, $R^2$ is H. In particular embodiments, $L^1$ is

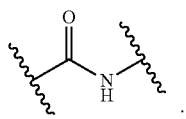 [SMILES: *NC(*)=O]

In further embodiments, $L^2$ is optionally substituted $C_{1-6}$ alkyl. In some embodiments, o is 1. In some embodiments, $R^3$ is halo. In certain embodiments, the compound is

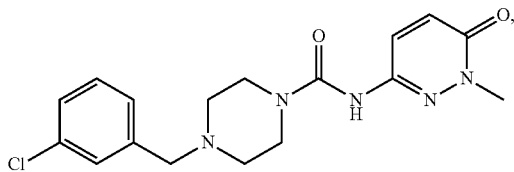

or a pharmaceutically acceptable salt thereof.

In yet other embodiments, the compound has the structure of formula (IV):

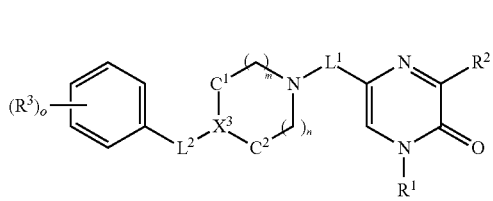

(IV)

wherein: m is 0 or 1; n is 0, 1, or 2; o is 0, 1, 2, 3, 4, or 5; $C^1$ and $C^2$ optionally combine to form a bond; each of $R^1$, $R^2$, $R^5$, and $R^6$ is, independently, H or optionally substituted $C_{1-6}$ alkyl; $R^3$ is halo, cyano, $C_{1-6}$ perfluoroalkyl, optionally substituted $C_{1-6}$ alkoxy, or optionally substituted $C_{1-6}$ alkyl; $X^3$ is $CR^4$ or N; or $X^3$ and $C^1$ or $C^2$ combine to form an optionally substituted alkene; $R^4$ is H, $OR^6$, optionally substituted $C_{1-6}$ alkyl, or halo; $L^1$ is optionally substituted $C_{5-10}$ heteroaryl or —C(O)—$X^5$—; $X^5$ is NH, O, or optionally substituted $C_{1-6}$ alkyl; and $L^2$ is O, $NR^5$, optionally substituted $C_{1-6}$ alkyl, optionally substituted $C_{1-6}$ heteroalkyl, or absent; or $X^3$ and $L^2$ combine to form an optionally substituted alkene, or a pharmaceutically acceptable salt thereof.

In further embodiments, the compound has the structure of formula (IV-A):

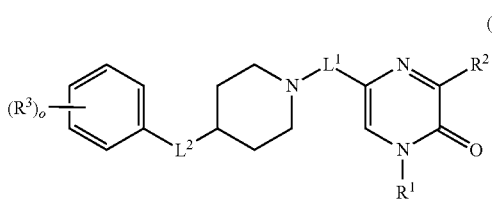

(IV-A)

wherein: o is 0, 1, 2, 3, 4, or 5; each of $R^1$, $R^2$, and $R^5$ is, independently, H or optionally substituted $C_{1-6}$ alkyl; $R^3$ is halo, cyano, $C_{1-6}$ perfluoroalkyl, optionally substituted $C_{1-6}$ alkoxy, or optionally substituted $C_{1-6}$ alkyl; $L^1$ is optionally substituted $C_{5-10}$ heteroaryl or —C(O)—$X^5$—; $X^5$ is NH, O, or optionally substituted $C_{1-6}$ alkyl; and $L^2$ is O, $NR^5$, optionally substituted $C_{1-6}$ alkyl, optionally substituted $C_{1-6}$ heteroalkyl, or absent; or a pharmaceutically acceptable salt thereof.

In some embodiments, $R^2$ is H. In further embodiments, $R^1$ is methyl. In some embodiments, $L^1$ is

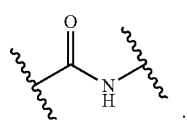 [SMILES: *NC(*)=O]

.

In certain embodiments, $L^2$ is optionally substituted $C_{1-6}$ alkyl. In some embodiments, o is 2. In further embodiments, $R^3$ is halo. In some embodiments, the compound is

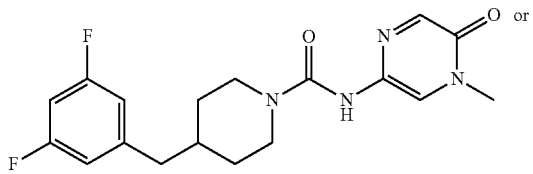

or

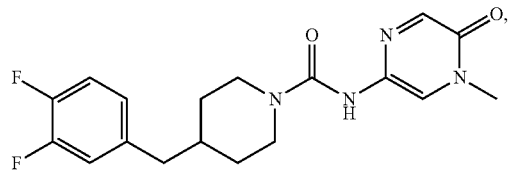

or a pharmaceutically acceptable salt thereof.

In some embodiments, the compound has the structure of formula (V):

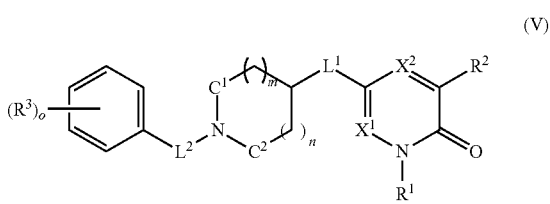

(V)

wherein: m is 0 or 1; n is 0, 1, or 2; o is 0, 1, 2, 3, 4, or 5; $C^1$ and $C^2$ optionally combine to form a bond; each of $R^1$, $R^2$, $R^5$, and $R^6$ is, independently, H or optionally substituted $C_{1-6}$ alkyl; $R^3$ is halo, cyano, $C_{1-6}$ perfluoroalkyl, optionally substituted $C_{1-6}$ alkoxy, or optionally substituted $C_{1-6}$ alkyl; each of $X^1$ and $X^2$ is, independently, CH or N, wherein $X^1$ and $X^2$ are not both N; $L^1$ is optionally substituted $C_{5-10}$ heteroaryl or —C(O)—$X^5$—; $X^5$ is NH, O, or optionally substituted $C_{1-6}$ alkyl; and $L^2$ is O, $NR^5$, optionally substituted $C_{1-6}$ alkyl, optionally substituted $C_{1-6}$ heteroalkyl, or absent; or a pharmaceutically acceptable salt thereof.

In certain embodiments, $X^1$ is N and $X^2$ is CH. In further embodiments, $R^2$ is H. In some embodiments, $R^1$ is methyl. In some embodiments, m is 1. In some embodiments, n is 1. In still further embodiments, $L^1$ is

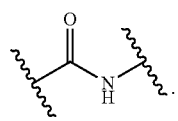 [SMILES: *NC(*)=O]

.

In particular embodiments, $L^2$ is optionally substituted $C_{1-6}$ alkyl. In some embodiments, o is 1. In some embodiments, $R^3$ is halo. In some embodiments, the compound is

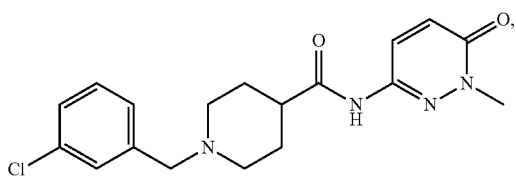 [SMILES: Cn1nc(NC(=O)C2CCN(Cc3cccc(Cl)c3)CC2)ccc1=O]
or a pharmaceutically acceptable salt thereof.
In some embodiments, the invention features a compound, or a pharmaceutically acceptable salt thereof, having the structure of any one of compounds 1-5, 7-11, 14-39, 41-105, 107-136 in Table 1.

TABLE 1-continued

Compounds of the Invention

| Compound | |
|---|---|
| 18 | (structure) |
| 19 | (structure) |
| 20 | (structure) |
| 21 | (structure) |
| 22 | (structure) |
| 23 | (structure) |
| 24 | (structure) |
| 25 | (structure) |
| 26 | (structure) |
| 27 | (structure) |
| 28 | (structure) |
| 29 | (structure) |
| 30 | (structure) |
| 31 | (structure) |
| 32 | (structure) |
| 33 | (structure) |
| 34 | (structure) |
| 35 | (structure) |

TABLE 1-continued

Compounds of the Invention

| Compound | |
|---|---|
| 36 | 3-chlorophenoxy-piperidine-acetyl-pyridazinone (NH) |
| 37 | 3-chlorobenzyl-piperidine-acetyl-N-methylpyridazinone |
| 38 | 3,5-difluorobenzyl-piperidine-acetyl-N-methylpyridazinone |
| 39 | 3-chlorophenoxy-piperidine-acetyl-N-methylpyridazinone |
| 40 | 3-chlorobenzyl-piperidine-carboxamide-N-methylpyridazinone |
| 41 | 3-fluorobenzyl-piperidine-carboxamide-N-methylpyridazinone |
| 42 | 2-chlorobenzyl-piperidine-carboxamide-N-methylpyridazinone |
| 43 | 4-chlorobenzyl-piperidine-carboxamide-N-methylpyridazinone |
| 44 | 4-fluorobenzyl-piperidine-carboxamide-N-methylpyridazinone |
| 45 | 3-fluorobenzyl-4-fluoropiperidine-carboxamide-N-methylpyridazinone |
| 46 | 3-chlorobenzyl-4-fluoropiperidine-carboxamide-N-methylpyridazinone |
| 47 | 3-fluorobenzyl-4-hydroxypiperidine-carboxamide-N-methylpyridazinone |
| 48 | 3-fluorobenzyl-4-methoxypiperidine-carboxamide-N-methylpyridazinone |
| 49 | 3,4-difluorobenzyl-piperidine-carboxamide-N-methylpyridazinone |
| 50 | 3-cyano-5-fluorobenzyl-piperidine-carboxamide-N-methylpyridazinone |
| 51 | 3,5-difluorobenzyl-piperidine-carboxamide-N-methylpyridazinone |
| 52 | 3-chloro-4-fluorobenzyl-piperidine-carboxamide-N-methylpyridazinone |
| 53 | 2,4-difluorobenzyl-piperidine-carboxamide-N-methylpyridazinone |
| 54 | 3-chloro-4-fluorobenzyl-piperidine-carboxamide-N-methylpyridazinone |
| 55 | 3-chloro-5-fluorobenzyl-piperidine-carboxamide-N-methylpyridazinone |

TABLE 1-continued
Compounds of the Invention
| Compound | |
|---|---|
| 56 | 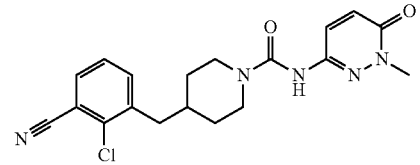 |
| 57 | 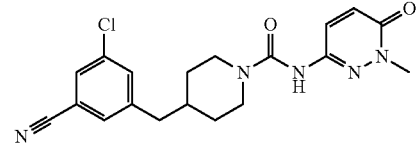 [SMILES: Cn1nc(NC(=O)N2CCC(Cc3cc(F)cc(C#N)c3)CC2)ccc1=O] |
| 58 | 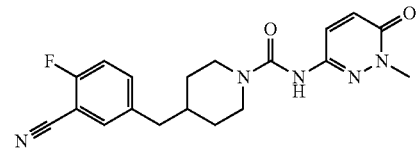 [SMILES: Cn1nc(NC(=O)N2CCC(Cc3ccc(F)c(C#N)c3)CC2)ccc1=O] |
| 59 | 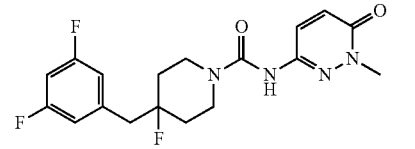 [SMILES: Cn1nc(NC(=O)N2CCC(F)(Cc3cc(F)cc(F)c3)CC2)ccc1=O] |
| 60 | 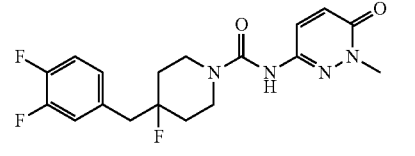 [SMILES: Cn1nc(NC(=O)N2CCC(F)(Cc3ccc(F)c(F)c3)CC2)ccc1=O] |
| 61 | 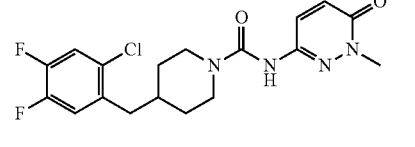 |
| 62 | 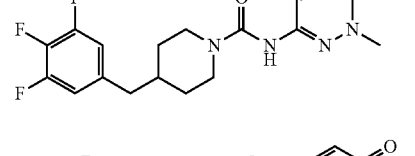 |
| 63 | 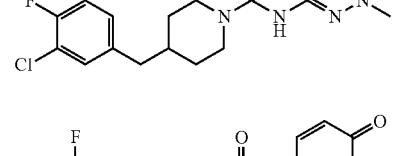 |
| 64 | 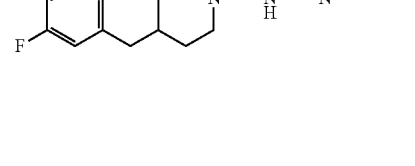 |
| 65 | 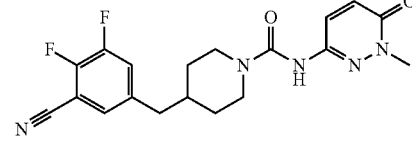 |
| 66 | 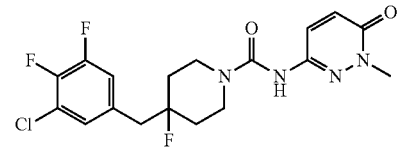 [SMILES: Cn1nc(NC(=O)N2CCC(F)(Cc3cc(F)c(F)c(Cl)c3)CC2)ccc1=O] |
| 67 | 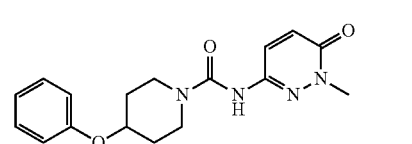 |
| 68 | 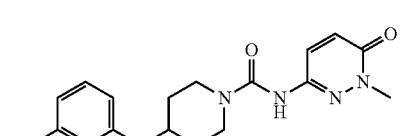 |
| 69 | 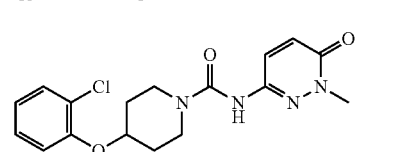 |
| 70 | 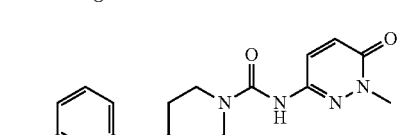 |
| 71 | 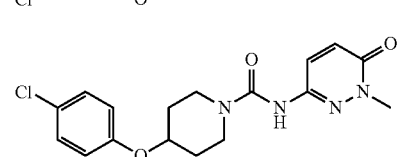 |
| 72 | 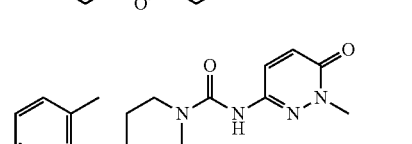 |
| 73 | 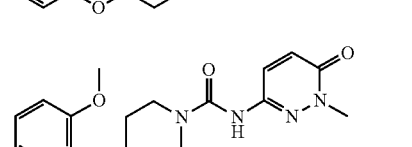 |
| 74 | 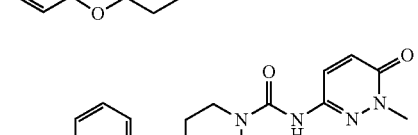 |

TABLE 1-continued

Compounds of the Invention

| Compound | |
|---|---|
| 75 | (structure) |
| 76 | (structure) |
| 77 | (structure) |
| 78 | (structure) |
| 79 | (structure) |
| 80 | (structure) |
| 81 | (structure) |
| 82 | (structure) |
| 83 | (structure) |
| 84 | (structure) |
| 85 | (structure) |
| 86 | (structure) |
| 87 | (structure) |
| 88 | (structure) |
| 89 | (structure) |
| 90 | (structure) |
| 91 | (structure) |

TABLE 1-continued

Compounds of the Invention

| Compound | |
|---|---|
| 92 | (structure) |
| 93 | (structure) |
| 94 | (structure) |
| 95 | (structure) |
| 96 | (structure) |
| 97 | (structure) |
| 98 | (structure) |
| 99 | (structure) |
| 100 | (structure) |
| 101 | (structure) |
| 102 | (structure) |
| 103 | (structure) |
| 104 | (structure) |
| 105 | (structure) |
| 106 | (structure) |

TABLE 1-continued

Compounds of the Invention

| Compound | |
|---|---|
| 107 | (structure) |
| 108 | (structure) |
| 109 | (structure) |
| 110 | (structure) |
| 111 | (structure) |
| 112 | (structure) |
| 113 | (structure) |
| 114 | (structure) |
| 115 | (structure) |
| 116 | (structure) |
| 117 | (structure) |
| 118 | (structure) |
| 119 | (structure) |
| 120 | (structure) |
| 121 | (structure) |
| 122 | (structure) |
| 123 | (structure) |
| 124 | (structure) |
| 125 | (structure) |

TABLE 1-continued

Compounds of the Invention

| Compound | |
|---|---|
| 126 | 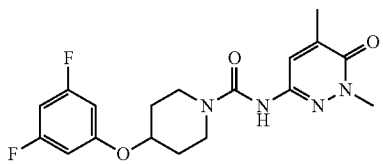 [SMILES: Cc1cc(NC(=O)N2CCC(Oc3cc(F)cc(F)c3)CC2)nn(C)c1=O] |
| 127 | 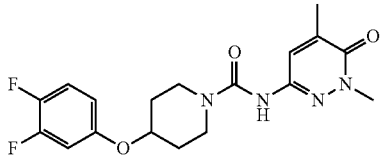 |
| 128 | 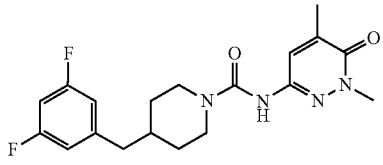 [SMILES: Cc1cc(NC(=O)N2CCC(Cc3cc(F)cc(F)c3)CC2)nn(C)c1=O] |
| 129 | 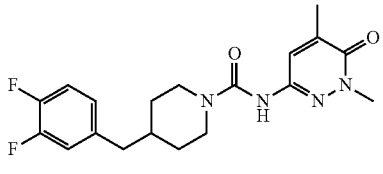 [SMILES: Cc1cc(NC(=O)N2CCC(Cc3ccc(F)c(F)c3)CC2)nn(C)c1=O] |
| 130 | 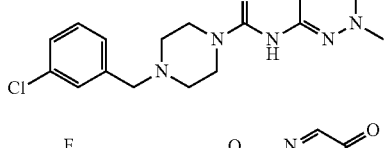 |
| 131 | 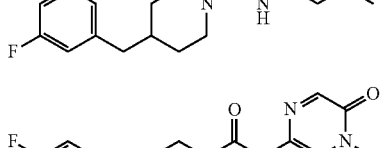 |
| 132 | 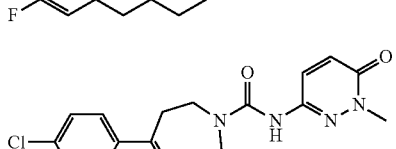 |
| 133 | 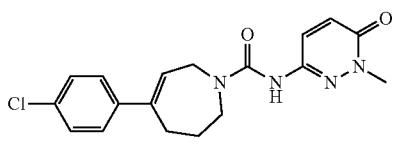 [SMILES: Cn1nc(NC(=O)N2CC=C(c3ccc(Cl)cc3)CCC2)ccc1=O] |
| 134 | 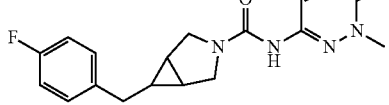 |
| 135 |  |
| 136 | 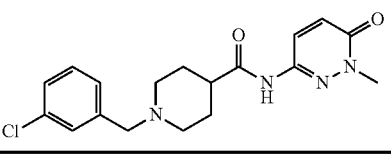 |

In some embodiments, the method includes administering a pharmaceutical composition including the compound disclosed herein, or a pharmaceutically acceptable salt thereof, and a pharmaceutically acceptable excipient.

In some embodiments, the pharmaceutical composition includes a compound of any one of formulas I-V and a pharmaceutically acceptable excipient.

In some embodiments, the primary brain cancer is a glioma. In some embodiments, the glioma is an astrocytoma. In some embodiments, the astrocytoma is a glioblastoma.

In some embodiments, the cancer is determined or predicted to be resistant to one or more chemotherapeutic agents. In some embodiments, the cancer has failed to respond to one or more chemotherapeutic agents. In some embodiments, one or more therapeutic agents is selected from the group of temozolomide, carmustine, bevacizumab, lomustine, everolimus, vincristine, or procarbazine. In some embodiments, one or more therapeutic agents is temozolomide.

In some embodiments, the subject is further administered one or more additional therapeutic interventions. In some embodiments, one or more additional therapeutic interventions comprises surgery, radiation, and/or one or more additional chemotherapeutic agents. In some embodiments, one or more additional therapeutic interventions is one or more chemotherapeutic agents. In some embodiments, one or more chemotherapeutic agents is selected from the group of temozolomide, carmustine, bevacizumab, lomustine, everolimus, vincristine, or procarbazine. In some embodiments, one or more chemotherapeutic agents is temozolomide.

Chemical Terms

It is to be understood that the terminology employed herein is for the purpose of describing particular embodiments and is not intended to be limiting.

The term "acyl," as used herein, represents a hydrogen or an alkyl group, as defined herein that is attached to a parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, or 1 to 6 carbon atoms). An alkylene is a divalent alkyl group.

The term "alkenyl," as used herein, alone or in combination with other groups, refers to a straight-chain or branched hydrocarbon residue having a carbon-carbon double bond and having 2 to 20 carbon atoms (e.g., 2 to 16 carbon atoms, 2 to 10 carbon atoms, 2 to 6, or 2 carbon atoms).

The term "alkynyl," as used herein, alone or in combination with other groups, refers to a straight-chain or branched hydrocarbon residue having a carbon-carbon triple bond and having 2 to 20 carbon atoms (e.g., 2 to 16 carbon atoms, 2 to 10 carbon atoms, 2 to 6, or 2 carbon atoms).

The term "amino," as used herein, represents —N($R^{N1}$)$_2$, wherein each $R^{N1}$ is, independently, H, OH, $NO_2$, N($R^{N2}$)$_2$, $SO_2OR^{N2}$, $SO_2R^{N2}$, $SOR^{N2}$, an N-protecting group, alkyl, alkoxy, aryl, arylalkyl, cycloalkyl, acyl (e.g., acetyl, trifluoroacetyl, or others described herein), wherein each of these recited $R^{N1}$ groups can be optionally substituted; or two $R^{N1}$ combine to form an alkylene or heteroalkylene, and wherein each $R^{N2}$ is, independently, H, alkyl, or aryl. The amino groups of the invention can be an unsubstituted amino (i.e., —$NH_2$) or a substituted amino (i.e., —N($R^{N1}$)$_2$).

The term "aryl," as used herein, refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl.

The term "arylalkyl," as used herein, represents an alkyl group substituted with an aryl group. Exemplary unsubstituted arylalkyl groups are from 7 to 30 carbons (e.g., from 7 to 16 or from 7 to 20 carbons, such as $C_{1-6}$ alkyl $C_{6-10}$ aryl, $C_{1-10}$ alkyl $C_{6-10}$ aryl, or $C_{1-20}$ alkyl $C_{6-10}$ aryl), such as, benzyl and phenethyl. In some embodiments, the akyl and the aryl each can be further substituted with 1, 2, 3, or 4 substituent groups as defined herein for the respective groups.

The term "azido," as used herein, represents a —N3 group.

The term "cyano," as used herein, represents a —CN group.

The terms "carbocyclyl," as used herein, refer to a non-aromatic $C_{3-12}$ monocyclic, bicyclic, or tricyclic structure in which the rings are formed by carbon atoms. Carbocyclyl structures include cycloalkyl groups and unsaturated carbocyclyl radicals.

The term "cycloalkyl," as used herein, refers to a saturated, non-aromatic, monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, and adamantyl.

The term "halogen," as used herein, means a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers alkyl-O— (e.g., methoxy and ethoxy). A heteroalkylene is a divalent heteroalkyl group.

The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers alkenyl-O—. A heteroalkenylene is a divalent heteroalkenyl group.

The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups. Examples of heteroalkynyl groups are an "alkynoxy" which, as used herein, refers alkynyl-O—. A heteroalkynylene is a divalent heteroalkynyl group.

The term "heteroaryl," as used herein, refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group. Examples of heteroaryl groups are pyridyl, pyrazoyl, benzooxazolyl, benzoimidazolyl, benzothiazolyl, imidazolyl, oxaxolyl, and thiazolyl.

The term "heteroarylalkyl," as used herein, represents an alkyl group substituted with a heteroaryl group. Exemplary unsubstituted heteroarylalkyl groups are from 7 to 30 carbons (e.g., from 7 to 16 or from 7 to 20 carbons, such as $C_{1-6}$ alkyl $C_{2-9}$ heteroaryl, $C_{1-10}$ alkyl $C_{2-9}$ heteroaryl, or $C_{1-20}$ alkyl $C_{2-9}$ heteroaryl). In some embodiments, the akyl and the heteroaryl each can be further substituted with 1, 2, 3, or 4 substituent groups as defined herein for the respective groups.

The term "heterocyclyl," as used herein, denotes a mono- or polycyclic radical having 3 to 12 atoms having at least one ring containing one, two, three, or four ring heteroatoms selected from N, O or S, wherein no ring is aromatic. Examples of heterocyclyl groups include, but are not limited to, morpholinyl, thiomorpholinyl, furyl, piperazinyl, piperidinyl, pyranyl, pyrrolidinyl, tetrahydropyranyl, tetrahydrofuranyl, and 1,3-dioxanyl.

The term "heterocyclylalkyl," as used herein, represents an alkyl group substituted with a heterocyclyl group. Exemplary unsubstituted heterocyclylalkyl groups are from 7 to 30 carbons (e.g., from 7 to 16 or from 7 to 20 carbons, such as $C_{1-6}$ alkyl $C_{2-9}$ heterocyclyl, $C_{1-10}$ alkyl $C_{2-9}$ heterocyclyl, or $C_{1-20}$ alkyl $C_{2-9}$ heterocyclyl). In some embodiments, the akyl and the heterocyclyl each can be further substituted with 1, 2, 3, or 4 substituent groups as defined herein for the respective groups.

The term "hydroxyl," as used herein, represents an —OH group.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999). N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —$NO_2$ group.

The term "thiol," as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: aryl (e.g., substituted and unsubstituted phenyl), carbocyclyl (e.g., substituted and unsubstituted cycloalkyl), halogen (e.g., fluoro), hydroxyl, heteroalkyl (e.g., substituted and unsubstituted methoxy, ethoxy, or thioalkoxy), heteroaryl, heterocyclyl, amino (e.g., $NH_2$ or mono- or dialkyl amino), azido, cyano, nitro, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99% or 99.9%) by weight relative to the other stereoisomers. When a single enantiomer is named or depicted by structure, the depicted or named enantiomer is at least 60%, 70%, 80%, 90%, 99% or 99.9% by weight optically pure. When a single diastereomer is named or depicted by structure, the depicted or named diastereomer is at least 60%, 70%, 80%, 90%, 99% or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99% or 99.9% by mole fraction pure relative to the other stereoisomers. When a single enantiomer is named or depicted by structure, the depicted or named enantiomer is at least 60%, 70%, 80%, 90%, 99% or 99.9% by mole fraction pure. When a single diastereomer is named or depicted by structure, the depicted or named diastereomer is at least 60%, 70%, 80%, 90%, 99% or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The invention embraces all of these forms.

Definitions

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

As used herein, the term "administration" refers to the administration of a composition (e.g., a compound, a complex or a preparation that includes a compound or complex as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

As used herein, the terms "approximately" and "about" are each intended to encompass normal statistical variation as would be understood by those of ordinary skill in the art as appropriate to the relevant context. In certain embodiments, the terms "approximately" or "about" each refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of a stated value, unless otherwise stated or otherwise evident from the context (e.g., where such number would exceed 100% of a possible value).

As used herein, the term "combination therapy" refers to those situations in which a subject is simultaneously exposed to two or more therapeutic agents. In some embodiments, two or more compounds may be administered simultaneously; in some embodiments, such compounds may be administered sequentially; in some embodiments, such compounds are administered in overlapping dosing regimens.

The term "dissemination" used herein refers to spread of a tumor beyond the primary tumor site. Dissemination may be near the primary tumor site (e.g., infiltration of surrounding tissues), within the same organ as the primary tumor (e.g., intracranial dissemination of a primary glioma), or within a different organ than the primary tumor (e.g., a metastasis).

In the practice of the methods of the present invention, an "effective amount" of any one of the compounds of the invention or a combination of any of the compounds of the invention or a pharmaceutically acceptable salt thereof, is administered via any of the usual and acceptable methods known in the art, either singly or in combination.

The term "glioma" used herein refers to a primary tumor that starts in the brain or the spinal cord and encompasses all the various types of glioma known in the art, including astrocytoma, ependymoma, oligodendroglioma, brainstem glioma, optic nerve glioma, and mixed glioma.

The terms "non-resectable tumor," "unresectable tumor," and "inoperable tumor" used herein refer to tumors that are unable to be surgically removed due to tumor site and/or extent of tumor dissemination.

The term "pharmaceutical composition," as used herein, represents a composition containing a compound described herein formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

A "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of the compound of formula (I). For example, pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

As used herein, the term "stearoyl-CoA desaturase (SCD)—associated disorder" refers to an undesired physiological condition, disorder, or disease that is associated with and/or mediated at least in part by an SCD protein. In some instances, SCD-associated disorders are associated with excess SCD levels and/or activity. SCDs introduce a double bond in the C9-C10 position of saturated fatty acids such as palmitoyl-CoA and stearoyl-CoA which are converted to palmitoleoyl-CoA and oleoyl-CoA, respectively. One SCD gene, SCD1, has been characterized in humans for which there are two isoforms, SCD1 and SCD5. An SCD-associated disorder may be associated with and/or mediated at least in part by SCD1 and/or SCD5. Exemplary SCD-associated disorders include SCD-associated disorders include, but are not limited to metabolic disorders (e.g., diabetes (e.g., Type I diabetes and Type II diabetes), hyperglycemia, metabolic syndrome, obesity, lipid disorders, fatty liver, nonalcoholic steatohepatitis (NASH), nonalcoholic fatty liver disease (NAFLD), and hypertension), cancer, cardiovascular diseases, cerebrovascular diseases, kidney diseases, liver diseases, skin disorders (e.g., acne (e.g., acne vulgaris)), central nervous system (CNS) disorders, dementia, multiple sclerosis, schizophrenia, mild cognitive impairment, Alzheimer's Disease, cerebral amyloid angiopathy, and dementia associated with Down Syndrome. Additional SCD-associated disorders are described herein or known in the art.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results.

Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment The term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." To give but one example, a refractory subject may have a low bioavailability such that clinical efficacy is not obtainable. In some embodiments, reference to a therapeutically effective amount may be a reference to an amount as measured in one or more specific tissues (e.g., a tissue affected by the disease, disorder or condition) or fluids (e.g., blood, saliva, serum, sweart, tears, urine, etc). Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

DETAILED DESCRIPTION OF THE INVENTION

The invention features compounds useful for the treatment of cancer, e.g., by inhibiting α-synuclein toxicity in a cell such as a neural cell. Exemplary compounds described herein include compounds having a structure according to one of formulas I-V:

Formula (I)

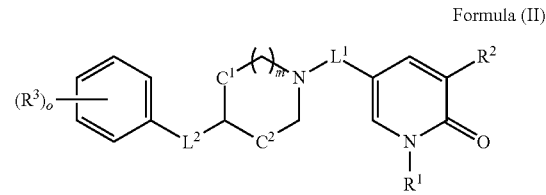

Formula (II)

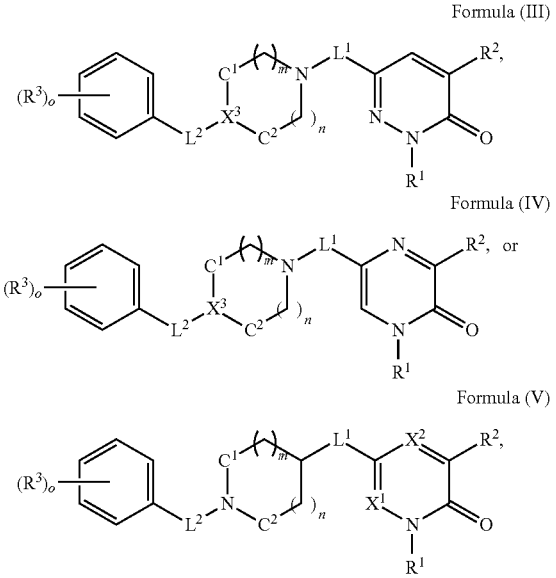

or pharmaceutically acceptable salts thereof. In some embodiments, the compound has the structure of any one of compounds 1-5, 7-11, 14-39, 41-105, 107-136 in Table 1.

Other embodiments, as well as exemplary methods for the synthesis or production of these compounds, are described herein.

Pharmaceutical Uses

The compounds described herein are useful in the methods of the invention and, while not bound by theory, are believed to exert their desirable effects through their ability to inhibit toxicity caused by protein aggregation, e.g., α-synuclein aggregation, in a cell.

The compounds described herein are useful as inhibitors of stearoyl-CoA desaturase (SCD), including SCD1 and/or SCD5. SCD inhibitors are known in the art to be useful in methods of treating and/or preventing SCD-associated disorders. SCD-associated disorders are described, for example, in U.S. Pat. No. 8,148,378, and in International Patent Application Publication Nos. WO 2011/047481, WO 2010/112520, WO 2010/045374, WO 2010/028761; WO 2009/150196, and WO 2009/106991. Accordingly, another aspect of the present invention relates to methods of treating and/or preventing an SCD-associated disorder in a subject in need thereof.

Cancer

Another aspect of the present invention relates to methods of treating and/or preventing cancer, including solid tumors or hematological malignancies (e.g., esophageal cancer, pancreatic cancer, endometrial cancer, kidney cancer, hepatoma, thyroid cancer, gallbladder cancer, prostate cancer, leukemia (e.g., lymphomas and myelomas), ENT-related cancer, primary brain cancer (e.g., a glioma, such as an astrocytoma, e.g., a glioblastoma), colon cancer, rectal cancer, colorectal cancer, ovarian cancer, uterine cancer, breast cancer, skin cancer, and prostate cancer), neoplasia, malignancy, metastases, tumors (benign or malignant), carcinogenesis, and hepatomas. Preferably, the method is for treating a primary brain cancer.

Glioma

A glioma is a type of tumor that starts in the brain or the spinal cord and arises from glial cells. Approximately half of all brain tumors are gliomas. There are four main types of glioma: astrocytoma, ependymoma, oligodendroglioma, and mixed glioma. Gliomas can be classified according to their location: infratentorial (i.e., located in the lower part of the brain) or supratentorial (i.e., located in the upper part of the brain). Gliomas are further categorized according to their grade, which is determined by pathologic evaluation of the tumor. The World Health Organization (WHO) has developed a grading system, from Grade I gliomas, which tend to be the least aggressive, to Grade IV gliomas, which tend to be the most aggressive and malignant. Examples of low grade (i.e., Grade I or Grade II) gliomas include pilocytic astrocytoma, fibrillary astrocytoma, pleomorphic xantroastrocytomoa, and desembryoplastic neuroepithelial tumor. High-grade gliomas encompass Grade III gliomas (e.g., anaplastic astrocytoma, AA) and Grade IV gliomas (e.g., glioblastoma multiforme, GBM). Anaplastic astrocytoma accounts for 4% of all brain tumors. Glioblastoma multiforme, the most invasive type of glial tumor, is most common in men and women in their 50s-70s and accounts for 23% of all primary brain tumors. The prognosis is the worst for Grade IV gliomas, with an average survival time of 12 months.

Gliomas are treated with surgery, radiation therapy and chemotherapy, often in combination; however, gliomas are rarely curable. More than 95% of the patients with gliomas die within 2 years following diagnosis despite aggressive therapy. Thus, there remains a need for new methods and compositions for treating gliomas.

Treatment of Primary Brain Cancer with SCD Inhibitors

SCD inhibitors are expected to be useful for inhibiting proliferation, survival, and invasiveness of cancer cells, thereby inhibiting tumor growth and dissemination in a subject suffering from a primary brain cancer (e.g., a glioma, such as an astrocytoma, e.g., a glioblastoma). Pharmaceutical compositions (e.g., the SCD inhibitors disclosed herein) may be administered either prior to or following surgical removal of a primary tumor and/or treatment such as administration of radiotherapy or conventional chemotherapeutic drugs (e.g., temozolomide). In certain embodiments, compounds of the present invention are used for the treatment of gliomas. A patient afflicted with a glioma may be diagnosed using criteria generally accepted in the art.

SCD1 was previously identified as a therapeutic target for the treat of gliomas (Dai et al., doi:10.3389/fphar.2017.00960; Tracz-Gaszewska and Dobrzyn, doi.org/10.3390/cancers11070948). Accordingly, SCD inhibitors can be used alone or in combination with one or more therapeutic interventions (e.g., surgery, radiotherapy, chemotherapy) for use in treating a subject suffering from a primary brain cancer (e.g., a glioma, such as an astrocytoma, e.g., a glioblastoma). In some embodiments, an SCD inhibitor can be used prior (e.g., about 1 minute, 5 minutes, 10 minutes, 20 minutes, 30 minutes, 40 minutes, 50 minutes, 1 hour, 2 hours, 3 hours, 4 hours, 5 hours, 6 hours, 8 hours, 10 hours, 12 hours, 16 hours, 20 hours, 1 day, 2 days, 3 days, 4 days, 5 days, 6 days, 1 week, 2 weeks, 4 weeks, 8 weeks, 12 weeks, 4 months, 5 months, 6 months, 8 months, 10 months, or 12 months) to one or more therapeutic interventions (e.g., surgery, radiotherapy, chemotherapy). In some embodiments, an SCD inhibitor can be used concurrently with one or more therapeutic interventions (e.g., surgery, radiotherapy, chemotherapy). In some embodiments, an SCD inhibitor can be used after (e.g., about 1 minute, 5 minutes, 10 minutes, 20 minutes, 30 minutes, 40 minutes, 50 minutes, 1 hour, 2 hours, 3 hours, 4 hours, 5 hours, 6 hours, 8 hours, 10 hours, 12 hours, 16 hours, 20 hours, 1 day, 2 days, 3 days, 4 days, 5 days, 6 days, 1 week, 2 weeks, 4 weeks, 8 weeks, 12 weeks, 4 months, 5 months, 6 months, 8 months, 10 months, or 12 months) one or more therapeutic interventions (e.g., surgery, radiotherapy, chemotherapy). For example, SCD inhibitors can be used concurrently with surgical resection of the tumor and prior to radiotherapy and chemotherapy. SCD inhibitors can also be used prior to surgical resection of the tumor, radiotherapy, and chemotherapy. SCD inhibitors can also be used concurrently with surgical resection of the tumor, radiotherapy, and chemotherapy. SCD inhibitors can also be used after surgical resection of the tumor, radiotherapy, and chemotherapy. SCD inhibitors can also be used concurrently with radiotherapy and prior to surgical resection of the tumor and chemotherapy. SCD inhibitors can also be used concurrently with post-resection radiotherapy and prior to chemotherapy. SCD inhibitors can also be used concurrently with chemotherapy and after surgical resection of the tumor and radiotherapy.

When SCD inhibitors, are used to treat a subject suffering from a glioma in combination with one or more appropriate therapeutics, the compounds within the combination can be administered as a combination product or can be administered substantially simultaneously or sequentially.

In one embodiment, an SCD inhibitor can be used in combination with one or more additional agents to treat glioblastoma multiforme. Examples of such agents include those selected from the group consisting of abarelix, actinomycin D, adriamycin, aldesleukin, alemtuzumab, alitretinoin, allopurinol, altretamine, amifostine, anakinra, anastrozole, arsenic trioxide, asparaginase, azacitidine, BCG Live, bevacuzimab, bexarotene, bleomycin, bortezomib, busulfan, calusterone, capecitabine, carboplatin, carmustine, celecoxib, cetuximab, chlorambucil, cisplatin, cladribine, clofarabine, cyclophosphamide, cytarabine, dacarbazine, dactinomycin, dalteparin (e.g., sodium), darbepoetin alfa, dasatinib, daunorubicin, daunomycin, decitabine, denileukin, denileukin diftitox, dexrazoxane, docetaxel, doxorubicin, dromostanolone propionate, eculizumab, epirubicin (e.g., HCl), epoetin alfa, erlotinib, estramustine, etoposide (e.g., phosphate), everolimus, exemestane, fentanyl (e.g., citrate), filgrastim, floxuridine, fludarabine, fluorouracil, 5-FU, fulvestrant, gefitinib, gemcitabine (e.g., HCl), gemtuzumab ozogamicin, goserelin (e.g., acetate), histrelin (e.g., acetate), hydroxyurea, ibritumomab tiuxetan, idarubicin, ifosfamide, imatinib (e.g., mesylate), interferon alfa-2b, irinotecan, lapatinib ditosylate, lenalidomide, letrozole, leucovorin, leuprolide (e.g., acetate), levamisole, lomustine, CCNU, meclorethamine (nitrogen mustard), megestrol, melphalan (L-PAM), mercaptopurine (6-MP), mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa-2b, pemetrexed (e.g., disodium), pentostatin, pipobroman, plicamycin (mithramycin), porfimer (e.g., sodium), procarbazine, quinacrine, rasburicase, rituximab, sargramostim, sorafenib, streptozocin, sunitinib (e.g., maleate), talc, tamoxifen, temozolomide, teniposide (VM-26), testolactone, thalidomide, thioguanine (6-TG), thiotepa, thiotepa, thiotepa, topotecan (e.g., hcl), toremifene, Tositumomab/I-131 (tositumomab), trastuzumab, tretinoin (ATRA), uracil mustard, valrubicin, vinblastine, vincristine, vinorelbine, vorinostat, zoledronate, and zoledronic acid. In some embodiments, an SCD inhibitor is used in combination with one or more of temozolomide, carmustine, bevacizumab, lomustine, everolimus, vincristine, and procarbazine, or biologically active variants, salts, and derivatives of any of the above.

In some embodiments, an SCD inhibitor when co-administered with a chemotherapeutic agent to a subject who has glioma, decreases the dosage of chemotherapeutic agent required for a therapeutic effect by, e.g., decreasing cancer cell growth rate, decreasing tumor size, decreasing survival of cancer cells, or increasing apoptosis by cancer cells. In one embodiment, the chemotherapeutic agent is temozolomide.

Treating primary brain cancer can result in a reduction in size or volume of a tumor. For example, after treatment, tumor size is reduced by about 5% or greater (e.g., about 10%, 20%, 30%, 40%, 50%, 60%, 70%, 80%, 90% or greater) relative to its size prior to treatment. Size of a tumor may be measured by any reproducible means of measurement. For example, the size of a tumor may be measured as a diameter of the tumor.

Treating primary brain cancer may further result in a decrease in number of tumors. For example, after treatment, tumor number is reduced by about 5% or greater (e.g., about 10%, 20%, 30%, 40%, 50%, 60%, 70%, 80%, 90% or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating primary brain cancer can result in a decrease in number of metastatic nodules in other tissues or organs distant from the primary tumor site. For example, after treatment, the number of metastatic nodules is reduced by about 5% or greater (e.g., about 10%, 20%, 30%, 40%, 50%, 60%, 70%, 80%, 90% or greater) relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating primary brain cancer can result in an increase in average survival time of a population of subjects treated according to the present invention in comparison to a population of untreated subjects. For example, the average survival time is increased by more than about 30 days (more than about 60 days, 90 days, or 120 days). An increase in average survival time of a population may be measured by any reproducible means. An increase in average survival time of a population may be measured, for example, by calculating for a population the average length of survival following initiation of treatment with the compound of the invention. An increase in average survival time of a population may also be measured, for example, by calculating for a population the average length of survival following completion of a first round of treatment with a pharmaceutically acceptable salt of the invention.

Treating primary brain cancer can also result in a decrease in the mortality rate of a population of treated subjects in comparison to an untreated population. For example, the mortality rate is decreased by more than about 2% (e.g., more than about 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of the invention. A decrease in the mortality rate of a population may also be measured, for example, by calculating for a population the average number of disease-related deaths per unit time following completion of a first round of treatment with a pharmaceutically acceptable salt of the invention.

Treating primary brain cancer can result in a decrease in recurrence of tumors in treated subjects in comparison to an untreated population. For example, after treatment, the time to tumor recurrence may be reduced by about 5% or greater (e.g., about 10%, 20%, 30%, 40%, 50%, 60%, 70%, 80%, 90% or greater) relative to the rate in the untreated population. The rate of recurrence may be measured, for example, by calculating for a population the average length of time from when the tumor could not be detected (e.g., after resection) to when a new tumor can be detected.

Treating primary brain cancer can result in a decrease in dissemination of cancer cells in treated subjects in comparison to an untreated population. For example, after treatment, the number of recurrent tumors at sites other than the original site of the tumor is reduced by about 5% or greater (e.g., about 10%, 20%, 30%, 40%, 50%, 60%, 70%, 80%, 90% or greater) relative to number present in the untreated population. A reduction in the number of recurrent tumors at sites other than the original site of the tumor can be measured by comparing the number of recurrent tumors at sites other than the original site in a treated population relative to the number in an untreated population.

Combination Formulations and Uses Thereof

The compounds of the invention can be combined with one or more therapeutic agents. In particular, the therapeutic agent can be one that treats or prophylactically treats any neurological disorder described herein.

Combination Therapies

A compound of the invention can be used alone or in combination with other agents that treat neurological disorders or symptoms associated therewith, or in combination with other types of treatment to treat, prevent, and/or reduce the risk of any neurological disorders. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., Neurology 65:S3-S6, 2005). In this case, dosages of the compounds when combined should provide a therapeutic effect.

Pharmaceutical Compositions

The compounds of the invention are preferably formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent, carrier, or excipient.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, and wafers.

A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003, $20^{th}$ ed.) and in The United States Pharmacopeia: The National Formulary (USP 24 NF19), published in 1999.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer. Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter.

The compounds of the invention may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of, for example, between 0.05 mg and 3000 mg (measured as the solid form). Dose ranges include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered. Preferred dose ranges include, for example, between 0.05-15 mg/kg or between 0.5-15 mg/kg.

Alternatively, the dosage amount can be calculated using the body weight of the patient. For example, the dose of a compound, or pharmaceutical composition thereof, administered to a patient may range from 0.1-50 mg/kg (e.g., 0.25-25 mg/kg). In exemplary, non-limiting embodiments, the dose may range from 0.5-5.0 mg/kg (e.g., 0.5, 1.0, 1.5, 2.0, 2.5, 3.0, 3.5, 4.0, 4.5, or 5.0 mg/kg) or from 5.0-20 mg/kg (e.g., 5.5, 6.0, 6.5, 7.0, 7.5, 8.0, 8.5, 9.0, 9.5, 10, 11, 12, 13, 14, 15, 16, 17, 18, 19, or 20 mg/kg).

EXAMPLES

The synthesis of compounds of this invention can be synthesized according to one or more of the general schemes 1-16 shown below.

General Scheme 1

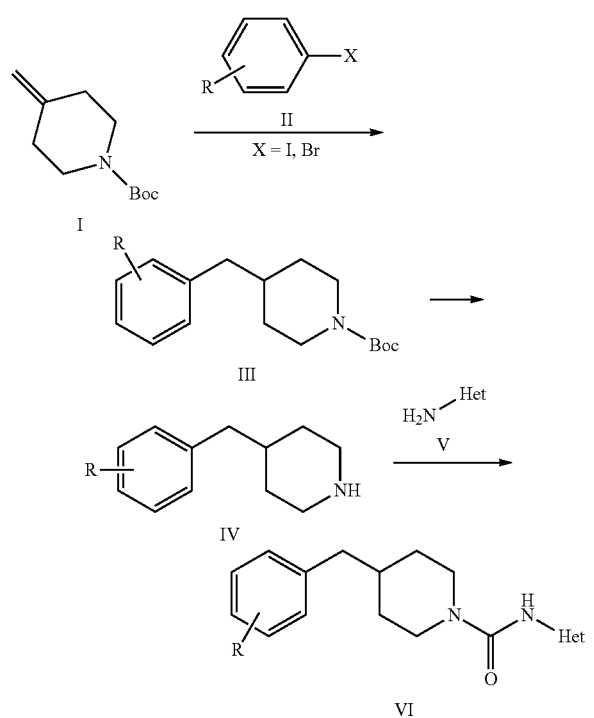

Hydroboration of piperidine I followed by Suzuki-Miyaura coupling with an appropriately substituted aromatic halide II affords Boc-protected intermediate III. Deprotection of piperidine III under acidic conditions (e.g., hydrochloric or trifluoroacetic acid) affords amine IV that can be reacted with an amino heterocycle V and an appropriate carbonyl synthon (e.g., triphosgene) to give appropriately substituted urea VI.

General Scheme 2

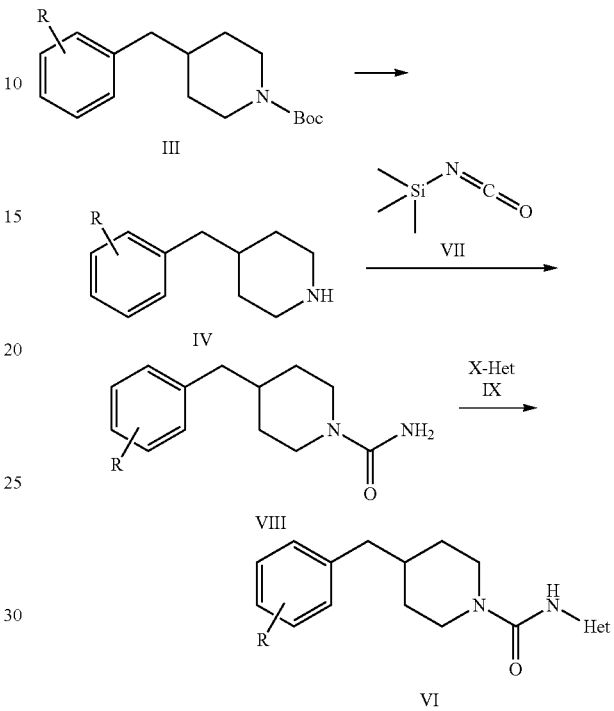

Alternatively, appropriately substituted Boc piperidine III can be deprotected using acidic conditions (e.g., hydrochloric or trifluoroacetic acid) to give free amine IV that can be coupled with trimethylsilyl isocyanate VII to give urethane VIII. Copper(I) mediated coupling of urea VIII with an aromatic halide IX (where X=halogen) affords appropriately substituted urea VI.

General Scheme 3

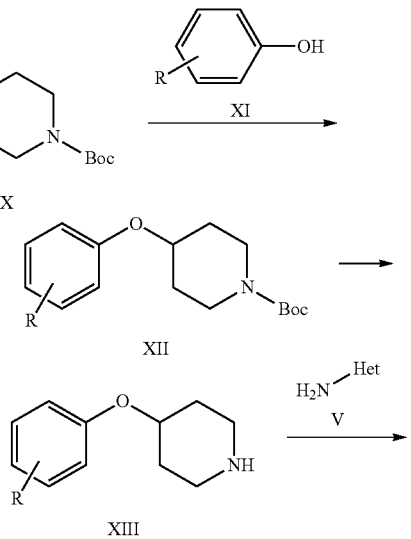

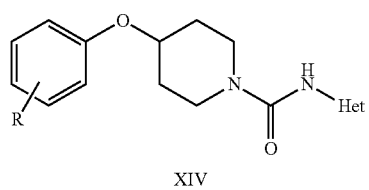

XIV

Condensation of piperidine alcohol X with appropriately substituted phenol XI under Mitsunobu conditions (e.g., diisopropyl azodicarboxylate) affords ether XII. Deprotection of XII under a variety of acidic conditions (e.g., hydrochloric or trifluoroacetic acid) affords amine XIII that can be reacted with an amino heterocycle V and an appropriate carbonyl synthon (e.g., triphosgene) to give appropriately substituted urea XIV.

General Scheme 4

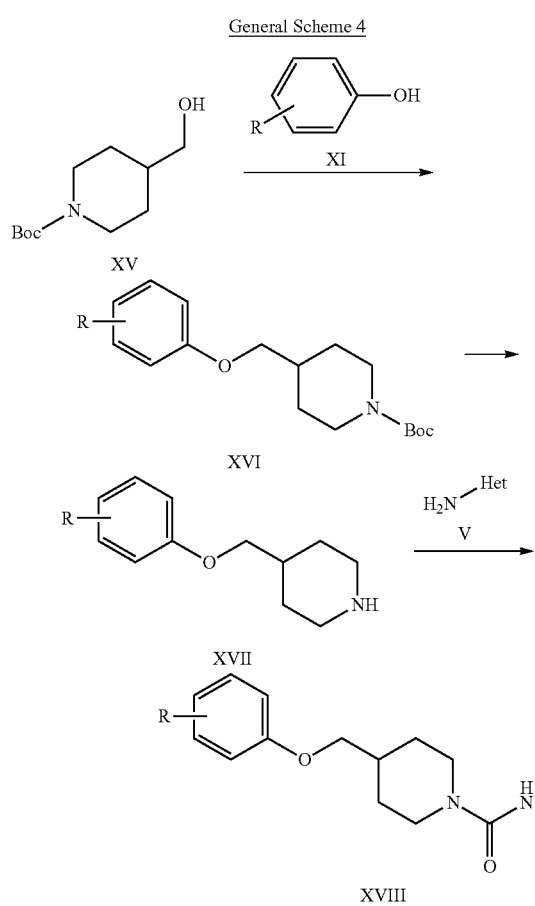

A reaction between piperidine alcohol XV and appropriately substituted phenol XI under Mitsunobu conditions (e.g., diisopropyl azodicarboxylate) affords homo piperidine ether XVI. Deprotection of XVI under a variety of acidic conditions (e.g., hydrochloric or trifluoroacetic acid) affords the free amine XVII that can be coupled with a heterocyclic amine V and an appropriate carbonyl synthon (e.g., triphosgene) to give appropriately substituted mixed urea XVIII.

General Scheme 5

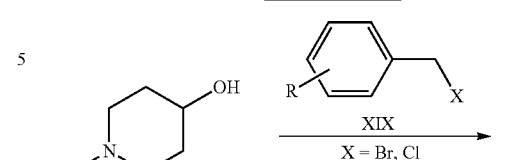

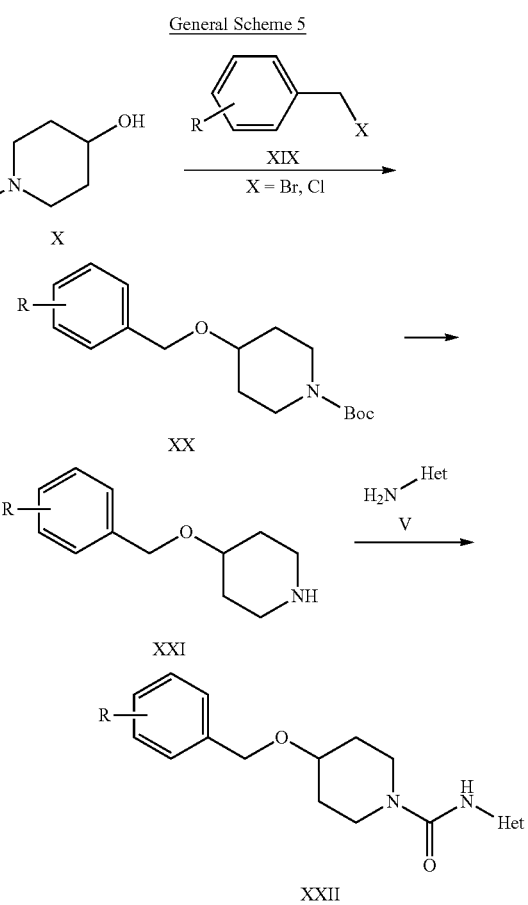

An alkylation of Boc-protected hydroxy piperidine X with an appropriately substituted benzyl halide XIX (where X=bromide or chloride) under strong basic conditions (e.g., sodium hydride) yields piperidine ether intermediate XX. Deprotection of XX under a variety of acidic conditions (e.g., hydrochloric or trifluoroacetic acid) affords the free amine XXI that can be coupled with a heterocyclic amine V and an appropriate carbonyl synthon (e.g., triphosgene) to give appropriately substituted urea XXII General Scheme 6

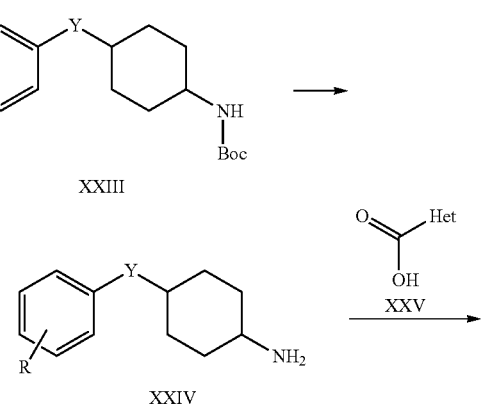

-continued

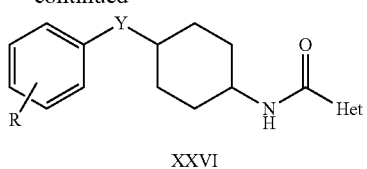

XXVI

Y = C, O

Deprotection of appropriately substituted Boc-protected amine XXIII under a variety of acidic conditions (e.g., hydrochloric or trifluoroacetic acid) affords primary amine XXIV. The reaction of amine XXIV and heterocyclic carboxylic acid XXV under a variety of peptide coupling conditions (e.g., HATU) yields an appropriately substituted amide XXVI.

General Scheme 7

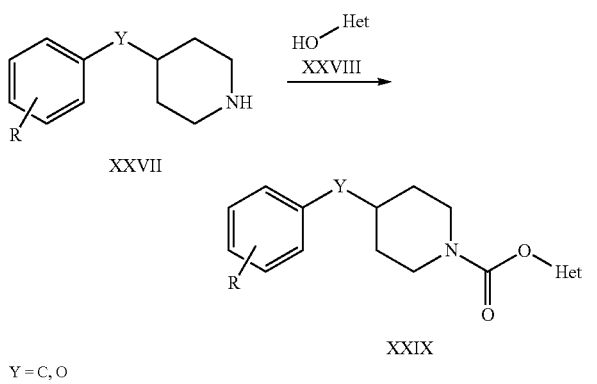

Y = C, O

An appropriately substituted piperidine XXVII can be coupled with a heterocyclic alcohol XXVIII using carbonyldiimidazole to afford carbamate XXIX.

General Scheme 8

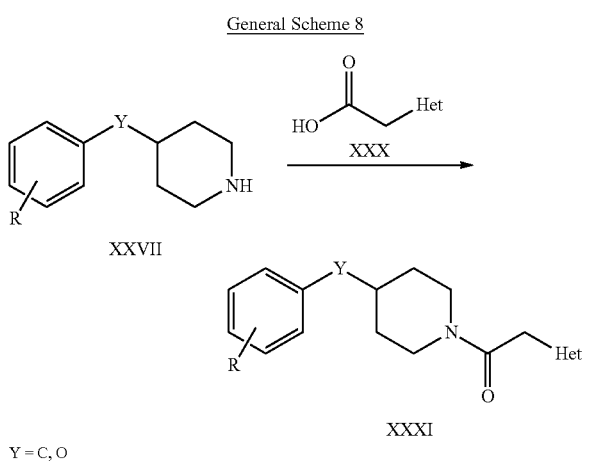

Y = C, O

Alternatively, intermediate XXVII can be reacted with carboxylic acid XXX under a variety of coupling conditions (e.g., HATU) to give an appropriately substituted amide XXXI.

General Scheme 9

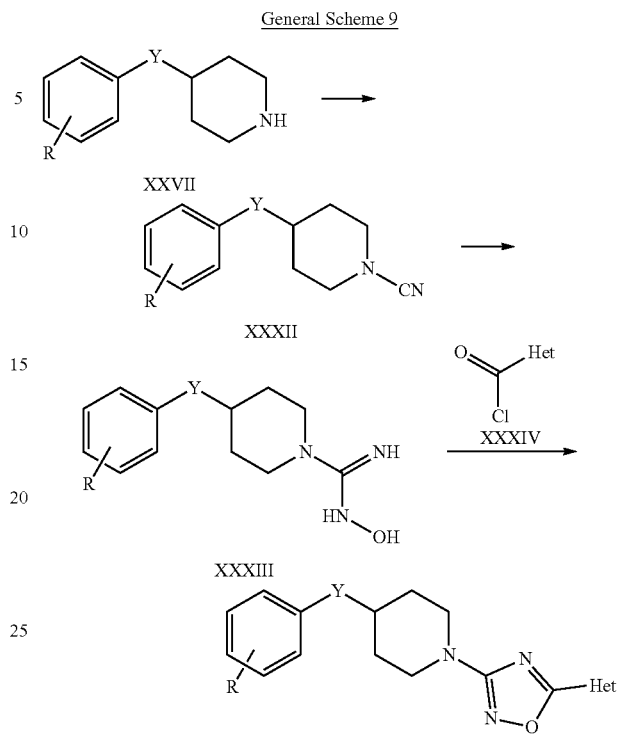

Y = C, O

A reaction between an appropriately substituted piperidine XXVII and cyanogen bromide yields nitrile XXXII that can be condensed with hydroxylamine to give amidoxime XXXIII. Coupling of intermediate XXXIII with a heterocyclic acyl chloride XXXIV gives appropriate 1,2,4-oxadiazole regioisomer XXXV.

General Scheme 10

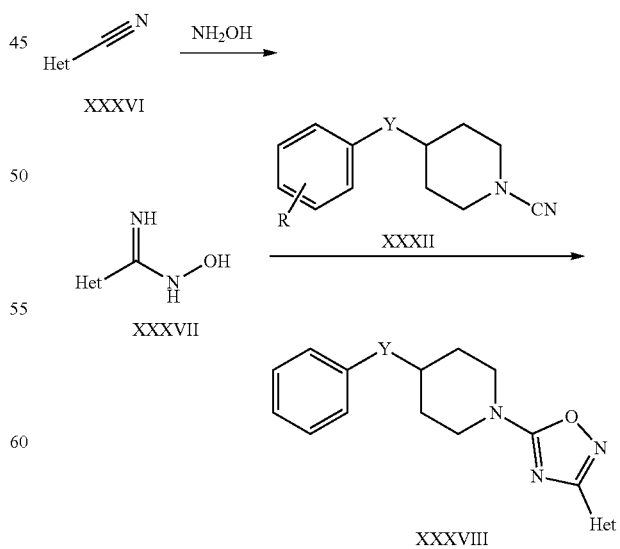

Y = C, O

A reaction between heterocyclic nitrile XXXVI and hydroxyl amine affords amidoxime XXXVII that can be reacted with appropriately substituted piperidine nitrile XXXII in the presence of zinc dichloride to yield appropriate 1,2,4-oxadiazole regioisomer XXXVIII.

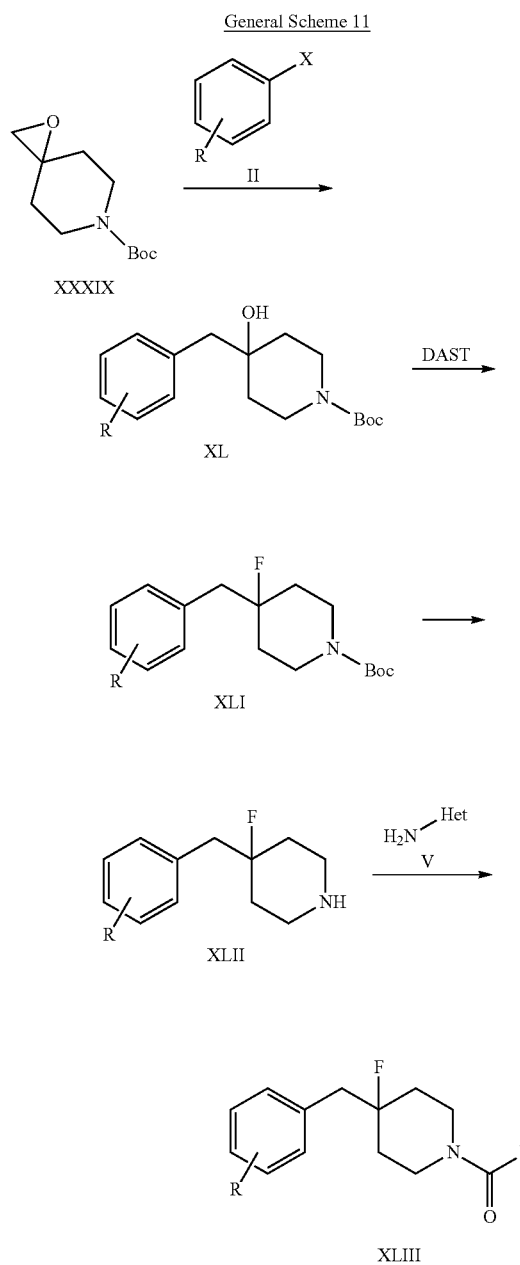

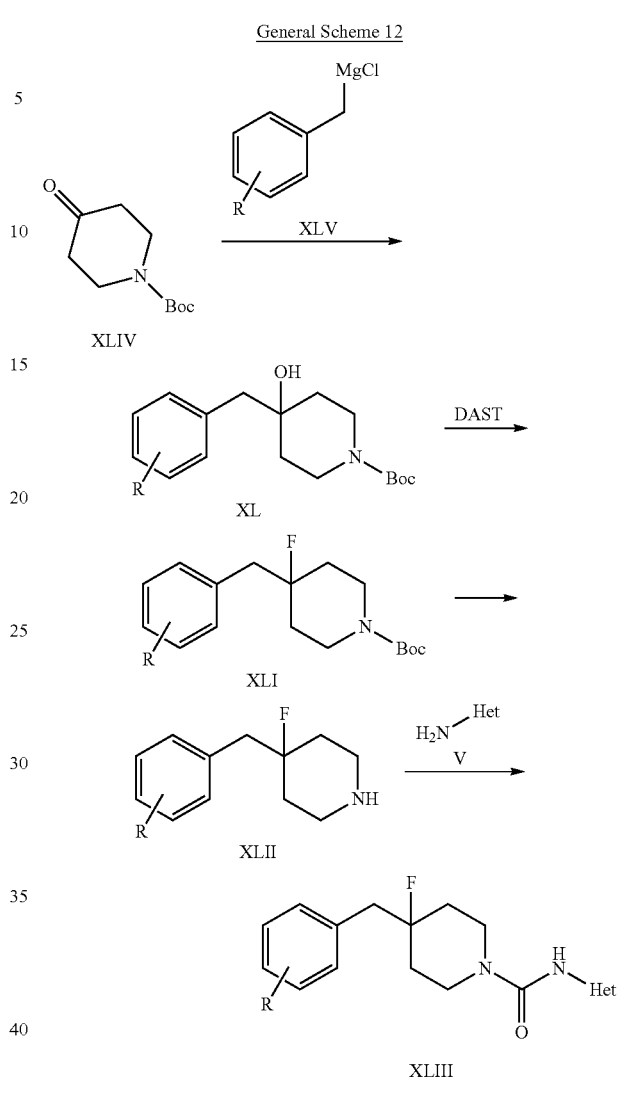

An appropriately substituted intermediate piperidine alcohol XL can be prepared from a Lewis acid catalyzed (e.g., boron trifluoride) ring opening of an epoxide XXXIX with an aromatic halide II. Alcohol XL can be converted to fluoride XLI using DAST. Deprotection of Boc-piperidine XLI under a variety of acidic conditions (e.g., hydrochloric or trifluoroacetic acid) affords the intermediate amine XLII that can be coupled to a heterocyclic amine V and an appropriate carbonyl synthon (e.g., triphosgene) to give appropriately substituted mixed urea XLIII.

Alternatively, substituted intermediate piperidine alcohol XL can be prepared from or a Grignard reaction between a ketone XLIV and an appropriately substituted benzyl magnesium chloride salt XLV. Alcohol XL can be converted to fluoride XLI using DAST. Deprotection of Boc-piperidine XLI under a variety of acidic conditions (e.g., hydrochloric or trifluoroacetic acid) affords the intermediate amine XLII that can be coupled to a heterocyclic amine V and an appropriate carbonyl synthon (e.g., triphosgene) to give appropriately substituted mixed urea XLIII.

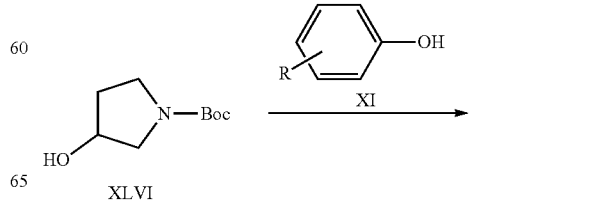

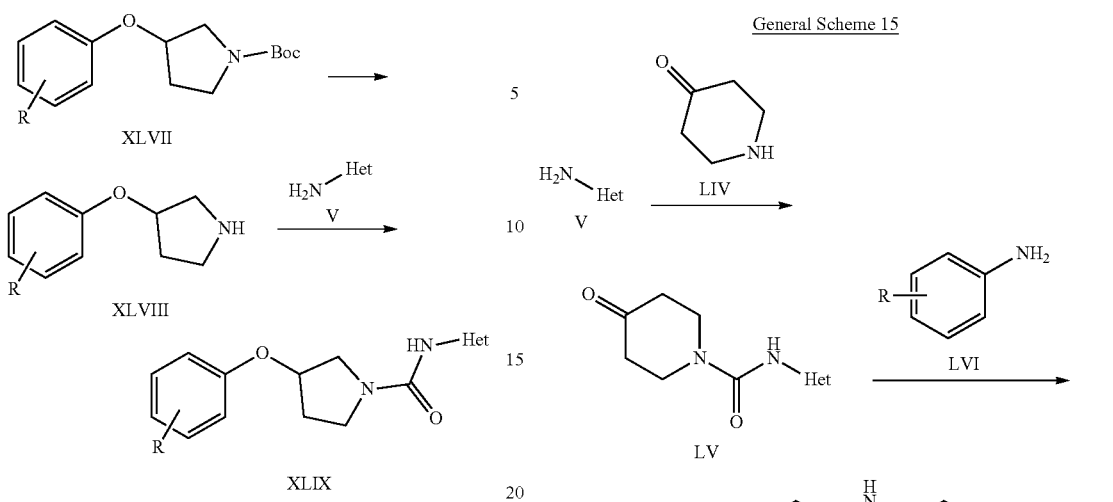

A reaction between pyrrolidine XLVI (chiral or racemic) and an appropriately substituted phenol XI under Mitsunobu conditions (e.g., diisopropyl azodicarboxylate) affords ether XLVII. Deprotection of XLVII under a variety of acidic conditions (e.g., hydrochloric or trifluoroacetic acid) affords a free amine XLVIII that can be coupled with heterocyclic amine V using triphosgene to give appropriately substituted urea XLIX.

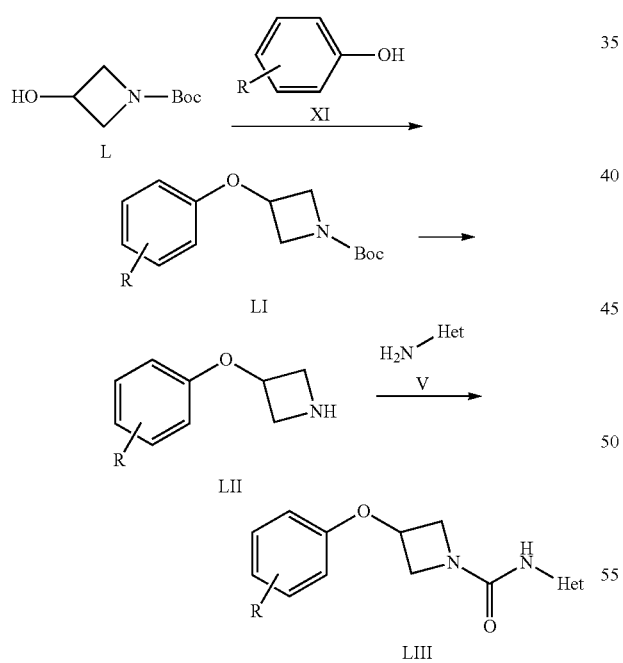

A reaction between azetidine L and appropriately substituted phenol XI under Mitsunobu conditions (e.g., diisopropyl azodicarboxylate) affords ether LI. Deprotection of LI under a variety of acidic conditions (e.g., hydrochloric or trifluoroacetic acid) affords a free amine LII that can be coupled with heterocyclic amine V using triphosgene to give appropriately substituted mixed urea LIII.

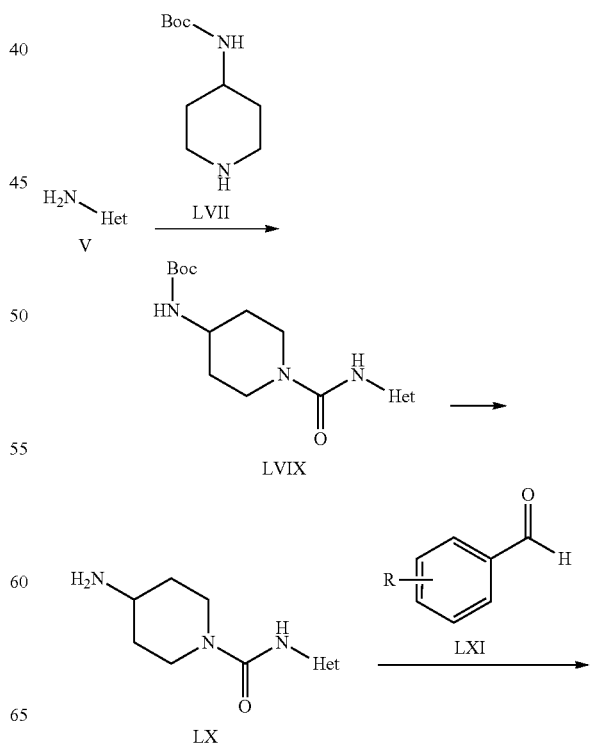

Urea LV can be obtained from a coupling between a heterocyclic amine V and piperidine ketone LIV. Reductive amination of ketone LV and appropriately substituted aniline LVI in the presence of a reducing agent (e.g., sodium cyanoborohydride) affords appropriately substituted N-linked compound LVII.

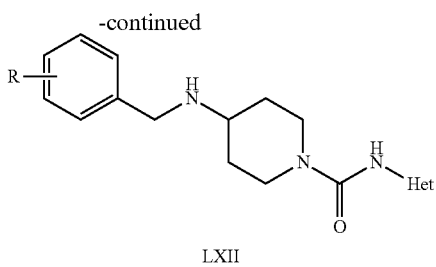

LXII

Coupling of a heterocyclic amine V with Boc-protected amino piperidine LVIII using triphosgene affords mixed urea intermediate LVIX. Deprotection of protecting group of LVIX under acidic conditions (e.g., hydrochloric acid) affords the free amine LX that can be alkylated with appropriately substituted benzaldehyde LXI in the presence of a reducing agent (e.g. sodium triacetoxyborohydride) to give amino piperidine LXII.

Example 1. Preparation of 4-(3-chlorobenzyl)-N-(1-methyl-6-oxo-1,6-dihydropyridazin-3-yl)piperidine-1-carboxamide (Compound 40)

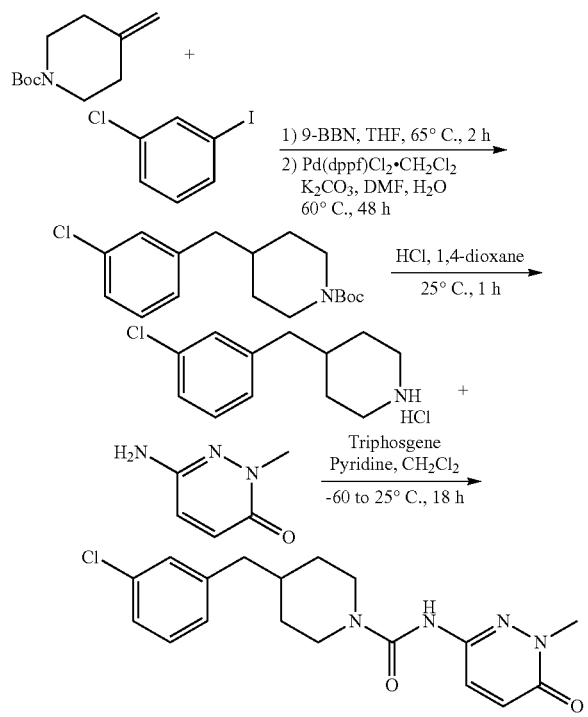

Step 1: Preparation of tert-butyl 4-(3-chlorobenzyl)piperidine-1-carboxylate

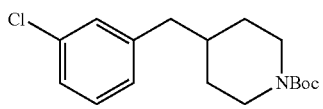 [SMILES: CC(C)(C)OC(=O)N1CCC(Cc2cccc(Cl)c2)CC1]

To a solution of 9-borabicyclo[3.3.1]nonane in tetrahydrofuran (40 mL, 20 mmol, 0.5 M) at 25° C. was added tert-butyl 4-methylenepiperidine-1-carboxylate (3.95 g, 20 mmol) under argon. The reaction mixture was stirred at 65° C. for 2 h, cooled to 25° C. and added to a solution of 1-chloro-3-iodobenzene (4.77 g, 20 mmol), potassium carbonate (3.6 g, 26 mmol) and 1,1'-bis(diphenylphosphino)ferrocene-palladium(II)dichloride dichloromethane complex (816 mg, 1.0 mmol) in N,N-dimethylformamide/water (30 mL/3 mL) at 25° C. The resulting mixture was heated at 60° C. for 48 h. The reaction mixture was quenched with aqueous 1 N aqueous sodium hydroxide solution and stirred at 25° C. for 1 h. The reaction solution was diluted with ethyl acetate (200 mL) and washed with brine (50 mL×3). The combined organic layers were dried over sodium sulfate, filtered and concentrated under reduced pressure. The crude residue was purified by column chromatography (silica gel, petroleum ether/ethyl acetate=15/1 to 10/1) to give tert-butyl 4-(3-chlorobenzyl)piperidine-1-carboxylate (3.46 g, 11.2 mmol, 56%) as a colorless oil. LCMS (ESI) m/z: 254.1 [M−56+H]$^+$.

Step 2: Preparation of 4-(3-chlorobenzyl)piperidine Hydrochloride

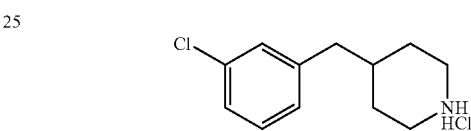

A solution of tert-butyl 4-(3-chlorobenzyl)piperidine-1-carboxylate (1.46 g, 4.72 mmol) and hydrochloric acid in 1,4-dioxane (50 mL, 4 M) was stirred at 25° C. for 1 h under nitrogen. The reaction mixture was concentrated under reduced pressure to yield 4-(3-chlorobenzyl)piperidine hydrochloride (1.05 g, 4.27 mmol, 90%) as a crude white solid. LCMS (ESI) m/z: 210.0 [M+H]$^+$. The intermediate was used in the next step without additional purification.

Step 3: Preparation of 4-(3-chlorobenzyl)-N-(1-methyl-6-oxo-1,6-dihydropyridazin-3-yl)piperidine-1-carboxamide

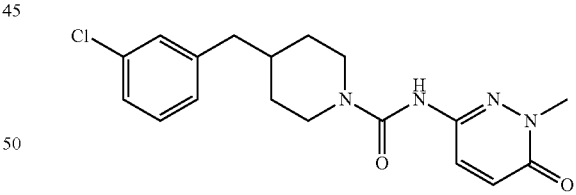

To a solution of triphosgene (119 mg, 0.4 mmol) in dichloromethane (10 mL) at −60° C. was added a solution of 6-amino-2-methylpyridazin-3(2H)-one (100 mg, 0.8 mmol) and pyridine (253 mg, 3.2 mmol) in dichloromethane (5 mL) under argon. The mixture was stirred at −60° C. for 30 min and a solution of 4-(3-chlorobenzyl)piperidine hydrochloride (236 mg, 0.96 mmol) and pyridine (253 mg, 3.2 mmol) in dichloromethane (5 mL) was added. The resulting mixture was warmed to 25° C. and stirred for 18 h. The reaction mixture was quenched with water (30 mL) and the aqueous layer was extracted with dichloromethane (50 mL×2). The combined organic layers were dried over sodium sulfate, filtered and concentrated under reduced pressure. The crude sample was dissolved in the minimum amount of N,N- dimethylformamide and purified by prep-HPLC (Boston C18, 10 μm, 21 mm×250 mm column, acetonitrile/10 mM ammonium acetate aqueous solution) to give 4-(3-chlorobenzyl)-N-(1-methyl-6-oxo-1,6-dihydropyridazin-3-yl) piperidine-1-carboxamide as a yellow solid (108 mg, 0.30 mmol, 37%). $^1$H NMR (400 MHz, Dimethylsulfoxide-$d_6$) δ 9.22 (s, 1H), 7.61 (d, J=9.6 Hz, 1H), 7.25-7.27 (m, 2H), 7.32 (t, J=7.6 Hz, 1H), 7.16 (d, J=7.6 Hz, 1H), 6.87 (d, J=9.6 Hz, 1H), 4.58 (d, J=13.2 Hz, 2H), 3.55 (s, 3H), 2.72 (t, J=12.4 Hz, 2H), 2.46-2.55 (m, 2H), 1.70-1.76 (m, 1H), 1.52-1.55 (m, 2H), 1.03-1.14 (m, 2H); LCMS (ESI) m/z: 361.1 [M+H]$^+$.

Example 2. Preparation of 4-(3-chloro-4-fluorobenzyl)-N-(1-methyl-6-oxo-1,6-dihydropyridazin-3-yl) piperidine-1-carboxamide (Compound 41)

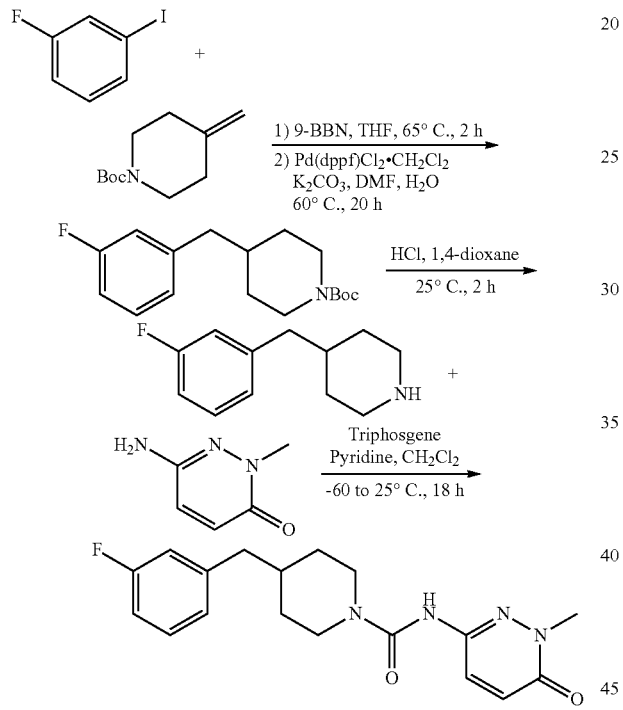

Step 1: Preparation of tert-butyl 4-(3-fluorobenzyl)piperidine-1-carboxylate

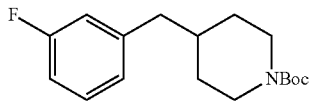

To a solution of 9-borabicyclo[3.3.1]nonane in tetrahydrofuran (40 mL, 20 mmol, 0.5 M) at 25° C. was added tert-butyl 4-methylenepiperidine-1-carboxylate (3.94 g, 20 mmol) under argon. The mixture was heated at 65° C. for 2 h, then the reaction mixture was cooled to 25° C. and added to a solution of 1-fluoro-3-iodobenzene (4.44 g, 20 mmol), potassium carbonate (3.59 g, 26 mmol) and 1,1'-bis(diphenylphosphino)ferrocene-palladium(II)dichloride dichloromethane complex (816 mg, 1.0 mmol) in N,N-dimethylformamide/water (32 mL/3.2 mL) at 25° C. The resulting mixture was heated at 60° C. for 20 h. The reaction was quenched with 1 N sodium hydroxide solution and stirred at 25° C. for 1 h. The reaction solution was diluted with ethyl acetate (200 mL) and washed with brine (200 mL×3). The combined organic layers were dried over sodium sulfate, filtered and concentrated under reduced pressure. The crude residue was purified by column chromatography (silica gel, petroleum ether/ethyl acetate=25/1) to give tert-butyl 4-(3-fluorobenzyl)piperidine-1-carboxylate (4 g, 13.7 mmol, 68%) as a colorless oil. LCMS (ESI) m/z: 238.2 [M-56+H]$^+$.

Step 2: Preparation of 4-(3-fluorobenzyl)piperidine

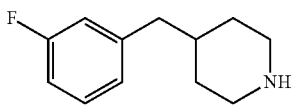

A solution of tert-butyl 4-(3-fluorobenzyl)piperidine-1-carboxylate (4.0 g, 13.7 mmol) and hydrochloric acid in 1,4-dioxane solution (40 mL, 4 M) was stirred at 25° C. for 2 h. The reaction mixture was concentrated under reduced pressure. The crude residue treated with aqueous sodium bicarbonate solution and extracted with dichloromethane (50 mL×2). The combined organic layers were dried over sodium sulfate, filtered and concentrated under reduced pressure. The crude 4-(3-fluorobenzyl)piperidine was used in the next step without further purification (2.6 g, 13.5 mmol, 99%). LCMS (ESI) m/z: 194.3 [M+H]$^+$.

Step 3: Preparation of 4-(3-fluorobenzyl)-N-(1-methyl-6-oxo-1,6-dihydropyridazin-3-yl)piperidine-1-carboxamide

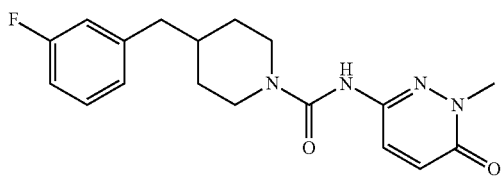 [SMILES: Cn1nc(NC(=O)N2CCC(Cc3cccc(F)c3)CC2)ccc1=O]

To a solution of triphosgene (148 mg, 0.5 mmol) in dichloromethane (13 mL) was added a solution of 6-amino-2-methylpyridazin-3(2H)-one (125 mg, 1.0 mmol) and pyridine (316 mg, 4.0 mmol) in dichloromethane (6 mL) at −60° C. under argon. The mixture was stirred at −60° C. for 0.5 h, then a solution of 4-(3-fluorobenzyl)piperidine (232 mg, 1.2 mmol) and pyridine (380 mg, 4.8 mmol) in dichloromethane (6 mL) was added at −60° C. The resulting mixture was stirred at 25° C. for 18 h. The reaction was quenched with water (30 mL) and the aqueous layer was extracted with dichloromethane (50 mL×2). The combined organic layers were dried over sodium sulfate, filtered and concentrated under reduced pressure. The crude sample was dissolved in the minimum amount of N,N-dimethylformamide and purified by prep-HPLC (BOSTON pHlex ODS, 21.2×250 mM, 10 μm, acetonitrile/0.1% aqueous formic acid)) to yield 4-(3-fluorobenzyl)-N-(1-methyl-6-oxo-1,6-dihydropyridazin-3-yl)piperidine-1-carboxamide (49.1 mg, 0.14 mmol, 14%) as a white solid. $^1$H NMR (400 MHz, Dimethylsulfoxide-$d_6$) δ 9.20 (s, 1H), 7.61 (d, J=9.6 Hz, 1H), 7.36-7.30 (m, 1H), 7.02 (t, J=8.2 Hz, 3H), 6.87 (d, J=9.6 Hz, 1H), 4.06 (d, J=13.6 Hz, 2H), 3.56 (s, 3H), 2.72 (t, J=12.2 Hz, 2H), 2.55 (d, J=7.2 Hz, 2H), 1.75-1.72 (m, 1H), 1.54 (d, J=12.0 Hz, 2H), 1.13-1.05 (m, 2H); LCMS (ESI) m/z: 345.1 [M+H]⁺.

Example 3. Preparation of 4-(3-chloro-5-fluorobenzyl)-N-(1-methyl-6-oxo-1,6-dihydropyridazin-3-yl)piperidine-1-carboxamide (Compound 55)

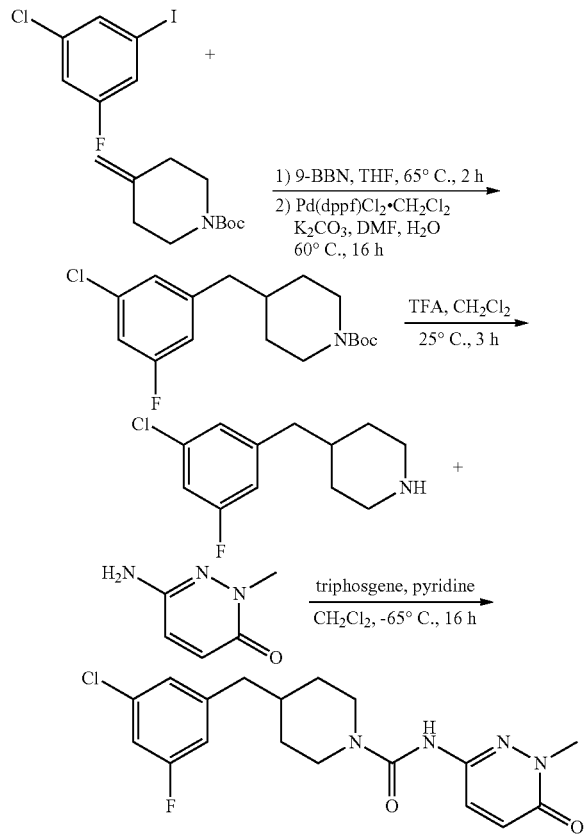

Step 1: Preparation of tert-butyl 4-(3-chloro-5-fluorobenzyl)piperidine-1-carboxylate

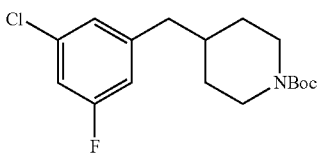 [SMILES: CC(C)(C)OC(=O)N1CCC(Cc2cc(F)cc(Cl)c2)CC1]

To a solution of 9-borabicyclo[3.3.1]nonane in tetrahydrofuran (50 mL, 25 mmol, 0.5 M) at 25° C. was added tert-butyl 4-methylenepiperidine-1-carboxylate (4.93 g, 25 mmol) under argon. The mixture was stirred at 65° C. for 2 h. The reaction mixture was cooled to 25° C. and added to a solution of 1-chloro-3-fluoro-5-iodobenzene (5.24 g, 20 mmol), potassium carbonate (4.49 g, 32.5 mmol) and 1,1'-bis(diphenylphosphino)ferrocene-palladium(II)dichloride dichloromethane complex (1.02 g, 1.25 mmol) in N,N-dimethylformamide/water (40 mL/4 mL) at 25° C. The resulting mixture was heated at 60° C. for 16 h. The reaction was cooled to room temperature and then quenched with aqueous 1 N aqueous sodium hydroxide solution and stirred at 25° C. for 1 h. The mixture was diluted with ethyl acetate (200 mL) and washed with brine (50 mL×3). The combined organic layers were dried over sodium sulfate, filtered and concentrated under reduced pressure. The crude residue was purified by column chromatography (silica gel, petroleum ether/ethyl acetate=15/1 to 10/1) to give tert-butyl 4-(3-chloro-5-fluorobenzyl)piperidine-1-carboxylate (4.36 g, 13.3 mmol, 53%) as a white solid. LCMS (ESI) m/z: 272.0 [M-56+H]⁺.

Step 2: Preparation of 4-(3-chloro-5-fluorobenzyl)piperidine

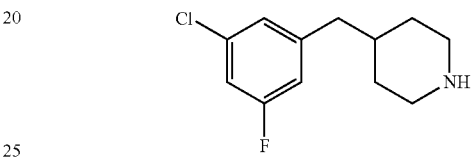

To a solution of tert-butyl 4-(3-chloro-5-fluorobenzyl)piperidine-1-carboxylate (4.36 g, 13.3 mmol) in dichloromethane (40 mL) was added trifluoroacetic acid (10 mL). The mixture was stirred at 25° C. for 3 h under nitrogen. The reaction mixture was basified to pH 9 with aqueous sodium bicarbonate solution and extracted with dichloromethane (100 mL×3). The combined organic layers were dried over sodium sulfate, filtered and concentrated under reduced pressure. The crude yellow solid was used in the next step without further purification (3.0 g, 13.2 mmol, 99%). LCMS (ESI) m/z: 228.0 [M+H]⁺.

Step 3: Preparation of 4-(3-chloro-5-fluorobenzyl)-N-(1-methyl-6-oxo-1,6-dihydropyridazin-3-yl)piperidine-1-carboxamide

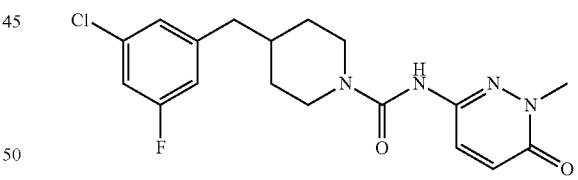

To a solution of triphosgene (119 mg, 0.4 mmol) in dichloromethane (10 mL) at −60° C. was added a solution of 6-amino-2-methylpyridazin-3(2H)-one (100 mg, 0.8 mmol) and pyridine (253 mg, 3.2 mmol) in dichloromethane (5 mL) under argon. The mixture was stirred at −60° C. for 30 min before a solution of 4-(3-chloro-5-fluorobenzyl)piperidine (219 mg, 0.96 mmol) and pyridine (253 mg, 3.2 mmol) in dichloromethane (5 mL) was added. The resulting mixture was warmed to 25° C. After 16 h, the reaction was quenched with water (30 mL) and the mixture was extracted with dichloromethane (50 mL×2). The combined organic layers were dried over sodium sulfate, filtered and concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 4-(3-chloro-5-fluorobenzyl)-N-(1-methyl-6-oxo-1,6-dihydropyridazin-3-yl)piperidine-1-carboxamide (26.7 mg, 0.07 mmol, 9%) as a white solid. $^1$H NMR (400 MHz, Dimethylsulfoxide-$d_6$) δ 9.22 (s, 1H), 7.61 (d, J=10.0 Hz, 1H), 7.24-7.27 (m, 1H), 7.16 (s, 1H), 7.08 (d, J=10.0 Hz, 1H), 6.87 (d, J=9.6 Hz, 1H), 4.05 (d, J=13.2 Hz, 2H), 3.56 (s, 3H), 2.72 (t, J=12.4 Hz, 2H), 2.55-2.57 (m, 2H), 1.74-1.79 (m, 1H), 1.52-1.55 (m, 2H), 1.04-1.14 (m, 2H); LCMS (ESI) m/z: 379.0 [M+H]$^+$.

Example 4. Preparation of 4-(3,5-difluorobenzyl)-N-(1-methyl-6-oxo-1,6-dihydropyridazin-3-yl)piperidine-1-carboxamide (Compound 51)

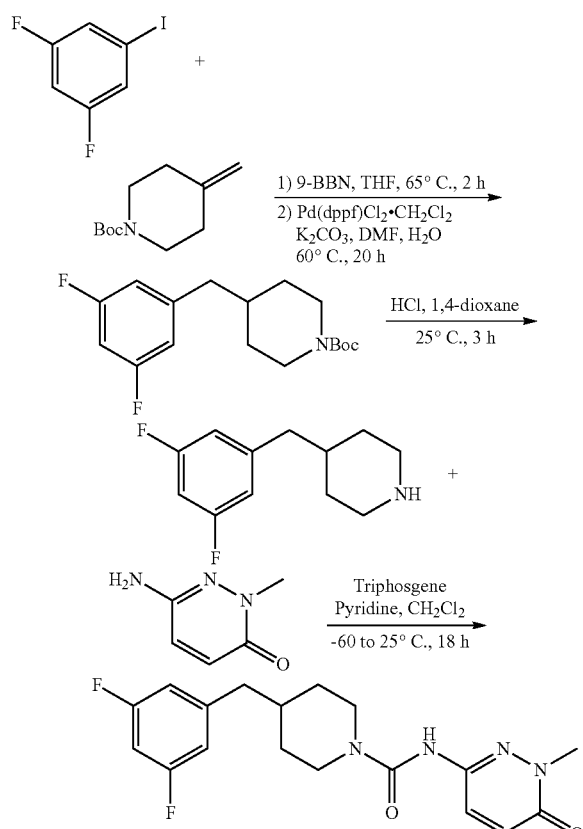

Step 1: Preparation of tert-butyl 4-(3,5-difluorobenzyl)piperidine-1-carboxylate

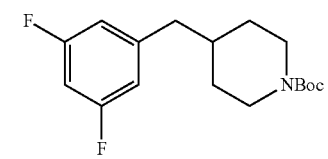

To a solution of 9-borabicyclo[3.3.1]nonane in tetrahydrofuran (120 mL, 60 mmol, 0.5 M) at 25° C. was added tert-butyl 4-methylenepiperidine-1-carboxylate (11.8 g, 60 mmol) under argon. The mixture was stirred at 65° C. for 2 h. The reaction mixture was cooled to 25° C. and added to a solution of 1,3-difluoro-5-iodobenzene (14.4 g, 60 mmol), potassium carbonate (10.8 g, 78 mmol) and 1,1'-bis(diphenylphosphino)ferrocene-palladium(II)dichloride dichloromethane complex (2.45 g, 3.0 mmol) in N,N-dimethylformamide/water (100 mL/10 mL) at 25° C. The resulting reaction solution was heated at 60° C. for 20 h. The reaction was cooled then quenched with 1 N aqueous sodium hydroxide solution and stirred at 25° C. for 1 h. The mixture was diluted with ethyl acetate (800 mL) and washed with brine (500 mL×3). The combined organic layers were dried over sodium sulfate, filtered and concentrated under reduced pressure. The crude residue was purified by column chromatography (silica gel, petroleum ether/ethyl acetate=20/1 to 10/1) to give tert-butyl 4-(3,5-difluorobenzyl)piperidine-1-carboxylate (9.5 g, 30.5 mmol, 51%) as a yellow solid. LCMS (ESI) m/z: 256.1 [M-56+H]$^+$.

Step 2: Preparation of 4-(3,5-difluorobenzyl)piperidine

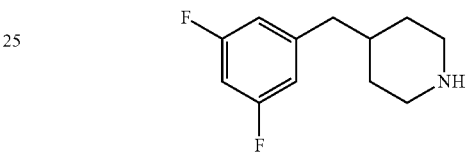

A solution of tert-butyl 4-(3,5-difluorobenzyl)piperidine-1-carboxylate (13.5 g, 43.3 mmol) and hydrochloric acid in 1,4-dioxane solution (100 mL, 4 M) was stirred at 25° C. for 3 h under nitrogen. The reaction solution was concentrated in vacuo and the crude residue was triturated with diethyl ether. The white solid was filtered and washed with diethyl ether (100 mL×2). The solid was suspended in aqueous sodium bicarbonate solution and extracted with dichloromethane (1000 mL×3). The combined organic layers were dried over sodium sulfate, filtered and concentrated under reduced pressure. The crude yellow solid was used in the next step without further purification (7.2 g, 34.1 mmol, 79%). LCMS (ESI) m/z: 212.1 [M+H]$^+$.

Step 3: Preparation of 4-(3,5-difluorobenzyl)-N-(1-methyl-6-oxo-1,6-dihydropyridazin-3-yl)piperidine-1-carboxamide

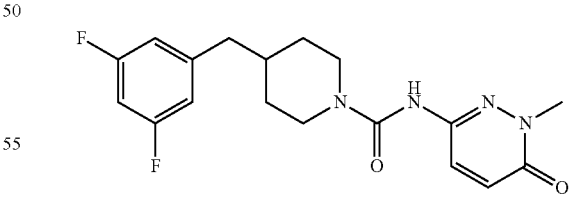

To a solution of triphosgene (3.71 g, 12.5 mmol) in dichloromethane (150 mL) was added a solution of 6-amino-2-methylpyridazin-3(2H)-one (3.13 g, 25 mmol) and pyridine (7.91 g, 100 mmol) in dichloromethane (50 mL) at −60° C. under argon. The mixture was stirred at −60° C. for 2 h and a solution of 4-(3,5-difluorobenzyl)piperidine (5.02 g, 23.75 mmol) and pyridine (7.91 g, 100 mmol) in dichloromethane (50 mL) was added at −60° C. The resulting mixture was stirred at 25° C. for 18 h. The reaction was quenched with water (200 mL) and the aqueous layer was extracted with dichloromethane (300 mL×2). The combined organic layers were dried over sodium sulfate, filtered and concentrated under reduced pressure. The crude residue was purified by column chromatography (silica gel, petroleum ether/ethyl acetate/ammonia in methanol (7 N) from 10/5/1 to 5/5/1) to give 4-(3,5-difluorobenzyl)-N-(1-methyl-6-oxo-1,6-dihydropyridazin-3-yl)piperidine-1-carboxamide as a yellow solid (4.7, 13.0 mmol, 55%). The yellow solid was further triturated in diethyl ether (200 mL), filtered and washed with diethyl ether to give 4-(3,5-difluorobenzyl)-N-(1-methyl-6-oxo-1,6-dihydropyridazin-3-yl)piperidine-1-carboxamide (4.25 g, 11.7 mmol, 49%) as an off-white solid. $^1$H NMR (400 MHz, Dimethylsulfoxide-d$_6$) δ 9.20 (s, 1H), 7.62 (d, J=9.6 Hz, 1H), 7.01-7.07 (m, 2H), 6.93-6.97 (m, 1H), 6.87 (d, J=10.0 Hz, 1H), 4.06 (d, J=13.2 Hz, 2H), 3.56 (s, 3H), 2.73 (t, J=12.0 Hz, 2H), 2.51-2.57 (m, 2H), 1.74-1.81 (m, 1H), 1.53-1.55 (m, 2H), 1.04-1.14 (m, 2H); LCMS (ESI) m/z: 363.2 [M+H]$^+$.

Example 5. Preparation of 4-(3,4-difluorobenzyl)-N-(1-methyl-6-oxo-1,6-dihydropyridazin-3-yl)piperidine-1-carboxamide (Compound 49)

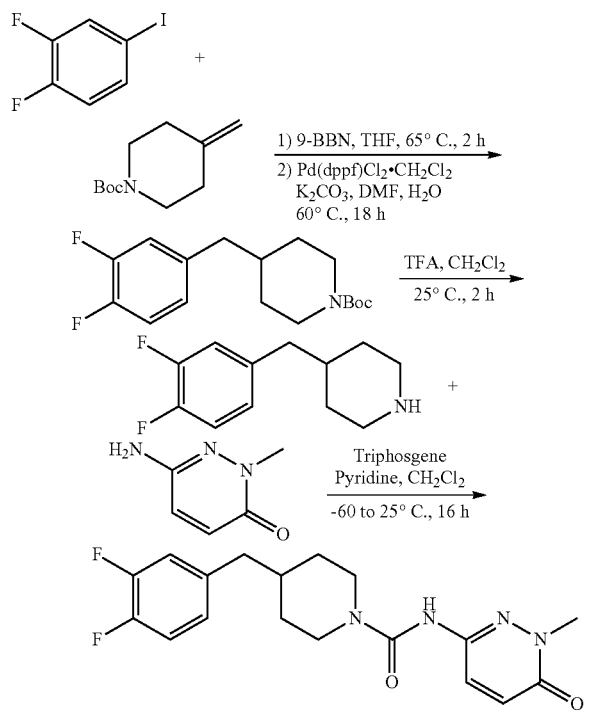

Step 1: Preparation of tert-butyl 4-(3,4-difluorobenzyl)piperidine-1-carboxylate

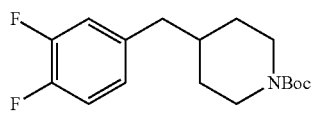

To a solution of 9-borabicyclo[3.3.1]nonane in tetrahydrofuran (36 mL, 18 mmol, 0.5 M) at 25° C. was added tert-butyl 4-methylenepiperidine-1-carboxylate (3.55 g, 18 mmol) under argon. The mixture was stirred at 65° C. for 2 h. The mixture was cooled to 25° C. and added to a solution of 1,2-difluoro-4-iodobenzene (4.32 g, 18 mmol), potassium carbonate (3.23 g, 23.4 mmol) and 1,1'-bis(diphenylphosphino)ferrocene-palladium(II)dichloride dichloromethane complex (735 mg, 0.9 mmol) in N,N-dimethylformamide/water (40 mL/4 mL) at 25° C. The resulting mixture was heated at 60° C. for 18 h. The reaction mixture was quenched with 1 N aqueous sodium hydroxide solution and the mixture was stirred at 25° C. for 1 h. Then reaction solution was diluted with ethyl acetate (200 mL) and washed with brine (50 mL×3). The combined organic layers were dried over sodium sulfate, filtered and concentrated under reduced pressure. The crude residue was purified by column chromatography (silica gel, petroleum ether/ethyl acetate from 10/1 to 5/1) to give tert-butyl 4-(3,4-difluorobenzyl)piperidine-1-carboxylate (1 g, 3.2 mmol, 18%) as a white solid. LCMS (ESI) m/z: 256.1 [M-56+H]$^+$.

Step 2: Preparation of 4-(3,4-difluorobenzyl)piperidine

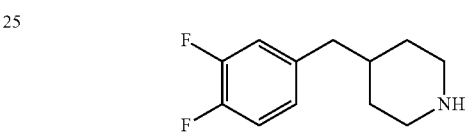

To a solution of tert-butyl 4-(3,4-difluorobenzyl)piperidine-1-carboxylate (1.16 g, 3.72 mmol) in dichloromethane (20 mL) was added trifluoroacetic acid (5 mL). The reaction mixture was stirred at 25° C. for 2 h under nitrogen and was concentrated under reduced pressure. The crude residue was treated with aqueous sodium bicarbonate solution. The aqueous layer was extracted with dichloromethane (50 mL×3). The combined organic layers were dried over sodium sulfate, filtered and concentrated under reduced pressure. The crude yellow solid was used in the next step without further purification (920 mg, 117%). LCMS (ESI) m/z: 212.1 [M+H]$^+$.

Step 3: Preparation of 4-(3,4-difluorobenzyl)-N-(1-methyl-6-oxo-1,6-dihydropyridazin-3-yl)piperidine-1-carboxamide

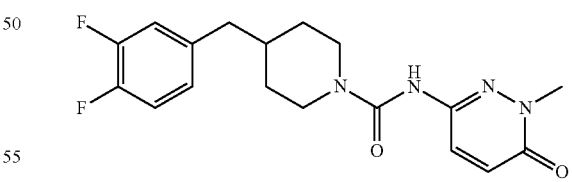

To a solution of triphosgene (119 mg, 0.4 mmol) in dichloromethane (10 mL) at −60° C. was added a solution of 6-amino-2-methylpyridazin-3(2H)-one (100 mg, 0.8 mmol) and pyridine (253 mg, 3.2 mmol) in dichloromethane (5 mL) under argon. The mixture was stirred at −60° C. for 30 min and then a solution of 4-(3,4-difluorobenzyl)piperidine (203 mg, 0.96 mmol) and pyridine (253 mg, 3.2 mmol) in dichloromethane (5 mL) was added at −60° C. The resulting mixture was stirred at 25° C. for 16 h. The reaction was quenched with water (30 mL) and the aqueous layer was extracted with dichloromethane (50 mL×2). The combined organic layers were dried over sodium sulfate, filtered and concentrated under reduced pressure. The crude sample was dissolved in the minimum amount of N,N-dimethylformamide and purified via prep-HPLC (Boston C18, 10 μm, 21 mm×250 mm column; acetonitrile/0.01% aqueous trifluoroacetic acid) to give 4-(3,4-difluorobenzyl)-N-(1-methyl-6-oxo-1,6-dihydropyridazin-3-yl)piperidine-1-carboxamide (90.3 mg, 0.25 mmol, 31%) as a white solid. $^{1}$H NMR (500 MHz, Dimethylsulfoxide-d$_6$) δ 9.20 (s, 1H), 7.61 (d, J=10.0 Hz, 1H), 7.26-7.36 (m, 2H), 7.02-7.04 (m, 1H), 6.87 (d, J=10.0 Hz, 1H), 4.05 (d, J=13.0 Hz, 2H), 3.56 (s, 3H), 2.72 (t, J=12.0 Hz, 2H), 2.50-2.53 (m, 2H), 1.71-1.74 (m, 1H), 1.53-1.55 (m, 2H), 1.05-1.12 (m, 2H); LCMS (ESI) m/z: 363.2 [M+H]$^{+}$.

Example 6. Preparation of 4-(3-chloro-4-fluorobenzyl)-N-(1-methyl-6-oxo-1,6-dihydropyridazin-3-yl)piperidine-1-carboxamide (Compound 54)

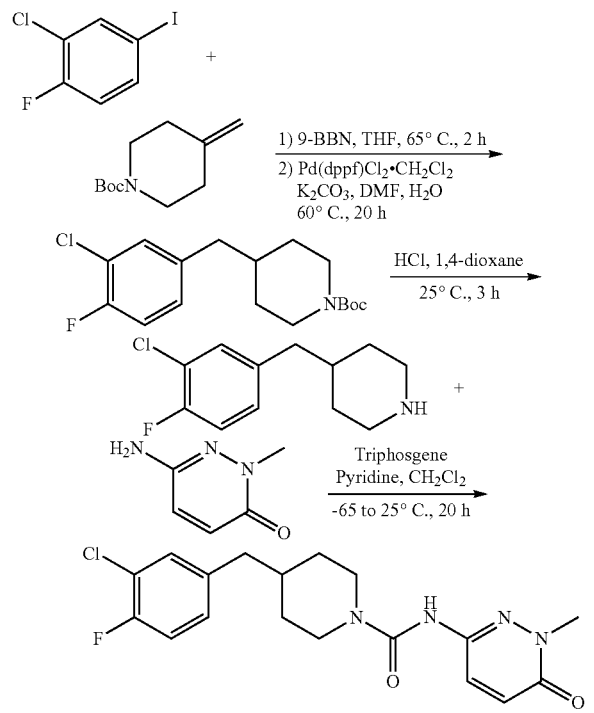

Step 1: Preparation of tert-butyl 4-(3-chloro-4-fluorobenzyl)piperidine-1-carboxylate

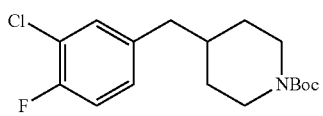 [SMILES: CC(C)(C)OC(=O)N1CCC(Cc2ccc(F)c(Cl)c2)CC1]

To a solution of tert-butyl 4-methylenepiperidine-1-carboxylate (3.95 g, 20 mmol) in tetrahydrofuran (40 mL) at 25° C. was added a solution of 9-borabicyclo[3.3.1]nonane in tetrahydrofuran (40 mL, 20 mmol, 0.5 M) under argon. The mixture was stirred at 65° C. for 2 h, then cooled to 25° C. and added to a solution of 2-chloro-1-fluoro-4-iodobenzene (5.13 g, 20 mmol), potassium carbonate (3.6 g, 26 mmol) and 1,1'-bis(diphenylphosphino)ferrocene-palladium (II)dichloride dichloromethane complex (816 mg, 1.0 mmol) in N,N-dimethylformamide/water (30 mL/3 mL). The resulting mixture was heated at 60° C. for 20 h. The reaction was quenched with 1 N aqueous sodium hydroxide and stirred at 25° C. for 1 h. The mixture was diluted with ethyl acetate (200 mL) and washed with brine (50 mL×3). The combined organic layers were dried over sodium sulfate, filtered and concentrated under reduced pressure. The crude residue was purified by column chromatography (silica gel, petroleum ether/ethyl acetate=15/1 to 10/1) to give tert-butyl 4-(3-chloro-4-fluorobenzyl)piperidine-1-carboxylate as a yellow solid (5.29 g, 16.1 mmol, 81%). LCMS (ESI) m/z: 272.1 [M-56+H]$^{+}$.

Step 2: Preparation of 4-(3-chloro-4-fluorobenzyl)piperidine

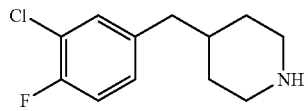 [SMILES: Fc1ccc(CC2CCNCC2)cc1Cl]

A solution of tert-butyl 4-(3-chloro-4-fluorobenzyl)piperidine-1-carboxylate (5.29 g, 16 mmol) and hydrochloric acid in 1,4-dioxane solution (50 mL, 4 M) was stirred at 25° C. for 3 h under nitrogen. The mixture was concentrated under reduced pressure. The crude residue was adjusted to pH=9 with sodium bicarbonate solution and extracted with dichloromethane (100 mL×3). The combined organic layers were dried over sodium sulfate, filtered and concentrated under reduced pressure. The crude yellow oil (3.5 g, 15.4 mmol, 96%) was used in the next step without further purification. LCMS (ESI) m/z: 228.0 [M+H]$^{+}$.

Step 3: Preparation of 4-(3-chloro-4-fluorobenzyl)-N-(1-methyl-6-oxo-1,6-dihydropyridazin-3-yl)piperidine-1-carboxamide

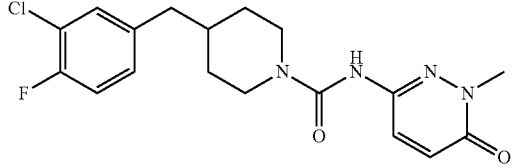 [SMILES: Cn1nc(NC(=O)N2CCC(Cc3ccc(F)c(Cl)c3)CC2)ccc1=O]

To a solution of triphosgene (297 mg, 1.0 mmol) in dichloromethane (30 mL) at −65° C. was added a solution of 6-amino-2-methylpyridazin-3(2H)-one (250 mg, 2.0 mmol) and pyridine (633 mg, 8.0 mmol) in dichloromethane (15 mL) under argon. The mixture was stirred at −65° C. for 0.5 h, then a solution of 4-(3-chloro-4-fluorobenzyl)piperidine (454 mg, 2.0 mmol) and pyridine (633 mg, 8.0 mmol) in dichloromethane (15 mL) was added at −65° C. The resulting mixture was warmed to 25° C. and stirred for 18 h. The reaction was diluted with water (50 mL) and the mixture was extracted with dichloromethane (100 mL×2). The combined organic layers were dried over sodium sulfate, filtered and concentrated under reduced pressure. The crude sample was dissolved in the minimum amount of N,N-dimethylformamide and purified by prep-HPLC (Boston C18, 10 µm, 21 mm×250 mm column, acetonitrile/10 mM ammonium acetate aqueous solution) to give 4-(3-chloro-4-fluorobenzyl)-N-(1-methyl-6-oxo-1,6-dihydropyridazin-3-yl)piperidine-1-carboxamide (190 mg, 0.50 mmol, 25%) as a yellow solid. $^1$H NMR (400 MHz, Dimethylsulfoxide-d$_6$) δ 9.19 (s, 1H), 7.62 (s, 1H), 7.42 (dd, J$_1$=2.0 Hz, J$_2$=7.2 Hz, 1H), 7.30-7.35 (m, 1H), 7.18-7.22 (m, 1H), 6.86 (d, J=10.0 Hz, 1H), 4.05 (d, J=13.6 Hz, 2H), 3.56 (s, 3H), 2.72 (t, J=12.0 Hz, 2H), 2.51-2.54 (m, 2H), 1.69-1.76 (m, 1H), 1.52-1.55 (m, 2H), 1.03-1.13 (m, 2H); LCMS (ESI) m/z: 379.0 [M+H]$^+$.

Example 7. Preparation of 4-(3-cyano-4-fluorobenzyl)-N-(1-methyl-6-oxo-1,6-dihydropyridazin-3-yl) piperidine-1-carboxamide (Compound 58)

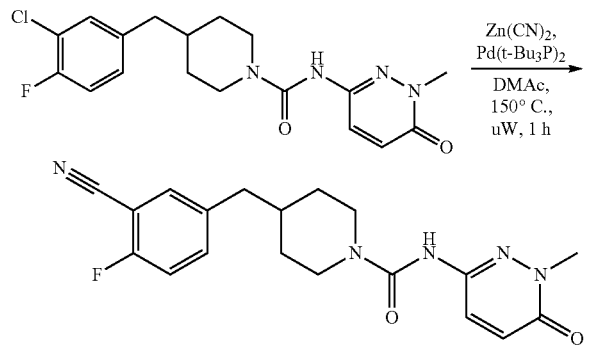

Step 1: Preparation of 4-(3-cyano-4-fluorobenzyl)-N-(1-methyl-6-oxo-1,6-dihydropyridazin-3-yl)piperidine-1-carboxamide

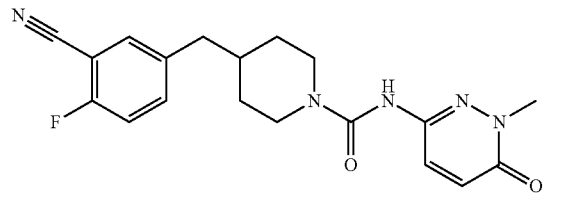 [SMILES: Cn1nc(NC(=O)N2CCC(Cc3ccc(F)c(C#N)c3)CC2)ccc1=O]

To a solution of 4-(3-chloro-4-fluorobenzyl)-N-(1-methyl-6-oxo-1,6-dihydropyridazin-3-yl)piperidine-1-carboxamide (114 mg, 0.3 mmol) and zinc cyanide (28 mg, 0.24 mmol) in N,N-dimethylaniline (3 mL) at 25° C. was added bis(tri-tert-butylphosphine)palladium(0) (16 mg, 0.03 mmol) under argon. The mixture was heated at 150° C. for 1 h under microwave irradiation. The reaction mixture was diluted with water (30 mL) and extracted with ethyl acetate (50 mL×3). The combined organic layers were dried over sodium sulfate, filtered and concentrated under reduced pressure. The crude sample was dissolved in the minimum amount of N,N-dimethylformamide and purified by prep-HPLC (Boston C18, 10 µm, 21 mm×250 mm column, acetonitrile/10 mM ammonium acetate aqueous solution) to give 4-(3-cyano-4-fluorobenzyl)-N-(1-methyl-6-oxo-1,6-dihydropyridazin-3-yl)piperidine-1-carboxamide (56.4 mg, 0.15 mmol, 50%) as a white solid. $^1$H NMR (400 MHz, Dimethylsulfoxide-d$_6$) δ 9.24 (s, 1H), 7.77 (dd, J$_1$=2.0 Hz, J$_2$=6.0 Hz, 1H), 7.60-7.64 (m, 2H), 7.44-7.49 (m, 1H), 6.87 (d, J=9.6 Hz, 1H), 4.06 (d, J=13.6 Hz, 2H), 3.56 (s, 3H), 2.71 (t, J=12.0 Hz, 2H), 2.57-2.59 (m, 2H), 1.72-1.77 (m, 1H), 1.51-1.54 (m, 2H), 1.03-1.13 (m, 2H); LCMS (ESI) m/z: 370.0 [M+H]$^+$.

Example 8. Preparation of 4-(3-chloro-4,5-difluorobenzyl)-N-(1-methyl-6-oxo-1,6-dihydropyridazin-3-yl)piperidine-1-carboxamide (Compound 63)

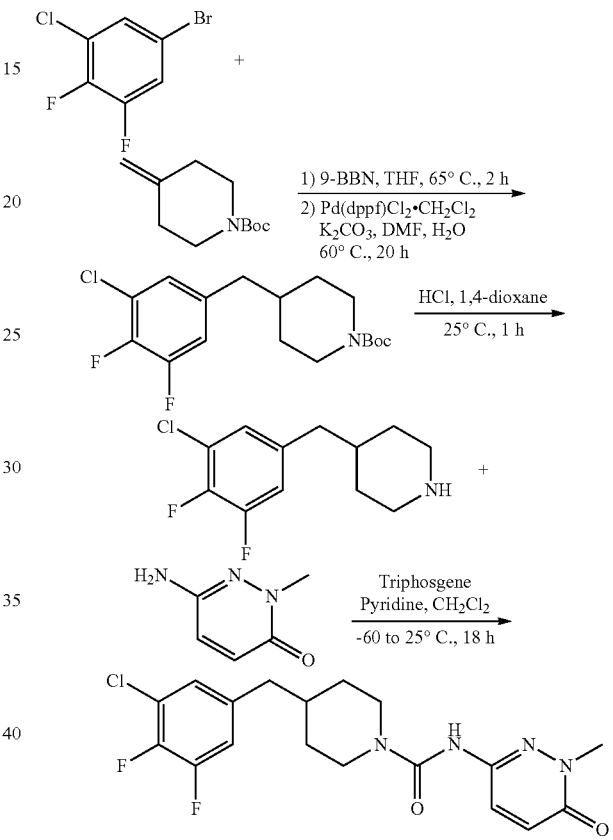

Step 1: Preparation of tert-butyl 4-(3-chloro-4,5-difluorobenzyl)piperidine-1-carboxylate

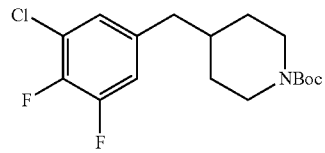 [SMILES: CC(C)(C)OC(=O)N1CCC(Cc2cc(F)c(F)c(Cl)c2)CC1]

To a solution of 9-borabicyclo[3.3.1]nonane in tetrahydrofuran (22 mL, 11 mmol, 0.5 M) at 25° C. was added tert-butyl 4-methylenepiperidine-1-carboxylate (2.17 g, 11 mmol) under argon. The mixture was stirred at 65° C. for 2 h. The mixture was cooled to 25° C. and added to a solution of 5-bromo-1-chloro-2,3-difluorobenzene (2.5 g, 11 mmol), potassium carbonate (1.97 g, 14.3 mmol) and 1,1'-bis(diphenylphosphino)ferrocene-palladium(II)dichloride dichloromethane complex (449 mg, 0.55 mmol) in N,N-dimethylformamide/water (18 mL/1.8 mL) at 25° C. The resulting mixture was heated at 60° C. for 20 h. The reaction was quenched with 1 N aqueous sodium hydroxide solution and the aqueous layer was stirred at 25° C. for 1 h. The reaction mixture was diluted with ethyl acetate (300 mL) and washed with brine (200 mL×3). The combined organic layers were dried over sodium sulfate, filtered and concentrated under reduced pressure. The crude residue was purified by column chromatography (silica gel, petroleum ether/ethyl acetate=25/1) to give tert-butyl 4-(3-chloro-4,5-difluorobenzyl)piperidine-1-carboxylate as a brown oil (1.25 g, 3.62 mmol, 33%). LCMS (ESI) m/z: 290.1 [M-56+H]$^+$.

Step 2: Preparation of 4-(3-chloro-4,5-difluorobenzyl)piperidine

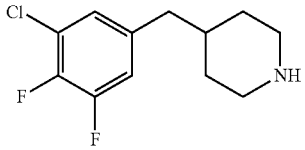

A solution of tert-butyl 4-(3-chloro-4,5-difluorobenzyl)piperidine-1-carboxylate (1.25 g, 3.62 mmol) in hydrochloric acid in dioxane solution (20 mL, 4M) was stirred at 25° C. for 1 h. The reaction mixture was concentrated under reduced pressure. The crude residue was adjusted to pH 9 with sodium bicarbonate solution and extracted with dichloromethane (100 mL×2). The combined organic layers were dried over sodium sulfate, filtered and concentrated under reduced pressure to give 4-(3-chloro-4,5-difluorobenzyl)piperidine as a brown oil, which was used in the next step without further purification (0.84 g, 3.43 mmol, 95%). LCMS (ESI) m/z: 246.1 [M+H]$^+$.

Step 3: Preparation of 4-(3-chloro-4,5-difluorobenzyl)-N-(1-methyl-6-oxo-1,6-dihydropyridazin-3-yl)piperidine-1-carboxamide

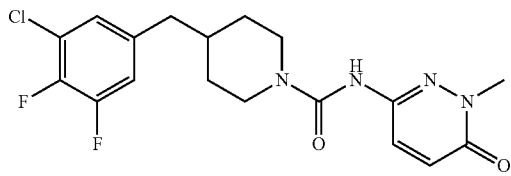 [SMILES: Cn1nc(NC(=O)N2CCC(Cc3cc(F)c(F)c(Cl)c3)CC2)ccc1=O]

To a solution of triphosgene (412 mg, 1.39 mmol) in dichloromethane (20 mL) was added a solution of 6-amino-2-methylpyridazin-3(2H)-one (347 mg, 2.78 mmol) and pyridine (880 mg, 11.1 mmol) in dichloromethane (30 mL) at −60° C. under argon. The mixture was stirred at −60° C. for 0.5 h, then a solution of 4-(3-chloro-4,5-difluorobenzyl)piperidine (680 mg, 2.78 mmol) and pyridine (1.06 g, 13.3 mmol) in dichloromethane (10 mL) was added at −60° C. The resulting mixture was warmed and then stirred at 25° C. for 18 h. The reaction mixture was quenched with water (60 mL) and the aqueous layer was extracted with dichloromethane (50 mL×2). The combined organic layers were dried over sodium sulfate, filtered and concentrated under reduced pressure. The crude residue was purified by column chromatography (silica gel, dichloromethane/ammonia in methanol (7 N)=50/1) to give 4-(3-chloro-4,5-difluorobenzyl)-N-(1-methyl-6-oxo-1,6-dihydropyridazin-3-yl)piperidine-1-carboxamide as a white solid (570 mg, 1.44 mmol, 52%). $^1$H NMR (400 MHz, Dimethylsulfoxide-d$_6$) δ 9.21 (s, 1H), 7.61 (d, J=9.6 Hz, 1H), 7.35-7.29 (m, 2H), 6.87 (d, J=9.6 Hz, 1H), 4.06 (d, J=13.2 Hz, 2H), 3.56 (s, 3H), 2.72 (t, J=12.4 Hz, 2H), 2.53 (d, J=7.6 Hz, 2H), 1.75 (s, 1H), 1.53 (d, J=12.4 Hz, 2H), 1.21-1.04 (m, 2H); LCMS (ESI) m/z: 396.9 [M+H]$^+$.

Example 9. Preparation of 4-(3-cyano-4,5-difluorobenzyl)-N-(1-methyl-6-oxo-1,6-dihydropyridazin-3-yl)piperidine-1-carboxamide (Compound 65)

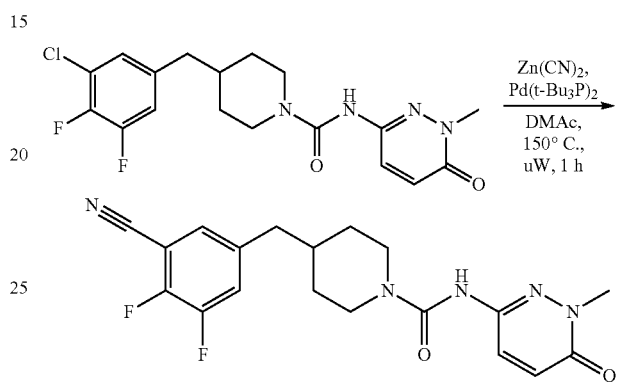

Step 1: Preparation of 4-(3-cyano-4,5-difluorobenzyl)-N-(1-methyl-6-oxo-1,6-dihydropyridazin-3-yl)piperidine-1-carboxamide

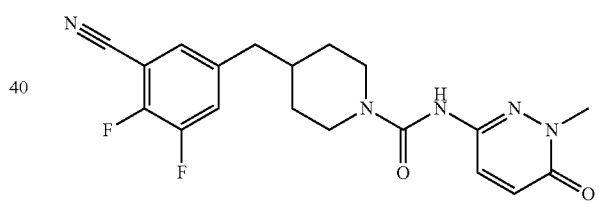

A solution of 4-(3-chloro-4,5-difluorobenzyl)-N-(1-methyl-6-oxo-1,6-dihydropyridazin-3-yl)piperidine-1-carboxamide (160 mg, 0.4 mmol), zinc(II) cyanide (37 mg, 0.32 mmol) and bis(tri-tert-butylphosphine)palladium(0) (20 mg, 0.04 mmol) in N,N-dimethylacetamide (3 mL) was stirred at 150° C. for 1 h under microwave irradiation. The reaction mixture was extracted with ethyl acetate (50 mL×2) and washed with brine (50 mL). The combined organic layers were dried over sodium sulfate, filtered and concentrated under reduced pressure. The crude sample was dissolved in the minimum amount of N,N-dimethylformamide and purified by prep-HPLC (BOSTON pHlex ODS, 10 μm, 21.2 mm×250 mm, acetonitrile/0.1% aqueous formic acid)) to yield 4-(3-cyano-4,5-difluorobenzyl)-N-(1-methyl-6-oxo-1,6-dihydropyridazin-3-yl)piperidine-1-carboxamide (31.0 mg, 0.08 mmol, 20%) as a white solid. $^1$H NMR (400 MHz, Dimethylsulfoxide-d$_6$) δ 9.22 (s, 1H), 7.79-7.74 (m, 1H), 7.62 (t, J=7.6 Hz, 2H), 6.87 (d, J=10.0 Hz, 1H), 4.06 (d, J=13.6 Hz, 2H), 3.56 (s, 3H), 2.72 (t, J=12.0 Hz, 2H), 2.58 (d, J=6.8 Hz, 2H), 1.80-1.75 (m, 1H), 1.53 (d, J=10.8 Hz, 2H), 1.13-1.03 (m, 2H); LCMS (ESI) m/z: 388.1 [M+H]$^+$.

Example 10. 4-(2-chlorobenzyl)-N-(1-methyl-6-oxo-1,6-dihydropyridazin-3-yl)piperidine-1-carboxamide (Compound 42)

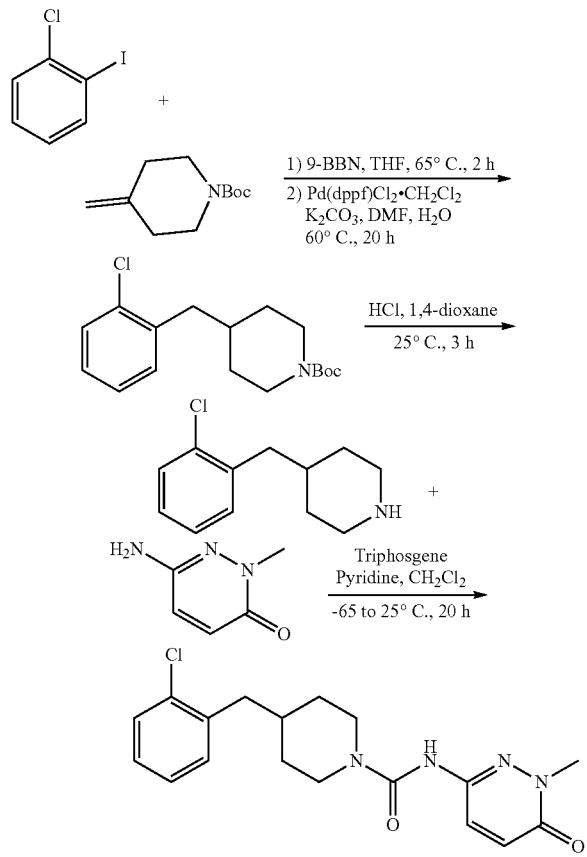

Step 1: Preparation of tert-butyl 4-(2-chlorobenzyl)piperidine-1-carboxylate

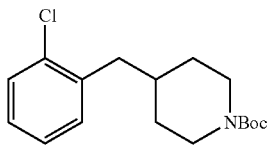 [SMILES: CC(C)(C)OC(=O)N1CCC(Cc2ccccc2Cl)CC1]

To a solution of 9-borabicyclo[3.3.1]nonane in tetrahydrofuran (45.6 mL, 22.8 mmol, 0.5 M) at 25° C. under argon was added tert-butyl 4-methylenepiperidine-1-carboxylate (4.5 g, 22.8 mmol). The mixture was stirred at 65° C. for 2 h. The mixture was cooled to 25° C. and added to a solution of 1-chloro-2-iodobenzene (5.44 g, 22.8 mmol), potassium carbonate (4.0 g, 29.0 mmol) and 1,1'-bis(diphenylphosphino)ferrocene-palladium(II)dichloride dichloromethane complex (930 mg, 1.14 mmol) in N,N-dimethylformamide/water (36 mL/4.5 mL) at 25° C. The resulting mixture was heated at 60° C. for 20 h. The reaction mixture was quenched with 1 N aqueous sodium hydroxide solution and the mixture was stirred at 25° C. for 1 h. The mixture was diluted with ethyl acetate (200 mL) and washed with brine (50 mL×2). The combined organic layers were dried over anhydrous sodium sulfate, filtered and concentrated under reduced pressure. The crude residue was purified by column chromatography (silica gel, petroleum ether/ethyl acetate=20/1 to 10/1) to give tert-butyl 4-(2-chlorobenzyl)piperidine-1-carboxylate (4.8 g, 15.5 mmol, 68%) as a red oil. LCMS (ESI) m/z: 332.1 [M+Na]$^+$.

Step 2: Preparation of 4-(2-chlorobenzyl)piperidine

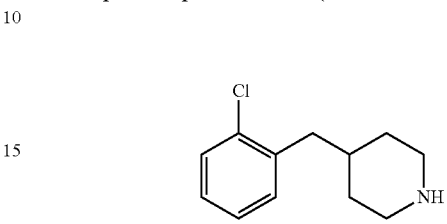

A mixture of tert-butyl 4-(2-chlorobenzyl)piperidine-1-carboxylate (4.7 g, 15.2 mmol) and hydrochloric acid in 1,4-dioxane (4 M, 30 mL) was stirred at 25° C. for 3 h. The reaction mixture was concentrated under reduced pressure. The residue was diluted with saturated sodium bicarbonate aqueous solution (50 mL) at 25° C. and extracted with dichloromethane (60 mL×5). The combined organic layers were dried over anhydrous sodium sulfate, filtered and concentrated under reduced pressure. The crude residue was purified by column chromatography (silica gel, dichloromethane/methanol from 100/0 to 100/20) to give 4-(2-chlorobenzyl)piperidine (2.0 g, 9.54 mmol, 63%) as a yellow oil. $^1$H NMR (400 MHz, Dimethylsulfoxide-d$_6$) δ 7.46-7.34 (m, 1H), 7.33-7.16 (m, 3H), 2.95-2.83 (m, 2H), 2.60 (d, J=7.1 Hz, 2H), 2.45-2.28 (m, 2H), 1.71-1.56 (m, 1H), 1.52-1.40 (m, 2H), 1.18-1.02 (m, 2H); LCMS (ESI) m/z: 210.1 [M+H]$^+$.

Step 3: Preparation of 4-(2-chlorobenzyl)-N-(1-methyl-6-oxo-1,6-dihydropyridazin-3-yl)piperidine-1-carboxamide

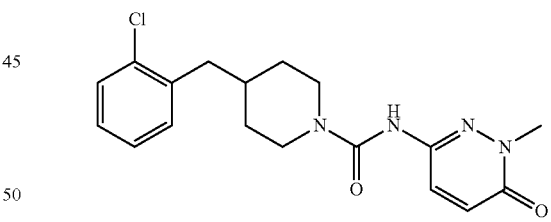

To a solution of triphosgene (148 mg, 0.5 mmol) in dichloromethane (5 mL) was added a solution of 6-amino-2-methylpyridazin-3(2H)-one (125 mg, 1.0 mmol) and pyridine (316 mg, 4.0 mmol) in dichloromethane (5 mL) at −65° C. under argon. The mixture was stirred at −65° C. for 0.5 h, then a solution of 4-(2-chlorobenzyl)piperidine (210 mg, 1.0 mmol) and pyridine (316 mg, 4.0 mmol) in dichloromethane (5 mL) was added at −65° C. The resulting mixture was stirred at 25° C. for 20 h. The reaction was quenched with water (100 mL) and extracted with dichloromethane (60 mL×2). The organics layer was dried over anhydrous sodium sulfate, filtered and concentrated under reduced pressure. The crude sample was dissolved in the minimum amount of N,N-dimethylformamide and purified via prep-HPLC (Boston C18, 10 μm, 21 mm×250 mm column, acetonitrile/0.01% aqueous formic acid) to give 4-(2-chlorobenzyl)-N-(1-methyl-6-oxo-1,6-dihydropyridazin-3-yl)piperidine-1-carboxamide (110.2 mg, 0.31 mmol, 31%) as a yellow solid. $^1$H NMR (400 MHz, Dimethylsulfoxide-d$_6$) δ 9.22 (s, 1H), 7.62 (d, J=9.9 Hz, 1H), 7.42 (dd, J=7.5, 1.6 Hz, 1H), 7.34-7.18 (m, 3H), 6.87 (d, J=9.9 Hz, 1H), 4.07 (d, J=13.1 Hz, 2H), 3.55 (s, 3H), 2.80-2.60 (m, 4H), 1.88-1.71 (m, 1H), 1.63-1.49 (m, 2H), 1.25-1.04 (m, 2H); LCMS (ESI) m/z: 361.1 [M+H]$^+$.

Example 11. Preparation of 4-(2-chloro-3,5-difluorobenzyl)-N-(1-methyl-6-oxo-1,6-dihydropyridazin-3-yl)piperidine-1-carboxamide (Compound 64)

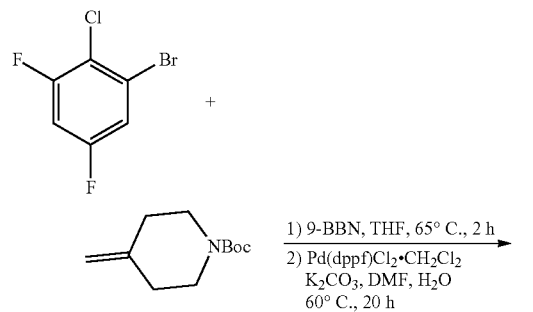

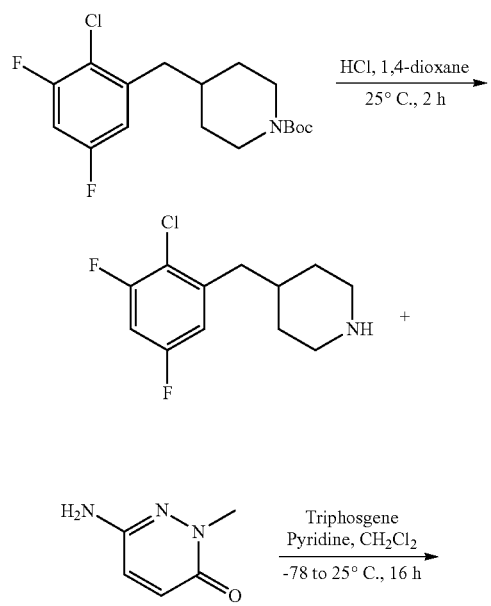

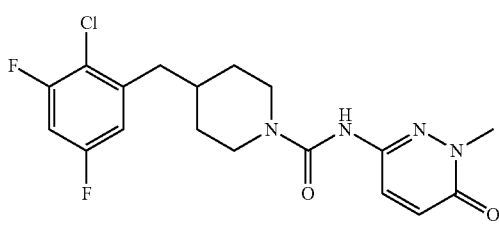 [SMILES: Cn1nc(NC(=O)N2CCC(Cc3cc(F)cc(F)c3Cl)CC2)ccc1=O]

Step 1: Preparation of tert-butyl 4-(2-chloro-3,5-difluorobenzyl)piperidine-1-carboxylate

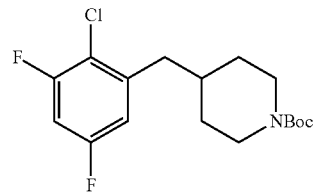

To a solution of 9-borabicyclo[3.3.1]nonane in tetrahydrofuran (36.2 mL, 18.1 mmol, 0.5 M) at 25° C. under argon was added tert-butyl 4-methylenepiperidine-1-carboxylate (3.47 g, 17.6 mmol). The mixture was stirred at 65° C. for 2 h. The mixture was cooled to 25° C. and added to a solution of 1-bromo-2-chloro-3,5-difluorobenzene (4 g, 17.6 mmol), potassium carbonate (3.16 g, 22.9 mmol), [1,1'-bis(diphenylphosphino)ferrocene]dichloropalladium(II) complex with dichloromethane (1.43 g, 1.76 mmol) in N,N-dimethylformamide/water (10 mL/10 mL) at 25° C. The resulting mixture was heated at 60° C. for 20 h. The reaction mixture was quenched with 1 N aqueous sodium hydroxide solution and the mixture was stirred at 25° C. for 0.5 h. The solution was diluted with ethyl acetate (200 mL) and washed with brine (50 mL×2). The combined organic layers were dried over sodium sulfate, filtered and concentrated under reduced pressure. The crude residue was purified by column chromatography (silica gel, petroleum ether/ethyl acetate=10/1) to give tert-butyl 4-(2-chloro-3,5-difluorobenzyl)piperidine-1-carboxylate (1.3 g, 93% purity, 16%) as a yellow solid. LCMS (ESI) m/z: 368.1 [M+Na]$^+$.

Step 2: Preparation of 4-(2-chloro-3,5-difluorobenzyl)piperidine

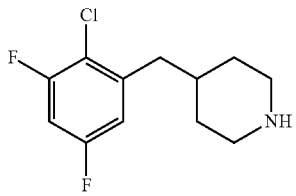

A solution of tert-butyl 4-(2-chloro-3,5-difluorobenzyl)piperidine-1-carboxylate (1.3 g, 3.7 mmol) and hydrochloric acid in 1,4-dioxane (20 mL, 4 M) was stirred at 25° C. for 2 h. The mixture was concentrated under reduced pressure. The residue was diluted with ethyl acetate (50 mL) and the aqueous phase was adjusted to pH 9 with aqueous sodium bicarbonate. The mixture was then extracted with ethyl acetate (30 mL×3). The combined organic layers were dried over sodium sulfate, filtered and concentrated under reduced pressure to give crude 4-(2-chloro-3,5-difluorobenzyl)piperidine (750 mg, 82%) as a yellow oil. This material was used in the next step without further purification. LCMS (ESI) m/z: 246.1 [M+H]$^+$.

Step 3: Preparation of 4-(2-chloro-3,5-difluorobenzyl)-N-(1-methyl-6-oxo-1,6-dihydropyridazin-3-yl)piperidine-1-carboxamide

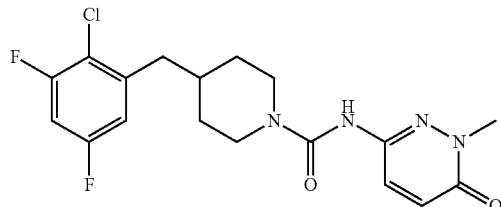

To a solution of triphosgene (30 mg, 0.1 mmol) in dichloromethane (3 mL) at −78° C. was added a mixture of 6-amino-2-methylpyridazin-3(2H)-one (25 mg, 0.2 mmol) and pyridine (63 mg, 0.8 mmol) in dichloromethane (2 mL). The reaction mixture was stirred for 0.5 h at −78° C., then a solution of 4-(2-chloro-3,5-difluorobenzyl)piperidine (38 mg, 0.2 mmol) and pyridine (63 mg, 0.8 mmol) in dichloromethane (2 mL) was added. The mixture was stirred at 25° C. for 4 h. The reaction was quenched with aqueous ammonium chloride and extracted with dichloromethane (20 mL). The combined organic layers were concentrated in vacuo. The crude sample was dissolved in the minimum amount of N,N-dimethylformamide and purified by prep-HPLC (Boston C18, 10 μm, 21 mm×250 mm column, acetonitrile/0.01% aqueous trifluoroacetic acid) to give 4-(2-chloro-3,5-difluorobenzyl)-N-(1-methyl-6-oxo-1,6-dihydropyridazin-3-yl)piperidine-1-carboxamide (36.4 mg, 0.092 mmol, 18%) as a yellow solid. $^1$H NMR (500 MHz, Dimethylsulfoxide-$d_6$) δ 9.21 (s, 1H), 7.61 (d, J=9.6 Hz, 1H), 7.40-7.35 (m, 1H), 7.17 (d, J=8.8 Hz, 1H), 6.86 (d, J=10 Hz, 1H), 4.07 (d, J=6.6 Hz, 1H), 3.55 (s, 3H), 2.75-2.70 (m, 4H), 1.84-1.82 (m, 1H), 1.56-1.53 (m, 2H), 1.23-1.14 (m, 2H); LCMS (ESI) m/z: 397.0 [M+H]$^+$.

Example 12. Preparation of 4-(2-chloro-4,5-difluorobenzyl)-N-(1-methyl-6-oxo-1,6-dihydropyridazin-3-yl)piperidine-1-carboxamide (Compound 61)

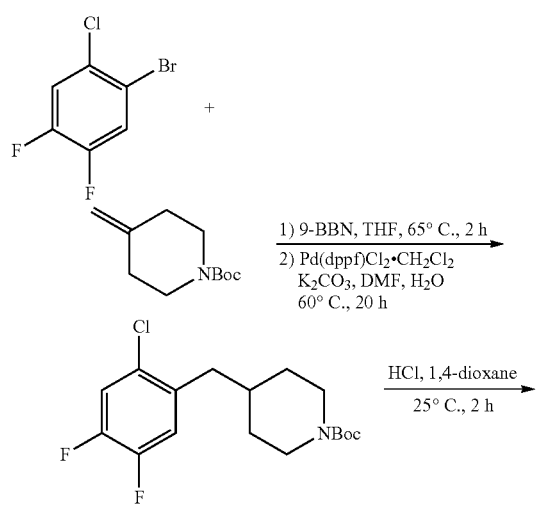

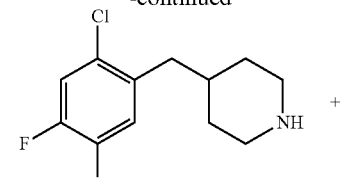

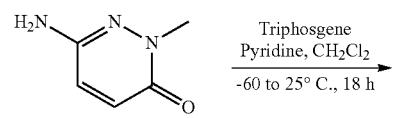

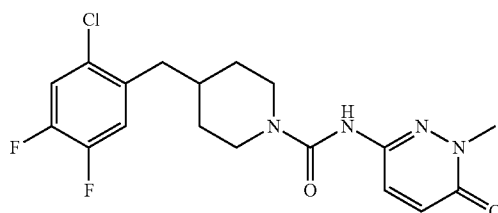

Step 1: Preparation of tert-butyl 4-(2-chloro-4,5-difluorobenzyl)piperidine-1-carboxylate

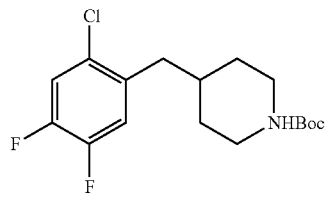

To a solution of 9-borabicyclo[3.3.1]nonane in tetrahydrofuran (22 mL, 11 mmol, 0.5 M) at 25° C. under argon was added tert-butyl 4-methylenepiperidine-1-carboxylate (2.17 g, 11 mmol). The mixture was stirred at 65° C. for 2 h. The mixture was cooled down to 25° C. and added to a solution of 1-bromo-2-chloro-4,5-difluorobenzene (2.5 g, 11 mmol), potassium carbonate (1.97 g, 14.3 mmol) and 1,1′-bis(diphenylphosphino)ferrocene-palladium(II)dichloride dichloromethane complex (449 mg, 0.55 mmol) in N,N-dimethylformamide/water (17.6 mL/1.76 mL) at 25° C. The resulting mixture was heated at 60° C. for 20 h. The reaction was quenched with 1 N aqueous sodium hydroxide solution and the aqueous layer was stirred at 25° C. for 1 h. The solution was diluted with ethyl acetate (200 mL) and washed with brine (150 mL×3). The combined organic layers were dried over sodium sulfate, filtered and concentrated under reduced pressure. The crude residue was purified by column chromatography (silica gel, petroleum ether/ethyl acetate=33/1) to give tert-butyl 4-(2-chloro-4,5-difluorobenzyl)piperidine-1-carboxylate (430 mg, 1.25 mmol, 11%) as a colorless oil. LCMS (ESI) m/z: 290.0 [M-56+H]$^+$.

Step 2: Preparation of 4-(2-chloro-4,5-difluorobenzyl)piperidine

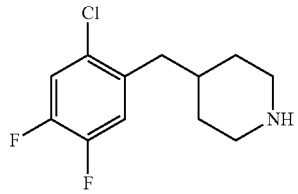 [SMILES: Fc1cc(Cl)c(CC2CCNCC2)cc1F]

A solution of tert-butyl 4-(2-chloro-4,5-difluorobenzyl) piperidine-1-carboxylate (430 mg, 1.25 mmol) and 4 N hydrochloric acid in 1,4-dioxane solution (10 mL) was stirred at 25° C. for 2 h. The reaction mixture was concentrated under reduced pressure. The crude residue was adjusted to pH 9 with sodium bicarbonate solution and extracted with dichloromethane (50 mL×2). The combined organic layers were dried over sodium sulfate, filtered and concentrated under reduced pressure. The crude 4-(2-chloro-4,5-difluorobenzyl)piperidine (0.3 g, 1.22 mmol, 98%) was used in the next step without further purification. LCMS (ESI) m/z: 246.1 [M+H]$^+$.

Step 3: Preparation of 4-(2-chloro-4,5-difluorobenzyl)-N-(1-methyl-6-oxo-1,6-dihydropyridazin-3-yl)piperidine-1-carboxamide

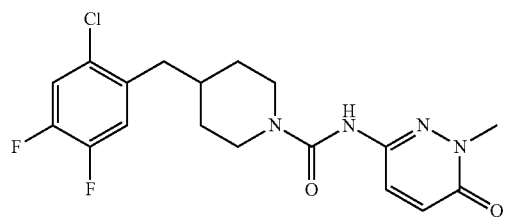 [SMILES: Cn1nc(NC(=O)N2CCC(Cc3cc(F)c(F)cc3Cl)CC2)ccc1=O]

To a solution of triphosgene (61 mg, 0.205 mmol) in dichloromethane (5 mL) at −60° C. was added a solution of 6-amino-2-methylpyridazin-3(2H)-one (51 mg, 0.41 mmol) and pyridine (130 mg, 1.64 mmol) in dichloromethane (6 mL) under argon. The mixture was stirred at −60° C. for 30 min, then a solution of 4-(2-chloro-4,5-difluorobenzyl)piperidine (100 mg, 0.41 mmol) and pyridine (156 mg, 1.97 mmol) in dichloromethane (4 mL) was added at −60° C. The resulting mixture was stirred at 25° C. for 18 h. The reaction was quenched with water (20 mL) and the aqueous layer was extracted with dichloromethane (30 mL×2). The combined organic layers were dried over sodium sulfate, filtered and concentrated under reduced pressure. The crude sample was dissolved in the minimum amount of N,N-dimethylformamide and purified by prep-HPLC (BOSTON pHlex ODS, 10 µm, 21.2 mm×250 mm, acetonitrile/0.1% aqueous formic acid) to yield 4-(2-chloro-4,5-difluorobenzyl)-N-(1-methyl-6-oxo-1,6-dihydropyridazin-3-yl)piperidine-1-carboxamide as a white solid (12 mg, 0.03 mmol, 7%). $^1$H NMR (400 MHz, Dimethylsulfoxide-d$_6$) δ 9.23 (s, 1H), 7.72-7.67 (m, 1H), 7.62 (d, J=9.6 Hz, 1H), 7.54-7.49 (m, 1H), 6.87 (d, J=10.0 Hz, 1H), 4.07 (d, J=13.2 Hz, 2H), 3.56 (s, 3H), 2.72 (t, J=11.8 Hz, 2H), 2.63 (d, J=7.2 Hz, 2H), 1.85-1.73 (m, 1H), 1.54 (d, J=11.2 Hz, 2H), 1.18-1.14 (m, 2H); LCMS (ESI) m/z: 397.0 [M+H]$^+$.

Example 13. Preparation of N-(1-methyl-6-oxo-1,6-dihydropyridazin-3-yl)-4-(3,4,5-trifluorobenzyl)piperidine-1-carboxamide (Compound 62)

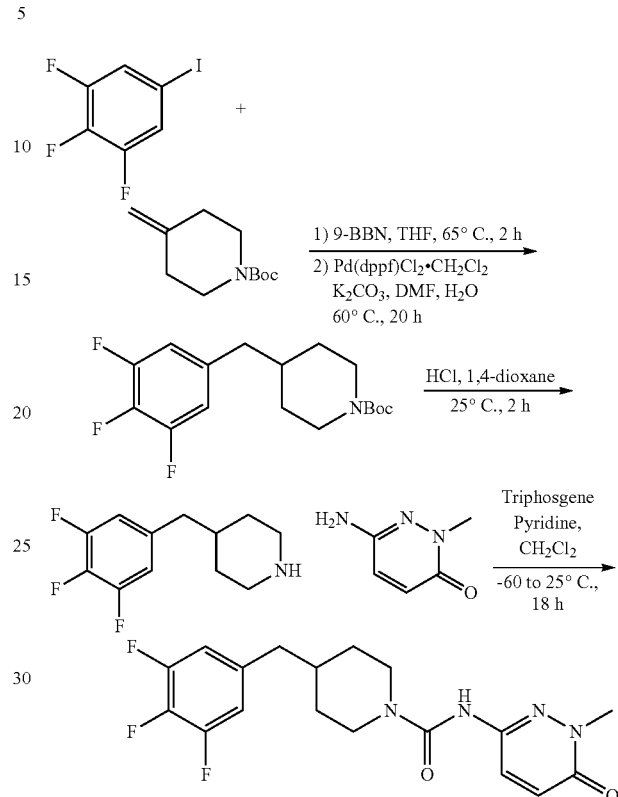

Step 1: Preparation of tert-butyl 4-(3,4,5-trifluorobenzyl)piperidine-1-carboxylate

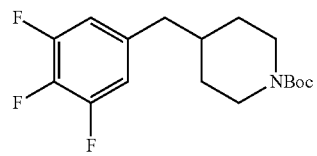

To a solution of 9-borabicyclo[3.3.1]nonane in tetrahydrofuran (18.7 mL, 9.34 mmol, 0.5 M) at 25° C. was added tert-butyl 4-methylenepiperidine-1-carboxylate (1.84 g, 9.34 mmol) under argon. The mixture was stirred at 65° C. for 2 h. The mixture was cooled to 25° C. and added to a solution of 1,2,3-trifluoro-5-iodobenzene (2.4 g, 9.34 mmol), potassium carbonate (1.66 g, 12 mmol) and 1,1'-bis(diphenylphosphino)ferrocene-palladium(II)dichloride dichloromethane complex (381 mg, 0.467 mmol) in N,N-dimethylformamide/water (15 mL/1.5 mL) at 25° C. The resulting mixture was heated at 60° C. for 20 h. The The reaction was quenched with 1 N aqueous sodium hydroxide solution and the mixture was stirred at 25° C. for 1 h. The solution was diluted with ethyl acetate (300 mL) and washed with brine (200 mL×3). The combined organic layers were dried over sodium sulfate, filtered and concentrated under reduced pressure. The crude residue was purified by column chromatography (silica gel, petroleum ether/ethyl acetate=20/1) to give tert-butyl 4-(3,4,5-trifluorobenzyl)piperidine-1-carboxylate (1.05 g, 3.2 mmol, 34%) as a brown oil. LCMS (ESI) m/z: 274.2 [M-56+H]$^+$.

Step 2: Preparation of 4-(3,4,5-trifluorobenzyl)piperidine

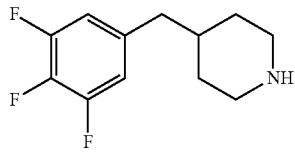

A solution of tert-butyl 4-(3,4,5-trifluorobenzyl)piperidine-1-carboxylate (1.05 g, 3.2 mmol) and 4 N hydrochloric acid in 1,4-dioxane (20 mL) was stirred at 25° C. for 1 h. The mixture was concentrated under reduced pressure. The crude residue was adjusted to pH 9 with sodium bicarbonate solution and extracted with dichloromethane (100 mL×2). The combined organic layers were dried over sodium sulfate, filtered and concentrated under reduced pressure. The crude product 4-(3,4,5-trifluorobenzyl)piperidine was used in the next step without further purification (0.67 g, 2.93 mmol, 91%). LCMS (ESI) m/z: 230.1 [M+H]$^+$.

Step 3: Preparation of N-(1-methyl-6-oxo-1,6-dihydropyridazin-3-yl)-4-(3,4,5-trifluorobenzyl)piperidine-1-carboxamide

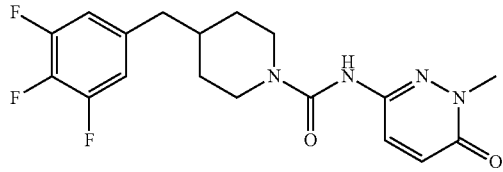 [SMILES: Cn1nc(NC(=O)N2CCC(Cc3cc(F)c(F)c(F)c3)CC2)ccc1=O]

To a solution of triphosgene (148 mg, 0.5 mmol) in dichloromethane (8 mL) at −60° C. was added a solution of 6-amino-2-methylpyridazin-3(2H)-one (125 mg, 1 mmol) and pyridine (316 mg, 4 mmol) in dichloromethane (10 mL) at −60° C. under argon. The mixture was stirred at −60° C. for 0.5 h, then a solution of 4-(3,4,5-trifluorobenzyl)piperidine (229 mg, 1 mmol) and pyridine (379 mg, 4.8 mmol) in dichloromethane (7 mL) was added at −60° C. The resulting mixture was stirred at 25° C. for 18 h. The reaction was quenched with water (50 mL) and the aqueous layer was extracted with dichloromethane (50 mL×2). The combined organic layers were dried over sodium sulfate, filtered and concentrated under reduced pressure. The crude sample was dissolved in the minimum amount of N,N-dimethylformamide and purified by prep-HPLC (BOSTON pHlex ODS, 10 μm, 21.2 mm×250 mm, acetonitrile/0.1% aqueous formic acid) to yield N-(1-methyl-6-oxo-1,6-dihydropyridazin-3-yl)-4-(3,4,5-trifluorobenzyl)piperidine-1-carboxamide as a yellow solid (138 mg, 0.36 mmol, 36%). $^1$H NMR (400 MHz, Dimethylsulfoxide-d$_6$) δ 9.21 (s, 1H), 7.61 (d, J=9.6 Hz, 1H), 7.18 (t, J=7.8 Hz, 2H), 6.87 (d, J=9.6 Hz, 1H), 4.06 (d, J=13.2 Hz, 2H), 3.56 (s, 3H), 2.72 (t, J=12.2 Hz, 2H), 2.53 (d, J=7.6 Hz, 2H), 1.75 (s, 1H), 1.53 (d, J=12.4 Hz, 2H), 1.12-1.04 (m, 2H); LCMS (ESI) m/z: 381.1 [M+H]$^+$.

Example 14. Preparation of 4-(4-chloro-3-fluorobenzyl)-N-(1-methyl-6-oxo-1,6-dihydropyridazin-3-yl)piperidine-1-carboxamide (Compound 52)

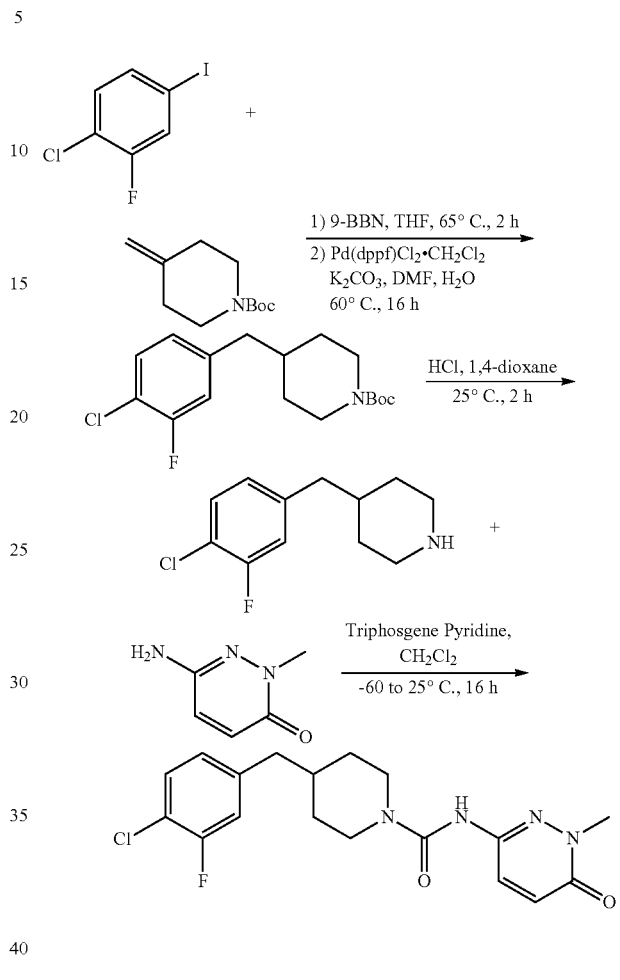

Step 1: Preparation of tert-butyl 4-(4-chloro-3-fluorobenzyl)piperidine-1-carboxylate

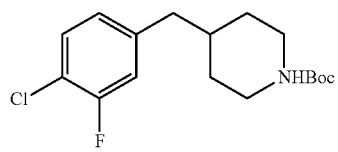

To a solution of 9-borabicyclo[3.3.1]nonane in tetrahydrofuran (40 mL, 20 mmol, 0.5 M) at 25° C. was added tert-butyl 4-methylenepiperidine-1-carboxylate (3.94 g, 20 mmol) under argon. The mixture was stirred at 65° C. for 2 h. The reaction was cooled to 25° C. and added to a solution of 1-chloro-2-fluoro-4-iodobenzene (5.12 g, 20 mmol), potassium carbonate (3.59 g, 26 mmol) and 1,1'-bis(diphenylphosphino)ferrocene-palladium(II)dichloride dichloromethane complex (816 mg, 1 mmol) in N,N-dimethylformamide/water (32 mL/3.2 mL) at 25° C. The resulting mixture was heated at 60° C. for 20 h. The reaction was quenched with 1 N aqueous sodium hydroxide solution and the mixture was stirred at 25° C. for 1 h. The solution was diluted with ethyl acetate (300 mL) and washed with brine (200 mL×3). The combined organic layers were dried over sodium sulfate, filtered and concentrated under reduced pressure. The crude residue was purified by column chromatography (silica gel, petroleum ether/ethyl acetate=30/1) to give tert-butyl 4-(4-chloro-3-fluorobenzyl)piperidine-1-carboxylate (2.5 g, 7.6 mmol, 38%) as a brown oil. LCMS (ESI) m/z: 272.1 [M-56+H]+.

Step 2: Preparation of 4-(4-chloro-3-fluorobenzyl)piperidine

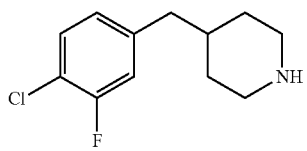 [SMILES: Fc1cc(CC2CCNCC2)ccc1Cl]

A solution of tert-butyl 4-(4-chloro-3-fluorobenzyl)piperidine-1-carboxylate (2.5 g, 7.6 mmol) and 4 N hydrochloric acid in 1,4-dioxane (40 mL) was stirred at 25° C. for 1 h. The mixture was concentrated under reduced pressure. The crude residue was adjusted to pH 9 with sodium bicarbonate solution and extracted with dichloromethane (100 mL×2). The combined organic layers were dried over sodium sulfate, filtered and concentrated under reduced pressure. The crude product 4-(4-chloro-3-fluorobenzyl)piperidine was used in the next step without further purification (1.48 g, 6.52 mmol, 85.8%). LCMS (ESI) m/z: 228.1 [M+H]+.

Step 3: Preparation of 4-(4-chloro-3-fluorobenzyl)-N-(1-methyl-6-oxo-1,6-dihydropyridazin-3-yl)piperidine-1-carboxamide

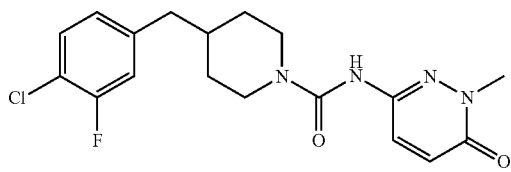 [SMILES: Cn1nc(NC(=O)N2CCC(Cc3ccc(Cl)c(F)c3)CC2)ccc1=O]

To a solution of triphosgene (148 mg, 0.5 mmol) in dichloromethane (6 mL) at −60° C. was added a solution of 6-amino-2-methylpyridazin-3(2H)-one (125 mg, 1 mmol) and pyridine (316 mg, 4 mmol) in dichloromethane (12 mL) under argon. The mixture was stirred at −60° C. for 0.5 h then a solution of 4-(4-chloro-3-fluorobenzyl)piperidine (227 mg, 1 mmol) and pyridine (380 mg, 4.8 mmol) in dichloromethane (7 mL) was added at −60° C. The resulting mixture was stirred at 25° C. for 18 h. The reaction was quenched with water (30 mL) and the aqueous layer was extracted with dichloromethane (50 mL×2). The combined organic layers were dried over sodium sulfate, filtered and concentrated under reduced pressure. The crude sample was dissolved in the minimum amount of N,N-dimethylformamide and purified by prep-HPLC (BOSTON pHlex ODS, 10 μm, 21.2 mm×250 mm, acetonitrile/0.1% aqueous formic acid) to yield 4-(4-chloro-3-fluorobenzyl)-N-(1-methyl-6-oxo-1,6-dihydropyridazin-3-yl)piperidine-1-carboxamide (132.5 mg, 0.35 mmol, 35%) as a yellow solid. 1H NMR (400 MHz, Dimethylsulfoxide-d6) δ 9.21 (s, 1H), 7.61 (d, J=9.6 Hz, 1H), 7.49 (t, J=8.0 Hz, 1H), 7.28 (dd, J=1.2, 10.4 Hz, 1H), 7.06 (dd, J=1.2, 8.0 Hz, 1H), 6.87 (d, J=10.0, 1H), 4.06 (d, J=13.2 Hz, 2H), 3.53 (s, 3H), 2.72 (t, J=12.0 Hz, 2H), 2.55 (d, J=7.6 Hz, 2H), 1.77-1.71 (m, 1H), 1.54 (d, J=11.2 Hz, 2H), 1.13-1.03 (m, 2H); LCMS (ESI) m/z: 379.0 [M+H]+.

Example 15. Preparation of 4-(4-fluorobenzyl)-N-(1-methyl-6-oxo-1,6-dihydropyridazin-3-yl)piperidine-1-carboxamide (Compound 44)

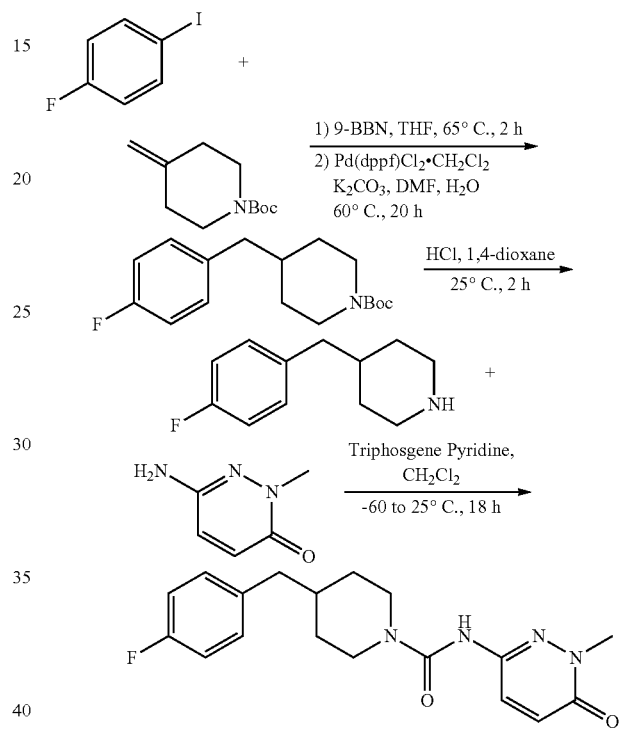

Step 1: Preparation of tert-butyl 4-(4-fluorobenzyl)piperidine-1-carboxylate

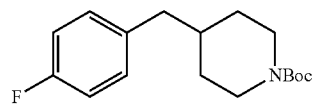

To a solution of 9-borabicyclo[3.3.1]nonane in tetrahydrofuran (40 mL, 20 mmol, 0.5 M) at 25° C. was added tert-butyl 4-methylenepiperidine-1-carboxylate (3.94 g, 20 mmol) under argon. The mixture was stirred at 65° C. for 2 h. The solution was cooled down to 25° C. and added to a mixture of 1-fluoro-4-iodobenzene (4.44 g, 20 mmol), potassium carbonate (3.59 g, 26 mmol) and 1,1'-bis(diphenylphosphino)ferrocene-palladium(II)dichloride dichloromethane complex (816 mg, 1 mmol) in N,N-dimethylformamide/water (32 mL/3.2 mL) at 25° C. The resulting mixture was heated at 60° C. for 20 h. The reaction was quenched with 1 N aqueous sodium hydroxide solution and the aqueous layer was stirred at 25° C. for 1 h. The mixture was diluted with ethyl acetate (300 mL) and washed with brine (200 mL×3). The combined organic layers were dried over sodium sulfate, filtered and concentrated under reduced pressure. The crude residue was purified by column chromatography (silica gel, petroleum ether/ethyl acetate=30/1) to give tert-butyl 4-(4-fluorobenzyl)piperidine-1-carboxylate as a colorless oil (2.2 g, 7.5 mmol, 38%). LCMS (ESI) m/z: 238.1 [M-56+H]$^+$.

Step 2: Preparation of 4-(4-fluorobenzyl)piperidine

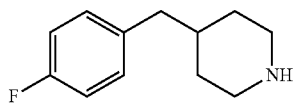

A solution of tert-butyl 4-(4-fluorobenzyl)piperidine-1-carboxylate (2.2 g, 7.5 mmol) and 4 N hydrochloric acid in 1,4-dioxane (40 mL) was stirred at 25° C. for 1 h. The mixture was concentrated under reduced pressure. The crude residue was adjusted to pH 9 with sodium bicarbonate solution and extracted with dichloromethane (100 mL×2). The combined organic layers were dried over sodium sulfate, filtered and concentrated under reduced pressure. The crude 4-(4-fluorobenzyl)piperidine was used in the next step without further purification (1.2 g, 6.2 mmol, 83%). LCMS (ESI) m/z: 194.1 [M+H]$^+$.

Step 3: Preparation of 4-(4-fluorobenzyl)-N-(1-methyl-6-oxo-1,6-dihydropyridazin-3-yl)piperidine-1-carboxamide

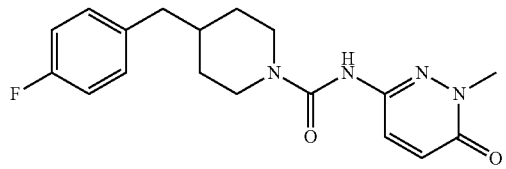 [SMILES: Cn1nc(NC(=O)N2CCC(Cc3ccc(F)cc3)CC2)ccc1=O]

To a solution of triphosgene (148 mg, 0.5 mmol) in dichloromethane (6 mL) at −60° C. was added a solution of 6-amino-2-methylpyridazin-3(2H)-one (125 mg, 1 mmol) and pyridine (316 mg, 4 mmol) in dichloromethane (12 mL) under argon. The mixture was stirred at −60° C. for 0.5 h, then a solution of 4-(4-fluorobenzyl)piperidine (193 mg, 1 mmol) and pyridine (380 mg, 4.8 mmol) in dichloromethane (7 mL) was added at −60° C. The resulting mixture was stirred at 25° C. for 18 h. The reaction was quenched with water (30 mL) and the aqueous layer was extracted with dichloromethane (50 mL×2). The combined organic layers were dried over sodium sulfate, filtered and concentrated under reduced pressure. The crude sample was dissolved in the minimum amount of N,N-dimethylformamide and purified by prep-HPLC (BOSTON pHlex ODS, 10 μm, 21.2 mm×250 mm, acetonitrile/0.1% aqueous formic acid) to yield 4-(4-fluorobenzyl)-N-(1-methyl-6-oxo-1,6-dihydropyridazin-3-yl)piperidine-1-carboxamide (95 mg, 0.28 mmol, 28%) as a yellow solid. $^1$H NMR (400 MHz, Dimethylsulfoxide-d$_6$) δ 9.21 (s, 1H), 7.61 (d, J=9.6 Hz, 1H), 7.23-7.19 (m, 2H), 7.14-6.88 (m, 2H), 6.87 (d, J=10.0 Hz, 1H), 4.06 (d, J=13.2 Hz, 2H), 3.55 (s, 3H), 2.71 (t, J=12.0 Hz, 2H), 2.52 (d, J=4.8 Hz, 2H), 1.71-1.69 (m, 1H), 1.54 (d, J=12.0 Hz, 2H), 1.13-1.06 (m, 2H); LCMS (ESI) m/z: 345.1 [M+H]$^+$.

Example 16. Preparation of 4-(2-chloro-3-cyanobenzyl)-N-(1-methyl-6-oxo-1,6-dihydropyridazin-3-yl)piperidine-1-carboxamide (Compound 56)

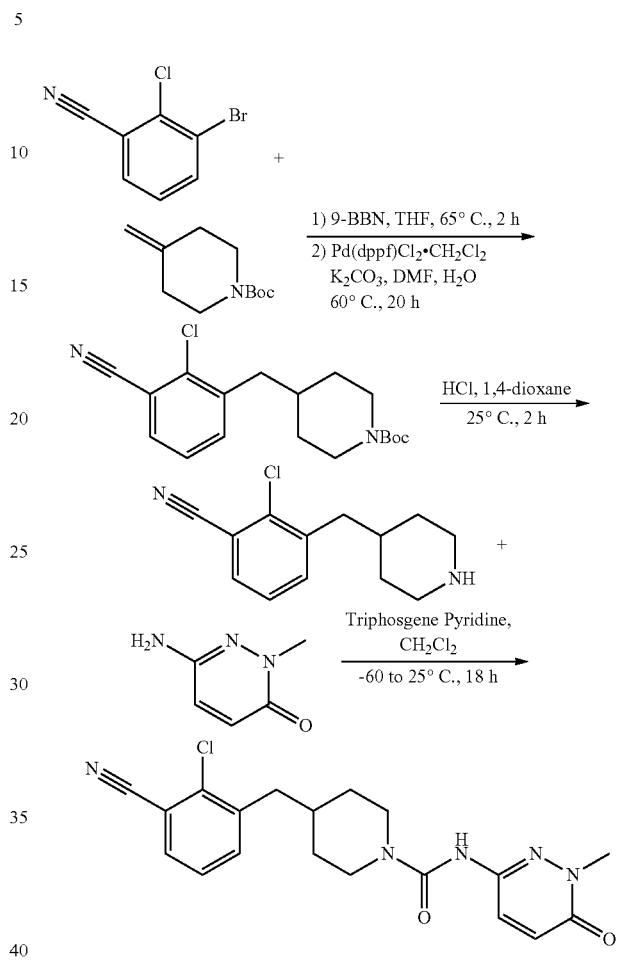

Step 1: Preparation of tert-butyl 4-(2-chloro-3-cyanobenzyl)piperidine-1-carboxylate

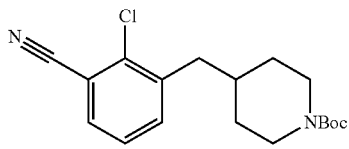 [SMILES: CC(C)(C)OC(=O)N1CCC(Cc2cccc(C#N)c2Cl)CC1]

A solution of tert-butyl 4-methylenepiperidine-1-carboxylate (1.0 g, 5.1 mmol) and 9-borabicyclo[3.3.1]nonane in tetrahydrofuran (12 mL, 6.0 mmol, 0.5 M) was stirred at 65° C. for 2 h. The mixture was cooled to 25° C. and added to a solution of 3-bromo-2-chlorobenzonitrile (1.0 g, 4.6 mmol), potassium carbonate (0.83 g, 6.0 mmol) and 1,1'-bis(diphenylphosphino)ferrocene-palladium(II)dichloride dichloromethane complex (188 mg, 0.23 mmol) in N,N-dimethylformamide/water (10 mL/1.5 mL) at 25° C. The resulting mixture was heated at 60° C. for 20 h. The reaction mixture was quenched with 1 N sodium hydroxide solution and stirred at 25° C. for 1 h. The mixture was diluted with ethyl acetate (200 mL) and washed with brine (50 mL×3).

The combined organic layers were dried over sodium sulfate, filtered and concentrated under reduced pressure. The crude residue was purified by column chromatography (silica gel, petroleum ether/ethyl acetate=15/1 to 10/1) to give tert-butyl 4-(2-chloro-3-cyanobenzyl)piperidine-1-carboxylate as a colorless oil (0.55 g, 1.65 mmol, 36%). LCMS (ESI) m/z: 279.1 [M-56+H]$^+$.

Step 2: Preparation of 2-chloro-3-(piperidin-4-ylmethyl)benzonitrile

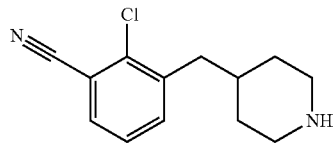 [SMILES: N#Cc1cccc(CC2CCNCC2)c1Cl]

To a solution of tert-butyl 4-(2-chloro-3-cyanobenzyl) piperidine-1-carboxylate (0.55 g, 1.65 mmol) in dichloromethane (10 mL) was added trifluoroacetic acid (3.0 mL). The mixture was stirred at 25° C. for 4 h under nitrogen. The reaction mixture was adjusted to pH 9 with aqueous sodium bicarbonate solution and extracted with dichloromethane (100 mL×3). The combined organic layers were dried over sodium sulfate, filtered and concentrated under reduced pressure. The crude yellow solid was used in the next step without further purification (360 mg, 1.54 mmol, 93%). LCMS (ESI) m/z: 235.2 [M+H]$^+$.

Step 3: Preparation of 4-(2-chloro-3-cyanobenzyl)-N-(1-methyl-6-oxo-1,6-dihydropyridazin-3-yl)piperidine-1-carboxamide formate salt

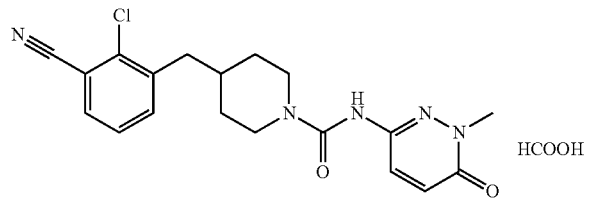 [SMILES: Cn1nc(NC(=O)N2CCC(Cc3cccc(C#N)c3Cl)CC2)ccc1=O ; "HCOOH"]

To a solution of triphosgene (119 mg, 0.4 mmol) in dichloromethane (10 mL) was added a solution of 6-amino-2-methylpyridazin-3(2H)-one (100 mg, 0.8 mmol) and pyridine (253 mg, 3.2 mmol) in dichloromethane (5 mL) at −60° C. under argon. The mixture was stirred at −60° C. for 0.5 h, then a solution of 2-chloro-3-(piperidin-4-ylmethyl)benzonitrile (225 mg, 0.96 mmol) and pyridine (253 mg, 3.2 mmol) in dichloromethane (5 mL) was added at −60° C. The resulting mixture was stirred at 25° C. for 18 h. The reaction was quenched with water (30 mL) and the aqueous layer was extracted with dichloromethane (50 mL×2). The combined organic layers were dried over sodium sulfate, filtered and concentrated under reduced pressure. The crude sample was dissolved in the minimum amount of N,N-dimethylformamide and purified via prep-HPLC (Boston C18, 10 μm, 21 mm×250 mm column, acetonitrile/0.01% aqueous formic acid) to give 4-(3-chloro-5-cyanobenzyl)-N-(1-methyl-6-oxo-1,6-dihydropyridazin-3-yl)piperidine-1-carboxamide formate salt (3.5 mg, 0.01 mmol, 1%) as a white solid. $^1$H NMR (400 MHz, Dimethylsulfoxide-d$_6$)$^1$H NMR (400 MHz, Dimethylsulfoxide-d$_6$) δ 9.21 (s, 1H), 8.46 (s, 1H, HCOOH), 7.85 (d, J=7.7 Hz, 1H), 7.69 (d, J=7.8 Hz, 1H), 7.61 (d, J=9.9 Hz, 1H), 7.50-7.46 (m, 1H), 6.87 (d, J=9.9 Hz, 1H), 4.06 (d, J=13.5 Hz, 2H), 3.55 (s, 3H), 2.72-2.68 (m, 4H), 1.82-1.80 (m, 1H), 1.53-1.50 (m, 2H), 1.29-1.10 (m, 2H); LCMS (ESI) m/z: 386.1 [M+H]$^+$.

Example 17. Preparation of 4-(3-chloro-5-cyanobenzyl)-N-(1-methyl-6-oxo-1,6-dihydropyridazin-3-yl)piperidine-1-carboxamide (Compound 57)

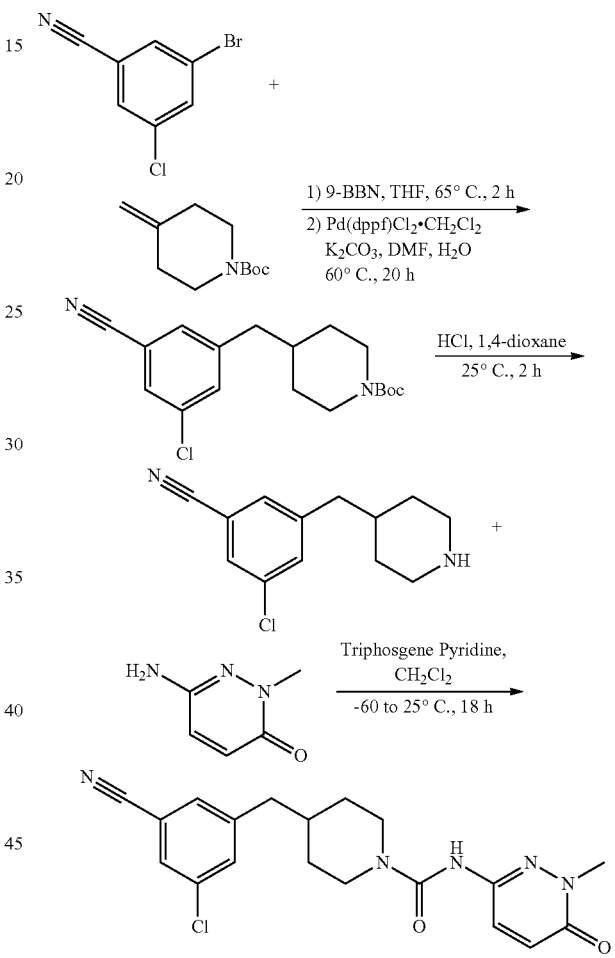

Step 1: Preparation of tert-butyl 4-(3-chloro-5-cyanobenzyl)piperidine-1-carboxylate

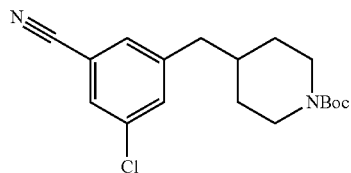 [SMILES: CC(C)(C)OC(=O)N1CCC(Cc2cc(Cl)cc(C#N)c2)CC1]

A solution of tert-butyl 4-methylenepiperidine-1-carboxylate (1.0 g, 5.1 mmol) and 9-borabicyclo[3.3.1]nonane in tetrahydrofuran (12 mL, 6.0 mmol, 0.5 M) was stirred at 65° C. for 2 h. The mixture was cooled to 25° C. and added to a solution of 3-bromo-5-chlorobenzonitrile (1.0 g, 4.6 mmol), potassium carbonate (0.83 g, 6.0 mmol) and 1,1'-bis(diphenylphosphino)ferrocene-palladium(II)dichloride dichloromethane complex (188 mg, 0.23 mmol) in N,N-dimethylformamide/water (10 mL/1.5 mL) at 25° C. The resulting mixture was heated at 60° C. for 20 h. The reaction mixture was quenched with 1 N aqueous sodium hydroxide solution and stirred at 25° C. for 1 h. The mixture was diluted with ethyl acetate (200 mL) and washed with brine (50 mL×3). The combined organic layers were dried over sodium sulfate, filtered and concentrated under reduced pressure. The crude residue was purified by column chromatography (silica gel, petroleum ether/ethyl acetate=15/1 to 10/1) to give tert-butyl 4-(3-chloro-5-cyanobenzyl)piperidine-1-carboxylate as a colorless oil (0.85 g, 2.5 mmol, 54%). LCMS (ESI) m/z: 279.1 [M-56+H]$^+$.

Step 2: Preparation of 3-chloro-5-(piperidin-4-ylmethyl)benzonitrile

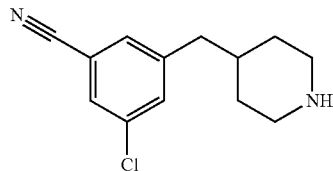 [SMILES: N#Cc1cc(Cl)cc(CC2CCNCC2)c1]

To a solution of tert-butyl 4-(3-chloro-5-cyanobenzyl)piperidine-1-carboxylate (0.85 g, 2.5 mmol) in dichloromethane (10 mL) was added trifluoroacetic acid (3.0 mL). The mixture was stirred at 25° C. for 4 h under nitrogen. The reaction solution was basified to pH 9 with sodium bicarbonate solution and the aqueous layer was extracted with dichloromethane (100 mL×3). The combined organic layers were dried over sodium sulfate, filtered and concentrated under reduced pressure. The crude yellow solid was used in the next step without further purification (0.51 g, 3.8 mmol, 76%). LCMS (ESI) m/z: 235.2 [M+H]$^+$.

Step 3: Preparation of 4-(3-chloro-5-cyanobenzyl)-N-(1-methyl-6-oxo-1,6-dihydropyridazin-3-yl)piperidine-1-carboxamide formate salt

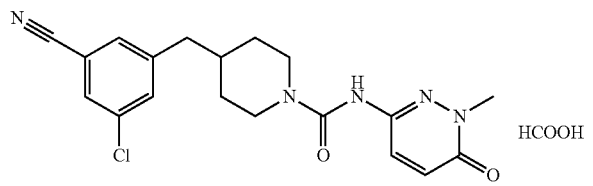 [SMILES: Cn1nc(NC(=O)N2CCC(Cc3cc(Cl)cc(C#N)c3)CC2)ccc1=O ; "HCOOH"]

To a solution of triphosgene (119 mg, 0.4 mmol) in dichloromethane (10 mL) at −60° C. was added a solution of 6-amino-2-methylpyridazin-3(2H)-one (100 mg, 0.8 mmol) and pyridine (253 mg, 3.2 mmol) in dichloromethane (5 mL) under argon. The mixture was stirred at −60° C. for 0.5 h, then a solution of 3-chloro-5-(piperidin-4-ylmethyl)benzonitrile (225 mg, 0.96 mmol) and pyridine (253 mg, 3.2 mmol) in dichloromethane (5 mL) was added. The resulting mixture was stirred at 25° C. for 18 h. The reaction was quenched with water (30 mL) and the aqueous layer was extracted with dichloromethane (50 mL×2). The combined organic layers were dried over sodium sulfate, filtered and concentrated under reduced pressure. The crude sample was dissolved in the minimum amount of N,N-dimethylformamide and purified via prep-HPLC (Boston C18, 10 μm, 21 mm×250 mm column, acetonitrile/0.01% aqueous formic acid) to give 4-(3-chloro-5-cyanobenzyl)-N-(1-methyl-6-oxo-1,6-dihydropyridazin-3-yl)piperidine-1-carboxamide formate salt (13.9 mg, 0.04 mmol, 4%) as a white solid. $^1$H NMR (400 MHz, Dimethylsulfoxide-d$_6$) δ 9.20 (s, 1H), 8.46 (s, 1H, HCOOH), 7.87 (s, 1H), 7.68 (d, J=5.7 Hz, 2H), 7.61 (d, J=9.9 Hz, 1H), 6.86 (d, J=9.9 Hz, 1H), 4.05 (d, J=13.3 Hz, 2H), 3.51 (d, J=36.3 Hz, 3H), 2.71-2.68 (m, 2H), 2.60-2.58 (m, 2H), 1.79-1.77 (m, 1H), 1.52-1.50 (m, 2H), 1.09-1.05 (m, 2H); LCMS (ESI) m/z: 386.1 [M+H]$^+$.

Example 18. Preparation of 4-(3,5-difluorobenzyl)-N-(1-ethyl-6-oxo-1,6-dihydropyridazin-3-yl)piperidine-1-carboxamide (Compound 125)

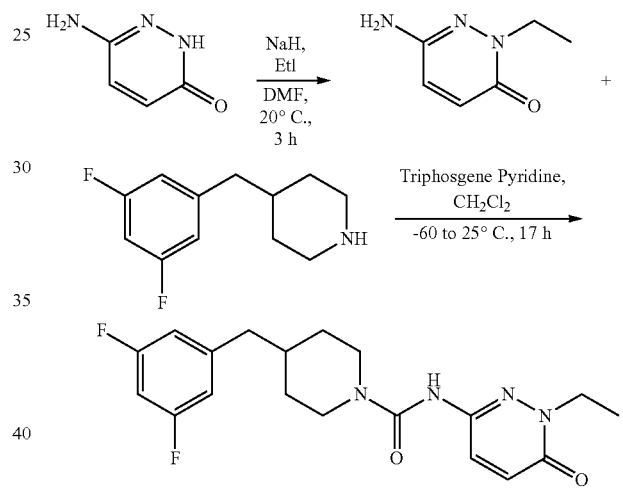

Step 1: Preparation of 6-amino-2-ethylpyridazin-3(2H)-one

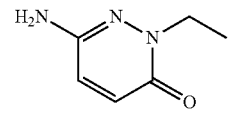

To a solution of 6-aminopyridazin-3(2H)-one (3 g, 27.0 mmol) in dry N,N-dimethylformamide (50 mL) was added sodium hydride (60% in mineral oil, 1.08 g, 27.0 mmol). The mixture was stirred at 20° C. for 1 h under nitrogen, then iodoethane (4.2 g, 27.0 mmol) was added to the mixture and stirred for 3 hr. The reaction mixture was concentrated under reduced pressure. The crude residue was purified by column chromatography (silica gel, dichloromethane/methanol=20/1) to give 6-amino-2-ethylpyridazin-3(2H)-one as a yellow solid (2.8 g, 20.1 mmol, 76%). LCMS (ESI) m/z: 139.8 [M+H]$^+$.

Step 2: Preparation of 4-(3,5-difluorobenzyl)-N-(1-ethyl-6-oxo-1,6-dihydropyridazin-3-yl)piperidine-1-carboxamide

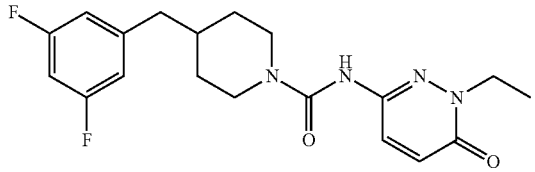 [SMILES: CCn1nc(NC(=O)N2CCC(Cc3cc(F)cc(F)c3)CC2)ccc1=O]

To a solution of triphosgene (169 mg, 0.57 mmol) in dichloromethane (5 mL) was added a solution of 6-amino-2-ethylpyridazin-3(2H)-one (264 mg, 1.9 mmol) and pyridine (300 mg, 3.8 mmol) in dichloromethane (10 mL) at −60° C. under argon. The mixture was stirred at −60° C. for 0.5 h, then a solution of 4-(3,5-difluorobenzyl)piperidine (200 mg, 0.95 mmol) and pyridine (300 mg, 3.8 mmol) in dichloromethane (15 mL) was added at −60° C. The resulting mixture was stirred at 25° C. for 17 h. The reaction was quenched with water (20 mL) and the mixture was extracted with dichloromethane (10 mL×3). The combined organic layers were dried over sodium sulfate, filtered and concentrated under reduced pressure. The crude sample was dissolved in the minimum amount of N,N-dimethylformamide and purified via prep-HPLC (Boston C18, 10 μm, 21 mm×250 mm column, acetonitrile/0.01% aqueous formic acid) to give 4-(3,5-difluorobenzyl)-N-(1-ethyl-6-oxo-1,6-dihydropyridazin-3-yl)piperidine-1-carboxamide (46.8 mg, 0.12 mmol, 13%) as a white solid. $^1$H NMR (400 MHz, Dimethylsulfoxide-$d_6$) δ 9.21 (s, 1H), 7.58 (d, J=9.8 Hz, 1H), 7.04 (dt, J=9.5, 2.3 Hz, 1H), 7.00-6.91 (m, 2H), 6.85 (d, J=9.8 Hz, 1H), 4.00 (dt, J=14.3, 10.2 Hz, 4H), 2.72 (t, J=11.8 Hz, 2H), 2.56 (d, J=7.2 Hz, 2H), 1.77 (ddd, J=11.2, 7.4, 3.7 Hz, 1H), 1.54 (d, J=10.9 Hz, 2H), 1.23 (t, J=7.1 Hz, 3H), 1.16-1.03 (m, 2H); LCMS (ESI) m/z: 377.4 [M+H]$^+$.

Example 19. Preparation of 4-(3-chlorobenzyl)-N-(1-methyl-6-oxo-1,6-dihydropyridin-3-yl)piperidine-1-carboxamide (Compound 6)

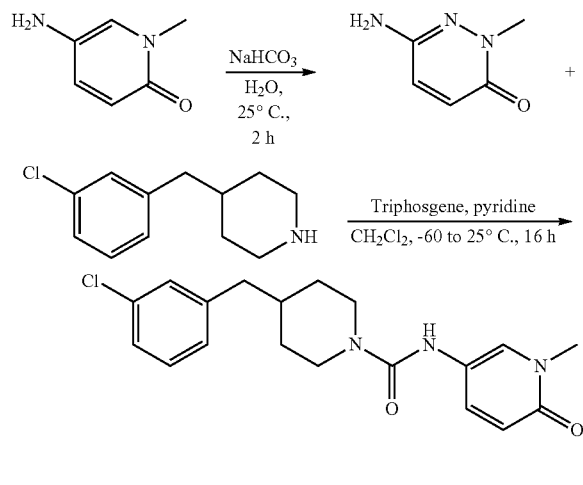

Step 1: Preparation of 5-amino-1-methylpyridin-2(1H)-one

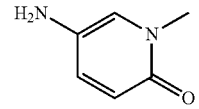

A solution of 5-amino-1-methylpyridin-2(1H)-one (1 g, 6.2 mmol) in aqueous sodium bicarbonate (30 mL) was stirred at 25° C. for 2 h under nitrogen. The reaction mixture was concentrated under reduced pressure. Ethanol (50 mL) and the aqueous layer was stirred for 2 h before it was filtered and washed with ethanol. The filtrate was concentrated and dried in vacuo to give 5-amino-1-methylpyridin-2(1H)-one (0.7 g, 5.65 mmol, 91%) as a black solid. LCMS (ESI) m/z: 125.2 [M+H]$^+$.

Step 2: Preparation of 4-(3-chlorobenzyl)-N-(1-methyl-6-oxo-1,6-dihydropyridin-3-yl)piperidine-1-carboxamide

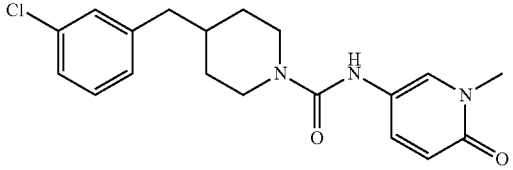 [SMILES: Cn1cc(NC(=O)N2CCC(Cc3cccc(Cl)c3)CC2)ccc1=O]

To a solution of triphosgene (119 mg, 0.4 mmol) in dichloromethane (10 mL) −60° C. was added a solution of 6-amino-2-methylpyridazin-3(2H)-one (100 mg, 0.8 mmol) and pyridine (253 mg, 3.2 mmol) in dichloromethane (5 mL) at under argon. The mixture was stirred at −60° C. for 30 min and a solution of 4-(3-chlorobenzyl)piperidine (200 mg, 0.96 mmol) and pyridine (253 mg, 3.2 mmol) in dichloromethane (5 mL) was added at −60° C. The resulting mixture was stirred at 25° C. for 16 h. The reaction was quenched with water (30 mL) and the aqueous layer was extracted with dichloromethane (50 mL×2). The combined organic layers were dried over sodium sulfate, filtered and concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 4-(3-chlorobenzyl)-N-(1-methyl-6-oxo-1,6-dihydropyridin-3-yl)piperidine-1-carboxamide (93.7 mg, 0.26 mmol, 33%) as a brown solid. $^1$H NMR (500 MHz, Dimethylsulfoxide-$d_6$) 8.14 (s, 1H), 7.75-7.75 (m, 1H), 7.40 (dd, $J_1$=2.5 Hz, $J_2$=9.0 Hz, 1H), 7.32 (t, J=8.0 Hz, 1H), 7.25-7.27 (m, 2H), 7.16 (d, J=8.0 Hz, 1H), 6.33 (d, J=9.5 Hz, 1H), 4.27 (d, J=13.5 Hz, 2H), 3.40 (s, 3H), 3.70 (t, J=12.0 Hz, 2H), 2.50-2.55 (m, 1H), 1.70-1.75 (m, 1H), 1.54-1.56 (m, 2H), 1.04-1.12 (m, 2H); LCMS (ESI) m/z: 360.1 [M+H]$^+$.

Example 20. Preparation of 4-(3-chloro-5-fluorobenzyl)-N-(1-methyl-6-oxo-1,6-dihydropyridin-3-yl)piperidine-1-carboxamide (Compound 8)

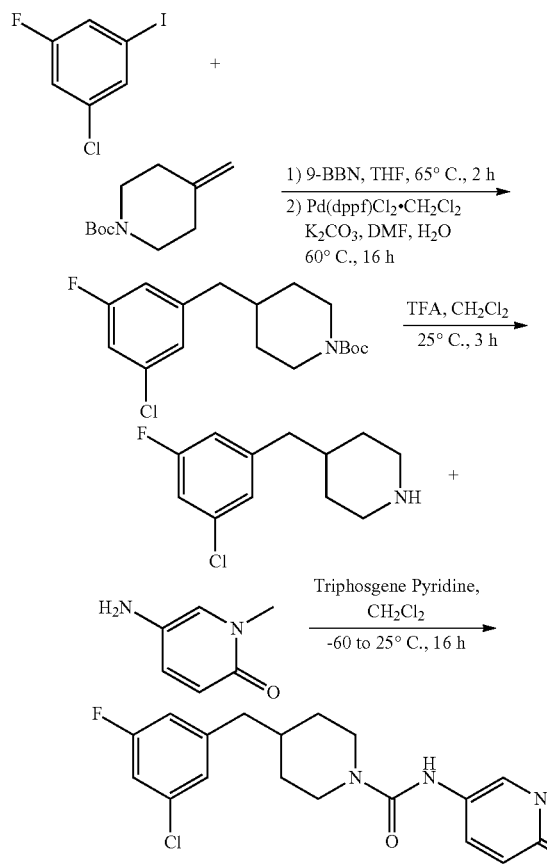

Step 1: Preparation of tert-butyl 4-(3-chloro-5-fluorobenzyl)piperidine-1-carboxylate

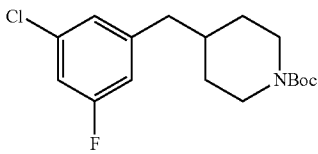 [SMILES: CC(C)(C)OC(=O)N1CCC(Cc2cc(F)cc(Cl)c2)CC1]

To a solution of 9-borabicyclo[3.3.1]nonane in tetrahydrofuran (50 mL, 25 mmol, 0.5 M) at 25° C. was added tert-butyl 4-methylenepiperidine-1-carboxylate (4.93 g, 25 mmol) under argon. The mixture was stirred at 65° C. for 2 h. The reaction mixture was cooled to 25° C. and added to a solution of 1-chloro-3-fluoro-5-iodobenzene (5.24 g, 25 mmol), potassium carbonate (4.49 g, 32.5 mmol) and 1,1'-bis(diphenylphosphino)ferrocene-palladium(II)dichloride dichloromethane complex (1.02 g, 1.25 mmol) in N,N-dimethylformamide/water (40 mL/4 mL) at 25° C. The resulting mixture was heated at 60° C. for 16 h. The reaction was quenched with 1 N aqueous sodium hydroxide solution and stirred at 25° C. for 1 h.

The reaction solution was diluted with ethyl acetate (200 mL) and washed with brine (50 mL×3). The combined organic layers were dried over sodium sulfate, filtered and concentrated under reduced pressure. The crude residue was purified by column chromatography (silica gel, petroleum ether/ethyl acetate=15/1 to 10/1) to give tert-butyl 4-(3-chloro-5-fluorobenzyl)piperidine-1-carboxylate (4.36 g, 13.3 mmol, 53%) as a white solid. LCMS (ESI) m/z: 272.0 [M-56+H]$^+$.

Step 2: Preparation of 4-(3-chloro-5-fluorobenzyl)piperidine

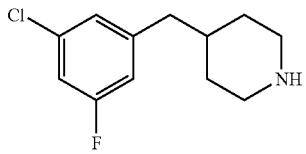 [SMILES: Fc1cc(Cl)cc(CC2CCNCC2)c1]

To a solution of tert-butyl 4-(3-chloro-5-fluorobenzyl)piperidine-1-carboxylate (4.36 g, 13.3 mmol) in dichloromethane (40 mL) was added trifluoroacetic acid (10 mL). The mixture was stirred at 25° C. for 3 h under nitrogen and then concentrated under reduced pressure. The crude residue was diluted with aqueous sodium bicarbonate solution and extracted with dichloromethane (100 mL×3). The combined organic layers were dried over sodium sulfate, filtered and concentrated under reduced pressure. The crude yellow solid was used in the next step without further purification (3.0 g, 13.2 mmol, 99%). LCMS (ESI) m/z: 228.0 [M+H]$^+$.

Step 3: Preparation of 4-(3-chloro-5-fluorobenzyl)-N-(1-methyl-6-oxo-1,6-dihydropyridin-3-yl)piperidine-1-carboxamide

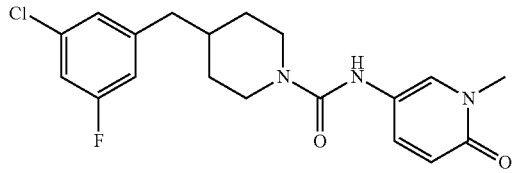

To a solution of triphosgene (119 mg, 0.4 mmol) in dichloromethane (10 mL) at −60° C. was added a solution of 5-amino-1-methylpyridin-2(1H)-one (100 mg, 0.8 mmol) and pyridine (253 mg, 3.2 mmol) in dichloromethane (5 mL) under argon. The mixture was stirred at −60° C. for 30 min and then a solution of 4-(3-chloro-5-fluorobenzyl)piperidine (219 mg, 0.96 mmol) and pyridine (253 mg, 3.2 mmol) in dichloromethane (5 mL) was added at −60° C. The resulting mixture was stirred at 25° C. for 16 h. The reaction was quenched with water (30 mL) and the aqueous layer was extracted with dichloromethane (50 mL×2). The combined organic layers were dried over sodium sulfate, filtered and concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 4-(3-chloro-5-fluorobenzyl)-N-(1-methyl-6-oxo-1,6-dihydropyridin-3-yl)piperidine-1-carboxamide (35.7 mg, 0.09 mmol, 12%) as a yellow solid. $^1$H NMR (400 MHz, Dimethylsulfoxide-d$_6$) δ 8.15 (s, 1H), 7.74 (d, J=2.8 Hz, 1H), 7.39 (dd, J1=3.2 Hz, J$_2$=9.6 Hz, 1H), 7.24-7.27 (m, 1H), 7.16 (s, 1H), 7.01-7.10 (m, 1H), 6.32 (d, J=10.0 Hz, 1H), 4.03 (d, J=10.0 Hz, 2H), 3.39 (s, 3H), 2.70 (t, J=11.6 Hz, 2H), 2.55-2.56 (m, 2H), 1.73-1.78 (m, 1H), 1.52-1.55 (m, 2H), 1.02-1.12 (m, 2H); LCMS (ESI) m/z: 378.0 [M+H]$^+$.

Example 21. Preparation of 4-(3,5-difluorobenzyl)-N-(4-methyl-5-oxo-4,5-dihydropyrazin-2-yl)piperidine-1-carboxamide (Compound 131)

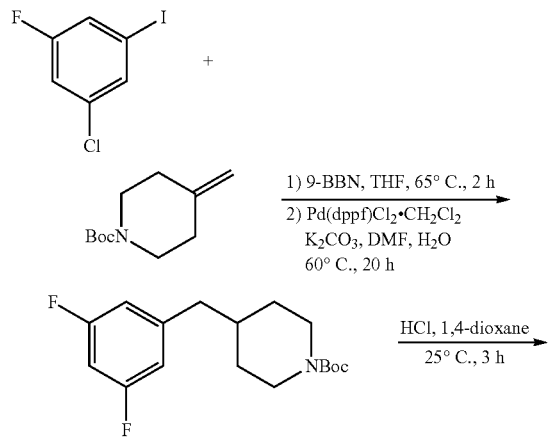

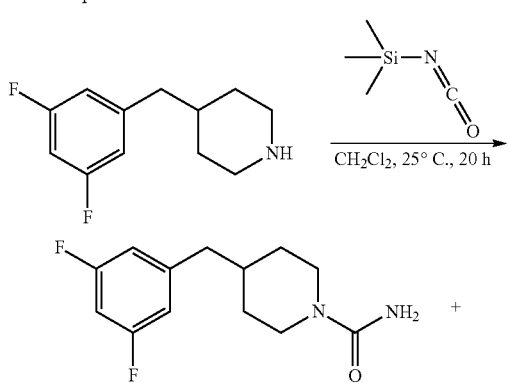

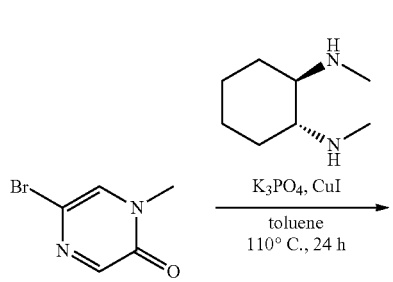

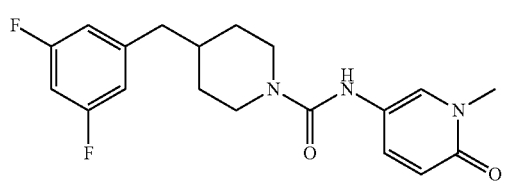

Step 1: Preparation of tert-butyl 4-(3,5-difluorobenzyl)piperidine-1-carboxylate

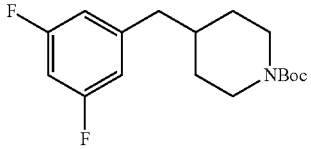

To a solution of 9-borabicyclo[3.3.1]nonane in tetrahydrofuran (100 mL, 50 mmol, 0.5 M) at 25° C. was added tert-butyl 4-methylenepiperidine-1-carboxylate (9.9 g, 50 mmol) under argon. The mixture was stirred at 65° C. for 2 h. The mixture was cooled to 25° C. and added to a solution of 1,3-difluoro-5-iodobenzene (12 g, 50 mmol), potassium carbonate (8.98 g, 65 mmol) and 1,1'-bis(diphenylphosphino)ferrocene-palladium(II)dichloride dichloromethane complex (2.04 g, 2.5 mmol) in N,N-dimethylformamide/water (80 mL/8 mL) at 25° C. The resulting mixture was heated at 60° C. for 20 h. The reaction mixture was quenchedThe reaction mixture was quenched with 1 N aqueous sodium hydroxide solution and the mixture was stirred at 25° C. for 1 h. The reaction solution was diluted with ethyl acetate (800 mL) and washed with brine (500 mL×3). The combined organic layers were dried over sodium sulfate, filtered and concentrated under reduced pressure. The crude residue was purified by column chromatography (silica gel, petroleum ether/ethyl acetate=20/1 to 10/1) to give tert-butyl 4-(3,5-difluorobenzyl)piperidine-1-carboxylate (7.9 g, 25.4 mmol, 51%) as a yellow solid. LCMS (ESI) m/z: 256.1 [M-56+H]$^+$.

Step 2: Preparation of 4-(3,5-difluorobenzyl)piperidine

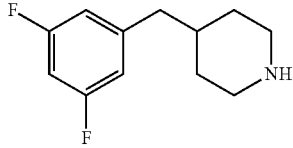

A solution of tert-butyl 4-(3,5-difluorobenzyl)piperidine-1-carboxylate (12.1 g, 38.8 mmol) and 4N hydrochloric acid in 1,4-dioxane solution (50 mL) was stirred at 25° C. under nitrogen. The mixture was concentrated under reduced pressure. The crude residue was basified to pH 9 with aqueous sodium bicarbonate solution and extracted with dichloromethane (1000 mL×3). The combined organic layers were dried over sodium sulfate, filtered and concentrated under reduced pressure. The crude product was purified by column chromatography (silica gel, dichloromethane/ammonia in methanol (7 N) from 20/1 to 10/1) to give 4-(3,5-difluorobenzyl)piperidine (6.5 g, 30.8 mmol, 79%) as a yellow solid. LCMS (ESI) m/z: 212.2 [M+H]$^+$.

Step 3: Preparation of 4-(3,5-difluorobenzyl)piperidine-1-carboxamide

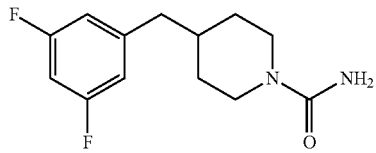 [SMILES: NC(=O)N1CCC(Cc2cc(F)cc(F)c2)CC1]

To a solution of 4-(3,5-difluorobenzyl)piperidine (2.11 g, 10 mmol) in dichloromethane (60 mL) was added trimethylsilyl isocyanate (2.31 g, 20 mmol) at 25° C. under nitrogen. The mixture was stirred at 25° C. for 20 h, then concentrated under reduced pressure. The crude residue was purified by column chromatography (silica gel, dichloromethane/ammonia in methanol (7 N)=20/1) to give 4-(3,5-difluorobenzyl)piperidine-1-carboxamide as a white solid (2 g, 7.87 mmol, 79%). LCMS (ESI) m/z: 255.1 [M+H]$^+$.

Step 4: Preparation of 4-(3,5-difluorobenzyl)-N-(4-methyl-5-oxo-4,5-dihydropyrazin-2-yl)piperidine-1-carboxamide

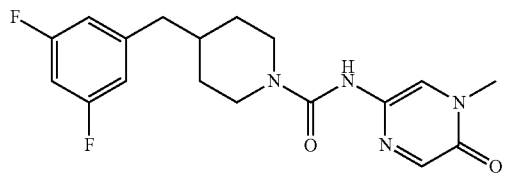 [SMILES: Cn1cc(NC(=O)N2CCC(Cc3cc(F)cc(F)c3)CC2)ncc1=O]

To a solution of 4-(3,5-difluorobenzyl)piperidine-1-carboxamide (127 mg, 0.5 mmol), 5-bromo-1-methylpyrazin-2(1H)-one (95 mg, 0.5 mmol), (1R,2R)—N1,N2-dimethyl-cyclohexane-1,2-diamine (15 mg, 0.1 mmol) and potassium phosphate (212 mg, 1.0 mmol) in toluene (15 mL) at 25° C. was added copper(I) iodide (5 mg, 0.025 mmol) under argon. The mixture was stirred at 110° C. for 24 h in a sealed tube. The reaction mixture was cooled to 25° C., water (20 mL) was added and the aqueous layer was extracted with dichloromethane (50 mL×2). The combined organic layers were dried over sodium sulfate, filtered and concentrated under reduced pressure.) The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 4-(3,5-difluorobenzyl)-N-(4-methyl-5-oxo-4,5-dihydropyrazin-2-yl)piperidine-1-carboxamideas (8.8 mg, 0.02 mmol, 5%) as a yellow solid. $^1$H NMR (400 MHz, Dimethylsulfoxide-d$_6$) δ 8.66 (s, 1H), 7.85-7.91 (m, 2H), 7.01-7.07 (m, 1H), 6.94-6.96 (m, 2H), 4.86 (d, J=13.2 Hz, 2H), 3.45 (s, 3H), 2.71 (t, J=12.0 Hz, 2H), 2.56 (d, J=7.2 Hz, 2H), 1.73-1.80 (m, 1H), 1.54 (d, J=11.6 Hz, 2H), 1.02-1.12 (m, 2H); LCMS (ESI) m/z: 363.1 [M+H]$^+$.

Example 22. Preparation of 4-(3,4-difluorobenzyl)-N-(4-methyl-5-oxo-4,5-dihydropyrazin-2-yl)piperidine-1-carboxamide (Compound 132)

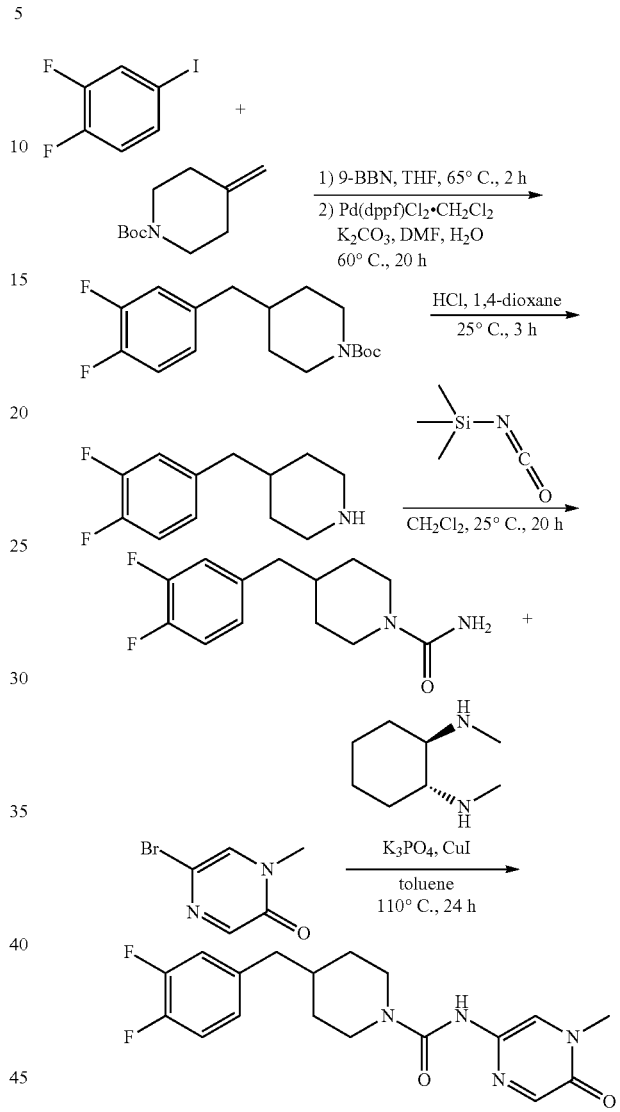

Step 1: Preparation of tert-butyl 4-(3,4-difluorobenzyl)piperidine-1-carboxylate

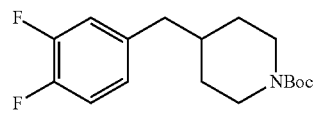

To a solution of 9-borabicyclo[3.3.1]nonane in tetrahydrofuran (78 mL, 39 mmol, 0.5 M) at 25° C. was added tert-butyl 4-methylenepiperidine-1-carboxylate (7.68 g, 39 mmol) under argon. The mixture was stirred at 65° C. for 2 h. The mixture was cooled to 25° C. and added to a solution of 1,2-difluoro-4-iodobenzene (7.2 g, 30 mmol), potassium carbonate (5.4 g, 39 mmol) and 1,1'-bis(diphenylphosphino)ferrocene-palladium(II)dichloride dichloromethane complex (2.45 g, 1.5 mmol) in N,N-dimethylformamide/water (40 mL/4 mL) at 25° C. The resulting mixture was heated at 60° C. for 4 h. The reaction mixture was quenched with 1 N aqueous sodium hydroxide solution and the mixture was stirred at 25° C. for 0.5 h. The mixture was diluted with ethyl acetate (800 mL) and washed with brine (500 mL×3). The combined organic layers were dried over sodium sulfate, filtered and concentrated under reduced pressure. The crude residue was purified by column chromatography (silica gel, petroleum ether/ethyl acetate=20/1 to 10/1) to give tert-butyl 4-(3,4-difluorobenzyl)piperidine-1-carboxylate (5.68 g, 18.2 mmol, 61%) as a yellow oil. LCMS (ESI) m/z: 256.1 [M-56+H]$^+$.

Step 2: Preparation of 4-(3,4-difluorobenzyl)piperidine

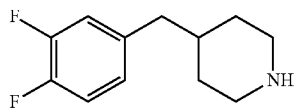

A solution of tert-butyl 4-(3,4-difluorobenzyl)piperidine-1-carboxylate (5.68 g, 18.2 mmol) and 4 N hydrochloric acid in 1,4-dioxane (50 mL) was stirred for 3 h at 25° C. under nitrogen. The reaction mixture was concentrated in vacuo, then the crude residue was triturated with diethyl ether. The resulting white solid was filtered and washed with diethyl ether (30 mL×2). The white solid was basified to pH 9 with sodium bicarbonate solution and extracted with dichloromethane (150 mL×3). The combined organic layers were dried over sodium sulfate, filtered and concentrated under reduced pressure. The crude yellow oil was used in the next step without further purification (3.18 g, 15.1 mmol, 83%). LCMS (ESI) m/z: 212.3 [M+H]$^+$.

Step 3: Preparation of 4-(3,4-difluorobenzyl)piperidine-1-carboxamide

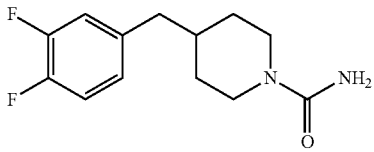 [SMILES: NC(=O)N1CCC(Cc2ccc(F)c(F)c2)CC1]

To a solution of 4-(3,4-difluorobenzyl)piperidine (1.06 g, 5.0 mmol) in dichloromethane (30 mL) at 25° C. was added trimethylsilyl isocyanate (1.15 g, 10.0 mmol) under nitrogen. The mixture was stirred at 25° C. for 16 h, then the mixture was concentrated under reduced pressure. The crude residue was purified by column chromatography (silica gel, dichloromethane/ammonia in methanol (7 N)=20/1) to give 4-(3,4-difluorobenzyl)piperidine-1-carboxamide (1.03 g, 4.05 mmol, 81%) as a white solid. LCMS (ESI) m/z: 255.1 [M+H]$^+$.

Step 4: Preparation of 4-(3,4-difluorobenzyl)-N-(4-methyl-5-oxo-4,5-dihydropyrazin-2-yl)piperidine-1-carboxamide

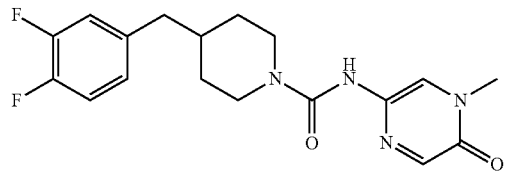 [SMILES: Cn1cc(NC(=O)N2CCC(Cc3ccc(F)c(F)c3)CC2)ncc1=O]

To a solution of 4-(3,4-difluorobenzyl)piperidine-1-carboxamide (254 mg, 1.0 mmol), 5-bromo-1-methylpyrazin-2(1H)-one (284 mg, 1.5 mmol), (1R,2R)—N1,N2-dimethylcyclohexane-1,2-diamine (57 mg, 0.4 mmol) and potassium phosphate (425 mg, 2.0 mmol) in toluene (5 mL) was added copper(I) iodide (19 mg, 0.1 mmol) at 25° C. under argon. The mixture was stirred at 110° C. for 24 h in a sealed tube. The reaction mixture was cooled to 25° C., diluted with water (20 mL) and the aqueous layer was extracted with dichloromethane (50 mL×2). The combined organic layers were dried over sodium sulfate, filtered and concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 4-(3,4-difluorobenzyl)-N-(4-methyl-5-oxo-4,5-dihydropyrazin-2-yl)piperidine-1-carboxamide as a yellow solid (59.2 mg, 0.16 mmol, 16%). $^1$H NMR (400 MHz, Dimethylsulfoxide-d$_6$) δ 8.66 (s, 1H), 7.85-7.91 (m, 2H), 7.25-7.37 (m, 2H), 7.01-7.04 (m, 1H), 4.08 (d, J=13.6 Hz, 2H), 3.45 (s, 3H), 2.70 (t, J=11.6 Hz, 2H), 2.50-2.53 (m, 2H), 1.69-1.75 (m, 1H), 1.52-1.55 (m, 2H), 1.01-1.11 (m, 2H); LCMS (ESI) m/z: 363.1 [M+H]$^+$.

Example 23. Preparation of 4-(2-chloro-3-cyanophenoxy)-N-(1-methyl-6-oxo-1,6-dihydropyridazin-3-yl)piperidine-1-carboxamide (Compound 87)

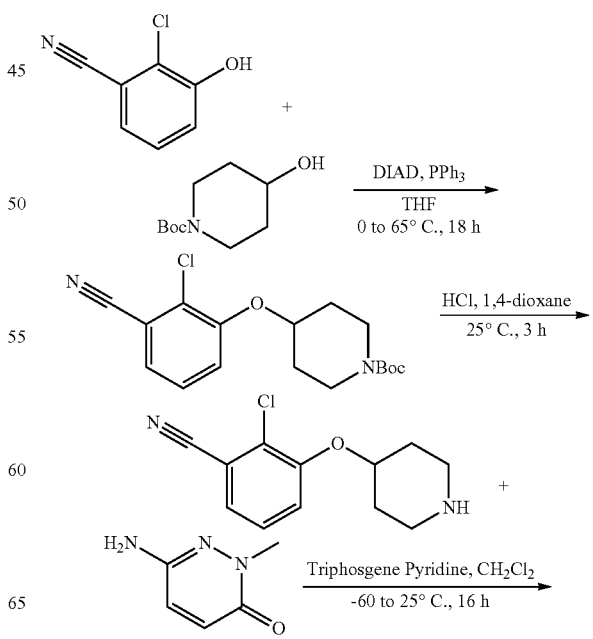

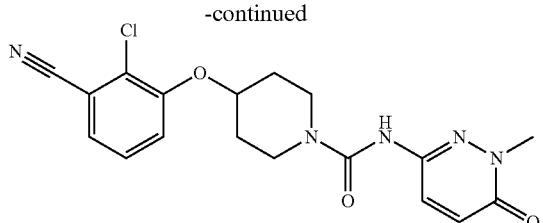

Step 1: Preparation of tert-butyl 4-(2-chloro-3-cyanophenoxy)piperidine-1-carboxylate

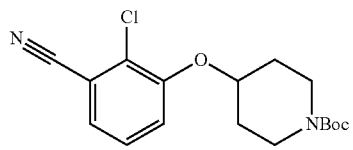 [SMILES: CC(C)(C)OC(=O)N1CCC(Oc2cccc(C#N)c2Cl)CC1]

To a solution of 2-chloro-3-hydroxybenzonitrile (2.53 g, 16.5 mmol), tert-butyl 4-hydroxypiperidine-1-carboxylate (3.02 g, 15 mmol) and triphenylphosphine (4.72 g, 18 mmol) in tetrahydrofuran (50 mL) at 0° C. was added diisopropyl azodicarboxylate (3.02 g, 18 mmol) under argon. The mixture was stirred at 65° C. for 18 h. The reaction mixture was cooled to 25° C. and concentrated under reduced pressure. The crude residue was triturated with petroleum ether (100 mL) and the mixture was stirred at 25° C. for 1 h, then filtered and washed with petroleum ether. The filtrate was concentrated under reduced pressure. The crude residue was purified by column chromatography (silica gel, petroleum ether/ethyl acetate=6/1 to 3/1) to give tert-butyl 4-(2-chloro-3-cyanophenoxy)piperidine-1-carboxylate (2.34 g, 6.92 mmol, 46%) as a colorless oil. LCMS (ESI) m/z: 281.1 [M-56+H]$^+$.

Step 2: Preparation of 2-chloro-3-(piperidin-4-yloxy)benzonitrile

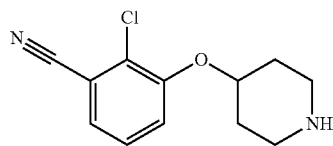

A solution of tert-butyl 4-(2-chloro-3-cyanophenoxy)piperidine-1-carboxylate (2.33 g, 6.92 mmol) and 4N hydrochloric acid in 1,4-dioxane solution (50 mL) was stirred for 3 h at 25° C. under nitrogen. The reaction mixture was concentrated under reduced pressure. The crude residue was triturated with diethyl ether, then the solid was collected by filtration and washed with diethyl ether. The white solid (1.66 g) was basified to pH 9 with sodium bicarbonate solution and extracted with dichloromethane (50 mL×3). The combined organic layers were dried over sodium sulfate, filtered and concentrated under reduced pressure. The crude white solid was used in the next step without further purification (1.3 g, 5.5 mmol, 80%). LCMS (ESI) m/z: 237.1 [M+H]$^+$.

Step 3: Preparation of 4-(2-chloro-3-cyanophenoxy)-N-(1-methyl-6-oxo-1,6-dihydropyridazin-3-yl)piperidine-1-carboxamide

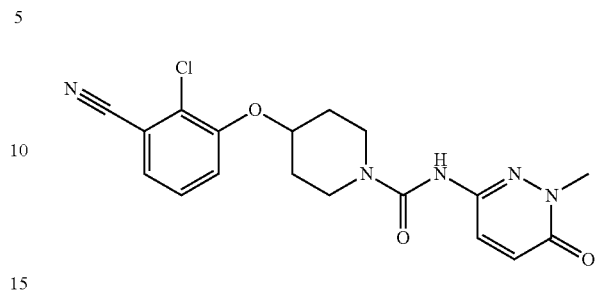

To a solution of triphosgene (119 mg, 0.4 mmol) in dichloromethane (10 mL) was added a solution of 6-amino-2-methylpyridazin-3(2H)-one (100 mg, 0.8 mmol) and pyridine (253 mg, 3.2 mmol) in dichloromethane (5 mL) at −60° C. under argon. The mixture was stirred at −60° C. for 0.5 h, then a solution of 2-chloro-3-(piperidin-4-yloxy)benzonitrile (218 mg, 0.8 mmol) and pyridine (253 mg, 3.2 mmol) in dichloromethane (5 mL) was added at −60° C. The resulting mixture was stirred at 25° C. for 18 h. The reaction was quenched with water (30 mL) and the aqueous layer was extracted with dichloromethane (50 mL×2). The combined organic layers were dried over sodium sulfate, filtered and concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 4-(2-chloro-3-cyanophenoxy)-N-(1-methyl-6-oxo-1,6-dihydropyridazin-3-yl)piperidine-1-carboxamide (34.1 mg, 0.09 mmol, 11%) as a yellow solid. $^1$H NMR (400 MHz, Dimethylsulfoxide-d$_6$) δ 9.37 (s, 1H), 7.64-7.67 (m, 2H), 7.49-7.57 (m, 2H), 6.89 (d, J=9.6 Hz, 1H), 4.83-4.85 (m, 1H), 3.66-3.71 (m, 2H), 3.57 (s, 3H), 3.36-3.44 (m, 2H), 1.93-1.95 (m, 2H), 1.63-1.70 (m, 2H); LCMS (ESI) m/z: 388.0 [M+H]$^+$.

Example 24. Preparation of 4-(3-chloro-4,5-difluorophenoxy)-N-(1-methyl-6-oxo-1,6-dihydropyridazin-3-yl)piperidine-1-carboxamide (Compound 89)

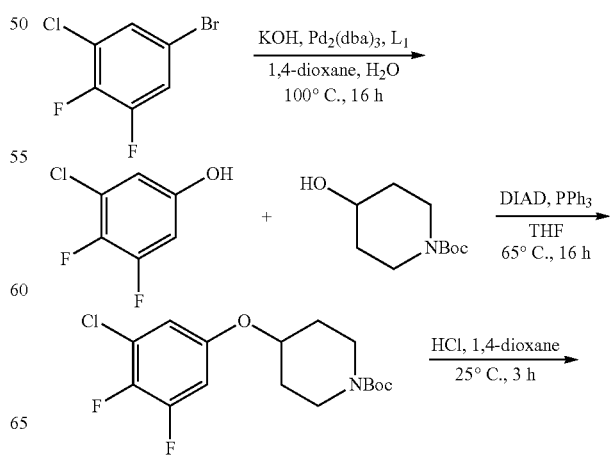

119

-continued

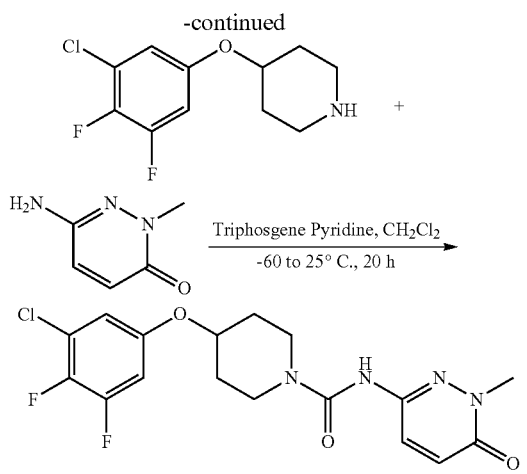

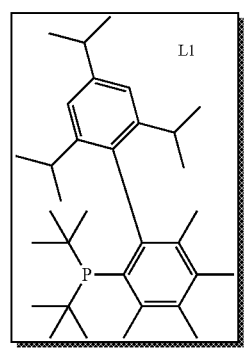

Step 1: Preparation of 3-chloro-4,5-difluorophenol

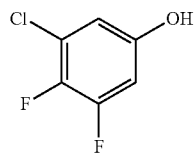

To a solution of 5-bromo-1-chloro-2,3-difluorobenzene (2.96 g, 13.0 mmol) and potassium hydroxide (2.60 g, 46.4 mmol) in 1,4-dioxane (20 mL) and water (20 mL) was added tris(dibenzylideneacetone)dipalladium(0) (120 mg, 0.13 mmol) and di-tert-butyl(2',4',6'-triisopropyl-3,4,5,6-tetramethyl-[1,1'-biphenyl]-2-yl)phosphane (125 mg, 0.26 mmol) under argon. The mixture was stirred at 100° C. under argon for 16 h. The reaction mixture was cooled to 25° C. and acidified to pH 5 with 1 N hydrochloric acid solution. The aqueous layer was extracted with dichloromethane (100 mL×3). The combined organic layers were dried over sodium sulfate, filtered and concentrated under reduced pressure. The crude residue was purified by column chromatography (silica gel, dichloromethane/methanol=80/1) to give 3-chloro-4,5-difluorophenol as a yellow oil (1.8 g, 10.9 mmol, 84%). $^1$H NMR (400 MHz, Dimethylsulfoxide-d$_6$) δ 10.29 (s, 1H), 6.77-6.81 (m, 1H), 6.73-6.76 (m, 1H).

120

Step 2: Preparation of tert-butyl 4-(3-chloro-4,5-difluorophenoxy)piperidine-1-carboxylate

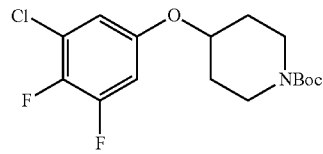 [SMILES: CC(C)(C)OC(=O)N1CCC(Oc2cc(F)c(F)c(Cl)c2)CC1]

To a solution of 3-chloro-4,5-difluorophenol (1.5 g, 9.1 mmol), tert-butyl 4-hydroxypiperidine-1-carboxylate (1.67 g, 8.3 mmol) and triphenylphosphine (2.6 g, 9.96 mmol) in tetrahydrofuran (80 mL) was added diisopropyl azodicarboxylate (2.01 g, 9.96 mmol) at 0° C. under argon. The mixture was stirred at 65° C. for 18 h. The reaction mixture was cooled to 25° C. and concentrated in vacuo. The crude material was dissolved in petroleum ether (150 mL) and the mixture was stirred at 25° C. for 1 h. The mixture was filtered, washed with petroleum ether and the filtrate was concentrated under reduced pressure. The crude residue was purified by column chromatography (silica gel, petroleum ether/ethyl acetate=20/1 to 10/1) to give tert-butyl 4-(3-chloro-4,5-difluorophenoxy)piperidine-1-carboxylate (1.95 g, 5.61 mmol, 67%) as a yellow oil. LCMS (ESI) m/z: 292.0 [M-56+H]$^+$.

Step 3: Preparation of 4-(3-chloro-4,5-difluorophenoxy)piperidine

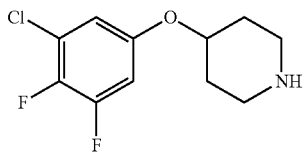 [SMILES: Fc1cc(OC2CCNCC2)cc(Cl)c1F]

A solution of tert-butyl 4-(3-chloro-4,5-difluorophenoxy)piperidine-1-carboxylate (2.37 g, 6.8 mmol) and hydrochloric acid in 1,4-dioxane (50 mL, 4 M) was stirred for 3 h at 25° C. under nitrogen. The mixture was concentrated under reduced pressure. The crude residue was triturated with diethyl ether, the solid was collected by filtration and washed with diethyl ether. The yellow solid was basified to pH 9 with sodium bicarbonate solution and extracted with dichloromethane (50 mL×3). The combined organic layers were dried over sodium sulfate, filtered and concentrated under reduced pressure. The crude yellow oil was used in the next step without further purification (1.5 g, 6.07 mmol, 89%). LCMS (ESI) m/z: 248.1 [M+H]$^+$.

Step 4: Preparation of 4-(3-chloro-4,5-difluorophenoxy)-N-(1-methyl-6-oxo-1,6-dihydropyridazin-3-yl)piperidine-1-carboxamide

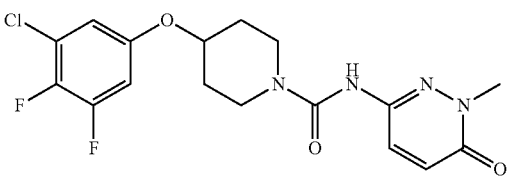 [SMILES: Cn1nc(NC(=O)N2CCC(Oc3cc(F)c(F)c(Cl)c3)CC2)ccc1=O]

To a solution of triphosgene (469 mg, 1.58 mmol) in dichloromethane (50 mL) was added a solution of 6-amino-2-methylpyridazin-3(2H)-one (395 mg, 3.16 mmol) and pyridine (999 mg, 12.6 mmol) in dichloromethane (25 mL) at −60° C. under argon. The mixture was stirred at −60° C. for 1 h, then a solution of 4-(3-chloro-4,5-difluorophenoxy)piperidine (743 mg, 3.0 mmol) and pyridine (999 mg, 12.6 mmol) in dichloromethane (25 mL) was added at −60° C. over 30 min. The resulting mixture was warmed then stirred at 25° C. for 6 h. The reaction was quenched with water (50 mL) and the aqueous layer was extracted with dichloromethane (100 mL×3). The combined organic layers were dried over sodium sulfate, filtered and concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 4-(3-chloro-4,5-difluorophenoxy)-N-(1-methyl-6-oxo-1,6-dihydropyridazin-3-yl)piperidine-1-carboxamide (280 mg, 0.70 mmol, 23%) as a white solid. $^1$H NMR (400 MHz, Dimethylsulfoxide-$d_6$) δ 9.34 (s, 1H), 7.64 (d, J=9.6 Hz, 1H), 7.19-7.25 (m, 1H), 7.12-7.15 (m, 1H), 6.89 (d, J=9.6 Hz, 1H), 4.62-4.66 (m, 1H), 3.76-3.81 (m, 2H), 3.56 (s, 3H), 3.23-3.30 (m, 2H), 1.92-1.95 (m, 2H), 1.51-1.59 (m, 2H); LCMS (ESI) m/z: 399.1 [M+H]$^+$.

Example 25. Preparation of 4-(3-cyano-4,5-difluorophenoxy)-N-(1-methyl-6-oxo-1,6-dihydropyridazin-3-yl)piperidine-1-carboxamide (Compound 90)

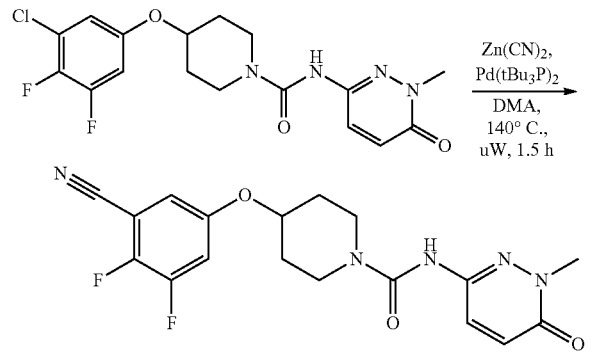

Step 1: Preparation of 4-(3-cyano-4,5-difluorophenoxy)-N-(1-methyl-6-oxo-1,6-dihydropyridazin-3-yl)piperidine-1-carboxamide

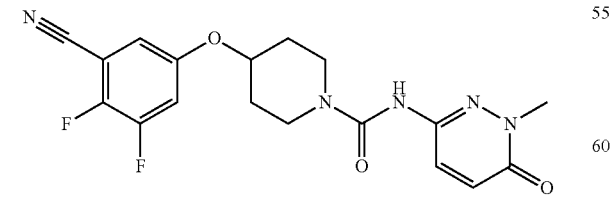

To a solution of 4-(3-chloro-4,5-difluorophenoxy)-N-(1-methyl-6-oxo-1,6-dihydropyridazin-3-yl)piperidine-1-carboxamide (150 mg, 0.38 mmol) and zinc cyanide (89 mg, 0.76 mmol) in N,N-dimethylaniline (5 mL) was added bis(tri-tert-butylphosphine)palladium(0) (21 mg, 0.04 mmol) under argon. The mixture was stirred at 140° C. for 100 min under microwave irradiation. The mixture was diluted with water (20 mL) and extracted with ethyl acetate (50 mL×2). The combined organic layers were dried over sodium sulfate, filtered and concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 4-(3-cyano-4,5-difluorophenoxy)-N-(1-methyl-6-oxo-1,6-dihydropyridazin-3-yl)piperidine-1-carboxamide (18.1 mg, 0.05 mmol, 12%) as a white solid. $^1$H NMR (400 MHz, Dimethylsulfoxide-$d_6$) δ 9.35 (s, 1H), 7.60-7.65 (m, 2H), 7.49-7.51 (m, 1H), 6.89 (d, J=9.6 Hz, 1H), 4.66-4.70 (m, 1H), 3.79-3.84 (m, 2H), 3.56 (s, 3H), 3.22-3.31 (m, 2H), 1.95-1.97 (m, 2H), 1.51-1.59 (m, 2H); LCMS (ESI) m/z: 390.1 [M+H]$^+$.

Example 26. Preparation of N-(1-methyl-6-oxo-1,6-dihydropyridazin-3-yl)-4-(4-(trifluoromethyl)phenoxy)piperidine-1-carboxamide (Compound 76)

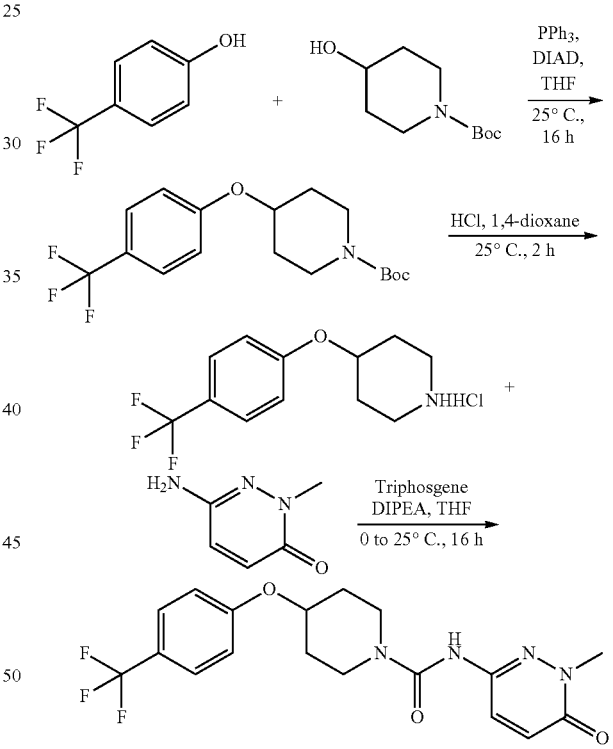

Step 1: Preparation of tert-butyl 4-(4-(trifluoromethyl)phenoxy)piperidine-1-carboxylate

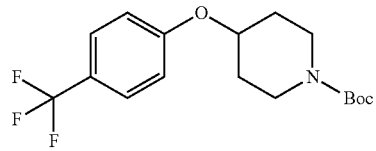 [SMILES: CC(C)(C)OC(=O)N1CCC(Oc2ccc(C(F)(F)F)cc2)CC1]

To a solution of 4-(trifluoromethyl)phenol (1.0 g, 6.17 mmol), tert-butyl 4-hydroxypiperidine-1-carboxylate (1.24 g, 6.17 mmol) and triphenylphosphine (1.94 g, 7.41 mmol) in tetrahydrofuran (15 mL) was added diisopropyl azodicarboxylate (1.49 g, 7.41 mmol) at 20° C. The mixture was stirred at 20° C. for 16 h. The volatiles were removed under reduced pressure and the residue was further purified by column chromatography (silica gel, petroleum ether/ethyl acetate=10/1) to give tert-butyl 4-(4-(trifluoromethyl)phenoxy)piperidine-1-carboxylate (1.6 g, 5.54 mmol, 90%) as a colorless oil. LCMS (ESI) m/z: 290.1 [M-56+H]$^+$.

Step 2: Preparation of 4-(4-(trifluoromethyl)phenoxy)piperidine hydrochloride

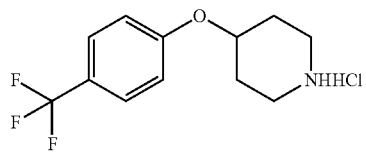

A solution of tert-butyl 4-(4-(trifluoromethyl)phenoxy)piperidine-1-carboxylate (1.6 g, 4.64 mmol) and 4M hydrochloric acid in 1,4-dioxane (6.0 mL, 24 mmol) was stirred at 20° C. for 2 h. The solution was concentrated to provide 4-(4-(trifluoromethyl)phenoxy)piperidine hydrochloride (800 mg, crude) as a white solid. This material was used in the next step without further purification. LCMS (ESI) m/z: 246.1 [M+H]$^+$.

Step 3: Preparation of N-(1-methyl-6-oxo-1,6-dihydropyridazin-3-yl)-4-(4-(trifluoromethyl)phenoxy)piperidine-1-carboxamide

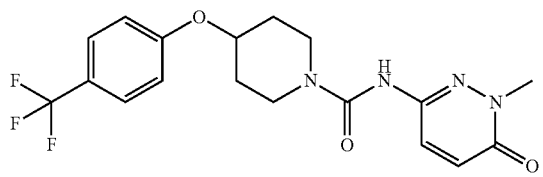 [SMILES: Cn1nc(NC(=O)N2CCC(Oc3ccc(C(F)(F)F)cc3)CC2)ccc1=O]

To a solution of triphosgene (176 mg, 0.600 mmol) in dichloromethane (10 mL) at 0° C. was added 6-amino-2-methylpyridazin-3(2H)-one (150 mg, 1.20 mmol) and diisopropylethylamine (310 mg, 2.40 mmol) in tetrahydrofuran (10 mL). The mixture was stirred at 0° C. for 1 h, then a solution of 4-(2-chloro-5-fluorophenoxy)piperidine hydrochloride (337 mg, 1.20 mmol) and diisopropylethylamine (310 mg, 2.40 mmol) in tetrahydrofuran (10 mL) was added. The reaction mixture was stirred at 25° C. for 16 h. The volatiles were removed under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 4-(5-fluoro-2-(trifluoromethyl)phenoxy)-N-(1-methyl-6-oxo-1,6-dihydropyridazin-3-yl)piperidine-1-carboxamide (134.9 mg, 0.341 mmol, 28%) as a white solid. $^1$H NMR (400 MHz, Dimethylsulfoxide-d$_6$) δ 9.35 (s, 1H), 7.66-7.63 (m, 3H), 7.18 (d, J=8.8 Hz, 2H), 6.89 (d, J=9.6 Hz, 1H), 4.76-4.72 (m, 1H), 3.83-3.77 (m, 2H), 3.56 (s, 3H), 3.33-3.27 (m, 2H), 2.00-1.96 (m, 2H), 1.64-1.57 (m, 2H); LCMS (ESI) m/z: 397.0 [M+H]$^+$.

Example 27. Preparation of 4-(2-chloro-5-fluorophenoxy)-N-(1-methyl-6-oxo-1,6-dihydropyridazin-3-yl)piperidine-1-carboxamide (Compound 86)

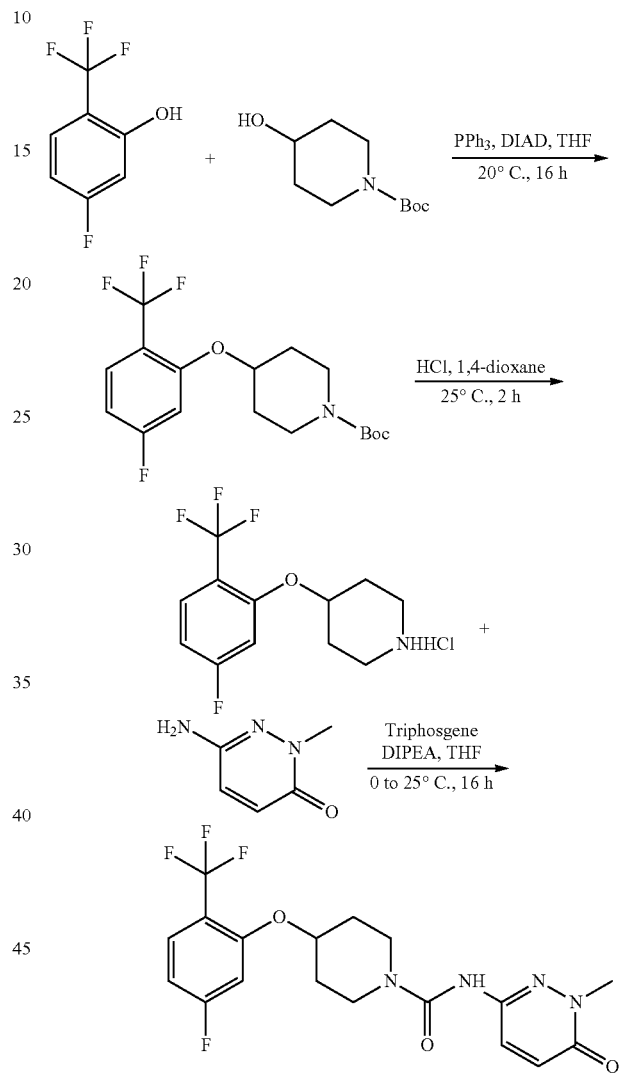

Step 1: Preparation of tert-butyl 4-(5-fluoro-2-(trifluoromethyl)phenoxy)piperidine-1-carboxylate

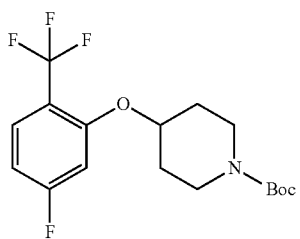 [SMILES: CC(C)(C)OC(=O)N1CCC(Oc2cc(F)ccc2C(F)(F)F)CC1]

To a solution of 5-fluoro-2-(trifluoromethyl)phenol (1.0 g, 5.55 mmol), tert-butyl 4-hydroxypiperidine-1-carboxylate (1.12 g, 5.55 mmol) and triphenylphosphine (1.75 g, 6.66 mmol) in tetrahydrofuran (15 mL) at 20° C. was added diisopropyl azodicarboxylate (1.34 g, 6.66 mmol). The mixture was stirred at 20° C. for 16 h. The volatiles were removed under reduced pressure. The crude residue was purified by column chromatography (silica gel, petroleum ether/ethyl acetate=10/1) to yield tert-butyl 4-(5-fluoro-2-(trifluoromethyl)phenoxy)piperidine-1-carboxylate (1.45 g, 3.99 mmol, 72%) as a colorless oil. LCMS (ESI) m/z: 274.1 [M−56+H]$^+$.

Step 2: Preparation of 4-(5-fluoro-2-(trifluoromethyl)phenoxy)piperidine hydrochloride

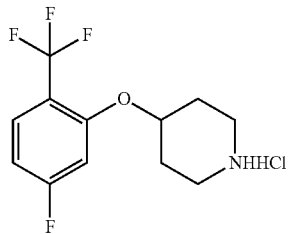

A solution of tert-butyl 4-(5-fluoro-2-(trifluoromethyl) phenoxy)piperidine-1-carboxylate (1.45 g, 3.99 mmol) and hydrochloric acid in 1,4-dioxane (6.0 mL, 24 mmol) was stirred at 20° C. for 2 h. The solution was concentrated in vacuo to give 4-(5-fluoro-2-(trifluoromethyl)phenoxy)piperidine hydrochloride (780 mg, crude) as a white solid. This material was used in the next step without further purification. LCMS (ESI) m/z: 264.1 [M+H]$^+$.

Step 3: Preparation of 4-(5-fluoro-2-(trifluoromethyl)phenoxy)-N-(1-methyl-6-oxo-1,6-dihydropyridazin-3-yl)piperidine-1-carboxamide

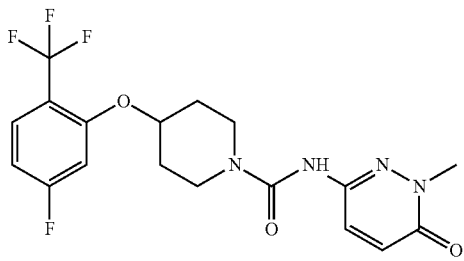 [SMILES: Cn1nc(NC(=O)N2CCC(Oc3cc(F)ccc3C(F)(F)F)CC2)ccc1=O]

To a solution of triphosgene (176 mg, 0.600 mmol) in dichloromethane (10 mL) at 0° C. was added 6-amino-2-methylpyridazin-3(2H)-one (150 mg, 1.20 mmol) and diisopropylethylamine (310 mg, 2.40 mmol) in tetrahydrofuran (10 mL). The mixture was stirred at 0° C. for 1 h, then a solution of 4-(2-chloro-5-fluorophenoxy)piperidine hydrochloride (359 mg, 1.20 mmol) and diisopropylethylamine (310 mg, 2.40 mmol) in tetrahydrofuran (10 mL) was added. The reaction mixture was stirred at 20° C. for 16 h.

The volatiles were removed under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 4-(5-fluoro-2-(trifluoromethyl)phenoxy)-N-(1-methyl-6-oxo-1, 6-dihydropyridazin-3-yl)piperidine-1-carboxamide (151.8 mg, 0.367 mmol, 37%) as a white solid. $^1$H NMR (400 MHz, Dimethylsulfoxide-d$_6$) δ 9.35 (s, 1H), 7.71-7.64 (m, 2H), 7.35 (d, J=11.2 Hz, 1H), 6.95-6.87 (m, 2H), 4.89 (m, 1H), 3.61-3.53 (m, 5H), 3.49-3.43 (m, 2H), 1.96-1.91 (m, 2H), 1.68-1.63 (m, 2H); LCMS (ESI) m/z: 415.0 [M+H]$^+$.

Example 28. Preparation of 4-(3-fluoro-4-(trifluoromethyl)phenoxy)-N-(1-methyl-6-oxo-1,6-dihydropyridazin-3-yl)piperidine-1-carboxamide (Compound 88)

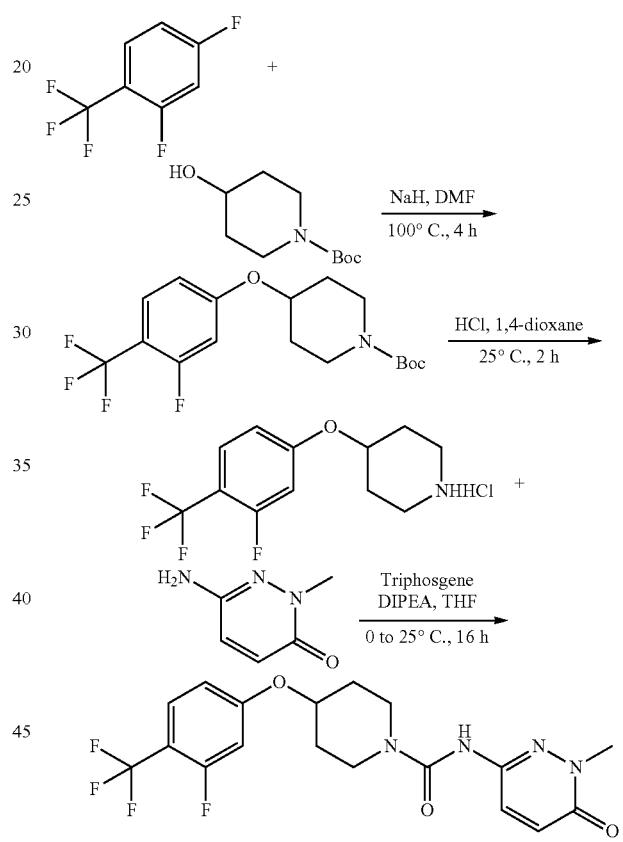

Step 1: Preparation of tert-butyl 4-(3-fluoro-4-(trifluoromethyl)phenoxy)piperidine-1-carboxylate

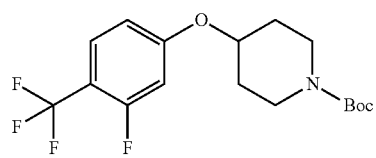 [SMILES: CC(C)(C)OC(=O)N1CCC(Oc2ccc(C(F)(F)F)c(F)c2)CC1]

To a solution of tert-butyl 4-hydroxypiperidine-1-carboxylate (2.1 g, 9.94 mmol) in N,N-dimethylformamide (50 mL) at 20° C. was added sodium hydride (440 mg, 10.9 mmol, 60% in mineral oil). The mixture was stirred at 20°

C. for 1 h and then a solution of 2,4-difluoro-1-(trifluoromethyl)benzene (1.99 g, 10.9 mmol) in N,N-dimethylformamide (10 mL) was added. The reaction mixture was heated to 100° C. and stirred for 4 h. The volatiles were removed under reduced pressure. The crude residue was purified by column chromatography (silica gel, petroleum ether/ethyl acetate=10/1) to give tert-butyl 4-(3-fluoro-4-(trifluoromethyl)phenoxy)piperidine-1-carboxylate (2.4 g, 7.79 mmol, 79%) as a cloudy oil. LCMS (ESI) m/z: 308.1 [M-56+H]⁺.

Step 2: Preparation of 4-(3-fluoro-4-(trifluoromethyl)phenoxy)piperidine hydrochloride

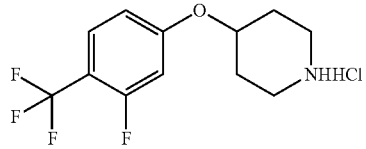

A solution of tert-butyl 4-(3-fluoro-4-(trifluoromethyl)phenoxy)piperidine-1-carboxylate (2.4 g, 6.61 mmol) and hydrochloric acid in 1,4-dioxane (10.0 mL, 40 mmol, 4 M) was stirred at 20° C. for 2 h, then the solution was concentrated under reduced pressure to give 4-(3-fluoro-4-(trifluoromethyl)phenoxy)piperidine hydrochloride (1.4 g, crude) as a white solid. This material was used in the next step without further purification. LCMS (ESI) m/z: 264.1 [M+H]⁺.

Step 3: Preparation of 4-(3-fluoro-4-(trifluoromethyl)phenoxy)-N-(1-methyl-6-oxo-1,6-dihydropyridazin-3-yl)piperidine-1-carboxamide

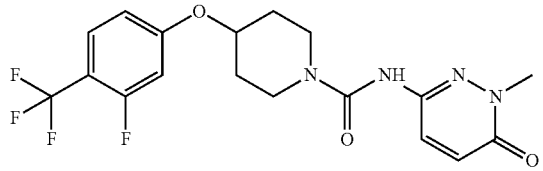 [SMILES: Cn1nc(NC(=O)N2CCC(Oc3ccc(C(F)(F)F)c(F)c3)CC2)ccc1=O]

To a solution of triphosgene (147 mg, 0.502 mmol) in dichloromethane (10 mL) at 0° C. was added a solution of 6-amino-2-methylpyridazin-3(2H)-one (125 mg, 1.00 mmol) and diisopropylethylamine (260 mg, 2.01 mmol) in tetrahydrofuran (10 mL). The mixture was stirred at 0° C. for 1 h, then a solution of 4-(3-fluoro-4-(trifluoromethyl)phenoxy)piperidine hydrochloride (300 mg, 1.00 mmol) and diisopropylethylamine (260 mg, 1.00 mmol) in tetrahydrofuran (10 mL) was added. The reaction mixture was stirred at 20° C. for 16 h. The reaction solution was concentrated under reduced pressure. The crude residue was dissolved in the minimum amount of methanol and purified by chiral-HPLC (SFC-80, Ad 20×250 mm, 10 μM column: CO₂/0.2% ammonia in methanol, 75/25) to give 4-(3-fluoro-4-(trifluoromethyl)phenoxy)-N-(1-methyl-6-oxo-1,6-dihydropyridazin-3-yl)piperidine-1-carboxamide (153.5 mg, 0.371 mmol, 37%) as a white solid. ¹H NMR (400 MHz, Dimethylsulfoxide-d₆) δ 9.34 (s, 1H), 7.65 (d, J=10.0 Hz, 1H), 7.53-7.48 (m, 2H), 7.42-7.39 (m, 1H), 6.89 (d, J=10.0 Hz, 1H), 4.83-4.81 (m, 1H), 3.63-3.56 (m, 5H), 3.47-3.41 (m, 2H), 1.95-1.90 (m, 2H), 1.67-1.62 (m, 2H); LCMS (ESI) m/z: 415.0 [M+H]⁺.

Example 29. Preparation of 4-((3-fluorophenoxy)methyl)-N-(1-methyl-6-oxo-1,6-dihydropyridazin-3-yl)piperidine-1-carboxamide (Compound 101)

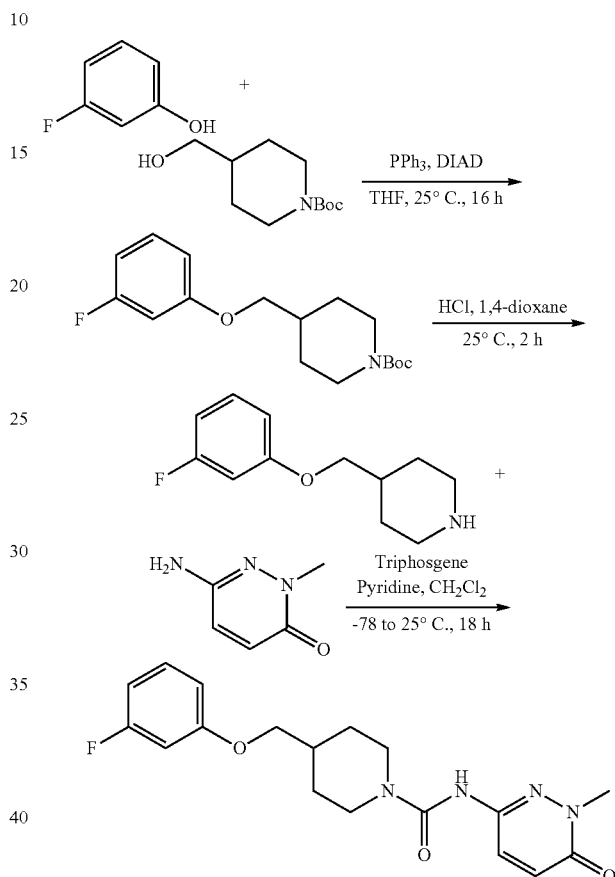

Step 1: Preparation of tert-butyl 4-((3-fluorophenoxy)methyl)piperidine-1-carboxylate

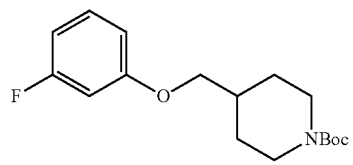

A mixture of triphenylphosphine (5.61 g, 21.4 mmol) and diisopropyl azodicarboxylate (4.33 g, 21.4 mmol) in tetrahydrofuran (80 mL) was stirred at 25° C. for 10 min, then tert-butyl 4-(hydroxymethyl)piperidine-1-carboxylate (3.84 g, 17.9 mmol) was added. The mixture was stirred at 25° C. for 20 min and 3-fluorophenol (2.0 g, 17.9 mmol) was added. The reaction was stirred at 25° C. for 15 h. The mixture was concentrated in vacuo then triturated in petroleum ether (200 mL) and stirred for 1 h. The solid was filtered and the filtrate was concentrated under reduced pressure. The crude material was purified by column chromatography (silica gel, petroleum ether/ethyl acetate=15/1) to give tert-butyl 4-((3-fluorophenoxy)methyl)piperidine-1-carboxylate (2.54 g, 8.22 mmol, 46%) as a white solid. LCMS (ESI) m/z: 332.1 [M+Na]$^+$.

Step 2: Preparation of 4-((3-fluorophenoxy)methyl)piperidine

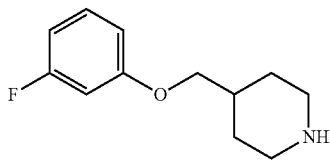 [SMILES: Fc1cccc(OCC2CCNCC2)c1]

A solution of tert-butyl 4-((3-fluorophenoxy)methyl)piperidine-1-carboxylate (2.54 g, 8.22 mmol) and 4N hydrochloric acid in 1,4-dioxane solution (50 mL) was stirred at 25° C. for 2 h under nitrogen. The reaction mixture was filtered and the white solid obtained was washed with petroleum ether (30 mL×2). The solid was dissolved in aqueous sodium bicarbonate solution and extracted with dichloromethane (250 mL×3). The combined organic layers were dried over sodium sulfate, filtered and concentrated to afford 4-((3-fluorophenoxy)methyl)piperidine (1.3 g, 6.22 mmol, 74%) as a yellow oil. LCMS (ESI) m/z: 210.1 [M+H]$^+$. The crude material was used without further purification in the next step.

Step 3: Preparation of 4-((3-fluorophenoxy)methyl)-N-(1-methyl-6-oxo-1,6-dihydropyridazin-3-yl)piperidine-1-carboxamide

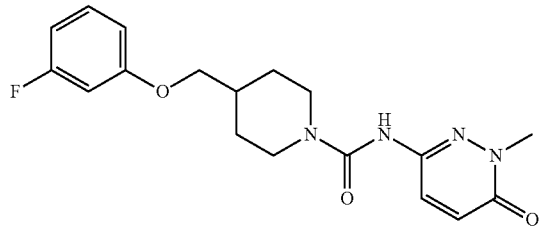 [SMILES: Cn1nc(NC(=O)N2CCC(COc3cccc(F)c3)CC2)ccc1=O]

To a solution of triphosgene (0.238 g, 0.8 mmol) in dichloromethane (10 mL) at −78° C. was added a solution of 6-hydroxy-2-methylpyridazin-3(2H)-one (0.2 g, 1.6 mmol) and pyridine (0.506 g, 6.4 mmol) in dichloromethane (5 mL) under argon. The mixture was stirred at −78° C. for 0.5 h, then a solution of 4-((2-fluorophenoxy)methyl)piperidine (0.34 g, 1.6 mmol) and pyridine (0.506 g, 6.4 mmol) in dichloromethane (5 mL) was added at −78° C. The resulting mixture was stirred at 25° C. for 18 h. The reaction was quenched with water (30 mL) and extracted with dichloromethane (50 mL×2). The combined organic layers were dried over sodium sulfate, filtered and concentrated under reduced pressure. The crude sample was dissolved in the minimum amount of N,N-dimethylformamide and purified via prep-HPLC (Boston C18, 10 μm, 21 mm×250 mm column; acetonitrile/0.01% aqueous trifluoroacetic acid) to afford 4-((3-fluorophenoxy)methyl)-N-(1-methyl-6-oxo-1,6-dihydropyridazin-3-yl)piperidine-1-carboxamide (0.023 g, 0.06 mmol, 4%) as a yellow solid. $^1$H NMR (400 MHz, Dimethylsulfoxide-d$_6$) δ 9.26 (s, 1H), 7.62 (d, J=9.9 Hz, 1H), 7.30 (q, J=7.9 Hz, 1H), 6.87 (d, J=9.9 Hz, 1H), 6.85-6.70 (m, 3H), 4.13 (d, J=13.2 Hz, 2H), 3.87 (d, J=6.3 Hz, 2H), 3.56 (s, 3H), 2.82 (t, J=12.1 Hz, 2H), 1.97 (s, 1H), 1.76 (d, J=11.3 Hz, 2H), 1.22 (dt, J=20.7, 10.5 Hz, 2H); LCMS (ESI) m/z: 361.1 [M+H]$^+$.

Example 30. Preparation of 4-(3-chloro-2-fluorophenoxy)-N-(1-methyl-6-oxo-1,6-dihydropyridazin-3-yl)piperidine-1-carboxamide (Compound 77)

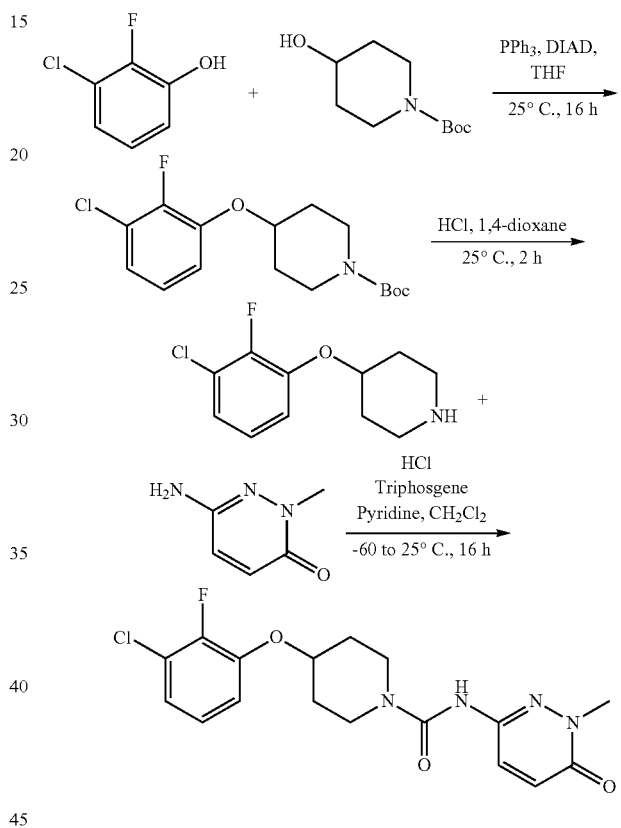

Step 1: Preparation of tert-butyl 4-(3-chloro-2-fluorophenoxy)piperidine-1-carboxylate

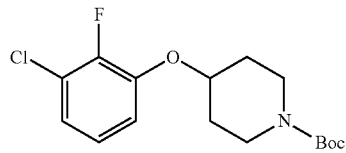 [SMILES: CC(C)(C)OC(=O)N1CCC(Oc2cccc(Cl)c2F)CC1]

To a solution of 3-chloro-2-fluorophenol (1.0 g, 6.85 mmol), tert-butyl 4-hydroxypiperidine-1-carboxylate (1.38 g, 6.85 mmol) and triphenylphosphine (2.15 g, 8.22 mmol) in tetrahydrofuran (15 mL) at 25° C. was added diisopropyl azodicarboxylate (1.65 g, 8.22 mmol). The mixture was stirred at 25° C. for 16 h, then the solvent was removed under reduced pressure. The crude residue was purified by column chromatography (silica gel, petroleum ether/ethyl acetate=10/1) to give tert-butyl 4-(3-chloro-2-fluorophenoxy)piperidine-1-carboxylate (1.28 g, crude) as a colorless oil. LCMS (ESI) m/z: 274.0 [M-56+H]⁺.

Step 2: Preparation of 4-(3-chloro-2-fluorophenoxy)piperidine Hydrochloride

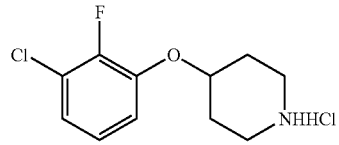

A solution of tert-butyl 4-(3-chloro-2-fluorophenoxy)piperidine-1-carboxylate (1.28 g, 3.89 mmol) and hydrochloric acid in 1,4-dioxane (6.0 mL, 24.0 mmol, 4 M) was stirred at 25° C. for 2 h. The reaction mixture was concentrated in vacuo to give 4-(3-chloro-2-fluorophenoxy)piperidine hydrochloride (870 mg, crude) as a white solid. This material was used in the next step without further purification. LCMS (ESI) m/z: 230.2 [M+H]⁺.

Step 3: Preparation of 4-(3-chloro-2-fluorophenoxy)-N-(1-methyl-6-oxo-1,6-dihydropyridazin-3-yl)piperidine-1-carboxamide

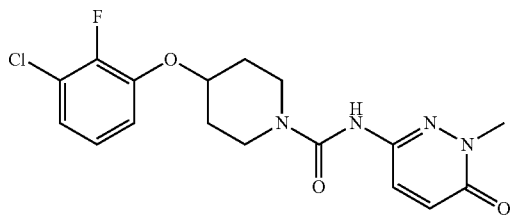

To a solution of triphosgene (166 mg, 0.566 mmol) in dichloromethane (10 mL) at 0° C. was added a solution of 6-amino-2-methylpyridazin-3(2H)-one (142 mg, 1.13 mmol) and diisopropylethylamine (293 mg, 2.26 mmol) in tetrahydrofuran (10 mL). The mixture was stirred at 0° C. for 1 h, then a solution of 4-(2-chloro-4-fluorophenoxy)piperidine hydrochloride (300 mg, 1.13 mmol) and diisopropylethylamine (293 mg, 2.26 mmol) in tetrahydrofuran (10 mL) was added. The reaction mixture was stirred at 25° C. for 16 h before it was concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 4-(3-chloro-2-fluorophenoxy)-N-(1-methyl-6-oxo-1,6-dihydropyridazin-3-yl)piperidine-1-carboxamide (208 mg, 0.547 mmol, 48%) as a white solid. ¹H NMR (400 MHz, Dimethylsulfoxide-d₆) δ 9.35 (s, 1H), 7.64 (d, J=10.0 Hz, 1H), 7.31-7.27 (m, 1H), 7.18-7.13 (m, 2H), 6.89 (d, J=10.0 Hz, 1H), 4.69-4.65 (m, 1H), 3.79-3.76 (m, 2H), 3.56 (s, 3H), 3.32-3.26 (m, 2H), 1.97-1.94 (m, 2H), 1.65-1.57 (m, 2H); LCMS (ESI) m/z: 380.9 [M+H]⁺.

Example 31. Preparation of N-(1-methyl-6-oxo-1,6-dihydropyridazin-3-yl)-4-(3-(trifluoromethyl)phenoxy)piperidine-1-carboxamide (Compound 74)

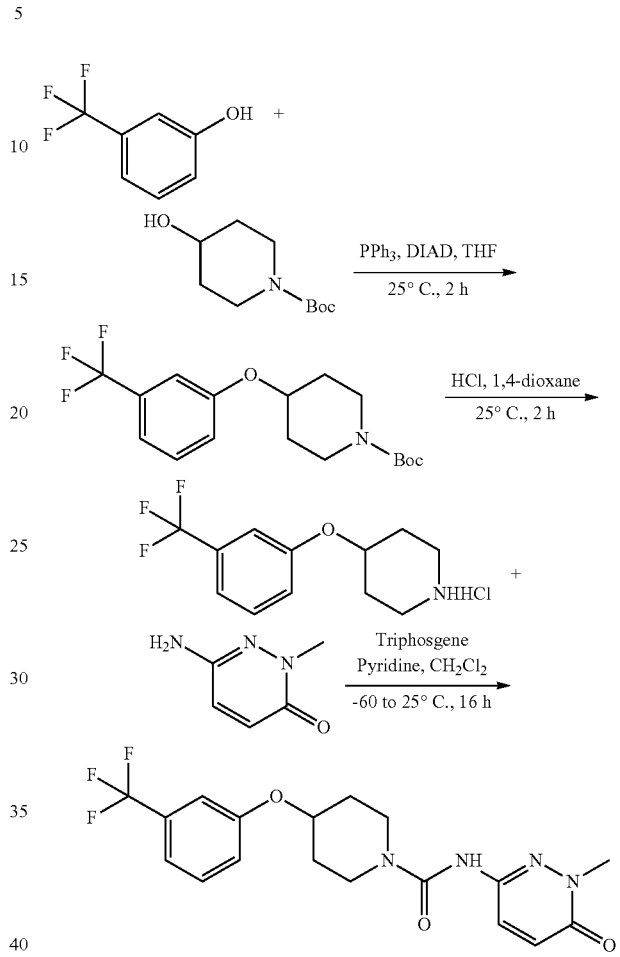

Step 1: Preparation of tert-butyl 4-(3-(trifluoromethyl)phenoxy)piperidine-1-carboxylate

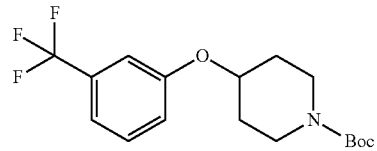 [SMILES: CC(C)(C)OC(=O)N1CCC(Oc2cccc(C(F)(F)F)c2)CC1]

To a solution of 3-(trifluoromethyl)phenol (1.0 g, 6.17 mmol), tert-butyl 4-hydroxypiperidine-1-carboxylate (1.24 g, 6.17 mmol) and triphenylphosphine (1.94 g, 7.41 mmol) in tetrahydrofuran (15 mL) was added diisopropyl azodicarboxylate (1.49 g, 7.41 mmol) at 25° C. The mixture was stirred at 25° C. for 16 h. The volatiles were removed under reduced pressure and the crude residue was purified by column chromatography (silica gel, petroleum ether/ethyl acetate=10/1) to give tert-butyl 4-(3-(trifluoromethyl)phenoxy)piperidine-1-carboxylate as a colorless oil (1.73 g, crude); LCMS (ESI) m/z: 263.0 [M-56+H]⁺.

Step 2: Preparation of 4-(3-(trifluoromethyl)phenoxy)piperidine hydrochloride

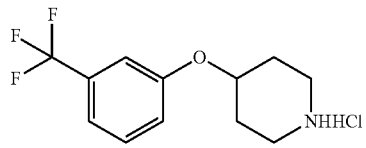

A solution of tert-butyl 4-(3-(trifluoromethyl)phenoxy)piperidine-1-carboxylate (1.73 g, 5.01 mmol) and hydrochloric acid in 1,4-dioxane (6.0 mL, 24.0 mmol, 4 M) was stirred at 25° C. for 2 h. The reaction mixture was concentrated in vacuo to give 4-(3-(trifluoromethyl)phenoxy)piperidine hydrochloride (900 mg, crude) as a white solid. This material was used in the next step without further purification. LCMS (ESI) m/z: 246.1 [M+H]$^+$.

Step 3: Preparation of N-(1-methyl-6-oxo-1,6-dihydropyridazin-3-yl)-4-(3-(trifluoromethyl)phenoxy)piperidine-1-carboxamide

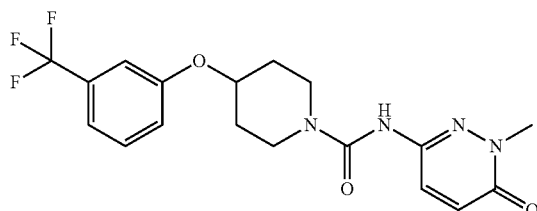

To a solution of triphosgene (166 mg, 0.566 mmol) in dichloromethane (10 mL) was added a solution of 6-amino-2-methylpyridazin-3(2H)-one (142 mg, 1.13 mmol) and diisopropylethylamine (293 mg, 2.26 mmol) in tetrahydrofuran (10 mL) at 0° C. The mixture was stirred at 0° C. for 1 h, then a solution of 4-(3-(trifluoromethyl)phenoxy)piperidine hydrochloride (318 mg, 1.13 mmol) and diisopropylethylamine (293 mg, 2.26 mmol) in tetrahydrofuran (10 mL) was added. The reaction mixture was stirred at 25° C. for 16 h before solvent was removed in vacuo. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give N-(1-methyl-6-oxo-1,6-dihydropyridazin-3-yl)-4-(3-(trifluoromethyl)phenoxy)piperidine-1-carboxamide (135.0 mg, 0.341 mmol, 30%) as a white solid. $^1$H NMR (400 MHz, Dimethylsulfoxide-d$_6$) δ 9.35 (s, 1H), 7.64 (d, J=9.6 Hz, 1H), 7.53 (t, J=8.2 Hz, 1H), 7.30 (t, J=10.0 Hz, 3H), 6.89 (d, J=9.6 Hz, 1H), 4.76-4.74 (m, 1H), 3.82-3.76 (m, 2H), 3.56 (s, 3H), 3.32-3.27 (m, 2H), 1.98-1.94 (m, 2H), 1.62-1.56 (m, 2H); LCMS (ESI) m/z: 397.0 [M+H]$^+$.

Example 32. Preparation of 4-(2-chloro-5-fluorophenoxy)-N-(1-methyl-6-oxo-1,6-dihydropyridazin-3-yl)piperidine-1-carboxamide (Compound 82)

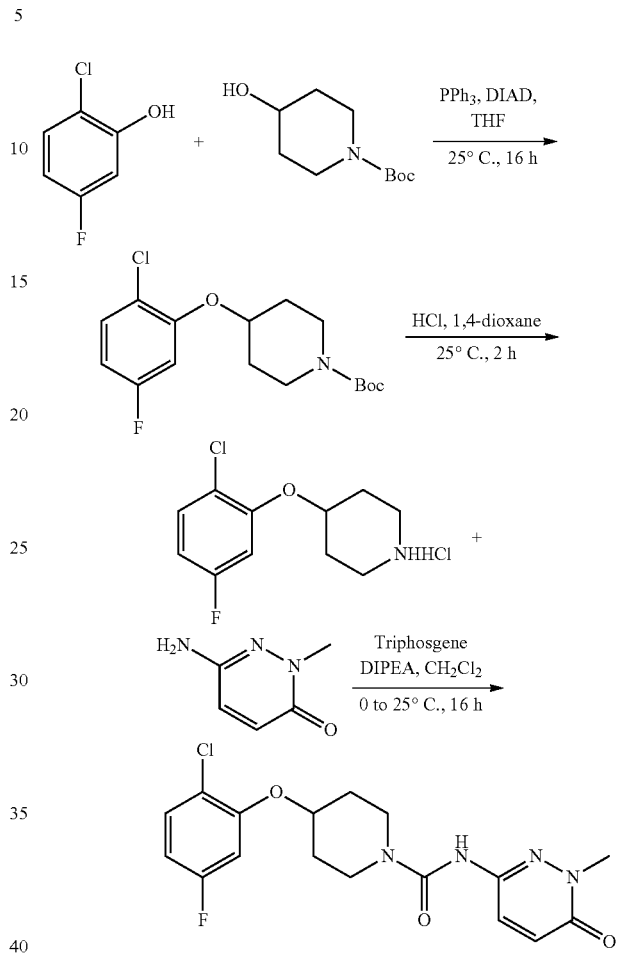

Step 1: Preparation of tert-butyl 4-(2-chloro-5-fluorophenoxy)piperidine-1-carboxylate

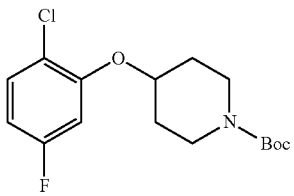 [SMILES: CC(C)(C)OC(=O)N1CCC(Oc2cc(F)ccc2Cl)CC1]

To a solution of 2-chloro-5-fluorophenol (2.0 g, 13.70 mmol), tert-butyl 4-hydroxypiperidine-1-carboxylate (2.76 g, 13.70 mmol), triphenylphosphine (4.31 g, 16.44 mmol) in tetrahydrofuran (15 mL) was added diisopropyl azodicarboxylate (3.32 g, 16.44 mmol) at 20° C. The mixture was stirred at 25° C. for 16 h. The volatiles were removed under reduced pressure and the residue was further purified by column chromatography (silica gel, petroleum ether/ethyl acetate=10/1) to give tert-butyl 4-(2-chloro-5-fluorophenoxy)piperidine-1-carboxylate as an opaque oil (4.0 g, crude); LCMS (ESI) m/z: 274.1 [M-56+H]$^+$.

Step 2: Preparation of 4-(2-chloro-5-fluorophenoxy)piperidine Hydrochloride

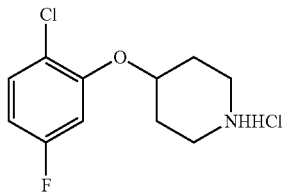

A solution of tert-butyl 4-(2-chloro-5-fluorophenoxy)piperidine-1-carboxylate (4.0 g, 12.15 mmol) and hydrochloric acid in 1,4-dioxane (9.1 mL, 36.5 mmol, 4N) was stirred at 25° C. for 2 h. The solution was concentrated to give 4-(2-chloro-5-fluorophenoxy)piperidine hydrochloride (3.0 g, crude) as a white solid. This material was used in the next step without further purification. LCMS (ESI) m/z: 230.1 [M+H]$^+$.

Step 3: Preparation of 4-(2-chloro-5-fluorophenoxy)-N-(1-methyl-6-oxo-1,6-dihydropyridazin-3-yl)piperidine-1-carboxamide

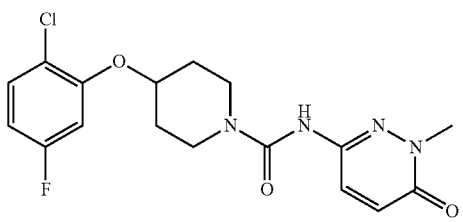 [SMILES: Cn1nc(NC(=O)N2CCC(Oc3cc(F)ccc3Cl)CC2)ccc1=O]

To a solution of triphosgene (111 mg, 0.378 mmol) in dichloromethane (10 mL) at 0° C. was added a solution of 6-amino-2-methylpyridazin-3(2H)-one (94 mg, 0.755 mmol) and diisopropylethylamine (195 mg, 1.51 mmol) in tetrahydrofuran (10 mL). The mixture was stirred at 0° C. for 1 h and a solution of 4-(2-chloro-5-fluorophenoxy)piperidine hydrochloride (200 mg, 0.755 mmol) and diisopropylethylamine (195 mg, 1.510 mmol) in tetrahydrofuran (10 mL) was added. The reaction mixture was stirred at 25° C. for 16 h. The volatiles were removed under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 4-(2-chloro-5-fluorophenoxy)-N-(1-methyl-6-oxo-1,6-dihydropyridazin-3-yl)piperidine-1-carboxamide (69.9 mg, 24%) as a white solid. $^1$H NMR (400 MHz, Dimethylsulfoxide-d$_6$) δ 9.35 (s, 1H), 7.65 (d, J=10.0 Hz, 1H), 7.47 (q, J=5.0 Hz, 1H), 7.26 (q, J=4.6 Hz, 1H), 6.89-6.81 (m, 2H), 4.79-4.75 (m, 1H), 3.71-3.67 (m, 2H), 3.56 (s, 3H), 3.43-3.37 (m, 2H), 1.96-1.91 (m, 2H), 1.67-1.60 (m, 2H); LCMS (ESI) m/z: 380.9 [M+H]$^+$.

Example 33. Preparation of 4-(2-chloro-4-fluorophenoxy)-N-(1-methyl-6-oxo-1,6-dihydropyridazin-3-yl)piperidine-1-carboxamide (Compound 83)

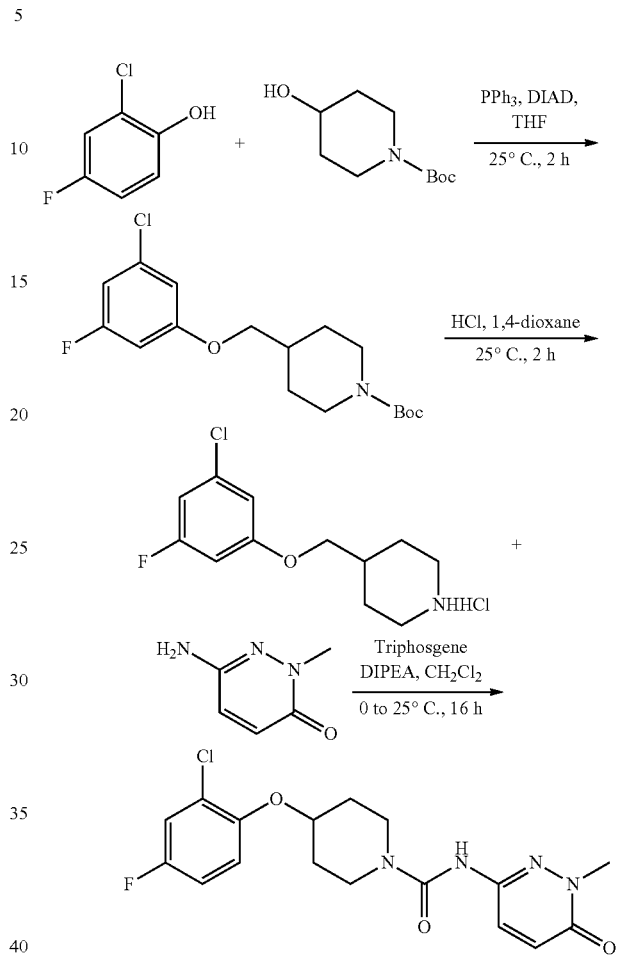

Step 1: Preparation of tert-butyl 4-(2-chloro-4-fluorophenoxy)piperidine-1-carboxylate

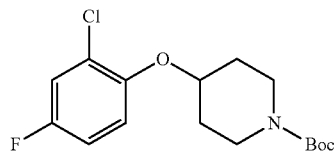 [SMILES: CC(C)(C)OC(=O)N1CCC(Oc2ccc(F)cc2Cl)CC1]

To a solution of 2-chloro-4-fluorophenol (2.0 g, 13.7 mmol), tert-butyl 4-hydroxypiperidine-1-carboxylate (2.76 g, 13.7 mmol) and triphenylphosphine (4.31 g, 16.4 mmol) in tetrahydrofuran (15 mL) at 25° C. was added diisopropyl azodicarboxylate (3.32 g, 16.4 mmol). The mixture was stirred at 25° C. for 16 h. The volatiles were removed under reduced pressure and the residue was further purified by column chromatography (silica gel, petroleum ether/ethyl acetate=10/1) to give tert-butyl 4-(2-chloro-4-fluorophenoxy)piperidine-1-carboxylate as an opaque oil (4.3 g, crude). LCMS (ESI) m/z: 274.1 [M-56+H]$^+$.

Step 2: Preparation of 4-(2-chloro-4-fluorophenoxy)piperidine Hydrochloride

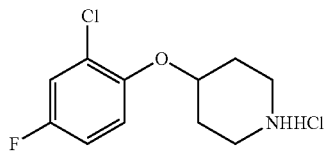

A solution of tert-butyl 4-(2-chloro-4-fluorophenoxy)piperidine-1-carboxylate (4.3 g, 13.1 mmol) and hydrochloric acid in 1,4-dioxane (9.8 mL, 39.2 mmol, 4 N) was stirred at 25° C. for 2 h. The solution was concentrated to give the crude 4-(2-chloro-4-fluorophenoxy)piperidine hydrochloride (3.1 g) as a white solid which was used in the next step without further purification. LCMS (ESI) m/z: 230.1 [M+H]$^+$.

Step 3: Preparation of 4-(2-chloro-4-fluorophenoxy)-N-(1-methyl-6-oxo-1,6-dihydropyridazin-3-yl)piperidine-1-carboxamide

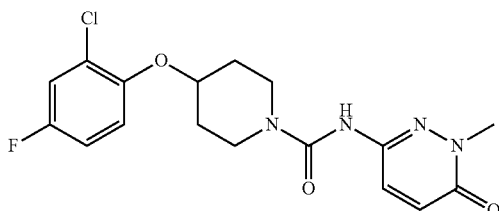

To a solution of triphosgene (183 mg, 0.622 mmol) in dichloromethane (10 mL) at 0° C. was added a solution of 6-amino-2-methylpyridazin-3(2H)-one (156 mg, 1.245 mmol) and diisopropylethylamine (322 mg, 2.49 mmol) in tetrahydrofuran (10 mL). The mixture was stirred at 0° C. for 1 h and a solution of 4-(2-chloro-4-fluorophenoxy)piperidine hydrochloride (330 mg, 1.25 mmol) and diisopropylethylamine (322 mg, 2.49 mmol) in tetrahydrofuran (10 mL) was added. The reaction was stirred at 25° C. for 16 h, then solvent was removed under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 4-(2-chloro-4-fluorophenoxy)-N-(1-methyl-6-oxo-1,6-dihydropyridazin-3-yl)piperidine-1-carboxamide (190.8 mg, 0.501 mmol, 40%) as a white solid. $^1$H NMR (400 MHz, Dimethylsulfoxide-d$_6$) δ 9.34 (s, 1H), 7.64 (d, J=10.0 Hz, 1H), 7.45 (q, J=3.8 Hz, 1H), 7.30 (q, J=4.8 Hz, 1H), 7.23 (m, 1H), 6.88 (d, J=10.0 Hz, 1H), 4.67-4.64 (m, 1H), 3.72-3.66 (m, 2H), 3.56 (s, 3H), 3.41-3.35 (m, 2H), 1.94-1.89 (m, 2H), 1.67-1.60 (m, 2H); LCMS (ESI) m/z: 380.9 [M+H]$^+$.

Example 34. 4-(3-fluorobenzyloxy)-N-(1-methyl-6-oxo-1,6-dihydropyridazin-3-yl)piperidine-1-carboxamide (Compound 96)

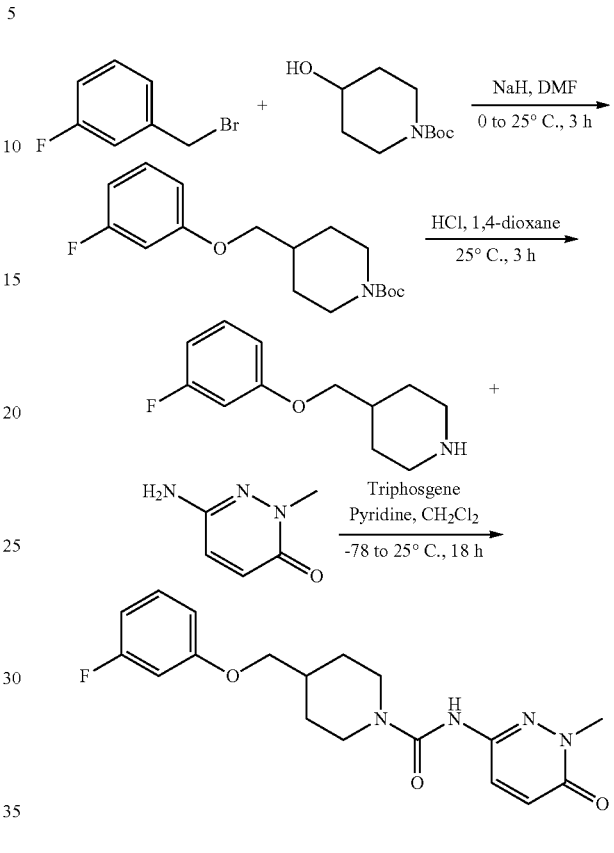

Step 1: Preparation of tert-butyl 4-(3-fluorobenzyloxy)piperidine-1-carboxylate

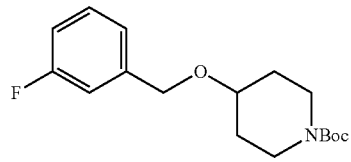 [SMILES: CC(C)(C)OC(=O)N1CCC(OCc2cccc(F)c2)CC1]

To a slurry of sodium hydride (800 mg, 20 mmol, 60% in mineral oil) in dry N,N-dimethylformamide (20 mL) was added a solution of tert-butyl 4-hydroxypiperidine-1-carboxylate (2.01 g, 10 mmol) in dry N,N-dimethylformamide (10 mL) at 0° C. under argon. The mixture was stirred at 0° C. for 20 min, then a solution of 1-(bromomethyl)-3-fluorobenzene (2.0 g, 10 mmol) in dry N,N-dimethylformamide (10 mL) was added at 0° C. The resulting mixture was stirred at 25° C. for 3 h. The mixture was poured into water (120 mL) and extracted with ethyl acetate (100 mL×2). The combined organic layers were concentrated under reduced pressure. The residue was purified by column chromatography silica gel, petroleum ether/ethyl acetate=15/1) to give tert-butyl 4-(32-fluorobenzyloxy)piperidine-1-carboxylate (2.3 g, 6.9 mmol, 74%) as a colorless oil. LCMS (ESI) m/z: 332.1 [M+Na]$^+$.

Step 2: Preparation of 4-(3-fluorobenzyloxy)piperidine

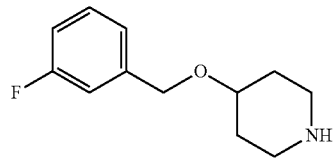 [SMILES: Fc1cccc(COC2CCNCC2)c1]

A solution of tert-butyl 4-(3-fluorobenzyloxy)piperidine-1-carboxylate (2.3 g, 1.61 mmol) and 4 M hydrochloric acid in 1,4-dioxane (30 mL) was stirred at 25° C. for 2 h. The mixture was concentrated under reduced pressure. The residue was diluted with ethyl acetate (50 mL) and water (50 mL) then was adjusted to pH 9 with aqueous sodium bicarbonate. The aqueous layer was extracted with ethyl acetate (30 mL×3). The combined organic layers were dried over sodium sulfate, filtered and concentrated to give 4-(2-fluorobenzyloxy)piperidine (1.3 g, crude) as a yellow oil. LCMS (ESI) m/z: 210.1 [M+H]$^+$.

Step 3: Preparation of 4-(3-fluorobenzyloxy)-N-(1-methyl-6-oxo-1,6-dihydropyridazin-3-yl)piperidine-1-carboxamide

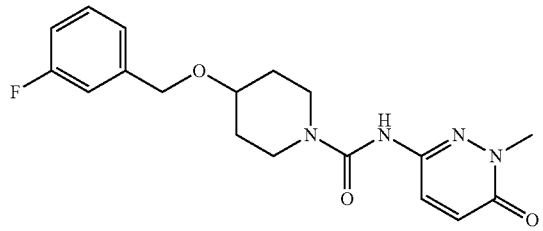

To a solution of triphosgene (150 mg, 0.5 mmol) in dichloromethane (3 mL) at −78° C. was added a mixture of 6-amino-2-methylpyridazin-3(2H)-one (125 mg, 1 mmol) and pyridine (316 mg, 4 mmol) in dichloromethane (2 mL). The reaction mixture was stirred for 0.5 h, then a solution of 4-(3-fluorobenzyloxy)piperidine (209 mg, 1 mmol) in pyridine (316 mg, 4 mmol) was added. The mixture was stirred at 25° C. for 18 h. The mixture was quenched with aqueous ammonium chloride and extracted with dichloromethane (20 mL×2). The combined organic layers were concentrated in vacuo. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 4-(3-fluorobenzyloxy)-N-(1-methyl-6-oxo-1,6-dihydropyridazin-3-yl)piperidine-1-carboxamide (83.8 mg, 0.232 mmol, 23%) as a yellow solid. $^1$H NMR (500 MHz, Dimethylsulfoxide-d$_6$) δ 9.28 (s, 1H), 7.62 (d, J=10 Hz, 1H), 7.42-7.36 (m, 1H), 7.12-7.07 (m, 3H), 6.87 (d, J=9.6 Hz, 1H), 4.55 (s, 2H), 3.78-3.72 (m, 2H), 3.62-3.57 (m, 1H), 3.55 (s, 3H), 3.18-3.12 (m, 2H), 1.88-1.84 (m, 2H), 1.51-1.42 (m, 2H); LCMS (ESI) m/z: 361.2 [M+H]$^+$.

Example 35. Preparation of 4-((2-fluorophenoxy)methyl)-N-(1-methyl-6-oxo-1,6-dihydropyridazin-3-yl)piperidine-1-carboxamide (Compound 99)

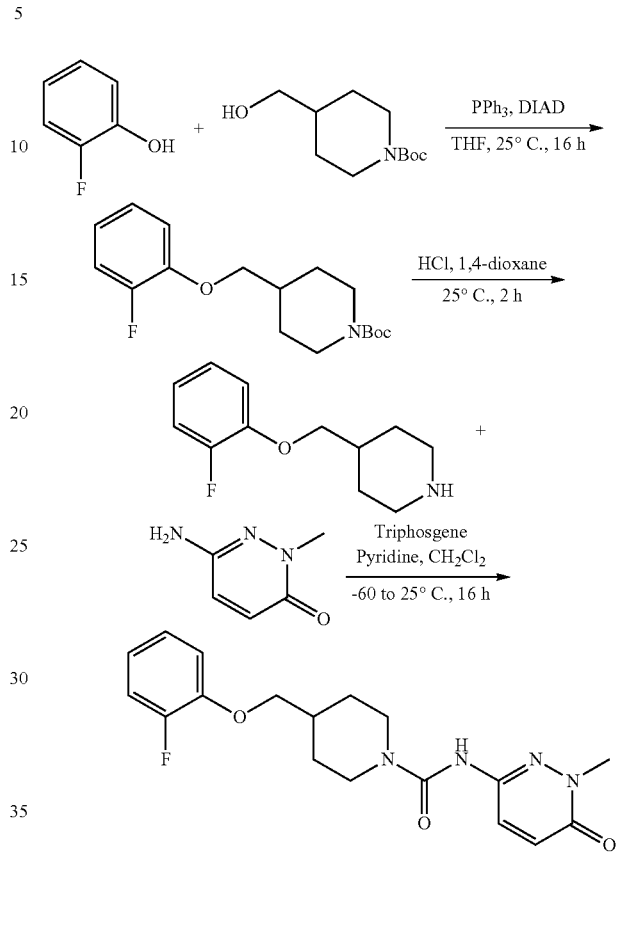

Step 1: Preparation of tert-butyl 4-((2-fluorophenoxy)methyl)piperidine-1-carboxylate

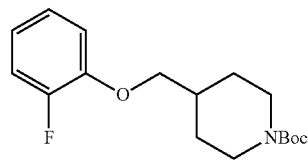 [SMILES: CC(C)(C)OC(=O)N1CCC(COc2ccccc2F)CC1]

A mixture of triphenylphosphine (5.61 g, 21.4 mmol), diisopropyl azodicarboxylate (4.33 g, 21.4 mmol) in tetrahydrofuran (80 mL) was stirred at 25° C. for 10 min, then tert-butyl 4-(hydroxymethyl)piperidine-1-carboxylate (3.84 g, 17.9 mmol) was added. The mixture was stirred at 25° C. for 20 min, then 2-fluorophenol (2 g, 17.9 mmol) was added. The mixture was stirred at 25° C. for 15 h. The reaction was concentrated then triturated in petroleum ether (200 mL) and stirred for 1 h. The mixture was filtered to remove the solid precipitate and the filtrate was concentrated in vacuo. The crude residue obtained was purified by column chromatography (silica gel, petroleum ether/ethyl acetate=15/1) to give tert-butyl 4-((2-fluorophenoxy)methyl)piperidine-1-carboxylate (1.95 g, 6.31 mmol, 35%) as a white solid. LCMS (ESI) m/z: 332.1 [M+Na]$^+$.

Step 2: Preparation of 4-((2-fluorophenoxy)methyl)piperidine

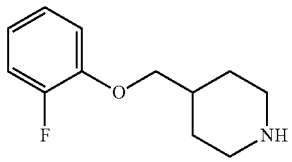 [SMILES: Fc1ccccc1OCC1CCNCC1]

A solution of tert-butyl 4-((2-fluorophenoxy)methyl)piperidine-1-carboxylate (1.95 g, 6.31 mmol) and hydrochloric acid in 1,4-dioxane (50 mL, 4 N) was stirred at 25° C. for 2 h under nitrogen. The reaction mixture was filtered and washed with petroleum ether (30 mL×2). The white solid was dissolved in pH 8 aqueous sodium bicarbonate solution and extracted with dichloromethane (250 mL×3). The combined organic layers were dried over sodium sulfate, filtered and concentrated in vacuo to afford 4-((2-fluorophenoxy)methyl)piperidine (1.18 g, 5.62 mmol, 89%) as a yellow oil. LCMS (ESI) m/z: 210.1 [M+H]$^+$.

Step 3: Preparation of 4-((2-fluorophenoxy)methyl)-N-(1-methyl-6-oxo-1,6-dihydropyridazin-3-yl)piperidine-1-carboxamide

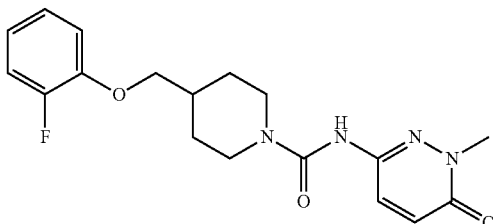

To a solution of triphosgene (0.238 g, 0.8 mmol) in dichloromethane (10 mL) at −60° C. was added a solution of 6-hydroxy-2-methylpyridazin-3(2H)-one (0.2 g, 1.6 mmol) and pyridine (0.506 g, 6.4 mmol) in dichloromethane (5 mL) under argon. The mixture was stirred at −60° C. for 0.5 h, then a solution of 4-((2-fluorophenoxy)methyl)piperidine (0.34 g, 1.6 mmol) and pyridine (0.506 g, 6.4 mmol) in dichloromethane (5 mL) was added at −60° C. The resulting mixture was stirred at 25° C. for 18 h. The reaction was quenched with water (30 mL) and extracted with dichloromethane (50 mL×2). The combined organic layers were dried over sodium sulfate, filtered and concentrated under reduced pressure. The crude sample was dissolved in the minimum amount of N,N-dimethylformamide and purified via prep-HPLC (Boston C18, 10 μm, 21 mm×250 mm column; acetonitrile/0.01% aqueous trifluoroacetic acid) to give 4-((2-fluorophenoxy)methyl)-N-(1-methyl-6-oxo-1,6-dihydropyridazin-3-yl)piperidine-1-carboxamide (0.012 g, 0.03 mmol, 2%) as a yellow solid. $^1$H NMR (400 MHz, Dimethylsulfoxide-d$_6$) δ 9.26 (s, 1H), 7.62 (d, J=9.8 Hz, 1H), 7.30 (dd, J=15.5, 8.1 Hz, 1H), 6.87 (d, J=9.8 Hz, 1H), 6.84-6.71 (m, 3H), 4.12 (d, J=12.9 Hz, 2H), 3.87 (d, J=6.4 Hz, 2H), 3.56 (s, 3H), 2.81 (t, J=12.0 Hz, 2H), 1.97 (s, 1H), 1.76 (d, J=11.0 Hz, 2H), 1.21 (dd, J=20.7, 12.0 Hz, 2H); LCMS (ESI) m/z: 361.0 [M+H]$^+$.

Example 36. 4-(2-fluorobenzyloxy)-N-(1-methyl-6-oxo-1,6-dihydropyridazin-3-yl)piperidine-1-carboxamide (Compound 97)

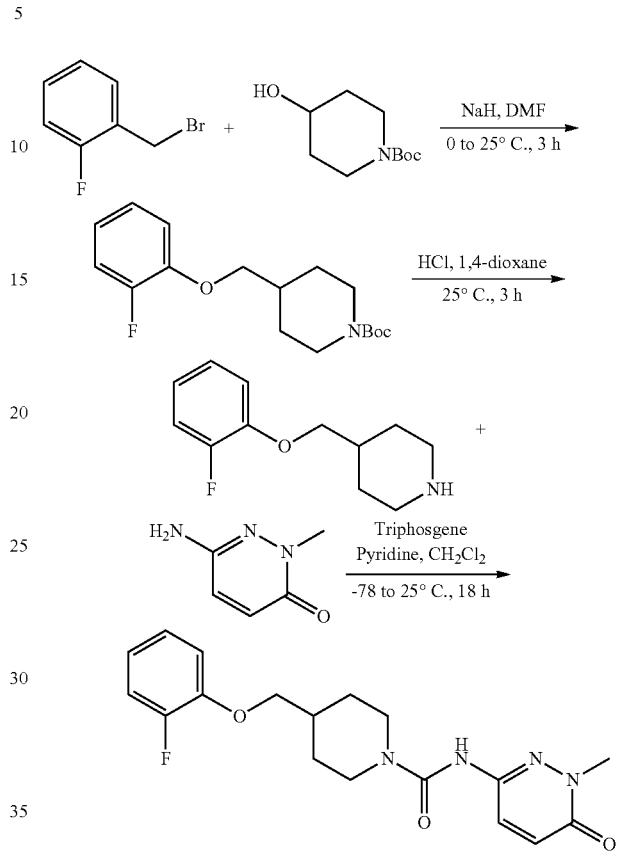

Step 1: Preparation of tert-butyl 4-(2-fluorobenzyloxy)piperidine-1-carboxylate

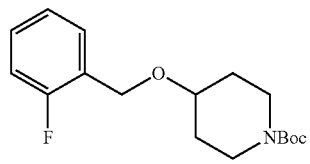 [SMILES: CC(C)(C)OC(=O)N1CCC(OCc2ccccc2F)CC1]

To a slurry of sodium hydride (800 mg, 20 mmol, 60% in mineral oil) in dry N,N-dimethylformamide (20 mL) was added a solution of tert-butyl 4-hydroxypiperidine-1-carboxylate (2.01 g, 10 mmol) in dry N,N-dimethylformamide (10 mL) at 0° C. under argon. The mixture was stirred at 0° C. for 20 min, then a solution of 1-(bromomethyl)-2-fluorobenzene (2.0 g, 10 mmol) in dry N,N-dimethylformamide (10 mL) was added at 0° C. The resulting mixture was stirred at 25° C. for 3 h. The reaction solution was poured into water (120 mL) and extracted with ethyl acetate (100 mL×2). The combined organic layers were concentrated under reduced pressure. The crude residue was purified by column chromatography (silica gel, petroleum ether/ethyl acetate=15/1) to give tert-butyl 4-(2-fluorobenzyloxy)piperidine-1-carboxylate (2.6 g, 8.41 mmol, 84%) as a colorless oil. LCMS (ESI) m/z 332.1 [M+Na]$^+$.

Step 2: Preparation of 4-(2-fluorobenzyloxy)piperidine

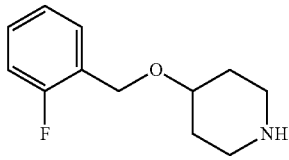 [SMILES: Fc1ccccc1COC1CCNCC1]

A solution of tert-butyl 4-(2-fluorobenzyloxy)piperidine-1-carboxylate (2.3 g, 1.61 mmol) and hydrochloric acid in 1,4-dioxane (30 mL, 4M) was stirred at 25° C. for 2 h. The reaction mixture was concentrated under reduced pressure. The residue was diluted with ethyl acetate (50 mL) and water (50 mL) and then the mixture was adjusted to pH 9 with aqueous sodium bicarbonate solution. The aqueous layer was extracted with ethyl acetate (30 mL×3). The combined organic layers were dried over sodium sulfate, filtered and concentrated to give 4-(2-fluorobenzyloxy)piperidine (1.3 g, crude) as a yellow oil. LCMS (ESI) m/z: 210.1 $[M+H]^+$.

Step 3: Preparation of 4-(2-fluorobenzyloxy)-N-(1-methyl-6-oxo-1,6-dihydropyridazin-3-yl)piperidine-1-carboxamide

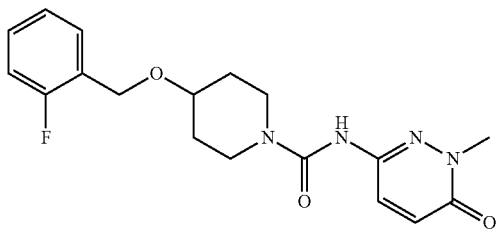 [SMILES: Cn1nc(NC(=O)N2CCC(OCc3ccccc3F)CC2)ccc1=O]

To a solution of triphosgene (30 mg, 0.1 mmol) in dichloromethane (3 mL) at −78° C. was added a mixture of 6-amino-2-methylpyridazin-3(2H)-one (25 mg, 0.2 mmol) and pyridine (63 mg, 0.8 mmol) in dichloromethane (2 mL). The reaction mixture was stirred for 0.5 h, then a mixture of 4-(2-fluorobenzyloxy)piperidine (38 mg, 0.2 mmol) in pyridine (63 mg, 0.8 mmol) was added. The mixture was warmed to 25° C. After 18 h, the mixture was quenched with aqueous ammonium chloride and then extracted with dichloromethane (20 mL). The organic layer was concentrated to give a crude residue that was dissolved in the minimum amount of N,N-dimethylformamide and purified via prep-HPLC (Boston C18, 10 μm, 21 mm×250 mm column; acetonitrile/0.01% aqueous trifluoroacetic acid) to give 4-(2-fluorobenzyloxy)-N-(1-methyl-6-oxo-1,6-dihydropyridazin-3-yl)piperidine-1-carboxamide (62.7 mg, 0.174 mmol, 87%) as a yellow solid. $^1$H NMR (500 MHz, Dimethylsulfoxide-$d_6$) δ 9.22 (s, 1H), 7.61 (d, J=10 Hz, 1H), 7.49-7.45 (m, 1H), 7.36-7.33 (m, 1H), 7.22-7.16 (m, 2H), 6.86 (d, J=9.6 Hz, 1H), 4.57 (s, 2H), 3.76-3.72 (m, 2H), 3.71-3.61 (m, 1H), 3.55 (s, 3H), 3.19-3.12 (m, 2H), 1.88-1.84 (m, 2H), 1.50-1.42 (m, 2H); LCMS (ESI) m/z: 361.2 $[M+H]^+$.

Example 37. Preparation of 4-((2-chlorophenoxy)methyl)-N-(1-methyl-6-oxo-1,6-dihydropyridazin-3-yl)piperidine-1-carboxamide (Compound 98)

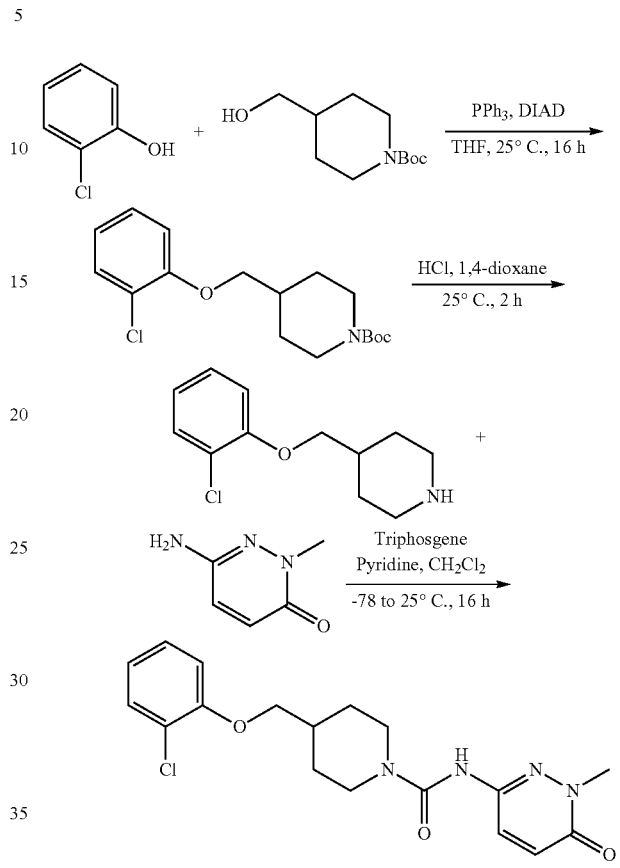

Step 1: Preparation of tert-butyl 4-((2-chlorophenoxy)methyl)piperidine-1-carboxylate

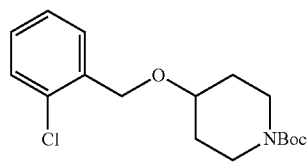 [SMILES: CC(C)(C)OC(=O)N1CCC(OCc2ccccc2Cl)CC1]

A mixture of triphenylphosphine (4.87 g, 18.6 mmol) and diisopropyl azodicarboxylate (3.76 g, 18.6 mmol) in tetrahydrofuran (80 mL) was stirred at 25° C. for 10 min, then tert-butyl 4-(hydroxymethyl)piperidine-1-carboxylate (3.33 g, 15.5 mmol) was added. The mixture was stirred at 25° C. for 20 min, then 2-chlorophenol (2 g, 15.5 mmol) was added. The mixture was stirred at 25° C. for 15 h. The reaction mixture was filtered and the filtrate was concentrated under reduced pressure. The crude oil was purified by column chromatography (silica gel, petroleum ether/ethyl acetate=15/1) and then triturated with petroleum ether (200 mL) to give tert-butyl 4-((2-chlorophenoxy)methyl)piperidine-1-carboxylate (1.92 g, 5.89 mmol, 38%) as a white solid. LCMS (ESI) m/z: 348.1 $[M+Na]^+$.

Step 2: Preparation of 4-((2-chlorophenoxy)methyl)piperidine

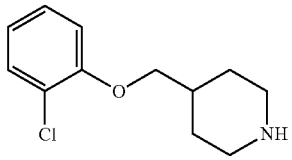 [SMILES: Clc1ccccc1OCC1CCNCC1]

A solution of tert-butyl 4-((2-chlorophenoxy)methyl)piperidine-1-carboxylate (1.92 g, 5.89 mmol) and 4N hydrochloric acid in 1,4-dioxane solution (50 mL) was stirred at 25° C. for 2 h under nitrogen. The reaction mixture was filtered, and the white solid then washed with petroleum ether (30 mL×2). The solid was suspended in aqueous sodium bicarbonate solution (pH 8) and the resulting mixture was extracted with dichloromethane (250 mL×3). The combined organic layers were dried over sodium sulfate, filtered and concentrated in vacuo to afford 4-((2-chlorophenoxy)methyl)piperidine (1.25 g, 5.54 mmol, 94%) as a yellow oil. LCMS (ESI) m/z: 226.2 [M+H]$^+$.

Step 3: Preparation of 4-((2-chlorophenoxy)methyl)-N-(1-methyl-6-oxo-1,6-dihydropyridazin-3-yl)piperidine-1-carboxamide

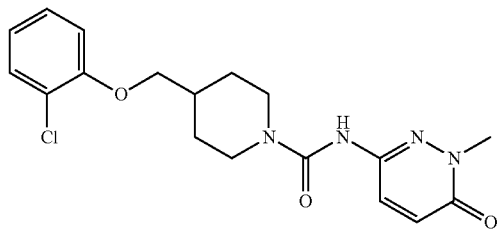 [SMILES: Cn1nc(NC(=O)N2CCC(COc3ccccc3Cl)CC2)ccc1=O]

To a solution of triphosgene (0.238 g, 0.8 mmol) in dichloromethane (10 mL) at −78° C. was added a solution of 6-hydroxy-2-methylpyridazin-3(2H)-one (0.2 g, 1.6 mmol) and pyridine (0.506 g, 6.4 mmol) in dichloromethane (5 mL) under argon. The mixture was stirred at −78° C. for 0.5 h, then a solution of 4-((2-chlorophenoxy)methyl)piperidine (0.36 g, 1.6 mmol) and pyridine (0.506 g, 6.4 mmol) in dichloromethane (5 mL) was added at −78° C. The resulting mixture was warmed to 25° C. After 18 h, the reaction was quenched with water (30 mL) and the aqueous layer was extracted with dichloromethane (50 mL×2). The combined organic layers were dried over sodium sulfate, filtered and concentrated under reduced pressure. The crude sample was dissolved in the minimum amount of N,N-dimethylformamide and purified via prep-HPLC (Boston C18, 10 μm, 21 mm×250 mm column; acetonitrile/0.01% aqueous trifluoroacetic acid) to give 4-((2-chlorophenoxy)methyl)-N-(1-methyl-6-oxo-1,6-dihydropyridazin-3-yl)piperidine-1-carboxamide (0.078 g, 0.20 mmol, 13%) as a yellow solid. $^1$H NMR (400 MHz, Dimethylsulfoxide-d$_6$) δ 9.27 (s, 1H), 7.62 (d, J=9.9 Hz, 1H), 7.42 (dd, J=7.9, 1.5 Hz, 1H), 7.34-7.25 (m, 1H), 7.18-7.10 (m, 1H), 6.95 (td, J=7.8, 1.2 Hz, 1H), 6.88 (d, J=9.9 Hz, 1H), 4.14 (d, J=13.3 Hz, 2H), 3.94 (d, J=6.3 Hz, 2H), 3.56 (s, 3H), 2.83 (t, J=11.9 Hz, 2H), 2.02 (s, 1H), 1.80 (d, J=11.0 Hz, 2H), 1.27 (qd, J=12.6, 4.0 Hz, 2H); LCMS (ESI) m/z: 377.0 [M+H]$^+$.

Example 38. Preparation of N-(1-methyl-6-oxo-1,6-dihydropyridazin-3-yl)-4-((2-(trifluoromethyl)phenoxy)methyl)piperidine-1-carboxamide (Compound 100)

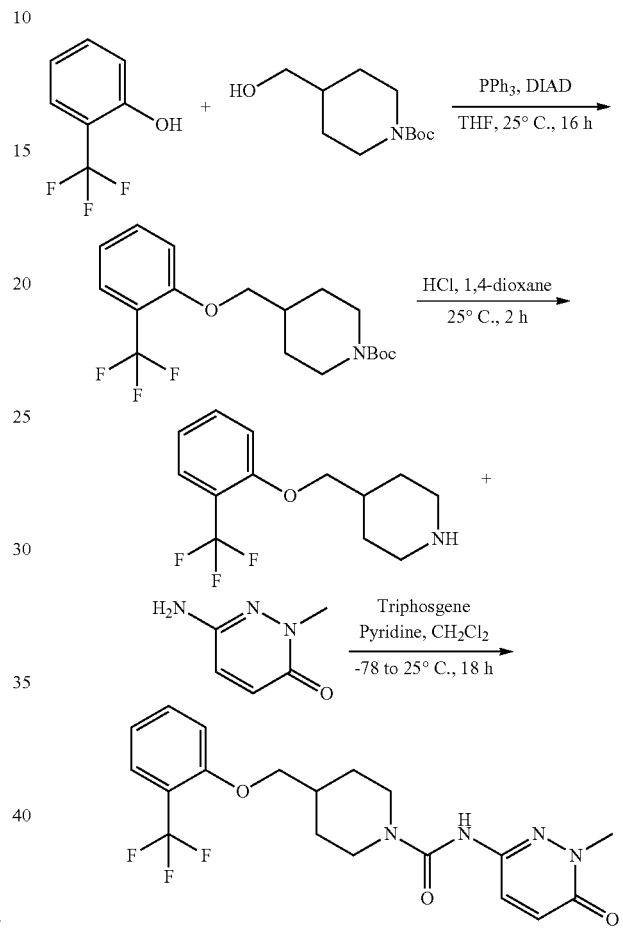

Step 1: Preparation of tert-butyl 4-((2-(trifluoromethyl)phenoxy)methyl)piperidine-1-carboxylate

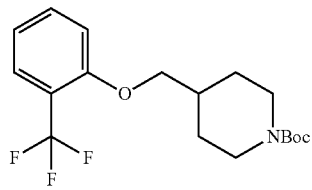 [SMILES: CC(C)(C)OC(=O)N1CCC(COc2ccccc2C(F)(F)F)CC1]

A mixture of triphenylphosphine (3.88 g, 14.8 mmol) and diisopropyl azodicarboxylate (2.99 g, 14.8 mmol) in tetrahydrofuran (80 mL) was stirred at 25° C. for 10 min then tert-butyl 4-(hydroxymethyl)piperidine-1-carboxylate (2.64 g, 12.3 mmol) was added. The mixture was stirred at 25° C. for 20 min then 2-(trifluoromethyl)phenol (2 g, 12.3 mmol) was added. The mixture was stirred at 25° C. for 15 h, then concentrated under reduced pressure, triturated with petroleum ether (200 mL), and stirred for about 1 h. The mixture was filtered, and the filtrate was concentrated under reduced pressure. The crude oil was purified by column chromatography (silica gel, petroleum ether/ethyl acetate=15/1) to give tert-butyl 4-((2-(trifluoromethyl)phenoxy)methyl)piperidine-1-carboxylate (1.77 g, 4.93 mmol, 40%) as a white solid. LCMS (ESI) m/z: 382.2 [M+Na]$^+$.

Step 2: Preparation of 4-((2-(trifluoromethyl)phenoxy)methyl)piperidine

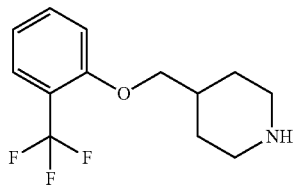 [SMILES: FC(F)(F)c1ccccc1OCC1CCNCC1]

A solution of tert-butyl 4-((2-(trifluoromethyl)phenoxy)methyl)piperidine-1-carboxylate (1.77 g, 4.93 mmol) and hydrochloric acid in 1,4-dioxane (50 mL, 4 M) was stirred at 25° C. for 2 h under nitrogen.

The reaction mixture was filtered and washed with petroleum ether (30 mL×2). The solid was suspended in aqueous sodium bicarbonate solution (pH 8) and extracted with dichloromethane (250 mL×3). The combined organic layers were dried over sodium sulfate, filtered and concentrated to afford 4-((2-(trifluoromethyl)phenoxy)methyl)piperidine (1.25 g, 5.54 mmol, 82%) as a yellow oil. LCMS (ESI) m/z: 260.3 [M+H]$^+$.

Step 3: Preparation of N-(1-methyl-6-oxo-1,6-dihydropyridazin-3-yl)-4-((2-(trifluoromethyl)phenoxy)methyl)piperidine-1-carboxamide

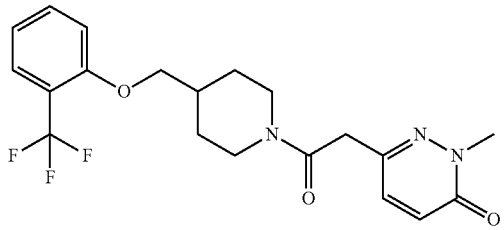 [SMILES: Cn1nc(CC(=O)N2CCC(COc3ccccc3C(F)(F)F)CC2)ccc1=O]

To a solution of triphosgene (0.238 g, 0.8 mmol) in dichloromethane (10 mL) at −78° C. was added a solution of 6-hydroxy-2-methylpyridazin-3(2H)-one (0.2 g, 1.6 mmol) and pyridine (0.506 g, 6.4 mmol) in dichloromethane (5 mL) under argon. The mixture was stirred at −78° C. for 0.5 h, then a solution of 4-((2-(trifluoromethyl)phenoxy)methyl)piperidine (0.41 g, 1.6 mmol) and pyridine (0.506 g, 6.4 mmol) in dichloromethane (5 mL) was added at −78° C. The resulting mixture was stirred at 25° C. for 18 h. The reaction mixture was quenched with water (30 mL) and the aqueous layer was extracted with dichloromethane (50 mL×2). The combined organic layers were dried over sodium sulfate, filtered and concentrated under reduced pressure. The crude sample was dissolved in the minimum amount of N,N-dimethylformamide and purified via prep-HPLC (Boston C18, 10 μm, 21 mm×250 mm column; acetonitrile/0.01% aqueous trifluoroacetic acid) to give N-(1-methyl-6-oxo-1,6-dihydropyridazin-3-yl)-4-((2-(trifluoromethyl)phenoxy)methyl)piperidine-1-carboxamide (0.008 g, 0.02 mmol, 1%) as a yellow solid. $^1$H NMR (400 MHz, Dimethylsulfoxide-d$_6$) δ 9.26 (s, 1H), 7.61 (m, 3H), 7.25 (d, J=8.5 Hz, 1H), 7.08 (t, J=7.6 Hz, 1H), 6.88 (d, J=9.8 Hz, 1H), 4.14 (d, J=13.1 Hz, 2H), 3.99 (d, J=5.9 Hz, 2H), 3.56 (s, 3H), 2.82 (t, J=12.2 Hz, 2H), 2.01 (s, 1H), 1.76 (d, J=13.4 Hz, 2H), 1.26 (m, 2H); LCMS (ESI) m/z: 411.1 [M+H]$^+$.

Example 39. Preparation of 4-(3-chlorophenoxy)-N-(1-methyl-6-oxo-1,6-dihydropyridazin-3-yl)piperidine-1-carboxamide (Compound 68)

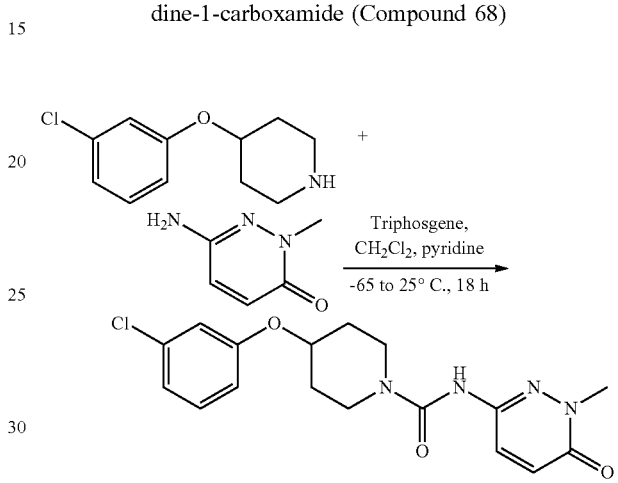

Step 1: Preparation of 4-(3-chlorophenoxy)-N-(1-methyl-6-oxo-1,6-dihydropyridazin-3-yl)piperidine-1-carboxamide

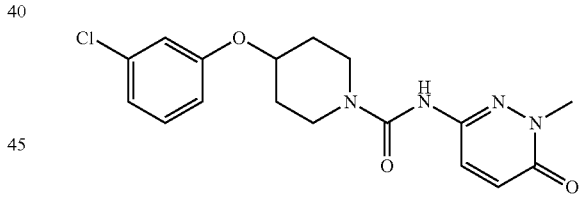

To a solution of triphosgene (5.93 g, 20 mmol) in dichloromethane (200 mL) at −65° C. was added a solution of 6-amino-2-methyl pyridazin-3(2H)-one (5.01 g, 40 mmol) and pyridine (12.7 g, 160 mmol) in dichloromethane (100 mL) under argon. The mixture was stirred at −65° C. for 4 h and a solution of 4-(3-chlorophenoxy)piperidine (8.04 g, 38 mmol) and pyridine (12.7 g, 160 mmol) in dichloromethane (100 mL) was added at −50° C. The resulting mixture was warmed and then stirred at 25° C. for 18 h. The reaction was quenched with water (400 mL) and the aqueous layer was extracted with dichloromethane (1000 mL×2). The combined organic layers were dried over sodium sulfate, filtered and concentrated under reduced pressure. The crude residue was purified by column chromatography (silica gel, petroleum ether/ethyl acetate/ammonia in methanol (7 N) from 10/5/1 to 5/5/1) to give crude product as a yellow solid (6.5 g, 18 mmol, 47%). The yellow solid was triturated in diethyl ether (200 mL), filtered and washed with diethyl ether to give a yellow solid, which was dissolved in N,N- dimethylformamide (20 mL) and the solution was added to water (500 mL) dropwise. The precipitate was collected by filtration and washed with water (100 mL) to give 4-(3-chlorophenoxy)-N-(1-methyl-6-oxo-1,6-dihydropyridazin-3-yl)piperidine-1-carboxamide as a yellow solid (5.0 g, 13.8 mmol, 36%). $^1$H NMR (400 MHz, Dimethylsulfoxide-d$_6$) δ 9.32 (s, 1H), 7.64 (d, J=9.6 Hz, 1H), 7.31 (t, J=8.0 Hz, 1H), 7.09 (d, J=2.0 Hz, 1H), 6.96-7.01 (m, 2H), 6.88 (d, J=10.0 Hz, 1H), 4.64-4.68 (m, 1H), 3.76-3.82 (m, 2H), 3.57 (s, 3H), 3.26-3.32 (m, 2H), 1.93-1.97 (m, 2H), 1.53-1.61 (m, 2H); LCMS (ESI) m/z: 363.0 [M+H]$^+$.

Example 40. Preparation of 4-(3,5-difluorophenoxy)-N-(1-methyl-6-oxo-1,6-dihydropyridazin-3-yl)piperidine-1-carboxamide (Compound 79)

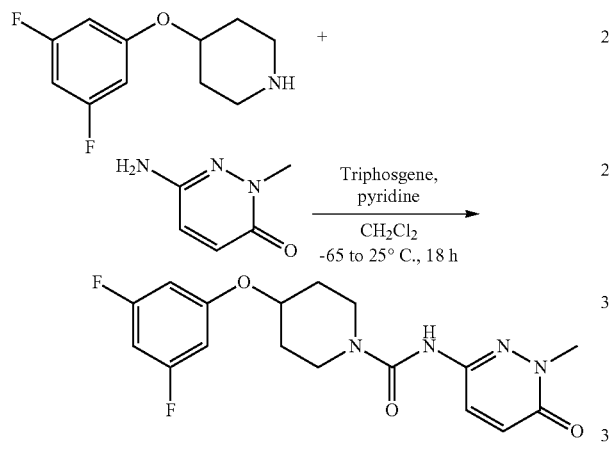

Step 1: Preparation of 4-(3,5-difluorophenoxy)-N-(1-methyl-6-oxo-1,6-dihydropyridazin-3-yl)piperidine-1-carboxamide

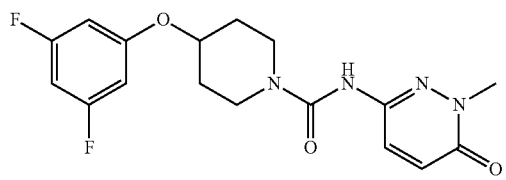 [SMILES: Cn1nc(NC(=O)N2CCC(Oc3cc(F)cc(F)c3)CC2)ccc1=O]

To a solution of triphosgene (119 mg, 0.4 mmol) in dichloromethane (10 mL) at −65° C. was added a solution of 6-amino-2-methylpyridazin-3(2H)-one (100 mg, 0.8 mmol) and pyridine (253 mg, 3.2 mmol) in dichloromethane (5 mL) under argon. The mixture was stirred at −65° C. for 30 min and a solution of 4-(3,5-difluorophenoxy)piperidine (170 mg, 0.8 mmol) and pyridine (253 mg, 3.2 mmol) in dichloromethane (5 mL) was added. The resulting mixture was stirred at 25° C. for 18 h. The reaction mixture was quenched with water (30 mL) and the aqueous layer was extracted with dichloromethane (50 mL×2). The combined organic layers were dried over sodium sulfate, filtered and concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 1-methyl-6-oxo-1,6-dihydropyridazin-3-yl 4-(3,5-difluorophenoxy)piperidine-1-carboxylate (118.3 mg, 0.32 mmol, 41%) as a white solid. $^1$H NMR (400 MHz, Dimethylsulfoxide-d$_6$) δ 9.34 (s, 1H), 7.64 (d, J=9.6 Hz, 1H), 6.88 (d, J=9.6 Hz, 1H), 6.74-6.80 (m, 3H), 4.64-4.69 (m, 1H), 3.77-3.83 (m, 2H), 3.56 (s, 3H), 3.24-3.30 (m, 2H), 1.94-1.98 (m, 2H), 1.52-1.60 (m, 2H); LCMS (ESI) m/z: 365.0 [M+H]$^+$.

Example 41. Preparation of 3-(3-chlorophenoxy)-N-(1-methyl-6-oxo-1,6-dihydropyridazin-3-yl)piperidine-1-carboxamide (Compound 70)

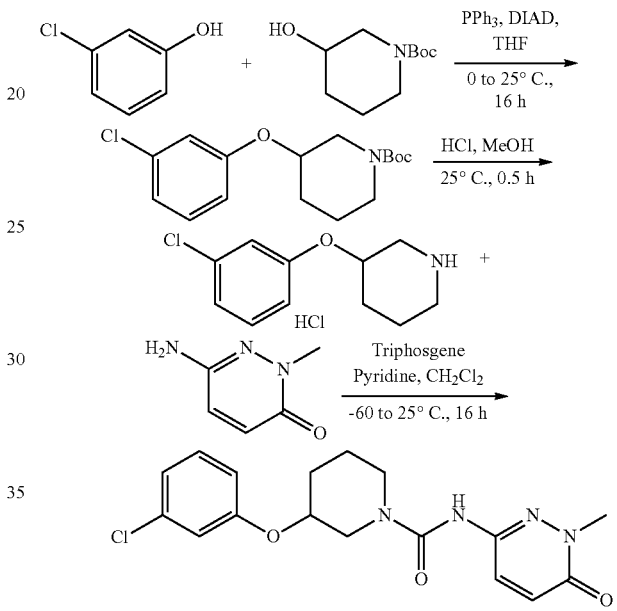

Step 1: Preparation of tert-butyl 3-(3-chlorophenoxy)piperidne-1-carboxylate

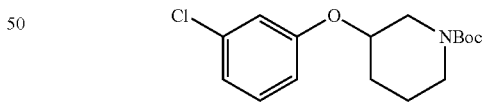

To a solution of 3-chlorophenol (5.2 g, 40.4 mmol), tert-butyl 3-hydroxypiperidine-1-carboxylate (8.12 g, 40.4 mmol) and triphenylphosphine (12.7 g, 48.5 mmol) in tetrahydrofuran (200 mL) at 0° C. was added diisopropyl azodicarboxylate (10.61 g, 52.5 mmol) dropwise. The reaction solution was stirred at 25° C. for 16 h. The volatiles were removed under reduced pressure and the residue was purified by column chromatography (silica gel, petroleum ether/ethyl acetate=4/1) to afford tert-butyl 3-(3-chlorophenoxy)piperidine-1-carboxylate as a yellow oil (4.2 g, 47% purity). LCMS (ESI) m/z: 334.0 [M+Na]$^+$. This material was used in the next step without further purification.

Step 2: Preparation of 3-(3-chlorophenoxy)piperidine Hydrochloride

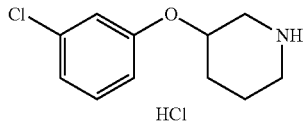 [SMILES: Clc1cccc(OC2CCCNC2)c1 ; Cl]

A mixture of tert-butyl 3-(3-chlorophenoxy)piperidine-1-carboxylate (3.8 g, crude) and hydrochloric acid (3 M in MeOH, 60 mL) was stirred at 25° C. for 1 h. The volatiles were removed under reduced pressure. The residue was treated with diethyl ether (80 mL). The resulting precipitate was collected by filtration and dried under vacuum to afford 3-(3-chlorophenoxy)piperidine hydrochloride (1.8 g, 80% purity, 18% over 2 steps) as a grey solid. LCMS (ESI) m/z: 212.1 [M+H]⁺. This material was used in the next step without further purification.

Step 3: Preparation of 3-(3-chlorophenoxy)-N-(1-methyl-6-oxo-1,6-dihydropyridazin-3-yl)piperidine-1-carboxamide

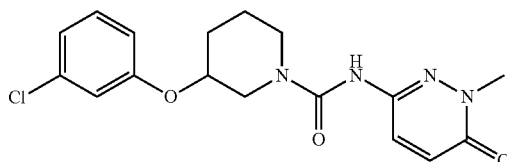

To a solution of triphosgene (296 mg, 1.0 mmol) in dichloromethane (20 mL) at −60° C. was added a solution of 6-amino-2-methylpyridazin-3(2H)-one (250 mg, 2.0 mmol) and pyridine (606 mg, 9.6 mmol) in dichloromethane (10 mL) under nitrogen. The mixture was stirred at −60° C. for 30 minutes, then a solution of 3-(3-chlorophenoxy)piperidine hydrochloride (250 mg, 2.0 mmol) and pyridine (506 mg, 8.0 mmol) in dichloromethane (10 mL) was added at −60° C. The resulting mixture was stirred at 25° C. for 18 h. The mixture was poured into water (100 mL) and the aqueous layer was extracted with dichloromethane (200 mL×2). The organic layers were dried over sodium sulfate, filtered and concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 3-(3-chlorophenoxy)-N-(1-methyl-6-oxo-1,6-dihydropyridazin-3-yl)piperidine-1-carboxamide (73.0 mg, 0.2 mmol, 10%) as a yellow solid. ¹H NMR (400 MHz, Dimethylsulfoxide-d₆) δ 9.31 (s, 1H), 7.63 (d, J=9.6 Hz, 1H), 7.29 (t, J=8.0 Hz, 1H), 7.05 (t, J=2.0 Hz, 1H), 6.99-6.93 (m, 2H), 6.88 (d, J=10.0 Hz, 1H), 4.49-4.85 (m, 1H), 3.84-3.80 (m, 1H), 3.56-3.54 (m, 4H), 3.40-3.29 (m, 2H), 2.02-1.97 (m, 1H), 1.78-1.65 (m, 2H), 1.55-1.49 (m, 1H); LCMS (ESI) m/z: 363.1 [M+H]⁺.

Example 42. Preparation of 4-(2,3-dichlorophenoxy)-N-(1-methyl-6-oxo-1,6-dihydropyridazin-3-yl)piperidine-1-carboxamide (Compound 81)

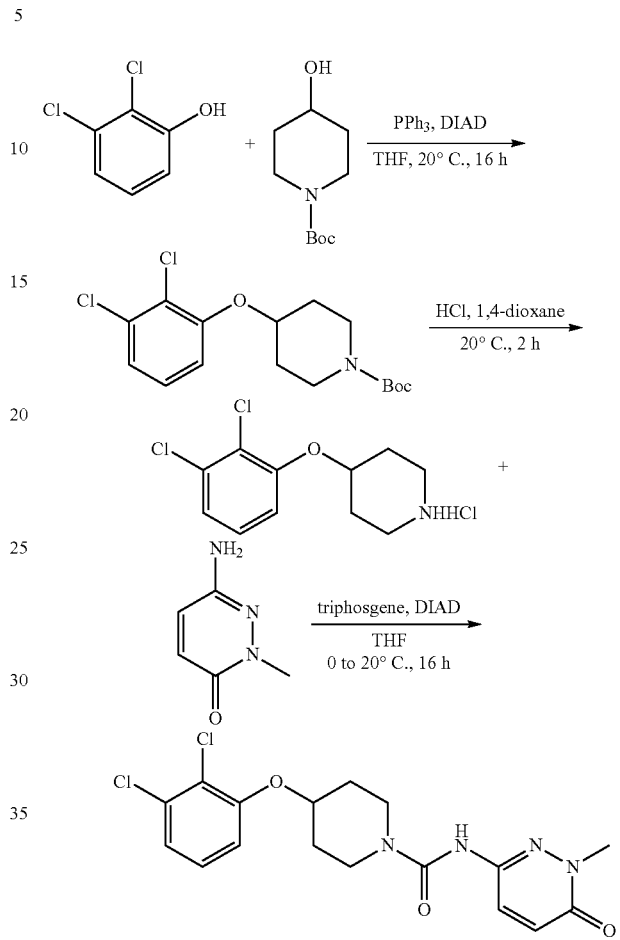

Step 1: Preparation of tert-butyl 4-(2,3-dichlorophenoxy)piperidine-1-carboxylate

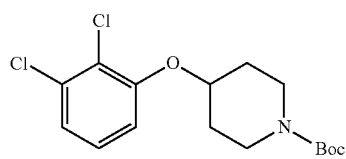

To a solution of 2,3-dichlorophenol (2.0 g, 12.35 mmol), tert-butyl 4-hydroxypiperidine-1-carboxylate (2.48 g, 12.4 mmol) and triphenylphosphine (3.88 g, 14.8 mmol) in tetrahydrofuran (15 mL) at 20° C. was added diisopropyl azodicarboxylate (2.99 g, 14.82 mmol). The mixture was stirred at 20° C. for 16 h. The volatiles were removed under reduced pressure and the residue was further purified by column chromatography (silica gel, petroleum ether/ethyl acetate=10/1) to give tert-butyl 4-(2,3-dichlorophenoxy)piperidine-1-carboxylate (3.3 g, crude) as an opaque oil. LCMS (ESI) m/z: 289.9 [M−56+H]⁺. The material was used in the next step without further purification.

Step 2: Preparation of 4-(2,3-dichlorophenoxy)piperidine Hydrochloride

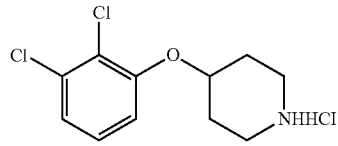

A solution of tert-butyl 4-(2,3-dichlorophenoxy)piperidine-1-carboxylate (3.3 g, 9.56 mmol) and hydrochloric acid in 1,4-dioxane (7.2 mL, 28.8 mmol, 4 M) was stirred at 20° C. for 2 h. The solution was concentrated to give 4-(2,3-dichlorophenoxy)piperidine hydrochloride (2.0 g, crude) as a white solid, which was used in the next step without further purification. LCMS (ESI) m/z: 246.0 [M+H]$^+$.

Step 3: Preparation of 4-(2,3-dichlorophenoxy)-N-(1-methyl-6-oxo-1,6-dihydropyridazin-3-yl)piperidine-1-carboxamide

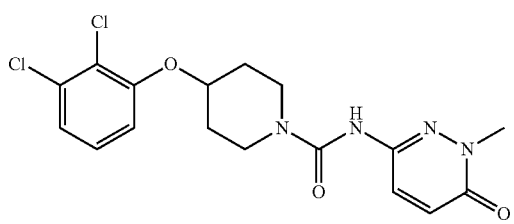 [SMILES: Cn1nc(NC(=O)N2CCC(Oc3cccc(Cl)c3Cl)CC2)ccc1=O]

To a solution of triphosgene (104 mg, 0.356 mmol) in dichloromethane (10 mL) at 0° C. was added a solution of 6-amino-2-methylpyridazin-3(2H)-one (89 mg, 0.712 mmol) and diisopropylethylamine (184 mg, 1.42 mmol) in tetrahydrofuran (10 mL). The mixture was stirred at 0° C. for 1 h before a solution of 4-(2,3-dichlorophenoxy)piperidine hydrochloride (200 mg, 0.712 mmol) and diisopropylethylamine (184 mg, 1.42 mmol) in tetrahydrofuran (10 mL) was added. The reaction was stirred at 20° C. for 16 h. The volatiles were removed under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 4-(2,3-dichlorophenoxy)-N-(1-methyl-6-oxo-1,6-dihydropyridazin-3-yl)piperidine-1-carboxamide (64.8 mg, 0.163 mmol, 23%) as a white solid. $^1$H NMR (400 MHz, Dimethylsulfoxide-d$_6$) δ 9.35 (s, 1H), 7.65 (d, J=10 Hz, 1H), 7.34-7.21 (m, 3H), 6.88 (d, J=9.6 Hz, 1H), 4.78 (s, 1H), 3.70-3.65 (m, 2H), 3.56 (s, 3H), 3.44-3.40 (m, 2H), 1.96-1.92 (m, 2H), 1.67-1.65 (m, 2H); LCMS (ESI) m/z: 397.0 [M+H]$^+$.

Example 43. Preparation of 4-(2-Chloro-3-fluorophenoxy)-N-(1-methyl-6-oxo-1,6-dihydropyridazin-3-yl)piperidine-1-carboxamide (Compound 78)

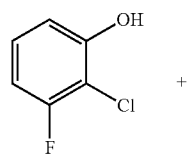

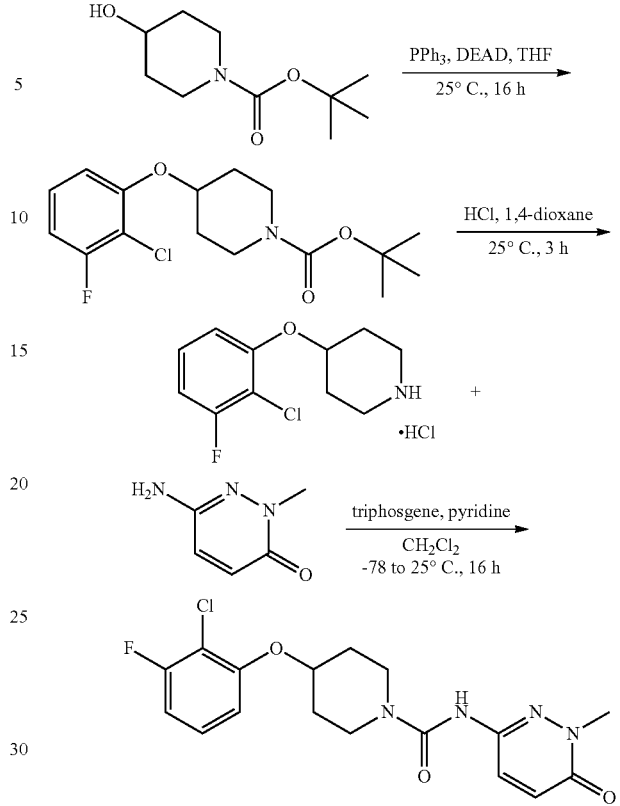

Step 1: Preparation of tert-butyl 4-(2-chloro-3-fluorophenoxy)piperidine-1-carboxylate

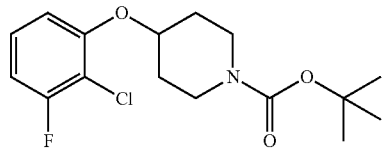 [SMILES: CC(C)(C)OC(=O)N1CCC(Oc2cccc(F)c2Cl)CC1]

To a solution of 2-chloro-3-fluorophenol (1.46 g, 9.94 mmol) in tetrahydrofuran (40 mL) at 25° C. was added tert-butyl 4-hydroxypiperidine-1-carboxylate (2.0 g, 9.94 mmol), diethyl azodicarboxylate (2.60 g, 14.9 mmol) and triphenylphosphine (3.91 g, 14.9 mmol). The reaction mixture was stirred at room temperature for 16 h. The The reaction was quenched with water (200 mL) and extracted with dichloromethane (80 mL×3). The combined organic layers were washed with brine (100 mL), dried over anhydrous sodium sulfate, filtered and concentrated. The crude material was purified by column chromatography (silica gel, petroleum ether/ethyl acetate=1/1) to afford tert-butyl 4-(2-chloro-3-fluorophenoxy)piperidine-1-carboxylate (2.0 g, 6.06 mmol, 61%) as a brown solid. LCMS (ESI) m/z: 330.1 [M+H]$^+$.

Step 2: Preparation of 4-(2-chloro-3-fluorophenoxy)piperidine Hydrochloride

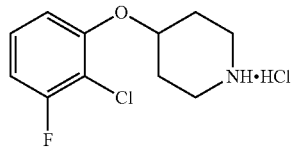

A solution of tert-butyl 4-(2-chloro-3-fluorophenoxy)piperidine-1-carboxylate (2.0 g, 6.06 mmol) and 4 N hydrochloric acid in 1,4-dioxane (30 mL) was stirred at room temperature for 3 h. The reaction mixture was concentrated in vacuo to afford 4-(2-chloro-3-fluorophenoxy)piperidine hydrochloride (1.3 g, 4.88 mmol, 80%) as a brown solid. LCMS (ESI) m/z: 230.1 [M+H]+.

Step 3: Preparation of 4-(2-Chloro-3-fluorophenoxy)-N-(1-methyl-6-oxo-1,6-dihydropyridazin-3-yl)piperidine-1-carboxamide

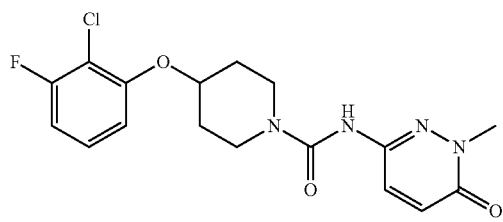 [SMILES: Cn1nc(NC(=O)N2CCC(Oc3cccc(F)c3Cl)CC2)ccc1=O]

To a solution of triphosgene (119.0 mg, 0.40 mmol) in anhydrous dichloromethane (8 mL) at −78° C. was added a solution of 6-amino-2-methylpyridazin-3(2H)-one (100 mg, 0.8 mmol) and pyridine (253.5 mg, 3.2 mmol) in dichloromethane (4 mL) under argon. The mixture was stirred at −78° C. for 0.5 h and then a solution of 4-(2-chloro-3-fluorophenoxy)piperidine hydrochloride (213 mg, 0.8 mmol) and pyridine (254 mg, 3.2 mmol) in dichloromethane (4 mL) was added. The resulting mixture was stirred at 25° C. for 16 h. The The reaction was quenched with water (100 mL) and extracted with dichloromethane (80 mL×3). The combined organic layers were washed with brine (100 mL), dried over anhydrous sodium sulfate, filtered and concentrated. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to afford 4-(2-chloro-3-fluorophenoxy)-N-(1-methyl-6-oxo-1,6-dihydropyridazin-3-yl)piperidine-1-carboxamide (105 mg, 0.276 mmol, 34%) as a white solid. $^1$H NMR (400 MHz, Dimethylsulfoxide-$d_6$) δ 9.36 (s, 1H), 7.64 (d, J=9.6 Hz, 1H), 7.34 (td, J=8.4, 6.7 Hz, 1H), 7.14 (d, J=8.4 Hz, 1H), 7.05-6.95 (m, 1H), 6.88 (d, J=10.0 Hz, 1H), 4.80-4.75 (m, 1H), 3.73-3.65 (m, 2H), 3.56 (s, 3H), 3.44-3.38 (m, 2H), 1.99-1.91 (m, 2H), 1.69-1.61 (m, 2H); LCMS (ESI) m/z: 381.1 [M+H]+

Example 44. Preparation of N-(1-methyl-6-oxo-1,6-dihydropyridazin-3-yl)-4-phenoxypiperidine-1-carboxamide (Compound 67)

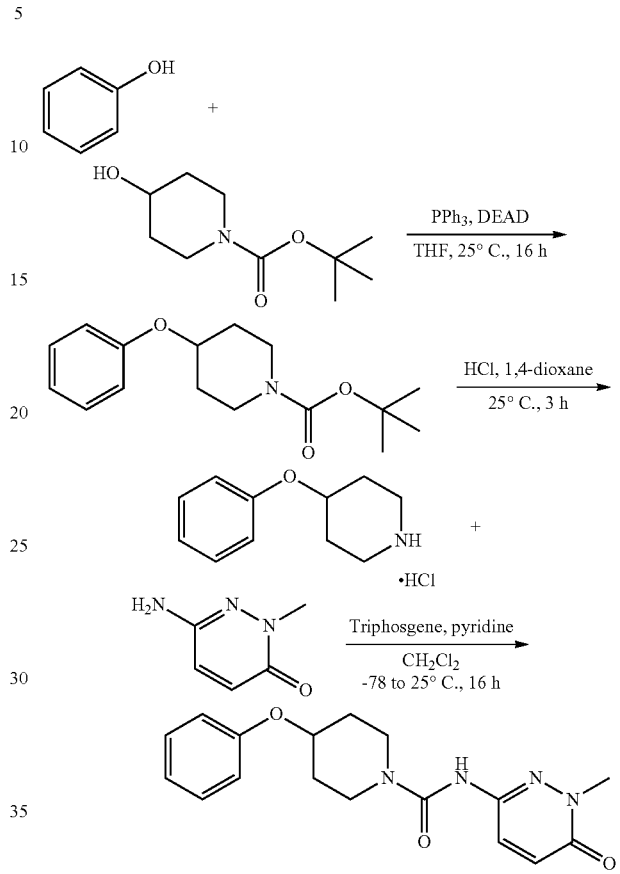

Step 1: Preparation of tert-butyl 4-phenoxypiperidine-1-carboxylate

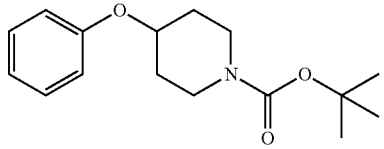 [SMILES: CC(C)(C)OC(=O)N1CCC(Oc2ccccc2)CC1]

To a solution of phenol (935 mg, 9.94 mmol) in tetrahydrofuran (40 mL) 25° C. was added tert-butyl 4-hydroxypiperidine-1-carboxylate (2.0 g, 9.94 mmol), diethyl azodicarboxylate (2.60 g, 14.9 mmol) and triphenylphosphine (3.91 g, 14.9 mmol). The reaction mixture was stirred at room temperature for 16 h. The reaction was quenched with water (200 mL) and extracted with dichloromethane (80 mL×3). The combined organic layers were washed with brine (100 mL), dried over anhydrous sodium sulfate, filtered and concentrated. The product was purified by column chromatography (silica gel, petroleum ether/ethyl acetate=1/1) to afford tert-butyl 4-phenoxypiperidine-1-carboxylate (1.0 g, 3.61 mmol, 36%) as a brown solid. LCMS (ESI) m/z: 278.2 [M+H]+.

Step 2: Preparation of 4-phenoxypiperidine Hydrochloride

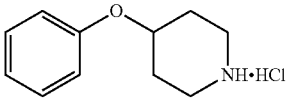

A solution of tert-butyl 4-phenoxypiperidine-1-carboxylate (1.0 g, 3.61 mmol) and 4 N hydrochloric acid in 1,4-dioxane (10 mL) was stirred at 0° C. to room temperature for 3 h. The reaction mixture was then concentrated in vacuo to afford 4-phenoxypiperidine hydrochloride (600 mg, 2.81 mmol, 78%) as a brown solid. LCMS (ESI) m/z: 178.2 [M+H]+. This material was used in the next step without further purification.

Step 3: Preparation of N-(1-methyl-6-oxo-1,6-dihydropyridazin-3-yl)-4-phenoxypiperidine-1-carboxamide

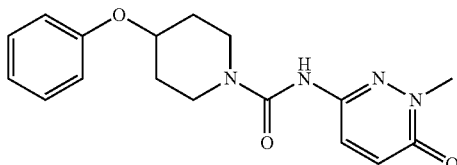

To a solution of triphosgene (119.0 mg, 0.40 mmol) in anhydrous dichloromethane (8 mL) at −78° C. was added a solution of 6-amino-2-methylpyridazin-3(2H)-one (100 mg, 0.8 mmol) and pyridine (253.5 mg, 3.2 mmol) in dichloromethane (4 mL) under argon. The mixture was stirred at −78° C. for 0.5 h and then a solution of 4-phenoxypiperidine hydrochloride (171 mg, 0.8 mmol) and pyridine (254 mg, 3.2 mmol) in dichloromethane (4 mL) was added at −78° C. The resulting mixture was stirred at 25° C. for 16 h. The reaction mixture was quenched with water (100 mL) and extracted with dichloromethane (80 mL×3). The combined organic layers were washed with brine (100 mL), dried over anhydrous sodium sulfate, filtered and concentrated. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to afford N-(1-methyl-6-oxo-1,6-dihydropyridazin-3-yl)-4-phenoxypiperidine-1-carboxamide (53 mg, 0.161 mmol, 20%) as a white solid. $^1$H NMR (400 MHz, Dimethylsulfoxide-d$_6$) δ 9.33 (s, 1H), 7.64 (d, J=10.0 Hz, 1H), 7.33-7.26 (m, 2H), 6.99 (d, J=7.8 Hz, 2H), 6.93 (t, J=7.2 Hz, 1H), 6.88 (d, J=10.0 Hz, 1H), 4.61-4.57 (m, 1H), 3.81-3.75 (m, 2H), 3.56 (s, 3H), 3.31-3.25 (m, 2H), 1.96-1.92 (m, 2H), 1.61-1.52 (m, 2H); LCMS (ESI) m/z: 329.1 [M+H]+.

Example 45. Preparation of N-(1-methyl-6-oxo-1,6-dihydropyridazin-3-yl)-4-(o-tolyloxy)piperidine-1-carboxamide (Compound 72)

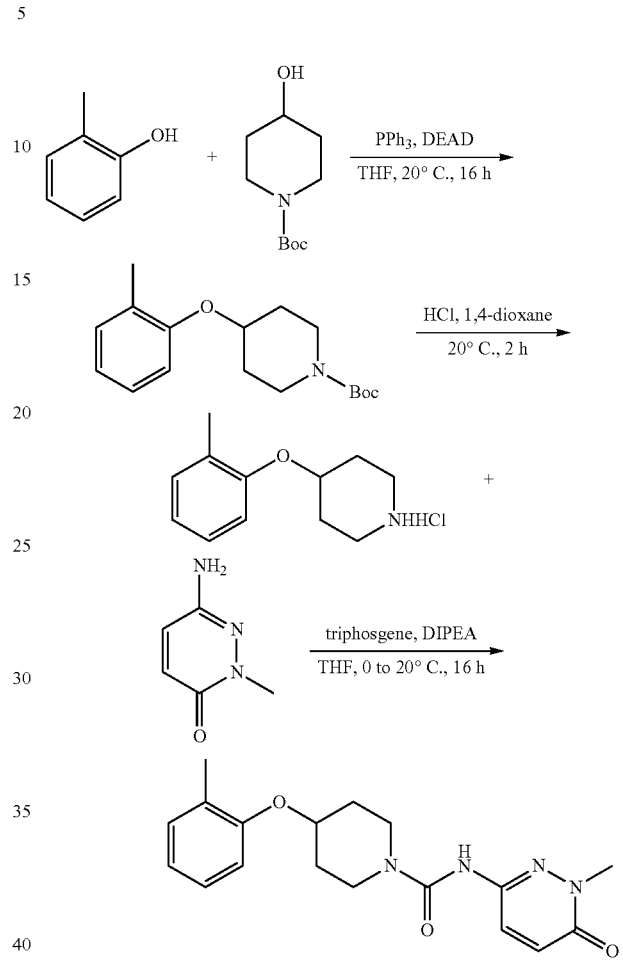

Step 1: Preparation of tert-butyl 4-(o-tolyloxy)piperidine-1-carboxylate

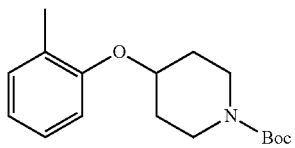 [SMILES: Cc1ccccc1OC1CCN(C(=O)OC(C)(C)C)CC1]

To a solution of o-cresol (2.0 g, 18.5 mmol), tert-butyl 4-hydroxypiperidine-1-carboxylate (3.72 g, 18.5 mmol) and triphenylphosphine (5.82 g, 22.2 mmol) in tetrahydrofuran (15 mL) at 20° C. was added diisopropyl azodicarboxylate (4.49 g, 22.20 mmol). The mixture was stirred at 20° C. for 16 h. The volatiles were removed under reduced pressure and the residue was further purified by column chromatography (silica gel, petroleum ether/ethyl acetate=10/1) to give tert-butyl 4-(o-tolyloxy)piperidine-1-carboxylate (4.2 g, crude) as an opaque oil; LCMS (ESI) m/z: 236.0 [M-56+H]+.

Step 2: Preparation of 4-(o-tolyloxy)piperidine Hydrochloride

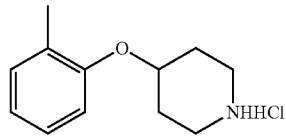

A solution of tert-butyl 4-(o-tolyloxy)piperidine-1-carboxylate (4.2 g, 14.4 mmol) and hydrochloric acid in 1,4-dioxane (10.8 mL, 43.2 mmol, 4M) was stirred at 20° C. for 2 h. The solution was concentrated in vacuo to give the crude 4-(o-tolyloxy)piperidine hydrochloride (2.5 g) as a white solid which was used in the next step without further purification. LCMS (ESI) m/z: 192.2 [M+H]$^+$.

Step 3: Preparation of N-(1-methyl-6-oxo-1,6-dihydropyridazin-3-yl)-4-(o-tolyloxy)piperidine-1-carboxamide

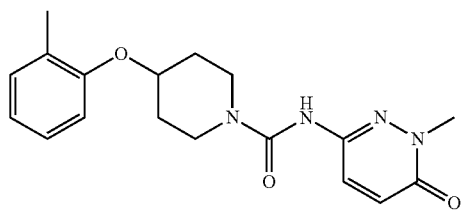 [SMILES: Cc1ccccc1OC1CCN(C(=O)Nc2ccc(=O)n(C)n2)CC1]

To a solution of triphosgene (129 mg, 0.440 mmol) in dichloromethane (10 mL) was added a solution of 6-amino-2-methylpyridazin-3(2H)-one (110 mg, 0.881 mmol) and diisopropylethylamine (228 mg, 1.76 mmol) in tetrahydrofuran (10 mL) at 0° C. The mixture was stirred at 0° C. for 1 h and a solution of 4-(o-tolyloxy)piperidine hydrochloride (200 mg, 0.881 mmol) and diisopropylethylamine (228 mg, 1.76 mmol) in tetrahydrofuran (10 mL) was added. The reaction mixture was stirred at 20° C. for 16 h. The crude sample was dissolved in the minimum amount of N,N-dimethylformamide and purified by prep-HPLC (Boston C18, 10 µm, 21 mm×250 mm column, acetonitrile/10 mM ammonium acetate aqueous solution) to give N-(1-methyl-6-oxo-1,6-dihydropyridazin-3-yl)-4-(o-tolyloxy)piperidine-1-carboxamide (47 mg, 0.137 mmol, 16%) as a white solid. $^1$H NMR (400 MHz, Dimethylsulfoxide-d$_6$) δ 9.33 (s, 1H), 7.65 (d, J=10 Hz, 1H), 7.14 (t, J=7.6 Hz, 1H), 7.00 (d, J=8.0 Hz, 1H), 6.90-6.81 (m, 2H), 4.63-4.59 (m, 1H), 3.71-3.66 (m, 2H), 3.56 (s, 3H), 3.43-3.37 (m, 2H), 2.17 (s, 3H), 1.94-1.89 (m, 2H), 1.67-1.60 (m, 2H); LCMS (ESI) m/z: 343.3 [M+H]$^+$.

Example 46. Preparation of N-(1-methyl-6-oxo-1,6-dihydropyridazin-3-yl)-4-(2-(trifluoromethyl)phenoxy)piperidine-1-carboxamide (Compound 75)

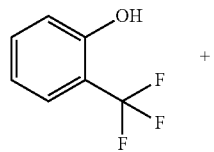

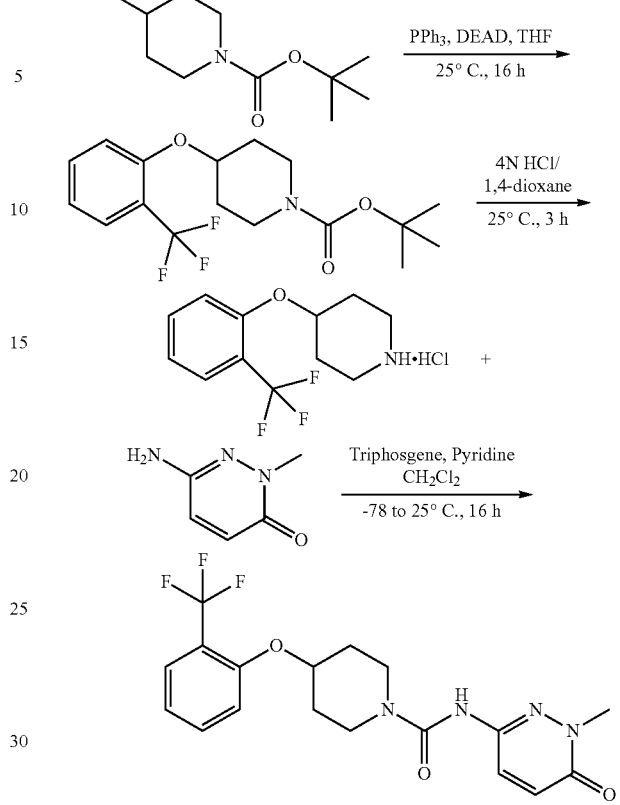

Step 1: Preparation of tert-butyl 4-(2-(trifluoromethyl)phenoxy)piperidine-1-carboxylate

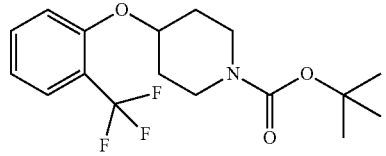 [SMILES: CC(C)(C)OC(=O)N1CCC(Oc2ccccc2C(F)(F)F)CC1]

To a solution of 2-(trifluoromethyl)phenol (1.61 g, 9.94 mmol) in tetrahydrofuran (40 mL) at 25° C. was added tert-butyl 4-hydroxypiperidine-1-carboxylate (2.0 g, 9.94 mmol), diethyl azodicarboxylate (2.60 g, 14.9 mmol) and triphenylphosphine (3.91 g, 14.9 mmol). The reaction mixture was stirred at room temperature for 16 h, then diluted with water (200 mL). The aqueous layer was extracted with dichloromethane (80 mL×3). The combined organic layers were washed with brine (100 mL), dried over anhydrous sodium sulfate, filtered and concentrated in vacuo. The crude material was purified by column chromatography (silica gel, petroleum ether/ethyl acetate=1/1) to afford tert-butyl 4-(2-(trifluoromethyl)phenoxy)piperidine-1-carboxylate (2.2 g, 6.37 mmol, 64%) as brown solid. LCMS (ESI) m/z: 346.2 [M+H]$^+$.

Step 2: Preparation of 4-(2-(trifluoromethyl)phenoxy)piperidine hydrochloride

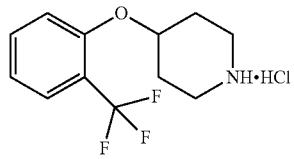

A solution of tert-butyl 4-(2-(trifluoromethyl)phenoxy)piperidine-1-carboxylate (2.0 g, 5.791 mmol) and hydrochloric acid in 1,4-dioxane (30 mL, 4M) was stirred at room temperature for 3 h. The reaction mixture was concentrated to afford 4-(2-(trifluoromethyl)phenoxy)piperidine hydrochloride (1.4 g, 4.97 mmol, 86%) as brown solid. LCMS (ESI) m/z: 246.1 [M+H]$^+$.

Step 3: Preparation of N-(1-methyl-6-oxo-1,6-dihydropyridazin-3-yl)-4-(2-(trifluoromethyl)phenoxy)piperidine-1-carboxamide

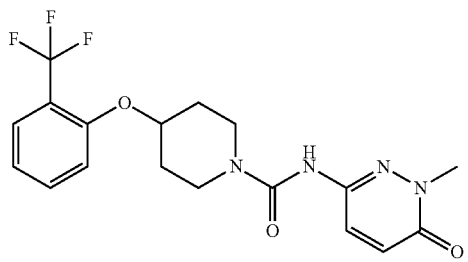 [SMILES: Cn1nc(NC(=O)N2CCC(Oc3ccccc3C(F)(F)F)CC2)ccc1=O]

To a solution of triphosgene (119 mg, 0.40 mmol) in anhydrous dichloromethane (8 mL) at −78° C. was added a solution of 6-amino-2-methylpyridazin-3(2H)-one (100 mg, 0.8 mmol) and pyridine (254 mg, 3.2 mmol) in dichloromethane (4 mL) under argon. The mixture was stirred at −78° C. for 30 min before a solution of 4-(2-(trifluoromethyl)phenoxy)piperidine hydrochloride (226 mg, 0.8 mmol) and pyridine (254 mg, 3.2 mmol) in dichloromethane (4 mL) was added at −78° C. The resulting mixture was stirred at 25° C. for 16 h and then diluted with water (100 mL). The aqueous layer was extracted with dichloromethane (80 mL×3). The combined organic layers were washed with brine (100 mL), dried over anhydrous sodium sulfate, filtered and concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to afford N-(1-methyl-6-oxo-1,6-dihydropyridazin-3-yl)-4-(2-(trifluoromethyl)phenoxy)piperidine-1-carboxamide (120 mg, 0.303 mmol, 38%) as a white solid. $^1$H NMR (400 MHz, Dimethylsulfoxide-d$_6$) δ 9.34 (s, 1H), 7.65-7.36 (m, 3H), 7.35 (d, J=8.8 Hz, 1H), 7.09 (t, J=7.6 Hz, 1H), 6.88 (d, J=10.0 Hz, 1H), 4.88-4.85 (m, 1H), 3.61-3.56 (m, 5H), 3.50-3.44 (m, 2H), 1.95-1.90 (m, 2H), 1.70-1.63 (m, 2H); LCMS (ESI) m/z: 397.2 [M+H]$^+$

Example 47. Preparation of 4-(2-methoxyphenoxy)-N-(1-methyl-6-oxo-1,6-dihydropyridazin-3-yl)piperidine-1-carboxamide (Compound 73)

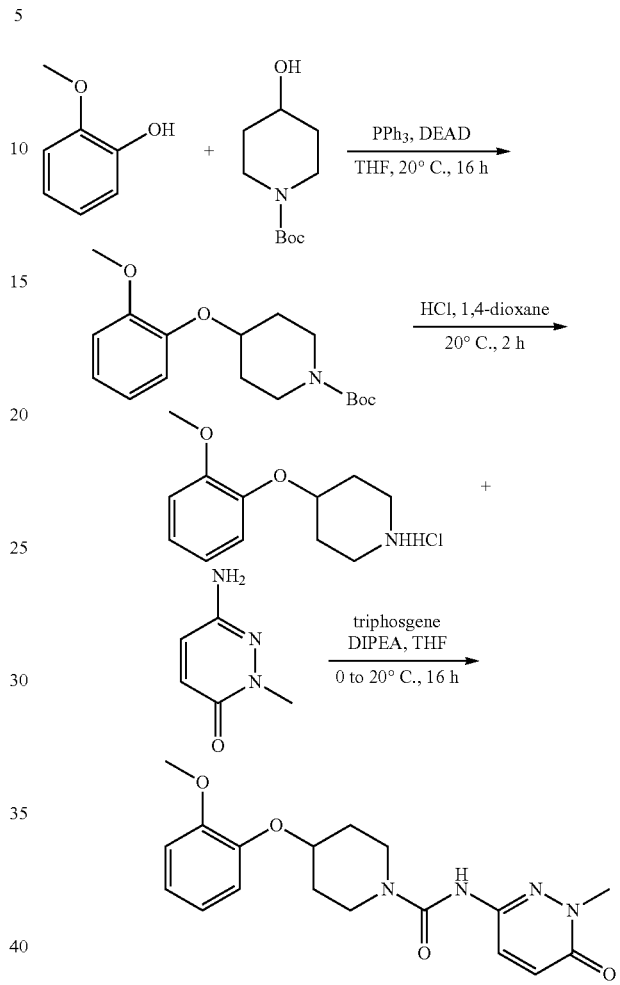

Step 1: Preparation of tert-butyl 4-(2-methoxyphenoxy)piperidine-1-carboxylate

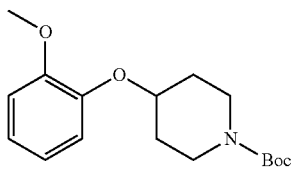 [SMILES: COc1ccccc1OC1CCN(C(=O)OC(C)(C)C)CC1]

To a solution of 2-methoxyphenol (2.0 g, 16.1 mmol), tert-butyl 4-hydroxypiperidine-1-carboxylate (3.24 g, 16.1 mmol) and triphenylphosphine (5.07 g, 19.4 mmol) in tetrahydrofuran (15 mL) was added diisopropyl azodicarboxylate (3.89 g, 19.4 mmol) at 20° C. The mixture was stirred at 20° C. for 3 h. The volatiles were removed under reduced pressure and the residue was further purified by column chromatography (silica gel, petroleum ether/ethyl acetate=10/1) to give tert-butyl 4-(2-methoxyphenoxy)piperidine-1-carboxylate as an opaque oil (3.6 g, crude); LCMS (ESI) m/z: 252.0 [M-56+H]$^+$.

Step 2: Preparation of 4-(2-methoxyphenoxy)piperidine hydrochloride

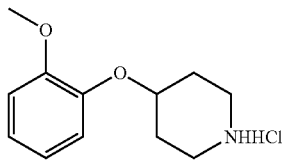

A solution of tert-butyl 4-(2-methoxyphenoxy)piperidine-1-carboxylate (3.6 g, 14.8 mmol) and hydrochloric acid in 1,4-dioxane (11.1 mL, 44.4 mmol, 4 M) was stirred at 20° C. for 2 h. The solution was concentrated in vacuo to give 4-(2-methoxyphenoxy)piperidine hydrochloride (2.1 g, crude) as a white solid which was used in the next step without further purification. LCMS (ESI) m/z: 208.2 [M+H]+.

Step 3: Preparation of 4-(2-methoxyphenoxy)N-(1-methyl-6-oxo-1,6-dihydropyridazin-3-yl)piperidine-1-carboxamide

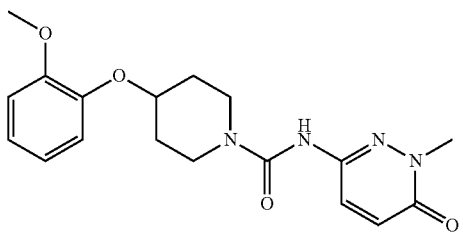 [SMILES: COc1ccccc1OC1CCN(C(=O)Nc2ccc(=O)n(C)n2)CC1]

To a solution of triphosgene (181 mg, 0.617 mmol) in dichloromethane (10 mL) at 0° C. was added a solution of 6-amino-2-methylpyridazin-3(2H)-one (154 mg, 1.23 mmol) and diisopropylethylamine (319 mg, 2.47 mmol) in tetrahydrofuran (10 mL). The mixture was stirred at 0° C. for 1 h and a solution of 4-(2-methoxyphenoxy)piperidine hydrochloride (300 mg, 1.23 mmol) and diisopropylethylamine (319 mg, 2.47 mmol) in tetrahydrofuran (10 mL) was added. The reaction mixture was stirred at 20° C. for 16 h. The volatiles were removed under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to afford 4-(2-methoxyphenoxy)-N-(1-methyl-6-oxo-1,6-dihydropyridazin-3-yl)piperidine-1-carboxamide (196 mg, 0.547 mmol, 44%) as a white solid. $^1$H NMR (400 MHz, Dimethylsulfoxide-$d_6$) δ 9.21 (s, 1H), 7.64 (d, J=10 Hz, 1H), 7.05-6.91 (m, 3H), 6.89-6.85 (m, 2H), 4.49-4.45 (m, 1H), 3.80-3.76 (m, 5H), 3.56 (s, 3H), 3.31-3.24 (m, 2H), 1.92-1.87 (m, 2H), 1.62-1.54 (m, 2H); LCMS (ESI) m/z: 359.2 [M+H]+.

Example 48. Preparation of 5-(2-(4-(3-chlorophenoxy)piperidin-1-yl)-2-oxoethyl)-1-methylpyridin-2(1H)-one (Compound 5)

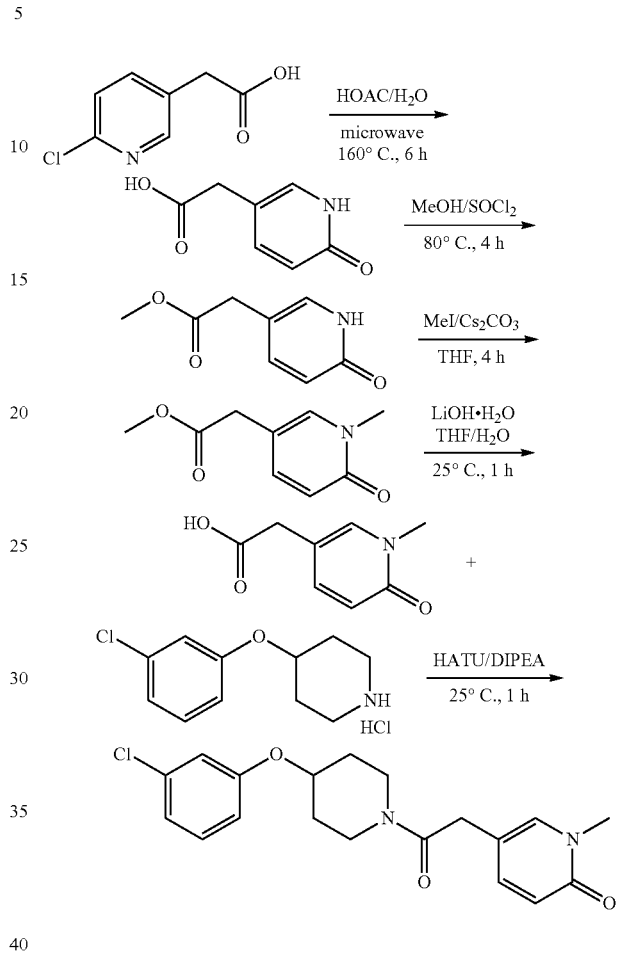

Step 1: Preparation of 2-(6-oxo-1,6-dihydropyridin-3-yl)acetic acid

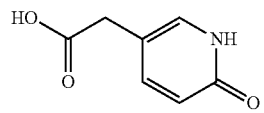

A mixture of 2-(6-chloropyridin-3-yl)acetic acid (1.0 g, 5.84 mmol), acetic acid (8 mL) and water (2 mL) was stirred at 160° C. under microwave irradiation for 6 h in duplicate. The two reaction mixtures were combined, poured into water, and extracted with ethyl acetate (100 mL×3). The aqueous phase was concentrated and dried under vacuum to afford 2-(6-oxo-1,6-dihydropyridin-3-yl)acetic acid (2.0 g, 13.07 mmol, 82.8%) as an off-white solid. LCMS (ESI) m/z: 154.1 [M+H]+.

Step 2: Preparation of methyl 2-(6-oxo-1,6-dihydropyridin-3-yl)acetate

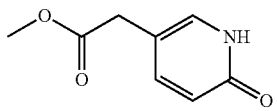

To a solution of 2-(6-oxo-1,6-dihydropyridin-3-yl)acetic acid (1.9 g, 12.4 mmol) in methanol (50 mL) at 0° C. was added thionyl chloride (2 mL) dropwise. The resulting solution was stirred at 80° C. for 4 h. The volatiles were removed under reduced pressure. The crude residue was poured into water and extracted with ethyl acetate/tetrahydrofuran mixture (150 mL/20 mL×3). The combined organic layers were dried over sodium sulfate, filtered and concentrated under reduced pressure to afford methyl 2-(6-oxo-1,6-dihydropyridin-3-yl)acetate (1.1 g, 6.58 mmol, 50%) as a grey solid. LCMS (ESI) m/z: 168.1 [M+H]$^+$.

Step 3: Preparation of methyl 2-(1-methyl-6-oxo-1,6-dihydropyridin-3-yl)acetate

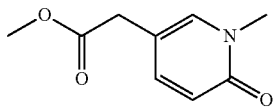

To a solution of methyl 2-(6-oxo-1,6-dihydropyridin-3-yl)acetate (1.0 g, 6.0 mmol) and cesium carbonate (2.34 g, 7.2 mmol) in tetrahydrofuran (20 mL) at 25° C. was added iodomethane (937 mg, 6.6 mmol). The reaction mixture was stirred for 4 h and was poured into water. The aqueous layer was extracted with ethyl acetate (100 mL×3) and the combined organic layers were concentrated under reduced pressure. The crude residue was purified by column chromatography (silica gel, 10% methanol in ethyl acetate) to afford methyl 2-(1-methyl-6-oxo-1,6-dihydropyridin-3-yl)acetate (900 mg, 4.97 mmol, 83%) as a yellow oil. $^1$H NMR (500 MHz, Chloroform-d) δ 7.28 (dd, J=9.0, 2.5 Hz, 1H), 7.22 (d, J=1.5 Hz, 1H), 6.56 (d, J=9.0 Hz, 1H), 3.72 (s, 3H), 3.53 (s, 3H), 3.36 (s, 2H); LCMS (ESI) m/z: 182.1 [M+H]$^+$.

Step 4: Preparation of 2-(1-methyl-6-oxo-1,6-dihydropyridin-3-yl)acetic acid

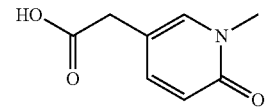

A mixture of methyl 2-(1-methyl-6-oxo-1,6-dihydropyridin-3-yl)acetate (800 mg, 4.42 mmol) and lithium hydroxide hydrate (557 mg, 13.3 mmol) in tetrahydrofuran (12 mL) and water (3 mL) was stirred at 25° C. for 1 h. The volatiles were removed under reduced pressure and the aqueous phase was acidified to pH 1-2 with hydrochloric acid (12 M) followed by concentration to dryness to afford 2-(1-methyl-6-oxo-1,6-dihydropyridin-3-yl)acetic acid (1.4 g, containing lithium chloride, crude) as a yellow green viscous oil. LCMS (ESI) m/z: 168.1 [M+H]$^+$.

Step 5: 5-(2-(4-(3-chlorophenoxy)piperidin-1-yl)-2-oxoethyl)-1-methylpyridin-2(1H)-one

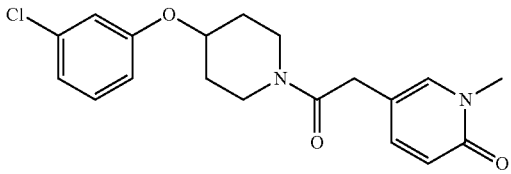 [SMILES: Cn1cc(CC(=O)N2CCC(Oc3cccc(Cl)c3)CC2)ccc1=O]

A mixture of 2-(1-methyl-6-oxo-1,6-dihydropyridin-3-yl)acetic acid (400 mg, crude), 4-(3-chlorophenoxy)piperidine hydrochloride (247 mg, 1.0 mmol), 2-(7-azabenzotriazol-1-yl)-N,N,N',N'-tetramethyluronium hexafluorophosphate (570 mg, 1.5 mmol), N-ethyl-N-isopropylpropan-2-amine (390 mg, 3.0 mmol) in N,N-dimethylformamide (5 mL) was stirred at 25° C. for 1 h. The crude sample was dissolved in the minimum amount of N,N-dimethylformamide and purified via prep-HPLC (Boston C18, 10 μm, 21 mm×250 mm column; acetonitrile/0.01% aqueous trifluoroacetic acid) to afford 5-(2-(4-(3-chlorophenoxy)piperidin-1-yl)-2-oxoethyl)-1-methylpyridin-2(1H)-one (276 mg, 0.76 mmol, 77%) as an off-white solid. $^1$H NMR (500 MHz, Dimethylsulfoxide-d$_6$) δ 7.52 (d, J=2.0 Hz, 1H), 7.32-7.28 (m, 2H), 7.09 (t, J=2.0 Hz, 1H), 6.99 (dd, J=7.5, 1.0 Hz, 1H), 6.96 (dd, J=8.0, 2.0 Hz, 1H), 6.35 (d, J=9.0 Hz, 1H), 4.70-4.65 (m, 1H), 3.88-3.85 (m, 1H), 3.78-3.75 (m, 1H), 3.41-3.37 (m, 4H), 3.28-3.22 (m, 1H), 1.93-1.89 (m, 2H), 1.93-1.89 (m, 2H), 1.59-1.47 (m, 2H); LCMS (ESI) m/z: 361.1 [M+H]$^+$.

Example 49. Preparation of 4-(3-chlorophenoxy)-N-(1-methyl-6-oxo-1,6-dihydropyridin-3-yl)piperidine-1-carboxamide (Compound 12)

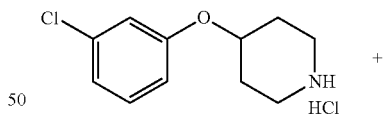

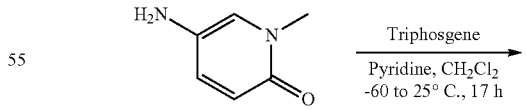

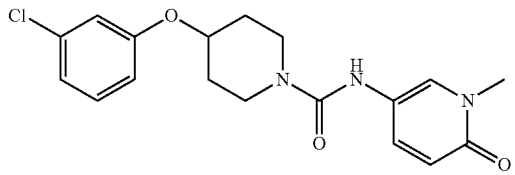

Step 1: Preparation of 4-(3-chlorophenoxy)-N-(1-methyl-6-oxo-1,6-dihydropyridin-3-yl)piperidine-1-carboxamide

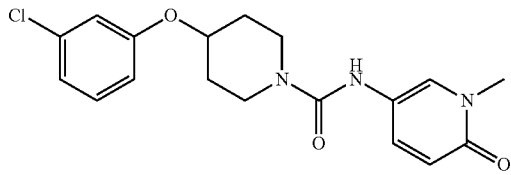

To a solution of triphosgene (178 mg, 0.6 mmol) in dichloromethane (5 mL) at −60° C. was added a solution of 5-amino-1-methylpyridin-2(1H)-one (238 mg, 1.92 mmol) and pyridine (379 mg, 4.8 mmol) in dichloromethane (10 mL) under argon. The mixture was stirred at −60° C. for 30 min and a solution of 4-(3-chlorophenoxy)piperidine hydrochloride (300 mg, 1.2 mmol) and pyridine (379 mg, 4.8 mmol) in dichloromethane (15 mL) was added at −60° C. The resulting mixture was stirred at 25° C. for 17 h. The reaction was quenched with water (20 mL) and the aqueous layer was extracted with dichloromethane (10 mL×3). The combined organic layers were dried over sodium sulfate, filtered and concentrated under reduced pressure. The crude sample was dissolved in the minimum amount of N,N-dimethylformamide and purified via prep-HPLC (Boston C18, 10 μm, 21 mm×250 mm column; acetonitrile/0.01% aqueous trifluoroacetic acid) to give 4-(3-chlorophenoxy)-N-(1-methyl-6-oxo-1,6-dihydropyridin-3-yl)piperidine-1-carboxamide (67.0 mg, 0.18 mmol, 15%) as a red solid. $^1$H NMR (400 MHz, Dimethylsulfoxide-$d_6$) δ 8.29 (s, 1H), 7.78 (d, J=2.7 Hz, 1H), 7.42 (dd, J=9.6, 2.8 Hz, 1H), 7.31 (t, J=8.1 Hz, 1H), 7.01 (ddd, J=22.5, 10.2, 2.0 Hz, 3H), 6.36 (d, J=9.6 Hz, 1H), 4.72-4.58 (m, 1H), 3.78 (dd, J=8.7, 5.2 Hz, 2H), 3.41 (s, 3H), 3.30-3.10 (m, 2H), 1.95 (d, J=12.0 Hz, 2H), 1.62-1.45 (m, 2H); LCMS (ESI) m/z: 362.0 [M+H]$^+$.

Example 50. Preparation of 1-methyl-6-oxo-1,6-dihydropyridin-3-yl 4-(3,5-difluorophenoxy)piperidine-1-carboxylate (Compound 14)

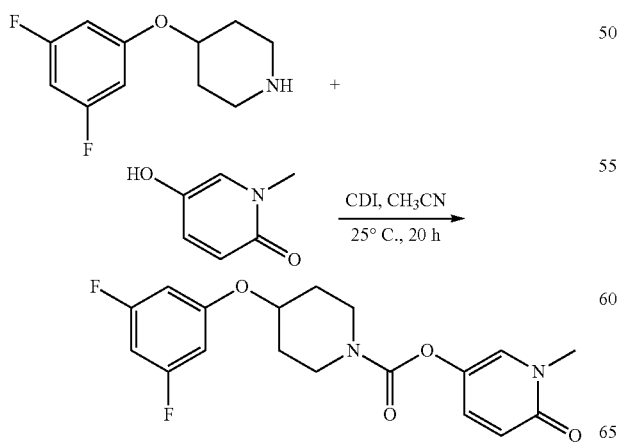

Step 1: Preparation of 1-methyl-6-oxo-1,6-dihydropyridin-3-yl 4-(3,5-difluorophenoxy)piperidine-1-carboxylate

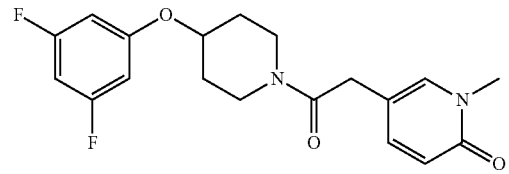 [SMILES: Cn1cc(CC(=O)N2CCC(Oc3cc(F)cc(F)c3)CC2)ccc1=O]

To a solution of 5-hydroxy-1-methylpyridin-2(1H)-one (100 mg, 0.8 mmol) in acetonitrile (20 mL) at 25° C. was added 1,1'-carbonyldiimidazole (143 mg, 0.88 mmol) under argon. The mixture was stirred at 25° C. for 2 h before 4-(3,5-difluorophenoxy)piperidine (170 mg, 0.8 mmol) was added. The resulting mixture was stirred at 25° C. for 20 h. The reaction mixture was quenched with water (30 mL) and extracted with dichloromethane (50 mL×2). The combined organic layers were dried over sodium sulfate, filtered and concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give to give 1-methyl-6-oxo-1,6-dihydropyridin-3-yl-4-(3,5-difluorophenoxy)piperidine-1-carboxylate (39 mg, 0.11 mmol, 13%) as a yellow solid. $^1$H NMR (400 MHz, Dimethylsulfoxide-$d_6$) δ 7.74 (d, J=2.8 Hz, 1H), 7.37 (dd, J1=3.2 Hz, J$_2$=9.6 Hz, 1H), 6.76-6.82 (m, 3H), 6.36 (d, J=10.0 Hz, 1H), 4.69-4.73 (m, 1H), 3.74-3.83 (m, 2H), 3.40 (s, 3H), 3.32-3.40 (m, 2H), 1.99 (s, 2H), 1.64 (s, 2H); LCMS (ESI) m/z: 365.0 [M+H]$^+$.

Example 51. Preparation of 5-(2-(4-(3-chlorobenzyl)piperidin-1-yl)-2-oxoethyl)-1-methylpyridin-2 (1H)-one (Compound 4)

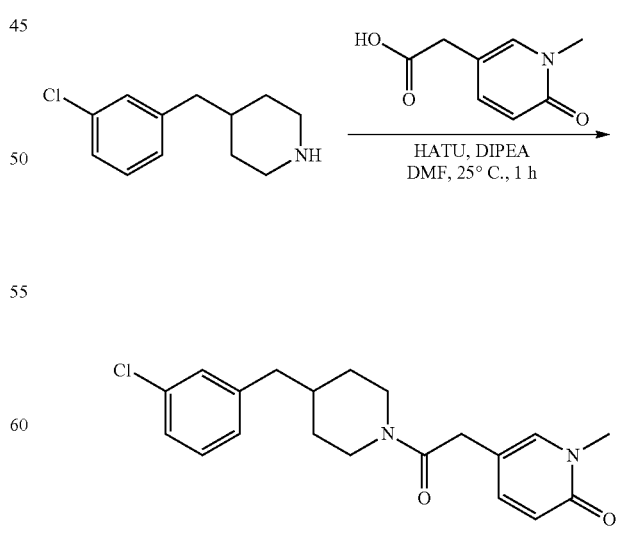

Step 1: Preparation of 5-(2-(4-(3-chlorobenzyl)piperidin-1-yl)-2-oxoethyl)-1-methylpyridin-2(1H)-one

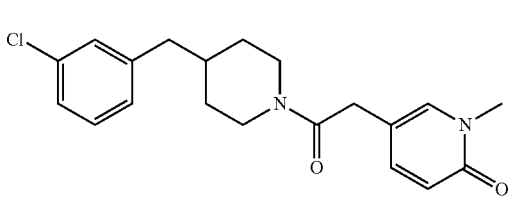

A mixture of 2-(1-methyl-6-oxo-1,6-dihydropyridin-3-yl)acetic acid (400 mg, crude), 4-(3-chlorobenzyl)piperidine (105 mg, 0.5 mmol), 2-(7-Azabenzotriazol-1-yl)-N,N,N',N'-tetramethyluronium hexafluorophosphate (285 mg, 0.75 mmol) and N-ethyl-N-isopropylpropan-2-amine (194 mg, 1.5 mmol) in N,N-dimethylformamide (4 mL) was stirred at 25° C. for 1 h. The mixture was purified by prep-HPLC Boston C18, 10 μm, 21 mm×250 mm column, acetonitrile/10 mM ammonium acetate aqueous solution) to give 5-(2-(4-(3-chlorobenzyl)piperidin-1-yl)-2-oxoethyl)-1-methylpyridin-2(1H)-one (76.3 mg, 0.21 mmol, 43%) as a white solid. $^1$H NMR (500 MHz, Dimethylsulfoxide-$d_6$) δ 7.48 (d, J=2.0 Hz, 1H), 7.33-7.30 (m, 1H), 7.26-7.24 (m, 3H), 7.15 (d, J=7.5 Hz, 1H), 6.32 (d, J=9.5 Hz, 1H), 4.33 (d, J=13.0 Hz, 1H), 3.92 (d, J=13.5 Hz, 1H), 3.42 (s, 2H), 3.38 (s, 3H), 2.97-2.92 (m, 1H), 2.53-2.47 (m, 3H), 1.80-1.74 (m, 1H), 1.58-1.54 (m, 2H), 1.10-0.93 (m, 2H); LCMS (ESI) m/z: 359.1 [M+H]$^+$.

Example 52. Preparation of 6-(2-(4-(3-chlorophenoxy)piperidin-1-yl)-2-oxoethyl)pyridazin-3(2H)-one (Compound 36)

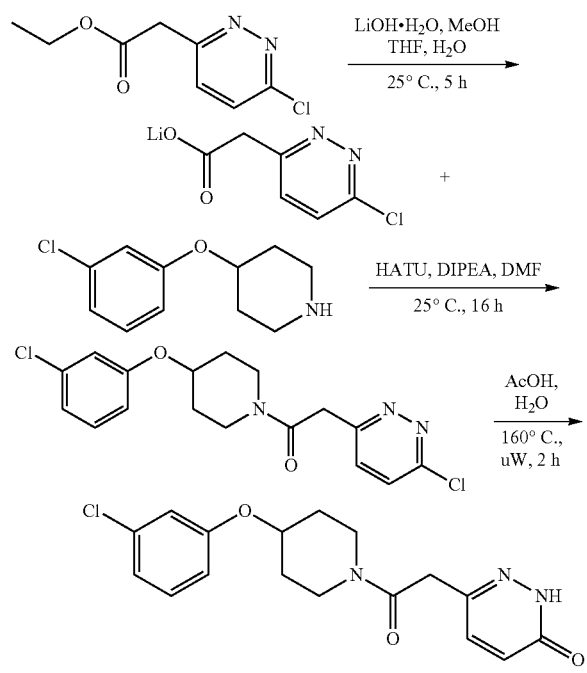

Step 1: Preparation of Lithium 2-(6-chloropyridazin-3-yl)acetate

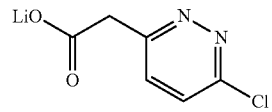

To a solution of ethyl 2-(6-chloropyridazin-3-yl)acetate (70 mg, 0.349 mmol) in methanol (1 mL) and tetrahydrofuran (1 mL) at 25° C., was added lithium hydroxide hydrate (18 mg, 0.419 mmol) and water (0.2 mL). The reaction mixture was stirred at 25° C. for 5 h. The residue was concentrated to afford lithium 2-(6-chloropyridazin-3-yl)acetate (90 mg, 0.349 mmol, crude) as a brown solid. LCMS (ESI) m/z: 173.1 [M-Li+H]$^+$.

Step 2: Preparation of 1-(4-(3-chlorophenoxy)piperidin-1-yl)-2-(6-chloropyridazin-3-yl)ethanone

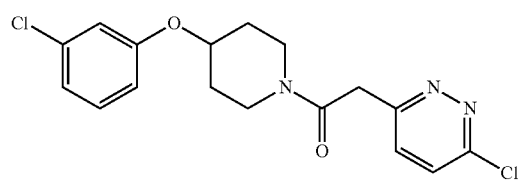 [SMILES: O=C(Cc1ccc(Cl)nn1)N1CCC(Oc2cccc(Cl)c2)CC1]

To a solution of lithium 2-(6-chloropyridazin-3-yl)acetate (90 mg, 0.349 mmol) in N,N-dimethylformamide (6 mL) at 0° C. was added 4-(3-chlorophenoxy)piperidine (74 mg, 0.349 mmol), 1-[bis(dimethylamino)methylene]-1H-1,2,3-triazolo[4,5-b]pyridinium 3-oxid hexafluorophosphate (199 mg, 0.524 mmol) and diisopropylethylamine (180 mg, 1.40 mmol). The mixture was stirred at 25° C. for 16 h. The reaction mixture was diluted with water and extracted with ethyl acetate (50 mL×3). The combined organic layers were washed with brine, dried over sodium sulfate, filtered and concentrated. The crude product was purified by column chromatography (silica gel, dichloromethane/methanol=20/1) to afford 1-(4-(3-chlorophenoxy)piperidin-1-yl)-2-(6-chloropyridazin-3-yl)ethanone (180 mg, 0.349 mmol, 99%) as a brown solid. LCMS (ESI) m/z: 366.1 [M+H]$^+$.

Step 3: Preparation of 6-(2-(4-(3-chlorophenoxy)piperidin-1-yl)-2-oxoethyl)pyridazin-3(2H)-one

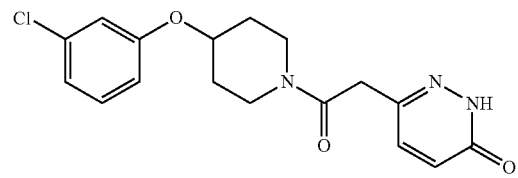

To a solution of 1-(4-(3-chlorophenoxy)piperidin-1-yl)-2-(6-chloropyridazin-3-yl)ethanone (180 mg, 0.349 mmol) in water (0.5 mL) at 25° C. was added acetic acid (5 mL) under nitrogen. The mixture was irradiated at 160° C. for 2 h in a microwave reactor. The crude sample was concentrated in vacuo, then dissolved in the minimum amount of N,N-dimethylformamide and purified by prep-HPLC (Boston C18, 10 μm, 21 mm×250 mm column, acetonitrile/10 mM ammonium acetate aqueous solution) to afford 6-(2-(4-(3-chlorophenoxy)piperidin-1-yl)-2-oxoethyl)pyridazin-3(2H)-one (18.2 mg, 0.276 mmol, 15%) as a white solid. ¹H NMR (400 MHz, Dimethylsulfoxide-d₆) δ 12.84 (s, 1H), 7.31 (t, J=8.2 Hz, 2H), 7.10 (t, J=2.2 Hz, 1H), 7.00-6.96 (m, 2H), 6.80-6.83 (m, 1H), 4.65-4.70 (m, 1H), 3.36-3.42 (m, 1H), 3.22-3.28 (m, 1H), 1.88-1.99 (m, 2H), 1.47-1.64 (m, 2H); LCMS (ESI) m/z: 348.0 [M+H]⁺.

Example 53. Preparation of 6-(2-(4-(3-chlorobenzyl)piperidin-1-yl)-2-oxoethyl)-2-methylpyridazin-3(2H)-one (Compound 37)

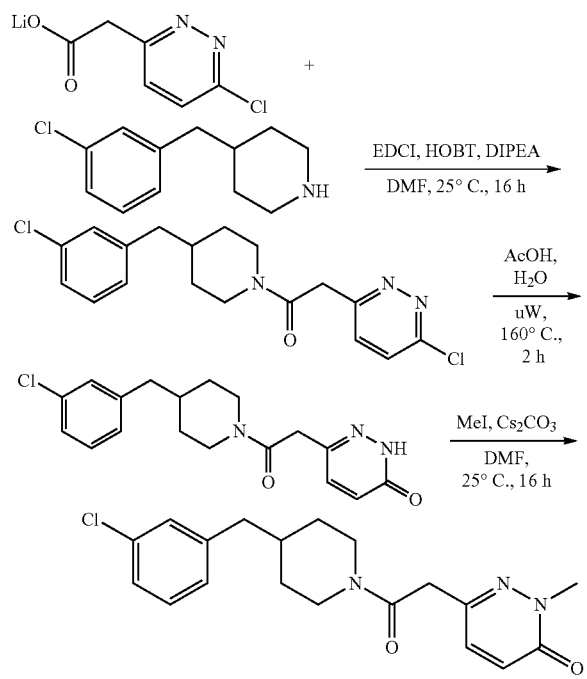

Step 1: Preparation of 1-(4-(3-chlorobenzyl)piperidin-1-yl)-2-(6-chloropyridazin-3-yl)ethanone

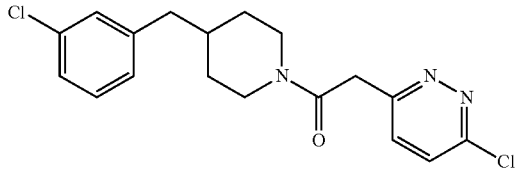 [SMILES: O=C(Cc1ccc(Cl)nn1)N1CCC(Cc2cccc(Cl)c2)CC1]

To a solution of lithium 2-(6-chloropyridazin-3-yl)acetate (1.2 g, 6.74 mmol), see preparation in Example 52 (Compound 36), 4-(3-chlorobenzyl)piperidine (1.13 g, 5.39 mmol), 3-(3-dimethylaminopropyl)-1-ethylcarbodiimide hydrochloride (1.55 g, 8.09 mmol) and 1-hydroxybenzotriazole (1.09 g, 8.09 mmol) in N,N-dimethylformamide (20 mL) at 25° C. was added N,N-diisopropylethylamine (2.61 g, 20.2 mmol). The reaction mixture was stirred for 16 h. The reaction solution was poured into ice-water (100 mL) and filtered. The filter cake was purified by column chromatography (silica gel, petroleum ether/ethyl acetate=10/1 to 3/1) to give 1-(4-(3-chlorobenzyl)piperidin-1-yl)-2-(6-chloropyridazin-3-yl)ethanone (990 mg, 2.72 mmol, 40%) as a brown solid. ¹H NMR (400 MHz, Methanol-d₄) δ 7.79 (d, J=8.8 Hz, 1H), 7.69 (d, J=8.8 Hz, 1H), 7.20-7.30 (m, 3H), 7.13 (d, J=7.2 Hz, 1H), 4.61 (s, 2H), 4.08-4.21 (m, 2H), 3.14 (t, J=12.0 Hz, 1H), 2.58-2.70 (m, 3H), 1.85-1.90 (m, 1H), 1.72 (t, J=13.6 Hz, 2H), 1.11-1.29 (m, 2H); LCMS (ESI) m/z: 364.0 [M+H]⁺.

Step 2: Preparation of 6-(2-(4-(3-chlorobenzyl)piperidin-1-yl)-2-oxoethyl)pyridazin-3(2H)-one

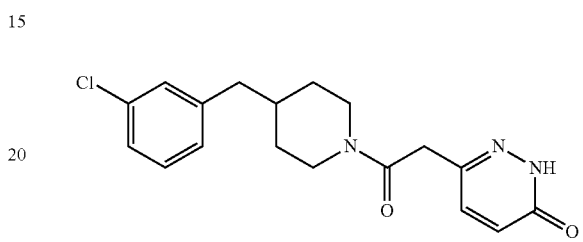

A solution of 1-(4-(3-chlorobenzyl)piperidin-1-yl)-2-(6-chloropyridazin-3-yl)ethanone (900 mg, 2.46 mmol) in acetic acid (9 mL) and water (1 mL) was irradiated in the microwave at 160° C. for 2 h. The reaction mixture was concentrated under reduced pressure. The crude residue was purified by prep-HPLC (SunFire C18, 4.6×50 mm, 3.5 μm column: Xbridge C18, 3.5 μm, 4.6×50 mm column, gradient of 5-95% over 1.5 min at 2 mL/min; acetonitrile in water/0.01% aqueous trifluoroacetic acid) to give 6-(2-(4-(3-chlorobenzyl)piperidin-1-yl)-2-oxoethyl)pyridazin-3(2H)-one (190 mg, 0.55 mmol, 22%) as a white solid. ¹H NMR (400 MHz, Dimethylsulfoxide-d₆) δ 12.81 (s, 1H), 7.25-7.34 (m, 4H), 7.15 (d, J=7.6 Hz, 1H), 6.80 (d, J=10.0 Hz, 1H), 4.32 (d, J=12.4 Hz, 1H), 3.88 (d, J=14.0 Hz, 1H), 3.67 (s, 2H), 2.97 (t, J=12.0 Hz, 1H), 2.51-2.54 (m, 3H), 1.74-1.80 (m, 1H), 1.56 (d, J=12.8 Hz, 2H), 0.98-1.15 (m, 2H); LCMS (ESI) m/z: 346.1 [M+H]⁺.

Step 3: Preparation of 6-(2-(4-(3-chlorobenzyl)piperidin-1-yl)-2-oxoethyl)-2-methylpyridazin-3(2H)-one

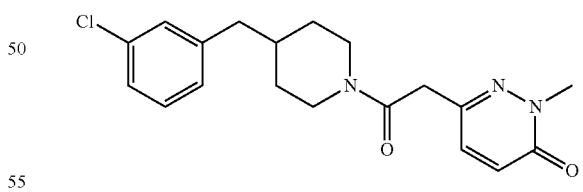

A solution of 6-(2-(4-(3-chlorobenzyl)piperidin-1-yl)-2-oxoethyl)pyridazin-3(2H)-one (160 mg, 0.46 mmol), iodomethane (131 mg, 0.92 mmol) and cesium carbonate (225 mg, 0.69 mmol) in N,N-dimethylformamide (5 mL) was stirred at 25° C. for 17 h. The reaction mixture was diluted with cold water (30 mL) and filtered. The filter cake was dried in vacuo to give 6-(2-(4-(3-chlorobenzyl)piperidin-1-yl)-2-oxoethyl)-2-methylpyridazin-3(2H)-one (107 mg, 0.30 mmol, 64%) as a brown solid. ¹H NMR (400 MHz, Dimethylsulfoxide-d₆) δ 7.25-7.34 (m, 4H), 7.15 (d, J=7.2 Hz, 1H), 6.87 (d, J=8.8 Hz, 1H), 4.32 (d, J=12.8 Hz, 1H), 3.88 (d, J=13.6 Hz, 1H), 3.70 (s, 2H), 3.59 (s, 3H), 2.98 (dt, J=14.4 Hz, J=2.4 Hz, 1H), 2.51-2.54 (m, 3H), 1.75-1.81 (m, 1H), 1.57 (t, J=8.4 Hz, 2H), 0.96-1.16 (m, 2H); LCMS (ESI) m/z: 360.1 [M+H]⁺.

Example 54. Preparation of 6-(2-(4-(3-chlorobenzyl)piperidin-1-yl)-2-oxoethyl)-2-methylpyridazin-3(2H)-one (Compound 38)

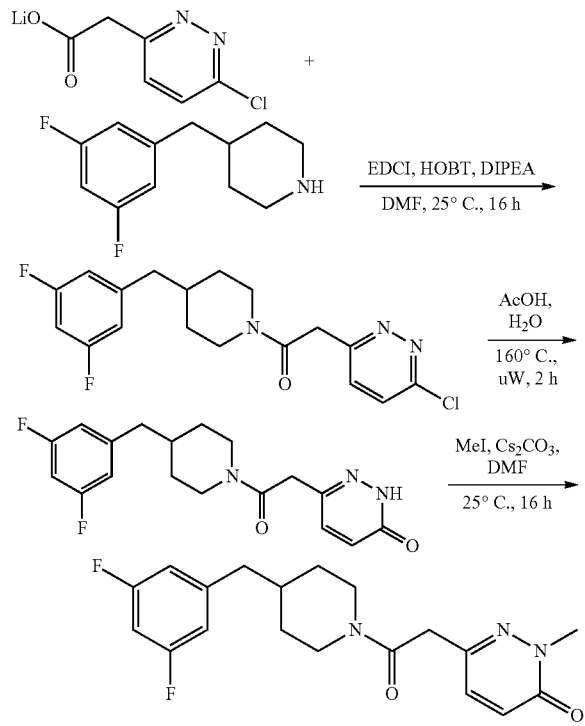

Step 1: Preparation of 2-(6-chloropyridazin-3-yl)-1-(4-(3,5-difluorobenzyl)piperidin-1-yl)ethanone

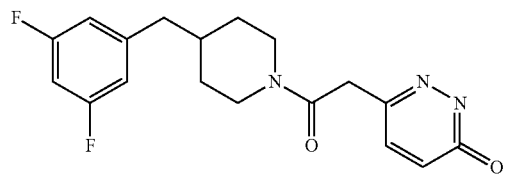

To a solution of lithium 2-(6-chloropyridazin-3-yl)acetate (1.24 g, 6.95 mmol), 4-(3,5-difluorobenzyl)piperidine (1.18 g, 5.57 mmol), 3-(3-dimethylaminopropyl)-1-ethylcarbodiimide hydrochloride (1.60 g, 8.34 mmol) and 1-hydroxybenzotriazole (1.13 g, 8.34 mmol) in N,N-dimethylformamide (20 mL) was added N,N-diisopropylethylamine (2.69 g, 20.9 mmol). The solution was stirred at 25° C. for 16 h and poured into ice-water (100 mL) and filtered. The filter cake was purified by column chromatography (silica gel, petroleum ether/ethyl acetate=10/1 to 3/1) to give 2-(6-chloropyridazin-3-yl)-1-(4-(3,5-difluorobenzyl)piperidin-1-yl)ethanone (980 mg, 2.68 mmol, 39%) as a brown solid. ¹H NMR (400 MHz, Methanol-d₄) δ 7.79 (d, J=8.8 Hz, 1H), 7.70 (d, J=8.8 Hz, 1H), 6.75-6.86 (m, 3H), 4.61 (s, 1H), 4.52 (d, J=11.2 Hz, 1H), 4.09-4.21 (m, 3H), 3.15 (dt, J=15.2 Hz, J=2.8 Hz, 1H), 2.61-2.72 (m, 3H), 1.86-1.93 (m, 1H), 1.72 (t, J=14.4 Hz, 2H), 1.14-1.30 (m, 2H); LCMS (ESI) m/z: 366.1 [M+H]⁺.

Step 2: Preparation of 6-(2-(4-(3,5-difluorobenzyl)piperidin-1-yl)-2-oxoethyl)pyridazin-3(2H)-one

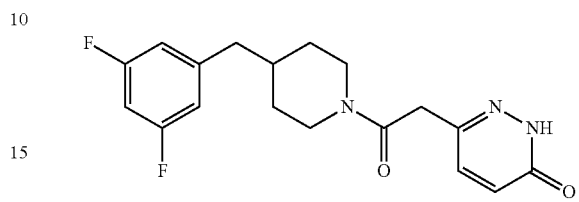

A solution of 2-(6-chloropyridazin-3-yl)-1-(4-(3,5-difluorobenzyl)piperidin-1-yl)ethanone (900 mg, 2.46 mmol) in acetic acid (9 mL) and water (1 mL) was irradiated in the microwave at 160° C. for 2 h. The crude sample was dissolved in the minimum amount of N,N-dimethylformamide and purified by prep-HPLC (column SunFire C18, 3.5 μm, 4.6 mm×50 mm; XBridge C18, 3.5 μm, 4.6 mm×50 mm, gradient of 5-95% over 1.5 min at 2 mL/min, acetonitrile/0.01% aqueous trifluoroacetic acid in water) to give 6-(2-(4-(3,5-difluorobenzyl)piperidin-1-yl)-2-oxoethyl)pyridazin-3(2H)-one (130 mg, 0.37 mmol, 15%) as a white solid. ¹H NMR (400 MHz, Dimethylsulfoxide-d₆) δ 12.81 (s, 1H), 7.27 (d, J=10.0 Hz, 1H), 7.01-7.07 (m, 1H), 6.93-6.95 (m, 2H), 6.80 (d, J=9.6 Hz, 1H), 4.32 (d, J=13.2 Hz, 1H), 3.88 (d, J=13.2 Hz, 1H), 3.67 (s, 2H), 2.97 (t, J=12.0 Hz, 1H), 2.51-2.56 (m, 3H), 1.78-1.84 (m, 1H), 1.54-1.56 (m, 2H), 0.98-1.15 (m, 2H); LCMS (ESI) m/z: 348.1 [M+H]⁺.

Step 3: Preparation of 6-(2-(4-(3,5-difluorobenzyl)piperidin-1-yl)-2-oxoethyl)-2-methylpyridazin-3(2H)-one

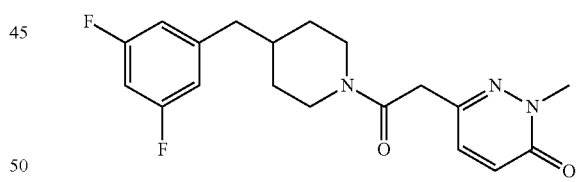

A mixture of 6-(2-(4-(3,5-difluorobenzyl)piperidin-1-yl)-2-oxoethyl)pyridazin-3(2H)-one (100 mg, 0.29 mmol), iodomethane (82 mg, 0.58 mmol) and cesium carbonate (141 mg, 0.43 mmol) in N,N-dimethylformamide (4 mL) was stirred at 25° C. for 17 h. The solution was diluted with cold water (30 mL) and filtered. The filter cake was dried in vacuo to give 6-(2-(4-(3,5-difluorobenzyl)piperidin-1-yl)-2-oxoethyl)-2-methylpyridazin-3(2H)-one (77 mg, 0.21 mmol, 74%) as a brown solid. ¹H NMR (400 MHz, Dimethylsulfoxide-d₆) δ 7.29 (d, J=9.6 Hz, 1H), 7.01-7.04 (m, 1H), 6.94 (d, J=6.8 Hz, 2H), 6.87 (d, J=7.2 Hz, 1H), 4.32 (d, J=13.2 Hz, 1H), 3.88 (d, J=13.6 Hz, 1H), 3.70 (s, 2H), 3.59 (s, 3H), 2.99 (t, J=11.6 Hz, 1H), 2.51-2.57 (m, 3H), 1.79-1.84 (m, 1H), 1.57 (t, J=10.4 Hz, 2H), 0.98-1.16 (m, 2H); LCMS (ESI) m/z: 362.1 [M+H]⁺.

Example 55. Preparation of 1-(3-chlorobenzyl)-N-(1-methyl-6-oxo-1,6-dihydropyridazin-3-yl)piperidine-4-carboxamide (Compound 136)

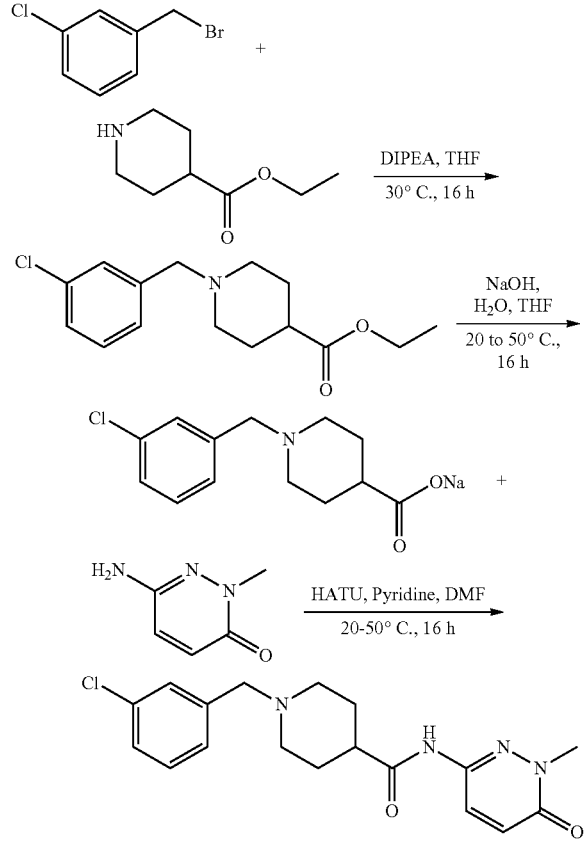

Step 1: Preparation of ethyl 1-(3-chlorobenzyl)piperidine-4-carboxylate

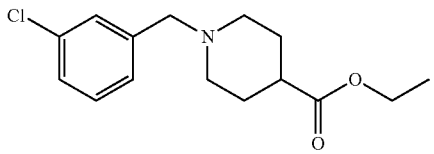 [SMILES: CCOC(=O)C1CCN(Cc2cccc(Cl)c2)CC1]

To a solution of 1-(bromomethyl)-3-chlorobenzene (1.57 g, 7.63 mmol) and diisopropylethylamine (3.95 g, 30.5 mmol) in tetrahydrofuran (25 mL) at 20° C. was added ethyl piperidine-4-carboxylate (1.2 g, 7.63 mmol). The mixture was stirred at 30° C. for 16 h. The residue was diluted with water and extracted with dichloromethane (50 mL×3). The combined organic layers were washed with brine, dried over sodium sulfate, filtered and concentrated under reduced pressure. The crude residue was purified by column chromatography (silica gel, petroleum ether/ethyl acetate=3/1) to afford ethyl 1-(3-chlorobenzyl)piperidine-4-carboxylate (1.54 g, 5.52 mmol, 72%) as a white solid. LCMS (ESI) m/z: 282.1 [M+H]+.

Step 2: Preparation of Sodium 1-(3-chlorobenzyl)piperidine-4-carboxylate

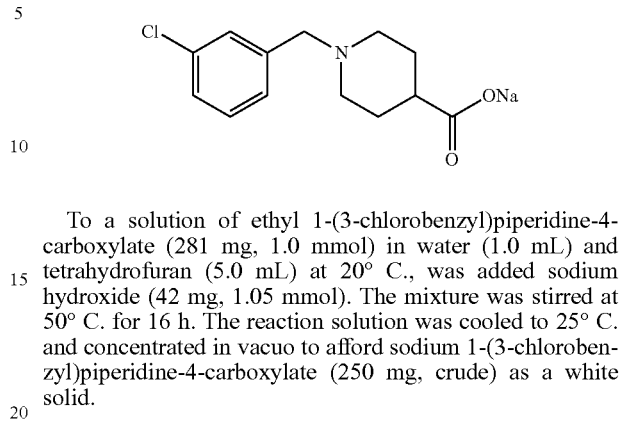

To a solution of ethyl 1-(3-chlorobenzyl)piperidine-4-carboxylate (281 mg, 1.0 mmol) in water (1.0 mL) and tetrahydrofuran (5.0 mL) at 20° C., was added sodium hydroxide (42 mg, 1.05 mmol). The mixture was stirred at 50° C. for 16 h. The reaction solution was cooled to 25° C. and concentrated in vacuo to afford sodium 1-(3-chlorobenzyl)piperidine-4-carboxylate (250 mg, crude) as a white solid.

Step 3: Preparation of 1-(3-chlorobenzyl)-N-(1-methyl-6-oxo-1,6-dihydropyridazin-3-yl)piperidine-4-carboxamide

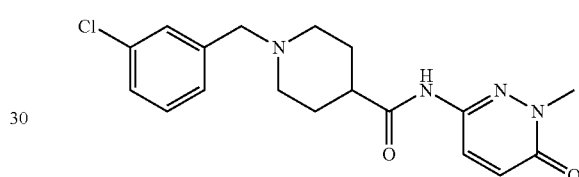

To a solution of 6-amino-2-methylpyridazin-3(2H)-one (114 mg, 0.907 mmol) in dimethylformamide (2 mL) at 20° C., was added sodium 1-(3-chlorobenzyl)piperidine-4-carboxylate (250 mg, 0.907 mmol), 2-(7-azabenzotriazol-1-yl)-N,N,N',N'-tetramethyluronium hexafluorophosphate (516 mg, 1.36 mmol) and pyridine (359 mg, 4.54 mmol). The mixture was stirred at 50° C. for 16 h. The mixture was diluted with water and the aqueous layer was extracted with dichloromethane (50 mL×3). The combined organic layers were washed with brine, dried over sodium sulfate, filtered and concentrated in vacuo. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 1-(3-chlorobenzyl)-N-(1-methyl-6-oxo-1,6-dihydropyridazin-3-yl)piperidine-4-carboxamide (70 mg, 0.194 mmol, 21%) as a white solid. $^1$H NMR (400 MHz, Dimethylsulfoxide-d$_6$) δ 10.48 (s, 1H), 7.96 (d, J=10.0 Hz, 1H), 7.26-7.38 (m, 4H), 6.95 (d, J=10.0 Hz, 1H), 3.56 (s, 3H), 3.47 (s, 2H), 2.82 (d, J=11.2 Hz, 2H), 2.34-2.41 (m, 1H), 1.92-1.97 (m, 2H), 1.72-1.75 (m, 2H), 1.56-1.66 (m, 2H); LCMS (ESI) m/z: 361.2 [M+H]+.

Example 56. Preparation of 6-(2-(4-(3,5-difluorobenzyl)piperidin-1-yl)oxazol-5-yl)-2-methylpyridazin-3(2H)-one (Compound 124)

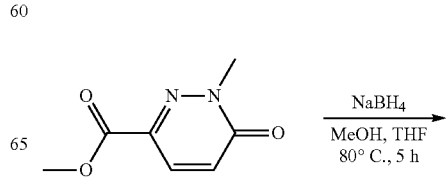

-continued

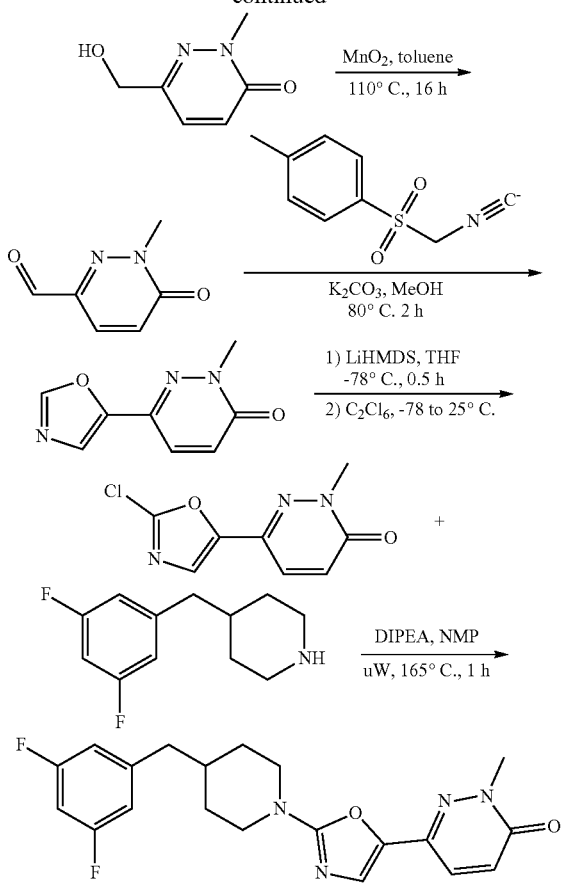

Step 1: Preparation of 6-(hydroxymethyl)-2-methylpyridazin-3(2H)-one

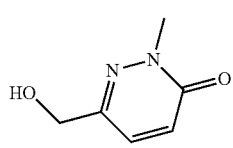

To a solution of methyl 1-methyl-6-oxo-1,6-dihydropyridazine-3-carboxylate (2 g, 11.9 mmol) in dry tetrahydrofuran (50 mL) was added methanol (10 mL) followed by sodium borohydride (0.45 g, 11.9 mmol) in portions. The reaction was heated to reflux and stirred under nitrogen for 5 h. The reaction was cooled to room temperature and then extracted with ethyl acetate (30 mL×2). The combined organic layers were washed with brine (40 mL), dried over sodium sulfate, filtered and concentrated to give 6-(hydroxymethyl)-2-methylpyridazin-3(2H)-one (1.24 g, 8.8 mmol, 74%) as a yellow solid. LCMS (ESI) m/z: 141.1 [M+H]$^+$.

Step 2: Preparation of 1-methyl-6-oxo-1,6-dihydropyridazine-3-carbaldehyde

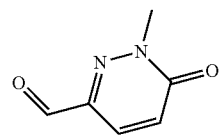

To a solution of 6-(hydroxymethyl)-2-methylpyridazin-3(2H)-one (1.2 g, 8.57 mmol) in dry toluene (100 mL) was added manganese dioxide (11.2 g, 129 mmol) slowly and the mixture was heated at reflux for 16 h. The reaction was cooled, filtered through a pad of Celite® and concentrated in vacuo to give 1-methyl-6-oxo-1,6-dihydropyridazine-3-carbaldehyde (0.6 g, 4.34 mmol, 51%) as a white solid. LCMS (ESI) m/z: 139.1 [M+H]$^+$.

Step 3: Preparation of 2-methyl-6-(oxazol-5-yl)pyridazin-3(2H)-one

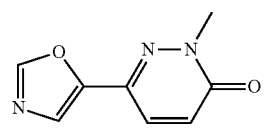

To a solution of 1-methyl-6-oxo-1,6-dihydropyridazine-3-carbaldehyde (0.56 g, 4 mmol) and 1-(isocyanomethylsulfonyl)-4-methylbenzene (0.79 g, 4 mmol) in methanol (20 mL) was added potassium carbonate (1.12 g, 8 mmol). The reaction mixture was heated at reflux for 2 h. The reaction was concentrated under reduced pressure. The crude material was diluted with water (40 mL) and extracted with ethyl acetate (40 mL×2). The combined organic layers were washed with brine (40 mL), dried over sodium sulfate, filtered and concentrated under reduced pressure. The residue was slurried with ethyl acetate/petroleum ether (5 mL/50 mL), filtered and dried to give 2-methyl-6-(oxazol-5-yl)pyridazin-3(2H)-one (0.64 g, 3.61 mmol, 90%) as a yellow solid. LCMS (ESI) m/z: 178.2 [M+H]$^+$.

Step 4: Preparation of 6-(2-chlorooxazol-5-yl)-2-methylpyridazin-3(2H)-one

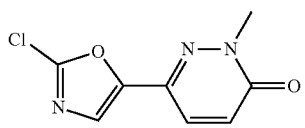

To a solution of 2-methyl-6-(oxazol-5-yl)pyridazin-3(2H)-one (0.26 g, 1.47 mmol) in dry tetrahydrofuran (25 mL) at −78° C. was added lithium bis(trimethylsilyl)amide (1 M tetrahydrofuran solution, 3 mL, 3 mmol) dropwise under nitrogen. The reaction was stirred at −78° C. for 30 min then a solution of perchloroethane (0.42 g, 1.76 mmol) in dry tetrahydrofuran (5 mL) was added dropwise. The reaction solution was warmed to 25° C. and then stirred for 16 h. The reaction was quenched with aqueous saturated ammonium chloride and extracted with ethyl acetate (40 mL×2). The combined organic layers were washed with brine (50 mL), dried over sodium sulfate, filtered and concentrated under reduced pressure. The residue was purified by Combi-Flash (Biotage, 40 g silica gel, eluted with ethyl acetate in petroleum ether from 10% to 20%) to give 6-(2-chlorooxazol-5-yl)-2-methylpyridazin-3(2H)-one (0.19 g, 0.9 mmol, 61%) as a yellow solid. LCMS (ESI) m/z: 212.1 [M+H]+.

Step 5: Preparation of 6-(2-(4-(3,5-difluorobenzyl)piperidin-1-yl)oxazol-5-yl)-2-methylpyridazin-3(2H)-one

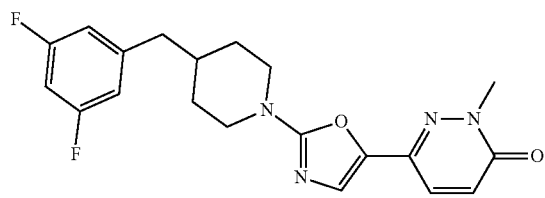 [SMILES: Cn1nc(-c2cnc(N3CCC(Cc4cc(F)cc(F)c4)CC3)o2)ccc1=O]

A mixture of 6-(2-chlorooxazol-5-yl)-2-methylpyridazin-3(2H)-one (70 mg, 0.33 mmol), 4-(3,5-difluorobenzyl)piperidine (77 mg, 0.36 mmol), N,N-diisopropylethylamine (64 mg, 0.50 mmol) in 1-methyl-2-pyrrolidinone (2 mL) was heated to 165° C. under microwave irradiation for 1 h. The reaction was cooled to 25° C., diluted with water (20 mL) and extracted with ethyl acetate (30 mL×2). The combined organic layers were washed with brine (50 mL), dried over sodium sulfate, filtered and concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 6-(2-(4-(3,5-difluorobenzyl)piperidin-1-yl)oxazol-5-yl)-2-methylpyridazin-3(2H)-one (90 mg, 0.23 mmol, 70%) as a white solid. $^1$H NMR (400 MHz, Dimethylsulfoxide-$d_6$) δ 7.75 (d, J=9.6 Hz, 1H), 7.52 (s, 1H), 6.92-7.09 (m, 4H), 4.00 (d, J=12.8 Hz, 2H), 3.64 (s, 3H), 2.91-3.06 (m, 2H), 2.58 (d, J=7.2 Hz, 2H), 1.73-1.88 (m, 1H), 1.64 (d, J=11.2 Hz, 2H), 1.13-1.29 (m, 2H); LCMS (ESI) m/z: 387.2 [M+H]+.

Example 57. Preparation of 6-(3-(4-(3-fluorobenzyl)piperidin-1-yl)-1,2,4-oxadiazol-5-yl)-2-methylpyridazin-3(2H)-one (Compound 114)

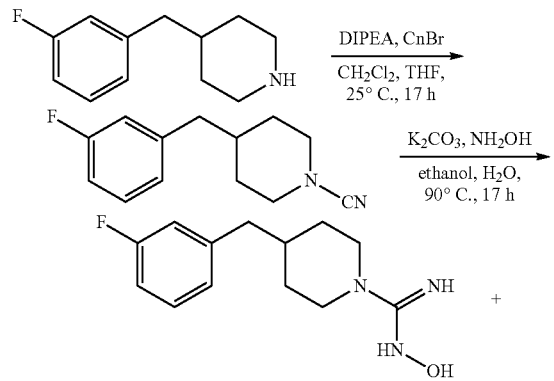

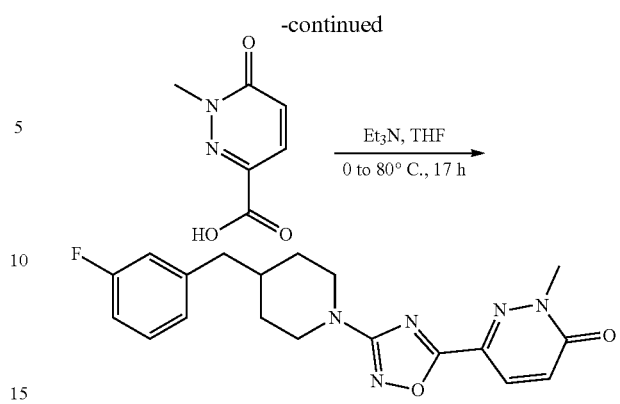

Step 1: Preparation of 4-(3-fluorobenzyl)piperidine-1-carbonitrile

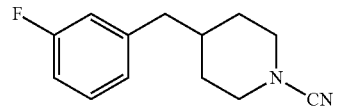 [SMILES: N#CN1CCC(Cc2cccc(F)c2)CC1]

To a solution of 4-(3-fluorobenzyl)piperidine (450 mg, 2.33 mmol) in tetrahydrofuran (10 mL) and dichloromethane (10 mL) under argon was added N,N-diisopropylethylamine (902 mg, 6.99 mmol) and cyanogen bromide (247 mg, 2.33 mmol). The mixture was stirred at 25° C. for 17 h. The reaction mixture was diluted with ethyl acetate (20 mL) and washed with water (10 mL×2) followed by brine (10 mL). The combined organic layers were dried over sodium sulfate, filtered and concentrated under reduced pressure to yield crude 4-(3-fluorobenzyl)piperidine-1-carbonitrile (420 mg, 1.93 mmol, 83%) as a yellow oil. LCMS (ESI) m/z: 219.3 [M+H]+.

Step 2: Preparation of 4-(3-fluorobenzyl)-N-hydroxypiperidine-1-carboximidamide

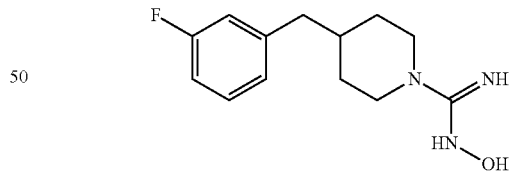

To a solution of 4-(3-fluorobenzyl)piperidine-1-carbonitrile (340 mg, 1.56 mmol) in ethanol (14 mL) and water (20 mL) under argon was added hydroxylamine hydrochloride (215 mg, 3.12 mmol) and potassium carbonate (646 mg, 4.68 mmol). The reaction mixture was stirred at 90° C. for 5 h and at 25° C. for 17 h. The volatiles were concentrated in vacuo and the residue was diluted with water (20 mL) and extracted with ethyl acetate (10 mL×3). The combined organic layers were washed with brine (10 mL), dried over sodium sulfate, filtered and concentrated under reduced pressure. The residue was purified by column chromatography (silica gel, dichloromethane/methanol=10/1) to give 4-(3-fluorobenzyl)-N-hydroxypiperidine-1-carboximidamide (200 mg, 0.79 mmol, 51%) as a yellow solid. LCMS (ESI) m/z: 252.2 [M+H]⁺.

Step 3: Preparation of 6-(3-(4-(3-fluorobenzyl)piperidin-1-yl)-1,2,4-oxadiazol-5-yl)-2-methylpyridazin-3(2H)-one

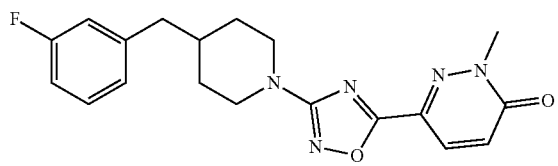 [SMILES: Cn1nc(-c2nc(N3CCC(Cc4cccc(F)c4)CC3)no2)ccc1=O]

A solution of 1-methyl-6-oxo-1,6-dihydropyridazine-3-carboxylic acid (86 mg, 0.56 mmol) in thionyl chloride (6 mL) under argon was stirred at 80° C. for 2 h, then concentrated in vacuo. The crude material was dissolved in tetrahydrofuran (5 mL) and added dropwise to a solution of 4-(3-fluorobenzyl)-N-hydroxypiperidine-1-carboximidamide (140 mg, 0.56 mmol) and triethylamine (170 mg, 1.68 mmol) in tetrahydrofuran (10 mL) at 0° C. The mixture was stirred at 80° C. for 17 h and then concentrated in vacuo. The crude sample was dissolved in the minimum amount of N,N-dimethylformamide and purified via prep-HPLC (Boston C18, 10 μm, 21 mm×250 mm column, acetonitrile/ 0.01% aqueous formic acid) to yield 6-(3-(4-(3-fluorobenzyl)piperidin-1-yl)-1,2,4-oxadiazol-5-yl)-2-methylpyridazin-3(2H)-one (22 mg, 0.06 mmol, 11%) as a white solid. ¹H NMR (400 MHz, Dimethylsulfoxide-d₆) δ 7.95 (d, J=9.7 Hz, 1H), 7.33 (dd, J=14.3, 7.9 Hz, 1H), 7.17-6.88 (m, 4H), 3.89 (d, J=12.9 Hz, 2H), 3.77 (s, 3H), 2.92 (t, J=11.4 Hz, 2H), 2.57 (d, J=7.2 Hz, 2H), 1.79 (s, 1H), 1.63 (d, J=11.2 Hz, 2H), 1.24 (t, J=12.0 Hz, 2H); LCMS (ESI) m/z: 370.3 [M+H]⁺.

Example 58. Preparation of 3-chloro-5-((1-(5-(1-methyl-6-oxo-1,6-dihydropyridazin-3-yl)-1,2,4-oxadiazol-3-yl)piperidin-4-yl)methyl)benzonitrile (Compound 117)

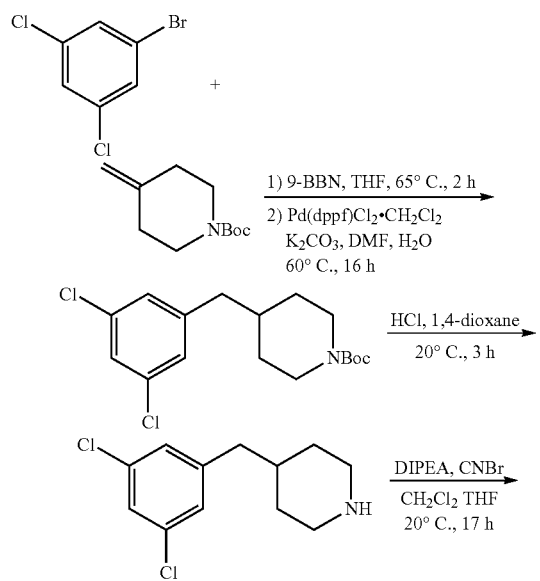

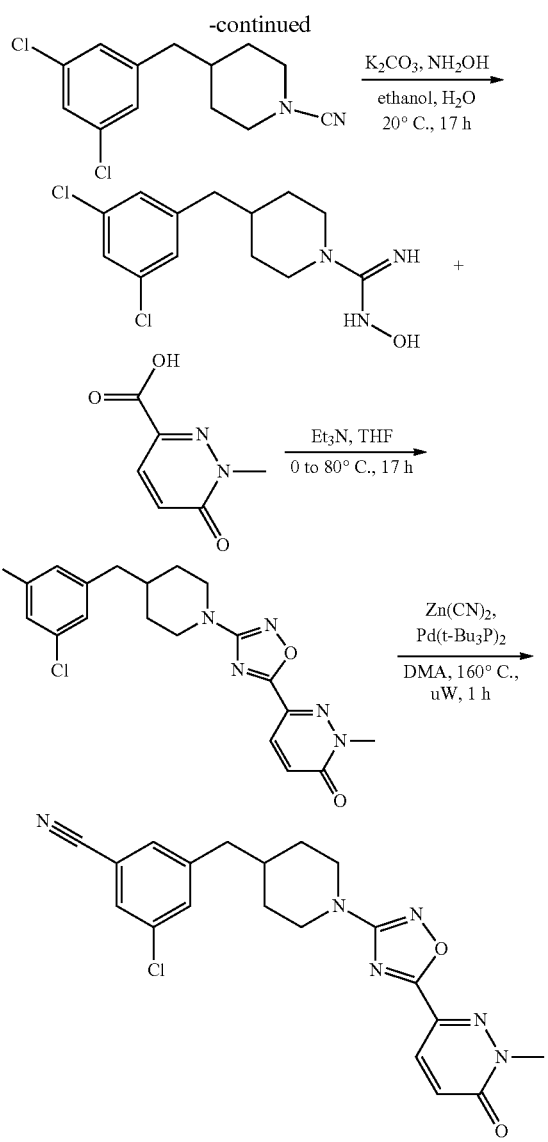

Step 1: Preparation of tert-butyl 4-(3,5-dichlorobenzyl)piperidine-1-carboxylate

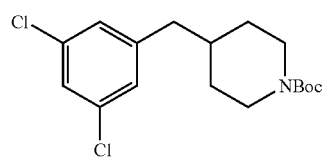

A solution of tert-butyl 4-methylenepiperidine-1-carboxylate (3.5 g, 17.8 mmol) and 9-borabicyclo[3.3.1]nonane in tetrahydrofuran (35.6 mL, 17.8 mmol, 0.5 M) was stirred at 65° C. for 2 h. The mixture was cooled to 25° C. and added to a solution of 1-bromo-3,5-dichlorobenzene (4 g, 17.8 mmol), potassium carbonate (3.2 g, 23.1 mmol) and 1,1'-bis(diphenylphosphino)ferrocene-palladium(II)dichloride dichloromethane complex (726 mg, 0.89 mmol) in N,N-dimethylformamide/water (30 mL/30 mL) at 25° C. The resulting mixture was heated at 60° C. for 20 h. The reaction was quenched with 1 N sodium hydroxide solution and stirred at 25° C. for 1 h. The reaction mixture was diluted with ethyl acetate (40 mL) and washed with brine (20 mL×3). The organic layer was dried over sodium sulfate, filtered and concentrated under reduced pressure. The crude residue was purified by column chromatography (silica gel, petroleum ether/ethyl acetate=50/1 to 30/1) to give tert-butyl 4-(3,5-dichlorobenzyl)piperidine-1-carboxylate (3.5 g, 10.2 mmol, 57%) as a yellow oil. LCMS (ESI) m/z: 288.1 [M-56+H]⁺.

Step 2: Preparation of 4-(3,5-dichlorobenzyl)piperidine Hydrochloride Salt

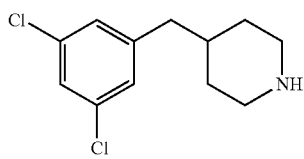

A solution of tert-butyl 4-(3,5-dichlorobenzyl)piperidine-1-carboxylate (3.4 g, 9.9 mmol) and 4N hydrochloric acid in 1,4-dioxane solution (40 mL) was stirred at 20° C. for 3 h under argon. The mixture was concentrated under reduced pressure. The crude residue was purified by column chromatography (silica gel, dichloromethane/methanol=15/1) to give 4-(3,5-dichlorobenzyl)piperidine hydrochloride salt (2.1 g, 8.61 mmol, 88%) as a white solid. LCMS (ESI) m/z: 244.1 [M+H]⁺.

Step 3: Preparation of 4-(3,5-dichlorobenzyl)piperidine-1-carbonitrile

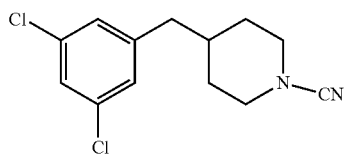 [SMILES: N#CN1CCC(Cc2cc(Cl)cc(Cl)c2)CC1]

To a solution of 4-(3,5-dichlorobenzyl)piperidine (2 g, 8.2 mmol) in tetrahydrofuran (20 mL) and dichloromethane (20 mL) under argon was added N,N-diisopropylethylamine (3.17 g, 24.6 mmol) and cyanogen bromide (868 mg, 8.2 mmol). The mixture was stirred at 20° C. for 17 h. The reaction mixture was washed with water (20 mL×2) followed by brine (20 mL). The combined organic layers were dried over sodium sulfate, filtered and concentrated under reduced pressure to yield 4-(3,5-dichlorobenzyl)piperidine-1-carbonitrile (1.8 g, 6.69 mmol, 82%) as a yellow oil. LCMS (ESI) m/z: 269.1 [M+H]⁺.

Step 4: Preparation of 4-(3,5-dichlorobenzyl)-N-hydroxypiperidine-1-carboximidamide

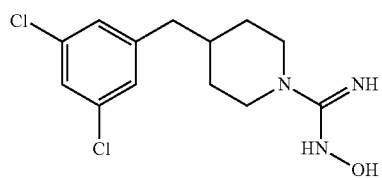 [SMILES: N=C(NO)N1CCC(Cc2cc(Cl)cc(Cl)c2)CC1]

To a solution of 4-(3,5-dichlorobenzyl)piperidine-1-carbonitrile (1.7 g, 6.3 mmol) in ethanol (14 mL) and water (20 mL) under argon was added hydroxylamine hydrochloride (869 mg, 12.6 mmol) and potassium carbonate (2.6 g, 18.9 mmol). The mixture was stirred at 90° C. for 5 h and then at 20° C. for 17 h. The volatiles were concentrated in vacuo. The crude residue was diluted with water (40 mL) then extracted with ethyl acetate (10 mL×3). The combined organic layers were washed with brine (10 mL), dried over sodium sulfate, filtered and concentrated under reduced pressure. The crude material was purified by column chromatography (silica gel, dichloromethane/methanol=15/1) to give 4-(3,5-dichlorobenzyl)-N-hydroxypiperidine-1-carboximidamide (1.0 g, 3.31 mmol, 53%) as a yellow solid. LCMS (ESI) m/z: 301.9 [M+H]⁺.

Step 5: Preparation of 6-(3-(4-(3,5-dichlorobenzyl)piperidin-1-yl)-1,2,4-oxadiazol-5-yl)-2-methylpyridazin-3(2H)-one

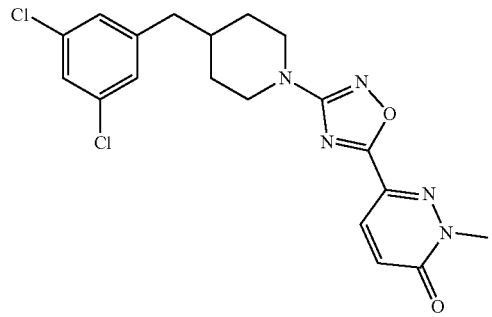 [SMILES: Cn1nc(-c2nc(N3CCC(Cc4cc(Cl)cc(Cl)c4)CC3)no2)ccc1=O]

A solution of 1-methyl-6-oxo-1,6-dihydropyridazine-3-carboxylic acid (458.9 mg, 2.98 mmol) in thionyl chloride (10 mL) under argon was stirred at 80° C. for 2 h. The volatiles were concentrated in vacuo. The crude material was dissolved in tetrahydrofuran (10 mL) and added dropwise to a solution of 4-(3,5-dichlorobenzyl)-N-hydroxypiperidine-1-carboximidamide (900 mg, 2.98 mmol) and triethylamine (903 mg, 8.94 mmol) in tetrahydrofuran (10 mL) under argon at 0° C. The mixture was stirred at 80° C. for 17 h and concentrated in vacuo. The crude sample was dissolved in the minimum amount of N,N-dimethylformamide and purified via prep-HPLC (Boston C18, 10 μm, 21 mm×250 mm column, acetonitrile/0.01% aqueous formic acid) to give 6-(3-(4-(3,5-dichlorobenzyl)piperidin-1-yl)-1,2,4-oxadiazol-5-yl)-2-methylpyridazin-3(2H)-one as a yellow solid (70 mg, 0.17 mmol, 6%). LCMS (ESI) m/z: 420.0 [M+H]⁺.

Step 6: Preparation of 3-chloro-5-((1-(5-(1-methyl-6-oxo-1,6-dihydropyridazin-3-yl)-1,2,4-oxadiazol-3-yl)piperidin-4-yl)methyl)benzonitrile

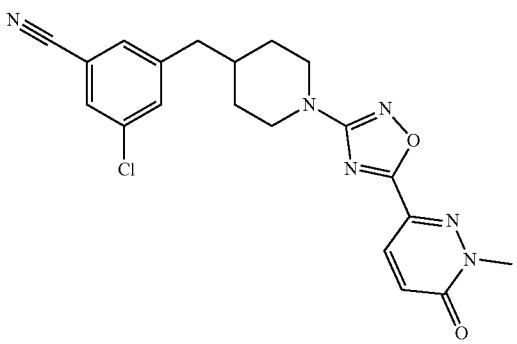 [SMILES: Cn1nc(-c2nc(N3CCC(Cc4cc(Cl)cc(C#N)c4)CC3)no2)ccc1=O]

To a solution of 6-(3-(4-(3,5-dichlorobenzyl)piperidin-1-yl)-1,2,4-oxadiazol-5-yl)-2-methylpyridazin-3(2H)-one (50 mg, 0.12 mmol) and zinc cyanide (28.2 mg, 0.24 mmol) in N,N-dimethylacetamide (5 mL) at 25° C. was added bis(tri-tert-butylphosphine)palladium(0) (61 mg, 0.12 mmol) under argon. The mixture was stirred at 160° C. for 1 h under microwave irradiation. The reaction solution was diluted with water (10 mL) and extracted with ethyl acetate (8 mL×3). The combined organic layers were dried over sodium sulfate, filtered and concentrated in vacuo. The crude sample was dissolved in the minimum amount of N,N-dimethylformamide and purified via prep-HPLC (Boston C18, 10 μm, 21 mm×250 mm column, acetonitrile/0.01% aqueous formic acid) to give 3-chloro-5-((1-(5-(1-methyl-6-oxo-1,6-dihydropyridazin-3-yl)-1,2,4-oxadiazol-3-yl)piperidin-4-yl)methyl)benzonitrile (5 mg, 0.01 mmol, 10%) as a white solid. $^1$H NMR (400 MHz, Dimethylsulfoxide-$d_6$) δ 8.01-7.84 (m, 2H), 7.71 (d, J=5.5 Hz, 2H), 7.11 (d, J=9.7 Hz, 1H), 3.90 (d, J=12.9 Hz, 2H), 3.77 (s, 3H), 2.92 (t, J=11.6 Hz, 2H), 2.62 (d, J=7.1 Hz, 2H), 1.84 (s, 1H), 1.60 (d, J=12.3 Hz, 2H), 1.19 (s, 2H); LCMS (ESI) m/z: 411.1 [M+H]$^+$.

Example 59. Preparation of 5-(3-(4-(3,5-difluorophenoxy)piperidin-1-yl)-1,2,4-oxadiazol-5-yl)-1-methylpyridin-2(1H)-one (Compound 15)

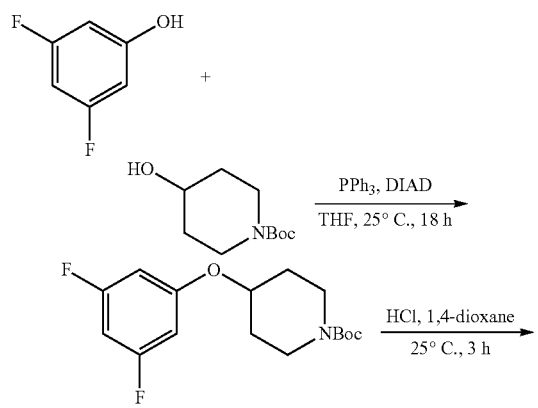

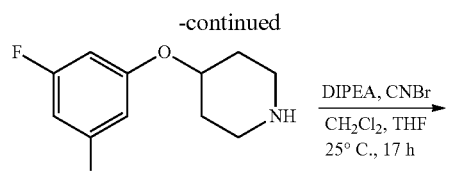

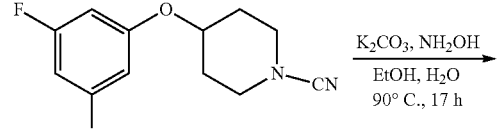

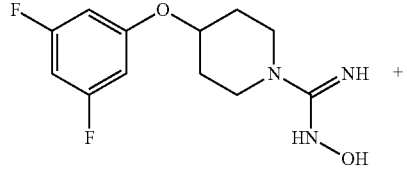

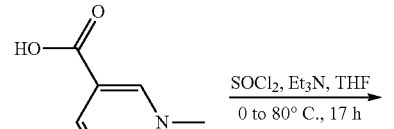

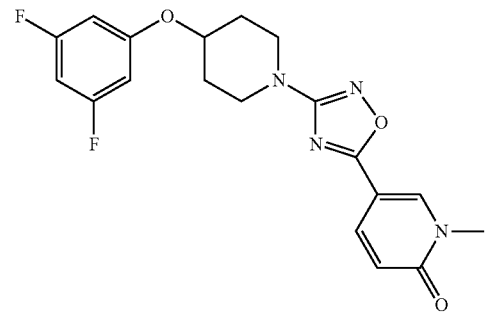

Step 1: Preparation of tert-butyl 4-(3,5-difluorophenoxy)piperidine-1-carboxylate

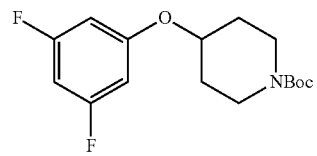

A solution of 3,5-difluorophenol (1.7 g, 13.1 mmol), tert-butyl 4-hydroxypiperidine-1-carboxylate (3.9 g, 19.6 mmol), triphenylphosphine (5.1 g, 19.6 mmol) and diisopropyl azodicarboxylate (3.9 g, 19.6 mmol) in tetrahydrofuran (30 mL) was stirred at 25° C. for 16 h under argon. The reaction mixture was filtered and concentrated under reduced pressure. The filtrate residue was purified by column chromatography (silica gel, petroleum ether/ethyl acetate=50/1) to give tert-butyl 4-(3,5-difluorophenoxy)piperidine-1-carboxylate (3.5 g, 11.2 mmol, 85%) as a yellow oil. LCMS (ESI) m/z: 258.2 [M-56+H]$^+$.

Step 2: Preparation of 4-(3,5-difluorophenoxy)piperidine

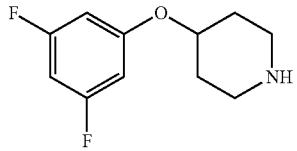

A solution of tert-butyl 4-(3,5-difluorophenoxy)piperidine-1-carboxylate (3.4 g, 10.9 mmol) and 4N hydrochloric acid in 1,4-dioxane solution (40 mL) was stirred at 25° C. for 3 h under argon. The mixture was concentrated under reduced pressure. The crude residue was purified by column chromatography (silica gel, dichloromethane/methanol=15/1) to give 4-(3,5-difluorophenoxy)piperidine (2.1 g, 9.86 mmol, 91%) as a white solid. LCMS (ESI) m/z: 214.2 $[M+H]^+$.

Step 3: Preparation of 4-(3,5-difluorophenoxy)piperidine-1-carbonitrile

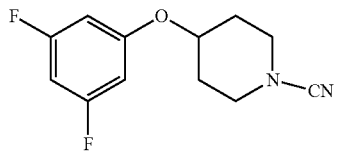 [SMILES: N#CN1CCC(Oc2cc(F)cc(F)c2)CC1]

To a solution of 4-(3,5-difluorophenoxy)piperidine (2 g, 9.3 mmol) in tetrahydrofuran (20 mL) and dichloromethane (20 mL) under argon was added N,N-diisopropylethylamine (3.6 g, 27.9 mmol) and cyanogen bromide (985 mg, 9.3 mmol). The mixture was stirred at 25° C. for 17 h. The reaction mixture was washed with water (10 mL×2) followed by brine (10 mL). The combined organic layers were dried over sodium sulfate, filtered and concentrated under reduced pressure to yield 4-(3,5-difluorophenoxy)piperidine-1-carbonitrile (1.8 g, 7.56 mmol, 82%) as a yellow oil. LCMS (ESI) m/z: 239.1 $[M+H]^+$.

Step 4: Preparation of 4-(3,5-difluorophenoxy)-N-hydroxypiperidine-1-carboximidamide

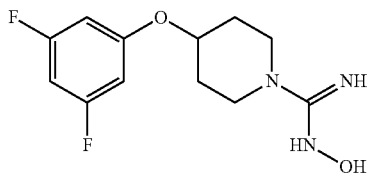

To a solution of 4-(3,5-difluorophenoxy)piperidine-1-carbonitrile (1.7 g, 7.1 mmol) in ethanol (21 mL) and water (30 mL) under argon was added hydroxylamine hydrochloride (980 mg, 14.2 mmol) and potassium carbonate (2.9 g, 21.3 mmol). The mixture was stirred at 90° C. for 5 h and at 25° C. for 17 h.

The volatiles were concentrated in vacuo. The crude residue was diluted with water (40 mL) and extracted with ethyl acetate (10 mL×3). The combined organic layers were washed with brine (10 mL), dried over sodium sulfate, filtered and concentrated under reduced pressure. The crude material was purified by column chromatography (silica gel, dichloromethane/methanol=15/1) to give 4-(3,5-difluorophenoxy)-N-hydroxypiperidine-1-carboximidamide (1.3 g, 4.79 mmol, 68%) as a white solid. LCMS (ESI) m/z: 272.2 $[M+H]^+$.

Step 5: Preparation of 5-(3-(4-(3,5-difluorophenoxy)piperidin-1-yl)-1,2,4-oxadiazol-5-yl)-1-methylpyridin-2(1H)-one

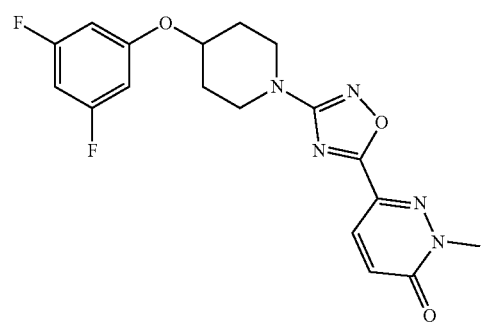

A solution of 1-methyl-6-oxo-1,6-dihydropyridine-3-carboxylic acid (91 mg, 0.59 mmol) in thionyl chloride (6 mL) was stirred at 80° C. for 2 h under argon. The volatiles were removed in vacuo. The crude product was dissolved in tetrahydrofuran (5 mL) and added dropwise to a solution of 4-(3,5-difluorophenoxy)-N-hydroxypiperidine-1-carboximidamide (160 mg, 0.59 mmol) and triethylamine (179 mg, 1.77 mmol) in tetrahydrofuran (15 mL) under argon at 0° C. The mixture was stirred at 80° C. for 17 h then concentrated in vacuo. The crude sample was dissolved in the minimum amount of N,N-dimethylformamide and purified via prep-HPLC (Boston C18, 10 μm, 21 mm×250 mm column, acetonitrile/0.01% aqueous formic acid) to give 5-(3-(4-(3,5-difluorophenoxy)piperidin-1-yl)-1,2,4-oxadiazol-5-yl)-1-methylpyridin-2(1H)-one (30 mg, 0.077 mmol, 13%) as a white solid. $^1$H NMR (400 MHz, Dimethylsulfoxide-$d_6$) δ 8.67 (d, J=2.3 Hz, 1H), 7.89 (dd, J=9.5, 2.4 Hz, 1H), 6.86-6.71 (m, 3H), 6.53 (d, J=9.5 Hz, 1H), 4.82-4.62 (m, 1H), 3.80-3.63 (m, 2H), 3.54 (s, 3H), 3.30 (s, 2H), 2.10-1.98 (m, 2H), 1.75-1.60 (m, 2H); LCMS (ESI) m/z: 389.1 $[M+H]^+$.

Example 60. Preparation of 5-(3-(4-(2-chloro-3-fluorophenoxy)piperidin-1-yl)-1,2,4-oxadiazol-5-yl)-1-methylpyridin-2(1H)-one (Compound 16)

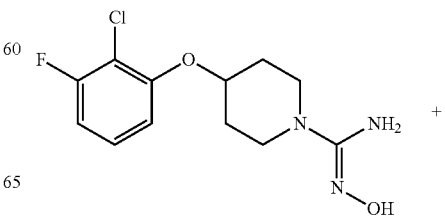

189

-continued

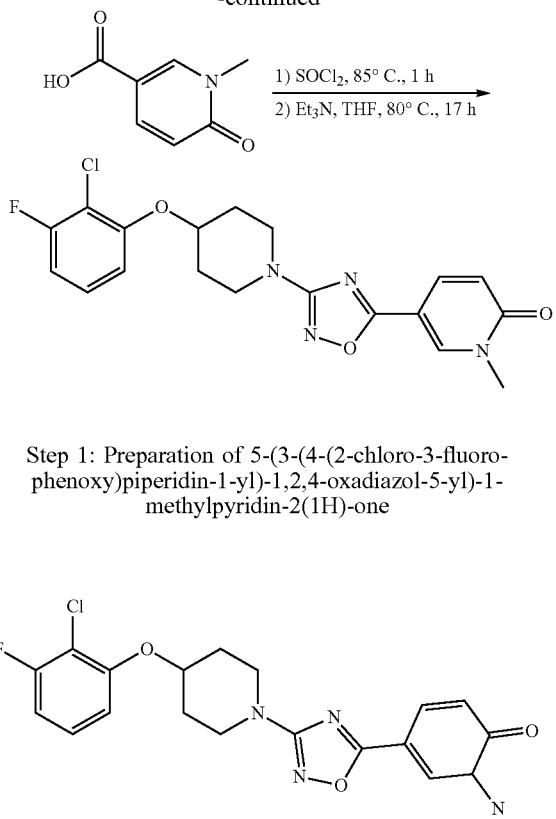

Step 1: Preparation of 5-(3-(4-(2-chloro-3-fluoro-phenoxy)piperidin-1-yl)-1,2,4-oxadiazol-5-yl)-1-methylpyridin-2(1H)-one A suspension of 1-methyl-6-oxo-1,6-dihydropyridine-3-carboxylic acid (199 mg, 1.3 mmol) in thionyl chloride (10 mL) was stirred at 85° C. for 1 h. The reaction mixture was concentrated under reduced pressure. The crude material was dissolved in tetrahydrofuran (5 mL) and added to a solution of (E)-4-(2-chloro-3-fluorophenoxy)-N-hydroxypiperidine-1-carboximidamide (287 mg, 1 mmol) and triethylamine (303 mg, 3 mmol) in tetrahydrofuran (10 mL) at 0° C. under argon. The mixture was stirred at 80° C. for 17 h and concentrated in vacuo. The crude sample was dissolved in the minimum amount of N,N-dimethylformamide and purified by prep-HPLC (BOSTON pHlex ODS, 10 μm, 21.2 mm×250 mm, acetonitrile/0.1% aqueous formic acid) to yield 5-(3-(4-(2-chloro-3-fluorophenoxy)piperidin-1-yl)-1,2,4-oxadiazol-5-yl)-1-methylpyridin-2(1H)-one (38.2 mg, 0.095 mmol, 10%) as a pink solid. $^1$H NMR (400 MHz, Dimethylsulfoxide-$d_6$) δ 8.68 (d, J=2.4 Hz, 1H), 7.89 (dd, J=4.8, 2.4 Hz, 1H), 7.38-7.32 (m, 1H), 7.15 (d, J=8.4 Hz, 1H), 7.01 (t, J=8.2 Hz, 1H), 6.53 (d, J=9.6 Hz, 1H), 4.84-4.80 (m, 1H), 3.70-3.62 (m, 2H), 3.55 (s, 3H), 3.45-3.39 (m, 2H), 2.06-2.01 (m, 2H), 1.80-1.74 (m, 2H); LCMS (ESI) m/z: 405.0 [M+H]$^+$.

Example 61. Preparation of 6-(3-(4-(2-chloro-3-fluorophenoxy)piperidin-1-yl)-1,2,4-oxadiazol-5-yl)-2-methylpyridazin-3(2H)-one (Compound 112)

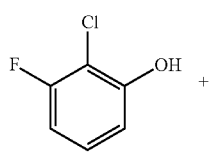

190

-continued

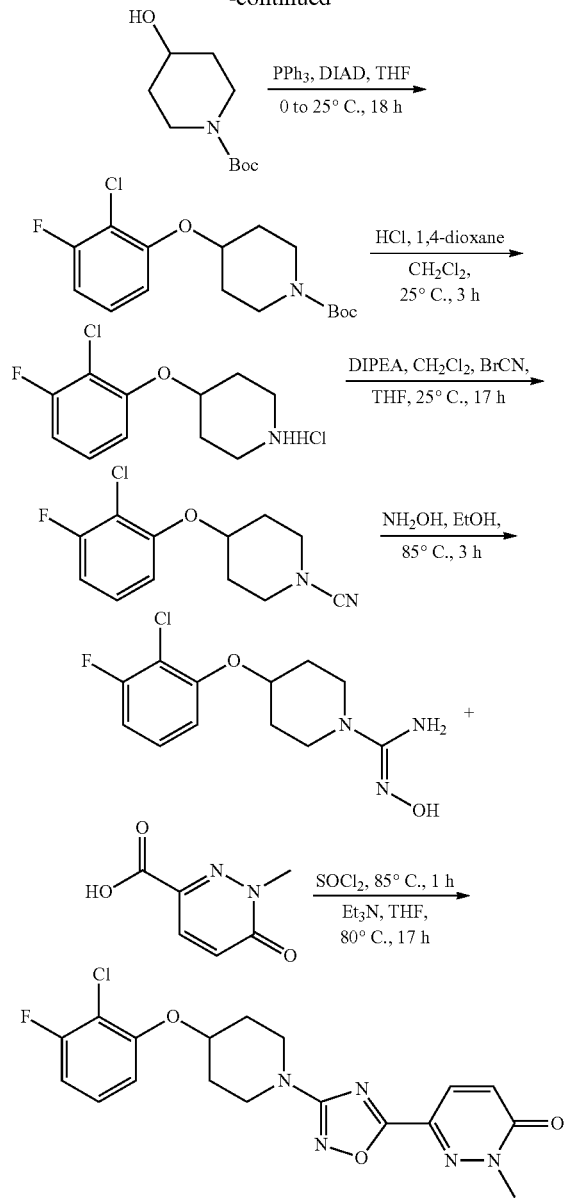

Step 1: Preparation of tert-butyl 4-(2-chloro-3-fluorophenoxy)piperidine-1-carboxylate To a solution of 2-chloro-3-fluorophenol (5.1 g×35 mmol), tert-butyl 4-hydroxypiperidine-1-carboxylate (7.04 g, 35 mmol) and triphenylphosphine (11 g, 42 mmol) in tetrahydrofuran (150 mL) was added diisopropyl azodicarboxylate (8.48 g, 42 mmol) at 0° C. The mixture was stirred at 25° C. for 18 h. The volatiles were removed under reduced pressure and petroleum ether (250 ml) was added. The resulting precipitate was filtered and the filtrate was concentrated and purified by column chromatography (silica gel, petroleum ether/ethyl acetate=17/1) to yield tert-butyl 4-(2-chloro-3-fluorophenoxy)piperidine-1-carboxylate as a brown oil (9.4 g, 28.6 mmol, 82%). LCMS (ESI) mz: 274.0 [M-56+H]⁺.

Step 2: Preparation of 4-(2-chloro-3-fluorophenoxy)piperidine Hydrochloride

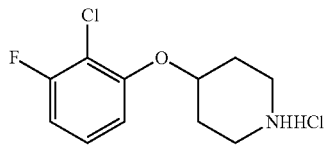

A solution of tert-butyl 4-(2-chloro-3-fluorophenoxy)piperidine-1-carboxylate (9.9 g, 30.1 mmol) and hydrochloric acid in 1,4-dioxane (30 mL, 4 N) in dichloromethane (30 ml) was stirred at 25° C. for 2 h. The reaction mixture was concentrated and methyl tert-butyl ether (100 mL) was added. The resulting precipitate was filtered to afford 4-(2-chloro-3-fluorophenoxy)piperidine hydrochloride (5.8 g, 21.8 mmol, 73%) as a white solid. LCMS (ESI) m/z: 230.1 [M+H]⁺.

Step 3: Preparation of 4-(2-chloro-3-fluorophenoxy) piperidine-1-carbonitrile

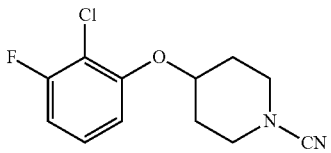 [SMILES: N#CN1CCC(Oc2cccc(F)c2Cl)CC1]

To a solution of 4-(2-chloro-3-fluorophenoxy)piperidine hydrochloride (5.78 g, 21.8 mmol) in tetrahydrofuran (80 mL) and dichloromethane (80 mL) under argon was added N,N-diisopropylethylamine (8.44 g, 65.4 mmol) and cyanogen bromide (2.31 g, 21.8 mmol) in dichloromethane (5 mL). The mixture was stirred at 25° C. for 17 h. The reaction mixture was washed with water (80 mL×2) followed by brine (40 mL). The combined organic layers were dried over sodium sulfate, filtered and concentrated under reduced pressure to yield crude 4-(2-chloro-3-fluorophenoxy)piperidine-1-carbonitrile (5.5 g, 21.7 mmol, 99%). LCMS (ESI) m/z: 255.1 [M+H]⁺. This material was used in the next step without further purification.

Step 4: Preparation of (E)-4-(2-chloro-3-fluorophenoxy)-N'-hydroxypiperidine-1-carboximidamide

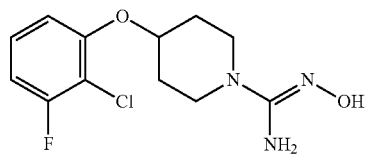 [SMILES: N/C(=N\O)N1CCC(Oc2cccc(F)c2Cl)CC1]

To a solution of 4-(2-chloro-3-fluorophenoxy)piperidine-1-carbonitrile (2.9 g, 11.4 mmol) in ethanol (50 mL) was added hydroxylamine (1.13 g, 34.3 mmol, 50% in water). The mixture was stirred at 85° C. for 3 h under argon. The reaction mixture was concentrated under reduced pressure. The crude residue was purified by column chromatography (silica gel, dichloromethane/ammonia in methanol (7 N)=55/45) to give (E)-4-(2-chloro-3-fluorophenoxy)-N'-hydroxypiperidine-1-carboximidamide (2.1 g, 7.3 mmol, 64%) as white solid. LCMS (ESI) m/z: 288.1 [M+H]⁺.

Step 5: Preparation of 6-(3-(4-(2-chloro-3-fluorophenoxy)piperidin-1-yl)-1,2,4-oxadiazol-5-yl)-2-methylpyridazin-3(2H)-one

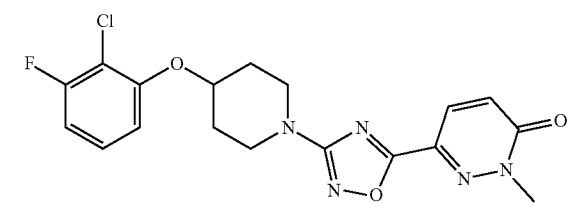 [SMILES: Cn1nc(-c2nc(N3CCC(Oc4cccc(F)c4Cl)CC3)no2)ccc1=O]

A solution of 1-methyl-6-oxo-1,6-dihydropyridazine-3-carboxylic acid (200 mg, 1.3 mmol) in thionyl chloride (10 mL) was stirred at 85° C. for 1 h. The reaction mixture was concentrated under reduced pressure. The crude material was dissolved in tetrahydrofuran (5 mL) and added to a solution of (E)-4-(2-chloro-3-fluorophenoxy)-N'-hydroxypiperidine-1-carboximidamide (287 mg, 1 mmol) and triethylamine (303 mg, 3 mmol) in tetrahydrofuran (10 mL) under argon at 0° C. The mixture was stirred at 80° C. for 17 h and concentrated in vacuo. The crude sample was dissolved in the minimum amount of N,N-dimethylformamide and purified by prep-HPLC (BOSTON pHlex ODS, 10 μm, 21.2 mm×250 mm, acetonitrile/0.1% aqueous formic acid) to yield 6-(3-(4-(2-chloro-3-fluorophenoxy)piperidin-1-yl)-1,2,4-oxadiazol-5-yl)-2-methylpyridazin-3(2H)-one (64.3 mg, 0.16 mmol, 16%) as a white solid. ¹H NMR (400 MHz, Dimethylsulfoxide-d₆) δ 7.97 (d, J=9.6 Hz, 1H), 7.38-7.32 (m, 1H), 7.16 (d, J=8.4 Hz, 1H), 7.12 (d, J=10.0 Hz, 1H), 7.02 (t, J=8.6 Hz, 1H), 4.86-4.82 (m, 1H), 3.78 (s, 3H), 3.72-3.66 (m, 2H), 3.49-3.43 (m, 2H), 2.07-2.02 (m, 2H), 1.82-1.74 (m, 2H); LCMS (ESI) m/z: 406.0 [M+H]⁺.

Example 62. Preparation of 6-(5-(4-(3,5-difluorobenzyl)piperidin-1-yl)-1,3,4-thiadiazol-2-yl)-2-methylpyridazin-3(2H)-one (Compound 121)

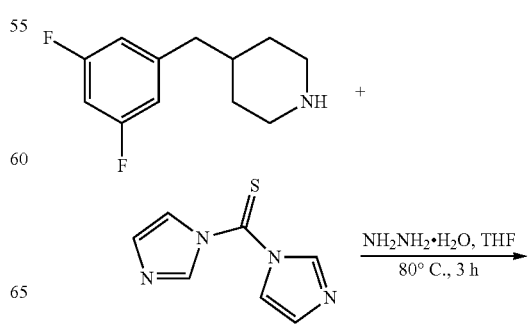

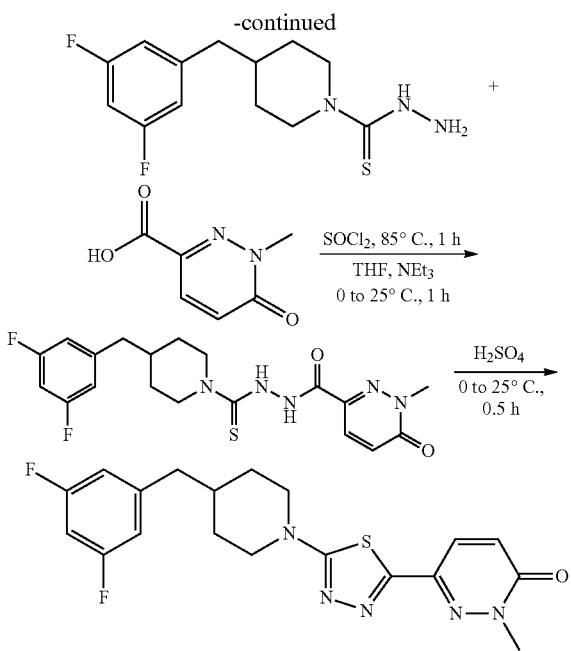

Step 1: Preparation of 4-(3,5-difluorobenzyl)piperidine-1-carbothiohydrazide

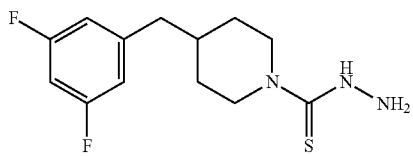 [SMILES: NNC(=S)N1CCC(Cc2cc(F)cc(F)c2)CC1]

To a solution of di(1H-imidazol-1-yl)methanethione (1.25 g, 7 mmol) in tetrahydrofuran (20 mL) was added 4-(3,5-difluorobenzyl)piperidine (1.48 g, 7 mmol) in tetrahydrofuran (5 mL) at 0° C. The reaction mixture was stirred at 25° C. for 2 h, then hydrazine hydrate (1.5 mL) was added and the reaction stirred at 80° C. for 3 h. The reaction solution was concentrated under reduced pressure, diluted with aqueous sodium bicarbonate solution (50 mL) and extracted with ethyl acetate (50 mL×2). The combined organic layers were washed with brine (50 mL), dried over sodium sulfate, filtered and concentrated in vacuo to give 4-(3,5-difluorobenzyl)piperidine-1-carbothiohydrazide (1.9 g, 6.7 mmol, 95%) as a brown oil. LCMS (ESI) m/z: 286.2 [M+H]$^+$.

Step 2: Preparation of N'-(4-(3,5-difluorobenzyl)piperidine-1-carbonothioyl)-1-methyl-6-oxo-1,6-dihydropyridazine-3-carbohydrazide

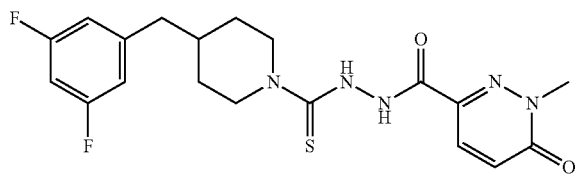 [SMILES: Cn1nc(C(=O)NNC(=S)N2CCC(Cc3cc(F)cc(F)c3)CC2)ccc1=O]

A suspension of 1-methyl-6-oxo-1,6-dihydropyridazine-3-carboxylic acid (200 mg, 1.3 mmol) in thionyl chloride (15 mL) was stirred at 85° C. for 1 h. The reaction mixture was concentrated, dissolved in tetrahydrofuran (5 mL) and added to a solution of 4-(3,5-difluorobenzyl)piperidine-1-carbothiohydrazide (285 mg, 1 mmol) and triethylamine (303 mg, 3 mmol) in tetrahydrofuran (15 mL) at 0° C. The reaction mixture was stirred at 85° C. for 20 h. The reaction mixture was cooled, poured into ice water and extracted with ethyl acetate (30 mL×2). The combined organic layers were washed with brine (30 mL), dried over sodium sulfate, filtered and concentrated under reduced pressure. The crude product was purified by column chromatography (silica gel, dichloromethane/ammonia in methanol (7 N)=50/1) to afford N'-(4-(3,5-difluorobenzyl)piperidine-1-carbonothioyl)-1-methyl-6-oxo-1,6-dihydropyridazine-3-carbohydrazide (190 mg, 0.45 mmol, 45%) as a yellow solid. LCMS (ESI) m/z: 422.1 [M+H]$^+$.

Step 3: Preparation of 6-(5-(4-(3,5-difluorobenzyl)piperidin-1-yl)-1,3,4-thiadiazol-2-yl)-2-methylpyridazin-3(2H)-one

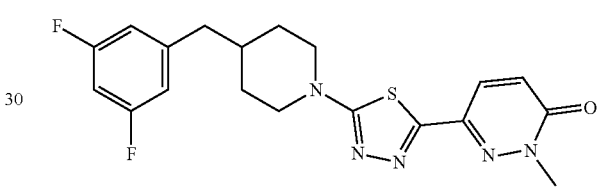

A solution of N'-(4-(3,5-difluorobenzyl)piperidine-1-carbonothioyl)-1-methyl-6-oxo-1,6-dihydropyridazine-3-carbohydrazide (140 mg, 0.33 mmol) and concentrated sulfuric acid (2.5 mL) was stirred at 0° C. and warmed to 25° C. for 0.5 h. The reaction mixture was poured into ice water and extracted with ethyl acetate (20 mL×3). The combined organic layers were washed with brine (20 mL), dried over sodium sulfate, filtered and concentrated. The crude sample was dissolved in the minimum amount of N,N-dimethylformamide and purified via prep-HPLC (Boston C18, 10 µm, 21 mm×250 mm column; acetonitrile/0.01% aqueous trifluoroacetic acid) to give 6-(5-(4-(3,5-difluorobenzyl)piperidin-1-yl)-1,3,4-thiadiazol-2-yl)-2-methylpyridazin-3(2H)-one (48 mg, 0.12 mmol, 36%) as a white solid. $^1$H NMR (400 MHz, Dimethylsulfoxide-d$_6$) δ 8.00 (d, J=9.6 Hz, 1H), 7.07 (d, J=9.6 Hz, 2H), 6.97 (d, J=6.8 Hz, 2H), 3.93 (d, J=9.2 Hz, 2H), 3.67 (s, 3H), 3.21-3.15 (m, 2H), 2.60 (d, J=7.2 Hz, 2H), 1.90-1.85 (m, 1H), 1.67 (d, J=12.8 Hz, 2H), 1.34-1.24 (m, 2H); LCMS (ESI) m/z: 404.1 [M+H]$^+$.

Example 63. Preparation of 5-(5-(4-(3,5-difluorobenzyl)piperidin-1-yl)-1,2,4-oxadiazol-3-yl)-1-methylpyridin-2(1H)-one (Compound 21)

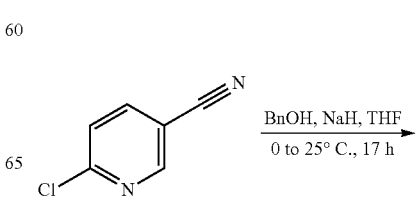

-continued

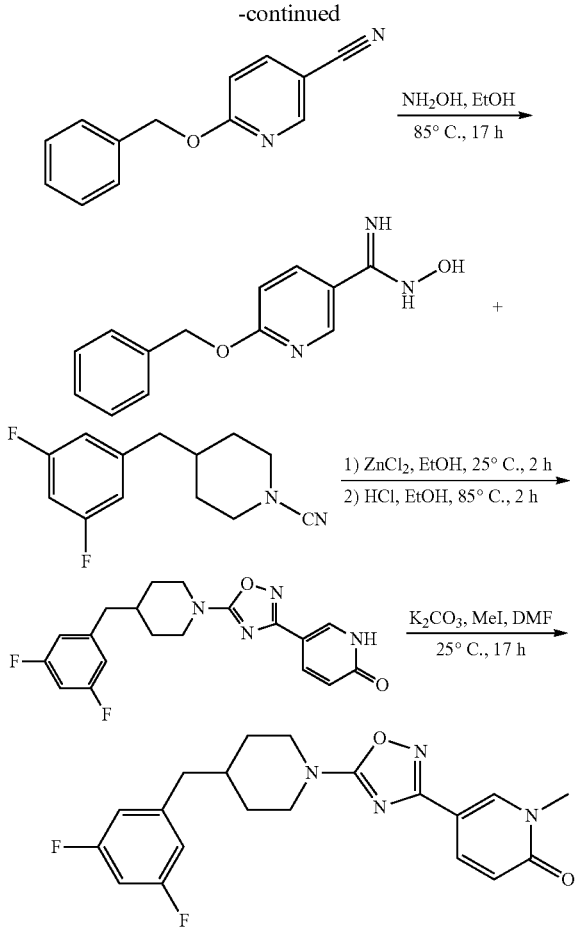

Step 1: Preparation of 6-(benzyloxy)nicotinonitrile

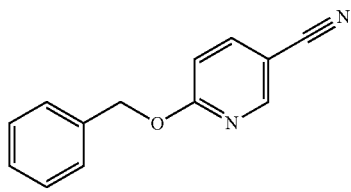 [SMILES: N#Cc1ccc(OCc2ccccc2)nc1]

To a solution of benzyl alcohol (8.61 g, 79.8 mmol) in tetrahydrofuran (150 mL) at 0° C. was added sodium hydride (3.19 g, 79.8 mmol, 60% in mineral oil). After 30 min, 6-chloronicotinonitrile (10.0 g, 72.5 mmol) was added and the solution was stirred at 25° C. for 17 h. The reaction mixture was poured into ice-water (200 mL) and neutralized to pH 7 with concentrated hydrochloric acid (2 mL). The aqueous layer was extracted with ethyl acetate (200 mL×2). The combined organic layers were concentrated and purified by column chromatography (silica gel, petroleum ether/ethyl acetate=20/1 to 5/1) to give 6-(benzyloxy)nicotinonitrile (14.0 g, 66.7 mmol, 92%) as a white solid. LCMS (ESI) m/z: 211.1 [M+H]$^+$.

Step 2: Preparation of 6-(benzyloxy)-N-hydroxynicotinamidine

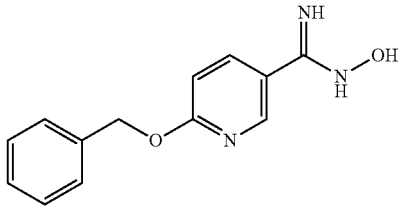 [SMILES: N=C(NO)c1ccc(OCc2ccccc2)nc1]

A solution of 6-(benzyloxy)nicotinonitrile (1.00 g, 4.76 mmol)) and hydroxylamine (2 mL, 50% in water) in ethanol (20 mL) was heated to 85° C. for 17 h. The mixture was concentrated to give 6-(benzyloxy)-N-hydroxynicotinamidine (1.16 g, 4.76 mmol, 100%) as a white solid. LCMS (ESI) m/z: 244.2 [M+H]$^+$. This material was used in the next step without further purification.

Step 3: Preparation of 5-(5-(4-(3,5-difluorobenzyl) piperidin-1-yl)-1,2,4-oxadiazol-3-yl)pyridin-2(1H)-one

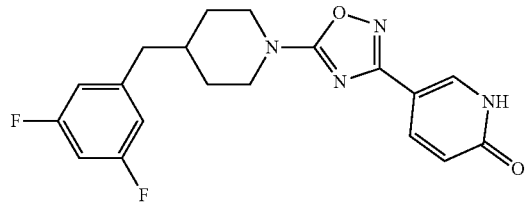 [SMILES: O=c1ccc(-c2noc(N3CCC(Cc4cc(F)cc(F)c4)CC3)n2)c[nH]1]

To a solution of 6-(benzyloxy)-N-hydroxynicotinamidine (309 mg, 1.27 mmol) and 4-(3,5-difluorobenzyl)piperidine-1-carbonitrile (300 mg, 1.27 mmol) in ethanol (10 mL) at 25° C. was added zinc chloride (346 mg, 2.54 mmol). The reaction mixture was stirred for 2 h, then concentrated hydrochloric acid (0.5 mL) was added and the solution was heated to 85° C. for 2 h. The reaction solution was diluted with water (50 mL) and extracted with ethyl acetate (50 mL×2). The combined organic layers were washed with brine (50 mL), dried over sodium sulfate, filtered and concentrated in vacuo. The crude sample was dissolved in the minimum amount of N,N-dimethylformamide and purified by prep-HPLC (column SunFire prep C18, 10 µm, 19 mm×250 mm, 40-50% over 7 min at 2 mL/min, acetonitrile/ 0.05% aqueous trifluoroacetic acid) to give 5-(5-(4-(3,5-difluorobenzyl)piperidin-1-yl)-1,2,4-oxadiazol-3-yl)pyridin-2(1H)-one (20 mg, 0.053 mmol, 4%) as a white solid. $^1$H NMR (400 MHz, Dimethylsulfoxide-d$_6$) δ 12.04 (s, 1H), 7.86 (s, 1H), 7.78 (d, J=9.6 Hz, 1H), 7.05 (t, J=8.4 Hz, 1H), 6.96 (d, J=7.2 Hz, 2H), 6.43 (d, J=7.6 Hz, 1H), 4.01 (d, J=12.8 Hz, 2H), 3.10 (t, J=12.4 Hz, 2H), 2.58 (d, J=7.2 Hz, 1H), 1.83-1.84 (m, 1H), 1.64 (d, J=13.2 Hz, 2H), 1.19-1.27 (m, 2H); LCMS (ESI) m/z: 373.2 [M+H]$^+$.

Step 4: Preparation of 5-(5-(4-(3,5-difluorobenzyl) piperidin-1-yl)-1,2,4-oxadiazol-3-yl)-1-methylpyridin-2(1H)-one

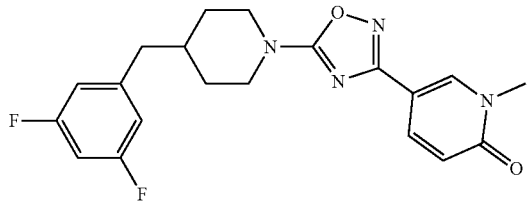

A mixture of 5-(5-(4-(3,5-difluorobenzyl)piperidin-1-yl)-1,2,4-oxadiazol-3-yl)pyridin-2(1H)-one (350 mg, 0.94 mmol), potassium carbonate (260 mg, 1.88 mmol) and iodomethane (267 mg, 1.88 mmol) in N,N-dimethylformamide (5 mL) was stirred at 25° C. for 17 h. The mixture was filtered and the filtrate was concentrated in vacuo. The crude sample was dissolved in the minimum amount of N,N-dimethylformamide and purified via prep-HPLC (Sunfire prep C18, 10 μm, 19 mm×250 mm; mobile phase:[water (0.05% trifluoroacetic acid)-acetonitrile]; B %: 40%-50%, 7 min) to give 5-(5-(4-(3,5-difluorobenzyl)piperidin-1-yl)-1, 2,4-oxadiazol-3-yl)-1-methylpyridin-2(1H)-one (81 mg, 0.21 mmol, 22%) as a white solid. $^1$H NMR (400 MHz, Dimethylsulfoxide-d$_6$) δ 8.30 (d, J=2.4 Hz, 1H), 7.78 (dd, J=9.6 Hz, J=2.4 Hz, 1H), 7.02-7.07 (m, 1H), 7.05 (t, J=8.4 Hz, 1H), 6.97 (d, J=6.8 Hz, 2H), 6.48 (d, J=9.2 Hz, 1H), 4.02 (d, J=12.8 Hz, 2H), 3.51 (s, 1H), 3.12 (t, J=10.8 Hz, 2H), 2.59 (d, J=7.2 Hz, 1H), 1.82-1.88 (m, 1H), 1.66 (d, J=12.0 Hz, 2H), 1.18-1.29 (m, 2H); LCMS (ESI) m/z: 387.1 [M+H]$^+$.

Example 64. Preparation of 6-(5-(4-(3,5-difluorobenzyl)piperidin-1-yl)-1,2,4-oxadiazol-3-yl)-2-methylpyridazin-3(2H)-one (Compound 122)

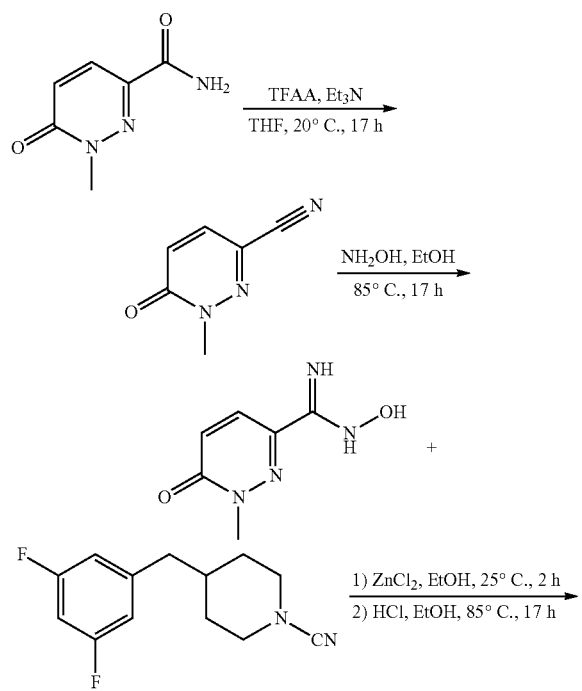

-continued

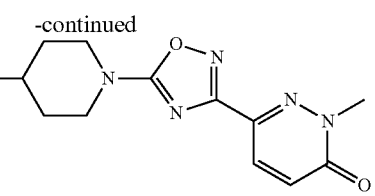

Step 1: Preparation of 1-methyl-6-oxo-1,6-dihydropyridazine-3-carbonitrile

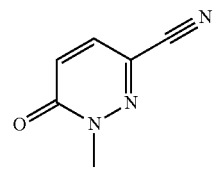

To a solution of 1-methyl-6-oxo-1,6-dihydropyridazine-3-carboxamide (600 mg, 0.31 mmol) and trifluoroacetic anhydride (1.65 g, 7.84 mmol) in tetrahydrofuran (20 mL) at 0° C. was added triethylamine (1.98 g, 19.6 mmol). The solution was stirred at 20° C. for 17 h, then it was concentrated in vacuo and purified by column chromatography (silica gel, petroleum ether/ethyl acetate=5/1 to 1/1) to give 1-methyl-6-oxo-1,6-dihydropyridazine-3-carbonitrile (520 mg, 3.85 mmol, 98%) as a white solid. LCMS (ESI) m/z: 136.2 [M+H]$^+$.

Step 2: Preparation of N-hydroxy-1-methyl-6-oxo-1,6-dihydropyridazine-3-carboximidamide

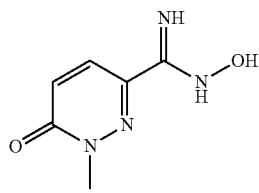

A solution of 1-methyl-6-oxo-1,6-dihydropyridazine-3-carbonitrile (480 mg, 3.56 mmol) and hydroxylamine (50% in water, 2 mL) in ethanol (15 mL) was heated to 85° C. for 17 h. The reaction mixture was concentrated in vacuo to give N-hydroxy-1-methyl-6-oxo-1,6-dihydropyridazine-3-carboximidamide as a white solid (597 mg, 3.56 mmol, 100%). LCMS (ESI) m/z: 169.2 [M+H]$^+$.

Step 3: Preparation of 6-(5-(4-(3,5-difluorobenzyl)piperidin-1-yl)-1,2,4-oxadiazol-3-yl)-2-methylpyridazin-3(2H)-one

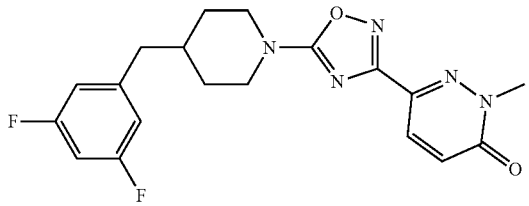

To a solution of N-hydroxy-1-methyl-6-oxo-1,6-dihydropyridazine-3-carboximidamide (170 mg, 1.02 mmol) and 4-(3,5-difluorobenzyl)piperidine-1-carbonitrile (200 mg, 0.84 mmol) in ethanol (10 mL) at 25° C. was added zinc chloride (229 mg, 1.68 mmol). The solution was stirred at 25° C. for 2 h, then concentrated hydrochloric acid (0.6 mL) was added and the solution was heated to 85° C. for 17 h. The solution was diluted with water (50 mL) and extracted with ethyl acetate (50 mL×2). The combined organic layers were washed with brine (50 mL), dried over sodium sulfate, filtered and concentrated in vacuo. The crude sample was dissolved in the minimum amount of N,N-dimethylformamide and purified by prep-HPLC (Sunfire prep C18, 10 μm, 19 mm×250 mm; mobile phase:[water (0.05% trifluoroacetic acid)-acetonitrile]; B %: 40%-50%, 8 min) to give 6-(5-(4-(3,5-difluorobenzyl)piperidin-1-yl)-1,2,4-oxadiazol-3-yl)-2-methylpyridazin-3(2H)-one a white solid (157 mg, 0.41 mmol, 48%). $^1$H NMR (400 MHz, Dimethylsulfoxide-d$_6$) δ 7.82 (d, J=9.6 Hz, 1H), 7.02-7.08 (m, 2H), 6.94-6.99 (m, 2H), 4.03 (d, J=13.2 Hz, 2H), 3.73 (s, 3H), 3.14 (td, J=13.2 Hz, J=2.8 Hz, 2H), 2.59 (d, J=7.2 Hz, 2H), 1.84-1.89 (m, 1H), 1.67 (d, J=11.2 Hz, 2H), 1.19-1.30 (m, 2H); LCMS (ESI) m/z: 388.2 [M+H]$^+$.

Example 65. Preparation of 5-(5-(4-(3,5-difluorobenzyl)piperidin-1-yl)-1,3,4-oxadiazol-2-yl)-1-methylpyridin-2(1H)-one (Compound 19)

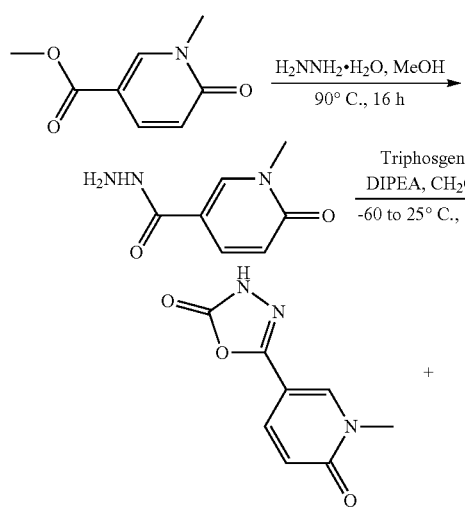

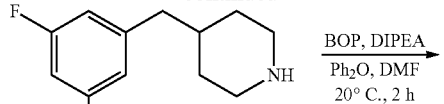

Step 1: Preparation of 1-methyl-6-oxo-1,6-dihydropyridine-3-carbohydrazide

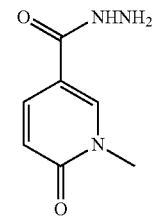

To a solution of methyl 1-methyl-6-oxo-1,6-dihydropyridine-3-carboxylate (3.0 g, 17.9 mmol) in methanol (20 mL) at 20° C. was added hydrazine monohydrate (5 mL). The mixture was heated at 90° C. for 16 h. The reaction solution was cooled to room temperature and filtered. The filtered solid was washed with methanol and dried to afford 1-methyl-6-oxo-1,6-dihydropyridine-3-carbohydrazide (2.1 g, 70%) as a white solid. This material was used in the next step without further purification.

Step 2: Preparation of 5-(1-methyl-6-oxo-1,6-dihydropyridin-3-yl)-1,3,4-oxadiazol-2(3H)-one

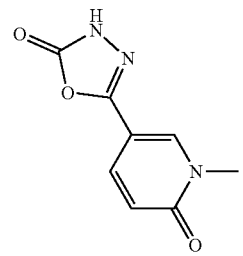

To a solution of 1-methyl-6-oxo-1,6-dihydropyridine-3-carbohydrazide (1.0 g, 5.99 mmol) and diisopropylethylamine (1.55 g, 11.97 mmol) in dichloromethane (50 mL) was added a solution of triphosgene (1.93 g, 6.58 mmol) in dichloromethane (10 mL). The mixture was stirred at 20° C. for 2 h. The solid was filtered and washed with dichlo-

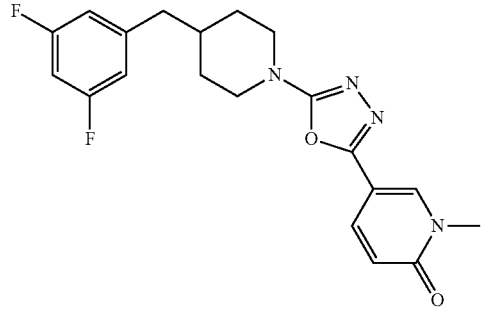

Step 3: Preparation of 5-(5-(4-(3,5-difluorobenzyl)piperidin-1-yl)-1,3,4-oxadiazol-2-yl)-1-methylpyridin-2(1H)-one

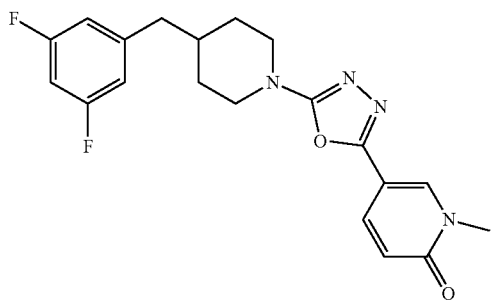 [SMILES: Cn1cc(-c2nnc(N3CCC(Cc4cc(F)cc(F)c4)CC3)o2)ccc1=O]

To a solution of 5-(1-methyl-6-oxo-1,6-dihydropyridin-3-yl)-1,3,4-oxadiazol-2(3H)-one (240 mg, 1.24 mmol), 4-(3,5-difluorobenzyl)piperidine (525 mg, 2.49 mmol), (benzotriazol1yloxy)tris(dimethylamino)phosphonium hexafluorophosphate (605 mg, 1.37) and diphenyl ether (423 mg, 2.49 mmol) in N,N-dimethylformamide (6 mL) at 20° C. was added diisopropylethylamine (321 mg, 2.49 mmol). The mixture was stirred at 20° C. for 2 h. The reaction was diluted with ethyl acetate (100 mL) and washed with water (50 mL) followed by brine (50 mL). The organic layer was concentrated in vacuo. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 5-(5-(4-(3,5-difluorobenzyl)piperidin-1-yl)-1,3,4-oxadiazol-2-yl)-1-methylpyridin-2(1H)-one (134 mg, 0.347 mmol, 26%) as a white solid. $^1$H NMR (400 MHz, Dimethylsulfoxide-$d_6$) δ 8.40 (d, J=2.4 Hz, 1H), 7.84-7.81 (m, 1H), 7.08-6.96 (m, 3H), 6.52 (d, J=9.6 Hz, 1H), 3.92 (d, J=13.2 Hz, 2H), 3.51 (s, 3H), 3.05-2.99 (m, 2H), 2.59 (d, J=6.8 Hz, 2H), 1.84-1.80 (m, 1H), 1.64 (d, J=11.6 Hz, 2H), 1.31-1.22 (m, 2H); LCMS (ESI) m/z: 387.1 [M+H]$^+$.

Example 66. Preparation of 5-(5-(4-(3-fluorobenzyl)piperidin-1-yl)-1,3,4-oxadiazol-2-yl)-1-methylpyridin-2(1H)-one (Compound 18)

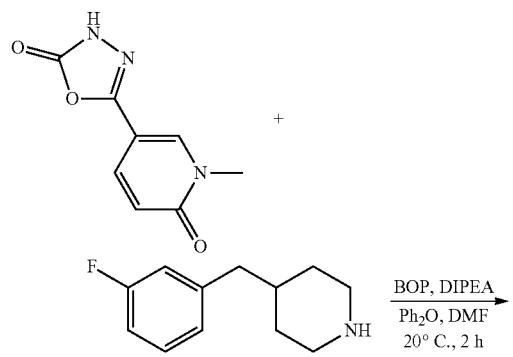

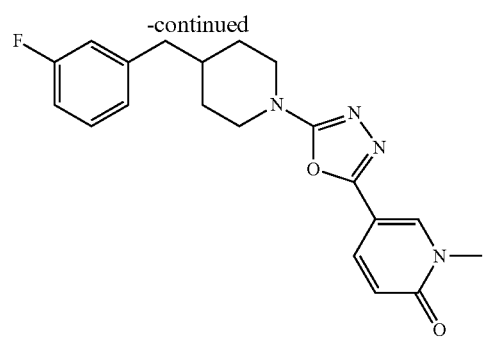

Step 1: Preparation of 5-(5-(4-(3-fluorobenzyl)piperidin-1-yl)-1,3,4-oxadiazol-2-yl)-1-methylpyridin-2(1H)-one

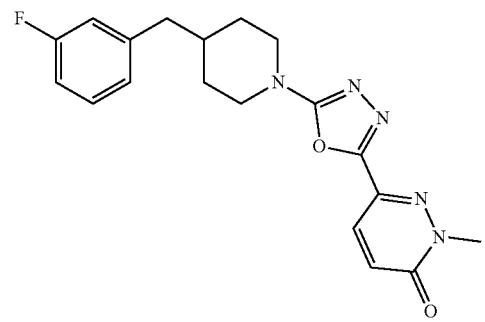 [SMILES: Cn1nc(-c2nnc(N3CCC(Cc4cccc(F)c4)CC3)o2)ccc1=O]

To a solution of 5-(1-methyl-6-oxo-1,6-dihydropyridin-3-yl)-1,3,4-oxadiazol-2(3H)-one (240 mg, 1.24 mmol), 4-(3-fluorobenzyl)piperidine (480 mg, 2.49 mmol), (benzotriazole-1-yloxy)tris(dimethylamino)phosphonium hexafluorophosphate (605 mg, 1.37) and diphenyl ether (423 mg, 2.49 mmol) in N,N-dimethylformamide (6 mL) was added diisopropylethylamine (321 mg, 2.49 mmol) at 20° C. The mixture was stirred at 20° C. for 2 h. The reaction was diluted with ethyl acetate (100 mL) and washed with water (50 mL) followed by brine (50 mL). The organic layer was concentrated in vacuo. The crude residue was dissolved in the minimum amount of methanol and purified by chiral-HPLC (SFC-80, Ad 20×250 mm, 10 μM column: $CO_2$/0.2% ammonia in methanol, 75/25) to give 5-(5-(4-(3-fluorobenzyl)piperidin-1-yl)-1,3,4-oxadiazol-2-yl)-1-methylpyridin-2(1H)-one (43.6 mg, 0.118 mmol, 9%) as a white solid. $^1$H NMR (400 MHz, Dimethylsulfoxide-$d_6$) δ 8.39 (d, J=2.4 Hz, 1H), 7.84-7.81 (m, 1H), 7.34 (q, J=7.2 Hz, 1H), 7.06-7.01 (m, 3H), 6.52 (d, J=9.6 Hz, 1H), 3.92 (d, J=12.8 Hz, 2H), 3.51 (s, 3H), 3.01 (t, J=11.8 Hz, 2H), 2.58 (d, J=7.6 Hz, 2H), 1.81-1.77 (m, 1H), 1.65 (d, J=13.2 Hz, 2H), 1.31-1.21 (m, 2H); LCMS (ESI) m/z: 369.1 [M+H]$^+$.

Example 67. Preparation of 5-(5-(4-(3,4-difluorobenzyl)piperidin-1-yl)-1,2,4-oxadiazol-3-yl)-1-methylpyridin-2(1H)-one (Compound 20)

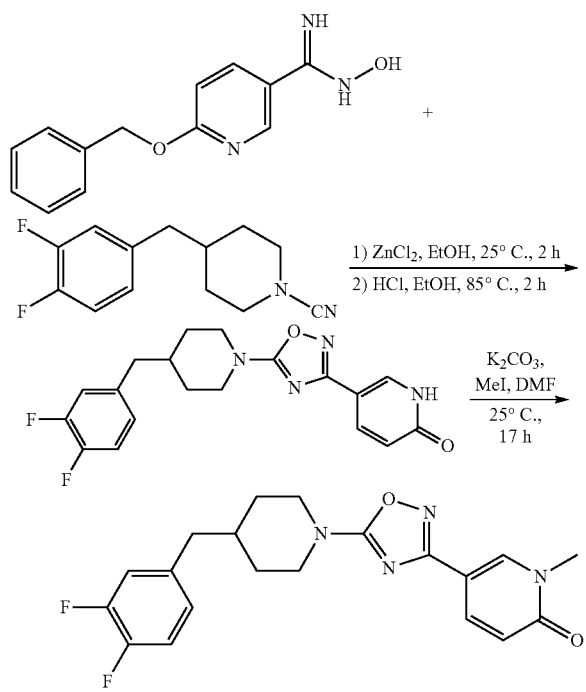

Step 1: Preparation of 5-(5-(4-(3,4-difluorobenzyl)piperidin-1-yl)-1,2,4-oxadiazol-3-yl)pyridin-2(1H)-one To a solution of 6-(benzyloxy)-N-hydroxynicotinamidine (1.44 g, 5.93 mmol) and 4-(3,4-difluorobenzyl)piperidine-1-carbonitrile (1.40 g, 5.93 mmol) in ethanol (40 mL) was added zinc chloride (1.62 g, 11.9 mmol). The reaction mixture was stirred at 25° C. for 2 h, then concentrated hydrochloric acid (0.5 mL) was added and the reaction was heated to 85° C. for 2 h. The reaction was diluted with water (150 mL) and extracted with ethyl acetate (150 mL×2). The combined organic layers were washed with brine (150 mL), dried over sodium sulfate and concentrated in vacuo. The crude sample was dissolved in the minimum amount of N,N-dimethylformamide and purified via prep-HPLC (Sunfire prep C18, 10 μm, 19×250 mm; mobile phase: [water (0.05% trifluoroacetic acid)-acetonitrile]; B %: 40-50%, 7 min) to give 5-(5-(4-(3,4-difluorobenzyl)piperidin-1-yl)-1,2,4-oxadiazol-3-yl)pyridin-2(1H)-one (270 mg, 0.73 mmol, 12%) as a white solid. $^1$H NMR (400 MHz, Dimethylsulfoxide-d$_6$) δ 12.04 (s, 1H), 7.86 (s, 1H), 7.77-7.85 (m, 1H), 7.26-7.38 (m, 2H), 7.04 (s, 1H), 6.43 (d, J=9.6 Hz, 1H), 4.00 (d, J=13.2 Hz, 2H), 3.09 (t, J=10.4 Hz, 2H), 2.55 (d, J=7.2 Hz, 1H), 1.88-1.82 (m, 1H), 1.64 (d, J=11.6 Hz, 2H), 1.17-1.27 (m, 2H); LCMS (ESI) m/z: 373.2 [M+H]$^+$.

Step 2: Preparation of 5-(5-(4-(3,4-difluorobenzyl)piperidin-1-yl)-1,2,4-oxadiazol-3-yl)-1-methylpyridin-2(1H)-one

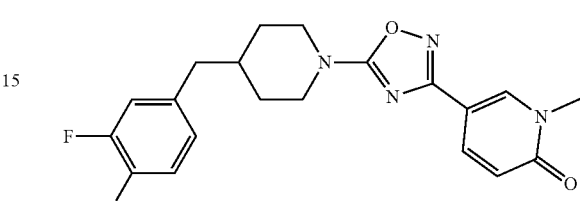

A mixture of 5-(5-(4-(3,4-difluorobenzyl)piperidin-1-yl)-1,2,4-oxadiazol-3-yl)pyridin-2(1H)-one (200 mg, 0.54 mmol), potassium carbonate (149 mg, 1.08 mmol) and iodomethane (153 mg, 1.08 mmol) in N,N-dimethylformamide (4 mL) was stirred at 25° C. for 17 h. The mixture was filtered and the filtrate was concentrated in vacuo. The crude sample was dissolved in the minimum amount of N,N-dimethylformamide and purified via prep-HPLC (Sunfire prep C18, 10 μm, 19×250 mm; mobile phase: [water (0.05% trifluoroacetic acid)-acetonitrile]; B %: 40-50%, 7 min) to give 5-(5-(4-(3,4-difluorobenzyl)piperidin-1-yl)-1,2,4-oxadiazol-3-yl)-1-methylpyridin-2(1H)-one as a white solid (120 mg, 0.31 mmol, 58%). $^1$H NMR (400 MHz, Dimethylsulfoxide-d$_6$) δ 8.29 (d, J=2.4 Hz, 1H), 7.78 (dd, J=9.6 Hz, J=2.4 Hz, 1H), 7.26-7.38 (m, 2H), 7.02-7.05 (m, 1H), 6.48 (d, J=9.2 Hz, 1H), 4.02 (d, J=12.8 Hz, 2H), 3.51 (s, 1H), 3.12 (dt, J=12.4 Hz, J=2.0 Hz, 2H), 2.55 (d, J=7.2 Hz, 1H), 1.77-1.83 (m, 1H), 1.66 (d, J=11.2 Hz, 2H), 1.18-1.28 (m, 2H); LCMS (ESI) m/z: 387.1 [M+H]$^+$.

Example 68. Preparation of 6-(5-(4-(3,4-difluorobenzyl)piperidin-1-yl)-1,2,4-oxadiazol-3-yl)-2-methylpyridazin-3(2H)-one (Compound 123)

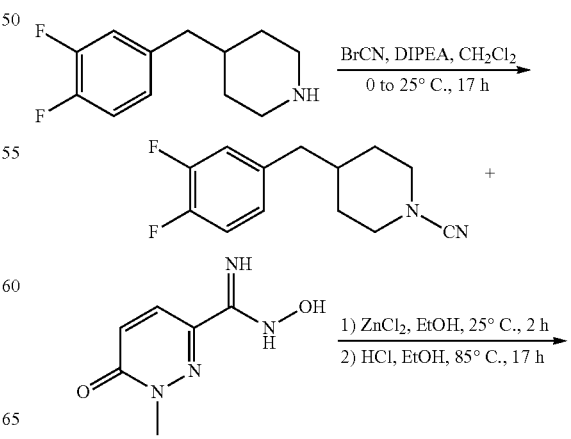

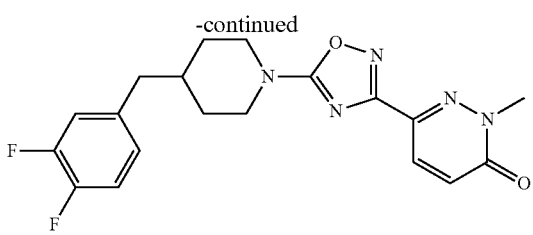

Step 1: Preparation of
4-(3,4-difluorobenzyl)piperidine-1-carbonitrile

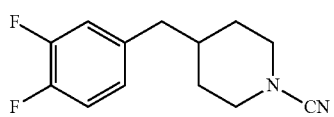 [SMILES: N#CN1CCC(Cc2ccc(F)c(F)c2)CC1]

To a solution of 4-(3,4-difluorobenzyl)piperidine (2.11 g, 10.0 mmol) in dichloromethane (40 mL) at 0° C. was added cyanogen bromide (1.59 g, 15.0 mmol) and N,N-diisopropylethylamine (2.58 g, 20.0 mmol). The reaction mixture was stirred at 25° C. for 17 h. The solution was concentrated under reduced pressure. The crude material was purified by column chromatography (silica gel, petroleum ether/ethyl acetate=10/1 to 3/1) to give 4-(3,4-difluorobenzyl)piperidine-1-carbonitrile (1.8 g, 7.63 mmol, 76%) as a brown solid. LCMS (ESI) m/z: 237.1 [M+H]$^+$.

Step 2: Preparation of 6-(5-(4-(3,4-difluorobenzyl)piperidin-1-yl)-1,2,4-oxadiazol-3-yl)-2-methylpyridazin-3(2H)-one

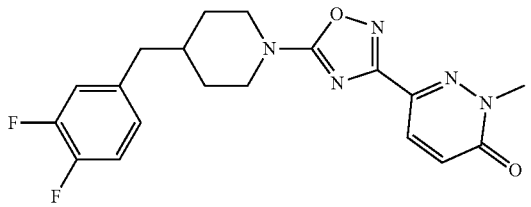 [SMILES: Cn1nc(-c2noc(N3CCC(Cc4ccc(F)c(F)c4)CC3)n2)ccc1=O]

To a solution of N-hydroxy-1-methyl-6-oxo-1,6-dihydropyridazine-3-carboximidamide (257 mg, 1.53 mmol) and 4-(3,5-difluorobenzyl)piperidine-1-carbonitrile (300 mg, 1.27 mmol) in ethanol (10 mL) was added zinc chloride (346 mg, 2.54 mmol). The solution was stirred at 25° C. for 2 h, then concentrated hydrochloric acid (0.7 mL) was added. The solution was heated to 85° C. for 17 h. The solution was diluted with water (50 mL) and extracted with ethyl acetate (50 mL×2). The combined organic layers were washed with brine (50 mL), dried over sodium sulfate, filtered and concentrated in vacuo. The crude sample was dissolved in the minimum amount of N,N-dimethylformamide and purified via prep-HPLC (Sunfire prep C18, 10 μm, 19×250 mm; mobile phase: [water (0.05% trifluoroacetic acid)-acetonitrile]; B %: 40-50%, 8 min) to give 6-(5-(4-(3,4-difluorobenzyl)piperidin-1-yl)-1,2,4-oxadiazol-3-yl)-2-methylpyridazin-3(2H)-one a white solid (251 mg, 0.65 mmol, 51%). $^1$H NMR (400 MHz, Dimethylsulfoxide-d$_6$) δ 7.82 (d, J=10.0 Hz, 1H), 7.27-7.38 (m, 2H), 7.05 (d, J=10.0 Hz, 1H), 4.03 (d, J=13.2 Hz, 2H), 3.73 (s, 3H), 3.13 (t, J=11.2 Hz, 2H), 2.55 (d, J=7.2 Hz, 2H), 1.79-1.84 (m, 1H), 1.67 (d, J=12.4 Hz, 2H), 1.18-1.29 (m, 2H); LCMS (ESI) m/z: 388.2 [M+H]$^+$.

Example 69. Preparation of 6-(5-(4-(3,5-difluorobenzyl)piperidin-1-yl)-1,3,4-oxadiazol-2-yl)-2-methylpyridazin-3(2H)-one (Compound 118)

Step 1: Preparation of methyl 1-methyl-6-oxo-1,6-dihydropyridazine-3-carboxylate

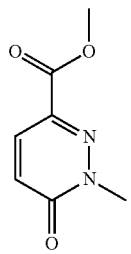

To a solution of methyl 6-oxo-1,6-dihydropyridazine-3-carboxylate (10 g, 64.9 mmol) and potassium carbonate (17.9 g, 130 mmol) in N,N-dimethylformamide (100 mL) at 25° C. was added iodomethane (9.2 g, 64.9 mmol). The mixture was stirred at 25° C. for 16 h. The reaction was diluted with ethyl acetate (500 mL) and washed with water (200 mL) and aqueous sodium chloride (200 mL). The combined organic layers were dried over sodium sulfate, filtered and concentrated. The crude material was purified by column chromatography (silica gel, petroleum ether/ethyl acetate=1/2) to give methyl 1-methyl-6-oxo-1,6-dihydropyridazine-3-carboxylate (4.2 g, 25.0 mmol, 39%) as a white solid. LCMS (ESI) m/z: 169.0 [M+H]$^+$.

Step 2: Preparation of 1-methyl-6-oxo-1,6-dihydropyridazine-3-carbohydrazide

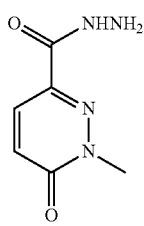

To a solution of methyl 6-oxo-1,6-dihydropyridazine-3-carboxylate (3.6 g, 21.4 mmol) in methanol (20 mL) at 20° C. was added hydrazine monohydrate (5 mL). The mixture was heated to 90° C. and stirred for 4 h. The reaction mixture was cooled to 20° C. and filtered. The solid was washed with methanol and dried to give 1-methyl-6-oxo-1,6-dihydropyridazine-3-carbohydrazide (1.9 g, 11.3 mmol, 53%) as a white solid.

Step 3: Preparation of 5-(1-methyl-6-oxo-1,6-dihydropyridazin-3-yl)-1,3,4-oxadiazol-2(3H)-one

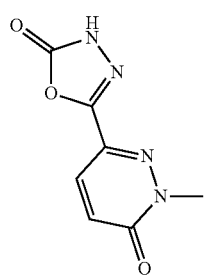

To a solution of 1-methyl-6-oxo-1,6-dihydropyridazine-3-carbohydrazide (1.7 g, 10.1 mmol) and diisopropylethylamine (2.61 g, 20.2 mmol) in dichloromethane (100 mL) was added a solution of triphosgene (3.27 g, 11.13 mmol) in dichloromethane (10 mL). The mixture was stirred at 25° C. for 2 h and filtered. The solid was washed with dichloromethane to give 5-(1-methyl-6-oxo-1,6-dihydropyridazin-3-yl)-1,3,4-oxadiazol-2(3H)-one (1.5 g) as a white solid. This material was used in the next step without further purification. LCMS (ESI) m/z: 195.0 [M+H]$^+$.

Step 4: Preparation of 4-(3,5-difluorobenzyl)piperidine

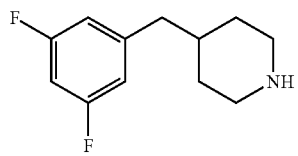 [SMILES: Fc1cc(F)cc(CC2CCNCC2)c1]

A solution of tert-butyl 4-(3,5-difluorobenzyl)piperidine-1-carboxylate (2.5 g, 8.03 mmol) and hydrochloric acid in 1,4-dioxane (12.0 mL, 48.0 mmol, 4 M) was stirred at 20° C. for 2 h. The reaction solution was concentrated in vacuo. The crude material was dissolved in dichloromethane (50 mL) and washed with aqueous sodium bicarbonate (50 mL). The combined organic layers were dried over sodium sulfate, filtered and concentrated to give crude 4-(3,5-difluorobenzyl)piperidine (1.5 g, crude) as a colorless oil. LCMS (ESI) m/z: 212.3 [M+H]$^+$.

Step 5: Preparation of 6-(5-(4-(3,5-difluorobenzyl)piperidin-1-yl)-1,3,4-oxadiazol-2-yl)-2-methylpyridazin-3(2H)-one

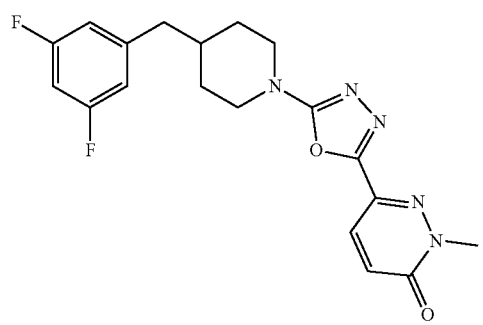 [SMILES: Cn1nc(-c2nnc(N3CCC(Cc4cc(F)cc(F)c4)CC3)o2)ccc1=O]

To a solution of 5-(1-methyl-6-oxo-1,6-dihydropyridazin-3-yl)-1,3,4-oxadiazol-2(3H)-one (100 mg, 0.515 mmol), 4-(3,5-difluorobenzyl)piperidine (218 mg, 1.03 mmol), (benzotriazol1yloxy)tris(dimethylamino)phosphonium hexafluorophosphate (251 mg, 0.567) and diphenyl ether (175 mg, 1.03 mmol) in N,N-dimethylformamide (6 mL) at 20° C. was added diisopropylethylamine (133 mg, 1.03 mmol). The mixture was stirred at 20° C. for 2 h. The reaction was diluted with ethyl acetate (100 mL) and washed with water (50 mL) followed by brine (50 mL). The combined organic layers were concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 6-(5-(4-(3,5-difluorobenzyl)piperidin-1-yl)-1,3,4-oxadiazol-2-yl)-2-methylpyridazin-3(2H)-one (42.8 mg, 0.111 mmol, 11%) as a white solid. ¹H NMR (400 MHz, Dimethylsulfoxide-d₆) δ 7.93 (d, J=10.0 Hz, 1H), 7.09-6.96 (m, 4H), 3.92 (d, J=12.4 Hz, 2H), 3.71 (s, 3H), 3.10-3.04 (m, 2H), 2.59 (d, J=7.2 Hz, 2H), 1.86-1.81 (m, 1H), 1.66 (d, J=12.4 Hz, 2H), 1.31-1.21 (m, 2H); LCMS (ESI) m/z: 388.2 [M+H]⁺.

Example 70. Preparation of 6-(5-(4-(3-fluorobenzyl)piperidin-1-yl)-1,3,4-oxadiazol-2-yl)-2-methylpyridazin-3(2H)-one (Compound 119)

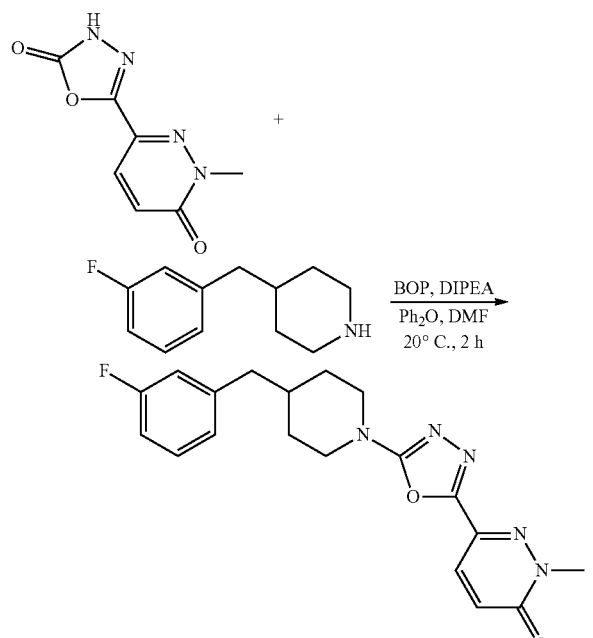

Step 1: Preparation of 6-(5-(4-(3-fluorobenzyl)piperidin-1-yl)-1,3,4-oxadiazol-2-yl)-2-methylpyridazin-3(2H)-one To a solution of 5-(1-methyl-6-oxo-1,6-dihydropyridazin-3-yl)-1,3,4-oxadiazol-2(3H)-one (200 mg, 1.03 mmol), 4-(3-fluorobenzyl)piperidine (398 mg, 2.06 mmol), (benzotriazol1yloxy)tris(dimethylamino)phosphonium hexafluorophosphate (502 mg, 1.13) and diphenyl ether (350 mg, 2.06 mmol) in N,N-dimethylformamide (6 mL) at 20° C. was added diisopropylethylamine (266 mg, 2.06 mmol). The mixture was stirred at 20° C. for 2 h before it was diluted with ethyl acetate (100 mL). The organic layer was washed with water (50 mL) followed by brine (50 mL) and concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 6-(5-(4-(3-fluorobenzyl)piperidin-1-yl)-1,3,4-oxadiazol-2-yl)-2-methylpyridazin-3(2H)-one (87.5 mg, 0.237 mmol, 23%) as a white solid. ¹H NMR (400 MHz, Dimethylsulfoxide-d₆) δ 7.93 (d, J=10.0 Hz, 1H), 7.34 (q, J=7.2 Hz, 1H), 7.09-7.01 (m, 4H), 3.92 (d, J=13.2 Hz, 2H), 3.71 (s, 3H), 3.07 (t, J=11.4 Hz, 2H), 2.57 (d, J=7.2 Hz, 2H), 1.82-1.80 (m, 1H), 1.67 (d, J=12.4 Hz, 2H), 1.31-1.21 (m, 2H); LCMS (ESI) m/z: 370.1 [M+H]⁺.

Example 71. Preparation of 6-(3-(4-(3,5-difluorobenzyl)piperidin-1-yl)-1,2,4-oxadiazol-5-yl)-2-methylpyridazin-3(2H)-one (Compound 115)

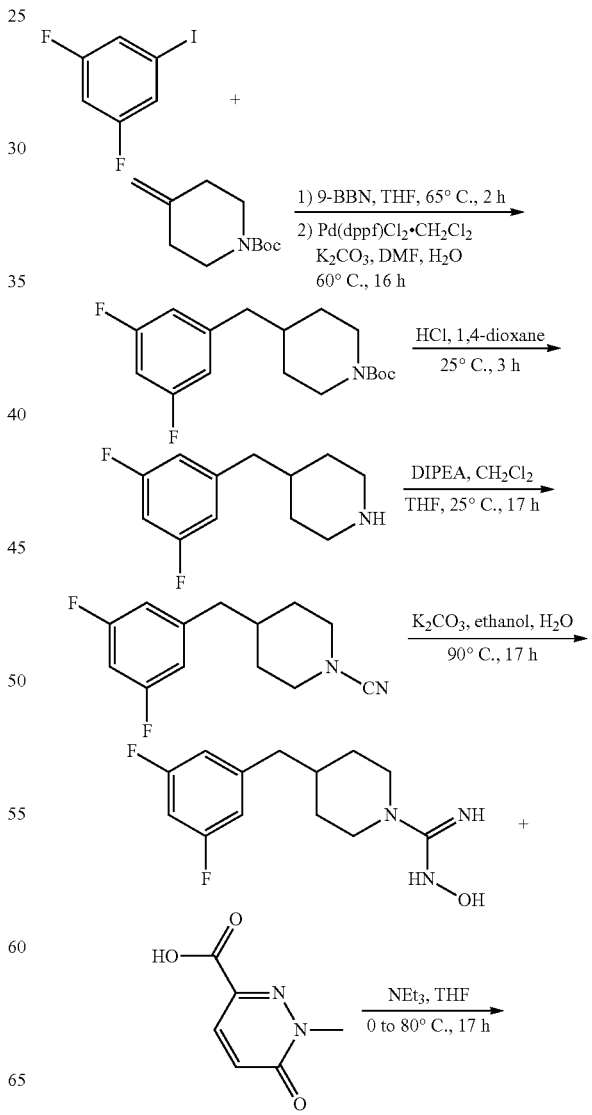

211

-continued

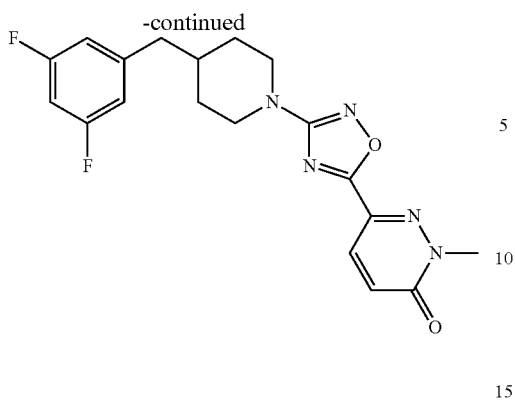

Step 1: Preparation of tert-butyl 4-(3,5-difluorobenzyl)piperidine-1-carboxylate

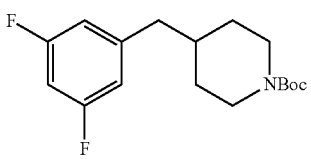

To a solution of 9-borabicyclo[3.3.1]nonane in tetrahydrofuran (100 mL, 50 mmol, 0.5 M) at 25° C. was added tert-butyl 4-methylenepiperidine-1-carboxylate (9.9 g, 50 mmol) under argon. The mixture was heated at 65° C. for 2 h. The mixture was cooled to 25° C. and added to a solution of 1,3-difluoro-5-iodobenzene (12.0 g, 50 mmol), potassium carbonate (8.98 g, 65 mmol) and 1,1'-bis(diphenylphosphino)ferrocene-palladium(II)dichloride dichloromethane complex (2.0 g, 2.5 mmol) in N,N-dimethylformamide/water (80 mL/8 mL). The resulting mixture was heated at 60° C. for 20 h. The reaction mixture was quenched with 1 N aqueous sodium hydroxide solution and stirred at 25° C. for 1 h. The mixture was diluted with ethyl acetate (800 mL) and washed with brine (500 mL×3). The combined organic layers were dried over sodium sulfate, filtered and concentrated under reduced pressure. The crude residue was purified by column chromatography (silica gel, petroleum ether/ethyl acetate=60/1 to 50/1) to give tert-butyl 4-(3,5-difluorobenzyl)piperidine-1-carboxylate as a yellow solid (8.0 g, 25.7 mmol, 52%). LCMS (ESI) m/z: 256.3 [M-56+H]+.

Step 2: Preparation of 4-(3,5-difluorobenzyl)piperidine

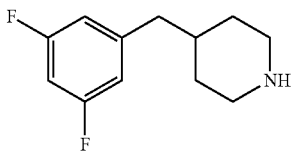

A solution of tert-butyl 4-(3,5-difluorobenzyl)piperidine-1-carboxylate (8 g, 25.7 mmol) in hydrochloric acid in 1,4-dioxane (20 mL, 4 M) was stirred at 25° C. for 3 h under nitrogen. The mixture was concentrated under reduced pressure. The crude residue was purified by column chromatography (silica gel, dichloromethane/methanol=20/1) to give 4-(3,5-difluorobenzyl)piperidine (5.2 g, 24.6 mmol, 96%) as a yellow oil. LCMS (ESI) m/z: 212.1 [M+H]+.

Step 3: Preparation of 4-(3,5-difluorobenzyl)piperidine-1-carbonitrile

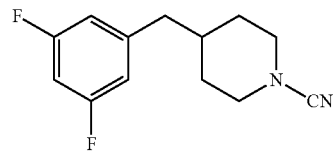 [SMILES: N#CN1CCC(Cc2cc(F)cc(F)c2)CC1]

To a solution of 4-(3,5-difluorobenzyl)piperidine (5.0 g, 23.7 mmol) in tetrahydrofuran (40 mL) and dichloromethane (40 mL) under argon was added N,N-diisopropylethylamine (9.2 g, 71.1 mmol) and cyanogen bromide (2.5 g, 23.7 mmol). The mixture was stirred at 25° C. for 17 h. The reaction mixture was washed with water (40 mL×2) followed by brine (40 mL). The combined organic layers were dried over sodium sulfate, filtered and concentrated under reduced pressure. The crude 4-(3,5-difluorobenzyl)piperidine-1-carbonitrile (4.8 g, crude) was used in the next step without further purification. LCMS (ESI) m/z: 237.1 [M+H]+.

Step 4: Preparation of 4-(3,5-difluorobenzyl)-N-hydroxypiperidine-1-carboximidamide

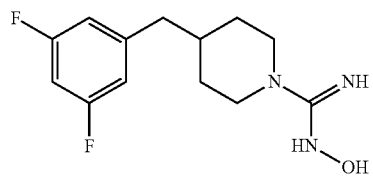

To a solution of 4-(3,5-difluorobenzyl)piperidine-1-carbonitrile (4.7 g, 19.9 mmol) in ethanol (35 mL) and water (50 mL) under argon was added hydroxylamine hydrochloride (2.7 g, 39.8 mmol) and potassium carbonate (8.2 g, 59.7 mmol). The mixture was stirred at 90° C. for 5 h then cooled to 25° C.

After 17 h, the reaction mixture was concentrated in vacuo. The crude material was treated with water (40 mL) and extracted with ethyl acetate (10 mL×3). The combined organic layers were washed with brine (10 mL), dried over sodium sulfate, filtered and concentrated under reduced pressure. The residue was purified by column chromatography (silica gel, dichloromethane/methanol=30/1) to give 4-(3,5-difluorobenzyl)-N-hydroxypiperidine-1-carboximidamide (1.1 g, 4.1 mmol, 21%) as a white solid. LCMS (ESI) m/z: 270.1 [M+H]+.

Step 5: Preparation of 6-(3-(4-(3,5-difluorobenzyl)piperidin-1-yl)-1,2,4-oxadiazol-5-yl)-2-methylpyridazin-3(2H)-one

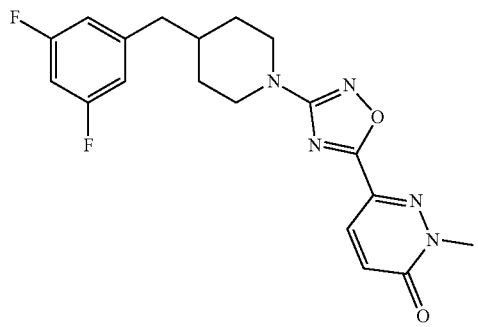 [SMILES: Cn1nc(-c2nc(N3CCC(Cc4cc(F)cc(F)c4)CC3)no2)ccc1=O]

A solution of 1-methyl-6-oxo-1,6-dihydropyridazine-3-carboxylic acid (114 mg, 0.74 mmol) in thionyl chloride (8 mL) under argon was stirred at 80° C. for 2 h. The reaction mixture was concentrated in vacuo. The crude residue was dissolved in tetrahydrofuran (5 mL) and added dropwise to a solution of 4-(3,5-difluorobenzyl)-N-hydroxypiperidine-1-carboximidamide (200 mg, 0.74 mmol) and triethylamine (224 mg, 2.22 mmol) in tetrahydrofuran (15 mL) at 0° C. under argon. The mixture was stirred at 80° C. for 17 h and then concentrated in vacuo. The crude sample was dissolved in the minimum amount of N,N-dimethylformamide and purified via prep-HPLC (Boston C18, 10 μm, 21 mm×250 mm column; acetonitrile/0.01% aqueous trifluoroacetic acid) to give 6-(3-(4-(3,5-difluorobenzyl)piperidin-1-yl)-1,2,4-oxadiazol-5-yl)-2-methylpyridazin-3(2H)-one as a white solid (16.9 mg, 0.04 mmol, 6%). $^1$H NMR (400 MHz, Dimethylsulfoxide-$d_6$) δ 7.95 (d, J=9.7 Hz, 1H), 7.18-6.91 (m, 4H), 3.90 (d, J=12.8 Hz, 2H), 3.77 (s, 3H), 2.92 (t, J=12.0 Hz, 2H), 2.58 (d, J=7.2 Hz, 2H), 1.82 (s, 1H), 1.62 (d, J=13.0 Hz, 2H), 1.23 (d, J=8.2 Hz, 2H); LCMS (ESI) m/z: 388.3 [M+H]$^+$.

Example 72. Preparation of 6-(3-(4-(3,5-difluorophenoxy)piperidin-1-yl)-1,2,4-oxadiazol-5-yl)-2-methylpyridazin-3(2H)-one (Compound 111)

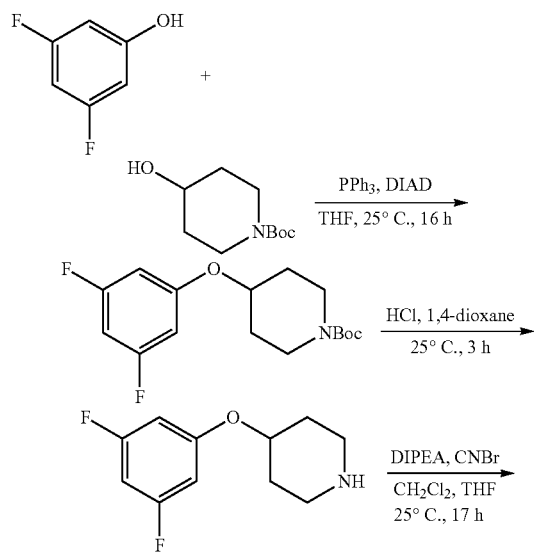

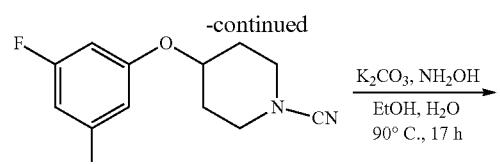

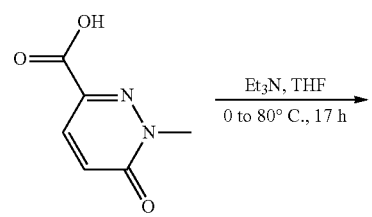

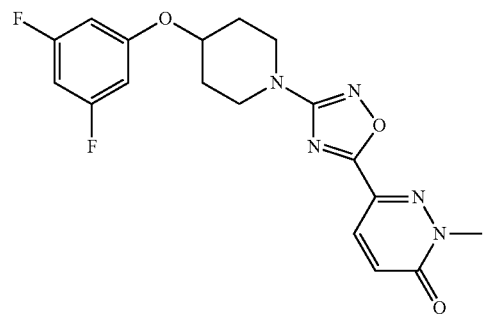

Step 1: Preparation of tert-butyl 4-(3,5-difluorophenoxy)piperidine-1-carboxylate

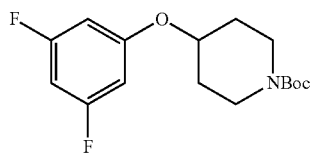

A solution of 3,5-difluorophenol (1.7 g, 13.1 mmol), tert-butyl 4-hydroxypiperidine-1-carboxylate (3.9 g, 19.6 mmol), triphenylphosphine (5.1 g, 19.6 mmol) and diisopropyl azodicarboxylate (3.9 g, 19.6 mmol) in tetrahydrofuran (30 mL) was stirred at 25° C. for 16 h under argon. The reaction mixture was filtered and concentrated under reduced pressure. The residue was purified by column chromatography (silica gel, petroleum ether/ethyl acetate=50/1) to give tert-butyl 4-(3,5-difluorophenoxy)piperidine-1-carboxylate (3.5 g, 11.2 mmol, 85%) as a yellow oil. LCMS (ESI) m/z: 258.2 [M-56+H]$^+$.

Step 2: Preparation of 4-(3,5-difluorophenoxy)piperidine

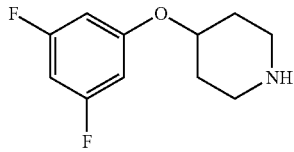 [SMILES: Fc1cc(F)cc(OC2CCNCC2)c1]

A solution of tert-butyl 4-(3,5-difluorophenoxy)piperidine-1-carboxylate (3.4 g, 10.9 mmol) and 4N hydrochloric acid in 1,4-dioxane solution (40 mL) was stirred at 25° C. for 3 h under argon. The reaction mixture was concentrated under reduced pressure. The crude residue was purified by column chromatography (silica gel, dichloromethane/methanol=15/1) to give 4-(3,5-difluorophenoxy)piperidine (2.1 g, 9.86 mmol, 91%) as a white solid. LCMS (ESI) m/z: 214.2 [M+H]$^+$.

Step 3: Preparation of 4-(3,5-difluorophenoxy)piperidine-1-carbonitrile

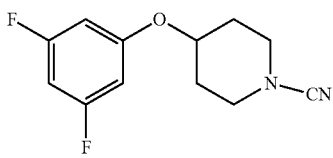 [SMILES: N#CN1CCC(Oc2cc(F)cc(F)c2)CC1]

To a solution of 4-(3,5-difluorophenoxy)piperidine (2 g, 9.3 mmol) in tetrahydrofuran (20 mL) and dichloromethane (20 mL) under argon was added N,N-diisopropylethylamine (3.6 g, 27.9 mmol) and cyanogen bromide (985 mg, 9.3 mmol). The reaction mixture was stirred at 25° C. for 17 h. The reaction solution was washed with water (10 mL×2) followed by brine (10 mL). The combined organic layers were dried over sodium sulfate, filtered and concentrated under reduced pressure to give 4-(3,5-difluorophenoxy)piperidine-1-carbonitrile (1.8 g, 7.56 mmol, 82%) as a yellow oil. LCMS (ESI) m/z: 239.1 [M+H]$^+$.

Step 4: Preparation of 4-(3,5-difluorophenoxy)-N-hydroxypiperidine-1-carboximidamide

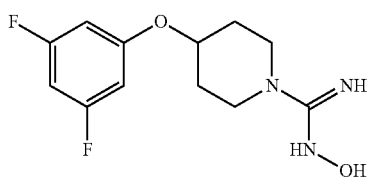

To a solution of 4-(3,5-difluorophenoxy)piperidine-1-carbonitrile (1.7 g, 7.1 mmol) in ethanol (21 mL) and water (30 mL) under argon was added hydroxylamine hydrochloride (980 mg, 14.2 mmol) and potassium carbonate (2.9 g, 21.3 mmol). The mixture was stirred at 90° C. for 5 h and at 25° C. for 17 h. The reaction solution was concentrated in vacuo. The residue was diluted with water (40 mL) and extracted with ethyl acetate (10 mL×3). The combined organic layers were washed with brine (10 mL), dried over sodium sulfate, filtered and concentrated under reduced pressure. The crude material was purified by column chromatography (silica gel, dichloromethane/methanol=15/1) to give 4-(3,5-difluorophenoxy)-N-hydroxypiperidine-1-carboximidamide (1.3 g, 4.79 mmol, 68%) as a white solid. LCMS (ESI) m/z: 272.2 [M+H]$^+$.

Step 5: Preparation of 6-(3-(4-(3,5-difluorophenoxy)piperidin-1-yl)-1,2,4-oxadiazol-5-yl)-2-methylpyridazin-3(2H)-one

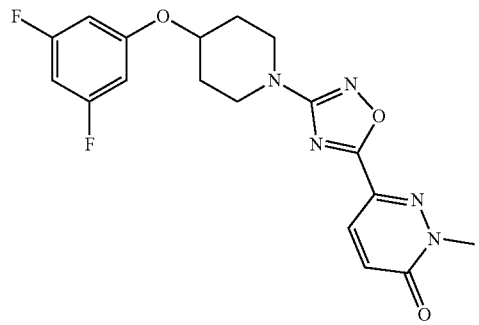 [SMILES: Cn1nc(-c2nc(N3CCC(Oc4cc(F)cc(F)c4)CC3)no2)ccc1=O]

A solution of 1-methyl-6-oxo-1,6-dihydropyridazine-3-carboxylic acid (91 mg, 0.59 mmol) and thionyl chloride (6 mL) was stirred at 80° C. for 2 h under argon. The reaction mixture was concentrated in vacuo. The crude solid was dissolved in tetrahydrofuran (5 mL) and added dropwise to a solution of 4-(3,5-difluorophenoxy)-N-hydroxypiperidine-1-carboximidamide (160 mg, 0.59 mmol) and triethylamine (179 mg, 1.77 mmol) in tetrahydrofuran (15 mL) under argon at 0° C. The reaction mixture was stirred at 80° C. for 17 h and concentrated in vacuo. The crude sample was dissolved in the minimum amount of N,N-dimethylformamide and purified via prep-HPLC (Boston C18, 10 μm, 21 mm×250 mm column, acetonitrile/0.01% aqueous formic acid) to give 6-(3-(4-(3,5-difluorophenoxy)piperidin-1-yl)-1,2,4-oxadiazol-5-yl)-2-methylpyridazin-3(2H)-one (47 mg, 0.12 mmol, 21%) as a white solid. $^1$H NMR (400 MHz, Dimethylsulfoxide-d$_6$) δ 7.97 (d, J=9.7 Hz, 1H), 7.11 (d, J=9.7 Hz, 1H), 6.88-6.69 (m, 3H), 4.81-4.60 (m, 1H), 3.84-3.61 (m, 5H), 3.46-3.37 (m, 2H), 2.05 (dd, J=12.3, 5.6 Hz, 2H), 1.77-1.60 (m, 2H); LCMS (ESI) m/z: 389.9 [M+H]$^+$.

Example 73. Preparation of 6-(3-(4-benzylpiperidin-1-yl)-1,2,4-oxadiazol-5-yl)-2-methylpyridazin-3(2H)-one (Compound 113)

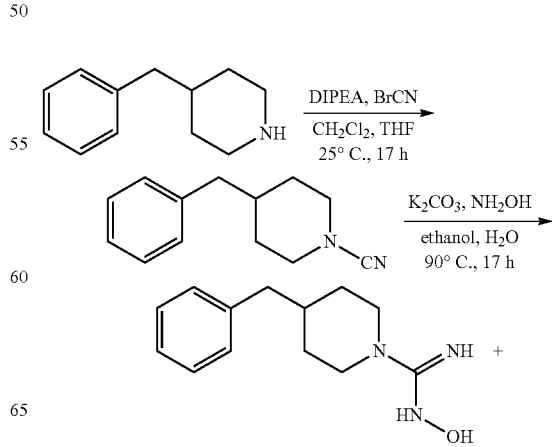

217

-continued

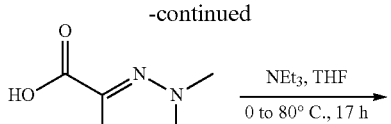

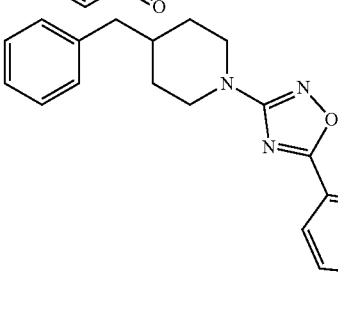

Step 1: Preparation of 4-benzylpiperidine-1-carbonitrile

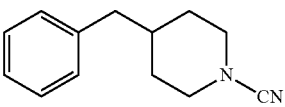 [SMILES: N#CN1CCC(Cc2ccccc2)CC1]

To a solution of 4-benzylpiperidine (3.0 g, 17.1 mmol) in tetrahydrofuran (30 mL) and dichloromethane (30 mL) under argon was added N,N-diisopropylethylamine (5.2 g, 51.3 mmol) and cyanogen bromide (1.8 g, 17.1 mmol). The mixture was stirred at 25° C. for 17 h. The reaction mixture was diluted with dichloromethane (20 mL) and washed with water (40 mL) and brine. The combined organic layers were dried over sodium sulfate, filtered and concentrated under reduced pressure. The crude 4-benzylpiperidine-1-carbonitrile (2.8 g, crude) was used in the next step without further purification. LCMS (ESI) m/z: 201.2 [M+H]+.

Step 2: Preparation of 4-benzyl-N-hydroxypiperidine-1-carboximidamide

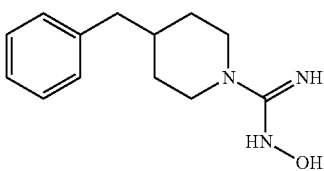 [SMILES: N=C(NO)N1CCC(Cc2ccccc2)CC1]

To a solution of 4-benzylpiperidine-1-carbonitrile (2.7 g, 13.5 mmol) in ethanol (35 mL) and water (50 mL) under argon was added hydroxylamine hydrochloride (1.9 g, 27.0 mmol) and potassium carbonate (5.6 g, 40.5 mmol). The mixture was stirred at 90° C. for 5 h and then cooled to 25° C. and stirred for 17 h. The reaction mixture was concentrated in vacuo and diluted with water (40 mL). The aqueous layer was extracted with ethyl acetate (10 mL×3). The combined organic layers were washed with brine (10 mL), dried over sodium sulfate, filtered and concentrated under reduced pressure. The residue was purified by column chromatography (silica gel, dichloromethane/methanol=20/1) to give 4-benzyl-N-hydroxypiperidine-1-carboximidamide (0.9 g, 3.9 mmol, 29%) as a white solid. LCMS (ESI) m/z: 234.2 [M+H]+.

Step 3: Preparation of 6-(3-(4-benzylpiperidin-1-yl)-1,2,4-oxadiazol-5-yl)-2-methylpyridazin-3(2H)-one

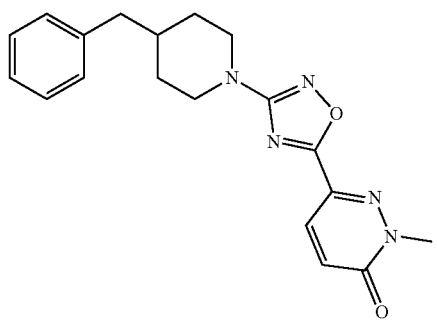 [SMILES: Cn1nc(-c2nc(N3CCC(Cc4ccccc4)CC3)no2)ccc1=O]

To a solution of 1-methyl-6-oxo-1,6-dihydropyridazine-3-carboxylic acid (132 mg, 0.86 mmol) in thionyl chloride (8 mL) under argon. The mixture was stirred at 80° C. for 2 h and concentrated in vacuo. The crude product (132 mg) was used in the next step without further purification. The crude residue in tetrahydrofuran (5 mL) was added dropwise to a solution of 4-benzyl-N-hydroxypiperidine-1-carboximidamide (200 mg, 0.86 mmol) in tetrahydrofuran (20 mL) under argon at 0° C. was added triethylamine (261 mg, 2.58 mmol). The mixture was stirred at 80° C. for 17 h and concentrated in vacuo. The crude sample was dissolved in the minimum amount of N,N-dimethylformamide and purified via prep-HPLC (Boston C18, 10 μm, 21 mm×250 mm column; acetonitrile/0.01% aqueous formic acid) to give 6-(3-(4-benzylpiperidin-1-yl)-1,2,4-oxadiazol-5-yl)-2-methylpyridazin-3(2H)-one (30 mg, 0.08 mmol, 10%) as a white solid. 1H NMR (400 MHz, Dimethylsulfoxide-d6) δ 7.95 (d, J=9.7 Hz, 1H), 7.36-7.24 (m, 2H), 7.19 (d, J=7.9 Hz, 3H), 7.10 (d, J=9.7 Hz, 1H), 3.89 (d, J=13.1 Hz, 2H), 3.76 (s, 3H), 2.91 (t, J=11.4 Hz, 2H), 2.54 (d, J=7.2 Hz, 2H), 1.76 (s, 1H), 1.65 (d, J=13.0 Hz, 2H), 1.24 (t, J=10.0 Hz, 2H); LCMS (ESI) m/z: 352.3 [M+H]+.

Example 74. Preparation of 6-(3-(4-(3,4-difluorobenzyl)piperidin-1-yl)-1,2,4-oxadiazol-5-yl)-2-methylpyridazin-3(2H)-one (Compound 116)

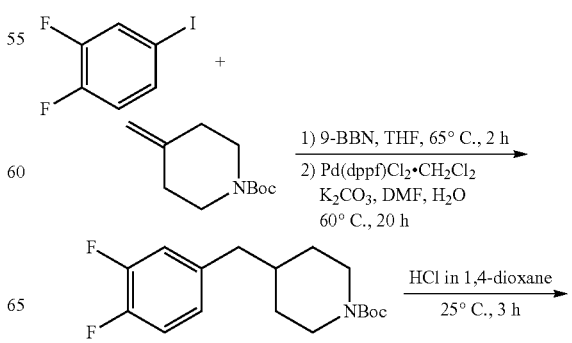

-continued

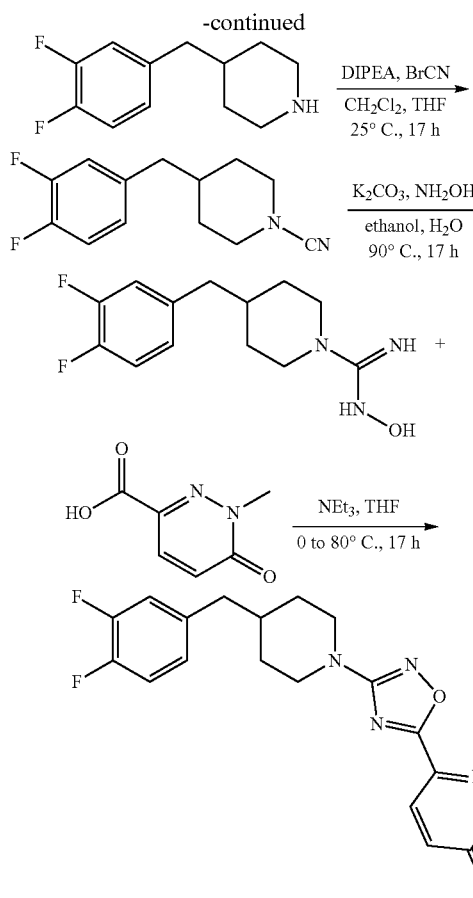

Step 1: Preparation of tert-butyl 4-(3,4-difluorobenzyl)piperidine-1-carboxylate

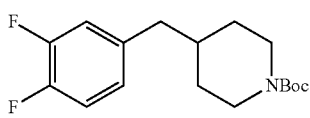 [SMILES: CC(C)(C)OC(=O)N1CCC(Cc2ccc(F)c(F)c2)CC1]

To a solution of 9-borabicyclo[3.3.1]nonane in tetrahydrofuran (100 mL, 50 mmol, 0.5 M) at 25° C. was added tert-butyl 4-methylenepiperidine-1-carboxylate (9.9 g, 50 mmol) under argon. The mixture was stirred at 65° C. for 2 h. The mixture was cooled to 25° C. and added to a solution of 1,2-difluoro-4-iodobenzene (12.0 g, 50 mmol), potassium carbonate (8.98 g, 65 mmol) and 1,1'-bis(diphenylphosphino)ferrocene-palladium(II)dichloride dichloromethane complex (2.0 g, 2.5 mmol) in N,N-dimethylformamide/water (80 mL/8 mL) at 25° C. The reaction mixture was heated at 60° C. for 20 h before 1 N sodium hydroxide solution was added and stirred at 25° C. for 1 h. The reaction was diluted with ethyl acetate (800 mL) and washed with brine (500 mL×3). The combined organic layers were dried over sodium sulfate, filtered and concentrated under reduced pressure. The crude residue was purified by column chromatography (silica gel, petroleum ether/ethyl acetate=20/1 to 10/1) to give tert-butyl 4-(3,4-difluorobenzyl)piperidine-1-carboxylate (7.5 g, 24.1 mmol, 48%) as a yellow solid. LCMS (ESI) m/z: 256.0 [M-56+H]$^+$.

Step 2: Preparation of 4-(3,4-difluorobenzyl)piperidine

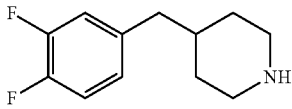

A solution of tert-butyl 4-(3,4-difluorobenzyl)piperidine-1-carboxylate (7.3 g, 23.5 mmol) in hydrochloric acid in 1,4-dioxane (20 mL, 4 M) was stirred at 25° C. for 3 h under nitrogen. The reaction solution was concentrated under reduced pressure. The crude residue was purified by column chromatography (silica gel, dichloromethane/methanol=20/1) to give 4-(3,4-difluorobenzyl)piperidine (4.2 g, 19.9 mmol, 86%). as a yellow oil. LCMS (ESI) m/z: 212.3 [M+H]$^+$.

Step 3: Preparation of 4-(3,4-difluorobenzyl)piperidine-1-carbonitrile

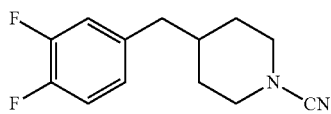 [SMILES: N#CN1CCC(Cc2ccc(F)c(F)c2)CC1]

To a solution of 4-(3,4-difluorobenzyl)piperidine (2 g, 9.48 mmol) in tetrahydrofuran (20 mL) and dichloromethane (20 mL) under argon was added N,N-diisopropylethylamine (3.7 g, 28.4 mmol) and cyanogen bromide (1.0 g, 9.48 mmol). The mixture was stirred at 25° C. for 17 h. The reaction mixture was washed with water (30 mL×2) and brine (20 mL). The combined organic layers were dried over sodium sulfate, filtered and concentrated under reduced pressure. The crude 4-(3,4-difluorobenzyl)piperidine-1-carbonitrile (1.9 g, crude) was used in the next step without further purification. LCMS (ESI) m/z: 237.3 [M+H]$^+$.

Step 4: Preparation of 4-(3,4-difluorobenzyl)-N-hydroxypiperidine-1-carboximidamide

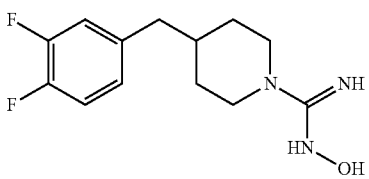 [SMILES: N=C(NO)N1CCC(Cc2ccc(F)c(F)c2)CC1]

To a solution of 4-(3,4-difluorobenzyl)piperidine-1-carbonitrile (1.9 g, 8.05 mmol) in ethanol (14 mL) and water (20 mL) under argon was added hydroxyamine hydrochloride (1.1 g, 16.1 mmol) and potassium carbonate (3.3 g, 24.1 mmol). The mixture was stirred at 90° C. for 5 h and at 25° C. for 17 h. The reaction solution was concentrated in vacuo and then diluted with water (40 mL). The aqueous layer was extracted with ethyl acetate (10 mL×3). The combined organic layers were washed with brine (10 mL), dried over sodium sulfate, filtered and concentrated under reduced pressure. The residue was purified by column chromatography (silica gel, dichloromethane/methanol=20/1) to give 4-(3,4-difluorobenzyl)-N-hydroxypiperidine-1-carboximidamide (0.7 g, 2.6 mmol, 33%) as a yellow solid. LCMS (ESI) m/z: 270.2 [M+H]+.

Step 5: Preparation of 6-(3-(4-(3,4-difluorobenzyl) piperidin-1-yl)-1,2,4-oxadiazol-5-yl)-2-methylpyridazin-3(2H)-one

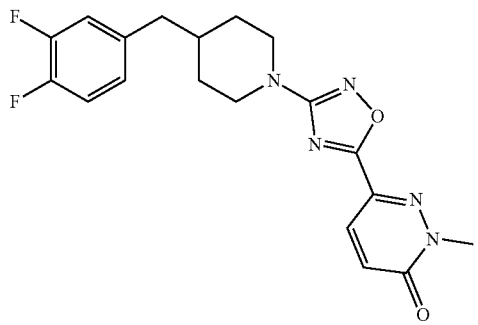 [SMILES: Cn1nc(-c2nc(N3CCC(Cc4ccc(F)c(F)c4)CC3)no2)ccc1=O]

A solution of 1-methyl-6-oxo-1,6-dihydropyridazine-3-carboxylic acid (114 mg, 0.74 mmol) in thionyl chloride (8 mL) was stirred at 80° C. for 2 h. The reaction was cooled and then concentrated in vacuo. The crude material was dissolved in tetrahydrofuran (5 mL) and added dropwise to a solution of 4-(3,4-difluorobenzyl)-N-hydroxypiperidine-1-carboximidamide (200 mg, 0.74 mmol) and triethylamine (224 mg, 2.22 mmol) in tetrahydrofuran (15 mL) at 0° C. under argon. The mixture was stirred at 80° C. for 17 h and then concentrated in vacuo. The crude sample was dissolved in the minimum amount of N,N-dimethylformamide and purified via prep-HPLC (Boston C18, 10 μm, 21 mm×250 mm column; acetonitrile/0.01% aqueous formic acid) to give 6-(3-(4-(3,4-difluorobenzyl)piperidin-1-yl)-1,2,4-oxadiazol-5-yl)-2-methylpyridazin-3(2H)-one as a white solid (5.6 mg, 0.01 mmol, 2%). 1H NMR (400 MHz, Dimethylsulfoxide-d6) δ 7.96 (d, J=9.7 Hz, 1H), 7.43-7.24 (m, 2H), 7.17-6.96 (m, 2H), 3.90 (d, J=12.8 Hz, 2H), 3.77 (s, 3H), 2.92 (t, J=11.7 Hz, 2H), 2.55 (d, J=7.1 Hz, 2H), 1.78 (s, 1H), 1.63 (d, J=12.5 Hz, 2H), 1.25 (d, J=10.4 Hz, 2H); LCMS (ESI) m/z: 388.0 [M+H]+.

Example 75. Preparation of 5-(3-(4-(3,5-difluorobenzyl)piperidin-1-yl)-1,2,4-oxadiazol-5-yl)-1-methylpyridin-2(1H)-one (Compound 17)

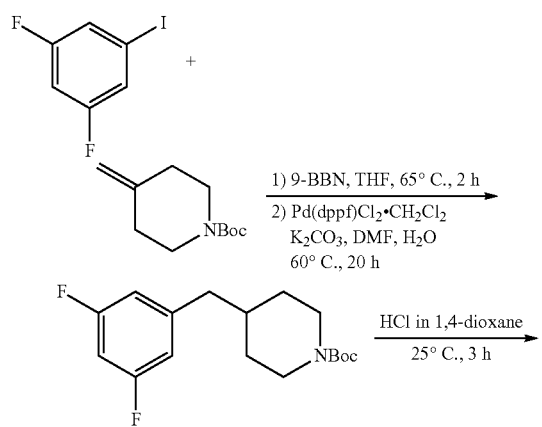

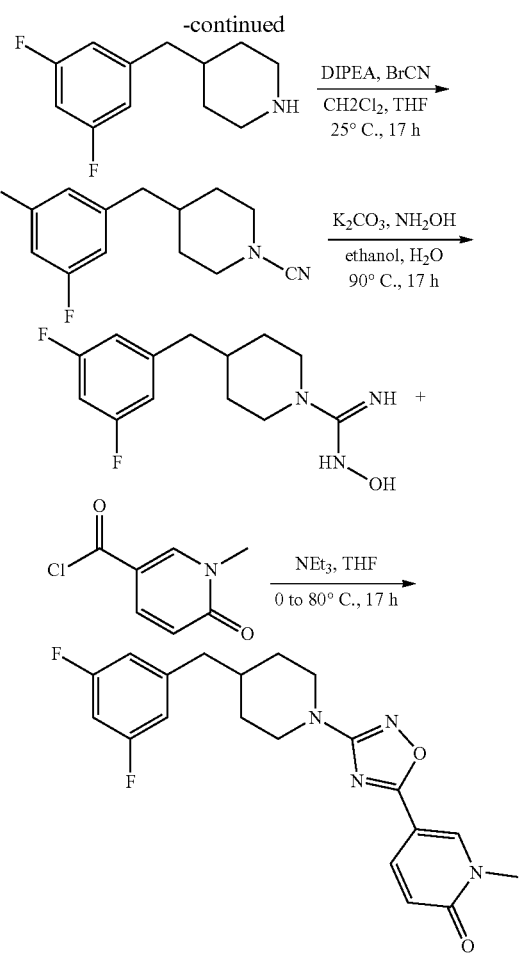

Step 1: Preparation of tert-butyl 4-(3,5-difluorobenzyl)piperidine-1-carboxylate

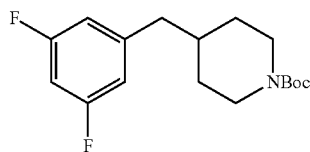

To a solution of 9-borabicyclo[3.3.1]nonane in tetrahydrofuran (100 mL, 50 mmol, 0.5 M) at 25° C. was added tert-butyl 4-methylenepiperidine-1-carboxylate (9.9 g, 50 mmol) under argon. The mixture was stirred at 65° C. for 2 h. The mixture was cooled to 25° C. and added to a solution of 1,3-difluoro-5-iodobenzene (12.0 g, 50 mmol), potassium carbonate (8.98 g, 65 mmol) and 1,1'-bis(diphenylphosphino)ferrocene-palladium(II)dichloride dichloromethane complex (2.0 g, 2.5 mmol) in N,N-dimethylformamide/water (80 mL/8 mL) at 25° C. The resulting mixture was heated at 60° C. for 20 h. The reaction mixture was quenched with 1 N sodium hydroxide solution and stirred at 25° C. for 1 h. The mixture was diluted with ethyl acetate (800 mL) and washed with brine (500 mL×3). The combined organic layers were dried over sodium sulfate, filtered and concentrated under reduced pressure. The crude residue was purified by column chromatography (silica gel, petroleum ether/ethyl acetate=60/1 to 50/1) to give tert-butyl 4-(3,5-difluorobenzyl)piperidine-1-carboxylate (8.0 g, 25.7 mmol, 52%) as a yellow solid. LCMS (ESI) m/z: 256.3 [M-56+H]$^+$.

Step 2: Preparation of 4-(3,5-difluorobenzyl)piperidine

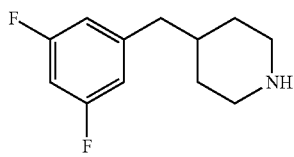

A solution of tert-butyl 4-(3,5-difluorobenzyl)piperidine-1-carboxylate (8 g, 25.7 mmol) in hydrochloric acid in 1,4-dioxane (20 mL, 4 M) was stirred at 25° C. for 3 h under nitrogen. The reaction mixture was concentrated under reduced pressure. The crude residue was purified by column chromatography (silica gel, dichloromethane/methanol=20/1) to give 4-(3,5-difluorobenzyl)piperidine as a yellow oil (5.2 g, 24.6 mmol, 96%). LCMS (ESI) m/z: 212.1 [M+H]$^+$.

Step 3: Preparation of 4-(3,5-difluorobenzyl)piperidine-1-carbonitrile

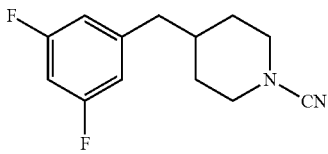 [SMILES: N#CN1CCC(Cc2cc(F)cc(F)c2)CC1]

To a solution of 4-(3,5-difluorobenzyl)piperidine (5 g, 23.7 mmol) in tetrahydrofuran (40 mL) and dichloromethane (40 mL) under argon was added N,N-diisopropylethylamine (9.2 g, 71.1 mmol) and cyanogen bromide (2.5 g, 23.7 mmol). The mixture was stirred at 25° C. for 17 h. The reaction mixture was washed with water (40 mL×2) and brine (40 mL). The combined organic layers were dried over sodium sulfate, filtered and concentrated under reduced pressure. The crude 4-(3,5-difluorobenzyl)piperidine-1-carbonitrile (4.8 g, crude) was used in the next step without further purification. LCMS (ESI) m/z: 237.1 [M+H]$^+$.

Step 4: Preparation of 4-(3,5-difluorobenzyl)-N-hydroxypiperidine-1-carboximidamide

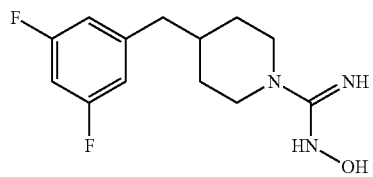 [SMILES: N=C(NO)N1CCC(Cc2cc(F)cc(F)c2)CC1]

To a solution of 4-(3,5-difluorobenzyl)piperidine-1-carbonitrile (4.7 g, 19.9 mmol) in ethanol (35 mL) and water (50 mL) under argon was added hydroxylamine hydrochloride (2.7 g, 39.8 mmol) and potassium carbonate (8.2 g, 59.7 mmol). The mixture was stirred at 90° C. for 5 h and at 25° C. for 17 h. The reaction solution was concentrated in vacuo. The residue was diluted with water (40 mL) and extracted with ethyl acetate (10 mL×3). The combined organic layers were washed with brine (10 mL), dried over sodium sulfate, filtered and concentrated under reduced pressure. The crude product was purified by column chromatography (silica gel, dichloromethane/methanol=30/1) to give 4-(3,5-difluorobenzyl)-N-hydroxypiperidine-1-carboximidamide (1.1 g, 4.1 mmol, 21%) as a white solid. LCMS (ESI) m/z: 270.1 [M+H]$^+$.

Step 5: Preparation of 5-(3-(4-(3,5-difluorobenzyl)piperidin-1-yl)-1,2,4-oxadiazol-5-yl)-1-methylpyridin-2(1H)-one

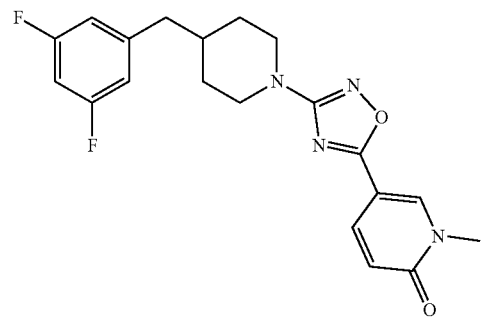 [SMILES: Cn1cc(-c2nc(N3CCC(Cc4cc(F)cc(F)c4)CC3)no2)ccc1=O]

A solution of 1-methyl-6-oxo-1,6-dihydropyridine-3-carbonyl chloride (127 mg, 0.74 mmol) in tetrahydrofuran (5 mL) at 0° C. was added dropwise to a solution of 4-(3,5-difluorobenzyl)-N-hydroxypiperidine-1-carboximidamide (200 mg, 0.74 mmol) and triethylamine (224 mg, 2.22 mmol) in tetrahydrofuran (15 mL) under argon. The mixture was stirred at 80° C. for 17 h and concentrated in vacuo. The crude sample was dissolved in the minimum amount of N,N-dimethylformamide and purified via prep-HPLC (Boston C18, 10 μm, 21 mm×250 mm column; acetonitrile/0.01% aqueous formic acid) to give 5-(3-(4-(3,5-difluorobenzyl)piperidin-1-yl)-1,2,4-oxadiazol-5-yl)-1-methylpyridin-2(1H)-one (31 mg, 0.08 mmol, 11%) as a white solid. $^1$H NMR (400 MHz, Dimethylsulfoxide-d$_6$) δ 8.65 (d, J=2.3 Hz, 1H), 7.87 (dd, J=9.5, 2.5 Hz, 1H), 7.11-6.83 (m, 3H), 6.52 (d, J=9.5 Hz, 1H), 3.88 (d, J=12.8 Hz, 2H), 3.54 (s, 3H), 2.88 (t, J=11.5 Hz, 2H), 2.57 (d, J=7.2 Hz, 2H), 1.80 (s, 1H), 1.61 (d, J=12.0 Hz, 2H), 1.23 (t, J=10.4 Hz, 2H); LCMS (ESI) m/z: 387.2 [M+H]$^+$.

Example 76. Preparation of 4-fluoro-4-(3-fluorobenzyl)-N-(1-methyl-6-oxo-1,6-dihydropyridazin-3-yl)piperidine-1-carboxamide (Compound 45)

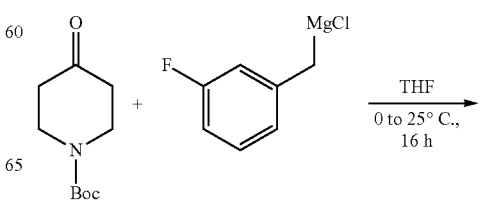

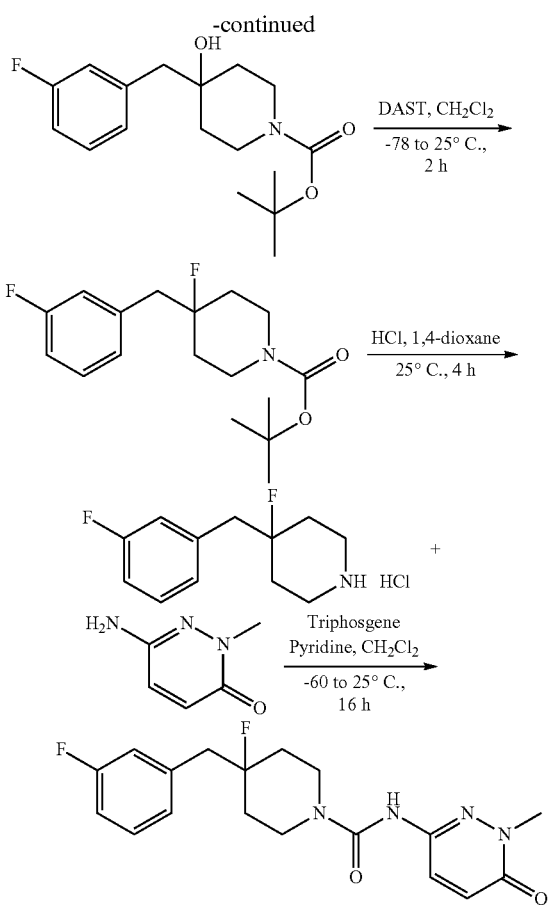

Step 1: Preparation of tert-butyl 4-(3-fluorobenzyl)-4-hydroxypiperidine-1-carboxylate

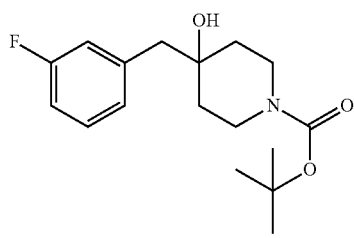 [SMILES: CC(C)(C)OC(=O)N1CCC(O)(Cc2cccc(F)c2)CC1]

To a solution of (3-fluorobenzyl)magnesium chloride (0.5 M in tetrahydrofuran, 12 mL, 6 mmol) in dry tetrahydrofuran (20 mL) at 0° C., was added a solution of tert-butyl 4-oxopiperidine-1-carboxylate (1 g, 5 mmol) in dry tetrahydrofuran (10 mL) dropwise under argon. The reaction mixture was stirred at 25° C. for 16 h. The reaction was quenched with aqueous ammonium chloride solution, diluted with ethyl acetate/water (20 mL/20 mL) and extracted with ethyl acetate (30 mL×2). The combined organic layers were washed with brine (50 mL), dried over sodium sulfate, filtered and concentrated under reduced pressure. The crude residue was purified by Combi-Flash (Biotage, 40 g silica gel, eluted with ethyl acetate in petroleum ether from 30% to 40%) to give tert-butyl 4-(3-fluorobenzyl)-4-hydroxypiperidine-1-carboxylate (0.65 g, 2.1 mmol, 42%) as a colorless oil. $^1$H NMR (400 MHz, Chloroform-d) δ 7.28-7.35 (m, 1H), 6.90-7.03 (m, 3H), 3.78-4.04 (m, 2H), 3.02-3.21 (m, 2H), 2.77 (s, 2H), 1.41-1.54 (m, 13H); LCMS (ESI) m/z: 236.1 [M-56+H]$^+$.

Step 2: Preparation of tert-butyl 4-fluoro-4-(3-fluorobenzyl)piperidine-1-carboxylate

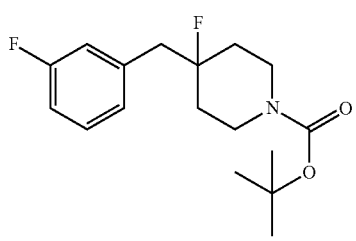 [SMILES: CC(C)(C)OC(=O)N1CCC(F)(Cc2cccc(F)c2)CC1]

To a solution of diethylamino sulfur trifluoride (0.57 mL, 4.33 mmol) in dry dichloromethane (20 mL), cooled to −78° C., was added a solution of tert-butyl 4-(3-fluorobenzyl)-4-hydroxypiperidine-1-carboxylate (0.67 g, 2.17 mmol) in dry dichloromethane (10 mL) dropwise under nitrogen. After the addition, the reaction was warmed to ambient temperature and stirred for 2 h. The reaction was quenched with saturated sodium bicarbonate aqueous solution and extracted with dichloromethane (30 mL×2). The combined organic layers were washed with brine (40 mL), dried over sodium sulfate, filtered and concentrated under reduced pressure. The residue was purified by Combi-Flash (Biotage, 40 g silica gel, eluted with ethyl acetate in petroleum ether from 5% to 10%) to give tert-butyl 4-fluoro-4-(3-fluorobenzyl)piperidine-1-carboxylate (0.32 g, 1.03 mmol, 48%) as colorless oil. $^1$H NMR (400 MHz, Dimethylsulfoxide-d$_6$) δ 7.29-7.42 (m, 1H), 6.98-7.15 (m, 3H), 3.70-3.85 (m, 2H), 2.81-3.04 (m, 4H), 1.48-1.68 (m, 4H), 1.39 (s, 9H); LCMS (ESI) m/z: 256.1 [M-56+H]$^+$.

Step 3: Preparation of 4-fluoro-4-(3-fluorobenzyl)piperidine Hydrochloride

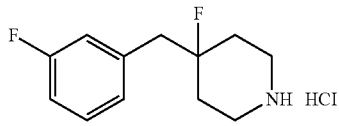

A solution of tert-butyl 4-fluoro-4-(3-fluorobenzyl)piperidine-1-carboxylate (0.3 g, 0.96 mmol) and 4 M hydrochloric acid in 1,4-dioxane (10 mL) was stirred at 25° C. for 4 h. The reaction was concentrated and dried in vacuo to give 4-fluoro-4-(3-fluorobenzyl)piperidine hydrochloride (0.2 g, 0.81 mmol, 84%) as a white solid. LCMS (ESI) m/z: 212.1 [M+H]$^+$.

Step 4: Preparation of 4-fluoro-4-(3-fluorobenzyl)-N-(1-methyl-6-oxo-1,6-dihydropyridazin-3-yl)piperidine-1-carboxamide

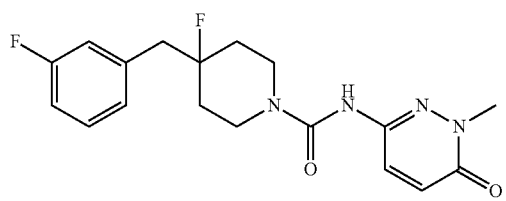 [SMILES: Cn1nc(NC(=O)N2CCC(F)(Cc3cccc(F)c3)CC2)ccc1=O]

To a solution of triphosgene (90 mg, 0.3 mmol) in dichloromethane (10 mL) at −60° C. was added 6-amino-2-methylpyridazin-3(2H)-one (76 mg, 0.6 mmol) and pyridine (192 mg, 2.4 mmol) in dichloromethane (5 mL) under argon. The mixture was stirred at −60° C. for 0.5 h, then a solution of 4-fluoro-4-(3-fluorobenzyl)piperidine hydrochloride (180 mg, 0.73 mmol) and pyridine (230 mg, 2.92 mmol) in dichloromethane (5 mL) was added at −60° C. The resulting mixture was stirred at 25° C. for 18 h. The reaction was quenched with water (30 mL) and was then extracted with dichloromethane (50 mL×2). The combined organic layers were dried over sodium sulfate, filtered and concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 4-fluoro-4-(3-fluorobenzyl)-N-(1-methyl-6-oxo-1,6-dihydropyridazin-3-yl)piperidine-1-carboxamide (55 mg, 0.15 mmol, 25%) as a white solid. $^1$H NMR (400 MHz, Dimethylsulfoxide-$d_6$) δ 9.31 (br. s, 1H), 7.62 (d, J=10.0 Hz, 1H), 7.30-7.42 (m, 1H), 7.00-7.16 (m, 3H), 6.88 (d, J=10 Hz, 1H), 3.94 (d, J=13.6 Hz, 2H), 3.56 (s, 3H), 2.91-3.09 (m, 4H), 1.55-1.77 (m, 4H); LCMS (ESI) m/z: 363.2 [M+H]$^+$.

Example 77. Preparation of 4-(3,4-difluorobenzyl)-4-fluoro-N-(1-methyl-6-oxo-1,6-dihydropyridazin-3-yl)piperidine-1-carboxamide (Compound 60)

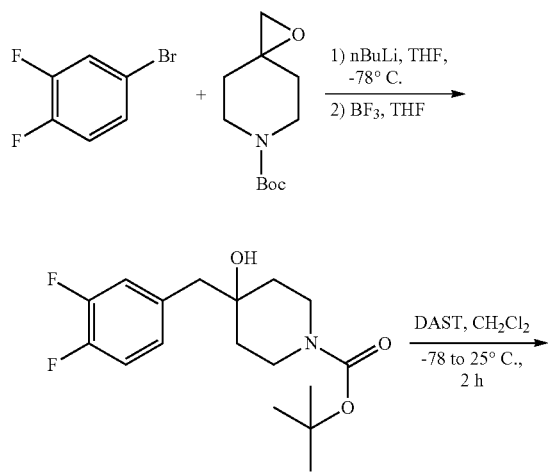

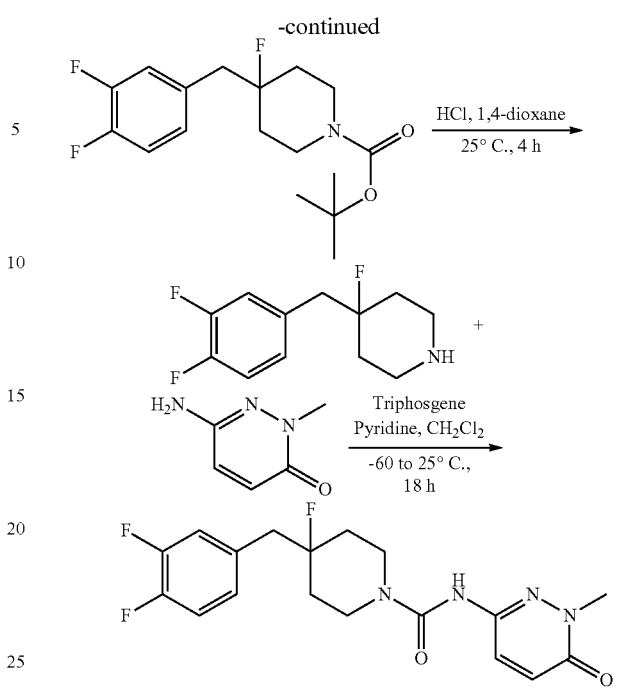

Step 1: Preparation of tert-butyl 4-(3,4-difluorobenzyl)-4-hydroxypiperidine-1-carboxylate

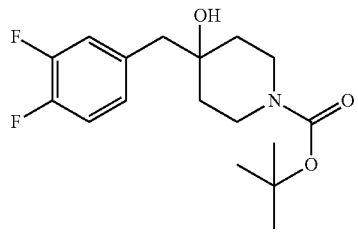 [SMILES: CC(C)(C)OC(=O)N1CCC(O)(Cc2ccc(F)c(F)c2)CC1]

To a solution of 4-bromo-1,2-difluorobenzene (3.78 g, 19.6 mmol) in dry tetrahydrofuran (60 mL) at −78° C., was added n-butyllithium (8.6 mL, 21.5 mmol, 2.5 M in hexanes) dropwise under argon. The reaction was stirred at −78° C. for 1.5 h, then boron trifluoride diethyl etherate (5.5 mL, 20.2 mmol, 47% by weight) was added slowly and the reaction was stirred for additional 15 min before a solution of tert-butyl 1-oxa-6-azaspiro[2.5]octane-6-carboxylate (4.18 g, 19.6 mmol) in dry tetrahydrofuran (20 mL) was added dropwise. After the addition, the reaction was stirred at −78° C. for 2 h and stirred at 25° C. for 18 h. The reaction was quenched with saturated aqueous ammonium chloride solution, then basified with aqueous 2 N sodium hydroxide solution and extracted with ethyl acetate (60 mL×2). The combined organic layers were washed with brine (50 mL), dried over sodium sulfate, filtered and concentrated under reduced pressure. The crude residue was purified by Combi-Flash (Biotage, 80 g silica gel, eluted with ethyl acetate in petroleum ether from 20% to 30%) to give tert-butyl 4-(3,4-difluorobenzyl)-4-hydroxypiperidine-1-carboxylate (3.1 g, 9.48 mmol, 48%) as a colorless oil. LCMS (ESI) m/z: 272.1 [M-56+H]$^+$.

Step 2: Preparation of tert-butyl 4-(3,4-difluorobenzyl)-4-fluoropiperidine-1-carboxylate

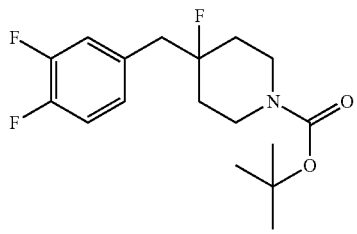 [SMILES: CC(C)(C)OC(=O)N1CCC(F)(Cc2ccc(F)c(F)c2)CC1]

To a solution of diethylaminosulfur trifluoride (2.5 mL, 19.0 mmol) in dry dichloromethane (50 mL), at −78° C., was added a solution of tert-butyl 4-(3,4-difluorobenzyl)-4-hydroxypiperidine-1-carboxylate (3 g, 9.17 mmol) in dry dichloromethane (20 mL) dropwise under nitrogen. After the addition, the reaction was warmed to ambient temperature and stirred for 2 h. The reaction was quenched with saturated sodium bicarbonate aqueous solution and extracted with dichloromethane (50 mL×2). The combined organic layers were washed with brine (40 mL), dried over sodium sulfate, filtered and concentrated under reduced pressure. The residue was purified by Combi-Flash (Biotage, 80 g silica gel, eluted with ethyl acetate in petroleum ether from 10% to 20%) to give tert-butyl 4-(3,4-difluorobenzyl)-4-fluoropiperidine-1-carboxylate (1.6 g, 4.86 mmol, 51%) as a yellow oil. LCMS (ESI) m/z: 274.2 [M-56+H]$^+$.

Step 3: Preparation of 4-(3,4-difluorobenzyl)-4-fluoropiperidine

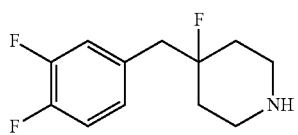

A solution of tert-butyl 4-(3,4-difluorobenzyl)-4-fluoropiperidine-1-carboxylate (1.55 g, 4.71 mmol) and hydrochloric acid in 1,4-dioxane solution (50 mL, 4 M) was stirred at 25° C. for 4 h. The reaction was concentrated under reduced pressure. The residue was diluted with dichloromethane (50 mL), neutralized with aqueous sodium bicarbonate solution and extracted with dichloromethane (30 mL×2). The combined organic layers were washed with brine (40 mL), dried over sodium sulfate, filtered and concentrated to give 4-(3,4-difluorobenzyl)-4-fluoropiperidine (1 g, 4.37 mmol, 93%) as a yellow oil. LCMS (ESI) m/z: 230.3 [M+H]$^+$.

Step 4: Preparation of 4-(3,4-difluorobenzyl)-4-fluoro-N-(1-methyl-6-oxo-1,6-dihydropyridazin-3-yl)piperidine-1-carboxamide

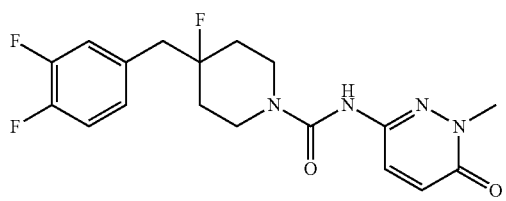 [SMILES: Cn1nc(NC(=O)N2CCC(F)(Cc3ccc(F)c(F)c3)CC2)ccc1=O]

To a solution of triphosgene (0.18 g, 0.6 mmol) in dichloromethane (20 mL) at −60° C. was added 6-amino-2-methylpyridazin-3(2H)-one (0.15 g, 1.2 mmol) and pyridine (0.25 g, 3.2 mmol) in dichloromethane (10 mL) under argon. The mixture was stirred at −60° C. for 0.5 h, then a solution of 4-(3,4-difluorobenzyl)-4-fluoropiperidine (0.33 g, 1.44 mmol) and pyridine (0.45 g, 5.76 mmol) in dichloromethane (10 mL) was added at −60° C. The resulting mixture was stirred at 25° C. for 18 h. The reaction was quenched with water (40 mL) and the mixture was extracted with dichloromethane (40 mL×2). The combined organic layers were dried over sodium sulfate, filtered and concentrated under reduced pressure. The residue was purified by Combi-Flash (Biotage, 40 g silica gel, eluted with 7 N ammonia methanol/dichloromethane=⅛ in dichloromethane from 20% to 30%) to afford 110 mg of impure product. The sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 4-(3,4-difluorobenzyl)-4-fluoro-N-(1-methyl-6-oxo-1,6-dihydropyridazin-3-yl)piperidine-1-carboxamide (45 mg, 0.12 mmol, 10%) as a white solid. $^1$H NMR (400 MHz, Dimethylsulfoxide-d$_6$) δ 9.30 (br. s, 1H), 7.63 (d, J=10.0 Hz, 1H), 7.29-7.41 (m, 1H), 7.09-7.23 (m, 2H), 6.88 (d, J=10 Hz, 1H), 3.96 (d, J=13.2 Hz, 2H), 3.56 (s, 3H), 2.91-3.11 (m, 4H), 1.60-1.82 (m, 4H); LCMS (ESI) m/z: 381.1 [M+H]$^+$.

Example 78. Preparation of 4-(3,5-difluorobenzyl)-4-fluoro-N-(1-methyl-6-oxo-1,6-dihydropyridazin-3-yl)piperidine-1-carboxamide (Compound 59)

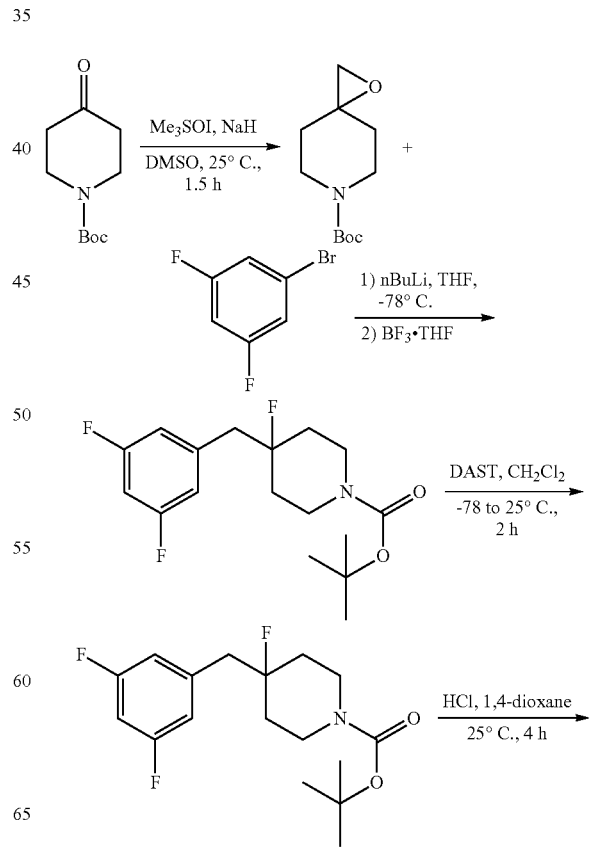

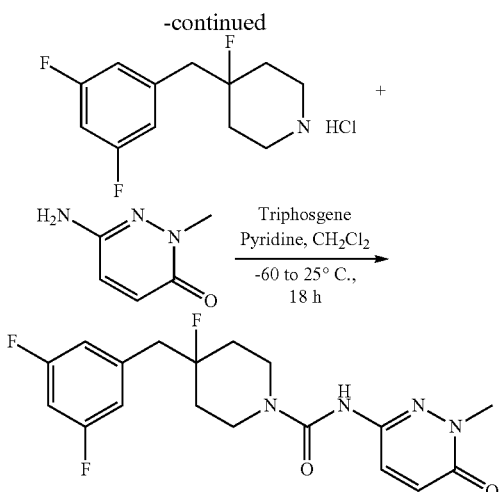

Step 1: Preparation of tert-butyl 1-oxa-6-azaspiro[2.5]octane-6-carboxylate

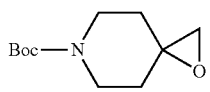

A suspension of sodium hydride (1.2 g, 30.2 mmol, 60% by weight) in dry dimethyl sulfoxide (30 mL) at 5° C. was treated with trimethylsulfonium iodide (6.63 g, 30.2 mmol). The reaction mixture was stirred for 30 min then tert-butyl 4-oxopiperidine-1-carboxylate (5 g, 25.1 mmol) was added in portions.

After the addition, the reaction was stirred at 25° C. for 1.5 h. The mixture was partitioned between water/diethyl ether (20 mL/20 mL), extracted with diethyl ether (30 mL) twice. The combined organic layers were washed with sodium sulfate, filtered and dried to afford tert-butyl 4-oxopiperidine-1-carboxylate (4.18 g, 19.6 mmol, 78%) as a colorless oil, which solidified on standing over ~15 h.

Step 2: Preparation of tert-butyl 4-(3,5-difluorobenzyl)-4-hydroxypiperidine-1-carboxylate

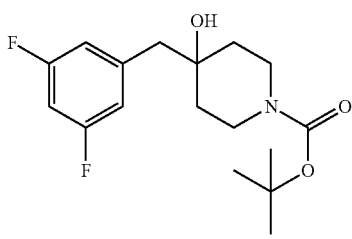 [SMILES: CC(C)(C)OC(=O)N1CCC(O)(Cc2cc(F)cc(F)c2)CC1]

To a solution of 1-bromo-3,5-difluorobenzene (3.78 g, 19.6 mmol) in dry tetrahydrofuran (60 mL), at −78° C., was added n-butyllithium (8.6 mL, 21.5 mmol, 2.5 M in hexanes) dropwise under argon. After the addition, the reaction was stirred at −78° C. for 1.5 h. Boron trifluoride diethyl etherate (5.5 mL, 20.2 mmol, 47% by weight) was added slowly. The reaction was stirred −78° C. for 15 min, then a solution of 1-oxaspiro[2.5]octan-6-one (4.18 g, 19.6 mmol) in dry tetrahydrofuran (20 mL) was added dropwise. After the addition, the reaction was stirred at −78° C. for 2 h, warmed to 25° C. and stirred for 18 h. The reaction was quenched with saturated aqueous ammonium chloride solution, basified with aqueous 2 N sodium hydroxide solution and extracted with ethyl acetate (60 mL×2). The combined organic layers were washed with brine (50 mL), dried over sodium sulfate, filtered and concentrated under reduced pressure.

The crude residue was purified by Combi-Flash (Biotage, 80 g silica gel, eluted with ethyl acetate in petroleum ether from 20% to 30%) to give tert-butyl 4-(3,5-difluorobenzyl)-4-hydroxypiperidine-1-carboxylate (2.19 g, 6.70 mmol, 34%) as a colorless oil. LCMS (ESI) m/z: 254.2 [M-56-OH+H]$^+$.

Step 3: Preparation of tert-butyl 4-(3,5-difluorobenzyl)-4-fluoropiperidine-1-carboxylate

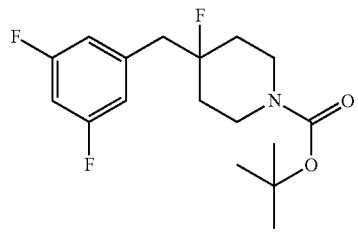 [SMILES: CC(C)(C)OC(=O)N1CCC(F)(Cc2cc(F)cc(F)c2)CC1]

To a solution of diethylaminosulfur trifluoride (1.77 mL, 13.4 mmol) in dry dichloromethane (40 mL) at −78° C. was added a solution of tert-butyl 4-(3,5-difluorobenzyl)-4-hydroxypiperidine-1-carboxylate (2.19 g, 6.7 mmol) in dry dichloromethane (20 mL) dropwise under nitrogen. After the addition, the reaction was warmed to ambient temperature and stirred for 2 h. The reaction was quenched with aqueous saturated sodium bicarbonate solution and extracted with dichloromethane (50 mL×2). The combined organic layers were washed with brine (40 mL), dried over sodium sulfate, filtered and concentrated under reduced pressure. The residue was purified by Combi-Flash (Biotage, 40 g silica gel, eluted with ethyl acetate in petroleum ether from 5% to 10%) to give tert-butyl 4-(3,5-difluorobenzyl)-4-fluoropiperidine-1-carboxylate (0.67 g, 2.04 mmol, 30%) as a colorless oil. LCMS (ESI) m/z: 274.2 [M-56+H]$^+$.

Step 4: Preparation of 4-(3,5-difluorobenzyl)-4-fluoropiperidine Hydrochloride

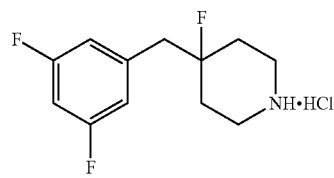

A solution of tert-butyl 4-(3,5-difluorobenzyl)-4-fluoropiperidine-1-carboxylate (0.67 g, 2.04 mmol) and hydrochloric acid in 1,4-dioxane solution (20 mL, 4 M) was stirred at 25° C. for 4 h. The reaction solution was concentrated in vacuo to give 4-(3,5-difluorobenzyl)-4-fluoropiperidine hydrochloride (0.53 g, 2 mmol, 98%) as a white solid. LCMS (ESI) m/z: 230.3 [M+H]+. The material was used in the next step without further purification.

Step 5: Preparation of 4-(3,5-difluorobenzyl)-4-fluoro-N-(1-methyl-6-oxo-1,6-dihydropyridazin-3-yl)piperidine-1-carboxamide

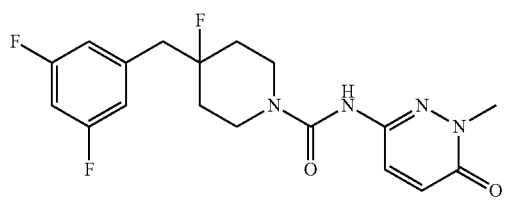 [SMILES: Cn1nc(NC(=O)N2CCC(F)(Cc3cc(F)cc(F)c3)CC2)ccc1=O]

solved in the minimum amount of N,N-dimethylformamide and purified by prep-HPLC (Boston C18, 10 μm, 21 mm×250 mm column, acetonitrile/10 mM ammonium acetate aqueous solution) to give 4-(3,5-difluorobenzyl)-4-fluoro-N-(1-methyl-6-oxo-1,6-dihydropyridazin-3-yl)piperidine-1-carboxamide (25 mg, 0.013 mmol, 7%) as a white solid. $^1$H NMR (400 MHz, Methanol-$d_4$) δ 7.78 (d, J=10.0 Hz, 1H), 7.29-7.42 (m, 1H), 6.91-7.07 (m, 3H), 4.02 (d, J=13.6 Hz, 2H), 3.70 (s, 3H), 3.12-3.24 (m, 2H), 3.08 (d, J=19.6 Hz, 2H), 1.67-1.90 (m, 4H); LCMS (ESI) m/z: 381.1 [M+H]+.

Example 79. 4-(4-chlorophenyl)-N-(1-methyl-6-oxo-1,6-dihydropyridazin-3-yl)-2,3,6,7-tetrahydro-1H-azepine-1-carboxamide (Compound 133) and 5-(4-chlorophenyl)-N-(1-methyl-6-oxo-1,6-dihydropyridazin-3-yl)-2,3,4,7-tetrahydro-1H-azepine-1-carboxamide (Compound 134)

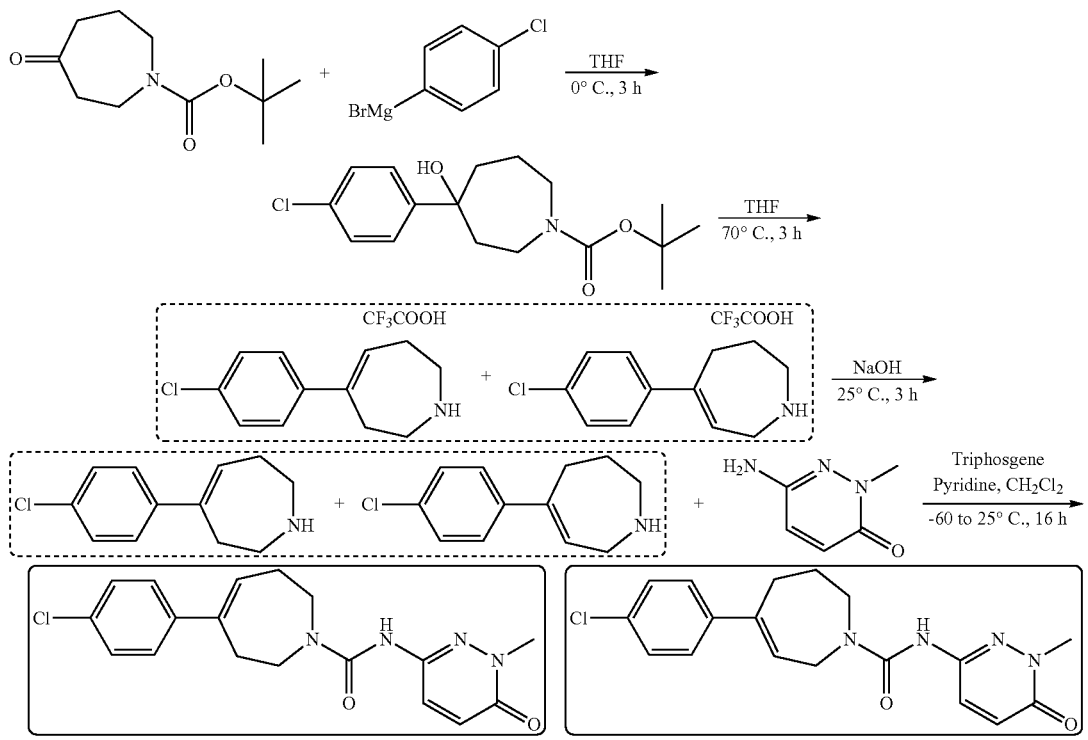

To a solution of triphosgene (0.14 g, 0.48 mmol) in dichloromethane (15 mL) at −60° C. was added a solution of 6-amino-2-methylpyridazin-3(2H)-one (0.12 g, 0.96 mmol) and pyridine (0.3 g, 3.84 mmol) in dichloromethane (5 mL) under argon. The mixture was stirred at −60° C. for 0.5 h, then a solution of 4-(3,5-difluorobenzyl)-4-fluoropiperidine hydrochloride (0.3 g, 1.15 mmol) and pyridine (0.36 g, 4.6 mmol) in dichloromethane (5 mL) was added at −60° C. The resulting mixture was stirred at 25° C. for 18 h. The reaction mixture was quenched with water (20 mL) and extracted with dichloromethane (30 mL×2). The combined organic layers were dried over sodium sulfate, filtered and concentrated under reduced pressure. The crude sample was dis- Step 1: Preparation of tert-butyl 4-(4-chlorophenyl)-4-hydroxyazepane-1-carboxylate

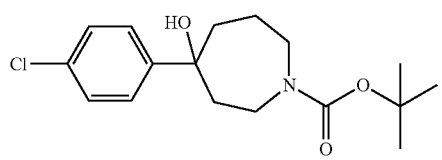 [SMILES: CC(C)(C)OC(=O)N1CCCC(O)(c2ccc(Cl)cc2)CC1]

To a solution of tert-butyl 4-oxoazepane-1-carboxylate (2.0 g, 9.38 mmol) in dry tetrahydrofuran (20 mL) at 0° C. was added (4-chlorophenyl)magnesium bromide (12.2 mL, 1.0 M in tetrahydrofuran). The mixture was stirred at 0° C. for 3 h, then quenched with ammonium chloride (100 mL) and the aqueous layer was extracted with ethyl acetate (100 mL×2). The combined organic layers were dried over sodium sulfate, filtered and concentrated under reduced pressure. The residue was purified by column chromatography (silica gel, petroleum ether/ethyl acetate=5/1) to give tert-butyl 4-(3,5-difluorophenyl)-4-hydroxyazepane-1-carboxylate (1.0 g, 3.07 mmol, 33%) as a yellow oil. LCMS (ESI) m/z: 348.1 [M+Na]+.

Step 2: Preparation of 4-(4-chlorophenyl)-2,3,6,7-tetrahydro-1H-azepine 2,2,2-trifluoroacetate and 5-(4-chlorophenyl)-2,3,4,7-tetrahydro-1H-azepine 2,2,2-trifluoroacetate

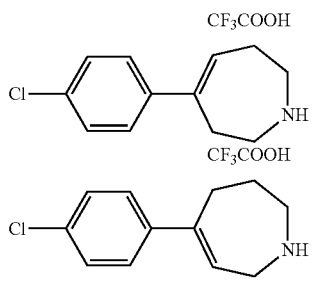

A suspension of tert-butyl 4-(3,5-difluorophenyl)-4-hydroxyazepane-1-carboxylate (1.5 g, 4.6 mmol) in 2,2,2-trifluoroacetic acid (20 mL) was stirred at 70° C. for 3 h. The reaction mixture was concentrated to afford the mixture of 4-(4-chloro phenyl)-2,3,6,7-tetrahydro-1H-azepine 2,2,2-trifluoroacetate and 5-(4-chlorophenyl)-2,3,4,7-tetrahydro-1H-azepine 2,2,2-trifluoroacetate (1.3 g, 4.04 mmol, 88%) as a white solid. LCMS (ESI) m/z: 208.2 [M+H]+.

Step 3: Preparation of 4-(4-chlorophenyl)-2,3,6,7-tetrahydro-1H-azepine and 5-(4-chlorophenyl)-2,3,4,7-tetrahydro-1H-azepine

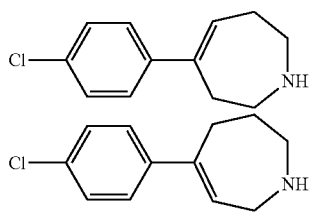

A solution of (E)-4-(4-chlorophenyl)-2,3,6,7-tetrahydro-1H-azepine 2,2,2-trifluoroacetate and (E)-5-(4-chlorophenyl)-2,3,4,7-tetrahydro-1H-azepine 2,2,2-trifluoroacetate (500 mg, 1.55 mmol) and sodium hydroxide (248 mg, 6.2 mmol) in water (20 mL) was stirred at 25° C. for 3 h. The reaction mixture was extracted with dichloromethane (100 mL×5). The combined organic layers were dried over anhydrous sodium sulfate, filtered and concentrated under reduced pressure. The crude residue was purified by column chromatography (silica gel, dichloromethane/methanol from 100/0 to 100/25) to give a mixture of 4-(4-chlorophenyl)-2,3,6,7-tetrahydro-1H-azepine and 5-(4-chloro phenyl)-2,3,4,7-tetrahydro-1H-azepine (300 mg, 1.44 mmol, 93%) as a white solid. LCMS (ESI) m/z: 208.2 [M+H]+.

Step 4: Preparation of 4-(4-chlorophenyl)-N-(1-methyl-6-oxo-1,6-dihydropyridazin-3-yl)-2,3,6,7-tetrahydro-1H-azepine-1-carboxamide and 5-(4-chlorophenyl)-N-(1-methyl-6-oxo-1,6-dihydropyridazin-3-yl)-2,3,4,7-tetrahydro-1H-azepine-1-carboxamide

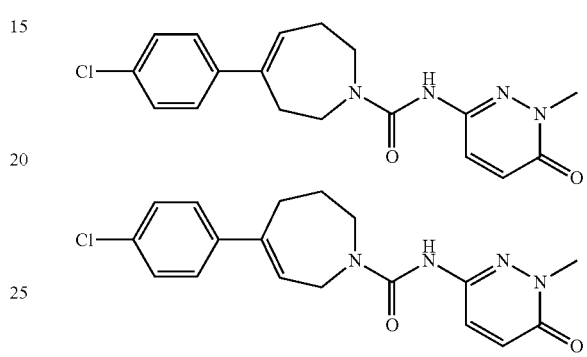

To a solution of triphosgene (395 mg, 1.33 mmol) in dichloromethane (20 mL) was added 6-amino-2-methyl pyridazin-3(2H)-one (332 mg, 2.65 mmol) and pyridine (838 mg, 10.6 mmol) in dichloromethane (20 mL) at −60° C. under argon. The mixture was stirred at −60° C. for 0.5 h, then a solution of (E)-4-(4-chlorophenyl)-2,3,6,7-tetrahydro-1H-azepine and (E)-5-(4-chlorophenyl)-2,3,4,7-tetrahydro-1H-azepine (550 mg, 2.65 mmol) and pyridine (838 mg, 10.6 mmol) in dichloromethane (20 mL) was added at −60° C. The resulting mixture was stirred at 25° C. for 20 h. The reaction was quenched with water (100 mL) and the aqueous layer was extracted with dichloromethane (100 mL×2). The combined organic layers were dried over anhydrous sodium sulfate, filtered and concentrated under reduced pressure. The crude residue was purified by column chromatography (silica gel, dichloromethane/methanol from 100/0 to 100/25) to give a mixture of 4-(4-chlorophenyl)-N-(1-methyl-6-oxo-1,6-dihydropyridazin-3-yl)-2,3,6,7-tetrahydro-1H-azepine-1-carboxamide and 5-(4-chlorophenyl)-N-(1-methyl-6-oxo-1,6-dihydropyridazin-3-yl)-2,3,4,7-tetrahydro-1H-azepine-1-carboxamide (600 mg, 1.67 mmol, 63%) as a yellow solid.

The yellow solid was dissolved in the minimum amount of methanol and purified by chiral-HPLC (SFC-80, Ad 20×250 mm, 10 μM column: $CO_2$/0.2% ammonia in methanol, 75/25) to give 4-(4-chlorophenyl)-N-(1-methyl-6-oxo-1,6-dihydropyridazin-3-yl)-2,3,6,7-tetrahydro-1H-azepine-1-carboxamide as a yellow solid (192.8 mg, 0.54 mmol, 32%). $^1$H NMR (400 MHz, Dimethylsulfoxide-$d_6$) δ 9.16 (s, 1H), 7.66 (d, J=10.0 Hz, 1H), 7.37 (s, 4H), 6.88 (d, J=9.6 Hz, 1H), 6.06 (t, J=5.6 Hz, 1H), 3.69 (t, J=5.2 Hz, 2H), 3.57-3.62 (m, 5H), 2.73 (s, 2H), 2.47-2.51 (m, 2H); LCMS (ESI) m/z: 359.1[M+H]+; and 5-(4-chlorophenyl)-N-(1-methyl-6-oxo-1,6-dihydropyridazin-3-yl)-2,3,4,7-tetrahydro-1H-azepine-1-carboxamide as a yellow solid (115.4 mg, 0.32 mmol, 19%). $^1$H NMR (400 MHz, Dimethylsulfoxide-$d_6$) δ 9.13 (s, 1H), 7.64 (d, J=9.6 Hz, 1H), 7.38 (s, 4H), 6.87 (d, J=9.6 Hz, 1H), 6.14 (t, J=4.8 Hz, 1H), 4.13 (d, J=4.8 Hz, 2H), 3.68 (t, J=5.6 Hz, 2H), 3.56 (s, 3H), 2.64 (t, J=4.8 Hz, 2H), 1.88 (s, 2H); LCMS (ESI) m/z: 359.1 [M+H]+.

Example 80. Preparation of 4-(3-chlorobenzyl)-N-(1-methyl-6-oxo-1,6-dihydropyridazin-3-yl)piperazine-1-carboxamide (Compound 130)

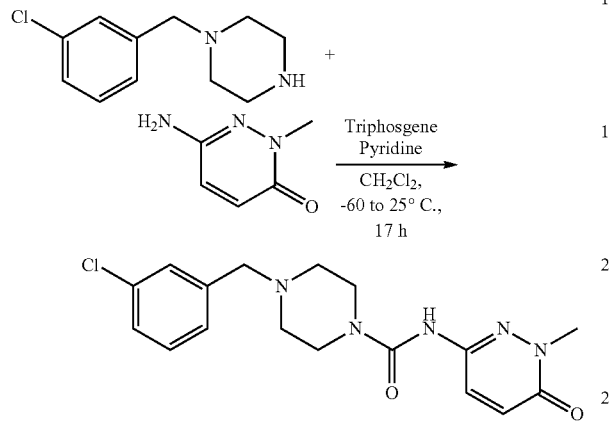

Step 1: Preparation of 4-(3-chlorobenzyl)-N-(1-methyl-6-oxo-1,6-dihydropyridazin-3-yl)piperazine-1-carboxamide

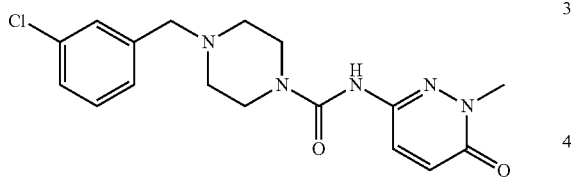

To a solution of triphosgene (139 mg, 0.47 mmol) in dichloromethane (5 mL) at −60° C. was added a solution of 6-amino-2-methylpyridazin-3(2H)-one (176 mg, 1.41 mmol) and pyridine (297 mg, 3.76 mmol) in dichloromethane (5 mL) under argon. The mixture was stirred at −60° C. for 30 min and a solution of 1-(3-chlorobenzyl)piperazine (200 mg, 0.94 mmol) and pyridine (297 mg, 3.76 mmol) in dichloromethane (10 mL) was added. The resulting mixture was stirred at 25° C. for 17 h. The reaction mixture was quenched with water (20 mL) and extracted with dichloromethane (10 mL×3). The combined organic layers were dried over sodium sulfate, filtered and concentrated under reduced pressure. The crude sample was dissolved in the minimum amount of N,N-dimethylformamide and purified via prep-HPLC (Boston C18, 10 μm, 21 mm×250 mm column; acetonitrile/0.01% aqueous trifluoroacetic acid) to give 4-(3-chlorobenzyl)-N-(1-methyl-6-oxo-1,6-dihydropyridazin-3-yl)piperazine-1-carboxamide as a white solid (36.8 mg, 0.10 mmol, 11%). ¹H NMR (400 MHz, Dimethylsulfoxide-d6) δ 9.27 (s, 1H), 7.62 (d, J=9.9 Hz, 1H), 7.34 (ddt, J=16.1, 14.5, 6.4 Hz, 4H), 6.87 (d, J=9.9 Hz, 1H), 3.55 (s, 3H), 3.51 (s, 2H), 3.47-3.38 (m, 4H), 2.40-2.26 (m, 4H); LCMS (ESI) m/z: 362.0 [M+H]+.

Example 81. Preparation of 4-(3,5-difluorobenzylidene)-N-(1-methyl-6-oxo-1,6-dihydropyridazin-3-yl)piperidine-1-carboxamide (Compound 33)

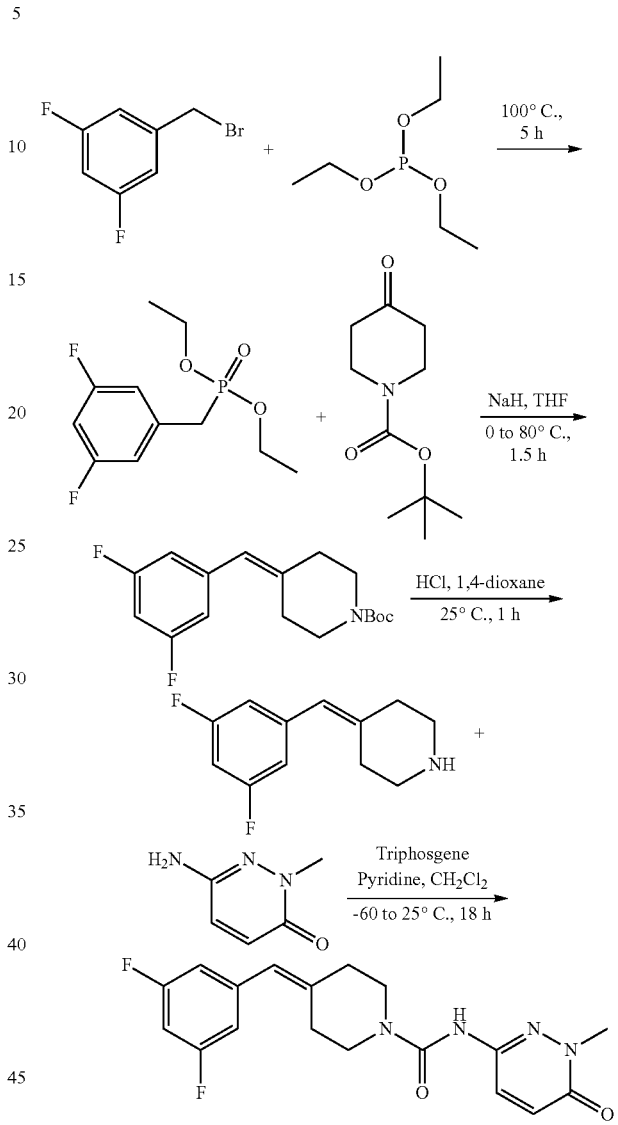

Step 1: Preparation of diethyl 3,5-difluorobenzylphosphonate

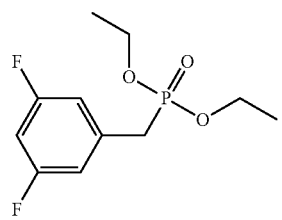 [SMILES: CCOP(=O)(Cc1cc(F)cc(F)c1)OCC]

A solution of 1-(bromomethyl)-3,5-difluorobenzene (4.14 g, 20 mmol) and triethyl phosphite (3.32 g, 20 mmol) was stirred at 100° C. for 5 h. The reaction mixture was concentrated to give diethyl 3,5-difluorobenzylphosphonate (5.17 g, 19.6 mmol, 97.9%) as a colorless oil. LCMS (ESI) m/z: 265.0 [M+H]+.

Step 2: Preparation of tert-butyl 4-(3,5-difluorobenzylidene)piperidine-1-carboxylate

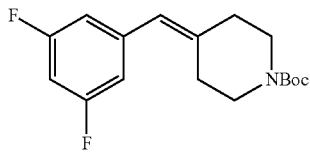

To a solution of tert-butyl 4-(4-fluorobenzyl)piperidine-1-carboxylate (4.8 g, 18.2 mmol) and tert-butyl 4-oxopiperidine-1-carboxylate (4.34 g, 21.8 mmol) in tetrahydrofuran (90 mL) at 0° C. was added sodium hydride (2.55 g, 63.7 mmol, 60% in mineral oil). The reaction mixture was stirred at 80° C. for 2 h, then poured into ice water and extracted with ethyl acetate (50 mL×2). The combined organic layers were washed with brine (50 mL), dried over sodium sulfate, filtered and concentrated under reduced pressure. The crude residue was purified by column chromatography (silica gel, petroleum ether/ethyl acetate=20/1) to give tert-butyl 4-(3,5-difluorobenzylidene)piperidine-1-carboxylate (2.1 g, 6.83 mmol, 38%) as a colorless oil. LCMS (ESI) m/z: 254.1 [M-56+H]+.

Step 3: Preparation of 4-(3,5-difluorobenzylidene)piperidine

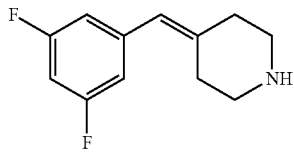 [SMILES: Fc1cc(F)cc(C=C2CCNCC2)c1]

A solution of tert-butyl 4-(3,5-difluorobenzylidene)piperidine-1-carboxylate (2.1 g, 6.8 mmol) and hydrochloric acid in dioxane solution (14 mL, 4 M) in dichloromethane (14 mL) was stirred at 25° C. for 1 h. The volatiles were concentrated under reduced pressure. The crude residue was treated with ether (100 mL) to give a precipitate that was filtered. The solid was dissolved in aqueous sodium bicarbonate solution (50 mL) and extracted with dichloromethane (100 mL×2). The combined organic layers were dried over sodium sulfate, filtered and concentrated under reduced pressure to yield crude 4-(3,5-difluorobenzylidene)piperidine (1.3 g, 6.2 mmol, 92%). LCMS (ESI) m/z: 210.1 [M+H]+. This material was used in the next step without additional purification.

Step 4: Preparation of 4-(3,5-difluorobenzylidene)-N-(1-methyl-6-oxo-1,6-dihydropyridazin-3-yl)piperidine-1-carboxamide

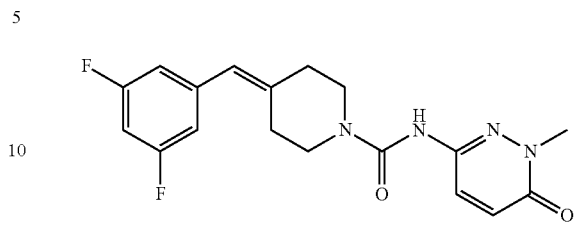

To a solution of triphosgene (148 mg, 0.5 mmol) in dichloromethane (6 mL) at −60° C. was added 6-amino-2-methylpyridazin-3(2H)-one (125 mg, 1 mmol) and pyridine (316 mg, 4 mmol) in dichloromethane (12 mL) under argon. The mixture was stirred at −60° C. for 0.5 h, then a solution of 4-(3,5-difluorobenzylidene)piperidine (209 mg, 1 mmol) and pyridine (380 mg, 4.8 mmol) in dichloromethane (7 mL) was added at −60° C. The resulting mixture was stirred at 25° C. for 3 h. The reaction was quenched with water (30 mL) and the aqueous layer was extracted with dichloromethane (30 mL×2). The combined organic layers were dried over sodium sulfate, filtered and concentrated under reduced pressure. The crude sample was dissolved in the minimum amount of N,N-dimethylformamide and purified by prep-HPLC (BOSTON pHlex ODS, 10 µm, 21.2 mm×250 mm, acetonitrile/0.1% aqueous formic acid) to yield 4-(3,5-difluorobenzylidene)-N-(1-methyl-6-oxo-1,6-dihydropyridazin-3-yl)piperidine-1-carboxamide (70.7 mg, 0.20 mmol, 20%) as a yellow solid. $^1$H NMR (400 MHz, Dimethylsulfoxide-d$_6$) δ 9.35 (s, 1H), 7.65 (d, J=10 Hz, 1H), 7.12-7.06 (m, 1H), 6.97-6.95 (m, 2H), 6.89 (d, J=10.4 Hz, 1H), 6.38 (s, 1H), 3.57 (s, 3H), 3.54 (t, J=5.8 Hz, 2H), 3.48 (t, J=5.4 Hz, 2H), 2.45 (t, J=5.4 Hz, 2H), 2.36 (t, J=5.6 Hz, 2H); LCMS (ESI) m/z: 361.1 [M+H]+.

Example 82. 3-(3-chlorobenzyl)-N-(1-methyl-6-oxo-1,6-dihydropyridazin-3-yl)pyrrolidine-1-carboxamide (Compound 25)

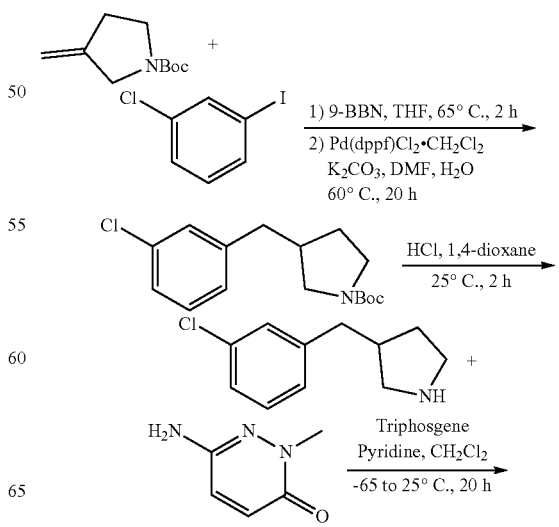

Step 1: Preparation of tert-butyl 3-(3-chlorobenzyl)pyrrolidine-1-carboxylate

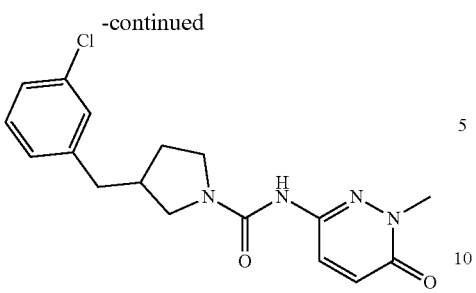

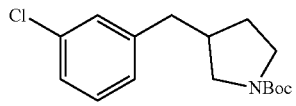 [SMILES: CC(C)(C)OC(=O)N1CCC(Cc2cccc(Cl)c2)C1]

To a solution of 9-borabicyclo[3.3.1]nonane in tetrahydrofuran (11.5 mL, 5.73 mmol, 0.5 M) at 25° C. was added tert-butyl 3-methylenepyrrolidine-1-carboxylate (1.0 g, 5.46 mmol) under argon. The mixture was stirred at 65° C. for 2 h. The mixture was cooled to 25° C. and added to a solution of 1-chloro-3-iodobenzene (1.3 g, 5.46 mmol), potassium carbonate (981 mg, 7.1 mmol) and 1,1'-bis(diphenylphosphino)ferrocene-palladium(II)dichloride dichloromethane complex (446 mg, 0.546 mmol) in N,N-dimethylformamide/water (8 mL/1 mL) at 25° C. The resulting mixture was heated at 60° C. for 20 h. The reaction was quenched wit 1 N aqueous sodium hydroxide solution and stirred at 25° C. for 1 h.

The reaction solution was diluted with ethyl acetate (100 mL) and washed with brine (50 mL×2). The combined organic layers were dried over anhydrous sodium sulfate, filtered and concentrated under reduced pressure. The crude residue was purified by column chromatography (silica gel, petroleum ether/ethyl acetate=20/1 to 10/1) to give tert-butyl 3-(3-chlorobenzyl)pyrrolidine-1-carboxylate (1.3 g, 4.39 mmol, 81%) as a red oil. LCMS (ESI) m/z: 318.1 [M+Na]⁺.

Step 2: Preparation of 3-(3-chlorobenzyl)pyrrolidine

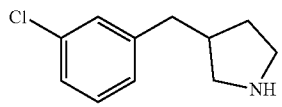 [SMILES: Clc1cccc(CC2CCNC2)c1]

A solution of tert-butyl 3-(3-chlorobenzyl)pyrrolidine-1-carboxylate (1.3 g, 4.39 mmol) and hydrochloric acid in 1,4-dioxane (20 mL, 4 M) was stirred at 25° C. for 3 h. The reaction mixture was concentrated in vacuo. The residue was diluted with saturated sodium bicarbonate aqueous solution (50 mL) and extracted with ethyl acetate (60 mL×5). The combined organic layers were dried over anhydrous sodium sulfate, filtered and concentrated under reduced pressure. The crude residue was purified by column chromatography (silica gel, dichloromethane/methanol from 100/0 to 100/20) to give 3-(3-chlorobenzyl)pyrrolidine (505 mg, 2.58 mmol, 59%) as a yellow oil. ¹H NMR (400 MHz, Methanol-d₄) δ 7.34-7.08 (m, 4H), 3.02-2.79 (m, 3H), 2.69 (d, J=7.6 Hz, 2H), 2.58-2.46 (m, 1H), 2.45-2.27 (m, 1H), 1.96-1.82 (m, 1H), 1.54-1.36 (m, 1H); LCMS (ESI) m/z: 196.2 [M+H]⁺.

Step 3: Preparation of 3-(3-chlorobenzyl)-N-(1-methyl-6-oxo-1,6-dihydropyridazin-3-yl)pyrrolidine-1-carboxamide

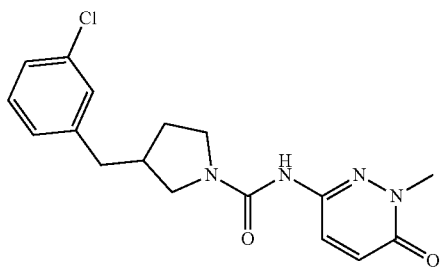 [SMILES: Cn1nc(NC(=O)N2CCC(Cc3cccc(Cl)c3)C2)ccc1=O]

To a solution of triphosgene (190 mg, 0.64 mmol) in dichloromethane (5 mL) at −60° C. was added a solution of 6-amino-2-methylpyridazin-3(2H)-one (160 mg, 1.28 mmol) and pyridine (405 mg, 5.12 mmol) in dichloromethane (5 mL) under argon. The mixture was stirred at −60° C. for 30 min and a solution of 3-(3-chlorobenzyl)pyrrolidine (250 mg, 1.28 mmol) and pyridine (405 mg, 5.12 mmol) in dichloromethane (5 mL) was added. The resulting mixture was stirred at 25° C. for 20 h. The reaction was quenched with water (50 mL) and extracted with dichloromethane (50 mL×2). The combined organic layers were dried over anhydrous sodium sulfate, filtered and concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 3-(3-chlorobenzyl)-N-(1-methyl-6-oxo-1,6-dihydropyridazin-3-yl)pyrrolidine-1-carboxamide (81 mg, 0.23 mmol, 18%) as a yellow solid. ¹H NMR (400 MHz, Dimethylsulfoxide-d₆) δ 8.93 (s, 1H), 7.73 (d, J=9.9 Hz, 1H), 7.39-7.16 (m, 4H), 6.88 (d, J=9.9 Hz, 1H), 3.55 (s, 3H), 3.55-3.40 (m, 2H), 3.39-3.23 (m, 1H), 3.08-2.96 (m, 1H), 2.75-2.62 (m, 2H), 2.48-2.37 (m, 1H), 1.98-1.84 (m, 1H), 1.64-1.47 (m, 1H); LCMS (ESI) m/z: 347.1 [M+H]⁺.

Example 83. 3-(3,5-difluorobenzyl)-N-(1-methyl-6-oxo-1,6-dihydropyridazin-3-yl)pyrrolidine-1-carboxamide (Compound 26)

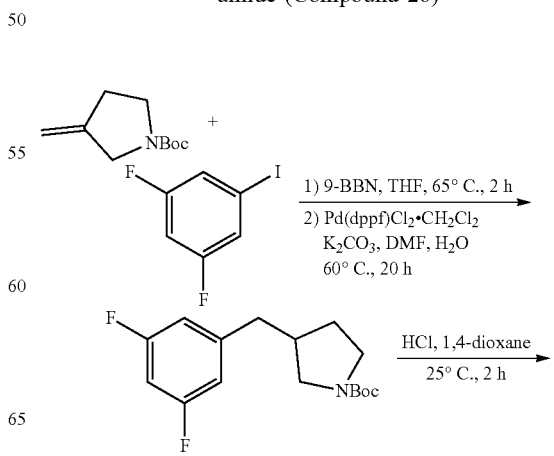

-continued

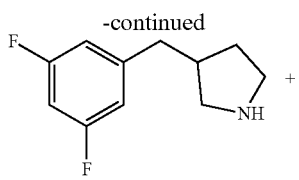

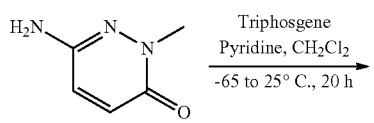

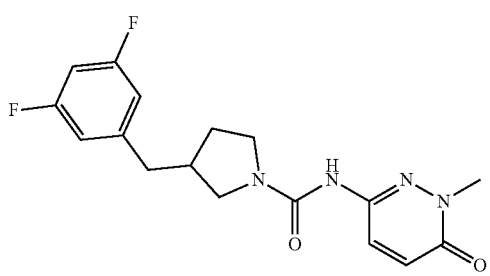

Step 1: Preparation of tert-butyl 3-(3,5-difluorobenzyl)pyrrolidine-1-carboxylate

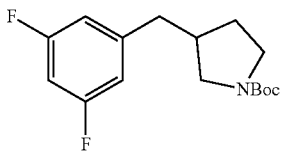 [SMILES: CC(C)(C)OC(=O)N1CCC(Cc2cc(F)cc(F)c2)C1]

To a solution of 9-borabicyclo[3.3.1]nonane in tetrahydrofuran (4.16 mL, 2.08 mmol, 0.5 M) at 25° C. was added tert-butyl 3-methylenepyrrolidine-1-carboxylate (381 mg, 2.08 mmol) under argon. The mixture was stirred at 65° C. for 2 h. The reaction mixture was cooled to 25° C. and added to a solution of 1,3-difluoro-5-iodobenzene (500 mg, 2.08 mmol), potassium carbonate (373 mg, 2.7 mmol) and 1,1'-bis(diphenylphosphino)ferrocene-palladium(II)dichloride dichloromethane complex (171 mg, 0.21 mmol) in N,N-dimethylformamide/water ((8 mL/1 mL). The resulting mixture was heated at 60° C. for 20 h. The reaction was quenched with 1 N aqueous sodium hydroxide solution and stirred at 25° C. for 1 h. The reaction solution was diluted with ethyl acetate (100 mL) and washed with brine (50 mL×2). The combined organic layers were dried over anhydrous sodium sulfate, filtered and concentrated under reduced pressure. The crude residue was purified by column chromatography (silica gel, petroleum ether/ethyl acetate=20/1 to 10/1) to give tert-butyl 3-(3,5-difluorobenzyl)pyrrolidine-1-carboxylate as a red oil (510 mg, 1.72 mmol, 82%).

Step 2: Preparation of 3-(3,5-difluorobenzyl)pyrrolidine

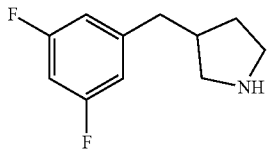 [SMILES: Fc1cc(F)cc(CC2CCNC2)c1]

A solution of tert-butyl 3-(3,5-difluorobenzyl)pyrrolidine-1-carboxylate (1.0 g, 3.36 mmol) and hydrochloric acid in 1,4-dioxane (20 mL, 4 M) was stirred at 25° C. for 3 h. The reaction mixture was concentrated in vacuo. The residue was diluted with saturated sodium bicarbonate aqueous solution (50 mL) at 25° C. and extracted with ethyl acetate (60 mL×5). The combined organic layers were dried over anhydrous sodium sulfate, filtered and concentrated under reduced pressure. The crude residue was purified by column chromatography (silica gel, dichloromethane/methanol from 100/0 to 100/20) to give 3-(3,5-difluorobenzyl)pyrrolidine (305 mg, 1.55 mmol, 45%) as a yellow oil. $^1$H NMR (400 MHz, Methanol-$d_4$) δ 6.92-6.81 (m, 2H), 6.81-6.73 (m, 1H), 3.04-2.95 (m, 2H), 2.95-2.84 (m, 1H), 2.71 (d, J=7.6 Hz, 2H), 2.56-2.49 (m, 1H), 2.46-2.34 (m, 1H), 1.98-1.86 (m, 1H), 1.55-1.41 (m, 1H); LCMS (ESI) m/z: 198.1 [M+H]$^+$.

Step 3: Preparation of 3-(3,5-difluorobenzyl)-N-(1-methyl-6-oxo-1,6-dihydropyridazin-3-yl)pyrrolidine-1-carboxamide

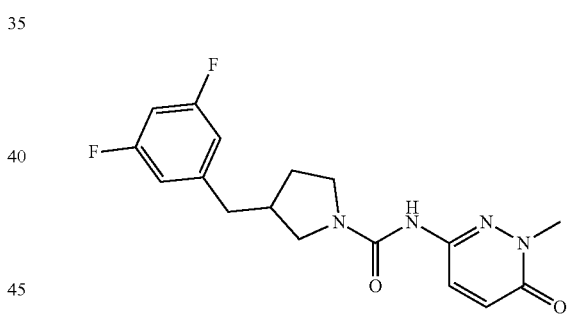

To a solution of triphosgene (77 mg, 0.26 mmol) in dichloromethane (5 mL) at −60° C. was added a solution of 6-amino-2-methylpyridazin-3(2H)-one (64 mg, 0.51 mmol) and pyridine (161 mg, 2.04 mmol) in dichloromethane (3 mL) under argon. The mixture was stirred at −60° C. for 30 min and a solution of 3-(3,5-difluorobenzyl)pyrrolidine (100 mg, 0.51 mmol) and pyridine (161 mg, 2.04 mmol) in dichloromethane (3 mL) was added. The resulting mixture was stirred at 25° C. for 20 h. The reaction mixture was quenched with water (40 mL) and extracted with dichloromethane (30 mL×2). The combined organic layers were dried over anhydrous sodium sulfate, filtered and concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 3-(3,5-difluorobenzyl)-N-(1-methyl-6-oxo-1,6-dihydropyridazin-3-yl)pyrrolidine-1-carboxamide (47.6 mg, 0.14 mmol, 18%) as a white solid. $^1$H NMR (400 MHz, Dimethylsulfoxide-$d_6$) δ 8.90 (s, 1H), 7.73 (d, J=9.9 Hz, 1H), 7.13-6.95 (m, 3H), 6.87 (d, J=9.9 Hz, 1H), 3.55 (s, 3H), 3.54-3.42 (m, 2H), 3.35-3.33 (m, 1H), 3.03 (t, J=9.3 Hz, 1H), 2.78-2.62 (m, 2H), 2.49-2.41 (m, 1H), 1.99-1.82 (m, 1H), 1.64-1.48 (m, 1H); LCMS (ESI) m/z: 349.2 [M+H]⁺.

Example 84. 3-(3,5-difluorobenzyl)-N-(1-methyl-6-oxo-1,6-dihydropyridin-3-yl)pyrrolidine-1-carboxamide (Compound 3)

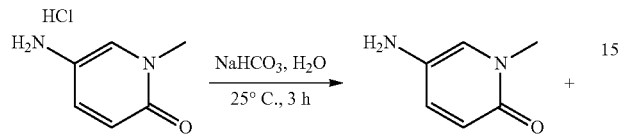

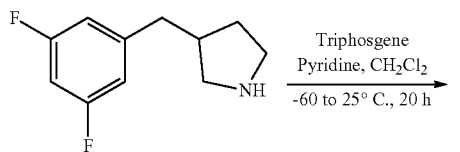

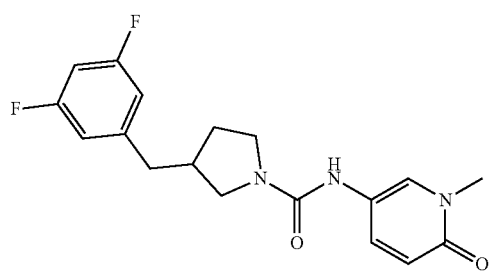 [SMILES: Cn1cc(NC(=O)N2CCC(Cc3cc(F)cc(F)c3)C2)ccc1=O]

Step 1: Preparation of 5-amino-1-methylpyridin-2(1H)-one

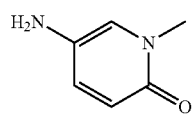

A solution of 5-amino-1-methylpyridin-2(1H)-one hydrochloride (2.0 g, 12.5 mmol) and sodium bicarbonate (2.09 g, 24.9 mmol) in water (50 mL) was stirred at 25° C. for 3 h. The reaction mixture was concentrated under reduced pressure. The crude residue was treated with ethanol (200 mL) and the reaction mixture was stirred at 25° C. for 2 h. The reaction mixture was filtered and washed with ethanol (200 mL). The filtrate was concentrated and dried in vacuo to give 5-amino-1-methylpyridin-2(1H)-one (1.55 g, 12.5 mmol, 100%) as a black solid. This material was used in the next step without further purification.

Step 2: Preparation of 3-(3,5-difluorobenzyl)-N-(1-methyl-6-oxo-1,6-dihydropyridin-3-yl)pyrrolidine-1-carboxamide

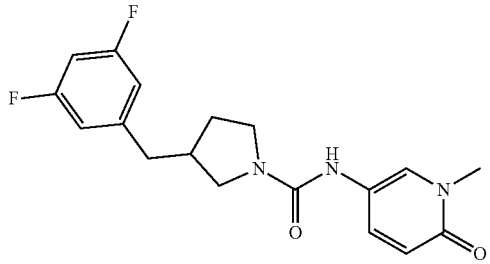

To a solution of triphosgene (119 mg, 0.40 mmol) in dichloromethane (5 mL) at −60° C. was added a solution of 5-amino-1-methylpyridin-2(1H)-one (98 mg, 0.79 mmol) and pyridine (250 mg, 3.16 mmol) in dichloromethane (5 mL) under argon. The mixture was stirred at −60° C. for 30 min and a solution of 3-(3,5-difluorobenzyl)pyrrolidine (155 mg, 0.79 mmol) and pyridine (250 mg, 3.16 mmol) in dichloromethane (5 mL) was added. The resulting mixture was stirred at 25° C. for 20 h. The reaction was quenched with water (50 mL) and extracted with dichloromethane (50 mL×2). The combined organic layers were dried over anhydrous sodium sulfate, filtered and concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 3-(3,5-difluorobenzyl)-N-(1-methyl-6-oxo-1,6-dihydropyridin-3-yl)pyrrolidine-1-carboxamide as a white solid (48.2 mg, 0.14 mmol, 18%). ¹H NMR (400 MHz, Dimethylsulfoxide-d₆) δ 7.84 (s, 1H), 7.75 (d, J=2.8 Hz, 1H), 7.42 (dd, J=9.7, 2.9 Hz, 1H), 7.10-6.97 (m, 3H), 6.31 (d, J=9.5 Hz, 1H), 3.50-3.39 (m, 2H), 3.38 (s, 3H), 3.30-3.20 (m, 1H), 3.00-2.92 (m, 1H), 2.75-2.68 (m, 2H), 2.49-2.44 (m, 1H), 1.98-1.86 (m, 1H), 1.64-1.50 (m, 1H); LCMS (ESI) m/z: 348.1 [M+H]⁺.

Example 85. (3R)-3-(3,4-difluorophenoxy)-N-(1-methyl-6-oxo-1,6-dihydropyridazin-3-yl)pyrrolidine-1-carboxamide (Compound 27)

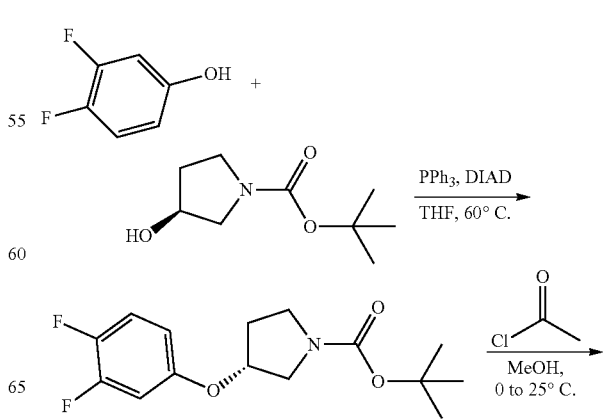

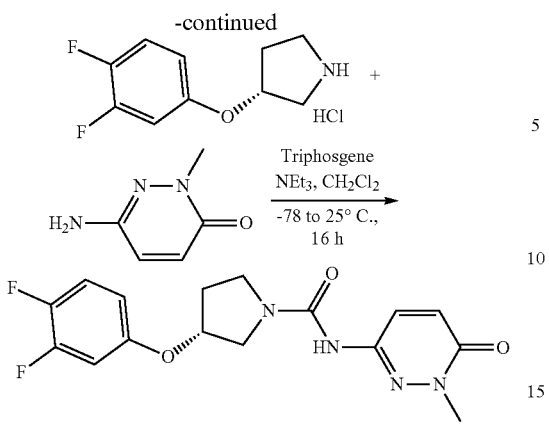

Step 1: Preparation of tert-butyl (3R)-3-(3,4-difluorophenoxy)pyrrolidine-1-carboxylate

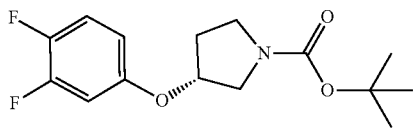 [SMILES: CC(C)(C)OC(=O)N1CC[C@@H](Oc2ccc(F)c(F)c2)C1]

To an ice-cooled solution of 3,4-difluorophenol (347 mg, 2.67 mmol), tert-butyl (3S)-3-hydroxypyrrolidine-1-carboxylate (500 mg, 2.67 mmol) and triphenylphosphine (768 mg, 2.93 mmol) in tetrahydrofuran (6.7 mL) was added diisopropyl azodicarboxylate (576 µL, 2.93 mmol). The reaction mixture was stirred at 60° C. for 48 h, then concentrated under reduced pressure. The crude oil was diluted with diethyl ether (10 mL) and 1 M aqueous sodium hydroxide (10 mL) was added. The aqueous layer was extracted with diethyl ether (10 mL×2). The combined organic layers were dried over magnesium sulfate, filtered and concentrated in vacuo. The crude material was purified via column chromatography (ISCO, 24 g silica gel, 0-20% ethyl acetate in hexanes over 20 min gradient) to give tert-butyl (3R)-3-(3,4-difluorophenoxy)pyrrolidine-1-carboxylate (0.638 g, 2.13 mmol, 80%) as a yellow solid. LCMS (ESI) m/z: 300.3 [M+H]⁺.

Step 2: Preparation of (3R)-3-(3,4-difluorophenoxy)pyrrolidine Hydrochloride

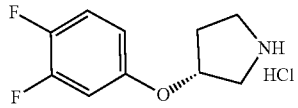

To a solution of tert-butyl (3R)-3-(3,4-difluorophenoxy) pyrrolidine-1-carboxylate (0.638 g, 2.13 mmol) in methanol (7.10 mL) at 0° C. was added acetyl chloride (756 µL, 10.6 mmol) dropwise. The reaction mixture was warmed to room temperature and stirred for 2 h. The volatiles were concentrated in vacuo to afford (3R)-3-(3,4-difluorophenoxy)pyrrolidine hydrochloride (370 mg, 1.57 mmol, 74%) as a light brown solid. The material was used in the next step without additional purification. ¹H NMR (300 MHz, Methanol-d₄) δ 10.14 (s, 2H), 7.09 (q, J=9.2 Hz, 1H), 6.77 (ddd, J=11.5, 6.5, 2.9 Hz, 1H), 6.63 (dtd, J=8.4, 3.2, 1.7 Hz, 1H), 4.96 (s, 1H), 3.52 (d, J=23.4 Hz, 4H), 2.46-2.09 (m, 2H); LCMS (ESI) m/z: 200.1 [M+H]⁺.

Step 3: Preparation of (3R)-3-(3,4-difluorophenoxy)-N-(1-methyl-6-oxo-1,6-dihydropyridazin-3-yl)pyrrolidine-1-carboxamide

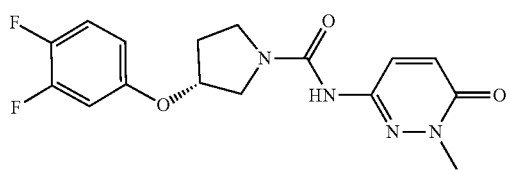 [SMILES: Cn1nc(NC(=O)N2CC[C@@H](Oc3ccc(F)c(F)c3)C2)ccc1=O]

To a solution of triphosgene (31.3 mg, 0.106 mmol) in methylene chloride (1.06 mL) at -78° C. was added a solution of 6-amino-2-methyl-2,3-dihydropyridazin-3-one (27.8 mg, 0.223 mmol) and triethylamine (118 µL, 0.848 mmol) in methylene chloride (530 µL). The mixture was stirred for 2 h at -78° C., then a solution of (3R)-3-(3,4-difluorophenoxy)pyrrolidine hydrochloride (0.050 g, 0.212 mmol) and triethylamine (118 µL, 0.848 mmol) in methylene chloride (530 µL) was added. The reaction mixture was warmed to room temperature and stirred for 18 h. The reaction was quenched with water (10 mL) and extracted with ethyl acetate (5 mL×2). The combined organic layers were washed with brine, dried over magnesium sulfate, filtered and concentrated under reduced pressure. The crude material was purified by column chromatography (ISCO, silica gel, 12 g, 0-4% methanol/dichloromethane, gradient over 20 minutes) to afford (3R)-3-(3,4-difluorophenoxy)-N-(1-methyl-6-oxo-1,6-dihydropyridazin-3-yl)pyrrolidine-1-carboxamide (61.6 mg, 0.176 mmol, 83%) as a yellow solid. ¹H NMR (300 MHz, Dimethylsulfoxide-d₆) δ 9.07 (s, 1H), 7.73 (d, J=9.9 Hz, 1H), 7.37 (dt, J=10.6, 9.3 Hz, 1H), 7.14 (ddd, J=12.8, 6.7, 3.0 Hz, 1H), 6.89 (d, J=9.9 Hz, 1H), 6.80 (dtd, J=9.0, 3.3, 1.7 Hz, 1H), 5.05 (s, 1H), 3.63 (m, 6H), 3.51-3.36 (m, 1H), 2.23-2.00 (m, 2H); LCMS (ESI) m/z: 351.2 [M+H]⁺.

Example 86. Preparation of (3R)-3-(3,5-difluorophenoxy)-N-(1-methyl-6-oxo-1,6-dihydropyridazin-3-yl)pyrrolidine-1-carboxamide (Compound 28)

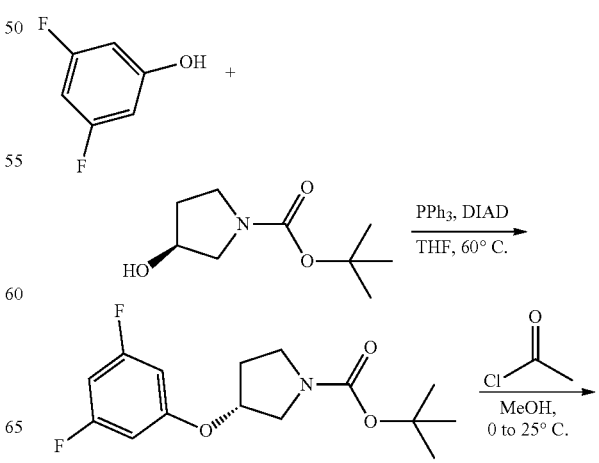

-continued

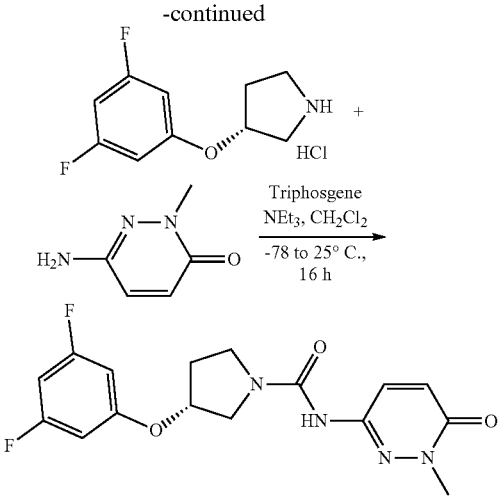

Step 1: Preparation of tert-butyl (3R)-3-(3,5-difluorophenoxy)pyrrolidine-1-carboxylate

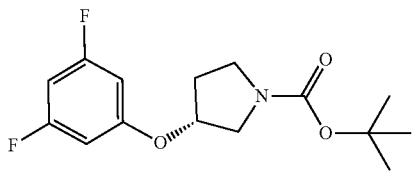 [SMILES: CC(C)(C)OC(=O)N1CC[C@@H](Oc2cc(F)cc(F)c2)C1]

To an ice-cooled solution of 3,5-difluorophenol (347 mg, 2.67 mmol), tert-butyl (3S)-3-hydroxypyrrolidine-1-carboxylate (500 mg, 2.67 mmol) and triphenylphosphine (768 mg, 2.93 mmol) in tetrahydrofuran (6.67 mL) at 60° C. was added diisopropyl azodicarboxylate (576 µL, 2.93 mmol) dropwise. The reaction mixture was stirred at 60° C. for 48 h, then concentrated under reduced pressure. The crude oil was diluted with diethyl ether (10 mL) and then 1 M aqueous sodium hydroxide (10 mL) was added. The aqueous layer was extracted with diethyl ether (10 mL×2). The combined organic layers were dried over magnesium sulfate, filtered and concentrated in vacuo (ISCO, 24 g silica gel, 0-20% ethyl acetate in hexanes over 20 min gradient) to give tert-butyl (3R)-3-(3,5-difluorophenoxy)pyrrolidine-1-carboxylate (650 mg, 2.17 mmol, 81%) as a colorless oil. $^1$H NMR (300 MHz, Chloroform-d) δ 6.51-6.30 (m, 3H), 3.70-3.40 (m, 1H), 2.29-2.03 (m, 1H), 1.44 (m, 3H); LCMS (ESI) m/z: 244.1 [M+H]$^+$.

Step 2: Preparation of (3R)-3-(3,5-difluorophenoxy)pyrrolidine Hydrochloride

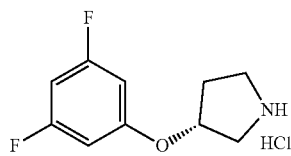 [SMILES: Fc1cc(F)cc(O[C@@H]2CCNC2)c1 ; Cl]

To a solution of tert-butyl (3R)-3-(3,5-difluorophenoxy)pyrrolidine-1-carboxylate (0.650 g, 2.17 mmol) in methanol (7.2 mL) at 0° C. was added acetyl chloride (770 µL, 10.8 mmol) dropwise. The reaction mixture was warmed to room temperature and stirred for 2 h. The volatiles were concentrated in vacuo to afford (3R)-3-(3,5-difluorophenoxy)pyrrolidine hydrochloride (509 mg, 2.15 mmol, 99%) as a light brown solid. The material was used in the next step without additional purification. $^1$H NMR (300 MHz, Methanol-d$_4$) δ 10.17 (s, 2H), 6.60-6.33 (m, 3H), 5.00 (s, 1H), 3.75-3.34 (m, 4H), 2.49-2.08 (m, 2H); LCMS (ESI) m/z: 200.1 [M+H]$^+$.

Step 3: Preparation of (3R)-3-(3,5-difluorophenoxy)-N-(1-methyl-6-oxo-1,6-dihydropyridazin-3-yl)pyrrolidine-1-carboxamide

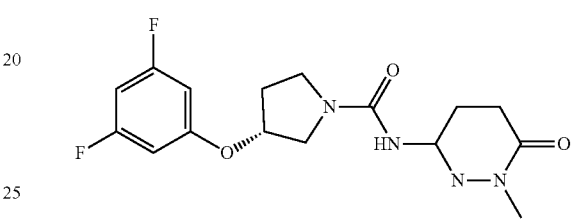

To a solution of triphosgene (62.9 mg, 0.212 mmol) in methylene chloride (2.12 mL) at −78° C. was added a solution of 6-amino-2-methyl-2,3-dihydropyridazin-3-one (55.7 mg, 0.446 mmol) and triethylamine (235 µL, 1.69 mmol) in methylene chloride (1.1 mL). The mixture was stirred for 2 h at −78° C., then a solution of (3R)-3-(3,5-difluorophenoxy)pyrrolidine hydrochloride (0.100 g, 0.424 mmol) and triethylamine (235 µL, 1.69 mmol) in methylene chloride (1.06 mL) was added. The reaction mixture was warmed to room temperature and stirred for 18 h. The reaction was quenched with water (10 mL) and extracted with ethyl acetate (5 mL×2). The combined organic layers were washed with brine, dried over magnesium sulfate, filtered and concentrated under reduced pressure. The crude material was purified by column chromatography (ISCO, silica gel, 12 g, 0-4% methanol/dichloromethane, gradient over 20 minutes) to afford (3R)-3-(3,5-difluorophenoxy)-N-(1-methyl-6-oxo-1,6-dihydropyridazin-3-yl)pyrrolidine-1-carboxamide (54.5 mg, 0.156 mmol, 37%) as a yellow solid. $^1$H NMR (300 MHz, Dimethylsulfoxide-d$_6$) δ 9.08 (s, 1H), 7.73 (d, J=9.9 Hz, 1H), 6.94-6.83 (m, 1H), 6.83-6.72 (m, 3H), 5.12 (s, 1H), 3.55 (m, 6H), 3.50-3.37 (m, 1H), 2.09 (s, 2H); LCMS (ESI) m/z: 351.2 [M+H]$^+$.

Example 87. Preparation of (3S)-3-(3,4-difluorophenoxy)-N-(1-methyl-6-oxo-1,6-dihydropyridazin-3-yl)pyrrolidine-1-carboxamide (Compound 29)

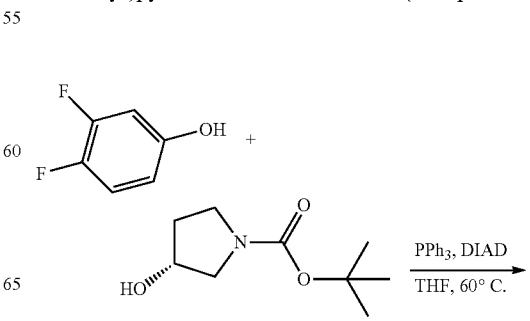

-continued

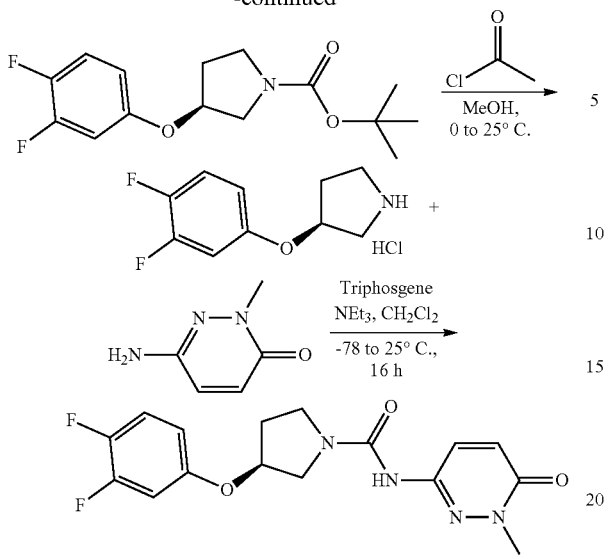

Step 1: Preparation of tert-butyl (3S)-3-(3,4-difluorophenoxy)pyrrolidine-1-carboxylate

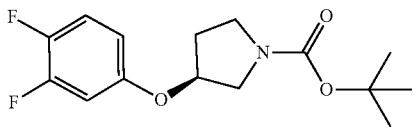 [SMILES: CC(C)(C)OC(=O)N1CC[C@H](Oc2ccc(F)c(F)c2)C1]

To an ice-cooled solution of 3,4-difluorophenol (0.250 g, 1.92 mmol), tert-butyl (3R)-3-hydroxypyrrolidine-1-carboxylate (359 mg, 1.92 mmol) and triphenylphosphine (553 mg, 2.11 mmol) in tetrahydrofuran (4.80 mL) at 25° C. was added diisopropyl azodicarboxylate (414 µL, 2.11 mmol) dropwise. The reaction mixture was stirred at 60° C. for 48 h, then concentrated under reduced pressure.

The crude oil was diluted with diethyl ether (10 mL) and then 1 M aqueous sodium hydroxide (10 mL) was added. The aqueous layer was extracted with diethyl ether (10 mL×2). The combined organic layers were dried over magnesium sulfate, filtered and concentrated in vacuo. The crude material was purified via column chromatography (ISCO, 24 g silica gel, 0-20% ethyl acetate in hexanes over 20 min gradient) to give tert-butyl (3S)-3-(3,4-difluorophenoxy)pyrrolidine-1-carboxylate (400 mg, 1.33 mmol, 70%) as a yellow solid. $^1$H NMR (300 MHz, Chloroform-d) δ 7.08 (dt, J=10.2, 9.1 Hz, 1H), 6.71 (ddd, J=11.9, 6.6, 3.0 Hz, 1H), 6.58 (dtd, J=9.2, 3.2, 1.8 Hz, 1H), 4.80 (dq, J=6.1, 2.5 Hz, 1H), 3.68-3.41 (m, 4H), 2.12 (dtd, J=18.1, 13.4, 9.8 Hz, 2H), 1.48 (s, 9H).

Step 2: Preparation of (3S)-3-(3,4-difluorophenoxy)pyrrolidine Hydrochloride

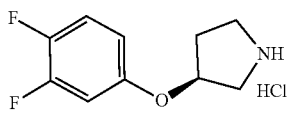 [SMILES: Fc1ccc(O[C@H]2CCNC2)cc1F ; Cl]

To a solution of tert-butyl (3S)-3-(3,4-difluorophenoxy)pyrrolidine-1-carboxylate (0.4 g, 1.33 mmol) in methanol (6.64 mL) at 0° C. was added acetyl chloride (936 µL, 13.2 mmol) dropwise. The reaction mixture was warmed to room temperature and stirred for 2 h. The volatiles were concentrated in vacuo to afford (3S)-3-(3,4-difluorophenoxy)pyrrolidine hydrochloride (370 mg, 1.57 mmol, >100%) as a light brown solid. The material was used in the next step without additional purification. $^1$H NMR (300 MHz, Chloroform-d) δ 10.14 (s, 2H), 7.10 (dt, J=9.8, 9.0 Hz, 1H), 6.79 (ddd, J=11.5, 6.5, 3.0 Hz, 1H), 6.64 (dtd, J=9.1, 3.2, 1.7 Hz, 1H), 4.98 (d, J=3.9 Hz, 1H), 3.66-3.41 (m, 4H), 2.45-2.18 (m, 2H); LCMS (ESI) m/z: 200.1 [M+H]$^+$.

Step 3: Preparation of (3S)-3-(3,4-difluorophenoxy)-N-(1-methyl-6-oxo-1,6-dihydropyridazin-3-yl)pyrrolidine-1-carboxamide

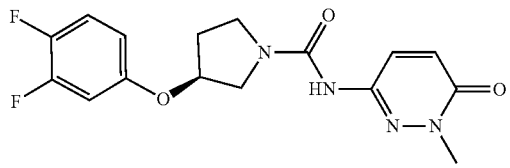 [SMILES: Cn1nc(NC(=O)N2CC[C@H](Oc3ccc(F)c(F)c3)C2)ccc1=O]

To a solution of triphosgene (62.9 mg, 0.212 mmol) in methylene chloride (2.12 mL) at −78° C. was added a solution of 6-amino-2-methyl-2,3-dihydropyridazin-3-one (55.7 mg, 0.446 mmol) and triethylamine (235 µL, 1.69 mmol) in methylene chloride (1.06 mL). The mixture was stirred for 2 h at −78° C., then a solution of (3S)-3-(3,4-difluorophenoxy)pyrrolidine hydrochloride (0.100 g, 0.424 mmol) and triethylamine (235 µL, 1.69 mmol) in methylene chloride (1.06 mL) was added. The reaction mixture was warmed to room temperature and stirred for 18 h. The reaction was quenched with water (10 mL) and extracted with ethyl acetate (5 mL×2). The combined organic layers were washed with brine, dried over magnesium sulfate, filtered and concentrated under reduced pressure. The crude material was purified by column chromatography (ISCO, silica gel, 12 g, 0-4% methanol/dichloromethane, gradient over 20 minutes) to afford (3S)-3-(3,4-difluorophenoxy)-N-(1-methyl-6-oxo-1,6-dihydropyridazin-3-yl)pyrrolidine-1-carboxamide (66.2 mg, 0.189 mmol, 45%) as a yellow solid. $^1$H NMR (300 MHz, Dimethylsulfoxide-d$_6$) δ 9.07 (s, 1H), 7.73 (d, J=9.9 Hz, 1H), 7.37 (dt, J=10.6, 9.4 Hz, 1H), 7.14 (ddd, J=12.8, 6.8, 3.1 Hz, 1H), 6.89 (d, J=9.9 Hz, 1H), 6.85-6.73 (m, 1H), 5.06 (s, 1H), 3.64 (m, 6H), 3.52-3.38 (m, 1H), 2.13 (q, J=9.4 Hz, 2H); LCMS (ESI) m/z: 351.2 [M+H]$^+$.

Example 88. Preparation of (3S)-3-(3,5-difluorophenoxy)-N-(1-methyl-6-oxo-1,6-dihydropyridazin-3-yl)pyrrolidine-1-carboxamide (Compound 30)

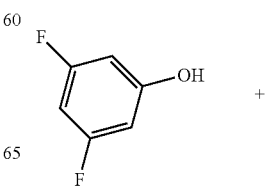

253

-continued

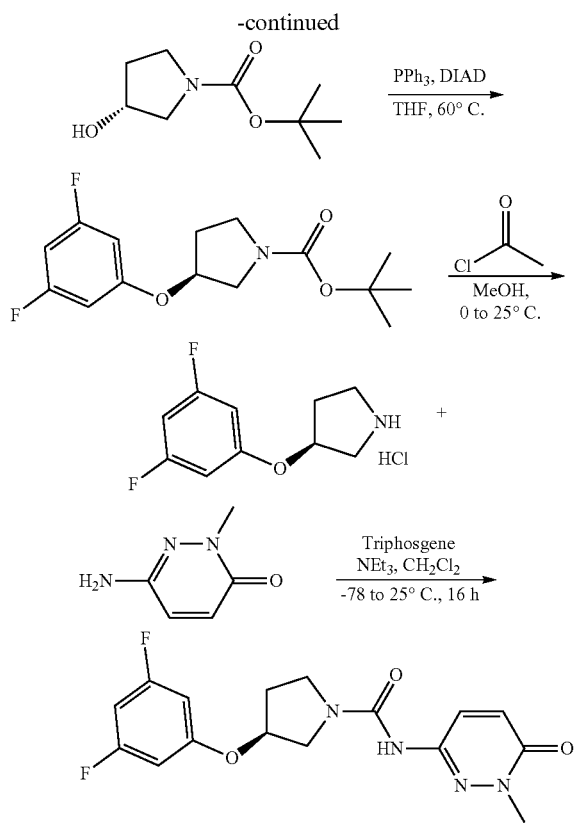

254

Step 2: Preparation of (3S)-3-(3,5-difluorophenoxy)pyrrolidine Hydrochloride

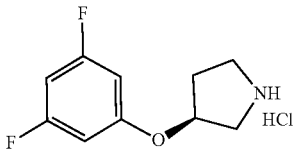

To a solution of tert-butyl (3S)-3-(3,5-difluorophenoxy) pyrrolidine-1-carboxylate (0.4 g, 1.33 mmol) in methanol (6.64 mL) at 0° C. was added acetyl chloride (936 µL, 13.2 mmol) dropwise. The reaction mixture was warmed to room temperature and stirred for 2 h. The volatiles were concentrated in vacuo to give (3S)-3-(3,5-difluorophenoxy)pyrrolidine hydrochloride (310 mg, 1.31 mmol, 99%) as a light brown solid. The material was used in the next step without additional purification. $^1$H NMR (300 MHz, Chloroform-d) δ 10.02 (s, 2H), 6.47 (ddt, J=10.7, 7.0, 2.1 Hz, 3H), 5.02 (s, 1H), 3.58 (m, 4H). 2.34 (m, 2H); LCMS (ESI) m/z: 200.1 [M+H]$^+$.

Step 3: Preparation of (3S)-3-(3,5-difluorophenoxy)-N-(1-methyl-6-oxo-1,6-dihydropyridazin-3-yl)pyrrolidine-1-carboxamide

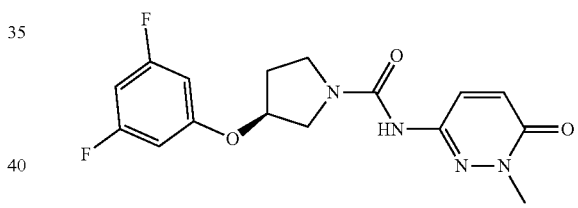

Step 1: Preparation of tert-butyl (3S)-3-(3,5-difluorophenoxy)pyrrolidine-1-carboxylate

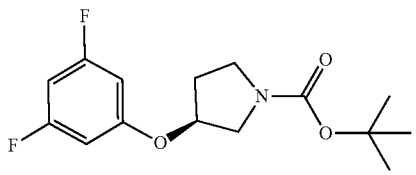 [SMILES: CC(C)(C)OC(=O)N1CC[C@H](Oc2cc(F)cc(F)c2)C1]

To an ice-cooled solution of 3,5-difluorophenol (0.250 g, 1.92 mmol), tert-butyl (3R)-3-hydroxypyrrolidine-1-carboxylate (359 mg, 1.92 mmol) and triphenylphosphine (553 mg, 2.11 mmol) in tetrahydrofuran (4.80 mL) at 60° C. was added diisopropyl azodicarboxylate (414 µL, 2.11 mmol) dropwise. The reaction mixture was stirred at 60° C. for 48 h. The reaction mixture was then concentrated under reduced pressure. The crude oil was diluted with diethyl ether (10 mL) and 1 M aqueous sodium hydroxide (10 mL) was added. The aqueous layer was extracted with diethyl ether (10 mL×2). The combined organic layers were dried over magnesium sulfate, filtered and concentrated in vacuo. The crude material was purified via column chromatography (ISCO, 24 g, 0-20% ethyl acetate in hexanes) to give tert-butyl (3S)-3-(3,5-difluorophenoxy)pyrrolidine-1-carboxylate (409 mg, 1.36 mmol, 71%) as a clear oil. $^1$H NMR (300 MHz, Chloroform-d) δ 6.51-6.31 (m, 3H), 4.83 (p, J=2.6 Hz, 1H), 3.73-3.38 (m, 4H), 2.26-2.01 (m, 2H), 1.48 (s, 9H).

To a solution of triphosgene (62.9 mg, 0.212 mmol) in methylene chloride (2.12 mL) at −78° C. was added a solution of 6-amino-2-methyl-2,3-dihydropyridazin-3-one (56 mg, 0.446 mmol) and triethylamine (235 µL, 1.69 mmol) in methylene chloride (1.1 mL). The mixture was stirred for 2 h at −78° C., then a solution of (3S)-3-(3,5-difluorophenoxy)pyrrolidine hydrochloride (0.100 g, 0.424 mmol) and triethylamine (235 µL, 1.69 mmol) in methylene chloride (1.06 mL) was added. The reaction mixture was warmed to room temperature and stirred for 18 h. The reaction was quenched with water (10 mL) and extracted with ethyl acetate (5 mL×2). The combined organic layers were washed with brine, dried over magnesium sulfate, filtered and concentrated under reduced pressure. The crude material was purified by column chromatography (ISCO, silica gel, 12 g, 0-4% methanol/dichloromethane, gradient over 20 minutes) to afford (3S)-3-(3,5-difluorophenoxy)-N-(1-methyl-6-oxo-1,6-dihydropyridazin-3-yl)pyrrolidine-1-carboxamide (48.4 mg, 0.138 mmol, 33%) as a yellow solid. $^1$H NMR (300 MHz, Dimethylsulfoxide-d$_6$) δ 9.08 (s, 1H), 7.73 (d, J=9.9 Hz, 1H), 6.89 (d, J=9.9 Hz, 1H), 6.84-6.71 (m, 3H), 5.12 (s, 1H), 3.55 (s, 6H), 3.50-3.37 (m, 1H), 2.25-2.01 (m, 2H); LCMS (ESI) m/z: 351.2 [M+H]$^+$.

Example 89. Preparation of 6-(3-fluorobenzyl)-N-(1-methyl-6-oxo-1,6-dihydropyridazin-3-yl)-3-azabicyclo[3.1.0]hexane-3-carboxamide (Compound 135)

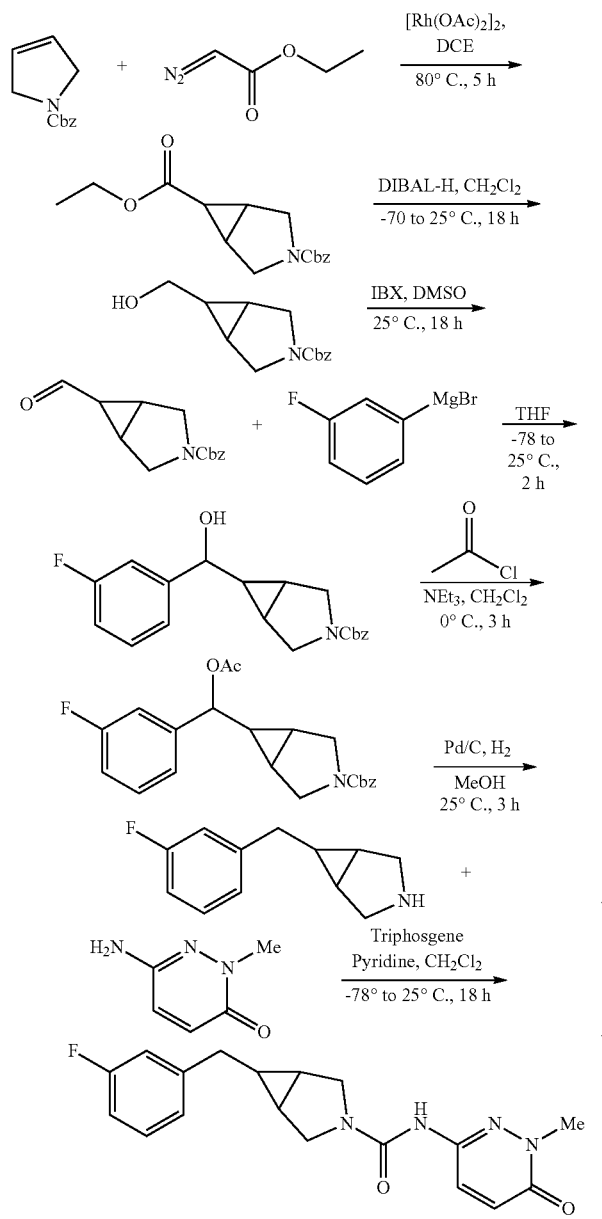

Step 1: Preparation of 3-benzyl 6-ethyl 3-azabicyclo[3.1.0]hexane-3,6-dicarboxylate

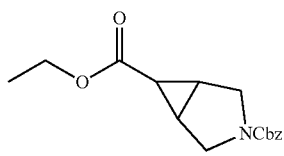 [SMILES: CCOC(=O)C1C2CN(C(=O)OCc3ccccc3)CC21]

To a solution of benzyl 2,5-dihydro-1H-pyrrole-1-carboxylate (5.3 mL, 26 mmol) and rhodium(II) acetate dimer (70 mg, 0.16 mmol) in dry 1,2-dichloroethane (60 mL) at 80° C. was added ethyl 2-diazoacetate (15.5 mL, 130 mmol) in dry dichloroethane (124 mL) slowly over 5 h. The reaction mixture was stirred at 80° C. for 1 h. The reaction solution was concentrated in vacuo. The crude residue was purified by column chromatography (silica gel, petroleum ether/ethyl acetate=6/4) to give 3-benzyl 6-ethyl 3-azabicyclo[3.1.0]hexane-3,6-dicarboxylate (6 g, 20.7 mmol, 80%) as a yellow oil. LCMS (ESI) m/z: 290.1 [M+H]$^+$.

Step 2: Preparation of benzyl 6-(hydroxymethyl)-3-azabicyclo[3.1.0]hexane-3-carboxylate

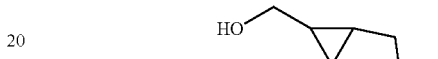

To a mixture of 3-benzyl 6-ethyl 3-azabicyclo[3.1.0]hexane-3,6-dicarboxylate (2.0 g, 6.9 mmol) in dry dichloromethane (30 mL) at −70° C. was added a solution of diisobutylaluminum hydride (27.6 mL, 27.6 mmol, 1 M). The mixture was stirred at −70° C. for 1 h and 25° C. for 1 h. The mixture was diluted with ethyl acetate (30 mL) and quenched with aqueous potassium sodium tartrate. The mixture was stirred at 25° C. for 1 h and extracted with ethyl acetate (2×30 mL). The combined organic layers were concentrated under pressure and purified via column chromatography to give benzyl 6-(hydroxymethyl)-3-azabicyclo[3.1.0]hexane-3-carboxylate (300 mg, 1.21 mmol, 18%) as a yellow oil. LCMS (ESI) m/z: 248.1 [M+H]$^+$.

Step 3: Preparation of Benzyl 6-formyl-3-azabicyclo[3.1.0]hexane-3-carboxylate

To a solution of benzyl 6-(hydroxymethyl)-3-azabicyclo[3.1.0]hexane-3-carboxylate (700 mg, 2.83 mmol) in dimethylsulfoxide (20 mL) at 25° C. was added iodoxybenzoic acid (1.58 g, 5.66 mmol). The mixture was stirred at 25° C. for 18 h. The mixture was quenched with water (50 mL) and ethyl acetate (50 mL), then stirred at 25° C. for 0.5 h. The solid was filtered and the organic layer was concentrated under reduced pressure. The crude residue was purified by column chromatography (silica gel, petroleum ether/ethyl acetate=1/1) to give benzyl 6-formyl-3-azabicyclo[3.1.0]hexane-3-carboxylate (500 mg, 2.04, 68%) as a yellow oil. LCMS (ESI) m/z: 268.1 [M+Na]$^+$.

Step 4: Preparation of benzyl 6-((3-fluorophenyl)(hydroxy)methyl)-3-azabicyclo[3.1.0]hexane-3-carboxylate

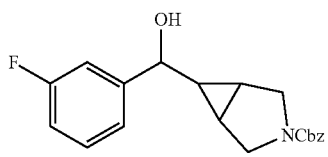 [SMILES: O=C(OCc1ccccc1)N1CC2C(C1)C2C(O)c1cccc(F)c1]

To a solution of (3-fluorophenyl)magnesium bromide (850 mg, 3.46 mmol) in dry tetrahydrofuran (20 mL) at −78° C. was added benzyl 6-formyl-3-azabicyclo[3.1.0]hexane-3-carboxylate (7 mL, 1 M, 7.0 mmol). The mixture was stirred at −78° C. for 3 h. The reaction mixture was quenched with aqueous ammonium chloride solution. The mixture was extracted with ethyl acetate (30 mL×2) and the organic layer was concentrated under reduced pressure. The crude residue was purified by column chromatography (silica gel, 100% ethyl acetate) to give benzyl 6-((3-fluorophenyl)(hydroxy)methyl)-3-azabicyclo[3.1.0]hexane-3-carboxylate (1.0 g, 2.74 mmol, 80%) as a yellow oil. LCMS (ESI) m/z: 364.1 [M+Na]⁺.

Step 5: Preparation of benzyl 6-(acetoxy(3-fluorophenyl)methyl)-3-azabicyclo[3.1.0]hexane-3-carboxylate

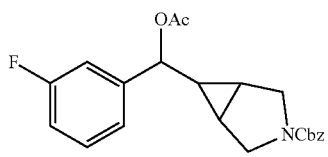 [SMILES: CC(=O)OC(c1cccc(F)c1)C1C2CN(C(=O)OCc3ccccc3)CC21]

To a mixture of benzyl 6-((3-fluorophenyl)(hydroxy)methyl)-3-azabicyclo[3.1.0]hexane-3-carboxylate (800 mg, 5.6 mmol) and triethylamine (2.5 mL, 16.8 mmol) in dichloromethane (20 mL) at 0° C. was added acetyl chloride (1 mL, 14 mmol) in dichloromethane (10 mL). The reaction mixture was stirred at 25° C. for 3 h. Water was added and the aqueous layer was extracted with dichloromethane (50 mL). The combined organic layers were concentrated in vacuo and the residue was purified by column chromatography (silica gel, petroleum ether/ethyl acetate=5/1) to give benzyl 6-(acetoxy(3-fluorophenyl)methyl)-3-azabicyclo[3.1.0]hexane-3-carboxylate (400 mg, 0.985 mmol, 18%) as yellow oil. LCMS (ESI) m/z: 406.1 [M+Na]⁺.

Step 6: Preparation of 6-(3-fluorobenzyl)-3-azabicyclo[3.1.0]hexane

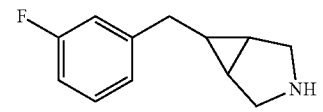

To a solution of benzyl 6-(acetoxy(3-fluorophenyl)methyl)-3-azabicyclo[3.1.0]hexane-3-carboxylate (400 mg, 1.04 mmol) in methanol (40 mL) was added palladium on carbon (300 mg, 10% wt). The reaction mixture was stirred at 25° C. for 3 h under hydrogen atmosphere. The mixture was filtered and the filtrate was concentrated under reduced pressure. The residue was diluted with dichloromethane (50 mL) and water (30 mL), and the aqueous layer was adjusted to pH 3 with 1 N hydrochloric acid. The aqueous layer was adjusted to pH-8 with sodium bicarbonate and extracted with ethyl acetate (30 mL×3). The combined organic layers were dried over sodium sulfate, filtered and concentrated to give crude 6-(3-fluorobenzyl)-3-azabicyclo[3.1.0]hexane (170 mg, 0.884 mmol, 85%) as a yellow oil. LCMS (ESI) m/z: 192.2 [M+H]⁺.

Step 7: Preparation of 6-(3-fluorobenzyl)-N-(1-methyl-6-oxo-1,6-dihydropyridazin-3-yl)-3-azabicyclo[3.1.0]hexane-3-carboxamide

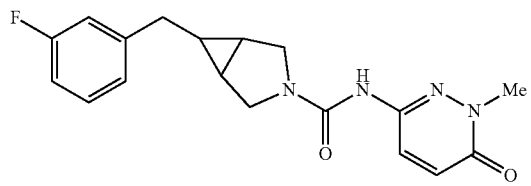 [SMILES: Cn1nc(NC(=O)N2CC3C(Cc4cccc(F)c4)C3C2)ccc1=O]

To a solution of 6-amino-2-methylpyridazin-3(2H)-one (85 mg, 0.68 mmol) in pyridine (215 mg, 2.72 mmol) and dichloromethane (5 mL) at −78° C. was added a solution of triphosgene (100 mg, 0.68 mmol) in dichloromethane (5 mL). The reaction was stirred for 0.5 h before 6-(3-fluorobenzyl)-3-azabicyclo[3.1.0]hexane (130 mg, 0.68 mmol) in pyridine (215 mg, 2.72 mmol) and dichloromethane (5 mL) was added. The mixture was stirred at 25° C. for 18 h. Water (30 mL) was added and the aqueous layer was extracted with dichloromethane (30 mL×2). The combined organic layers were concentrated under reduced pressure. The crude sample was dissolved in the minimum amount of N,N-dimethylformamide and purified by prep-HPLC (Boston C18, 10 μm, 21 mm×250 mm column, acetonitrile/10 mM ammonium acetate aqueous solution) to give 6-(3-fluorobenzyl)-N-(1-methyl-6-oxo-1,6-dihydropyridazin-3-yl)-3-azabicyclo[3.1.0]hexane-3-carboxamide (42.9 mg, 0.125 mmol, 18%) as a yellow solid. ¹H NMR (400 MHz, Dimethylsulfoxide-d₆) δ 8.88 (s, 1H), 7.67 (d, J=10 Hz, 1H), 7.34-7.30 (m, 1H), 7.12-7.10 (m, 2H), 7.02 (t, J=8.0 Hz, 1H), 6.87 (d, J=10 Hz, 1H), 3.63-3.60 (m, 4H), 3.54 (s, 3H), 2.59 (d, J=7.2 Hz, 2H), 1.55 (m, 2H), 0.79 (m, 1H); LCMS (ESI) m/z: 343.2 [M+H]⁺.

Example 90. Preparation of 3-(3-chlorobenzyl)-N-(1-methyl-6-oxo-1,6-dihydropyridazin-3-yl)azetidine-1-carboxamide (Compound 22)

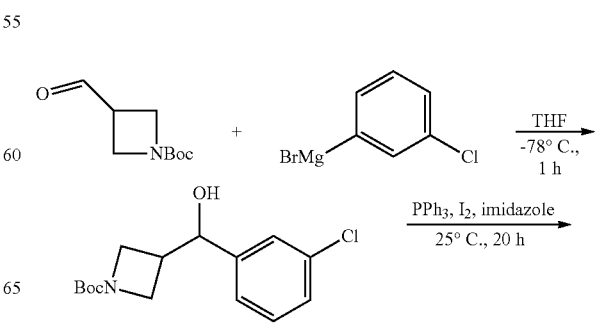

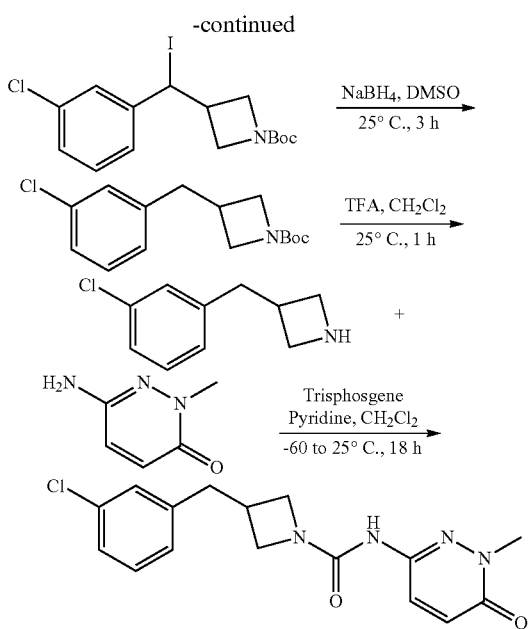

Step 1: Preparation of tert-butyl 3-((3-chlorophenyl)(hydroxy)methyl)azetidine-1-carboxylate

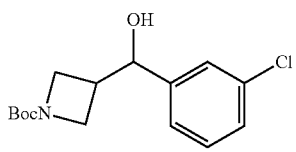 [SMILES: CC(C)(C)OC(=O)N1CC(C(O)c2cccc(Cl)c2)C1]

To a solution of tert-butyl 3-formylazetidine-1-carboxylate (800 mg, 4.3 mmol) in dry tetrahydrofuran (10 mL) at −78° C. was added (3-chlorophenyl)magnesium bromide (10.8 mL, 0.4 M in tetrahydrofuran). The reaction mixture was stirred at −78° C. for 1 h. The reaction mixture was quenched with aqueous saturated ammonium chloride (50 mL) and the aqueous layer was extracted with ethyl acetate (50 mL×2). The combined organic layers were concentrated under reduced pressure. The crude residue was purified by column chromatography (silica gel, petroleum ether/ethyl acetate=1/1) to give tert-butyl 3-((3-chlorophenyl)(hydroxy)methyl)azetidine-1-carboxylate (700 mg, 2.19 mmol, 51%) as a colorless oil. LCMS (ESI) m/z: 320.1 [M+Na]$^+$.

Step 2: Preparation of tert-butyl 3-((3-chlorophenyl)iodomethyl)azetidine-1-carboxylate

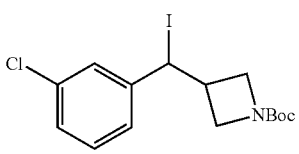 [SMILES: CC(C)(C)OC(=O)N1CC(C(I)c2cccc(Cl)c2)C1]

A suspension of triphenylphosphine (1.3 g, 5.0 mmol) and iodine (1.26 g, 5.0 mmol) in acetone (5 mL) and tetrahydrofuran (30 mL) was stirred at 25° C. for 15 min., then imidazole (340 mg, 5.0 mmol) was added followed by tert-butyl 3-((3-chlorophenyl)(hydroxy)methyl)azetidine-1-carboxylate (600 mg, 2.0 mmol) in tetrahydrofuran (15 mL). The reaction mixture was stirred at 25° C. for 20 h. The solvent was concentrated in vacuo. The crude residue was diluted with ethyl acetate (50 mL) and the organic layer was washed with aqueous sodium sulfite (30 mL) and brine (30 mL). The combined organic layers were dried over sodium sulfate, filtered and concentrated to give crude tert-butyl 3-((3-chlorophenyl)iodomethyl)azetidine-1-carboxylate (2.0 g, 2.0 mmol, crude) as a brown solid. LCMS (ESI) m/z: 429.9 [M+Na]$^+$.

Step 3: Preparation of tert-butyl 3-(3-chlorobenzyl)azetidine-1-carboxylate

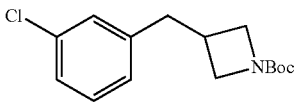 [SMILES: CC(C)(C)OC(=O)N1CC(Cc2cccc(Cl)c2)C1]

To a mixture of tert-butyl 3-((3-chlorophenyl)iodomethyl)azetidine-1-carboxylate (2.0 g, 2.0 mmol) in dimethyl sulfoxide (15 mL) was added sodium borohydride (151 mg, 4.0 mmol) at 0° C. and stirred at 25° C. for 3 h. Ethyl acetate (50 mL) and water (50 mL) was added and the aqueous layer was extracted with ethyl acetate. The combined organic layers were washed with brine, dried over sodium sulfate and concentrated under reduced pressure. The crude material was purified by column chromatography (silica gel, petroleum ether/ethyl acetate=5/1) to give tert-butyl 3-(3-chlorobenzyl)azetidine-1-carboxylate (100 mg, 15% over two steps) as a white solid. LCMS (ESI) m/z: 282.3 [M+H]$^+$.

Step 4: Preparation of 3-(3-chlorobenzyl)azetidine

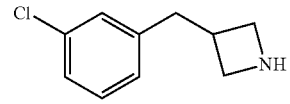 [SMILES: Clc1cccc(CC2CNC2)c1]

A mixture of tert-butyl 3-(3-chlorobenzyl)azetidine-1-carboxylate (100 mg, 0.35 mmol) and trifluoroacetic acid (1.0 mL) in dichloromethane (5 mL) at 25° C. was stirred for 1 h. The reaction mixture was concentrated in vacuo and the residue was diluted with dichloromethane (20 mL) and water (20 mL). The aqueous phase was adjusted to ~pH 9 with aqueous saturated sodium bicarbonate and extracted with dichloromethane. The combined organic layers were washed with brine, dried over sodium sulfate, filtered and concentrated to give crude 3-(3-chlorobenzyl)azetidine (65 mg) as a yellow oil. LCMS (ESI) m/z: 182.1 [M+H]$^+$.

Step 5: Preparation of 3-(3-chlorobenzyl)-N-(1-methyl-6-oxo-1,6-dihydropyridazin-3-yl)azetidine-1-carboxamide

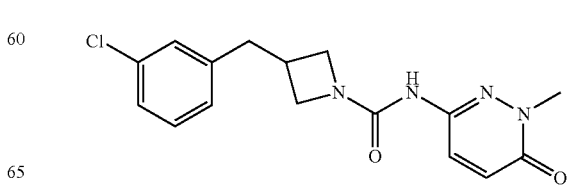

To a solution of triphosgene (53 mg, 0.18 mmol) in dry dichloromethane (3 mL) −78° C. was added 6-amino-2-methylpyridazin-3(2H)-one (45 mg, 0.36 mmol) and pyridine (114 mg, 1.44 mmol) in dry dichloromethane (4 mL). The mixture was stirred at −78° C. for 0.5 h before 3-(3-chlorobenzyl)azetidine (65 mg, 0.36 mmol) and pyridine (114 mg, 1.44 mmol) in dry dichloromethane (3 mL) was added. The reaction mixture was stirred at 25° C. for 18 h. The reaction solution was washed with water (10 mL) and the organic layer was concentrated under reduced pressure. The crude sample was dissolved in the minimum amount of N,N-dimethylformamide and then purified by prep-HPLC (Boston C18, 10 μm, 21 mm×250 mm column, acetonitrile/10 mM ammonium acetate aqueous solution) to give 3-(3-chlorobenzyl)-N-(1-methyl-6-oxo-1,6-dihydropyridazin-3-yl)azetidine-1-carboxamide (23.1 mg, 0.069 mmol, 19%) as a white solid. $^1$H NMR (400 MHz, Dimethylsulfoxide-$d_6$) δ 10.13 (s, 1H), 8.35 (d, J=2.0 Hz, 1H), 8.08 (d, J=8.8 Hz, 1H), 7.94 (d, J=10.0 Hz, 1H), 7.77 (dd, J1=2.0 Hz, J$_2$=8.4 Hz, 1H), 7.24-7.28 (m, 2H), 7.15-7.18 (m, 1H), 7.06 (d, J=10.0 Hz, 1H), 3.98 (s, 2H), 3.78 (s, 3H); LCMS (ESI) m/z: 333.2 [M+H]$^+$.

Example 91. Preparation of 3-(3,4-difluorophenoxy)-N-(1-methyl-6-oxo-1,6-dihydropyridazin-3-yl)azetidine-1-carboxamide (Compound 23)

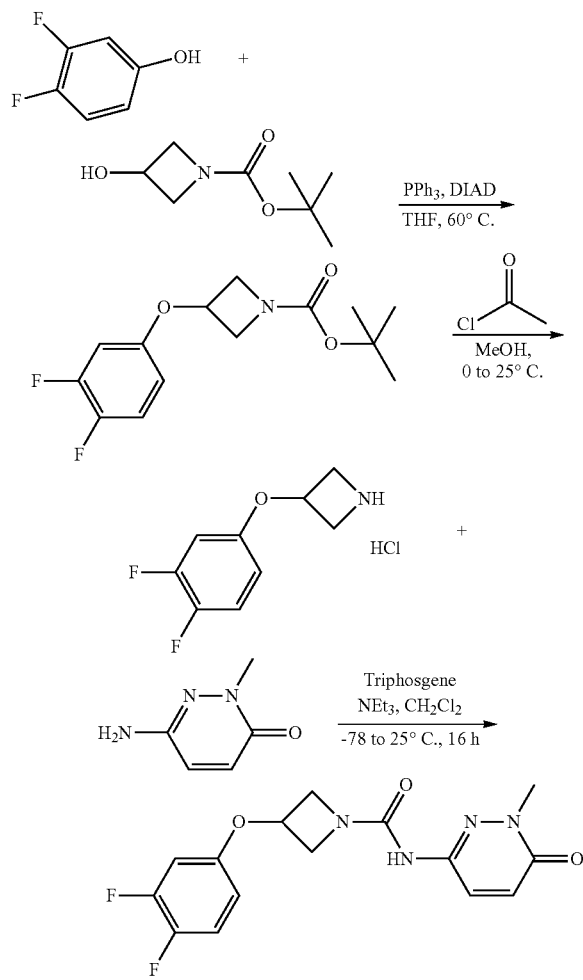

Step 1: Preparation of tert-butyl 3-(3,4-difluorophenoxy)azetidine-1-carboxylate

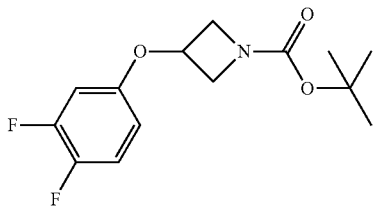 [SMILES: CC(C)(C)OC(=O)N1CC(Oc2ccc(F)c(F)c2)C1]

To an ice-cooled solution of 3,4-difluorophenol (411 mg, 3.16 mmol), tert-butyl 3-hydroxyazetidine-1-carboxylate (500 mg, 2.88 mmol) and triphenylphosphine (904 mg, 3.45 mmol) in tetrahydrofuran (7.19 mL) at 0° C. was added diisopropyl azodicarboxylate (621 μL, 3.16 mmol) dropwise.

The reaction was stirred at 60° C. for 48 h. The reaction mixture was then concentrated under reduced pressure and partitioned between water and diethyl ether (50 mL). The combined organic layers were extracted with diethyl ether (20 mL×2), dried over magnesium sulfate, filtered and concentrated under reduced pressure. The crude material was purified by column chromatography (ISCO, 24 g, 0-30% ethyl acetate/hexanes, gradient over 20 minutes) to afford tert-butyl 3-(3,4-difluorophenoxy)azetidine-1-carboxylate (694 mg, 2.43 mmol, 70%) as a white solid. $^1$H NMR (300 MHz, Chloroform-d) δ 7.08 (dt, J=10.0, 9.0 Hz, 1H), 6.59 (ddd, J=11.6, 6.5, 3.0 Hz, 1H), 6.44 (dtd, J=9.1, 3.2, 1.8 Hz, 1H), 4.82 (tt, J=6.4, 4.1 Hz, 1H), 4.30 (ddd, J=9.7, 6.4, 1.1 Hz, 2H), 3.99 (ddd, J=9.7, 4.1, 1.1 Hz, 2H), 1.45 (d, J=1.3 Hz, 9H); LCMS (ESI) m/z: 186.1 [M-Boc+H]$^+$.

Step 2: Preparation of 3-(3,4-difluorophenoxy)azetidine Hydrochloride

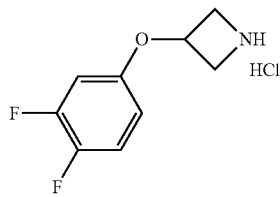 [SMILES: Fc1ccc(OC2CNC2)cc1F ; Cl]

To a solution of tert-butyl 3-(3,4-difluorophenoxy)azetidine-1-carboxylate (0.695 g, 2.43 mmol) in methanol (8.10 mL) at 0° C. was added acetyl chloride (862 μL, 12.1 mmol) dropwise. The reaction mixture was warmed to room temperature and stirred for 2 h. The volatiles were concentrated in vacuo to afford 3-(3,4-difluorophenoxy)azetidine hydrochloride (563 mg, 2.54 mmol) as a yellow solid. The material was used in the next step without additional purification. $^1$H NMR (300 MHz, Methanol-$d_4$) δ 10.04 (s, 2H), 7.20-6.98 (m, 1H), 6.63 (ddd, J=11.2, 6.4, 3.0 Hz, 1H), 6.55-6.34 (m, 1H), 5.07 (s, 1H), 4.46 (s, 2H), 4.23 (s, 2H); LCMS (ESI) m/z: 186.1 [M+H]$^+$.

Step 3: Preparation of 3-(3,4-difluorophenoxy)-N-(1-methyl-6-oxo-1,6-dihydropyridazin-3-yl)azetidine-1-carboxamide

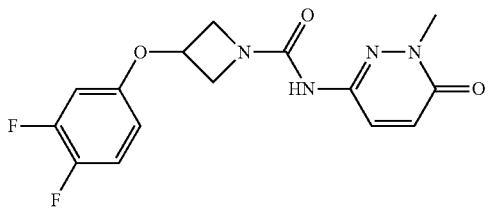 [SMILES: Cn1nc(NC(=O)N2CC(Oc3ccc(F)c(F)c3)C2)ccc1=O]

To a solution of triphosgene (63.5 mg, 0.2139 mmol) in methylene chloride (2.14 mL) at −78° C. was added a solution of 6-amino-2-methyl-2,3-dihydropyridazin-3-one (56.3 mg, 0.4500 mmol) and triethylamine (238 μL, 1.71 mmol) in methylene chloride (1.07 mL). The mixture was stirred for 2 h at −78° C., then a solution of 3-(3,4-difluorophenoxy)azetidine hydrochloride (0.095 g, 0.429 mmol) and triethylamine (238 μL, 1.71 mmol) in methylene chloride (1.07 mL) was added. The reaction mixture was warmed to room temperature and stirred for 18 h. The reaction was quenched with water (10 mL) and extracted with ethyl acetate (5 mL×2). The combined organic layers were washed with brine, dried over magnesium sulfate, filtered and concentrated under reduced pressure. The crude material was purified by column chromatography (ISCO, silica gel, 12 g, 0-4% methanol/dichloromethane, gradient over 20 minutes) to afford 3-(3,4-difluorophenoxy)-N-(1-methyl-6-oxo-1,6-dihydropyridazin-3-yl)azetidine-1-carboxamide (56.6 mg, 0.169 mmol, 39%) as a yellow solid. $^1$H NMR (300 MHz, Dimethylsulfoxide-$d_6$) δ 9.44 (s, 1H), 7.84 (d, J=9.9 Hz, 1H), 7.39 (dt, J=10.7, 9.3 Hz, 1H), 7.03 (ddd, J=12.4, 6.7, 3.0 Hz, 1H), 6.91 (d, J=9.9 Hz, 1H), 6.70 (dtd, J=9.1, 3.3, 1.7 Hz, 1H), 5.09-4.95 (m, 1H), 4.49-4.34 (m, 2H), 3.89 (dd, J=10.0, 3.7 Hz, 2H), 3.55 (s, 3H); LCMS (ESI) m/z: 337.2 [M+H]$^+$.

Example 92. Preparation of 3-(3,5-difluorophenoxy)-N-(1-methyl-6-oxo-1,6-dihydropyridazin-3-yl)azetidine-1-carboxamide (Compound 24)

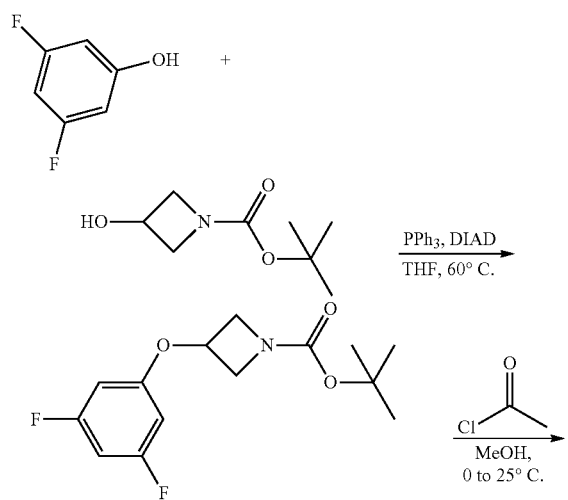

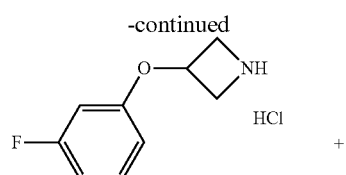

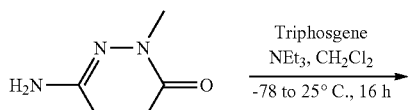

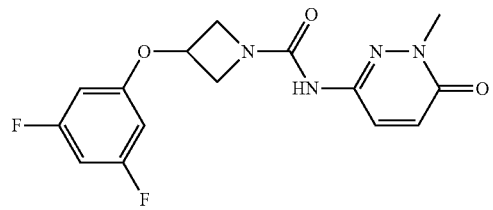

Step 1: Preparation of tert-butyl 3-(3,5-difluorophenoxy)azetidine-1-carboxylate

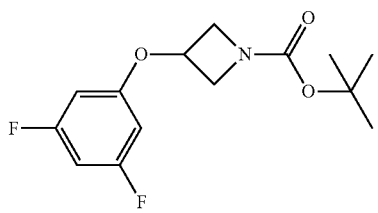 [SMILES: CC(C)(C)OC(=O)N1CC(Oc2cc(F)cc(F)c2)C1]

To an ice-cooled solution of 3,5-difluorophenol (411 mg, 3.16 mmol), tert-butyl 3-hydroxyazetidine-1-carboxylate (500 mg, 2.88 mmol) and triphenylphosphine (904 mg, 3.45 mmol) in tetrahydrofuran (7.19 mL) at 0° C. was added diisopropyl azodicarboxylate (621 μL, 3.16 mmol) dropwise.

The reaction mixture was stirred at 60° C. for 48 h. The reaction mixture was then concentrated under reduced pressure and partitioned between water and diethyl ether (50 mL). The combined organic layers were extracted with diethyl ether (20 mL×2), dried over magnesium sulfate, filtered and concentrated under reduced pressure. The crude material was purified via column chromatography (ISCO, 24 g, 0-30% ethyl acetate/hexanes, gradient over 20 minutes) to afford tert-butyl 3-(3,5-difluorophenoxy)azetidine-1-carboxylate (770 mg, 2.69 mmol, 94%) as a clear oil. $^1$H NMR (300 MHz, Chloroform-d) δ 6.47 (tt, J=9.0, 2.2 Hz, 1H), 6.35-6.16 (m, 2H), 4.83 (tt, J=6.4, 4.1 Hz, 1H), 4.31 (ddd, J=9.7, 6.4, 1.1 Hz, 2H), 4.00 (ddd, J=9.7, 4.1, 1.1 Hz, 2H), 1.46 (s, 9H); LCMS (ESI) m/z: 286.4 [M+H]$^+$.

Step 2: Preparation of 3-(3,5-difluorophenoxy)azetidine Hydrochloride

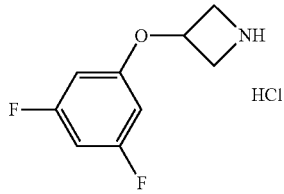 [SMILES: Fc1cc(F)cc(OC2CNC2)c1 ; Cl]

To a solution of tert-butyl 3-(3,5-difluorophenoxy)azetidine-1-carboxylate (0.695 g, 2.43 mmol) in methanol (8.1 mL) at 0° C. was added acetyl chloride (860 µL, 12.1 mmol) dropwise. The reaction mixture was warmed to room temperature and stirred for 2 h. The volatiles were concentrated in vacuo to afford 3-(3,4-difluorophenoxy)azetidine hydrochloride (563 mg, 2.54 mmol) as a yellow solid. The material was used in the next step without additional purification. $^1$H NMR (300 MHz, Methanol-$d_4$) δ 10.04 (s, 2H), 7.20-6.98 (m, 1H), 6.63 (ddd, J=11.2, 6.4, 3.0 Hz, 1H), 6.55-6.34 (m, 1H), 5.07 (s, 1H), 4.46 (s, 2H), 4.23 (s, 2H); LCMS (ESI) m/z: 186.1 [M+H]$^+$.

Step 3: Preparation of 3-(3,5-difluorophenoxy)-N-(1-methyl-6-oxo-1,6-dihydropyridazin-3-yl)azetidine-1-carboxamide

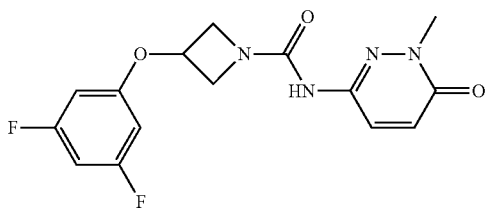 [SMILES: Cn1nc(NC(=O)N2CC(Oc3cc(F)cc(F)c3)C2)ccc1=O]

To a solution of triphosgene (66.9 mg, 0.226 mmol) in methylene chloride (2.25 mL) at −78° C. was added a solution of 6-amino-2-methyl-2,3-dihydropyridazin-3-one (59.2 mg, 0.474 mmol) and triethylamine (250 µL, 1.80 mmol) in methylene chloride (1.12 mL). The mixture was stirred for 2 h at −78° C., then a solution of 3-(3,5-difluorophenoxy)azetidine hydrochloride (0.100 g, 0.451 mmol) and triethylamine (250 µL, 1.80 mmol) in methylene chloride (1.12 mL) was added. The reaction mixture was warmed to room temperature and stirred for 18 h. The reaction was quenched with water (10 mL) and extracted with ethyl acetate (5 mL×2). The combined organic layers were washed with brine, dried over magnesium sulfate, filtered and concentrated under reduced pressure. The crude material was purified by column chromatography (ISCO, silica gel, 12 g, 0-4% methanol/dichloromethane, gradient over 20 minutes) to afford 3-(3,5-difluorophenoxy)-N-(1-methyl-6-oxo-1,6-dihydropyridazin-3-yl)azetidine-1-carboxamide (30.4 mg, 0.091 mmol, 23%) as a yellow solid. $^1$H NMR (300 MHz, Dimethylsulfoxide-$d_6$) δ 9.45 (s, 1H), 7.84 (d, J=9.9 Hz, 1H), 6.91 (d, J=9.9 Hz, 1H), 6.84 (dt, J=9.5, 2.3 Hz, 1H), 6.68 (dd, J=9.2, 2.2 Hz, 2H), 5.05 (td, J=6.4, 3.4 Hz, 1H), 4.43 (dd, J=9.6, 6.4 Hz, 2H), 3.90 (dd, J=9.9, 3.8 Hz, 2H), 3.55 (s, 3H); LCMS (ESI) m/z: 337.2 [M+H]$^+$.

Example 93. Preparation of 4-(3,5-difluorophenylamino)-N-(1-methyl-6-oxo-1,6-dihydropyridin-3-yl)piperidine-1-carboxamide (Compound 11)

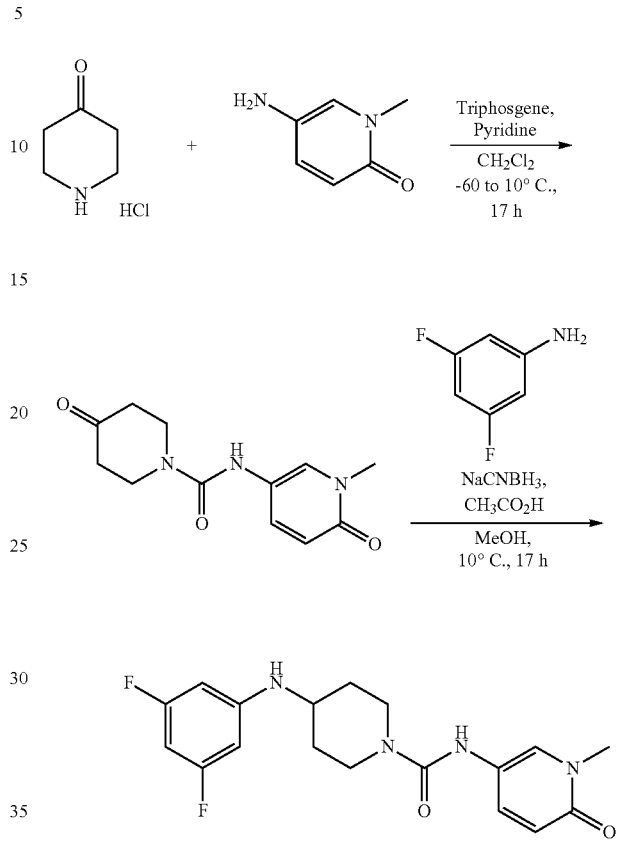

Step 1: Preparation of N-(1-methyl-6-oxo-1,6-dihydropyridin-3-yl)-4-oxopiperidine-1-carboxamide

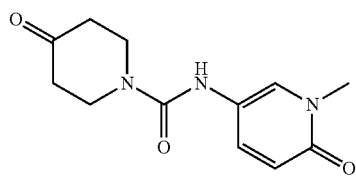 [SMILES: Cn1cc(NC(=O)N2CCC(=O)CC2)ccc1=O]

To a solution of triphosgene (549 mg, 1.85 mmol) in dichloromethane (10 mL) was added a solution of 5-amino-1-methylpyridin-2(1H)-one (0.595 mg, 3.7 mmol) and pyridine (1.17 g, 14.8 mmol) in dichloromethane (10 mL) at −60° C. under argon. The mixture was stirred at −60° C. for 30 min. Then a solution of piperidin-4-one hydrochloride (500 mg, 3.7 mmol) and pyridine (1.17 g, 14.8 mmol) in dichloromethane (20 mL) was added at −60° C. The resulting mixture was stirred at 10° C. for 17 h. After completion, water (20 mL) was added. The mixture was extracted with dichloromethane (10 mL×3). The organic layer was dried over sodium sulfate, filtered and concentrated. The crude residue was purified by TLC (dichloromethane/methanol=10/1) to give N-(1-methyl-6-oxo-1,6-dihydropyridin-3-yl)-4-oxopiperidine-1-carboxamide (280 mg, 1.12 mmol, 30%) as a yellow solid. LCMS (ESI) m/z: 250.1 [M+H]$^+$.

Step 2: Preparation of 4-(3,5-difluorophenylamino)-N-(1-methyl-6-oxo-1,6-dihydropyridin-3-yl)piperidine-1-carboxamide

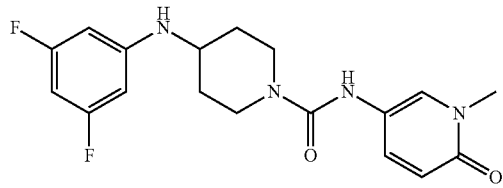 [SMILES: Cn1cc(NC(=O)N2CCC(Nc3cc(F)cc(F)c3)CC2)ccc1=O]

To a solution of N-(1-methyl-6-oxo-1,6-dihydropyridin-3-yl)-4-oxopiperidine-1-carboxamide (120 mg, 0.48 mmol) in methyl alcohol (15 mL) were added 3,5-difluoroaniline (124 mg, 0.96 mmol) and acetic acid (14.4 mg, 0.24 mmol). The mixture was stirred at 10° C. for 1 h. Then sodium cyanoborohydride (90.4 mg, 1.44 mmol) was added. The resulting mixture was stirred at 10° C. for 17 h. The reaction mixture was concentrated under reduced pressure. The crude residue was dissolved in the minimal amount of N,N-dimethylformamide and purified by prep-HPLC (Boston C18, 21×250 mm 10 μm column: acetonitrile/0.01% aqueous FA) to give 4-(3,5-difluorophenylamino)-N-(1-methyl-6-oxo-1,6-dihydropyridin-3-yl)piperidine-1-carboxamide (10.4 mg, 0.02 mmol, 6.0%) as a white solid. $^1$H NMR (400 MHz, Dimethylsulfoxide-$d_6$) δ 8.23 (s, 1H), 7.75 (d, J=2.8 Hz, 1H), 7.40 (dd, J=9.6, 2.9 Hz, 1H), 6.37-6.07 (m, 5H), 3.98 (d, J=13.5 Hz, 2H), 3.45 (d, J=8.1 Hz, 1H), 3.39 (s, 3H), 2.96 (t, J=11.3 Hz, 2H), 1.89 (d, J=10.0 Hz, 2H), 1.25 (dd, J=20.6, 10.1 Hz, 2H); LCMS (ESI) m/z: 363.2 [M+H]$^+$.

Example 94. Preparation of 4-((3-chloro-5-fluorophenyl)amino)-N-(1-methyl-6-oxo-1,6-dihydropyridazin-3-yl)piperidine-1-carboxamide (Compound 93)

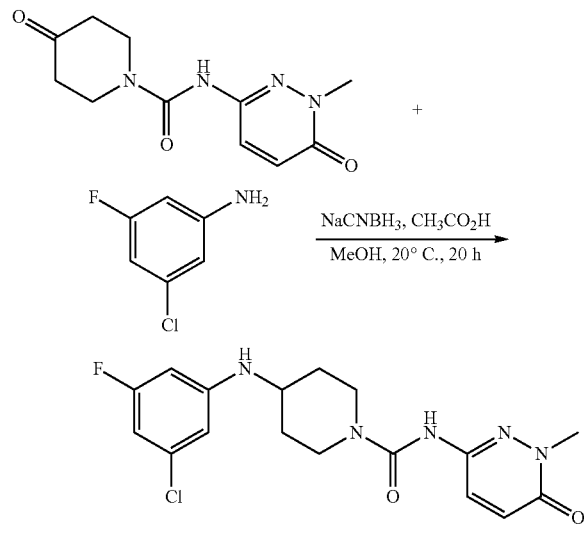

Step 1: Preparation of 4-((3-chloro-5-fluorophenyl)amino)-N-(1-methyl-6-oxo-1,6-dihydropyridazin-3-yl)piperidine-1-carboxamide

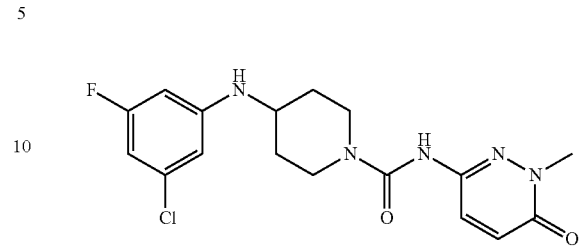

To a solution of N-(1-methyl-6-oxo-1,6-dihydropyridazin-3-yl)-4-oxopiperidine-1-carboxamide (0.15 g, 0.6 mmol) and 3-chloro-5-fluoroaniline (0.174 g, 1.2 mmol) in methanol (15 mL) at 20° C. was added acetic acid (1 drop) under argon. The mixture was stirred at 20° C. for 1 h, then sodium cyanoborohydride (0.113 g, 1.8 mmol) was added, the mixture was stirred at 20° C. for 20 h. The reaction mixture was concentrated in vacuo. The crude residue was dissolved in the minimal amount of N,N-dimethylformamide and purified by prep-HPLC (Boston 018, 21×250 mm, 10 μm column: acetonitrile/10 mM ammonium acetate aqueous solution) to give 4-((3-chloro-5-fluorophenyl)amino)-N-(1-methyl-6-oxo-1,6-dihydropyridazin-3-yl)piperidine-1-carboxamide (0.026 g, 0.068 mmol, 11%) as a white solid. $^1$H NMR (400 MHz, Dimethylsulfoxide-$d_6$) δ 9.31 (s, 1H), 7.63 (d, J=9.9 Hz, 1H), 6.87 (d, J=9.9 Hz, 1H), 6.47 (d, J=1.7 Hz, 1H), 6.43-6.34 (m, 2H), 6.24 (d, J=8.1 Hz, 1H), 4.01 (d, J=13.5 Hz, 2H), 3.56 (s, 3H), 3.51-3.44 (m, 1H), 2.99 (t, J=11.4 Hz, 2H), 1.88 (d, J=10.1 Hz, 2H), 1.26 (dd, J=20.7, 9.9 Hz, 2H); LCMS (ESI) m/z: 380.1 [M+H]$^+$.

Example 95. Preparation of N-(1-methyl-6-oxo-1,6-dihydropyridazin-3-yl)-4-(phenylamino)piperidine-1-carboxamide (Compound 91)

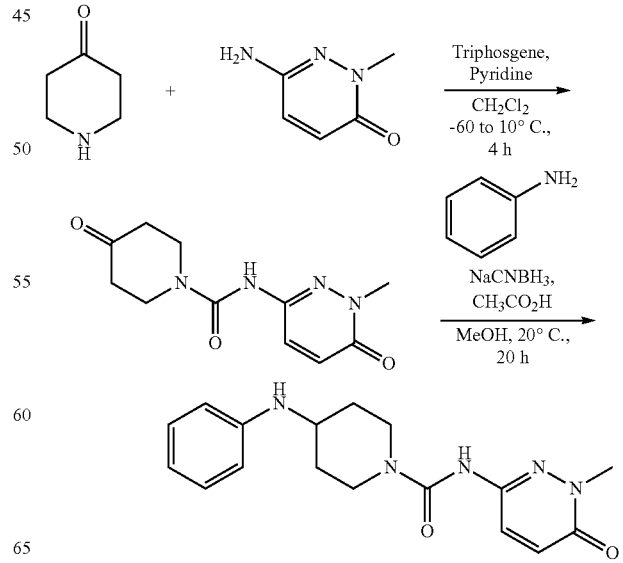

Step 1: Preparation of N-(1-methyl-6-oxo-1,6-dihydropyridazin-3-yl)-4-oxopiperidine-1-carboxamide

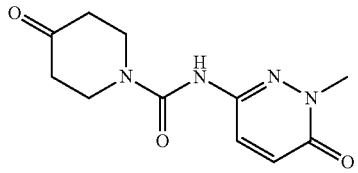 [SMILES: Cn1nc(NC(=O)N2CCC(=O)CC2)ccc1=O]

To a suspension of 6-amino-2-methylpyridazin-3(2H)-one (2.50 g, 20.0 mmol) and pyridine (6.4 mL, 80.0 mmol) in dry dichloromethane (100 mL) at −60° C. was added triphosgene (2.96 g, 10.0 mmol) under argon. The mixture was stirred at −60° C. for 1 h and slowly warmed to −10° C. over 1 h to obtain a clear yellow solution. The mixture was cooled to −60° C. and a solution of piperidin-4-one hydrochloride (2.70 g, 20.0 mmol) and pyridine (6.4 mL, 80.0 mmol) in dichloromethane (10 mL) was added. The resulting mixture was stirred at 25° C. for 2 h. The reaction mixture was quenched with methanol (50 mL) and concentrated in vacuo. The crude residue was purified by column chromatography (silica gel, dichloromethane/methanol=10/1) to obtain N-(1-methyl-6-oxo-1,6-dihydropyridazin-3-yl)-4-oxopiperidine-1-carboxamide (3.15 g, 12.6 mmol, 63%) as a yellow solid. LCMS (ESI) m/z: 251.1 [M+H]$^+$.

Step 2: Preparation of N-(1-methyl-6-oxo-1,6-dihydropyridazin-3-yl)-4-(phenylamino)piperidine-1-carboxamide

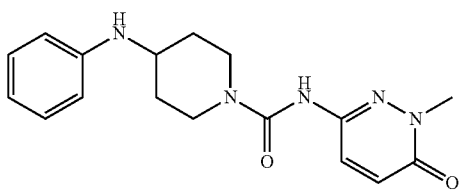 [SMILES: Cn1nc(NC(=O)N2CCC(Nc3ccccc3)CC2)ccc1=O]

To a solution of N-(1-methyl-6-oxo-1,6-dihydropyridazin-3-yl)-4-oxopiperidine-1-carboxamide (200 mg, 0.8 mmol) and aniline (206 mg, 1.6 mmol) in methanol (10 mL) at 20° C. was added acetic acid (1 drop) under argon. The mixture was stirred at 20° C. for 1 h, then sodium cyanoborohydride (150 mg, 2.4 mmol) was added. The reaction mixture was stirred at 20° C. for 20 h and concentrated in vacuo. The crude residue was dissolved in the minimum amount of N,N-dimethylformamide and purified by prep-HPLC (Boston C18, 21×250 mm, 10 μm column: acetonitrile/10 mM ammonium acetate aqueous solution) to give N-(1-methyl-6-oxo-1,6-dihydropyridazin-3-yl)-4-(phenylamino)piperidine-1-carboxamide (75.2 mg, 0.23 mmol, 29%) as a white solid. $^1$H NMR (400 MHz, Dimethylsulfoxide-d$_6$) δ 9.29 (s, 1H), 7.63 (d, J=9.9 Hz, 1H), 7.06 (t, J=7.8 Hz, 2H), 6.88 (d, J=9.9 Hz, 1H), 6.59 (d, J=7.9 Hz, 2H), 6.50 (t, J=7.2 Hz, 1H), 5.47 (d, J=7.9 Hz, 1H), 4.01 (d, J=13.4 Hz, 2H), 3.56 (s, 3H), 3.43 (s, 1H), 2.99 (t, J=11.5 Hz, 2H), 1.90 (d, J=10.6 Hz, 2H), 1.28 (dd, J=20.8, 9.9 Hz, 2H); LCMS (ESI) m/z: 328.2 [M+H]$^+$.

Example 96. Preparation of N-(1-methyl-6-oxo-1,6-dihydropyridazin-3-yl)-4-(2-(trifluoromethyl)phenylamino)piperidine-1-carboxamide (Compound 92)

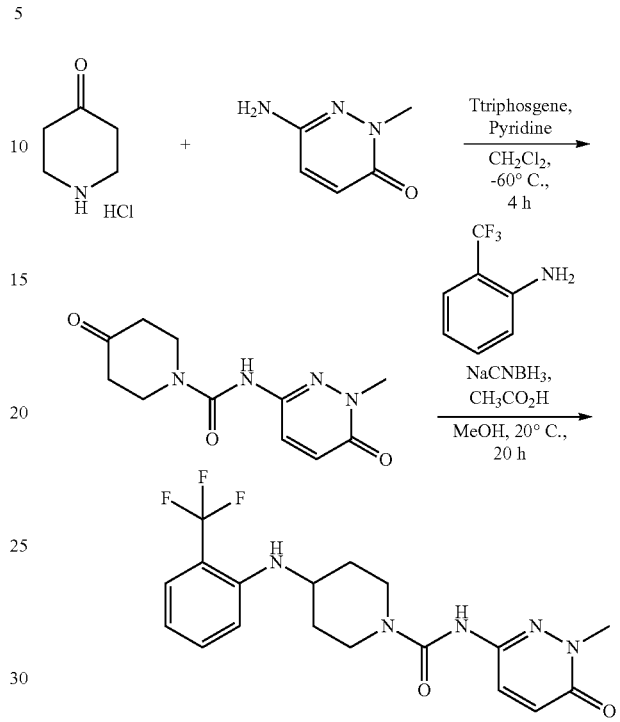

Step 1: Preparation of N-(1-methyl-6-oxo-1,6-dihydropyridazin-3-yl)-4-oxopiperidine-1-carboxamide

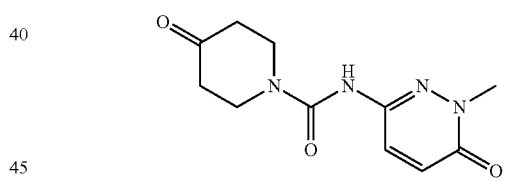

To a suspension of 6-amino-2-methylpyridazin-3(2H)-one (2.50 g, 20.0 mmol) and pyridine (6.4 mL, 80.0 mmol) in dry dichloromethane (100 mL) at −60° C. was added triphosgene (2.96 g, 10.0 mmol) under argon. The mixture was stirred at −60° C. for 1 h then slowly warmed to −10° C. over 1 h to obtain a clear yellow solution. The mixture was cooled to −60° C. and a solution of piperidin-4-one hydrochloride (2.70 g, 20.0 mmol) and pyridine (6.4 mL, 80.0 mmol) in dichloromethane (10 mL) was added. The resulting mixture was stirred at 25° C. for 2 h. After completion, the mixture was quenched with methanol (50 mL) and concentrated in vacuo. The crude residue was purified by column chromatography (silica gel, dichloromethane/methanol=10/1) to obtain N-(1-methyl-6-oxo-1,6-dihydropyridazin-3-yl)-4-oxopiperidine-1-carboxamide (3.15 g, 12.6 mmol, 63%) as a pale yellow solid. LCMS (ESI) m/z: 251.1 [M+H]$^+$.

Step 2: Preparation of N-(1-methyl-6-oxo-1,6-dihydropyridazin-3-yl)-4-(2-(trifluoromethyl)phenylamino)piperidine-1-carboxamide

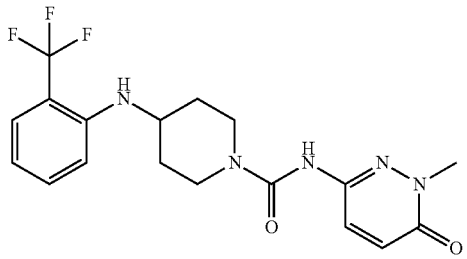 [SMILES: Cn1nc(NC(=O)N2CCC(Nc3ccccc3C(F)(F)F)CC2)ccc1=O]

To a solution of N-(1-methyl-6-oxo-1,6-dihydropyridazin-3-yl)-4-oxopiperidine-1-carboxamide (0.2 g, 0.8 mmol) and 2-(trifluoromethyl)aniline (0.258 g, 1.6 mmol) in methanol (10 mL) at 20° C. was added acetic acid (1 drop) under argon. The mixture was stirred at 20° C. for 1 h, then sodium cyanoborohydride (0.15 g, 2.4 mmol) was added. The reaction mixture was stirred at 20° C. for 20 h and concentrated in vacuo. The crude residue was dissolved in the minimum amount of N,N-dimethylformamide and purified by prep-HPLC (Boston C18, 21×250 mm, 10 μm column: acetonitrile/10 mM ammonium acetate aqueous solution) to give N-(1-methyl-6-oxo-1,6-dihydropyridazin-3-yl)-4-(2-(trifluoromethyl)phenylamino)piperidine-1-carboxamide (0.007 g, 0.019 mmol, 2%) as a white solid. $^1$H NMR (400 MHz, Dimethylsulfoxide-$d_6$) δ 9.31 (s, 1H), 7.64 (d, J=9.8 Hz, 1H), 7.42 (dd, J=7.5, 5.3 Hz, 2H), 6.99 (d, J=8.8 Hz, 1H), 6.89 (d, J=9.8 Hz, 1H), 6.71 (t, J=7.5 Hz, 1H), 4.70 (d, J=7.8 Hz, 1H), 4.06 (d, J=13.6 Hz, 2H), 3.68 (s, 1H), 3.56 (s, 3H), 2.97 (t, J=11.8 Hz, 2H), 1.90 (d, J=10.2 Hz, 2H), 1.46 (dd, J=20.7, 11.0 Hz, 2H); LCMS (ESI) m/z: 396.1 [M+H]$^+$.

Example 97. Preparation of 4-(3,5-difluorobenzylamino)-N-(1-methyl-6-oxo-1,6-dihydropyridazin-3-yl)piperidine-1-carboxamide (Compound 104)

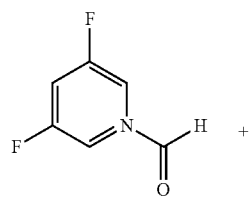

+

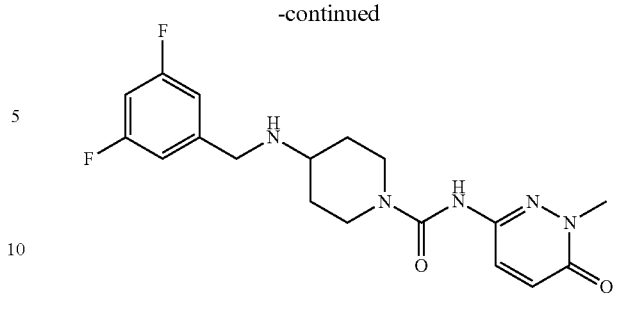

Step 1: Preparation of 4-(3,5-difluorobenzylamino)-N-(1-methyl-6-oxo-1,6-dihydropyridazin-3-yl)piperidine-1-carboxamide

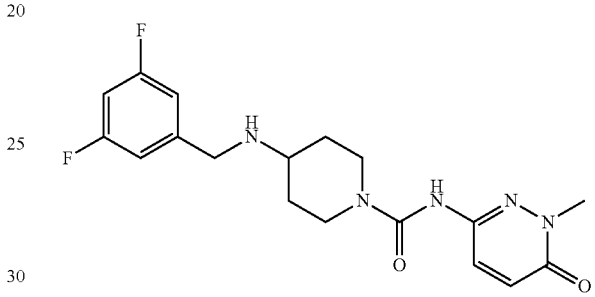

A solution of 4-amino-N-(1-methyl-6-oxo-1,6-dihydropyridazin-3-yl)piperidine-1-carboxamide (251 mg, 1.0 mmol) and 3,5-difluorobenzaldehyde (142 mg, 1.0 mmol) in dichloroethane (9 mL) and acetic acid (0.1 mL) was stirred at 25° C. for 1 h before sodium borohydride acetate (318 mg, 1.5 mmol) was added. The reaction mixture was stirred at 25° C. for 16 h and filtered. The filtrate was concentrated in vacuo. The crude material was dissolved in the minimum amount of N,N-dimethylformamide and purified by prep-HPLC (SunFire C18, 4.6×50 mm, 3.5 μm column: Xbridge C18, 3.5 μm 4.6×50 mm column: used a gradient of 5-95% over 1.5 min at 2 mL/min [acetonitrile/0.01% aqueous formic acid]) to afford 4-(3,5-difluorobenzylamino)-N-(1-methyl-6-oxo-1,6-dihydropyridazin-3-yl)piperidine-1-carboxamide (29.4 mg, 0.08 mmol, 8%) as a white solid. $^1$H NMR (400 MHz, Dimethylsulfoxide-$d_6$) δ 9.22 (s, 1H), 8.24 (s, 1H), 7.61-7.59 (d, J=9.9 Hz, 1H), 7.26-7.00 (m, 3H), 6.87 (d, J=9.9 Hz, 1H), 3.94-3.90 (m, 2H), 3.77 (s, 2H), 3.55 (s, 3H), 2.87 (t, J=11.2 Hz, 2H), 2.57-2.53 (m, 1H), 1.80 (d, J=10.2 Hz, 2H), 1.20-1.17 (m, 2H); LCMS (ESI) m/z: 378.1 [M+H]$^+$.

Example 98. Preparation of 4-((3,5-difluorophenyl)amino)-N-(1-methyl-6-oxo-1,6-dihydropyridazin-3-yl)piperidine-1-carboxamide (Compound 94)

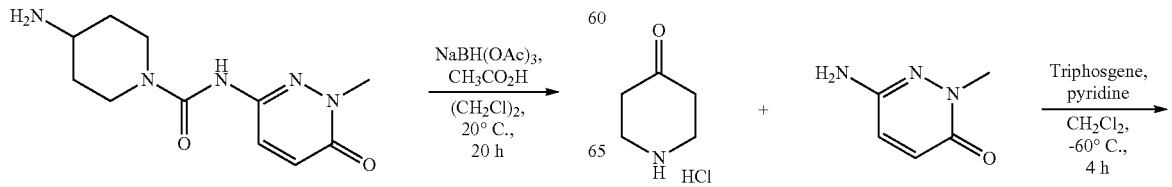

Step 1: Preparation of N-(1-methyl-6-oxo-1,6-dihydropyridazin-3-yl)-4-oxopiperidine-1-carboxamide

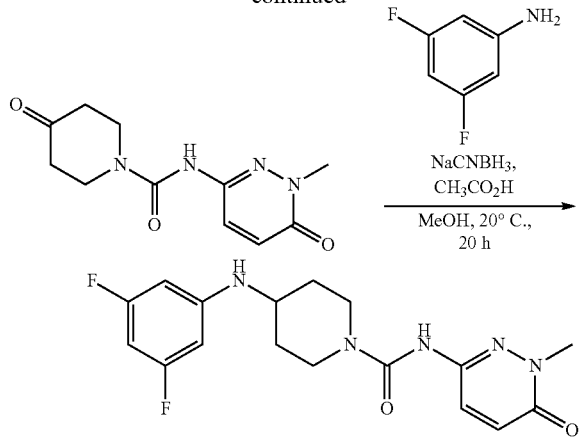

To a suspension of 6-amino-2-methylpyridazin-3(2H)-one (2.50 g, 20.0 mmol) and pyridine (6.4 mL, 80.0 mmol) in dry dichloromethane (100 mL) at −60° C. was added triphosgene (2.96 g, 10.0 mmol) under argon. The mixture was stirred at −60° C. for 1 h, and slowly warmed to −10° C. over 1 h. The reaction mixture was cooled to −60° C. and a solution of piperidin-4-one hydrochloride (2.70 g, 20.0 mmol) and pyridine (6.4 mL, 80.0 mmol) in dichloromethane (10 mL) was added. The resulting mixture was stirred at 25° C. for 2 h. The reaction mixture was quenched with methanol (50 mL) and concentrated in vacuo. The crude residue was purified by column chromatography (silica gel, dichloromethane/methanol=10/1) to give N-(1-methyl-6-oxo-1,6-dihydropyridazin-3-yl)-4-oxopiperidine-1-carboxamide (3.15 g, 12.6 mmol, 63%) as a yellow solid. LCMS (ESI) m/z: 251.1 [M+H]$^+$.

Step 2: Preparation of 4-((3,5-difluorophenyl)amino)-N-(1-methyl-6-oxo-1,6-dihydropyridazin-3-yl)piperidine-1-carboxamide

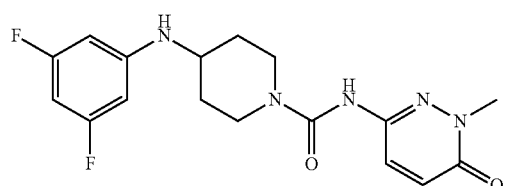

To a solution of N-(1-methyl-6-oxo-1,6-dihydropyridazin-3-yl)-4-oxopiperidine-1-carboxamide (100 mg, 0.4 mmol) and 3,5-difluoroaniline (103 mg, 0.8 mmol) in methanol (10 mL) at 20° C. was added acetic acid (1 drop) under argon. The mixture was stirred at 20° C. for 1 h, then sodium cyanoborohydride (75 mg, 1.2 mmol) was added, the mixture was stirred at 20° C. for 20 h. The reaction mixture was concentrated in vacuo. The crude residue was dissolved in the minimum amount of N,N-dimethylformamide and purified by prep-HPLC (Boston C18, 21×250 mm, 10 μm column; 10 mM ammonium acetate aqueous solution) to give 4-((3,5-difluorophenyl)amino)-N-(1-methyl-6-oxo-1,6-dihydropyridazin-3-yl)piperidine-1-carboxamide (20 mg, 0.06 mmol, 14%) as a white solid. $^1$H NMR (400 MHz, Dimethylsulfoxide-d$_6$) δ 7.63 (d, J=9.9 Hz, 1H), 6.88 (d, J=9.9 Hz, 1H), 6.30-6.15 (m, 4H), 4.01 (d, J=13.4 Hz, 2H), 3.56 (s, 3H), 3.46 (d, J=8.1 Hz, 1H), 2.99 (t, J=11.5 Hz, 2H), 1.88 (d, J=10.1 Hz, 2H), 1.26 (dd, J=20.5, 10.2 Hz, 2H); LCMS (ESI) m/z: 364.1 [M+H]$^+$.

Example 99. Preparation of N-(1-methyl-6-oxo-1,6-dihydropyridazin-3-yl)-4-(2 (trifluoromethyl)benzylamino)piperidine-1-carboxamide (Compound 105)

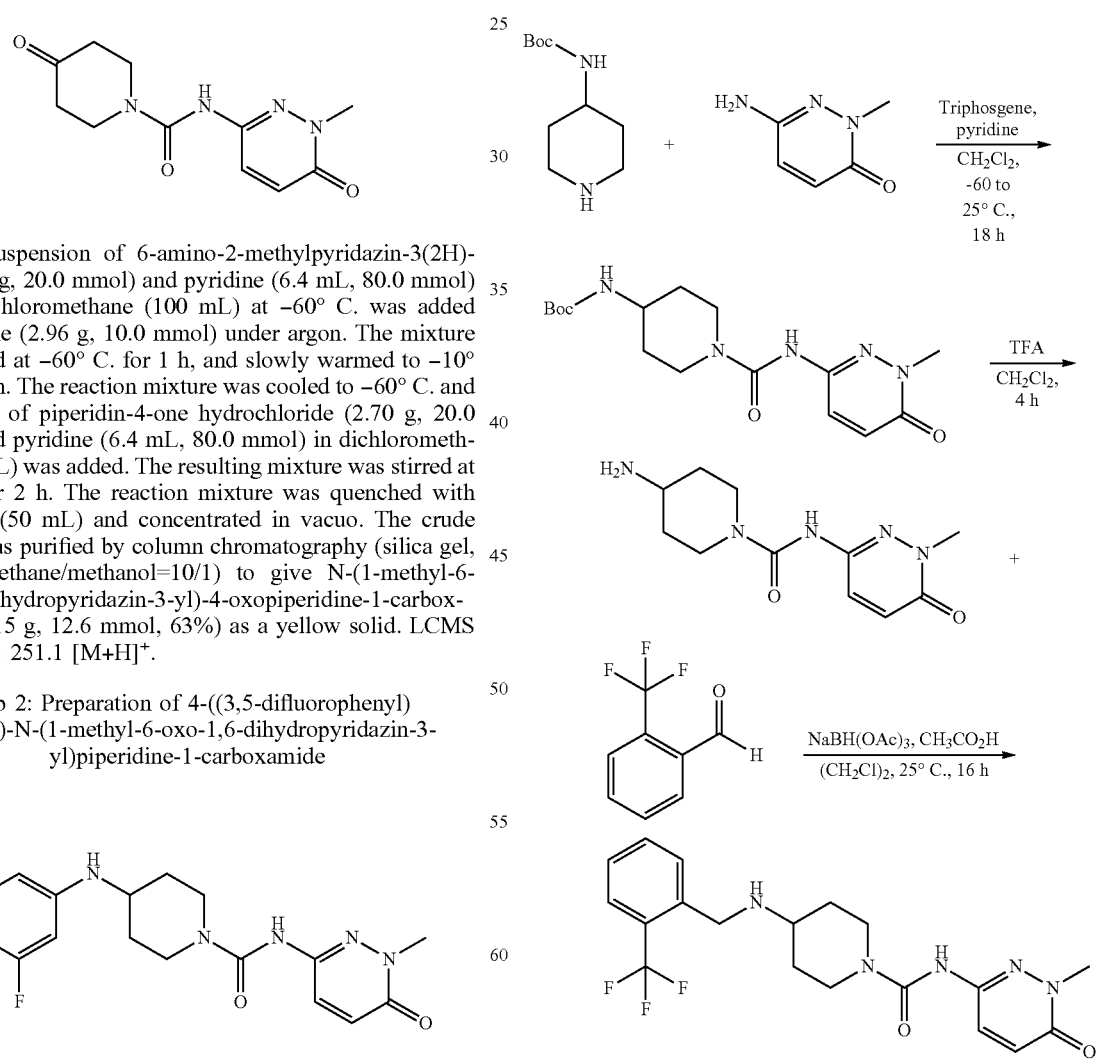

Step 1: Preparation of tert-butyl 1-(1-methyl-6-oxo-1,6-dihydropyridazin-3-ylcarbamoyl)piperidin-4-ylcarbamate

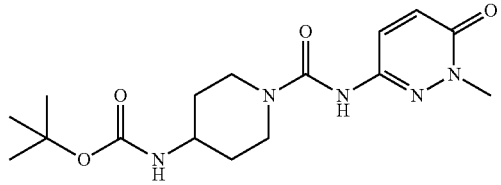 [SMILES: Cn1nc(NC(=O)N2CCC(NC(=O)OC(C)(C)C)CC2)ccc1=O]

To a solution of triphosgene (3.0 g, 10.0 mmol) in dichloromethane (150 mL) was added a solution of 6-amino-2-methylpyridazin-3(2H)-one (2.5 g, 20.0 mmol) and pyridine (7.6 g, 96 mmol) in dichloromethane (25 mL) at −60° C. under argon. The mixture was stirred at −60° C. for 30 min and then at 0° C. for 30 min, before a solution of tert-butyl piperidin-4-ylcarbamate (4.0 g, 20.0 mmol) and pyridine (7.6 g, 96 mmol) in dichloromethane (25 mL) was added at −60° C. The resulting mixture was stirred at 25° C. for 18 h. The reaction mixture was quenched with water (30 mL) and extracted with dichloromethane (500 mL×2). The organic layer was dried over sodium sulfate, filtered and concentrated. The crude residue was purified by column chromatography (silica gel, dichloromethane/methanol from 50/1 to 20/1) to give tert-butyl 1-(1-methyl-6-oxo-1,6-dihydropyridazin-3-ylcarbamoyl)piperidin-4-ylcarbamate (4.6 g, 13.1 mmol, 66%) as a brown solid. LCMS (ESI) m/z: 352.2 [M+H]$^+$.

Step 2: Preparation of 4-amino-N-(1-methyl-6-oxo-1,6-dihydropyridazin-3-yl)piperidine-1-carboxamide

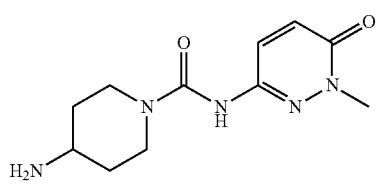 [SMILES: Cn1nc(NC(=O)N2CCC(N)CC2)ccc1=O]

To a solution of tert-butyl 1-(1-methyl-6-oxo-1,6-dihydropyridazin-3-ylcarbamoyl)piperidin-4-ylcarbamate (1.2 g, 3.4 mmol) in dichloromethane (10 mL) was added trifluoroacetic acid (3.0 mL). The mixture was stirred at 25° C. for 4 h under nitrogen. After completion, the crude residue was adjusted pH=9 with sodium bicarbonate solution and extracted with dichloromethane (100 mL×3). The organic layer was dried over sodium sulfate, filtered and concentrated in vacuo. The crude solid was purified by column chromatography (silica gel, dichloromethane/methanol from 20/1 to 10/1) to give 4-amino-N-(1-methyl-6-oxo-1,6-dihydropyridazin-3-yl)piperidine-1-carboxamide (0.67 g, 2.7 mmol, 78%) as a brown solid. $^1$H NMR (400 MHz, Dimethylsulfoxide-d$_6$) δ 9.21 (s, 1H), 7.61-7.58 (d, J=9.9 Hz, 1H), 6.86-6.84 (d, J=9.9 Hz, 1H), 4.06-3.89 (m, 2H), 3.55 (s, 3H), 3.32 (s, 2H), 2.95-2.80 (m, 2H), 2.76-7.74 (m, 1H), 1.69-1.65 (m, 2H), 1.14-1.11 (m, 2H); LCMS (ESI) m/z: 252.1 [M+H]$^+$.

Step 3: Preparation of N-(1-methyl-6-oxo-1,6-dihydropyridazin-3-yl)-4-(2-(trifluoromethyl)benzylamino)piperidine-1-carboxamide

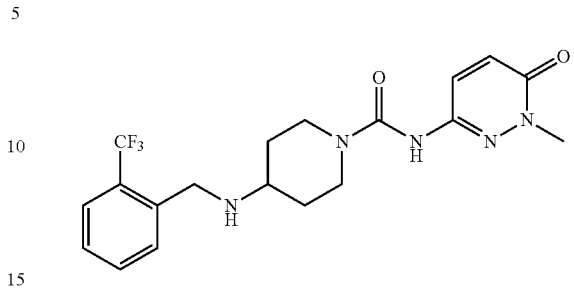

A solution of 4-amino-N-(1-methyl-6-oxo-1,6-dihydropyridazin-3-yl)piperidine-1-carboxamide (251 mg, 1.0 mmol) and 2-(trifluoromethyl)benzaldehyde (174 mg, 1.0 mmol) in dichloroethane (9 mL) and acetic acid (0.1 mL) was stirred at 25° C. for 1 h. Then sodium borohydride acetate (318 mg, 1.5 mmol) was added to the reaction mixture and stirred at 25° C. for 16 h. The reaction mixture was filtered, and the filtrate was concentrated in vacuo. The crude material was dissolved in the minimum amount of N,N-dimethylformamide and purified by prep-HPLC (SunFire C18, 4.6×50 mm, 3.5 μm column: Xbridge C18 3.5 μm, 4.6×50 mm column; gradient of 5-95% over 1.5 min at 2 mL/min, acetonitrile/0.01% aqueous formic acid) to afford N-(1-methyl-6-oxo-1,6-dihydropyridazin-3-yl)-4-(2-(trifluoromethyl)benzylamino)piperidine-1-carboxamide (57.8 mg, 0.14 mmol, 14%) as a white solid. $^1$H NMR (400 MHz, Dimethylsulfoxide-d$_6$) δ 9.22 (s, 1H), 7.83 (d, J=7.7 Hz, 1H), 7.73-7.57 (m, 3H), 7.44 (t, J=7.6 Hz, 1H), 6.87 (d, J=9.9 Hz, 1H), 3.94 (d, J=13.5 Hz, 2H), 3.90 (s, 2H), 3.55 (s, 3H), 2.88 (t, J=11.2 Hz, 2H), 2.61 (d, J=9.3 Hz, 1H), 2.21-2.19 (m, 1H), 1.81 (d, J=10.1 Hz, 2H), 1.22-1.20 (m, 2H); LCMS (ESI) m/z: 410.1 [M+H]$^+$.

Example 100. Preparation of 4-(3-chloro-4,5-difluorobenzyl)-4-fluoro-N-(1-methyl-6-oxo-1,6-dihydropyridazin-3-yl)piperidine-1-carboxamide (Compound 66)

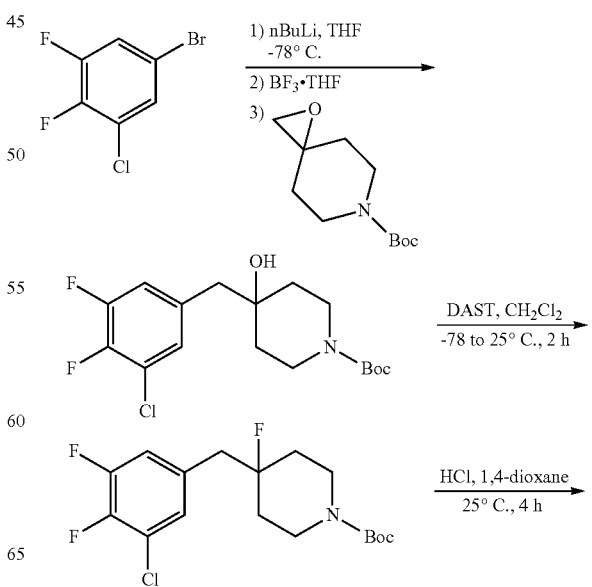

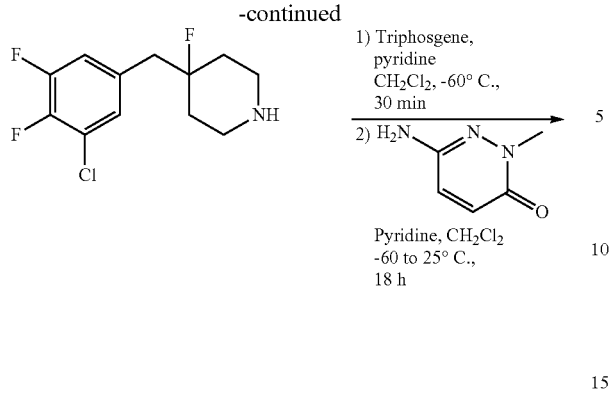

Step 1: Preparation of tert-butyl 4-(3-chloro-4,5-difluorobenzyl)-4-hydroxypiperidine-1-carboxylate

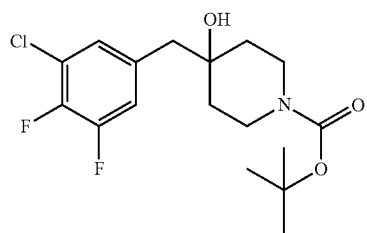 [SMILES: CC(C)(C)OC(=O)N1CCC(O)(Cc2cc(F)c(F)c(Cl)c2)CC1]

To a solution of 5-bromo-1-chloro-2,3-difluorobenzene (4.5 g, 19.9 mmol) in dry tetrahydrofuran (60 mL) at −78° C. was added n-butyllithium (2.5 M, 8.7 mL, 21.9 mmol) drop-wise under argon. The reaction mixture was stirred at −78° C. for 1.5 h, then boron trifluoride etherate (47% wt, 5.6 mL, 20.6 mmol) was added slowly. The reaction solution was stirred for 15 min before a solution of tert-butyl 1-oxa-6-azaspiro[2.5]octane-6-carboxylate (4.2 g, 19.9 mmol) in dry tetrahydrofuran (20 mL) was added drop-wise. The reaction mixture was stirred at −78° C. for 2 h and then at 25° C. for 18 h. The reaction solution was quenched with saturated ammonium chloride aqueous solution and basified to pH=9 with 2 N sodium hydroxide aqueous solution. The aqueous layer was extracted with ethyl acetate (60 mL×2). The combined organic phase was washed with brine (50 mL), dried over sodium sulfate, filtered and concentrated in vacuo. The crude residue was purified by Combi-Flash (Biotage, 80 g silica gel, eluted with ethyl acetate in petroleum ether from 20 to 30%) to give tert-butyl 4-(3-chloro-4,5-difluorobenzyl)-4-hydroxypiperidine-1-carboxylate (4 g, 11.08 mmol, 55%) as a colorless oil. LCMS (ESI) m/z: 306.2 [M−56+H]$^+$.

Step 2: Preparation of tert-butyl 4-(3-chloro-4,5-difluorobenzyl)-4-fluoropiperidine-1-carboxylate

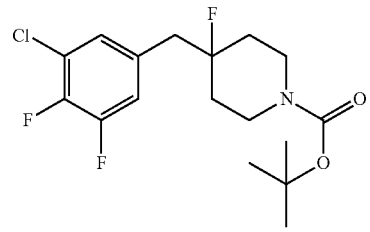 [SMILES: CC(C)(C)OC(=O)N1CCC(F)(Cc2cc(F)c(F)c(Cl)c2)CC1]

To a solution of diethylamino sulfur trifluoride (2.85 mL, 21.6 mmol) in dry dichloromethane (80 mL) at −78° C. was added a solution of tert-butyl 4-(3-chloro-4,5-difluorobenzyl)-4-hydroxypiperidine-1-carboxylate (3.9 g, 10.8 mmol) in dry dichloromethane (20 mL) drop-wise under nitrogen. After the addition, the reaction was warmed up to ambient temperature and stirred for 2 h. The reaction was quenched with saturated sodium bicarbonate aqueous solution and extracted with dichloromethane (50 mL×2). The combined organic phases were washed with brine (40 mL), dried over sodium sulfate, filtered and concentrated. The residue was purified by Combi-Flash (Biotage, 80 g silica gel, eluted with ethyl acetate in petroleum ether from 10 to 20%) to give tert-butyl 4-(3-chloro-4,5-difluorobenzyl)-4-fluoropiperidine-1-carboxylate (1.8 g, 4.96 mmol, 46%) as colorless oil. LCMS (ESI) m/z: 308.1 [M−56+H]$^+$.

Step 3: Preparation of 4-(3-chloro-4,5-difluorobenzyl)-4-fluoropiperidine

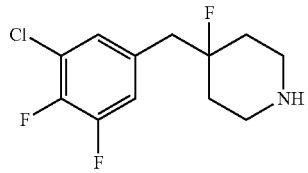 [SMILES: Fc1cc(CC2(F)CCNCC2)cc(Cl)c1F]

A solution of tert-butyl 4-(3-chloro-4,5-difluorobenzyl)-4-fluoropiperidine-1-carboxylate (1.7 g, 4.68 mmol) and hydrochloric acid in 1,4-dioxane solution (4 M, 40 mL) was stirred at 25° C. for 4 h. The reaction mixture was concentrated in vacuo. The residue was diluted with dichloromethane (50 mL), neutralized with sodium bicarbonate aqueous solution and extracted with dichloromethane (30 mL×2).

The combined organic phases were washed with brine (40 mL), dried over sodium sulfate, filtered and concentrated to give 4-(3-chloro-4,5-difluorobenzyl)-4-fluoropiperidine (0.8 g, 3.04 mmol, 65%) as a yellow oil. LCMS (ESI) m/z: 264.1 [M+H]$^+$.

Step 4: Preparation of 4-(3-chloro-4,5-difluorobenzyl)-4-fluoro-N-(1-methyl-6-oxo-1,6-dihydropyridazin-3-yl)piperidine-1-carboxamide

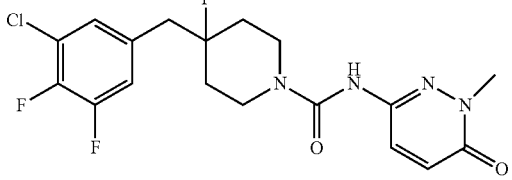

To a solution of triphosgene (0.18 g, 0.6 mmol) in dichloromethane (20 mL) at −60° C. was added a solution of 6-amino-2-methylpyridazin-3(2H)-one (0.15 g, 1.2 mmol) and pyridine (0.38 g, 4.8 mmol) in dichloromethane (10 mL) under argon. The mixture was stirred at −60° C. for 30 min. Then a solution of 4-(3-chloro-4,5-difluorobenzyl)-4-fluoropiperidine (0.38 g, 1.44 mmol) and pyridine (0.45 g, 5.78 mmol) in dichloromethane (10 mL) was added at −60° C. The resulting mixture was stirred at 25° C. for 18 h. The reaction mixture was quenched with water (40 mL) and the aqueous layer was extracted with dichloromethane (40 mL×2). The combined organic layers were dried over sodium sulfate, filtered and concentrated. The crude residue was dissolved in the minimum amount of N,N-dimethylformamide and purified by prep-HPLC (Boston C18, 21×250 mm, 10 μm column; acetonitrile/10 mM ammonium acetate aqueous solution) to give 4-(3-chloro-4,5-difluorobenzyl)-4-fluoro-N-(1-methyl-6-oxo-1,6-dihydropyridazin-3-yl)piperidine-1-carboxamide (140 mg, 0.34 mmol, 28%) as a white solid. $^1$H NMR (400 MHz, Dimethylsulfoxide-$d_6$) δ 7.63 (d, J=9.6, 1H), 7.38-7.45 (m, 1H), 7.14-7.23 (m, 1H), 6.88 (d, J=9.6 Hz, 1H), 3.96 (d, J=13.6 Hz, 2H), 3.56 (s, 3H), 2.91-3.12 (m, 4H), 1.60-1.84 (m, 4H); LCMS (ESI) m/z: 415.0 [M+H]$^+$.

Example 101. Preparation of 4-(3-fluorobenzyl)-4-hydroxy-N-(1-methyl-6-oxo-1,6-dihydropyridazin-3-yl)piperidine-1-carboxamide (Compound 47)

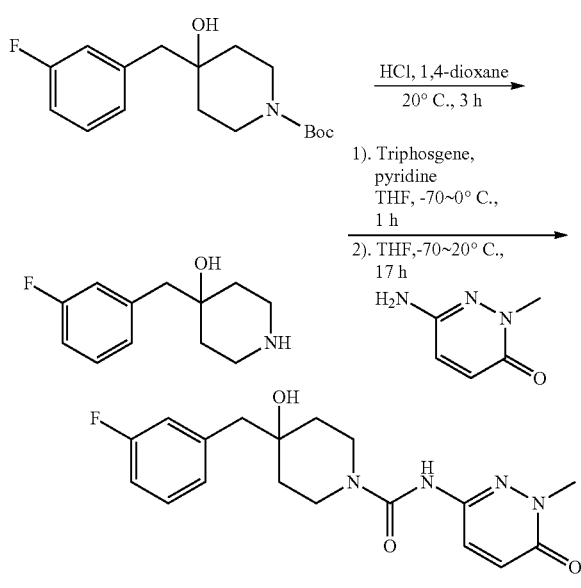

Step 1: Preparation of 4-(3-fluorobenzyl)piperidin-4-ol

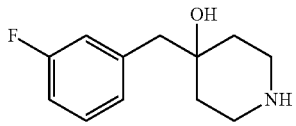 [SMILES: OC1(Cc2cccc(F)c2)CCNCC1]

A solution of tert-butyl 4-(3-fluorobenzyl)-4-hydroxypiperidine-1-carboxylate (2.0 g, 6.47 mmol) and hydrochloric acid in 1,4-dioxane (20 mL, 4 M) was stirred at 20° C. for 3 h. The reaction mixture was concentrated to remove the volatiles. The crude residue was diluted with methanol (30 mL) and potassium carbonate (2.0 g) was added. The mixture was stirred at 20° C. for 1 h and filtered, the filtrate was concentrated to give 4-(3-fluorobenzyl)piperidin-4-ol (1.20 g, 5.74 mmol, 88%) as a brown oil. LCMS (ESI) m/z: 210.2 [M+H]$^+$.

Step 2: Preparation of 4-(3-fluorobenzyl)-4-hydroxy-N-(1-methyl-6-oxo-1,6-dihydropyridazin-3-yl)piperidine-1-carboxamide

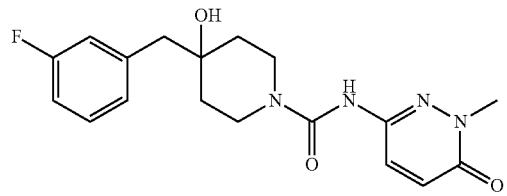

To a solution of triphosgene (136 mg, 0.46 mmol) in tetrahydrofuran (10 mL) at −70° C. was added a solution of 6-amino-2-methylpyridazin-3(2H)-one (144 mg, 1.15 mmol) and pyridine (363 mg, 4.6 mmol) in tetrahydrofuran (5 mL) under argon. The mixture was warmed from −70° C. to 20° C. for 1 h. The reaction mixture was cooled to −70° C., then a solution of 4-(3-fluorobenzyl)piperidin-4-ol (240 mg, 1.15 mmol) in tetrahydrofuran (5 mL) was added at −70° C. The resulting mixture was stirred at 25° C. for 18 h. The reaction solution was quenched with water (30 mL) and extracted with ethyl acetate (50 mL×2). The combined organic layers were dried over sodium sulfate, filtered and concentrated. The crude residue was dissolved in the minimum amount of N,N-dimethylformamide and purified by prep-HPLC (Boston C18, 21×250 mm, 10 μm column; acetonitrile/10 mM ammonium acetate aqueous solution) to give 4-(3-fluorobenzyl)-4-hydroxy-N-(1-methyl-6-oxo-1,6-dihydropyridazin-3-yl)piperidine-1-carboxamide (76 mg, 0.21 mmol, 18%) as a white solid. $^1$H NMR (400 MHz, Dimethylsulfoxide-$d_6$) δ 9.18 (s, 1H), 7.60 (d, J=10.0 Hz, 1H), 7.30 (q, J=10.0 Hz, 1H), 7.00-7.07 (m, 3H), 6.86 (d, J=10.0 Hz, 1H), 4.49 (s, 1H), 3.79 (d, J=13.2 Hz, 2H), 3.55 (s, 3H), 3.09 (t, J=11.2 Hz, 2H), 2.71 (s, 2H), 1.33-1.47 (m, 4H); LCMS (ESI) m/z: 361.2 [M+H]$^+$.

Example 102. Preparation of 4-(3-fluorobenzyl)-4-methoxy-N-(1-methyl-6-oxo-1,6-dihydropyridazin-3-yl)piperidine-1-carboxamide (Compound 48)

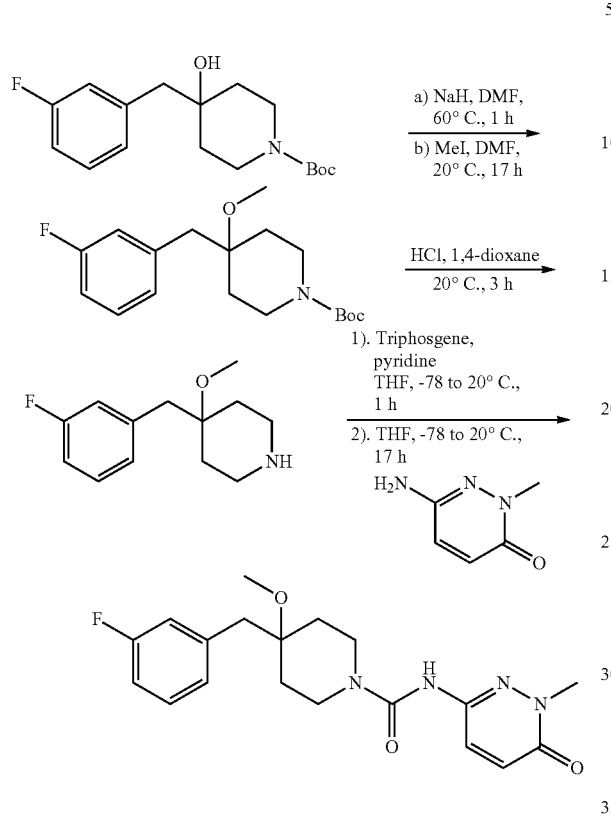

Step 1: Preparation of tert-butyl 4-(3-fluorobenzyl)-4-methoxypiperidine-1-carboxylate

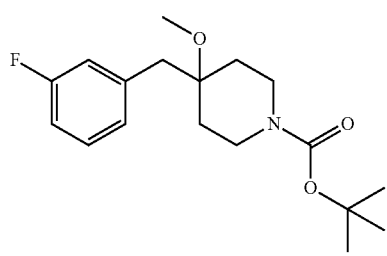 [SMILES: COC1(Cc2cccc(F)c2)CCN(C(=O)OC(C)(C)C)CC1]

To a solution of tert-butyl 4-(3-fluorobenzyl)-4-hydroxypiperidine-1-carboxylate (700 mg, 2.26 mmol) in N,N-dimethylformamide (20 mL) at 20° C. was added sodium hydride (271 mg, 6.79 mmol). The reaction mixture was heated to 60° C. for 1 h, then cooled to 20° C. and iodomethane (964 mg, 6.79 mmol) was added. The reaction mixture was stirred at 20° C. for 17 h. The reaction solution was poured into cool water (100 mL) and extracted with ethyl acetate (100 mL). The combined organic layers were washed with water (100 mL×2), brine (100 mL) and concentrated in vacuo. The crude tert-butyl 4-(3-fluorobenzyl)-4-methoxypiperidine-1-carboxylate (702 mg, 2.17 mmol, 96%) was obtained as a brown oil. LCMS (ESI) m/z: 224.3 [M-100+H]+. The material was used in the next step without additional purification.

Step 2: Preparation of 4-(3-fluorobenzyl)-4-methoxypiperidine

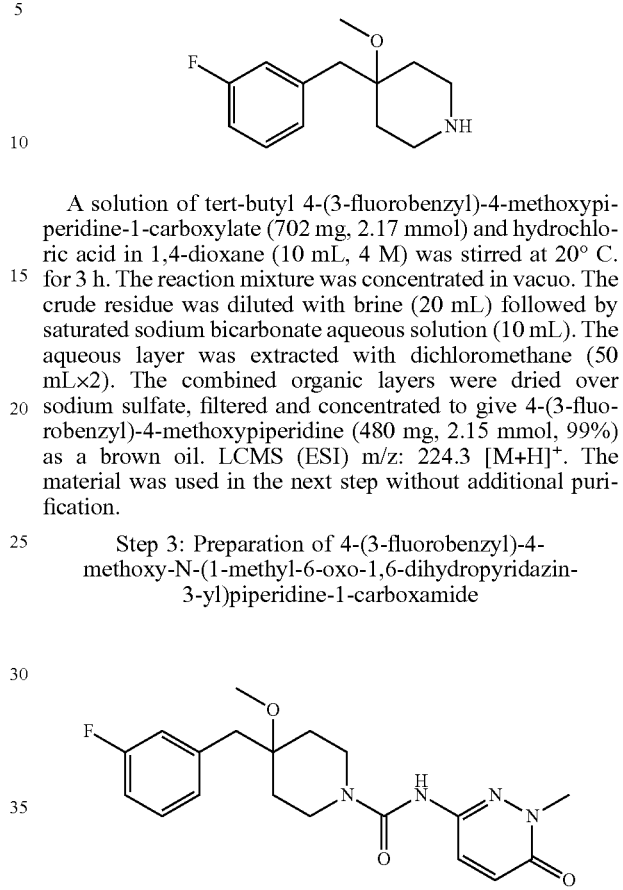

A solution of tert-butyl 4-(3-fluorobenzyl)-4-methoxypiperidine-1-carboxylate (702 mg, 2.17 mmol) and hydrochloric acid in 1,4-dioxane (10 mL, 4 M) was stirred at 20° C. for 3 h. The reaction mixture was concentrated in vacuo. The crude residue was diluted with brine (20 mL) followed by saturated sodium bicarbonate aqueous solution (10 mL). The aqueous layer was extracted with dichloromethane (50 mL×2). The combined organic layers were dried over sodium sulfate, filtered and concentrated to give 4-(3-fluorobenzyl)-4-methoxypiperidine (480 mg, 2.15 mmol, 99%) as a brown oil. LCMS (ESI) m/z: 224.3 [M+H]+. The material was used in the next step without additional purification.

Step 3: Preparation of 4-(3-fluorobenzyl)-4-methoxy-N-(1-methyl-6-oxo-1,6-dihydropyridazin-3-yl)piperidine-1-carboxamide To a solution of triphosgene (212 mg, 0.72 mmol) in tetrahydrofuran (20 mL) at −70° C. was added a solution of 6-amino-2-methylpyridazin-3(2H)-one (224 mg, 1.79 mmol) and pyridine (566 mg, 7.16 mmol) in tetrahydrofuran (10 mL) under argon. The reaction mixture was warmed from −70° C. to 20° C. for 1 h. The reaction solution was cooled to −70° C., then a solution of 4-(3-fluorobenzyl)piperidin-4-ol (480 mg, 2.15 mmol) in tetrahydrofuran (10 mL) was added at −70° C. The resulting mixture was stirred at 25° C. for 18 h. The reaction mixture was concentrated in vacuo. The crude product was diluted with acetonitrile (15 mL), poured into cool water (40 mL) and acidified to pH 3~4 with 6 M aqueous hydrochloric acid solution. The reaction solution was filtered and the filter cake was dried in vacuo to give 4-(3-fluorobenzyl)-4-methoxy-N-(1-methyl-6-oxo-1,6-dihydropyridazin-3-yl)piperidine-1-carboxamide as a white solid (354 mg, 0.95 mmol, 53%). $^1$H NMR (400 MHz, Dimethylsulfoxide-$d_6$) δ 9.21 (s, 1H), 7.59 (d, J=10.0 Hz, 1H), 7.32 (dd, J=14.8 Hz, J=9.6 Hz, 1H), 6.99-7.05 (m, 3H), 6.86 (d, J=10.0 Hz, 1H), 3.81 (d, J=12.8 Hz, 2H), 3.55 (s, 3H), 3.27 (s, 3H), 2.97 (t, J=12.0 Hz, 2H), 2.81 (s, 2H), 1.60 (d, J=13.6 Hz, 2H) 1.36-1.43 (m, 2H); LCMS (ESI) m/z: 375.1 [M+H]+.

Example 103. Characterization Data of Compounds of the Invention

The following compounds were synthesized by methods similar to those described above.

Compound 1

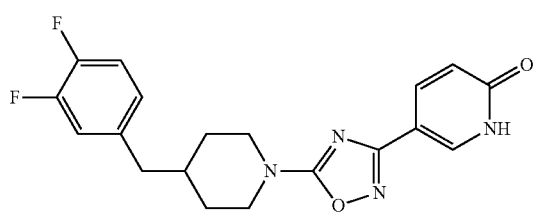

¹H NMR (400 MHz, Dimethylsulfoxide-d₆) δ 12.04 (s, 1H), 7.86 (s, 1H), 7.78 (d, J=9.6 Hz, 1H), 7.05 (t, J=8.4 Hz, 1H), 6.96 (d, J=7.2 Hz, 2H), 6.43 (d, J=7.6 Hz, 1H), 4.01 (d, J=12.8 Hz, 2H), 3.10 (t, J=12.4 Hz, 2H), 2.58 (d, J=7.2 Hz, 1H), 1.83-1.84 (m, 1H), 1.64 (d, J=13.2 Hz, 2H), 1.19-1.27 (m, 2H); LCMS (ESI) m/z: 373.2 [M+H]⁺.

Compound 2

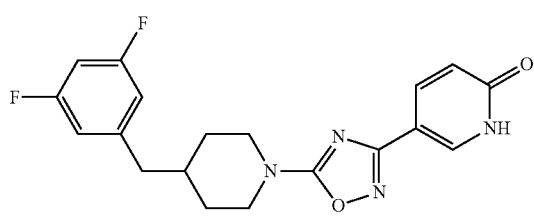

¹H NMR (400 MHz, Dimethylsulfoxide-d₆) δ 12.04 (s, 1H), 7.86 (s, 1H), 7.77-7.85 (m, 1H), 7.26-7.38 (m, 2H), 7.04 (s, 1H), 6.43 (d, J=9.6 Hz, 1H), 4.00 (d, J=13.2 Hz, 2H), 3.09 (t, J=10.4 Hz, 2H), 2.55 (d, J=7.2 Hz, 1H), 1.878-1.82 (m, 1H), 1.64 (d, J=11.6 Hz, 2H), 1.17-1.27 (m, 2H); LCMS (ESI) m/z: 373.2 [M+H]⁺.

Compound 4

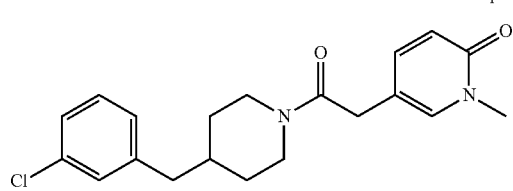

¹H NMR (500 MHz, Dimethylsulfoxide-d₆) δ 7.48 (d, J=2.0 Hz, 1H), 7.33-7.30 (m, 1H), 7.26-7.24 (m, 3H), 7.15 (d, J=7.5 Hz, 1H), 6.32 (d, J=9.5 Hz, 1H), 4.33 (d, J=13.0 Hz, 1H), 3.92 (d, J=13.5 Hz, 1H), 3.42 (s, 2H), 3.38 (s, 3H), 2.97-2.92 (m, 1H), 2.53-2.47 (m, 3H), 1.80-1.74 (m, 1H), 1.58-1.54 (m, 2H), 1.10-0.93 (m, 2H); LCMS (ESI) m/z: 359.1 [M+H]⁺.

Compound 7

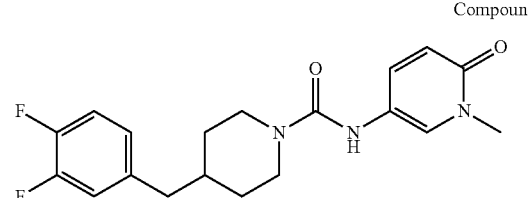

¹H NMR (500 MHz, Dimethylsulfoxide-d₆) δ 8.15 (s, 1H), 7.75 (d, J=3.0 Hz, 1H), 7.38-7.41 (m, 1H), 7.31-7.36 (m, 1H), 7.26-7.30 (m, 1H), 7.02-7.04 (m, 1H), 6.33 (d, J=9.5 Hz, 1H), 4.03 (d, J=13.5 Hz, 2H), 3.39 (s, 3H), 2.67-2.72 (m, 2H), 2.51-2.53 (m, 2H), 1.70-1.74 (m, 1H), 1.53-1.55 (m, 2H), 1.03-1.11 (m, 2H); LCMS (ESI) m/z: 362.1 [M+H]⁺.

Compound 9

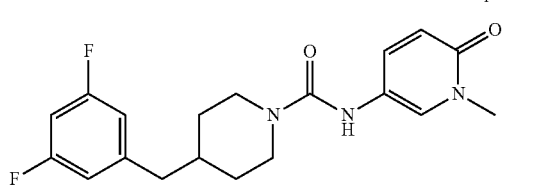

¹H NMR (500 MHz, Dimethylsulfoxide-d₆) δ 8.14 (s, 1H), 7.74 (d, J=3.0 Hz, 1H), 7.39 (dd, J1=3.0 Hz, J₂=10.0 Hz, 1H), 7.02-7.07 (m, 1H), 6.94-6.97 (m, 2H), 6.32 (d, J=10.0 Hz, 1H), 4.03 (d, J=13.0 Hz, 2H), 3.39 (s, 3H), 2.67-2.73 (m, 2H), 2.55-2.57 (m, 2H), 1.74-1.79 (m, 1H), 1.53-1.55 (m, 2H), 1.03-1.17 (m, 2H); LCMS (ESI) m/z: 362.1 [M+H]⁺.

Compound 10

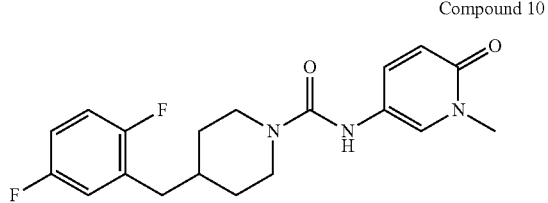 [SMILES: Cn1cc(NC(=O)N2CCC(Cc3cc(F)ccc3F)CC2)ccc1=O]

¹H NMR (400 MHz, Dimethylsulfoxide-d₆) δ 8.15 (s, 1H), 7.72 (d, J=2.2 Hz, 1H), 7.38 (d, J=7.0 Hz, 1H), 7.19-7.15 (m, 2H), 7.09 (d, J=8.5 Hz, 1H), 6.31 (d, J=9.6 Hz, 1H), 4.03-4.00 (m, 2H), 3.38 (s, 3H), 2.70-2.68 (m, 2H), 2.55 (d, J=7.2 Hz, 2H), 1.75-1.72 (m, 1H), 1.54 (d, J=12.5 Hz, 2H), 1.10-1.08 (m, 2H); LCMS (ESI) m/z: 362.1 [M+H]⁺.

Compound 13

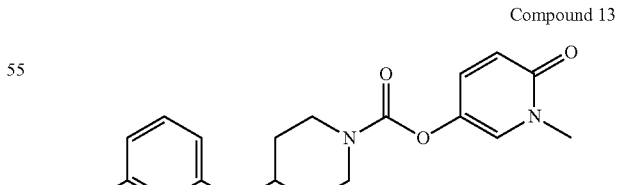

¹H NMR (500 MHz, Dimethylsulfoxide-d₆) δ 7.46 (d, J=9.8 Hz, 1H), 7.31 (t, J=8.2 Hz, 1H), 7.11 (d, J=2.0 Hz, 1H), 7.07-6.87 (m, 3H), 4.75-4.68 (m, 1H), 3.76-3.73 (m, 2H), 3.57 (s, 3H), 3.52-3.32 (m, 2H), 1.99-1.96 (m, 2H), 1.67-1.65 (m, 2H); LCMS (ESI) m/z: 363.1 [M+H]⁺.

Compound 31

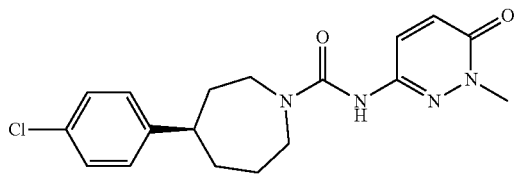

¹H NMR (400 MHz, Dimethylsulfoxide-d₆) δ 9.03 (s, 1H), 7.69 (d, J=9.9 Hz, 1H), 7.36-7.29 (m, 2H), 7.27-7.19 (m, 2H), 6.89 (d, J=9.9 Hz, 1H), 3.79-3.69 (m, 1H), 3.65-3.52 (m, 4H), 3.50-3.41 (m, 1H), 3.37-3.29 (m, 1H), 2.74-2.62 (m, 1H), 1.96-1.55 (m, 6H); LCMS (ESI) m/z: 361.2 [M+H]⁺.

Compound 32

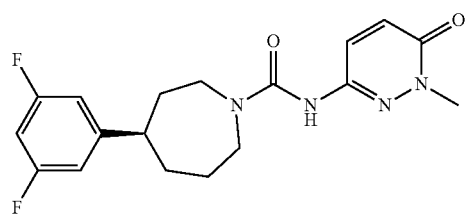

¹H NMR (400 MHz, Dimethylsulfoxide-de) δ 9.02 (s, 1H), 7.70 (d, J=9.9 Hz, 1H), 7.06-6.95 (m, 3H), 6.89 (d, J=9.9 Hz, 1H), 3.78-3.68 (m, 1H), 3.64-3.52 (m, 4H), 3.48-3.38 (m, 2H), 2.78-2.68 (m, 1H), 1.96-1.60 (m, 6H); LCMS (ESI) m/z: 363.1 [M+H]⁺.

Compound 34

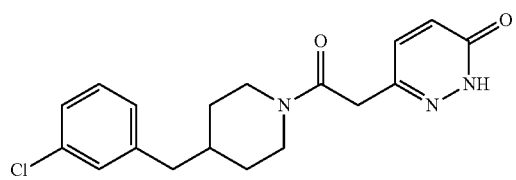

¹H NMR (400 MHz, Dimethylsulfoxide-d₆) δ 9.20 (s, 1H), 7.61 (d, J=9.6 Hz, 1H), 7.36-7.30 (m, 1H), 7.02 (t, J=8.2 Hz, 3H), 6.87 (d, J=9.6 Hz, 1H), 4.06 (d, J=13.6 Hz, 2H), 3.56 (s, 3H), 2.72 (t, J=12.2 Hz, 2H), 2.55 (d, J=7.2 Hz, 2H), 1.75-1.72 (m, 1H), 1.54 (d, J=12.0 Hz, 2H), 1.13-1.05 (m, 2H); LCMS (ESI) m/z: 346.1[M+H]⁺.

Compound 35

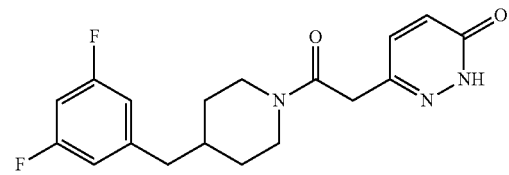

¹H NMR (400 MHz, Dimethylsulfoxide-d₆) δ 12.81 (s, 1H), 7.27 (d, J=10.0 Hz, 1H), 7.01-7.07 (m, 1H), 6.93-6.95 (m, 2H), 6.80 (d, J=9.6 Hz, 1H), 4.32 (d, J=13.2 Hz, 1H), 3.88 (d, J=13.2 Hz, 1H), 3.67 (s, 2H), 2.97 (t, J=12.0 Hz, 1H), 2.51-2.56 (m, 3H), 1.78-1.84 (m, 1H), 1.54-1.56 (m, 2H), 0.98-1.15 (m, 2H); LCMS (ESI) m/z: 348.1[M+H]⁺.

Compound 39

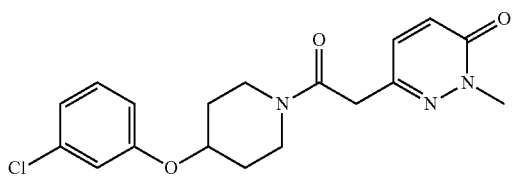

¹H NMR (400 MHz, Dimethylsulfoxide-d₆) δ 7.31 (dd, J=13.1, 5.6 Hz, 2H), 7.09 (d, J=2.0 Hz, 1H), 6.98 (dd, J=13.3, 4.9 Hz, 2H), 6.88 (d, J=9.5 Hz, 1H), 4.79-4.52 (m, 1H), 3.90-3.81 (m, 1H), 3.75 (d, J=11.3 Hz, 3H), 3.60 (s, 3H), 3.41 (dd, J=8.8, 5.0 Hz, 1H), 3.30-3.16 (m, 1H), 2.05-1.81 (m, 2H), 1.57 (dd, J=42.3, 8.7 Hz, 2H); LCMS (ESI) m/z: 362.1 [M+H]⁺.

Compound 43

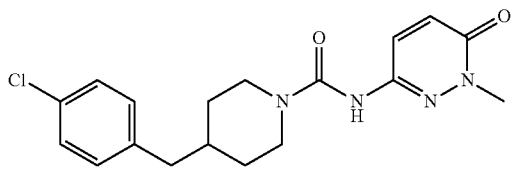

¹H NMR (400 MHz, Dimethylsulfoxide-d₆) δ 9.19 (s, 1H), 7.60-7.58 (d, J=9.8 Hz, 1H), 7.34-7.31 (d, J=8.3 Hz, 2H), 7.21-7.20 (d, J=8.3 Hz, 2H), 6.86-6.84 (d, J=9.8 Hz, 1H), 4.05-4.02 (m, 2H), 3.55 (s, 3H), 2.71-2.70 (t, J=12.0 Hz, 2H), 2.53-2.50 (m, 2H), 1.70-1.68 (m, 1H), 1.54-1.52 (d, J=12.2 Hz, 2H), 1.19-0.99 (m, 2H); LCMS (ESI) m/z: 361.2 [M+H]⁺.

Compound 46

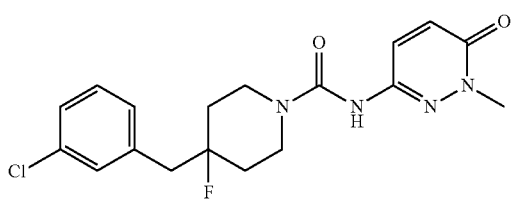

¹H NMR (400 MHz, Dimethylsulfoxide-d₆) δ 9.32 (br. s, 1H), 7.62 (d, J=10.0 Hz, 1H), 7.28-7.40 (m, 3H), 7.17-7.23 (m, 1H), 6.88 (d, J=10 Hz, 1H), 3.94 (d, J=13.6 Hz, 2H), 3.56 (s, 3H), 2.91-3.06 (m, 4H), 1.55-1.77 (m, 4H); LCMS (ESI) m/z: 379.1 [M+H]⁺.

Compound 50

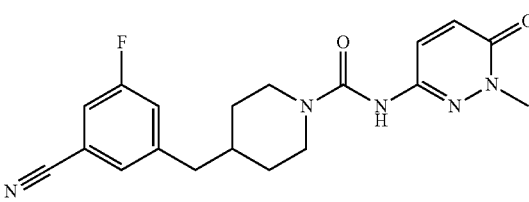

¹H NMR (400 MHz, Dimethylsulfoxide-d₆) δ 9.21-9.22 (m, 1H), 7.67-7.70 (m, 1H), 7.61 (d, J=10.0 Hz, 1H), 7.58 (s, 1H), 7.50 (dd, J₁=1.2 Hz, J₂=10.0 Hz, 1H), 6.87 (d, J=10.0 Hz, 1H), 4.06 (d, J=13.2 Hz, 2H), 3.56 (s, 3H), 2.72 (t, J=12.0 Hz, 2H), 2.61-2.63 (m, 2H), 1.77-1.83 (m, 1H), 1.51-1.54 (m, 2H), 1.04-1.15 (m, 2H); LCMS (ESI) m/z: 370.0 [M+H]⁺.

Compound 51

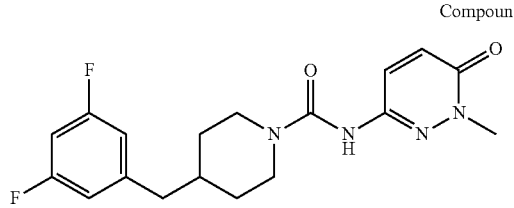

¹H NMR (500 MHz, Dimethylsulfoxide-d₆) δ 9.22 (s, 1H), 7.61 (d, J=10.0 Hz, 1H), 7.02-7.07 (m, 1H), 6.93-6.97 (m, 2H), 6.87 (d, J=9.5 Hz, 1H), 4.06 (d, J=13.5 Hz, 2H), 3.56 (s, 3H), 2.72 (t, J=12.0 Hz, 2H), 2.51-2.57 (m, 2H), 1.75-1.79 (m, 1H), 1.53-1.55 (m, 2H), 1.05-1.13 (m, 2H); LCMS (ESI) m/z: 363.1 [M+H]⁺.

Compound 53

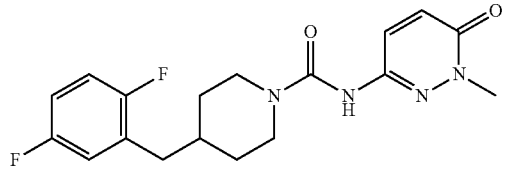

¹H NMR (400 MHz, Dimethylsulfoxide-d₆) δ 9.20 (s, 1H), 7.61-7.60 (d, J=9.8 Hz, 1H), 7.19-7.15 (m, 2H), 7.14-7.03 (m, 1H), 6.86-6.85 (d, J=9.9 Hz, 1H), 4.06-4.02 (m, 2H), 3.55 (s, 3H), 2.72-2.70 (t, J=12.1 Hz, 2H), 2.56-2.53 (m, 2H), 1.76-1.74 (m, 1H), 1.55-1.52 (d, J=12.2 Hz, 2H), 1.30-0.99 (m, 2H); LCMS (ESI) m/z: 363.1 [M+H]⁺.

Compound 69

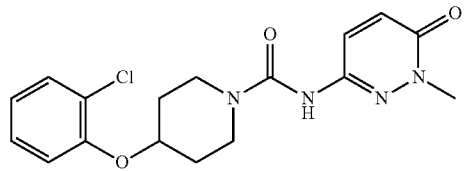

¹H NMR (400 MHz, Dimethylsulfoxide-d₆) δ 9.35 (s, 1H), 7.65 (d, J=10.0 Hz, 1H), 7.44 (dd, J1=1.2 Hz, J₂=7.6 Hz, 1H), 7.25-7.33 (m, 2H), 6.95-6.99 (m, 1H), 6.89 (d, J=9.6 Hz, 1H), 4.72-4.75 (m, 1H), 3.66-3.72 (m, 2H), 3.57 (s, 3H), 3.38-3.44 (m, 2H), 1.90-1.96 (m, 2H), 1.61-1.69 (m, 2H); LCMS (ESI) m/z: 363.1 [M+H]⁺.

Compound 70

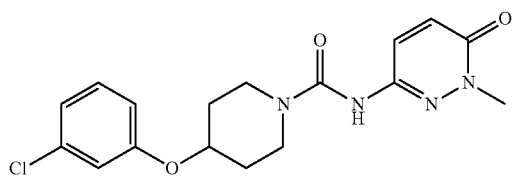

¹H NMR (400 MHz, Dimethylsulfoxide-d₆) δ 9.31 (s, 1H), 7.63 (d, J=9.6 Hz, 1H), 7.29 (t, J=8.0 Hz, 1H), 7.05 (t, J=2.0 Hz, 1H), 6.99-6.93 (m, 2H), 6.88 (d, J=10.0 Hz, 1H), 4.49-4.85 (m, 1H), 3.84-3.80 (m, 1H), 3.56-3.54 (m, 4H), 3.40-3.29 (m, 2H), 2.02-1.97 (m, 1H), 1.78-1.65 (m, 2H), 1.55-1.49 (m, 1H); LCMS (ESI) m/z: 363.1 [M+H]⁺.

Compound 71

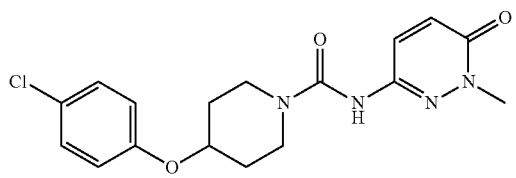

¹H NMR (400 MHz, Dimethylsulfoxide-d₆) δ 9.32 (s, 1H), 7.62 (d, J=9.8 Hz, 1H), 7.31 (d, J=8.9 Hz, 2H), 7.01 (d, J=8.9 Hz, 2H), 6.87 (d, J=9.8 Hz, 1H), 4.58-4.55 (m, 1H), 3.76 (d, J=13.7 Hz, 2H), 3.56 (s, 3H), 3.25 (d, J=9.9 Hz, 2H), 1.92-1.90 (m, 2H), 1.69-1.42 (m, 2H); LCMS (ESI) m/z: 363.1 [M+H]⁺.

Compound 80

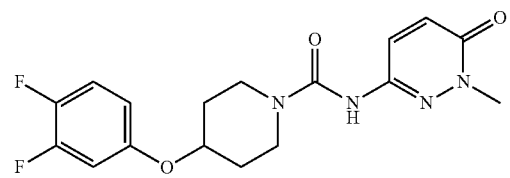

¹H NMR (400 MHz, Dimethylsulfoxide-d₆) δ 7.63 (d, J=10.0 Hz, 1H), 7.34 (dd, J₁=9.6 Hz, J₂=20.0 Hz, 1H), 7.13-7.19 (m, 1H), 6.88 (d, J=10.0 Hz, 1H), 6.81-6.85 (m, 1H), 4.56-4.60 (m, 1H), 3.76-3.81 (m, 2H), 3.56 (s, 3H), 3.24-3.33 (m, 2H), 1.91-1.96 (m, 2H), 1.51-1.60 (m, 2H); LCMS (ESI) m/z: 365.0 [M+H]⁺.

Compound 84

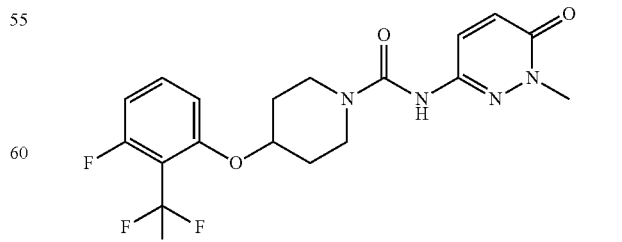

¹H NMR (400 MHz, Dimethylsulfoxide-d₆) δ 9.33 (s, 1H), 7.78-7.51 (m, 2H), 7.21 (d, J=8.6 Hz, 1H), 6.98-6.95

(m, 1H), 6.87 (d, J=9.9 Hz, 1H), 4.88-4.85 (m, 1H), 3.60-3.58 (m, 2H), 3.56 (s, 3H), 3.51-3.41 (m, 2H), 2.05-1.84 (m, 2H), 1.79-1.54 (m, 2H); LCMS (ESI) m/z: 415.1 [M+H]⁺.

Compound 85

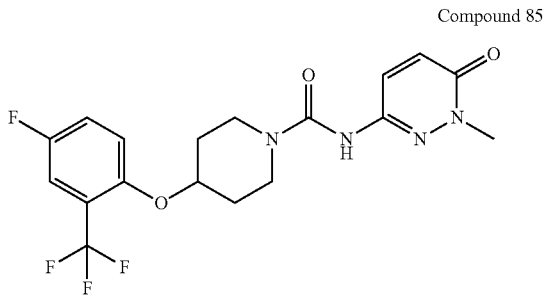 [SMILES: Cn1nc(NC(=O)N2CCC(Oc3ccc(F)cc3C(F)(F)F)CC2)ccc1=O]

¹H NMR (400 MHz, Dimethylsulfoxide-d₆) δ 9.32 (s, 1H), 7.63 (d, J=9.9 Hz, 1H), 7.50 (t, J=8.7 Hz, 2H), 7.39 (dd, J=8.8, 4.2 Hz, 1H), 6.86 (d, J=9.9 Hz, 1H), 4.82-4.80 (m, 1H), 3.60-3.58 (dd, J=10.9, 7.1 Hz, 2H), 3.57 (s, 3H), 3.48-3.39 (m, 2H), 2.00-1.78 (m, 2H), 1.77-1.45 (m, 2H); LCMS (ESI) m/z: 415.0 [M+H]⁺.

Compound 106

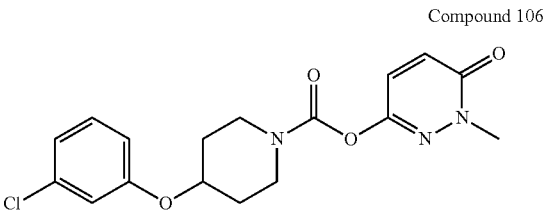 [SMILES: Cn1nc(OC(=O)N2CCC(Oc3cccc(Cl)c3)CC2)ccc1=O]

¹H NMR (500 MHz, Dimethylsulfoxide-d₆) δ 7.46 (d, J=9.8 Hz, 1H), 7.31 (t, J=8.2 Hz, 1H), 7.10 (d, J=2.0 Hz, 1H), 7.03 (d, J=9.8 Hz, 1H), 7.02-6.93 (m, 2H), 4.75-4.67 (m, 1H), 3.76-3.74 (m, 2H), 3.57 (s, 3H), 3.53-3.30 (m, 2H), 1.99-1.97 (m, 2H), 1.67-1.65 (m, 2H); LCMS (ESI) m/z: 364.0 [M+H]⁺.

Compound 107

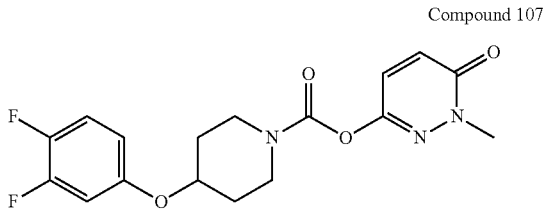 [SMILES: Cn1nc(OC(=O)N2CCC(Oc3ccc(F)c(F)c3)CC2)ccc1=O]

¹H NMR (400 MHz, Dimethylsulfoxide-d₆) δ 7.47 (d, J=10.0 Hz, 1H), 7.36 (dd, J1=9.2 Hz, J₂=20.0 Hz, 1H), 7.16-7.21 (m, 1H), 7.05 (d, J=9.6 Hz, 1H), 6.83-6.87 (m, 1H), 4.61-4.67 (m, 1H), 3.80-3.84 (m, 1H), 3.70-3.75 (m, 1H), 3.57 (s, 3H), 3.44-3.49 (m, 1H), 3.33-3.40 (m, 1H), 1.99-2.05 (m, 2H), 1.64-1.69 (m, 2H); LCMS (ESI) m/z: 366.0 [M+H]⁺.

Compound 108

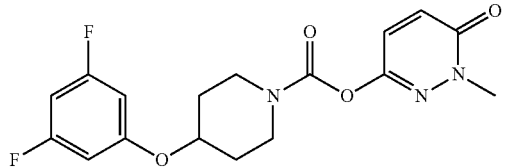

¹H NMR (400 MHz, Dimethylsulfoxide-d₆) δ 7.47 (d, J=9.6 Hz, 1H), 7.04 (d, J=9.6 Hz, 1H), 6.76-6.82 (m, 3H), 4.70-4.74 (m, 1H), 3.82-3.85 (m, 1H), 3.73-3.75 (m, 1H), 3.58 (s, 3H), 3.45-3.49 (m, 1H), 3.33-3.37 (m, 1H), 1.95-2.02 (m, 2H), 1.67-1.70 (m, 2H); LCMS (ESI) m/z: 366.0 [M+H]⁺.

Compound 109

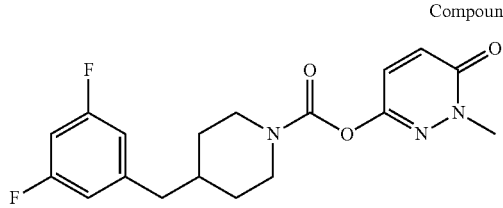

¹H NMR (400 MHz, Dimethylsulfoxide-d₆) δ 7.43 (d, J=9.6 Hz, 1H), 7.02-7.09 (m, 2H), 6.95-6.99 (m, 2H), 3.94-4.06 (m, 2H), 3.57 (s, 3H), 2.95-3.01 (m, 1H), 2.81-2.87 (m, 1H), 2.58-2.60 (m, 2H), 1.78-1.86 (m, 1H), 1.60-1.64 (m, 2H), 1.12-1.24 (m, 2H); LCMS (ESI) m/z: 364.2 [M+H]⁺.

Compound 126

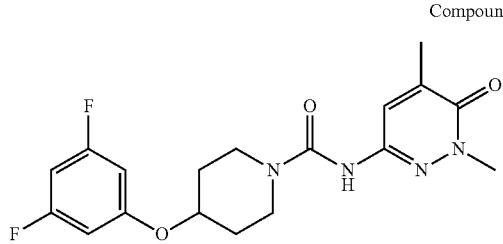

¹H NMR (400 MHz, Dimethylsulfoxide-d₆) δ 9.21 (s, 1H), 7.53 (s, 1H), 6.76 (t, J=11.1 Hz, 3H), 4.66-4.63 (m, 1H), 3.78 (d, J=13.5 Hz, 2H), 3.57 (s, 3H), 3.29-3.20 (m, 2H), 2.07 (s, 3H), 1.94 (d, J=9.3 Hz, 2H), 1.67-1.39 (m, 2H); LCMS (ESI) m/z: 379.1 [M+H]⁺.

Compound 127

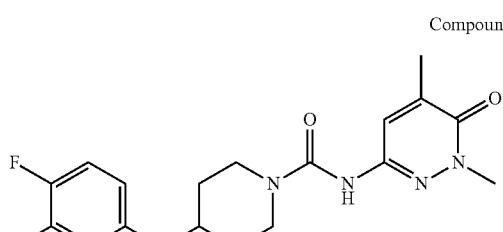

¹H NMR (400 MHz, Dimethylsulfoxide-d₆) δ 9.19 (s, 1H), 7.53 (s, 1H), 7.33 (dd, J=19.6, 9.7 Hz, 1H), 7.25-7.06

(m, 1H), 6.82-6.81 (d, J=9.6 Hz, 1H), 4.57-4.55 (m, 1H), 3.78-3.76 (d, J=14.3 Hz, 2H), 3.57 (s, 3H), 3.24-3.21 (m, 2H), 2.07 (s, 3H), 1.91-1.90 (m, 2H), 1.54-1.52 (m, 2H); LCMS (ESI) m/z: 379.0 [M+H]+.

Compound 128

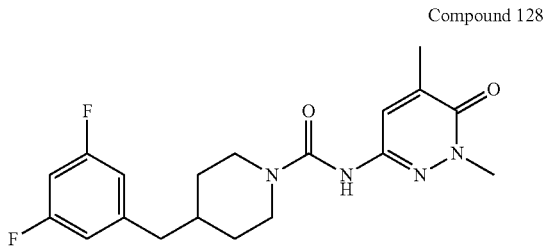 [SMILES: Cc1cc(NC(=O)N2CCC(Oc3cc(F)cc(F)c3)CC2)nn(C)c1=O]

$^{1}$H NMR (400 MHz, Dimethylsulfoxide-d$_{6}$) δ 9.07 (s, 1H), 7.51 (s, 1H), 7.03 (t, J=8.9 Hz, 1H), 6.94 (d, J=7.1 Hz, 2H), 4.04 (d, J=13.1 Hz, 2H), 3.56 (s, 3H), 2.71 (t, J=12.6 Hz, 2H), 2.55 (d, J=6.8 Hz, 2H), 2.06 (s, 3H), 1.77-1.75 (m, 1H), 1.53-1.50 (m, 2H), 1.21-0.99 (m, 2H); LCMS (ESI) m/z: 377.1 [M+H]+.

Compound 129

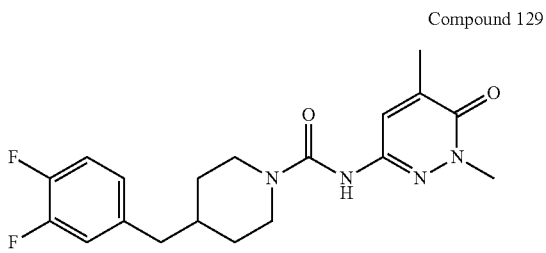 [SMILES: Cc1cc(NC(=O)N2CCC(Oc3ccc(F)c(F)c3)CC2)nn(C)c1=O]

$^{1}$H NMR (400 MHz, Dimethylsulfoxide-d$_{6}$) δ 9.06 (s, 1H), 7.51 (s, 1H), 7.30-7.28 (m, 2H), 7.03 (s, 1H), 4.04 (d, J=13.3 Hz, 2H), 3.56 (s, 3H), 2.71 (t, J=12.2 Hz, 2H), 2.53-2.51 (m, 2H), 2.03 (s, 3H), 1.72-1.70 (m, 1H), 1.53-1.50 (m, 2H), 1.23-0.94 (m, 2H); LCMS (ESI) m/z: 377.1 [M+H]+.

Example 104: Stearoyl-CoA Desaturase (SCD) is the Target of the Compounds of the Invention Materials and Methods
Strain Construction and OLE1 Replacement with SCD1 or SCD5

Strain GMYF was constructed from the ABC16/Green monster strain described in Suzuki et al. *Nat. Methods* 8(2):159-164, 2011. In this strain, YAP1 was deleted using a HIS3-MX6 cassette, and FLR1 was deleted using a NAT-MX6 cassette using standard methods. The knockout cassettes were PCR-amplified from plasmid templates (see, e.g., Bahler et al. Yeast 14(10):943-951, 1998; Longtine et al. Yeast 14(10):953-961, 1998) and transformed into yeast using lithium acetate-based transformation (Gietz et al. *Methods Mol. Biol.* 1205:1-12, 2014). The yap1::his3 deletion strain was selected on media lacking histidine and flr1::NAT on plates containing 100 µg/mL nourseothricin. All strains were confirmed by diagnostic PCR. Strain W303 pdr1Δ pdr3Δ was constructed from W303-1A (American Type Culture Collection (ATCC) 208352) by deleting PDR1 and PDR3 with kan-MX6 cassettes separately in MATa and MATα W303a isolates, mating, sporulating, and identifying double deletion haploids by tetrad dissection and identification of non-parental ditype tetrads. Strain W-erg3 was derived from W303 pdr1Δ pdr3Δ by deleting SNQ2 with NAT-MX6, YAP1 with HIS3-MX6, and ERG3 with BleMX.

Strain ApoE-mga2Δ was generated by amplifying 1000 base pairs (bp) upstream and downstream of the MGA2 ORF in a strain in which MGA2 was deleted using a G418 (GENETICIN®) resistance cassette (kanMX) (Piotrowski et al. *Proc. Natl. Acad. Sci.* USA 112(12):E1490-1497, 2015) and transforming the resulting deletion cassette into the ApoE4 strain in the BY4741 (ATCC 201388) genetic background. The ApoE strain is described, for example, in International Patent Application Publication No. WO 2016/040794, which is incorporated herein by reference in its entirety.

The alpha-synuclein expression strain was made in the same manner as described in Su et al. *Dis. Model Mech.* 3(3-4):194-208, 2010, except that the alpha-synuclein construct lacked the green fluorescent protein (GFP) tag.

Strain ole1Δ (yeast ole1 deletion mutant) was constructed by deleting OLE1 with NAT-MX6 in BY4741, amplifying the deletion cassette from the genomic DNA of the resulting strain with primers flanking the ORF by 1000 bp upstream and downstream, transforming the resulting deletion cassette into W303 pdr1Δ pdr3Δ, and plating transformants on YPD media containing G418 (200 µg/mL) and nourseothricin (100 µg/mL) with 0.01% TWEEN®-20 and 0.5 mM oleic and palmitoleic acids.

To generate yeast strains expressing SCD1 or SCD5 as the sole desaturase, the human SCD1 and SCD5 genes were cloned from cDNAs (Harvard PlasmID database Clone ID HsCD00340237 for SCD1 and HsCD00342695 for SCD5) into yeast plasmid pRS316 (ATCC 77145) between the yeast TDH3 promoter and the CYC1 terminator. The coding sequence of yeast OLE1 was also cloned into this plasmid). These clones were then transformed into the ole1Δ strain and plated on CSM-Ura media (CSM lacking uracil) with 2% glucose (w/v) and independent colonies were isolated and amplified.

Compound Profiling Methods

All compound profiling experiments were performed using the same basic protocol. Different genetic backgrounds (e.g., gene deletions) or conditions (e.g., addition of oleic and palmitoleic acid) were replaced as indicated below.

Yeast were cultured using standard techniques in complete synthetic media (CSM) and yeast nitrogen base supplemented with 2% (w/v) carbon source (glucose, raffinose, or galactose) to regulate the expression of the toxic disease protein. An initial starter culture was inoculated in 3 mL CSM-Glucose media and incubated overnight in a 30° C. shaker incubator (225 rpm). Saturated morning cultures were then diluted 1:20 in fresh CSM-Raffinose media and grown for 6 h to an OD$_{600}$ (optical density) of ~0.4-0.8 at 30° C. with shaking.

Compound stocks (10 mM in 100% DMSO) were arrayed into 384 round well, v-bottom polypropylene plates and diluted according to indicated dilution factors. Compound administration was performed in two separate steps. First, 15 µL of CSM-Galactose (induces expression of toxic protein) was dispensed into clear 384 well assay plates using a MULTIDROP™ Combi reagent dispenser. The diluted compound stock plates were then applied to the assay plates using an automated workstation (Perkin Elmer JANUS™) outfitted with a 384 pin tool containing slotted pins that deliver 100 nL of compound. The cultures described above were then diluted to a 2× concentration (0.03 and 0.08 for alpha-synuclein and ApoE, final OD$_{600}$ of 0.015 and 0.04) in CSM-Galactose. For wild-type and Ole1/SCD1/SCD5 plasmid-containing strains, the 2× cell density was 0.02. In all experiments, 15 μL culture was then dispensed into the pinned assay plate to achieve 30 μL of the 1× $OD_{600}$ culture and a top drug concentration of 33.3 μM.

After yeast delivery, assay plates were incubated under humidified conditions at 30° C. for 24 to 40 h. ApoE4 rescue experiments were stopped at 24 h, aSyn experiments at 40 h, Ole1 at 24 h, and SCD1/SCD5 at 40 h. The growth of yeast was monitored by reading the $OD_{600}$ of each well using a microplate reader (Perkin Elmer EnVision™). Data were analyzed as follows. For model rescue experiments, raw data were processed by background subtracting and calculating a fold-change relative to DMSO control [(EXP-0.035)/(DMSO-0.035)—where 0.035 is the $OD_{600}$ contributed by an empty well containing 30 μL of media alone]. For growth inhibition of wild-type cells, raw data were processed by background subtracting and converting values to a percent of the nontreated condition for that strain [(EXP-0.035)/(DMSO-0.035)×100%].

Compound Sources

Compounds were sourced as follows: cycloheximide (Sigma Aldrich), A939572 (Abcam), CAY10566 (Abcam), MF-438 (Calbiochem), MK-8245 (Selleckchem), oleic acid (Sigma Aldrich), palmitoleic acid (Acros organics), mycophenolic acid (Sigma Aldrich), and tunicamycin (Cayman Chemical).

Drug Resistant Mutant Selection

Strains GMYF and W-erg3 were grown to saturation in CSM-glucose, centrifuged, resuspended in phosphate-buffered Saline (PBS), and plated at a density of $10^7$ cells/plate on solid 15 cm petri dishes containing CSM with 2% galactose (w/v), 2% (w/v) agar, and 10 μM Compound 155, and incubated at 30° C. Resistant colonies were isolated after 5-7 days, re-streaked on the same media, and resistance reconfirmed. Cultures of validated strains were then inoculated for genomic DNA isolation using a YeaStar™ yeast genomic DNA kit (Zymo Research).

Libraries were prepared for sequencing using the Illumina NEXTERA™ library prep kit and sequenced via Illumina HiSeq™ 2500 1X50 bp (single end reads). Sequences were aligned to the *S. cerevisiae* reference genome (S288CCR64-1-1, *Saccharomyces* Genome Database (SGD)) using Burrows-Wheeler Aligner (BWA, see, e.g., Li et al. *Bioinformatics* 25:1754-1760, 2009; Li et al. *Bioinformatics* 2010, Epub (PMID 20080505)). The BWA output SAI files were converted to SAM files using BWA. The SAM files were sorted using SAMtools 1.3.1 (Li et al. *Bioinformatics* 25:2079-2079, 2009). Variants (single-nucleotide polymorphisms (SNPs), indels) were identified using Freebayes (see, e.g., arXiv:1207.3907). Variant locations were summarized using snpEFF (Cingolani et al. Fly (Austin) 6(2):80-92, 2012).

Quantitative Lipid Profiling

Overnight cultures of yeast strain W303 pdr1Δ pdr3Δ were diluted into CSM media with 2% (w/v) raffinose, $OD_{600}$ 0.25, and grown for 4 h before resuspending at an $OD_{600}$ of 0.2 in CSM media with 2% (w/v) galactose and adding Compound 95 or DMSO at the indicated concentrations. Cells were grown for the indicated timepoints before centrifugation, washing once in PBS, and freezing pellets. Lipids were extracted from pellets by resuspending the pellets in 600 μL methanol, 300 μL water, and 400 μL chloroform, followed by cell lysis by vortexing with glass beads for 1 min. Samples were then centrifuged at 10,000×g for 10 mM, and the bottom layer that formed (organic/lipids) was moved into a new tube and evaporated. Samples were then analyzed by LC/MS/MS using a Thermo Scientific Q Exactive™ Orbitrap™ coupled to a Dionex UltiMate® 3000 ultra-high performance liquid chromatography system, following the method described in Tafesse et al. PLoS Pathog. 11(10): el 005188, 2015.

Example 105. Inhibition of SDC1, and SCD5 by Compounds of the Invention

Using the methods described above, the inhibition of SCD1 and SCD5 was tested for the compounds of the invention. The results are shown in Table 2.

TABLE 2

Inhibition of SCD1 and SCD5 by Compounds of the Invention

| # | SCD1 IC50 (μM) | SCD5 IC50 (μM) | # | SCD1 IC50 (μM) | SCD5 IC50 (μM) |
|---|---|---|---|---|---|
| 27 | 17.00 | >45 | 53 | 1.18 | 0.13 |
| 28 | 8.10 | >45 | 89 | 0.26 | 0.06 |
| 29 | 0.42 | 2.80 | 90 | 10.34 | 7.18 |
| 30 | 0.33 | 2.90 | 71 | 13.31 | 4.96 |
| 23 | 1.30 | 1.80 | 70 | >45 | >45 |
| 24 | 1.10 | 2.90 | 62 | 0.39 | 0.02 |
| 5 | >45 | >45 | 52 | 2.40 | 0.33 |
| 39 | 1.35 | 1.38 | 44 | 2.21 | 1.17 |
| 12 | 27.05 | 6.94 | 125 | 4.96 | 1.15 |
| 68 | 0.26 | 0.06 | 45 | 1.68 | 0.22 |
| 13 | 3.86 | 2.11 | 59 | >45 | 11.00 |
| 106 | 1.17 | 0.57 | 133 | >45 | >45 |
| 4 | >45 | 24.66 | 134 | >45 | >45 |
| 37 | 12.67 | 4.36 | 36 | 25.50 | 5.35 |
| 6 | 22.84 | 3.12 | 82 | 0.05 | 0.02 |
| 40 | 0.54 | 0.05 | 83 | 4.36 | 6.21 |
| 55 | 0.16 | 0.02 | 101 | >45 | >45 |
| 51 | 0.68 | 0.06 | 96 | >45 | 26.38 |
| 49 | 8.10 | 0.43 | 99 | 32.48 | 6.87 |
| 8 | 2.32 | 0.83 | 97 | >45 | 26.09 |
| 9 | 14.39 | 4.22 | 84 | 0.43 | 0.17 |
| 7 | >45 | 5.01 | 85 | 0.08 | 0.05 |
| 69 | 0.42 | 0.15 | 86 | 0.01 | 0.01 |
| 136 | >45 | >45 | 98 | 5.18 | 1.35 |
| 130 | >45 | 15.84 | 100 | 4.49 | 0.22 |
| 79 | 0.48 | 0.20 | 131 | 6.80 | 2.00 |
| 80 | 1.98 | 1.19 | 132 | 11.00 | 4.00 |
| 58 | >45 | 10.37 | 57 | 9.20 | 2.60 |
| 50 | 17.11 | 2.46 | 77 | 0.91 | 0.74 |
| 109 | >45 | 4.85 | 74 | 0.02 | 0.04 |
| 14 | 4.70 | 2.76 | 76 | 9.77 | 4.80 |
| 108 | 9.00 | 5.01 | 87 | >45 | >45 |
| 107 | >45 | 7.93 | 56 | >45 | >45 |
| 33 | 0.44 | 0.14 | 15 | 12.36 | 0.86 |
| 41 | 2.71 | 0.14 | 111 | >45 | 0.61 |
| 25 | 2.75 | 5.29 | 117 | 2.00 | 0.03 |
| 26 | 4.15 | 5.68 | 16 | 0.35 | 0.59 |
| 3 | 11.27 | 20.75 | 112 | 0.50 | 0.60 |
| 135 | 1.70 | 5.08 | 123 | 4.90 | 1.40 |
| 31 | 39.00 | >45 | 20 | 2.70 | 1.40 |
| 32 | 7.20 | 21.00 | 21 | 10.00 | 3.00 |
| 22 | 2.59 | 0.95 | 124 | 26.00 | 0.14 |
| 115 | 0.45 | 0.01 | 114 | 1.70 | 0.01 |
| 122 | 13.56 | 1.73 | 19 | 9.72 | 1.00 |
| 113 | >45 | 0.38 | 118 | 26.32 | 0.07 |
| 116 | 0.86 | 0.01 | 121 | 0.18 | 0.01 |
| 17 | 0.72 | 0.01 | 119 | >45 | 0.16 |
| 38 | 17.18 | 6.37 | 18 | >45 | 1.93 |
| 128 | 0.05 | 0.02 | 34 | >45 | 8.20 |
| 129 | 0.31 | 0.08 | 35 | >45 | 20.35 |
| 126 | 0.04 | 0.04 | 88 | 0.07 | 0.03 |
| 127 | 0.20 | 0.20 | 60 | 3.90 | 1.10 |
| 81 | 0.06 | 0.15 | 46 | 0.64 | 0.03 |
| 78 | 0.17 | 0.01 | 66 | 6.50 | 0.92 |
| 67 | 3.98 | 2.10 | 47 | >45 | >45 |
| 72 | 0.43 | 0.28 | 48 | >45 | >45 |
| 75 | 0.22 | 0.07 | 1 | 14.00 | 3.80 |
| 73 | 31.90 | 12.54 | 2 | >45 | >45 |
| 54 | 0.44 | 0.04 | 94 | >45 | >45 |
| 63 | 0.13 | 0.01 | 95 | >45 | 12.00 |

TABLE 2-continued

Inhibition of SCD1 and SCD5 by Compounds of the Invention

| # | SCD1 IC50 (µM) | SCD5 IC50 (µM) | # | SCD1 IC50 (µM) | SCD5 IC50 (µM) |
|---|---|---|---|---|---|
| 65 | 8.15 | 1.49 | 93 | >45 | 15.00 |
| 42 | 0.44 | 0.03 | 92 | 2.40 | 0.39 |
| 43 | 8.58 | 2.24 | 91 | >45 | >45 |
| 64 | 0.05 | 0.01 | 104 | >45 | >45 |
| 61 | 0.08 | 0.04 | 11 | >45 | >45 |
| 10 | >45 | >45 | 105 | >45 | >45 |

Other Embodiments

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A method of treating a primary brain cancer in a subject in need thereof, the method comprising administering an effective amount of the compound of formula (I):

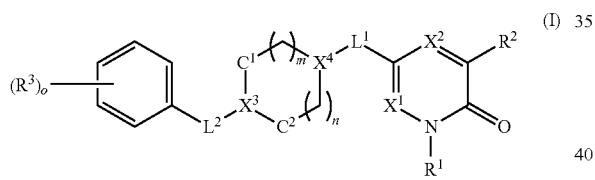

wherein:
m is 0 or 1;
n is 0, 1, or 2;
o is 0, 1, 2, 3, 4, or 5;
$C^1$ and $C^2$ optionally combine to form a bond;
each of $R^1$, $R^2$, $R^5$, and $R^6$ is, independently, H or optionally substituted $C_{1-6}$ alkyl;
$R^3$ is halo, cyano, $C_{1-6}$ perfluoroalkyl, optionally substituted $C_{1-6}$ alkoxy, or optionally substituted $C_{1-6}$ alkyl;
each of $X^1$ and $X^2$ is, independently, CH or N, wherein $X^1$ and $X^2$ are not both N;
$X^3$ is $CR^4$ or N; or $X^3$ and $C^1$ or $C^2$ combine to form an optionally substituted alkene;
$X^4$ is CH or N;
wherein at least one of $X^3$ and $X^4$ is N;
$R^4$ is H, $OR^6$, optionally substituted $C_{1-6}$ alkyl, or halo;
$L^1$ is —C(O)—$X^5$— or optionally substituted $C_{5-10}$ heteroaryl;
$X^5$ is NH, O, or optionally substituted $C_{1-6}$ alkyl; and
$L^2$ is O, $NR^5$, optionally substituted $C_{1-6}$ alkyl, optionally substituted $C_{1-6}$ heteroalkyl, or absent; or $X^3$ and $L^2$ combine to form an optionally substituted alkene,
or a pharmaceutically acceptable salt thereof;
wherein the compound does not have a structure selected from the group consisting of:

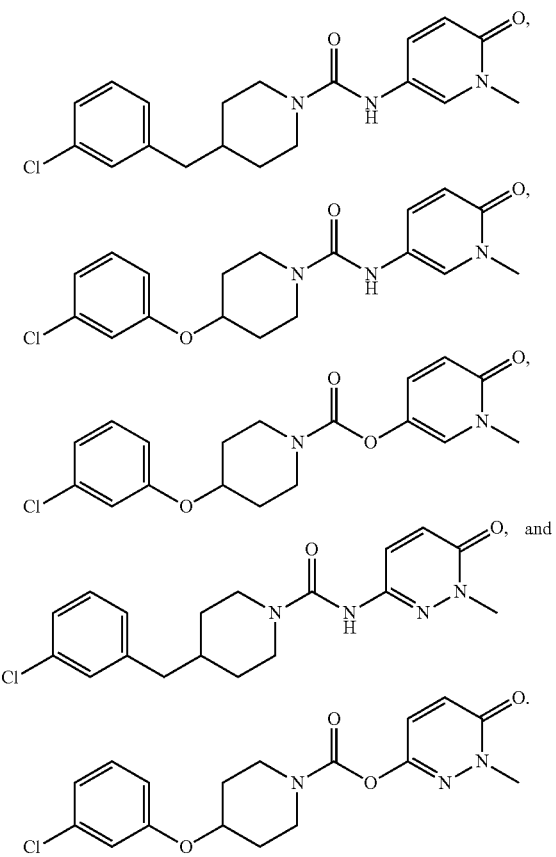

2. The method of claim 1, wherein the compound has the structure of formula (II):

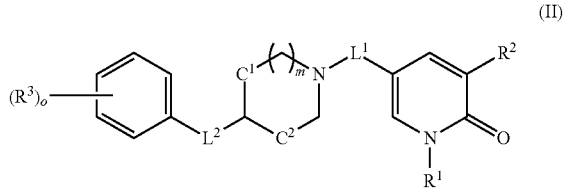

wherein:
m is 0 or 1;
o is 0, 1, 2, 3, 4, or 5;
$C^1$ and $C^2$ optionally combine to form a bond;
each of $R^1$, $R^2$, and $R^5$ is, independently, H or optionally substituted $C_{1-6}$ alkyl;
$R^3$ is halo, cyano, $C_{1-6}$ perfluoroalkyl, optionally substituted $C_{1-6}$ alkoxy, or optionally substituted $C_{1-6}$ alkyl;
$L^1$ is —C(O)—$X^5$— or optionally substituted $C_{5-10}$ heteroaryl;
$X^5$ is NH, O, or optionally substituted $C_{1-6}$ alkyl; and
$L^2$ is O, $NR^5$, optionally substituted $C_{1-6}$ alkyl, optionally substituted $C_{1-6}$ heteroalkyl, or absent;
or a pharmaceutically acceptable salt thereof;
wherein the compound does not have the structure selected from the group consisting of:

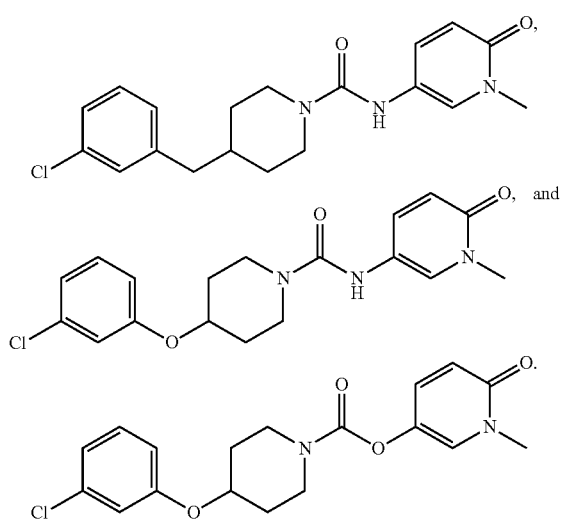

3. The method of claim 1, wherein the compound has the structure of formula (III):

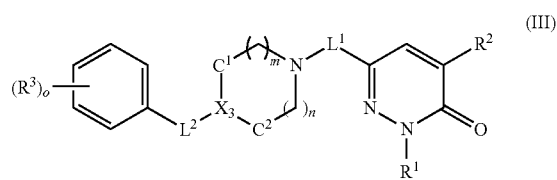

wherein:
m is 0 or 1;
n is 0, 1, or 2;
o is 0, 1, 2, 3, 4, or 5;
$C^1$ and $C^2$ optionally combine to form a bond;
each of $R^1$, $R^2$, $R^5$, and $R^6$ is, independently, H or optionally substituted $C_{1-6}$ alkyl;
$R^3$ is halo, cyano, $C_{1-6}$ perfluoroalkyl, optionally substituted $C_{1-6}$ alkoxy, or optionally substituted $C_{1-6}$ alkyl;
$X^3$ is $CR^4$ or N; or $X^3$ and $C^1$ or $C^2$ combine to form an optionally substituted alkene;
$R^4$ is H, $OR^6$, optionally substituted $C_{1-6}$ alkyl, or halo;
$L^1$ is —C(O)—$X^5$— or optionally substituted $C_{5-10}$ heteroaryl;
$X^5$ is NH, O, or optionally substituted $C_{1-6}$ alkyl; and
$L^2$ is O, $NR^5$, optionally substituted $C_{1-6}$ alkyl, optionally substituted $C_{1-6}$ heteroalkyl, or absent; or $X^3$ and $L^2$ combine to form an optionally substituted alkene,
or a pharmaceutically acceptable salt thereof;
wherein the compound does not have the structure selected from the group consisting of:

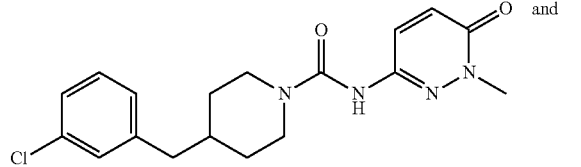

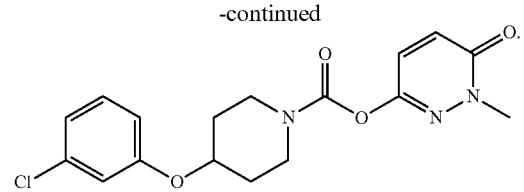

4. The method of claim 3, wherein the compound has the structure of formula (III-A):

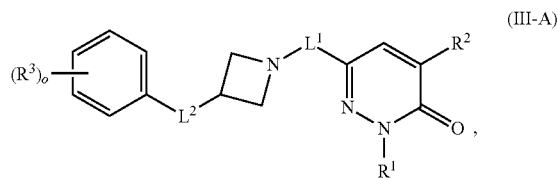

or
the structure of formula (III-B);

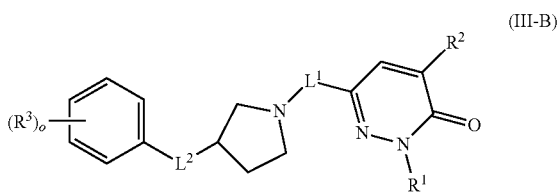

wherein:
o is 0, 1, 2, 3, 4, or 5;
each of $R^1$, $R^2$, and $R^5$ is, independently, H or optionally substituted $C_{1-6}$ alkyl;
$R^3$ is halo, cyano, $C_{1-6}$ perfluoroalkyl, optionally substituted $C_{1-6}$ alkoxy, or optionally substituted $C_{1-6}$ alkyl;
$L^1$ is —C(O)—$X^5$— or optionally substituted $C_{5-10}$ heteroaryl;
$X^5$ is NH, O, or optionally substituted $C_{1-6}$ alkyl; and
$L^2$ is O, $NR^5$, optionally substituted $C_{1-6}$ alkyl, optionally substituted $C_{1-6}$ heteroalkyl, or absent;
or a pharmaceutically acceptable salt thereof.

5. The method of claim 3, wherein the compound has the structure of formula (III-C):

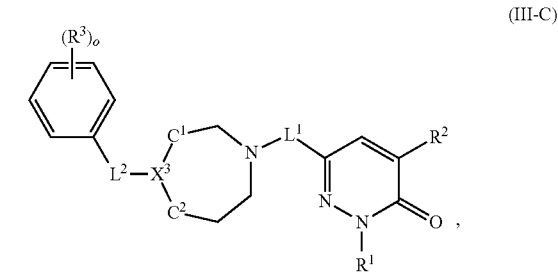

or the compound has the structure of formula (III-D):

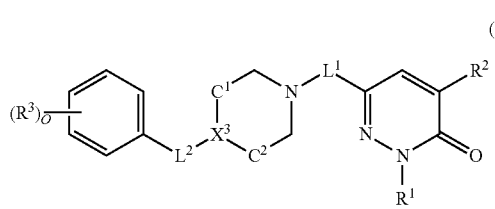
(III-D)

wherein:

o is 0, 1, 2, 3, 4, or 5;

$C^1$ and $C^2$ optionally combine to form a bond;

each of $R^1$, $R^2$, $R^5$, and $R^6$ is, independently, H or optionally substituted $C_{1-6}$ alkyl;

$R^3$ is halo, cyano, $C_{1-6}$ perfluoroalkyl, optionally substituted $C_{1-6}$ alkoxy, or optionally substituted $C_{1-6}$ alkyl;

$X^3$ is $CR^4$ or N; or $X^3$ and $C^1$ or $C^2$ combine to form an optionally substituted alkene;

$R^4$ is H, $OR^6$, optionally substituted $C_{1-6}$ alkyl, or halo;

$L^1$ is —C(O)—$X^5$— or optionally substituted $C_{5-10}$ heteroaryl;

$X^5$ is NH, O, or optionally substituted $C_{1-6}$ alkyl; and $L^2$ is O, $NR^5$, optionally substituted $C_{1-6}$ alkyl, optionally substituted $C_{1-6}$ heteroalkyl, or absent; or $X^3$ and $L^2$ combine to form an optionally substituted alkene, or a pharmaceutically acceptable salt thereof;

wherein the compound does not have the structure selected from the group consisting of:

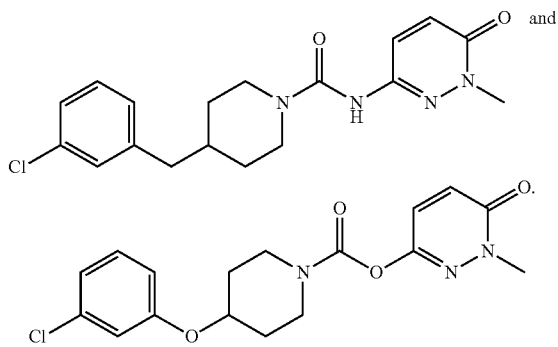

and

6. The method of claim 5, wherein the compound has the structure of formula (III-D-1):

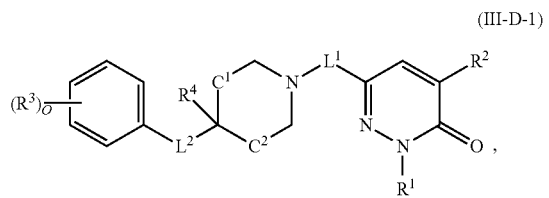
(III-D-1)

or the structure of formula (III-D-2):

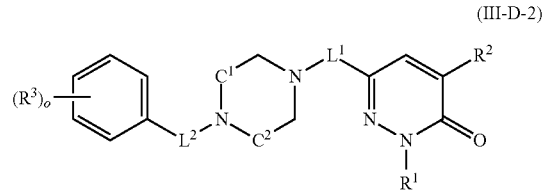
(III-D-2)

wherein:

o is 0, 1, 2, 3, 4, or 5;

$C^1$ and $C^2$ optionally combine to form a bond;

each of $R^1$, $R^2$, $R^5$, and $R^6$ is, independently, H or optionally substituted $C_{1-6}$ alkyl;

$R^3$ is halo, cyano, $C_{1-6}$ perfluoroalkyl, optionally substituted $C_{1-6}$ alkoxy, or optionally substituted $C_{1-6}$ alkyl;

$R^4$ is H, $OR^6$, optionally substituted $C_{1-6}$ alkyl, or halo;

$L^1$ is —C(O)—$X^5$— or optionally substituted $C_{5-10}$ heteroaryl;

$X^5$ is NH, O, or optionally substituted $C_{1-6}$ alkyl; and $L^2$ is O, $NR^5$, optionally substituted $C_{1-6}$ alkyl, optionally substituted $C_{1-6}$ heteroalkyl, or absent;

or a pharmaceutically acceptable salt thereof;

wherein the compound does not have the structure selected from the group consisting of:

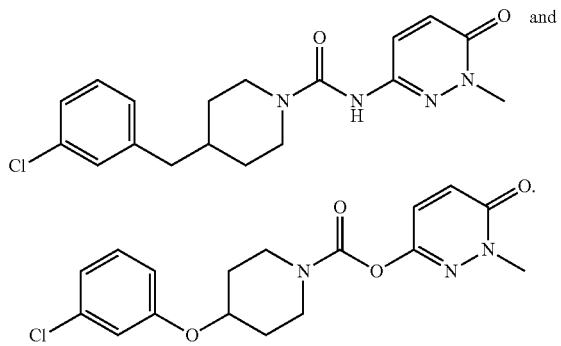

and

7. The method of claim 1, wherein the compound has the structure of formula (IV):

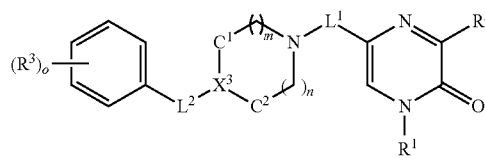
(IV)

wherein:

m is 0 or 1;

n is 0, 1, or 2;

o is 0, 1, 2, 3, 4, or 5;

$C^1$ and $C^2$ optionally combine to form a bond;

each of $R^1$, $R^2$, $R^5$, and $R^6$ is, independently, H or optionally substituted $C_{1-6}$ alkyl;

$R^3$ is halo, cyano, $C_{1-6}$ perfluoroalkyl, optionally substituted $C_{1-6}$ alkoxy, or optionally substituted $C_{1-6}$ alkyl;

$X^3$ is $CR^4$ or N; or $X^3$ and $C^1$ or $C^2$ combine to form an optionally substituted alkene;
$R^4$ is H, $OR^6$, optionally substituted $C_{1-6}$ alkyl, or halo;
$L^1$ is —C(O)—$X^5$— or optionally substituted $C_{5-10}$ heteroaryl;
$X^5$ is NH, O, or optionally substituted $C_{1-6}$ alkyl; and
$L^2$ is O, $NR^5$, optionally substituted $C_{1-6}$ alkyl, optionally substituted $C_{1-6}$ heteroalkyl, or absent; or $X^3$ and $L^2$ combine to form an optionally substituted alkene,
or a pharmaceutically acceptable salt thereof.

8. The method of claim 7, wherein the compound has the structure of formula (IV-A):

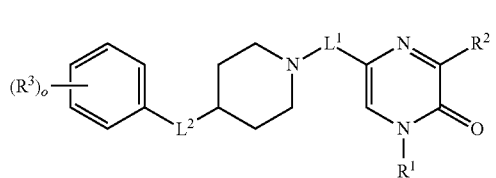

(IV-A)

wherein:
o is 0, 1, 2, 3, 4, or 5;
each of $R^1$, $R^2$, and $R^5$ is, independently, H or optionally substituted $C_{1-6}$ alkyl;
$R^3$ is halo, cyano, $C_{1-6}$ perfluoroalkyl, optionally substituted $C_{1-6}$ alkoxy, or optionally substituted $C_{1-6}$ alkyl;
$L^1$ is —C(O)—$X^5$— or optionally substituted $C_{5-10}$ heteroaryl;
$X^5$ is NH, O, or optionally substituted $C_{1-6}$ alkyl; and
$L^2$ is O, $NR^5$, optionally substituted $C_{1-6}$ alkyl, optionally substituted $C_{1-6}$ heteroalkyl, or absent;
or a pharmaceutically acceptable salt thereof.

9. The method of claim 1, wherein the compound has the structure of formula (V):

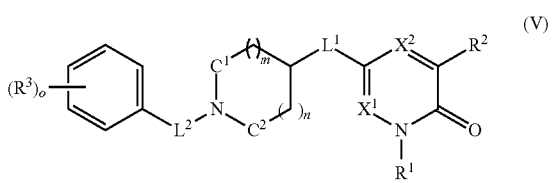

(V)

wherein:
m is 0 or 1;
n is 0, 1, or 2;
o is 0, 1, 2, 3, 4, or 5;
$C^1$ and $C^2$ optionally combine to form a bond;
each of $R^1$, $R^2$, $R^5$, and $R^6$ is, independently, H or optionally substituted $C_{1-6}$ alkyl;
$R^3$ is halo, cyano, $C_{1-6}$ perfluoroalkyl, optionally substituted $C_{1-6}$ alkoxy, or optionally substituted $C_{1-6}$ alkyl;
each of $X^1$ and $X^2$ is, independently, CH or N, wherein $X^1$ and $X^2$ are not both N;
$L^1$ is —C(O)—$X^5$— or optionally substituted $C_{5-10}$ heteroaryl;
$X^5$ is NH, O, or optionally substituted $C_{1-6}$ alkyl; and
$L^2$ is O, $NR^5$, optionally substituted $C_{1-6}$ alkyl, optionally substituted $C_{1-6}$ heteroalkyl, or absent;
or a pharmaceutically acceptable salt thereof.

10. The method of claim 1, wherein $R^1$ is H, methyl or ethyl, or $R^2$ is H or methyl.

11. The method of claim 1, wherein $L^1$ is

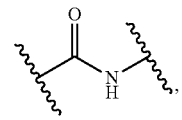

or $L^2$ is O or optionally substituted $C_{1-6}$ alkyl.

12. The method of claim 1, wherein o is 1 or 2.

13. The method of claim 1, wherein $R^3$ is halo.

14. The method of claim 1, wherein the compound is administered as a pharmaceutical composition comprising the compound, or a pharmaceutically acceptable salt thereof, and a pharmaceutically acceptable excipient.

15. The method of claim 1, wherein the primary brain cancer is a glioma.

16. The method of claim 15, wherein the glioma is an astrocytoma.

17. The method of claim 16, wherein the astrocytoma is a glioblastoma.

18. The method of claim 1, wherein the cancer is determined or predicted to be resistant to one or more chemotherapeutic agents.

19. The method of claim 1, wherein the cancer has failed to respond to one or more chemotherapeutic agents.

20. The method of claim 19, wherein the one or more chemotherapeutic agents is selected from the group consisting of: temozolomide, carmustine, bevacizumab, lomustine, everolimus, vincristine, and procarbazine.

21. The method of claim 20, wherein the one or more chemotherapeutic agents is temozolomide.

22. The method of claim 1, wherein the subject is further administered one or more additional therapeutic interventions.

23. The method of claim 22, wherein the one or more additional therapeutic interventions comprises surgery, radiation, and/or one or more additional chemotherapeutic agents.

24. The method of claim 1, wherein the compound is selected from the group consisting of:

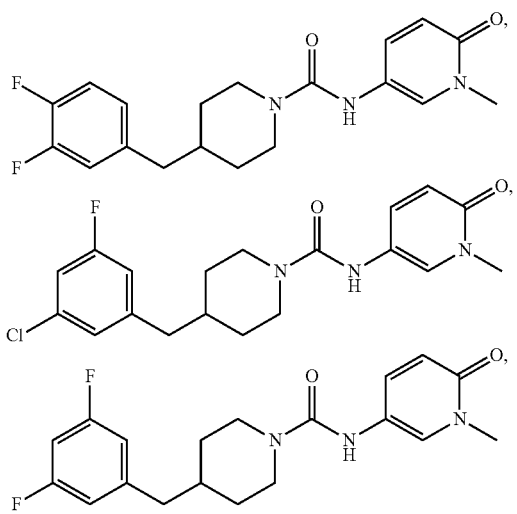

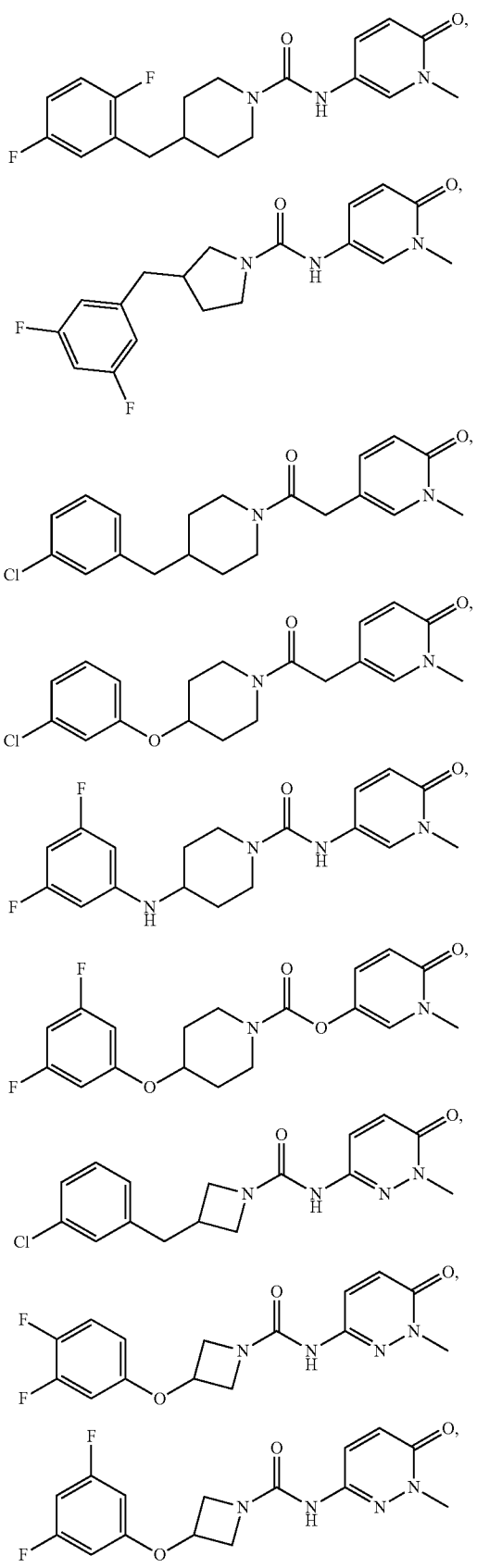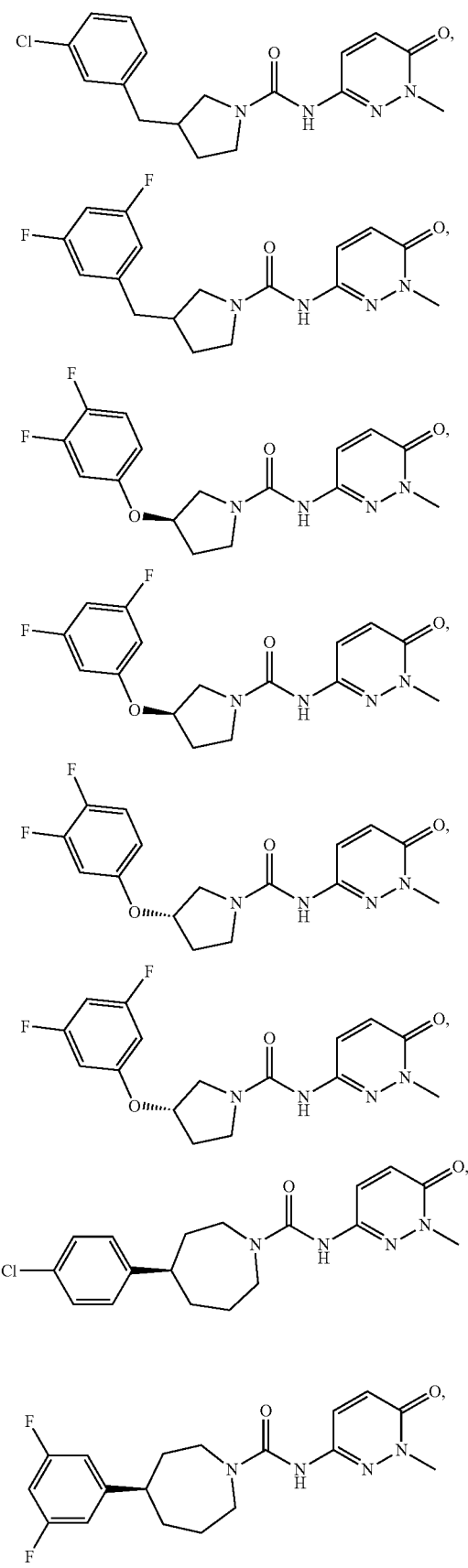

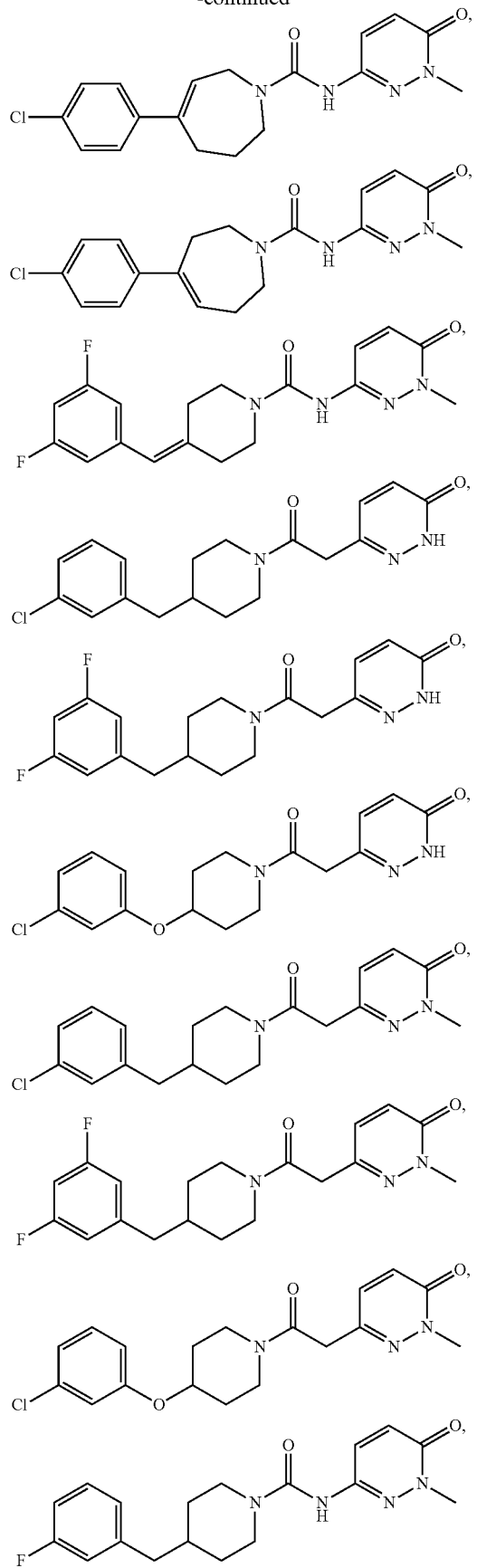
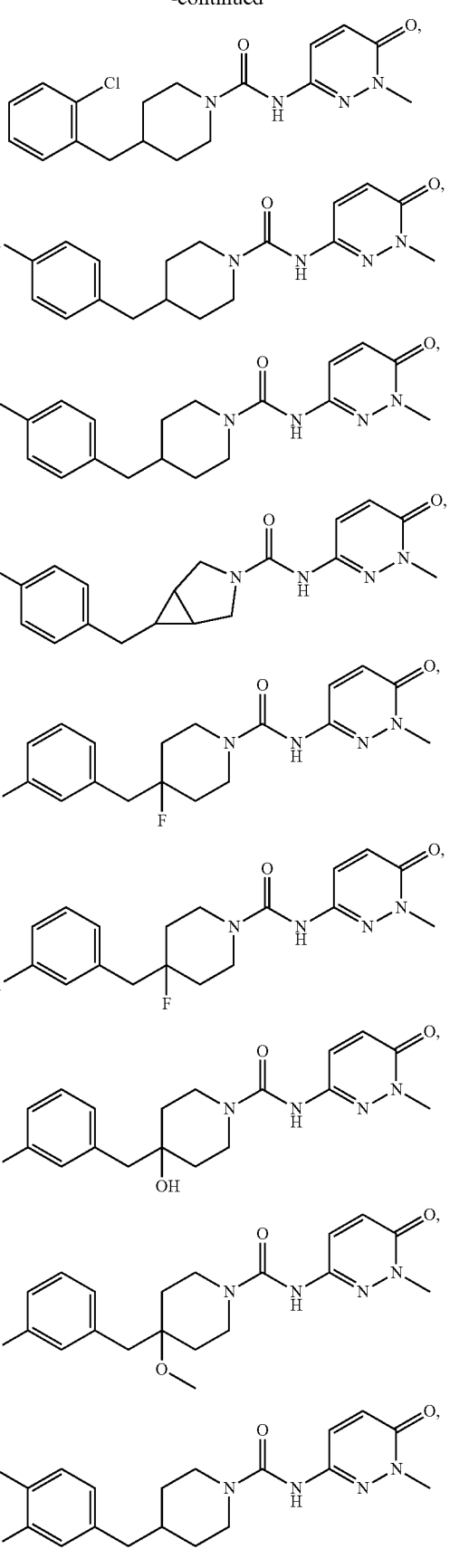

307
-continued
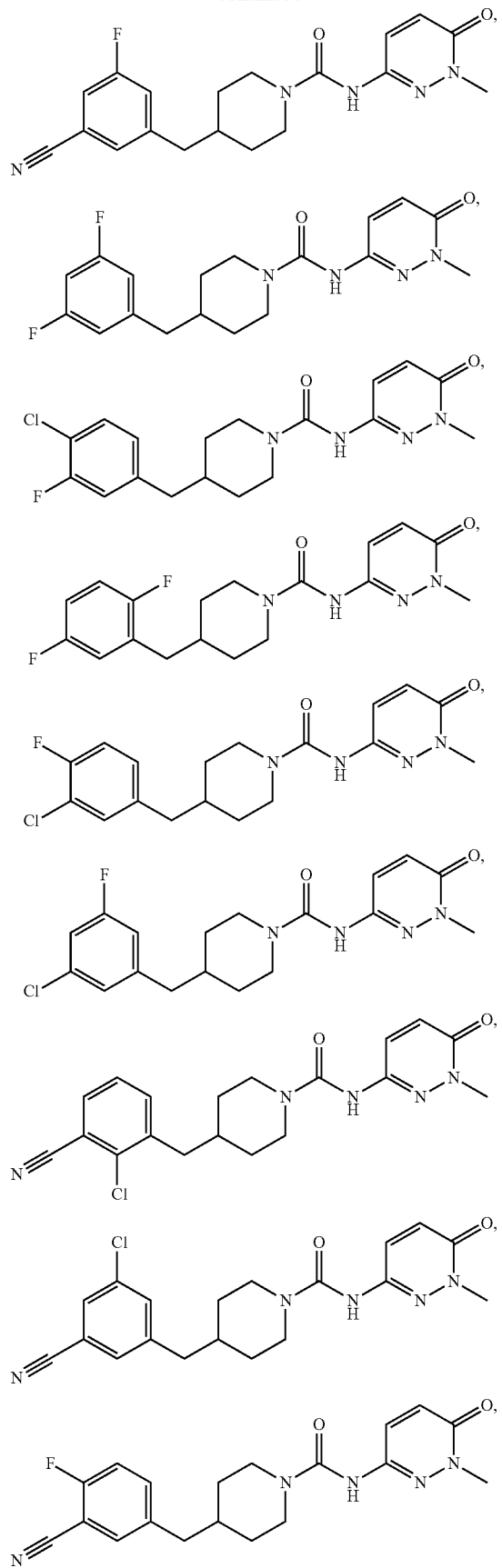
308
-continued
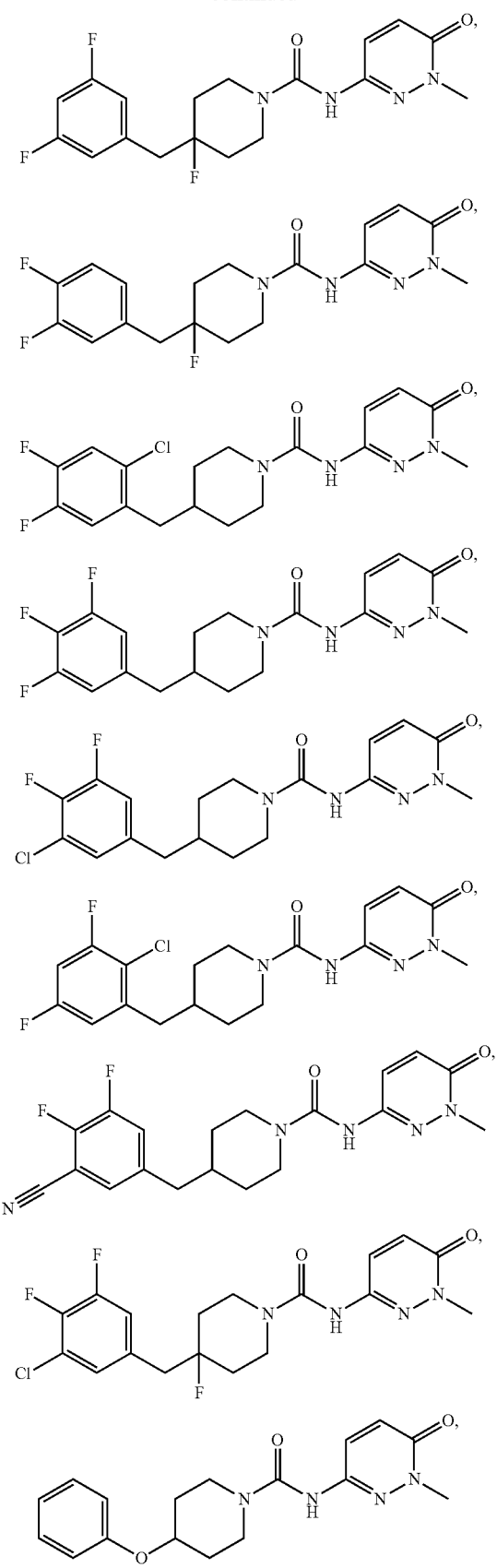

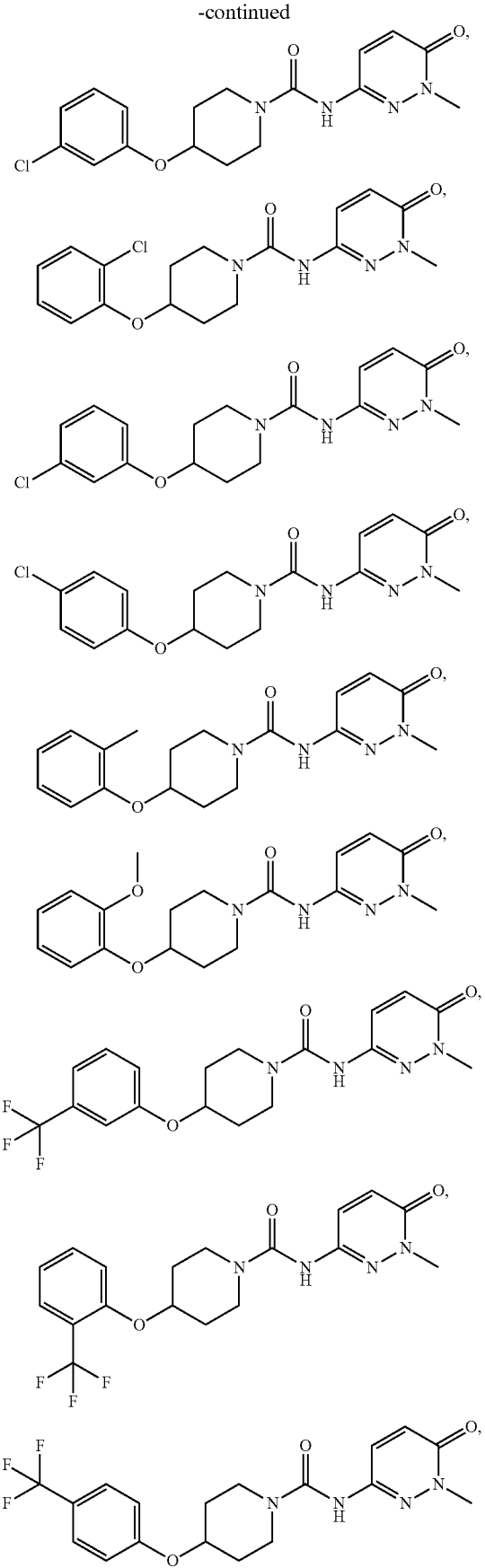
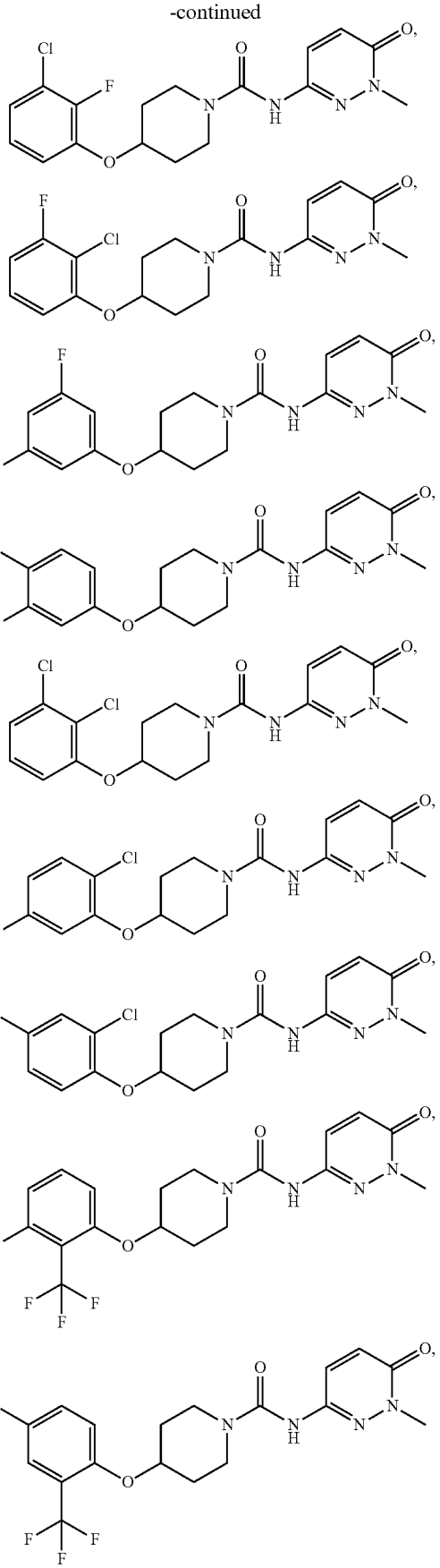

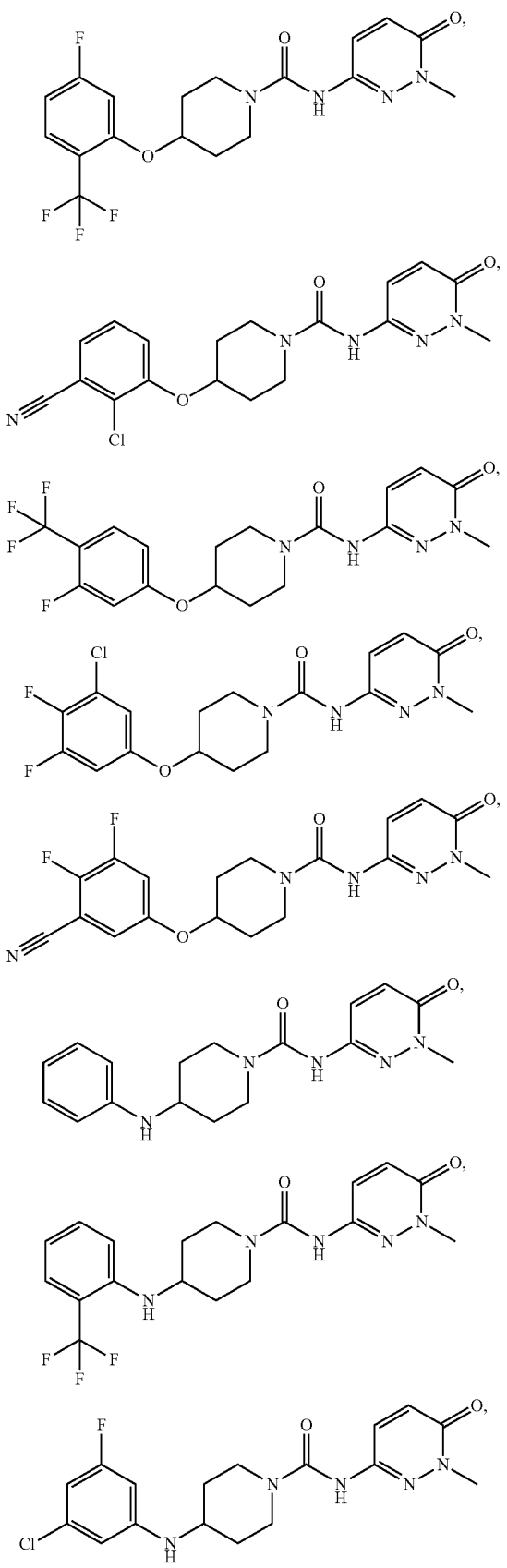
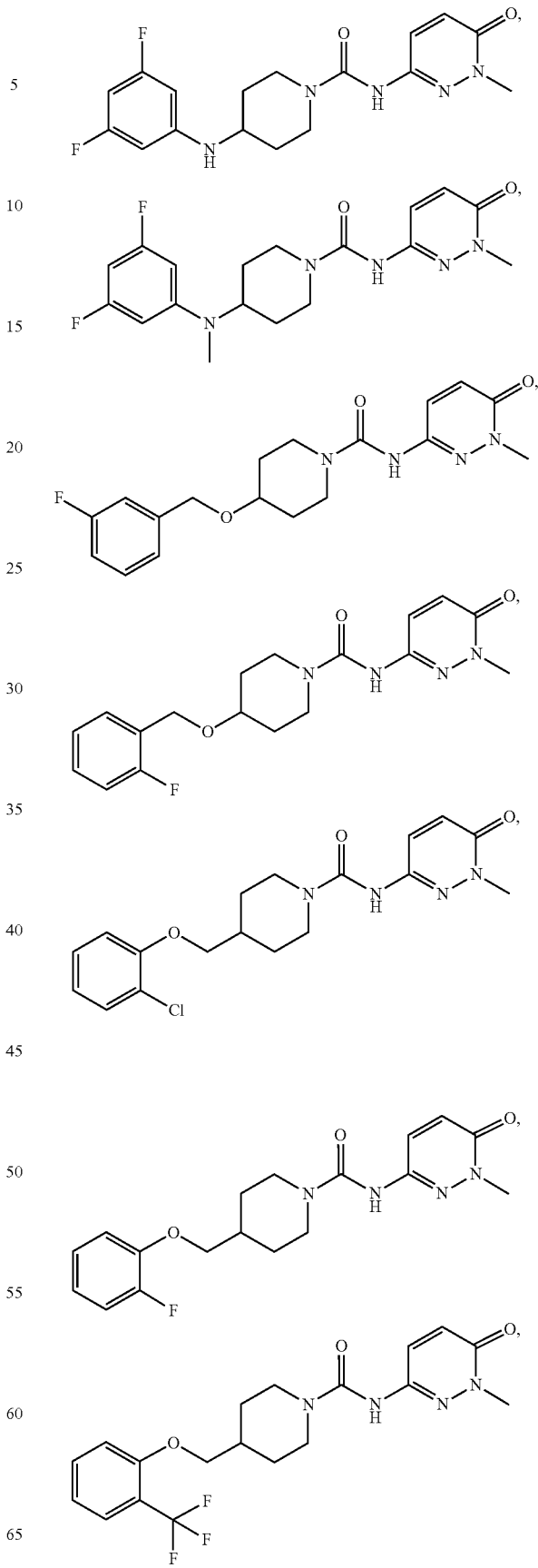

313
-continued
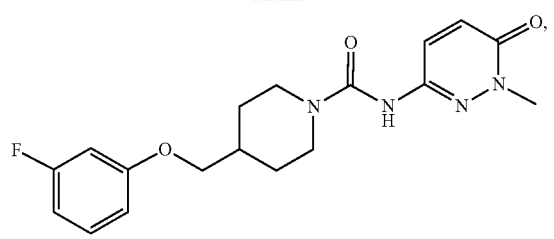
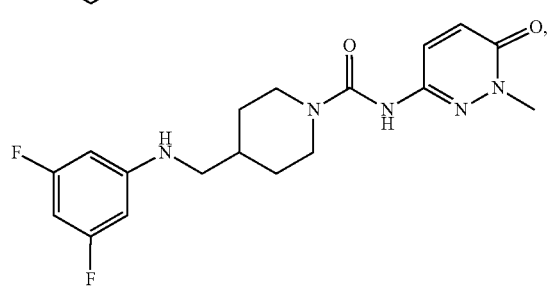
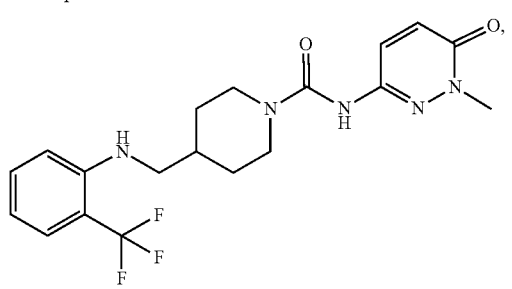
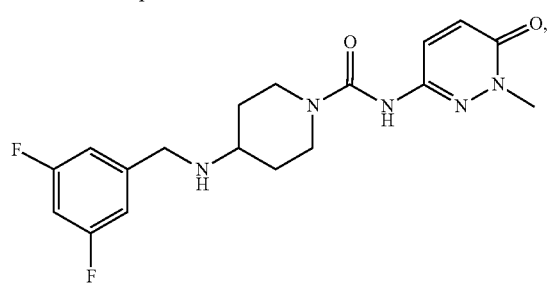
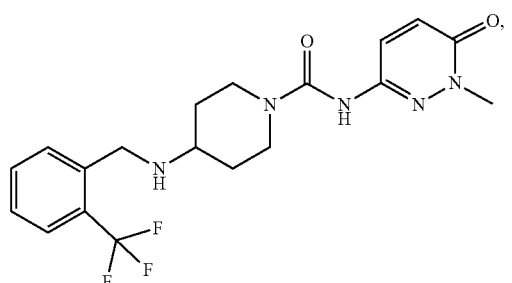
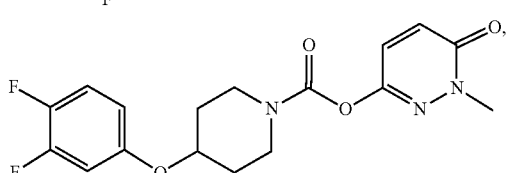
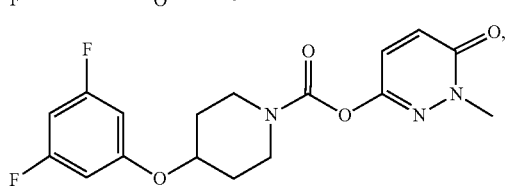
314
-continued
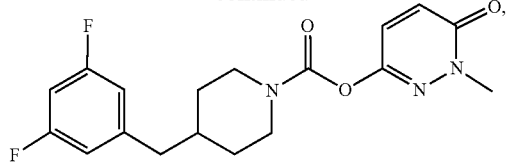
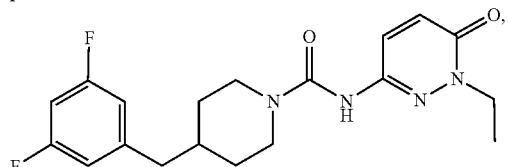
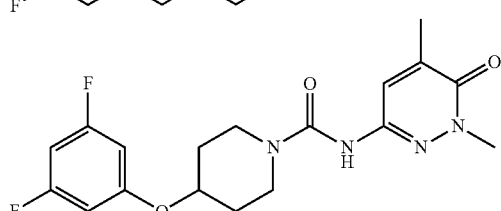
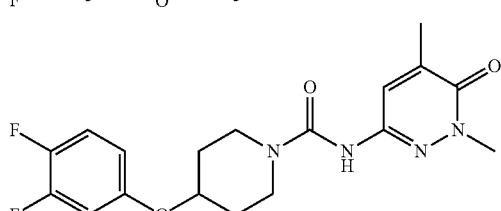
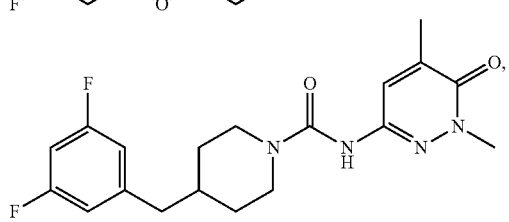
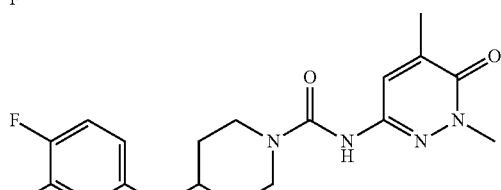
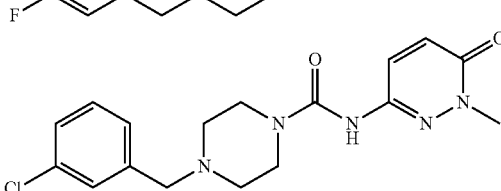
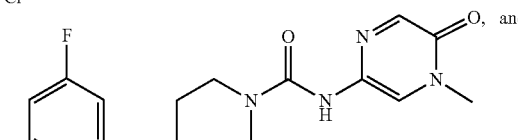
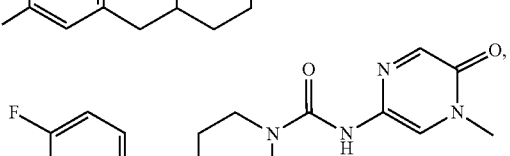
or a pharmaceutically acceptable salt thereof.

25. The method of claim 24, wherein the compound is:

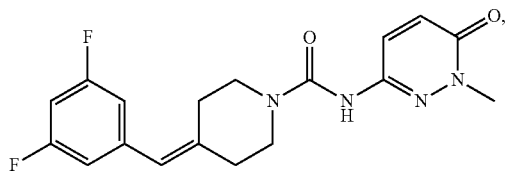 [SMILES: Cn1nc(NC(=O)N2CCC(=Cc3cc(F)cc(F)c3)CC2)ccc1=O]

or a pharmaceutically acceptable salt thereof.

26. The method of claim 24, wherein the compound is:

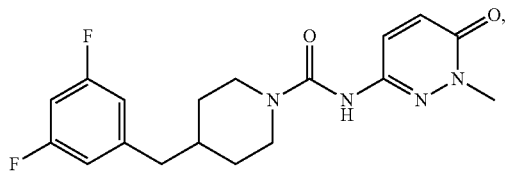 [SMILES: Cn1nc(NC(=O)N2CCC(Cc3cc(F)cc(F)c3)CC2)ccc1=O]

or a pharmaceutically acceptable salt thereof.

27. The method of claim 24, wherein the compound is:

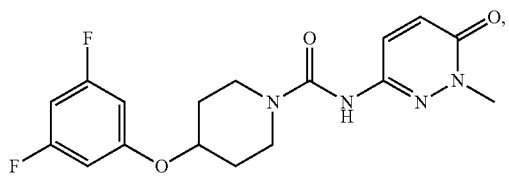 [SMILES: Cn1nc(NC(=O)N2CCC(Oc3cc(F)cc(F)c3)CC2)ccc1=O]

or a pharmaceutically acceptable salt thereof.

28. The method of claim 24, wherein the compound is:

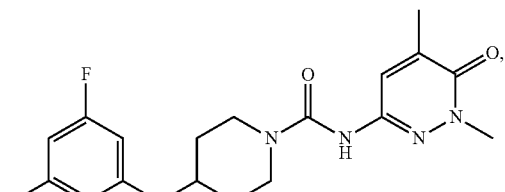

or a pharmaceutically acceptable salt thereof.

29. The method of claim 24, wherein the compound is:

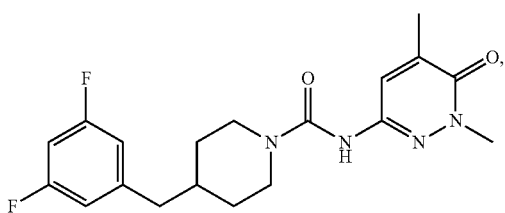 [SMILES: Cc1cc(NC(=O)N2CCC(Cc3cc(F)cc(F)c3)CC2)nn(C)c1=O]

or a pharmaceutically acceptable salt thereof.

* * * * *